United States Patent
Beaudenon-Huibregtse et al.

(10) Patent No.: US 11,118,231 B2
(45) Date of Patent: *Sep. 14, 2021

(54) MIRNAS AS BIOMARKERS FOR DISTINGUISHING BENIGN FROM MALIGNANT THYROID NEOPLASMS

(71) Applicant: INTERPACE DIAGNOSTICS, LLC, Parsippany, NJ (US)

(72) Inventors: Sylvie Beaudenon-Huibregtse, Austin, TX (US); Ashish Choudhary, Austin, TX (US)

(73) Assignee: INTERPACE DIAGNOSTICS, LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,769

(22) Filed: Nov. 13, 2018

(65) Prior Publication Data

US 2019/0309370 A1    Oct. 10, 2019

Related U.S. Application Data

(63) Continuation of application No. 13/299,226, filed on Nov. 17, 2011, now Pat. No. 10,150,999.

(60) Provisional application No. 61/414,778, filed on Nov. 17, 2010.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 7,888,010 B2 | 2/2011 | Brown et al. |
| 2001/0051344 A1 | 12/2001 | Shalon et al. |
| 2005/0059024 A1 | 3/2005 | Conrad |
| 2007/0161004 A1 | 7/2007 | Brown et al. |
| 2009/0092974 A1 | 4/2009 | Davison et al. |
| 2009/0131348 A1 | 5/2009 | Labourier et al. |
| 2009/0176723 A1 | 7/2009 | Brown et al. |
| 2010/0178653 A1 | 7/2010 | Aharonov et al. |
| 2010/0216139 A1 | 8/2010 | Galas et al. |
| 2011/0312530 A1 | 12/2011 | Aharonov et al. |
| 2013/0310276 A1 | 11/2013 | Johansen et al. |

FOREIGN PATENT DOCUMENTS

| | | |
|---|---|---|
| CN | 101423869 A | 5/2009 |
| WO | 2007148235 A2 | 12/2007 |
| WO | 2008002672 A2 | 1/2008 |
| WO | 2009066291 A2 | 5/2009 |
| WO | 2010073248 A2 | 7/2010 |
| WO | 2011154008 A1 | 12/2011 |
| WO | 2012068400 A2 | 5/2012 |
| WO | 2012129378 A1 | 9/2012 |

OTHER PUBLICATIONS

Szafranska et al. (Oncogoene (2007) 26, 4442-4452).
Szafranska et al (Clin. Chem. 54(10): 1716-1724, 2008).
Aherne et al., "Geographical mapping of a multifocal thyroid tumour using genetic alteration analysis & miRNA profiling," Molecular Cancer (2008) 7:89.
Kitano et al., "Expression profiling of difficult-to-diagnose thyroid histologic subtypes shows distinct expression profiles and identify candidate diagnostic microRNAs," Annals of Surgical Oncology (2011) 18(12):3443-3453.
Bernecker, et al., Thyroid. 22(12): 1294-5, 2012.
Dettmer, et al. , J Clin Endocrin Metab. 98:0000-0000, 2013.
Dorris, et al., "MIR141 expression differentiates Hashimoto thyroiditis from PTC and benign thyrocytes in Irish archival thyroid tissues," Front Endocrin. (2012) vol. 3 (102): 1-6.
Elton, et al., Gene. Doi: 10.10 16/j.gene.20 12. 12.009, 2012.
Geraldo, et al. Bras Endocrinol Metab. 56(8): 552-7, 2012.
Lee, et al. Gene. Doi: 10. 1016/j.genc.2012.11.068, 2012.
Lodewijk, et al., Cancer Biomarkers. 11:229-38, 2011/2012.
Morin, "MiRNAs in cancer: Non-coding RNAs as appealing biomarkers for malignancy," Cancer Biomarker (2012) 11:227-228.
Patrizia, et al., "MicroRNA Expression Profile Helps to Distinguish Benign Nodules from Pupillary Thyroid Carcinomas Starting from Cells of Fine Needle Aspiration." Euro Soc Endocrinol. 1-29, 2012.
Rossing, et al., "miRNAs in Follicular Thyroid Tumours." Society Endocrinol. 1-41, 2011.
Shen. et al., Thyroid. 22(1): 9-16, 2012.
Wang, et al. Mutagenesis. Doi: 10.1093/mutage/ges052: 1-10. 2012.
Yip, et al., Ann Surg Oncol. Doi: 10.1245/s10434-011-1733-0: 1-7, 2011.
Zhou,et al., Med Oncol. DO1: 10. 1007/s 12032-012-0315-8: 1-7, 2012.
Ambros, Cell. 107(7):823-826, 2001.
Brennecke et al., Cell, 113:25-36, 2003.
Calin et al., Proc. Natl. Acad. Sc. USA. 99:15524-15529,2002.
Carrington et al. Science. 301 (5631): 336-338, 2003.
Denli et al. Trends Biochem. Sci., 28:196, 2003.
Didenko, Biolechniques, 31(5): 1106-16, 1118, 1120-1, 2001.
Esquela-Kerscher and Slack, Nat Rev Cancer, 6(4):259-269, 2006.
Lagos-Quintana et al. Science, 294(5543):853-858, 2001.
Lau et al., Science, 294(5543):858-862, 2001.
Lee and Ambros, Science, 294(5543):862-864, 2001.
Lu et al., Nature, 435(7043):834-838, 2005.

(Continued)

*Primary Examiner* — Celine X Qian
(74) *Attorney, Agent, or Firm* — Troutman Pepper Hamilton Sanders LLP

(57) ABSTRACT

The present invention concerns methods and compositions for identifying a miRNA profile for a particular condition, such as thyroid nodules or thyroid cancer, and using the profile in the diagnosis of a patient for a condition, such as thyroid nodules or thyroid cancer.

6 Claims, 6 Drawing Sheets

(56) References Cited

OTHER PUBLICATIONS

Olsen et al., "The lin-4 Regulatory RNA Controls Developmental Timing in Caenorhabditis elegans by Blocking LIN-14 Protein Synthesis after the Initiation of Translation," Dev. Biol. (1999) 216:671-680.
Seggerson et al., "Two Genetic Circuits Repress the Caenorhabditis elegans Heterochronic Gene lin-28 after Translation Initiation," (2002) Dev. Biol. 243:215-225.
Xu et al., "The *Drosophila* MicroRNA Mir-14 Suppresses Cell Death and Is Required for Normal Fat Metabolism," Curr. Biol., (2003) 13:790-795.
Braun et al., "downregulation of microRNAs directs the EMT and invasive potential of anaplastic thyroid carcinmoas", Oncogene, p. 4237-44, 2010.
Kroese et al (Genetics in Medicine 6(6) :475-480, 2004).
Lucentini (The Scientist, 18(24):20, 2004).
Internation Search Report and Written Opinion in International Application No. PCT/US2011/061237 dated Nov. 2, 2012.
Schopman et al., "A miRNA-tRNA mix-up: tRNA origin of propsed miRNA", RNA Biology (2010) vol. 7, No. 5, pp. 573-576.
Chen, et al., "MicroRNA analysis as a potential diagnostic tool for papillary thyroid carcinoma," Mod. Pathol., 21:1139-46, 2008.
Eszlinger and Paschke, "Molecular fine-needle aspiration biopsy diagnosis of thyroid nodules by tumor specific mutations and gene expression patterns," Mol. Cell. Endocrinol., 322:29-37, 2010.
Gao, et al., "miRNA expression in a human papillary thyroid carcinoma cell line varies with invasiveness," Endocr. J., 57:81-6, 2010.
Griffiths-Jones, etal., "miRBase: microRNA sequences, targets and gene nomenclature," Nucleic Acids Res., 34:0140-4, 2006.
He, et al., "The role of micro RNA genes in papillary thyroid carcinoma," Proc. Natl. Acad. Sci. USA, 102:19075-80,2005.
Huber, et al., "Variance stabilization applied to microarray data calibration and to the quantification of differential expression," Bioinformatics, 18:896-104, 2002.
Jazdzewski, et al., "Common SNP in pre-miR-146a decreases mature miR expression and predisposes to papillary thyroid carcinoma," Proc. Nat/. Acad. Sci. USA, 105:7269-74, 2008.
Jazdzewski, et al., "Polymorphic mature microRNAs from passenger strand of pre-miR-146a contribute to thyroid cancer," Proc. Nat/. Acad. Sci. USA, 106:1502-5,2009.
Li, et al., "Comparison ofMicroRNA expression in thyroid neoplasms: an aid for diagnostic evaluation" United States and Canadian Academy Pathology 2010 Annual Meeting, Mar. 23, 2010.
Lubitz, et al., "Microarray analysis of thyroid nodule tine-needle aspirates accurately classifies benign and malignant lesions," J. Mol. Diagn., 8:490-8, 2006.
Menon and Khan "Micro-RNAs in thyroid neoplasms: molecular, diagnostic and therapeutic implications," J. Clin. Pathol., 62:978-85, 2009.
Mitomo, et al., "Downregulation ofmiR-138 is associated with overexpression ofhuman telomerase reverse transcriptase protein in human anaplastic thyroid carcinoma cell lines," Cancer Sci., 99:280-6, 2008.
Nikiforova, et al., "MicroRNA expression profiles in thyroid tumors," Endocr. Pathol., 20:85-91, 2009.
Nikiforova, et al., "MicroRNA expression profiling of thyroid tumors: biological significance and diagnostic utility," J. Clin. Endocrinol. Metab. (2008) 93:1600-8.
Pacifico, et al., "Nuclear factor-{kappa}B contributes to anaplastic thyroid carcinomas through up-regulation of rniR-146a," J. Clin. Endocrinol. Metab., 95:1421-30, 2010.
Pallante, et al., "Deregulation ofmicroRNA expression in follicular cell-derived human thyroid carcinomas" Endocr. Relat. Cancer, 17:F91-104, 2010.
Pallante, et al., "MicroRNA deregulation in human thyroid papillary carcinomas," Endocr. Relat. Cancer, 13:497-508, 2006.
Rippe, et al., "The two stem cell microRNA gene clusters C19MC and miR-371-3 are activated by specific chromosomal rearrangements in a subgroup of thyroid adenomas," PLoS One, 5:e9485, 2010.
Santarpia, et al., "Deregulation of miRNA-200 family in medullary thyroid carcinoma modulates the expression of cadherin members and mediates cell-adhesion and tight junctions," American Thyroid Association 2009 Annual Meeting, Sep. 26, 2009.
Schwertheim, et al., "Analysis of deregulated miRNAs is helpful to distinguish poorly differentiated thyroid carcinoma from papillary thyroid carcinoma," Horm. Metab. Res., 41:475-81,2009.
Sheu, et al., "Differential miRNA expression profiles in variants of papillary thyroid carcinoma and encapsulated follicular thyroid tumours," Br. J. Cancer, 102:376-82, 2010.
Sheu, et al., "Lack of correlation between BRAF V600E mutational status and the expression profile of a distinct set ofmiRNAs in papillary thyroid carcinoma," Horm. Metab. Res., 41:482-7, 2009.
Takakura, et al., "Oncogenic role of miR-17-92 cluster in anaplastic thyroid cancer cells," Cancer Sci., 99:1147-54, 2008.
Tetzlaff, et al., "Differential expression ofmiRNAs in papillary thyroid carcinoma compared to multinodular goiter using formalin fixed paraffin embedded tissues," Endocr. Pathol., 18:163-73,2007.
Visone, et al., "MicroRNAs (miR)-221 and miR-222, both overexpressed in human thyroid papillary carcinomas, regulate p27Kip1 protein levels and cell cycle," Endocr. Relat. Cancer, 14:791-8, 2007.
Visone, et al., "Specific microRNAs are downregulated in human thyroid anaplastic carcinomas," Oncogene, 26:7590-5,2007.
Vriens, et al., "Diagnostic markers and prognostic factors in thyroid cancer," Future Oncol., 5:1283-93, 2009.
Vriens, et al., "MicroRNA expression profiling is a potential diagnostic tool for thyroid cancer," Cancer, 2011.
Weber, et al., "A limited set of human MicroRNA is deregulated in follicular thyroid carcinoma," J. Clin. Endocrinol. Metab., 91:3584-91,2006.
Bargren et al (World J Surg (2010) 34:1254-1260).
Mazeh et al (Thyroid 21(2): 111-118, Feb. 2011).
Chou et al (Thyroid 20:489-94, 2010).
TaqMan Array Human MicroRNA Cards—Applied Biosystems [retreived from the internet on Apr. 18, 2016].
Non-final Office Action dated Oct. 18, 2016 in U.S. Appl. No. 13/662,450.
Non-final Office Action dated Jul. 17, 2017 in U.S. Appl. No. 13/662,450.
Notice of Allowance dated Jul. 26, 2018 in U.S. Appl. No. 13/299,226.
Deftereos et al., "The value of mutational profiling of the cytocentrifugation supernatant fluid from fine-needle aspiration of pancreatic solid mass lesions," Modern Pathology (2014) 27, 594-601.

MIRNAS AS BIOMARKERS FOR DISTINGUISHING BENIGN FROM MALIGNANT THYROID NEOPLASMS

This application is a continuation of U.S. patent application Ser. No. 13/299,266, filed Nov. 17, 2011, which claims the benefit of U.S. Provisional Patent Application 61/414,778 filed on Nov. 17, 2010, which is hereby incorporated by reference in its entirety.

BACKGROUND OF THE INVENTION

I. Field of the Invention

The present invention relates generally to the fields of molecular biology and oncology. More particularly, it concerns methods and compositions involving microRNA (miRNAs) molecules and cancer diagnosis and/or prognosis. Certain aspects include applications for miRNAs in diagnosis and prognosis of thyroid cancer.

II. Background

The vast majority of thyroid cancers occur randomly. However, several reports have shown that the incidence of thyroid cancer is higher in individuals exposed to radiation, whether the radiation is from treatment for disease (e.g., for Hodgkin's and Graves' diseases) or from accidental exposure. Childhood radiation exposure is the only well-documented risk factor for the development of thyroid cancer. Also, medullary thyroid cancers, a rare form of thyroid cancer, have been linked to a genetic predisposition, and approximately 5% of non-medullary thyroid cancers are hereditary. Patients with a history of Graves' disease, thyroiditis, goiter, or a family history of familial adenomatous polyposis (FAP) have an elevated risk of developing thyroid cancer. Most thyroid cancers are indolent and usually treatable when detected early. A subset of thyroid tumors can however behave aggressively.

Thyroid tumors encompass a variety of lesions that range from benign adenoma to malignant tumors. The cancers can be well-differentiated, poorly-differentiated, or undifferentiated (anaplastic). More than 95% of thyroid cancers are derived from thyroid follicular cells, 2-3% of cancers (medullary thyroid carcinomas) are derived from the thyroid C cells, and approximately 1% of tumors are anaplastic. Approximately 80% of all thyroid cancers are follicular-cell derived papillary thyroid carcinomas (PTC), which may spread to local lymph nodes. The tall cell variant (TCV) of PTC represents the most common aggressive form of PTC. The second most common tumor type, approximately 15% of all cancers, is follicular thyroid carcinoma (FTC), which may be of conventional or oncocytic (Hürthle) cell type. FTC can develop either de novo or from a pre-existing benign follicular adenoma and is characterized by haematogenous spread. Both PTC and FTC are well-differentiated cancers that are usually indolent and have a good prognosis. In contrast, poorly-differentiated carcinomas (PDC) and anaplastic thyroid cancers (ATC) are highly aggressive and lethal tumors that can develop de novo or from the progression of pre-existing PTC or FTC. Fortunately, ATC are rare, accounting for ~5% of all thyroid cancers, and easily diagnosed Although thyroid cancer is relatively rare, thyroid nodules are very common. Because the great majority of thyroid nodules are benign, a continuing challenge for physicians is to accurately distinguish benign nodules from malignant nodules. Cytology of fine needle aspiration biopsies, the current standard for evaluating malignancy of thyroid nodules, frequently lacks specificity and is incapable of determining malignancy in up to 40% of cases. Recently, molecular testing for mutations or translocations in genes such as BRAF, RAS, RET/PTC, and PAX8/PPARγ has been applied to thyroid cancer diagnosis. However, some thyroid cancers do not carry mutations in these genes and some of these markers have low specificity for malignancy.

Recently, microRNAs have been implicated in various cancers, including thyroid cancer. microRNAs (miRNAs) are short RNA molecules (16-29 nucleotides in length) that arise from longer precursors, which are transcribed from non-protein coding genes (Carrington et al., 2003). The precursors are processed by cellular proteins to generate short double-stranded miRNA. One of the miRNA strands is incorporated into a complex of proteins and miRNA called the RNA-induced silencing complex (RISC). The miRNA guides the RISC complex to a target mRNA, which is then cleaved or translationally silenced, depending on the degree of sequence complementarity of the miRNA or its target mRNA (Bagga et al., 2005; Lim et al., 2005).

A need exists for additional thyroid cancer markers that are capable of distinguishing benign from malignant thyroid nodules and distinguishing among the different types of thyroid cancers.

SUMMARY OF THE INVENTION

The inventors have recognized that additional methods to improve the preoperative assessment of thyroid nodules are a critical need. Novel methods for assessment would have a significant impact on clinical care by reducing the number of unnecessary thyroid surgeries and associated financial costs and morbidity. Additional methods for diagnosis and prognosis of thyroid cancer are provided, in certain aspects, by identifying miRNAs that are differentially expressed or mis-regulated in various types of diseased, normal, cancerous, and/or abnormal tissues, including but not limited to normal thyroid, benign thyroid conditions, and various types of thyroid cancers. Further, also described are methods for diagnosing thyroid cancer and identifying a thyroid cancer type that are based on determining levels (increased or decreased) of selected miRNAs in patient-derived samples.

In certain embodiments, methods are directed to detecting a pre-malignant or malignant thyroid nodule in a subject comprising measuring expression levels of one or more miRNAs selected from miR-1274a, miR-1274b, miR-720, miR-1260, miR-206, miR-92b*, miR-1202, miR-1300, miR-663, miR-149*, miR-631, miR-936, miR-187*, miR-1182, miR-198, miR-765, miR-648, miR-934, miR-142-5p, miR-146b-3p, miR-146b-5p, miR-181a-2*, miR-7, miR-204, miR-135b*, miR-1322, miR-145, miR-1470, miR-1227, miR-182*, miR-372, miR-491-3p, miR-554, miR-1228, miR-1258, miR-130a, miR-1912, miR-200a*, miR-376a or miR-379 in a thyroid sample from the subject, wherein a change in miRNA expression level in the sample relative to a reference level is indicative of a pre-malignant or malignant thyroid nodule.

"Reference level" as it relates to a biomarker, such as an miRNA, refers to a level or amount of a biomarker in a healthy individual or control population. The reference level or amount may be determined by obtaining a biological sample and detecting the biomarker in a healthy individual, or may be determined by taking the level or amount known or readily determined from a control population.

In certain aspects, an increase in miR-1274a, miR-1274b, miR-720, or miR-1260 levels in the sample relative to a reference level, or a decrease in miR-206, miR-92b*, miR-1202, miR-1300, miR-663, miR-149*, miR-631, miR-936, miR-187*, miR-1182, miR-198, miR-765, miR-648, or miR-934 levels relative to a reference level, or a combination thereof is indicative of a pre-malignant or malignant thyroid nodule.

In certain aspects levels of miR-1274a and one or more of miR-1274b, miR-720, miR-1260, miR-206, miR-92b*, miR-1202, miR-1300, miR-663, miR-149*, miR-631, miR-936, miR-187*, miR-1182, miR-198, miR-765, miR-648, or miR-934; or miR-1274b and one or more of miR-1274a, miR-720, miR-1260, miR-206, miR-92b*, miR-1202, miR-1300, miR-663, miR-149*, miR-631, miR-936, miR-187*, miR-1182, miR-198, miR-765, miR-648, or miR-934; or miR-720 and one or more of miR-1274a, miR-1274b, miR-1260, miR-206, miR-92b*, miR-1202, miR-1300, miR-663, miR-149*, miR-631, miR-936, miR-187*, miR-1182, miR-198, miR-765, miR-648, or miR-934; or miR-1260 and one or more of miR-1274a, miR-1274b, miR-720, miR-206, miR-92b*, miR-1202, miR-1300, miR-663, miR-149*, miR-631, miR-936, miR-187*, miR-1182, miR-198, miR-765, miR-648, or miR-934; or miR-206 and one or more of miR-1274a, miR-1274b, miR-720, miR-1260, miR-92b*, miR-1202, miR-1300, miR-663, miR-149*, miR-631, miR-936, miR-187*, miR-1182, miR-198, miR-765, miR-648, or miR-934; or miR-92b* and one or more of miR-1274a, miR-1274b, miR-720, miR-1260, miR-206, miR-1202, miR-1300, miR-663, miR-149*, miR-631, miR-936, miR-187*, miR-1182, miR-198, miR-765, miR-648, or miR-934; or miR-1202 and one or more of miR-1274a, miR-1274b, miR-720, miR-1260, miR-206, miR-92b*, miR-1300, miR-663, miR-149*, miR-631, miR-936, miR-187*, miR-1182, miR-198, miR-765, miR-648, or miR-934; or miR-1300 and one or more of miR-1274a, miR-1274b, miR-720, miR-1260, miR-206, miR-92b*, miR-1202, miR-663, miR-149*, miR-631, miR-936, miR-187*, miR-1182, miR-198, miR-765, miR-648, or miR-934; or miR-663 and one or more of miR-1274a, miR-1274b, miR-720, miR-1260, miR-206, miR-92b*, miR-1202, miR-1300, miR-149*, miR-631, miR-936, miR-187*, miR-1182, miR-198, miR-765, miR-648, or miR-934; or miR-149* and one or more of miR-1274a, miR-1274b, miR-720, miR-1260, miR-206, miR-92b*, miR-1202, miR-1300, miR-663, miR-631, miR-936, miR-187*, miR-1182, miR-198, miR-765, miR-648, or miR-934; or miR-631 and one or more of miR-1274a, miR-1274b, miR-720, miR-1260, miR-206, miR-92b*, miR-1202, miR-1300, miR-663, miR-149*, miR-936, miR-187*, miR-1182, miR-198, miR-765, miR-648, or miR-934; or miR-936 and one or more of miR-1274a, miR-1274b, miR-720, miR-1260, miR-206, miR-92b*, miR-1202, miR-1300, miR-663, miR-149*, miR-631, miR-187*, miR-1182, miR-198, miR-765, miR-648, or miR-934; or miR-187* and one or more of miR-1274a, miR-1274b, miR-720, miR-1260, miR-206, miR-92b*, miR-1202, miR-1300, miR-663, miR-149*, miR-631, miR-936, miR-1182, miR-198, miR-765, miR-648, or miR-934; or miR-1182 and one or more of miR-1274a, miR-1274b, miR-720, miR-1260, miR-206, miR-92b*, miR-1202, miR-1300, miR-663, miR-149*, miR-631, miR-936, miR-187*, miR-198, miR-765, miR-648, or miR-934; or miR-198 and one or more of miR-1274a, miR-1274b, miR-720, miR-1260, miR-206, miR-92b*, miR-1202, miR-1300, miR-663, miR-149*, miR-631, miR-936, miR-187*, miR-1182, miR-765, miR-648, or miR-934; or miR-765 and one or more of miR-1274a, miR-1274b, miR-720, miR-1260, miR-206, miR-92b*, miR-1202, miR-1300, miR-663, miR-149*, miR-631, miR-936, miR-187*, miR-1182, miR-198, miR-648, or miR-934; or miR-648 and one or more of miR-1274a, miR-1274b, miR-720, miR-1260, miR-206, miR-92b*, miR-1202, miR-1300, miR-663, miR-149*, miR-631, miR-936, miR-187*, miR-1182, miR-198, miR-765, or miR-934; or miR-934 and one or more of miR-1274a, miR-1274b, miR-720, miR-1260, miR-206, miR-92b*, miR-1.202, miR-1300, miR-663, miR-149*, miR-631, miR-936, miR-187*, miR-1182, miR-198, miR-765, or miR-648 are measured.

In a further aspect the levels of miR-1274a, miR-1274b, miR-720, miR-1260, miR-206, miR-92b*, miR-1202, miR-1300, miR-663, miR-149*, miR-631, miR-936, miR-187*, miR-1182, miR-198, miR-765, miR-648, and miR-934 are measured.

In certain aspects the malignant thyroid nodule is a papillary thyroid carcinoma (PTC), follicular thyroid carcinoma (FTC), or follicular variant of papillary thyroid carcinoma (FVPTC). In a further aspect an increase in miR-142-5p, miR-146b-3p, miR-146b-5p, or miR-181a-2* levels in the sample relative to a reference level; or a decrease in miR-7, miR-204, miR-135b*, miR-1322, miR-145, or miR-1470 levels in the sample relative to a reference level; or a combination thereof is indicative of a malignant thyroid nodule.

In a further aspect the levels of miR-142-5p and one or more of miR-146b-3p, miR-146b-5p, miR-181a-2*, miR-7, miR-204, miR-135b*, miR-1322, miR-145, or miR-1470; or miR-146b-3p and one or more of miR-142-5p, miR-146b-5p, miR-181a-2*, miR-7, miR-204, miR-135b*, miR-1322, miR-145, or miR-1470; or miR-146b-5p and one or more of miR-142-5p, miR-146b-3p, miR-181a-2*, miR-7, miR-204, miR-135b*, miR-1322, miR-145, or miR-1470; or miR-181a-2* and one or more of miR-142-5p, miR-146b-3p, miR-146b-5p, miR-7, miR-204, miR-135b*, miR-1322, miR-145, or miR-1470; or miR-7 and one or more of miR-142-5p, miR-146b-3p, miR-146b-5p, miR-181a-2*, miR-204, miR-135b*, miR-1322, miR-145, or miR-1470; or miR-204 and one or more of miR-142-5p, miR-146b-3p, miR-146b-5p, miR-181a-2*, miR-7, miR-135b*, miR-1322, miR-145, or miR-1470; or miR-135b* and one or more of miR-142-5p, miR-146b-3p, miR-146b-5p, miR-181a-2*, miR-7, miR-204, miR-1322, miR-145, or miR-1470; or miR-1322 and one or more of miR-142-5p, miR-146b-3p, miR-146b-5p, miR-181a-2*, miR-7, miR-204, miR-135b*, miR-145, or miR-1470; or miR-145 and one or more of miR-142-5p, miR-146b-3p, miR-146b-5p, miR-181a-2*, miR-7, miR-204, miR-135b*, miR-1322, or miR-1470; or miR-1470 and one or more of miR-142-5p, miR-146b-3p, miR-146b-5p, miR-181a-2*, miR-7, miR-204, miR-135b*, miR-1322, or miR-145 are measured.

In a certain aspect the levels of miR-142-5p, miR-146b-3p, miR-146b-5p, miR-181a-2*, miR-7, miR-204, miR-135b*, miR-1322, miR-145, and miR-1470 are measured.

In a certain aspect an increase in miR-1227, miR-182*, miR-372, miR-491-3p, miR-554 levels in the sample relative to a reference level; or a decrease in miR-1228, miR-1258, miR-130a, miR-1912, miR-200a*, miR-376a or miR- 379 levels in the sample relative to a reference level; or a combination thereof is indicative of a pre-malignant thyroid nodule.

In certain aspects the levels of miR-1227 and one or more of miR-182*, miR-372, miR-491-3p, miR-554, miR-1228, miR-1258, miR-130a, miR-1912, miR-200a*, miR-376a or miR-379, or miR-182* and one or more of miR-1227, miR-372, miR-491-3p, miR-554, miR-1228, miR-1258, miR-130a, miR-1912, miR-200a*, miR-376a or miR-379, or miR-372 and one or more of miR-1227, miR-182*, miR-491-3p, miR-554, miR-1228, miR-1258, miR-130a, miR-1912, miR-200a*, miR-376a or miR-379, or miR-491-3p and one or more of miR-1227, miR-182*, miR-372, miR-554, miR-1228, miR-1258, miR-130a, miR-1912, miR-200a*, miR-376a or miR-379, or miR-554 and one or more of miR-1227, miR-182*, miR-372, miR-491-3p, miR-1228, miR-1258, miR-130a, miR-1912, miR-200a*, miR-376a or miR-379, or miR-1228 and one or more of miR-1227, miR-182*, miR-372, miR-491-3p, miR-554, miR-1258, miR-130a, miR-1912, miR-200a*, miR-376a or miR-379, or miR-1258 and one or more of miR-1227, miR-182*, miR-372, miR-491-3p, miR-554, miR-1228, miR-130a, miR-1912, miR-200a*, miR-376a or miR-379, or miR-130a and one or more of miR-1227, miR-182*, miR-372, miR-491-3p, miR-554, miR-1228, miR-1258, miR-1912, miR-200a*, miR-376a or miR-379, or miR-1912 and one or more of miR-1227, miR-182*, miR-372, miR-491-3p, miR-554, miR-1228, miR-1258, miR-130a, miR-200a*, miR-376a or miR-379, or miR-200a* and one or more of miR-1227, miR-182*, miR-372, miR-491-3p, miR-554, miR-1228, miR-1258, miR-130a, miR-1912, miR-376a or miR-379, or miR-376a and one or more of miR-1227, miR-182*, miR-372, miR-491-3p, miR-554, miR-1228, miR-1258, miR-130a, miR-1912, miR-200a*, or miR-379, or miR-379 and one or more of miR-1227, miR-182*, miR-372, miR-491-3p, miR-554, miR-1228, miR-1258, miR-130a, miR-1912, miR-200a*, or miR-376a are measured.

In certain aspects the levels of miR-1227, miR-182*, miR-372, miR-491-3p, miR-554, miR-1228, miR-1258, miR-130a, miR-1912, miR-200a*, miR-376a and miR-379 are measured.

In certain aspects the pre-malignant thyroid nodule is a follicular adenoma (FA).

In certain aspects the reference level is an average level of expression of the measured miRNA in a hyperplastic nodule (NOD) reference samples. In further aspects the reference level is an average level of expression of the measured miRNA in a follicular adenoma (FA) reference samples.

In certain aspects miRNA expression levels are decreased or increased if they are at least 4, 6, 8, 10, 20, or 40 fold less or more than reference levels.

The sample can be isolated RNA, fresh tissue or cells, frozen tissue or cells, fixed tissue or cells, or embedded tissue or cells from a thyroid nodule. In certain aspects the sample is a biopsy, such as a surgical resection or a fine needle aspirate.

Embodiments may further comprise one or more of obtaining a sample from the subject; labeling miRNA from the sample; and/or hybridizing a labeled miRNA to one or more miRNA probes. In certain aspects the miRNA probes are coupled to a support. The support can be, but is not limited to glass, plastic, metal, or latex. In a further aspect the support is planar or is a bead.

The methods can further comprise one or more of diagnosing a subject with thyroid cancer if the miRNA level profile is indicative of a malignant thyroid nodule; providing a prognosis; providing a report of the miRNA levels; classifying a malignant thyroid nodule based on the measured miRNA levels; and/or assessing responsiveness of a thyroid nodule to therapy. As used herein, the term "diagnosis" refers to distinguishing between malignant and benign thyroid neoplasms. As used herein, the term "providing a prognosis" refers to providing a prediction of the probable course and outcome of the thyroid cancer.

In certain aspects the expression level of an miRNA is determined by an amplification assay or a hybridization assay. The amplification assay can be a quantitative amplification assay, such as but not limited to quantitative RT-PCR. The hybridization assay can be an array hybridization assay or a solution hybridization assay.

In some embodiments methods for evaluating a thyroid sample are provided in which methods involve measuring the level of expression of one or more miRNAs or the miRNA precursors, or one or more targets of the miRNA. In some embodiments, the thyroid sample has not been evaluated for any mutations associated with malignancy. In other embodiments, the thyroid sample has been tested for a BRAF V600E mutation. In certain cases, the thyroid sample from a patient has been determined to be negative for a BRAF V600E mutation. In further embodiments, the thyroid sample has been alternatively or additionally tested for a point mutation in one or more of the following: N-Ras, H-Ras or K-Ras and/or for the following genetic alterations: RET/PTC 1 (translocation), RET/PTC3 (translocation), and/or PAX8-PPARg Fusion Protein (PPFP) (translocation); these will be collectively referred to as mutations. In certain embodiments, a thyroid sample has been determined to be negative for a BRAF V600E mutation. In other embodiments, the thyroid sample has been determined to be negative for the following mutations: N-Ras, H-Ras, K-Ras, RET/PTC 1 (translocation), RET/PTC3 (translocation), PAX8-PPARg Fusion Protein (PPFP) (translocation). In further embodiments, however, a thyroid sample has been determined to be positive for a mutation related to thyroid malignancy, such as N-Ras, H-Ras, K-Ras, RET/PTC 1 (translocation), RET/PTC3 (translocation), PAX8-PPARg Fusion Protein (PPFP) (translocation). In some embodiments, a patient may be tested for a BRAF V600E mutation by having a thyroid sample assayed for miR-146b expression (Chou et al. 2010, which is hereby incorporated by reference).

In some embodiments, methods and steps discussed below are implemented on a thyroid sample that has been determined to be negative for a BRAF V600E mutation, to be positive for a mutation in N-Ras, H-Ras, K-Ras, RET/PTC 1 (translocation), RET/PTC3 (translocation), and/or PAX8-PPARg Fusion Protein (PPFP) (translocation), or to be negative for a mutation in BRAF V600E, N-Ras, H-Ras, K-Ras, RET/PTC 1 (translocation), RET/PTC3 (translocation), and PAX8-PPARg Fusion Protein (PPFP) (translocation), or to have an unknown mutation status related to BRAF V600E, N-Ras, H-Ras, K-Ras, RET/PTC 1 (translocation), RET/PTC3 (translocation), and PAX8-PPARg Fusion Protein (PPFP) (translocation). In some embodiments, methods include determining whether a thyroid sample has a BRAF V600E mutation. In even further embodiments, methods include assaying the sample for a BRAF V600E mutation. This assay may be performed before, after, or at the same time that the expression level of one or more miRNAs or other biomarkers is measured. Also, this assay may be performed before, after, or at the same time that a sample is assayed for a mutation in N-Ras, H-Ras, and/or K-Ras and/or for RET/PTC 1 (translocation), RET/PTC3 (translocation), and/or PAX8-PPARg Fusion Protein (PPFP) (translocation).

Measuring a microRNA or miRNA refers to measuring the amount of a mature microRNA or miRNA, though it is contemplated that in some embodiments a mature miRNA may be indirectly determined by measuring the level of an immature or unprocessed form of the miRNA, such as the double-stranded RNA molecule or RNA hairpin structure. Moreover, in some embodiments, amount of a mature miRNA is determined by measuring the amount of one or more of the miRNA's target or the targets complement. An miRNA's target refers to the endogenous RNA in the thyroid cell that is the target for the miRNA and whose expression is affected by the miRNA. Consequently, any embodiments discussed herein in the context of determining the amount of a microRNA (i.e., the mature form of a microRNA) can be implemented instead in some embodiments by measuring a precursor of the miRNA or one or more of the miRNA's target (or the complement thereof). Unless qualified, the term "measuring" refers to directly measuring. Mature miRNAs may be indirectly determined by directly measuring precursor microRNA molecules. It will be understood that the term "star" in the context of a miR refers to an asterisk (*); for example, miR-222-star is the same as miR-222*.

Methods also include evaluating the thyroid sample by calculating a score based on the compared expression levels, wherein the score indicates probability that the thyroid sample is benign, pre-malignant, or malignant.

Methods for treating a patient with thyroid cancer are also provided. In some embodiments such methods comprise: a) obtaining a diagnostic score based on expression levels of miRNAs in a thyroid sample from the patient, wherein the expression levels differ between malignant thyroid cancer cells compared to non-malignant, benign, or normal thyroid cells and wherein the thyroid sample has been determined to be negative for a BRAF V600E mutation; and, b) performing a thyroidectomy on a patient determined to have a diagnostic score indicative of malignant thyroid cancer. In certain embodiments, the diagnostic score indicates the sample is pre-malignant.

In some embodiments, a patient is also administered radioactive iodine, radiation and/or chemotherapy as part of a treatment regimen. In further embodiments, methods may involve determining the patient as having or likely having a benign thyroid condition, or determining the patient has not having or likely not having a malignancy. In such cases, a clinician may then decide not to subject the patient to surgery. In such cases, the patient may continue to be monitored. In certain embodiments, methods involve imaging an unresected thyroid growth or doing a biopsy before and/or after miRNA levels are measured. In further embodiments, the imaging or biopsy occurs after 1, 2, 3, 4, 5, 6 months following a test that involves measuring one or more miRNA expression levels.

In some embodiments, methods will involve determining or calculating a diagnostic score based on data concerning the expression level of one or more miRNAs, meaning that the expression level of the one or more miRNAs is at least one of the factors on which the score is based. A diagnostic score will provide information about the biological sample, such as the general probability that the thyroid sample is malignant and/or an aggressive tumor or that the thyroid sample is pre-malignant, or that the thyroid sample is benign or normal. In some embodiments, the diagnostic score represents the probability that the thyroid sample is more likely than not either malignant or non-malignant. In certain embodiments, a probability value is expressed as a numerical integer that represents a probability of 0% likelihood to 100% likelihood that a patient has a thyroid malignancy or a noncancerous thyroid condition. In some embodiments, the probability value is expressed as a numerical integer that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a particular type of thyroid condition or growth.

In some embodiments, methods include evaluating one or more values of differential miRNA expression using a scoring algorithm to generate a diagnostic score for the thyroid growth in terms of being malignant or being benign or normal or noncancerous, wherein the patient is identified as having or as not having such a growth based on the score. It is understood by those of skill in the art that the score is a predictive value about the classification of the thyroid growth. In some embodiments, a report is generated and/or provided that identifies the diagnostic score or the values that factor into such a score. In some embodiments, a cut-off score is employed to characterize a sample as likely having a thyroid malignancy (or alternatively a benign thyroid condition). In some embodiments, the risk score for the patient is compared to a cut-off score to characterize the biological sample from the patient with respect to a malignancy or a benign or normal condition.

Methods may involve obtaining from the patient a thyroid sample, which means the sample is obtained directly from the patient. In other embodiments, a patient's thyroid tissue sample may be obtained from an entity that is not the patient, such as the doctor, clinician, hospital or laboratory. In certain embodiments, methods involve a thyroid tissue sample or a thyroid cyst or nodule sample. In particular embodiments, the sample is a tissue sample, while in other embodiments, the sample is a cystic fluid sample. In some cases, methods involve fixing the tissue sample in formalin and embedding it in paraffin prior to measuring the level of expression of one or more miRNAs or diff pair miRNAs in the sample. In additional embodiments, the sample is obtained by fine needle aspirate or FNA. In other embodiments, the sample is retrieved from a biopsy, such as a fine needle aspiration biopsy (FNAB) or a needle aspiration biopsy (NAB).

In additional embodiments, methods involve determining a treatment for the patient based on expression levels of one or more miRNAs, particularly differential expression. In some embodiments, methods include determining a treatment for the patient based on a calculated diagnostic score. In some embodiments, a patient may be suspected of having a thyroid malignancy. In other embodiments, the patient may have previously had a thyroid condition suspected of being malignant that was then subsequently treated. In other embodiments, the patient has recurring thyroid growth, which may or may not be malignant. In still further embodiments, the patient has a familial history of thyroid growths, particularly malignant thyroid growths. In some circumstances, a patient also presents with symptoms of a thyroid growth, such as fatigue, change in appetite and other symptoms relating to a change in thyroid hormone levels.

Certain embodiments are directed to a kit for analysis of a thyroid sample by assessing miRNA profile for a sample comprising, in suitable container means, two or more miRNA hybridization or amplification reagents comprising one or more of the miRNAs described herein. The miRNA hybridization reagent can comprise hybridization probes that bind to the miRNAs described herein. The miRNA amplification reagent can comprise amplification primers for the miRNAs described herein.

Other embodiments are discussed throughout this application. Any embodiment discussed with respect to one aspect of the invention applies to other aspects as well and vice versa. The embodiments in the Example section are understood to be embodiments of the invention that are applicable to all aspects of the invention.

Some embodiments further involve isolating ribonucleic or RNA from a biological sample. Other steps may or may not include amplifying a nucleic acid in a sample and/or hybridizing one or more probes to an amplified or non-amplified nucleic acid. In certain embodiments, a microarray may be used to measure or assay the level of miRNA expression in a sample.

The term "miRNA" or "miR" is used according to its ordinary and plain meaning and refers to a microRNA molecule found in eukaryotes that is involved in RNA-based gene regulation. See, e.g., Carrington et al., 2003, which is hereby incorporated by reference. The term will be used to refer to the single-stranded RNA molecule processed from a precursor. Names of miRNAs and their sequences related to embodiments are provided herein.

Individual miRNAs have been identified and sequenced in different organisms, and they have been given names. Names of miRNAs that are related to the disclosed methods and compositions, as well as their sequences, are provided herein. The name of the miRNAs that are used in methods and compositions refers to an miRNA that is at least 90% identical to the named miRNA based on its mature sequence listed herein and that is capable of being detected under the conditions described herein using the designated ABI part number for the probe. In most embodiments, the sequence provided herein is the sequence that is being measured in methods described herein. In some methods, a step may involve using a nucleic acid with the sequence comprising or consisting of any of the complements of any of SEQ ID NOs or any sequence found herein to measure expression of a miRNA in the sample. Alternatively, probes directed to the immature form of these miRNAs may be used, as may be probes directed to the targets of the miRNAs.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to a level of expression in a thyroid sample from a patient of at least one of the following miR-1274a, miR-1274b, miR-720, miR-1260, miR-206, miR-92b*, miR-1202, miR-1300, miR-663, miR-149*, miR-631, miR-936, miR-187*, miR-1182, miR-198, miR-765, miR-648, miR-934, miR-142-5p, miR-146b-3p, miR-146b-5p, miR-181a-2*, miR-7, miR-204, miR-135b*, miR-1322, miR-145, miR-1470, miR-1227, miR-182*, miR-372, miR-491-3p, miR-554, miR-1228, miR-1258, miR-130a, miR-1912, miR-200a*, miR-376a or miR-379, wherein at least one of the miRNAs is a biomarker miRNA; and b) comparing the level of expression to a reference level, wherein a difference is indicative of whether the thyroid nodule is malignant or benign. In some embodiments, receiving information comprises receiving from a tangible data storage device information corresponding to a level of expression in a thyroid sample from a patient of at least one of the following miRNAs: miR-1274a, miR-1274b, miR-720, miR-1260, miR-206, miR-92b*, miR-1202, miR-1300, miR-663, miR-149*, miR-631, miR-936, miR-187*, miR-1182, miR-198, miR-765, miR-648, miR-934, miR-142-5p, miR-146b-3p, miR-146b-5p, miR-181a-2*, miR-7, miR-204, miR-135b*, miR-1322, miR-145, miR-1470, miR-1227, miR-182*, miR-372, miR-491-3p, miR-554, miR-1228, miR-1258, miR-130a, miR-1912, miR-200a*, miR-376a or miR-379, wherein at least one of the miRNAs is differentially expressed in a cancerous nodule when compared to a reference marker or level. In additional embodiments the medium further comprises computer-readable code that, when executed by a computer, causes the computer to perform one or more additional operations comprising: sending information corresponding to the biomarker diff pair value to a tangible data storage device. In specific embodiments, it further comprises computer-readable code that, when executed by a computer, causes the computer to perform one or more additional operations comprising: sending information corresponding to the different expression level to a tangible data storage device. In certain embodiments, receiving information comprises receiving from a tangible data storage device information corresponding to a level of expression in a thyroid sample from a patient of at least one of the following miRNAs: miR-1274a, miR-1274b, miR-720, miR-1260, miR-206, miR-92b*, miR-1202, miR-1300, miR-663, miR-149*, miR-631, miR-936, miR-187*, miR-1182, miR-198, miR-765, miR-648, miR-934, miR-142-5p, miR-146b-3p, miR-146b-5p, miR-181a-2*, miR-7, miR-204, miR-135b*, miR-1322, miR-145, miR-1470, miR-1227, miR-182*, miR-372, miR-491-3p, miR-554, miR-1228, miR-1258, miR-130a, miR-1912, miR-200a*, miR-376a or miR-379, wherein differential expression compared to a reference may be indicative of cancer. In even further embodiments, the tangible computer-readable medium has computer-readable code that, when executed by a computer, causes the computer to perform operations further comprising: c) calculating a diagnostic score for the thyroid sample, wherein the diagnostic score is indicative of the probability that the thyroid sample is malignant or cancerous or normal. It is contemplated that any of the methods described above may be implemented with tangible computer readable medium that has computer readable code, that when executed by a computer, causes the computer to perform operations related to the measuring, comparing, and/or calculating a diagnostic score related to the probability of a malignancy or a benign thyroid condition.

A processor or processors can be used in performance of the operations driven by the example tangible computer-readable media disclosed herein. Alternatively, the processor or processors can perform those operations under hardware control, or under a combination of hardware and software control. For example, the processor may be a processor specifically configured to carry out one or more those operations, such as an application specific integrated circuit (ASIC) or a field programmable gate array (FPGA). The use of a processor or processors allows for the processing of information (e.g., data) that is not possible without the aid of a processor or processors, or at least not at the speed achievable with a processor or processors. Some embodiments of the performance of such operations may be achieved within a certain amount of time, such as an amount of time less than what it would take to perform the operations without the use of a computer system, processor, or processors, including no more than one hour, no more than 30 minutes, no more than 15 minutes, no more than 10 minutes, no more than one minute, no more than one second, and no more than every time interval in seconds between one second and one hour.

Some embodiments of the present tangible computer-readable media may be, for example, a CD-ROM, a DVD-ROM, a flash drive, a hard drive, or any other physical storage device. Some embodiments of the present methods may include recording a tangible computer-readable medium with computer-readable code that, when executed by a computer, causes the computer to perform any of the operations discussed herein, including those associated with the present tangible computer-readable media. Recording the tangible computer-readable medium may include, for example, burning data onto a CD-ROM or a DVD-ROM, or otherwise populating a physical storage device with the data.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
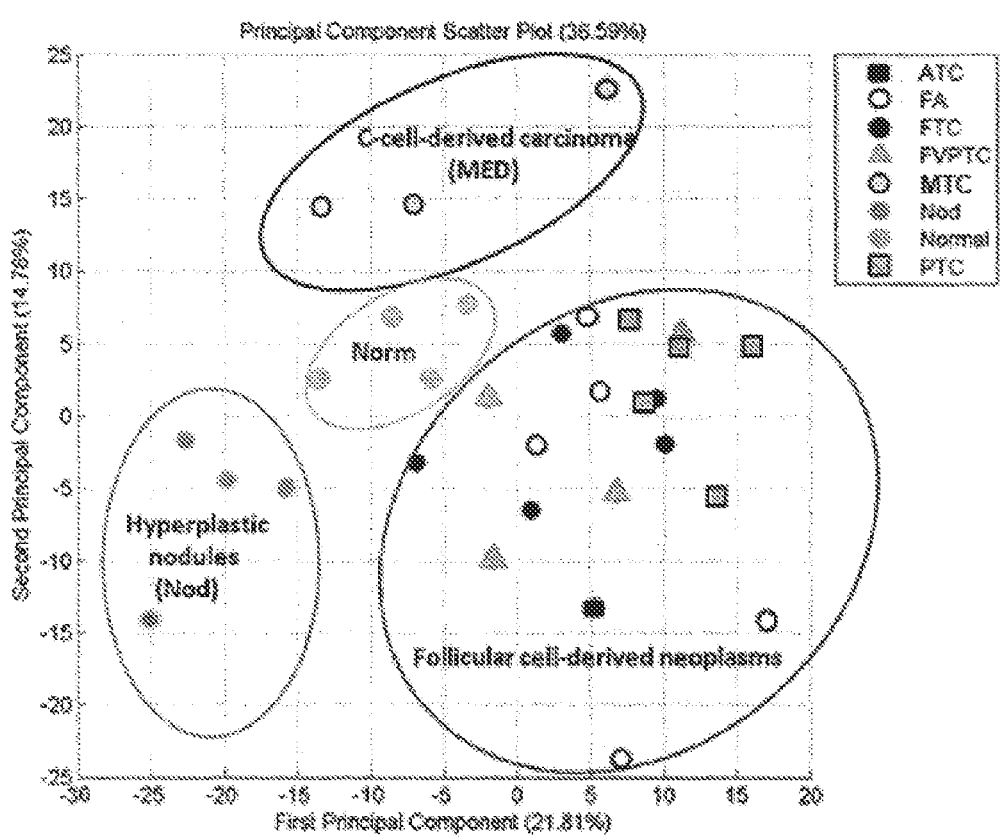
FIG. 1 miRNA expression profiles in normal, benign, and malignant thyroid tissues. Principal component analysis (PCA) on all detected miRNA probes between eight groups of thyroid samples. NOR, normal, N=4; NOD, hyperplastic nodules, N=4; FA, follicular adenoma, N=5; FTC, follicular thyroid carcinoma, N=5; PTC, papillary thyroid carcinoma, N=5; FVPTC, follicular variant of papillary thyroid carcinoma, N=4; ATC, anaplastic thyroid carcinoma, N=1; MTC, medullary thyroid carcinoma, N=3.

Embodiments are directed to compositions and methods relating to preparation and characterization of miRNAs, as well as use of miRNAs for prognostic and/or diagnostic applications, particularly those methods and compositions related to assessing and/or identifying thyroid disease. The present invention advances the current art for thyroid cancer diagnosis by describing the use of novel miRNA markers for thyroid cancer diagnosis and for distinguishing among different types of thyroid cancers.

I. Thyroid Conditions

Thyroid carcinoma represents 1% of all malignant diseases, but 90% of all neuroendocrine malignancies. It is estimated that 5-10% of the population will develop a clinically significant thyroid nodule during their life-time. The best available test in the evaluation of a patient with a thyroid nodule is fine needle aspiration biopsy (FNA). Of the malignant FNAs, the majority are from papillary thyroid cancers (PTC) or its follicular variant (FVPTC). These can be easily diagnosed if they have the classic cytologic features including abundant cellularity and enlarged nuclei containing intra-nuclear grooves and inclusions. Indeed, one third of the time these diagnoses are clear on FNA. Fine needle aspiration biopsy of thyroid nodules has greatly reduced the need for thyroid surgery and has increased the detection of malignant tumors among excised nodules. In addition, the diagnosis of malignant thyroid tumors, combined with effective therapy, has led to a marked decrease in morbidity due to thyroid cancer. Unfortunately, many thyroid FNAs are not definitively benign or malignant, yielding an "indeterminate" or "suspicious" diagnosis. The prevalence of indeterminate FNAs varies, but typically ranges from 10-25% of FNAs. In general, thyroid FNAs are indeterminate due to overlapping or undefined morphologic criteria for benign versus malignant lesions, or focal nuclear atypia within otherwise benign specimens. Of note, twice as many patients are referred for surgery for a suspicious lesion (10%) than for a malignant lesion (5%), an occurrence that is not widely appreciated since the majority of FNAs are benign. Therefore, when the diagnosis is unclear on FNA these patients are classified as having a suspicious or indeterminate lesion only. It is well known that frozen section analysis often yields no additional information.

The surgeon decides when to perform a thyroid lobectomy, which is appropriate for benign lesions or a total thyroidectomy, which is appropriate for malignant lesions when the diagnosis is uncertain both preoperatively and intra-operatively. Thyroid lobectomy as the initial procedure for every patient with a suspicious FNA could result in the patient with cancer having to undergo a second operation for completion thyroidectomy. Conversely, total thyroidectomy for all patients with suspicious FNA would result in a majority of patients undergoing an unnecessary surgical procedure, requiring lifelong thyroid hormone replacement and exposure to the inherent risks of surgery.

Several attempts to formulate a consensus about classification and treatment of thyroid carcinoma based on standard histopathologic analysis have resulted in published guidelines for diagnosis and initial disease management. In the past few, decades no improvement has been made in the differential diagnosis of thyroid tumors by FNA, specifically suspicious or indeterminate thyroid lesions, suggesting that a new approach to this should be explored. Thus, there is a compelling need to develop more accurate initial diagnostic tests for evaluating a thyroid nodule.

Thyroid cancer derived from the follicular epithelial cell is the most common endocrine cancer. Papillary thyroid carcinoma (PTC) and follicular thyroid carcinoma (FTC) account for the great majority of all thyroid malignancies. An estimated 7% of the adult population (275,000 in 1999 in the United States alone) develops clinically significant thyroid nodules during their lifetime. The advent of thyroid ultrasound now allows for an increasing number of nodules to be diagnosed, and it is now recognized that nodules are present in an estimated 50% of the general population and are detected at a subclinical level.

II. Evaluation of miRNA Levels

It is contemplated that a number of assays could be employed to analyze miRNAs in thyroid samples. Such assays include, but are not limited to, array hybridization, solution hybridization, nucleic amplification, polymerase chain reaction, quantitative PCR, RT-PCR, in situ hybridization, Northern hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), andlor Oligo Ligation Assay (OLA), hybridization, and array analysis.

U.S. patent applications Ser. No. 11/141,707, filed May 31, 2005; Ser. No. 11/857,948, filed Sep. 19, 2007; Ser. No. 11/273,640, filed Nov. 14, 2005 and provisional patent application 60/869,295, filed Dec. 8, 2006 are incorporated by reference in their entirety.

A. Sample Preparation

While endogenous miRNA is contemplated in compositions and methods, recombinant miRNA—including nucleic acids that are complementary or identical to endogenous miRNA or precursor miRNA—can also be handled and analyzed as described herein. Samples may be biological samples, in which case, they can be from lavage, biopsy, fine needle aspirates, exfoliates, blood, sputum, tissue, organs, semen, saliva, tears, urine, cerebrospinal fluid, body fluids, hair follicles, skin, or any sample containing or constituting biological cells of interest. In certain embodiments, samples may be, but are not limited to, fresh, frozen, fixed, formalin-fixed, preserved, RNAlater-preserved, paraffin-embedded, or formalin-fixed and paraffin-embedded thyroid samples.

B. Differential Expression Analyses

Methods can be used to detect differences in miRNA expression or levels between two samples, or a sample and a reference (e.g., a tissue or other biological reference or a digital reference representative of a non-cancerous state). Specifically contemplated applications include identifying and/or quantifying differences between miRNA from a sample that is normal and from a sample that is not normal, between a cancerous condition and a non-cancerous condition, or between two differently treated samples (e.g., a pretreatment versus a posttreatment sample). Also, miRNA may be compared between a sample believed to be susceptible to a particular therapy, disease, or condition and one believed to be not susceptible or resistant to that therapy, disease, or condition. A sample that is not normal is one exhibiting phenotypic trait(s) of a disease or condition or one believed to be not normal with respect to that disease or condition. It may be compared to a cell that is normal relative to that disease or condition. Phenotypic traits include symptoms of a disease or condition of which a component is or may or may not be genetic or caused by a hyperproliferative or neoplastic cell or cells, such as nodules or tumors.

It is specifically contemplated that embodiments can be used to evaluate differences between stages of disease, such as between hyperplasia, neoplasia, pre-cancer and cancer, or between a primary tumor and a metastasized tumor.

Phenotypic traits also include characteristics such as longevity, morbidity, susceptibility or receptivity to particular drugs or therapeutic treatments (drug efficacy), and risk of drug toxicity.

In certain embodiments, miRNA profiles may be generated to evaluate and correlate those profiles with pharmacokinetics. For example, miRNA profiles may be created and evaluated for patient tumor and blood samples prior to the patient's being treated or during treatment to determine if there are miRNAs whose expression correlates with the outcome of treatment. Identification of differential miRNAs can lead to a diagnostic assay involving them that can be used to evaluate tumor and/or blood samples to determine what drug regimen the patient should be provided. In addition, it can be used to identify or select patients suitable for a particular clinical trial. If a miRNA profile is determined to be correlated with drug efficacy or drug toxicity that determination may be relevant to whether that patient is an appropriate patient for receiving the drug or for a particular dosage of the drug.

In addition to the above assay, blood samples from patients can be evaluated to identify a disease or a condition based on miRNA levels, such as metastatic disease. A diagnostic assay can be created based on the profiles that doctors can use to identify individuals with a disease or who are at risk to develop a disease. Alternatively, treatments can be designed based on miRNA profiling. Examples of such methods and compositions are described in the U.S. Provisional Patent Application entitled "Methods and Compositions Involving miRNA and miRNA Inhibitor Molecules" filed on May 23, 2005, which is hereby incorporated by reference in its entirety.

C. Amplification

Many methods exist for evaluating miRNA levels by amplifying all or part of miRNA nucleic acid sequences such as mature miRNAs, precursor miRNAs, and primary miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method may be used, such as reverse transcription followed by real time PCR (Chen et al., 2005 and/or U.S. patent application Ser. No. 11/567,082, filed Dec. 5, 2006, which are incorporated herein by reference in its entirety).

A typical PCR reaction includes multiple amplification steps, or cycles that selectively amplify target nucleic acid species. A typical PCR reaction includes three steps: a denaturing step in which a target nucleic acid is denatured; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Typical PCR reactions include 20 or more cycles of denaturation, annealing, and elongation. In many cases, the annealing and elongation steps can be performed concurrently, in which case the cycle contains only two steps. Since mature miRNAs are single stranded, a reverse transcription reaction (which produces a complementary cDNA sequence) is performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length. In additional embodiments, a primer is at least 35 nucleotides in length.

In a further aspect, a forward primer can comprise at least one sequence that anneals to a target miRNA and alternatively can comprise an additional 5' noncomplementary region. In another aspect, a reverse primer can be designed to anneal to the complement of a reverse transcribed miRNA. The reverse primer may be independent of the miRNA sequence, and multiple miRNAs may be amplified using the same reverse primer. Alternatively, a reverse primer may be specific for a miRNA.

In some embodiments, two or more miRNAs or nucleic acids are amplified in a single reaction volume or multiple reaction volumes. In certain aspects, one or more miRNA or nucleic may be used as a normalization control or a reference nucleic acid for normalization. Normalization may be performed in separate or the same reaction volumes as other amplification reactions. One aspect includes multiplex q-PCR, such as qRT-PCR, which enables simultaneous amplification and quantification of at least one miRNA of interest and at least one reference nucleic acid in one reaction volume by using more than one pair of primers and/or more than one probe. The primer pairs comprise at least one amplification primer that uniquely binds each nucleic acid, and the probes are labeled such that they are distinguishable from one another, thus allowing simultaneous quantification of multiple miRNAs. Multiplex qRT-PCR has research and diagnostic uses, including but not limited to detection of miRNAs for diagnostic, prognostic, and therapeutic applications.

A single combined reaction for q-PCR, may be used to: (1) decrease risk of experimenter error, (2) reduce assay-to-assay variability, (3) decrease risk of target or product contamination, and (4) increase assay speed. The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619). For example, the components for a reverse transcriptase reaction and a PCR reaction may be sequestered using one or more thermoactivation methods or chemical alteration to improve polymerization efficiency (U.S. Pat. Nos. 5,550,044, 5,413,924, and 6,403,341).

To assess the expression of microRNAs, real-time RT-PCR detection can be used to screen nucleic acids or RNA isolated from samples of interest and a related reference such as, but not limited to a normal adjacent tissue (NAT) samples.

A panel of amplification targets is chosen for real-time RT-PCR quantification. The selection of the panel or targets can be based on the results of microarray expression analyses, such as with mirVana™ miRNA Bioarray V1 (Ambion), Human miRNA Microarrays (V3) (Agilent), miRLink™ Arrays (Asuragen), or any other suitable microarray. In one aspect, the panel of targets includes one or more miRNA described herein. One example of a normalization target is 5S rRNA and others can be included. Reverse transcription (RT) reaction components are typically assembled on ice prior to the addition of RNA template. Total RNA template is added and mixed. RT reactions are incubated in an appropriate PCR System at an appropriate temperature (15-30° C., including all values and ranges there between) for an appropriate time, 15 to 30 minutes or longer, then at a temperature of 35 to 42 to 50° C. for 10 to 30 to 60 minutes, and then at 80 to 85 to 95° C. for 5 minutes, then placed on wet ice. Reverse Transcription reaction components typically include nuclease-free water, reverse transcription buffer, dNTP mix, RT Primer, RNase Inhibitor, Reverse Transcriptase, and RNA.

PCR reaction components are typically assembled on ice prior to the addition of the cDNA from the RT reactions. Following assembly of the PCR reaction components a portion of the RT reaction is transferred to the PCR mix. PCR reaction are then typically incubated in an PCR system at an elevated temperature (e.g., 95° C.) for 1 minute or so, then for a number of cycles of denaturing, annealing, and extension (e.g., 40 cycles of 95° C. for 5 seconds and 60° C. for 30 seconds). Results can be analyzed, for example, with SDS V2.3 (Applied Biosystems). Real-time PCR components typically include Nuclease-free water, $MgCl_2$, PCR Buffer, dNTP mix, one or more primers, DNA Polymerase, cDNA from RT reaction and one or more detectable label.

Software tools such as NormFinder (Andersen et al., 2004) are used to determine targets for normalization with the targets of interest and tissue sample set. For normalization of the real-time RT-PCR results, the cycle threshold ($C_t$)

value (a log value) for the microRNA of interest is subtracted from the geometric mean $C_t$ value of normalization targets. Fold change can be determined by subtracting the $dC_t$ normal reference (N) from the corresponding $dC_t$ sample being evaluated (T), producing a $ddC_t$(T-N) value for each sample. The average $ddC_t$(T-N) value across all samples is converted to fold change by $2^{ddCt}$. The representative p-values are determined by a two-tailed paired Student's t-test from the $dC_t$ values of sample and normal reference.

D. Nucleic Acid Arrays

Certain aspects concern the preparation and use of miRNA arrays or miRNA probe arrays, which are ordered macroarrays or microarrays of nucleic acid molecules (probes) that are fully or nearly complementary or identical to a plurality of miRNA molecules or precursor miRNA molecules and are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO 0138580; WO 0168255; WO 03020898; WO 03040410; WO 03053586; WO 03087297; WO 03091426; WO 03100012; WO 04020085; WO 04027093; EP 373 203; EP 785 280; EP 799 897 and UK 8 803 000; the disclosures of which are all herein incorporated by reference. Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

E. Hybridization

After an array or a set of miRNA probes is prepared and the miRNA in the sample is labeled, the population of target nucleic acids is contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in many embodiments is the use of stringent conditions during hybridization. Stringent conditions are known to those of skill in the art.

III. Nucleic Acids

In certain aspects nucleic acids, e.g., miRNAs, typically include segments of sequence or complementary sequences to microRNA ("miRNA" or "miR") molecules, which are generally 21 to 22 nucleotides in length, though lengths of 16 and up to 35 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enable them to form a stem-loop- or fold-back-like structure, which is cleaved in animals by a ribonuclease III-like nuclease enzyme called Dicer. The processed miRNA is typically a portion of the stem.

The processed miRNA (also referred to as "mature miRNA") becomes part of a large complex to down-regulate a particular target gene. Examples of animal miRNAs include those that imperfectly basepair with the target, which halts translation (Olsen et al., 1999; Seggerson et al., 2002). siRNA molecules also are processed by Dicer, but from a long, double-stranded RNA molecule. siRNAs are not naturally found in animal cells, but they can direct the sequence-specific cleavage of an mRNA target through a RNA-induced silencing complex (RISC) (Denli et al., 2003). In certain aspects, nucleic acids in some embodiments are RNA or RNA analogs.

In some embodiments, there is a synthetic or isolated miRNA having a length of between 17 and 130 residues. Embodiments concern synthetic or non-synthetic miRNA molecules that are, are at least, or are at most 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more residues in length, including any integer or any range derivable therein.

In certain embodiments, nucleic acids have (a) a "miRNA region" whose sequence from 5' to 3' is identical to all or a segment of a mature miRNA sequence, and/or (b) a "complementary region" whose sequence from 5' to 3' is between 60% and 100% complementary to the miRNA sequence. In certain embodiments, these synthetic miRNA are also isolated, as defined above. The term "miRNA region" refers to a region on the synthetic miRNA that is at least 75, 80, 85, 90, 95, or 100% identical, including all integers there between, to the entire sequence of a mature, naturally occurring miRNA sequence. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA. Alternatively, the miRNA region can comprise 18, 19, 20, 21, 22, 23, 24, 25, 26, 27 or more nucleotide positions in common with a naturally-occurring miRNA as compared by sequence alignment algorithms and methods well known in the art.

The term "complementary region" refers to a region of a synthetic miRNA that is or is at least 60% complementary to the mature, naturally occurring miRNA sequence that the miRNA region is identical to. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. With single polynucleotide sequences, there may be a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

It is contemplated that synthetic miRNA may have one or more of the replacement, sugar modification, or noncomplementarity designs. In certain cases, synthetic RNA molecules have two of them, while in others these molecules have all three designs in place.

When the RNA molecule is a single polynucleotide, there is a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having a miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

In some embodiments, methods and compositions involving miRNA may concern miRNA and/or other nucleic acids. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, miRNA-containing vectors, control nucleic acids, and other probes and primers. In many embodiments, miRNA are 19-24 nucleotides in length, while miRNA probes are 5, 10, 15, 19, 20, 25, 30, to 35 nucleotides in length, including all values and ranges there between, depending on the length of the processed miRNA and any flanking regions added. miRNA precursors are generally between 62 and 110 nucleotides in humans.

Nucleic acids used in embodiments may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 110 contiguous nucleotides. It is further understood that the length of complementarity within a precursor miRNA or between a miRNA probe and a miRNA or a miRNA gene are such lengths. Moreover, the complementarity may be expressed as a percentage, meaning that the complementarity between a probe and its target is 90% identical or greater over the length of the probe. In some embodiments, complementarity is or is at least 90%, 95% or 100% identical. In particular, such lengths may be applied to any nucleic acid comprising a nucleic acid sequence identified in any of nucleic acids disclosed herein.

The term "recombinant" may be used and this generally refers to a molecule that has been manipulated in vitro or that is a replicated or expressed product of such a molecule.

The term "miRNA" generally refers to a single-stranded molecule, but in specific embodiments, molecules implemented in different embodiments may also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary. miRNA probes or nucleic acids may include, can be or can be at least 60, 65, 70, 75, 80, 85, 90, 95, 96, 97, 98, 99 or 100% complementary to their target.

Nucleic acids may be made by any technique known to one of ordinary skill in the art, such as for example, chemical synthesis, enzymatic production or biological production. It is specifically contemplated that miRNA probes are chemically synthesized in some embodiments.

In some embodiments, miRNAs are recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and it is specifically incorporated by reference herein. Generally, methods involve lysing cells with a solution having guanidinium and a detergent.

A. Isolation of Nucleic Acids

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

Methods may involve the use of organic solvents and/or alcohol to isolate nucleic acids, particularly miRNA used in methods and compositions of the invention. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

In specific embodiments, miRNA isolation processes include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried down and resuspended in a liquid and volume appropriate for subsequent manipulation.

B. Preparation of Nucleic Acids

Alternatively, nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite, or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In some methods, one or more oligonucleotide may be used. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee, 2002), a single-stranded precursor miRNA, or a single-stranded mature miRNA. In addition to the use of recombinant technology, such non-synthetic nucleic acids may be generated chemically, such as by employing technology used for creating oligonucleotides.

C. Labels and Labeling Techniques

In some embodiments, methods concern miRNA that are directly or indirectly labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In many embodiments, the label is non-radioactive. Generally, nucleic acids may be labeled by adding labeled nucleotides (one-step process) or adding nucleotides and labeling the added nucleotides (two-step process).

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to a miRNA, and the unlabeled nucleotide is modified with a chemical moiety that enables it to be subsequently labeled. In some embodiments, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNA is how to label the already existing molecule. In some methods, embodiments concern the use of an enzyme capable of using a di- or tri-phosphate ribonucleotide or deoxyribonucleotide as a substrate for its addition to a miRNA. Moreover, in specific embodiments, it involves using a modified di- or tri-phosphate ribonucleotide, which is added to the 3' end of a miRNA. The source of the enzyme is not limiting. Examples of sources for the enzymes include yeast, gram-negative bacteria such as *E. coli, Lactococcus lactis*, and sheep pox virus.

Enzymes capable of adding such nucleotides include, but are not limited to, poly(A) polymerase, terminal transferase, and polynucleotide phosphorylase. In specific embodiments, a ligase is contemplated as not being the enzyme used to add the label, and instead, a non-ligase enzyme is employed.

Terminal transferase catalyzes the addition of nucleotides to the 3' terminus of a nucleic acid.

Polynucleotide phosphorylase can polymerize nucleotide diphosphates without the need for a primer.

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}$I, $^{32}$P, $^{33}$P, and $^{35}$S. Examples of enzymatic labels include alkaline phosphatase, luciferase, horseradish peroxidase, and β-galactosidase. Labels can also be proteins with luminescent properties, e.g., green fluorescent protein and phycoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

A number of techniques for visualizing or detecting labeled nucleic acids are readily available. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize association of one or more nucleic acid. Furthermore, a person of ordinary skill in the art is well aware of ways of visualizing, identifying, and characterizing labeled nucleic acids, and accordingly, such protocols may be used as part of some embodiments. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

IV. Kits

Any of the compositions or components described herein may be comprised in a kit. In a non-limiting example, reagents for isolating miRNA, labeling miRNA, and/or evaluating a miRNA population using an array, nucleic acid amplification, and/or hybridization can be included in a kit, as well reagents for preparation of samples from colon samples. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. In certain aspects, the kit can include amplification reagents. In other aspects, the kit may include various supports, such as glass, nylon, polymeric beads, magnetic beads, and the like, and/or reagents for coupling any probes and/or target nucleic acids. It may also include one or more buffers, such as reaction buffer, labeling buffer, washing buffer, or a hybridization buffer, compounds for preparing the miRNA probes, and components for isolating miRNA. Other kits of the invention may include components for making a nucleic acid array comprising miRNA, and thus, may include, for example, a solid support.

Kits for implementing methods of the invention described herein are specifically contemplated. In some embodiments, there are kits for preparing miRNA for multi-labeling and kits for preparing miRNA probes and/or miRNA arrays. In these embodiments, kit comprise, in suitable container means, 1, 2, 3, 4, 5, 6, 7, 8, 9, 10, 11, 12 or more of the following: (1) poly(A) polymerase; (2) unmodified nucleotides (G, A, T, C, and/or U); (3) a modified nucleotide (labeled or unlabeled); (4) poly(A) polymerase buffer; and, (5) at least one microfilter; (6) label that can be attached to a nucleotide; (7) at least one miRNA probe; (8) reaction buffer; (9) a miRNA array or components for making such an array; (10) acetic acid; (11) alcohol; (12) solutions for preparing, isolating, enriching, and purifying miRNAs or miRNA probes or arrays. Other reagents include those generally used for manipulating RNA, such as formamide, loading dye, ribonuclease inhibitors, and DNase.

In specific embodiments, kits of the invention include an array containing miRNA probes, as described in the application. An array may have probes corresponding to all known miRNAs of an organism or a particular tissue or organ in particular conditions, or to a subset of such probes. The subset of probes on arrays of the invention may be or include those identified as relevant to a particular diagnostic, therapeutic, or prognostic application. For example, the array may contain one or more probes that is indicative or suggestive of (1) a disease or condition (thyroid cancer), (2) susceptibility or resistance to a particular drug or treatment; (3) susceptibility to toxicity from a drug or substance; (4) the stage of development or severity of a disease or condition (prognosis); and (5) genetic predisposition to a disease or condition.

For any kit embodiment, including an array, there can be nucleic acid molecules that contain or can be used to amplify a sequence that is a variant of, identical to or complementary to all or part of any of the sequences described herein. Any nucleic acid discussed above may be implemented as part of a kit.

The components of the kits may be packaged either in aqueous media or in lyophilized form. The container means of the kits will generally include at least one vial, test tube, flask, bottle, syringe or other container means, into which a component may be placed, and preferably, suitably aliquotted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 μg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that facilitate isolation of the labeled miRNA. It may also include components that preserve or maintain the miRNA or that protect against its degradation. Such components may be RNase-free or protect against RNases. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

It is contemplated that such reagents are embodiments of kits of the invention. Such kits, however, are not limited to the particular items identified above and may include any reagent used for the manipulation or characterization of miRNA.

TABLE 1 microRNA Accession Numbers. Accession numbers correspond to those listed in the Sanger miRBase version 12.0 database of microRNAs (Griffiths-Jones et al., 2006) and are hereby incorporated by reference in their entirety on Nov. 16, 2010, as well as the sequences represented in each database entry.

| Probe_ID | MicroRNA Accession Number | Precursor Accession Number |
| --- | --- | --- |
| hsa-let-7a | MIMAT0000062 | MI0000062 |
| hsa-let-7a* | MIMAT0004481 | MI0000062 |
| hsa-let-7b | MIMAT0000063 | MI0000063 |
| hsa-let-7b* | MIMAT0004482 | MI0000063 |
| hsa-let-7c | MIMAT0000064 | MI0000064 |
| hsa-let-7c* | MIMAT0004483 | MI0000064 |
| hsa-let-7d | MIMAT0000065 | MI0000065 |
| hsa-let-7d* | MIMAT0004484 | MI0000065 |
| hsa-let-7e | MIMAT0000066 | MI0000066 |
| hsa-let-7e* | MIMAT0004485 | MI0000066 |
| hsa-let-7f | MIMAT0000067 | MI0000068 |
| hsa-let-7f-1* | MIMAT0004486 | MI0000067 |
| hsa-let-7g | MIMAT0000414 | MI0000433 |
| hsa-let-7g* | MIMAT0004584 | MI0000433 |
| hsa-let-7i | MIMAT0000415 | MI0000434 |
| hsa-let-7i* | MIMAT0004585 | MI0000434 |
| hsa-miR-1 | MIMAT0000416 | MI0000437 |
| hsa-miR-100 | MIMAT0000098 | MI0000102 |
| hsa-miR-100* | MIMAT0004512 | MI0000102 |
| hsa-miR-101 | MIMAT0000099 | MI0000739 |
| hsa-miR-101* | MIMAT0004513 | MI0000103 |
| hsa-miR-103 | MIMAT0000101 | MI0000108 |
| hsa-miR-105 | MIMAT0000102 | MI0000112 |
| hsa-miR-105* | MIMAT0004516 | MI0000112 |
| hsa-miR-106b | MIMAT0000680 | MI0000734 |
| hsa-miR-107 | MIMAT0000104 | MI0000114 |
| hsa-miR-10a | MIMAT0000253 | MI0000266 |
| hsa-miR-10a* | MIMAT0004555 | MI0000266 |
| hsa-miR-10b | MIMAT0000254 | MI0000267 |
| hsa-miR-10b* | MIMAT0004556 | MI0000267 |
| hsa-miR-1180 | MIMAT0005825 | MI0006273 |
| hsa-miR-1181 | MIMAT0005826 | MI0006274 |

TABLE 1-continued microRNA Accession Numbers. Accession numbers correspond to those listed in the Sanger miRBase version 12.0 database of microRNAs (Griffiths-Jones et al., 2006) and are hereby incorporated by reference in their entirety on Nov. 16, 2010, as well as the sequences represented in each database entry.

| Probe_ID | MicroRNA Accession Number | Precursor Accession Number |
|---|---|---|
| hsa-miR-1182 | MIMAT0005827 | MI0006275 |
| hsa-miR-1183 | MIMAT0005828 | MI0006276 |
| hsa-miR-1185 | MIMAT0005798 | MI0003844 |
| hsa-miR-1201 | MIMAT0005864 | MI0006333 |
| hsa-miR-1202 | MIMAT0005865 | MI0006334 |
| hsa-miR-1203 | MIMAT0005866 | MI0006335 |
| hsa-miR-1207-5p | MIMAT0005871 | MI0006340 |
| hsa-miR-1208 | MIMAT0005873 | MI0006341 |
| hsa-miR-122 | MIMAT0000421 | MI0000442 |
| hsa-miR-122* | MIMAT0004590 | MI0000442 |
| hsa-miR-1224-5p | MIMAT0005458 | MI0003764 |
| hsa-miR-1225-3p | MIMAT0005573 | MI0006311 |
| hsa-miR-1225-5p | MIMAT0005572 | MI0006311 |
| hsa-miR-1226* | MIMAT0005576 | MI0006313 |
| hsa-miR-1227 | MIMAT0005580 | MI0006316 |
| hsa-miR-1228 | MIMAT0005583 | MI0006318 |
| hsa-miR-1228* | MIMAT0005582 | MI0006318 |
| hsa-miR-1229 | MIMAT0005584 | MI0006319 |
| hsa-miR-1234 | MIMAT0005589 | MI0006324 |
| hsa-miR-1237 | MIMAT0005592 | MI0006327 |
| hsa-miR-1238 | MIMAT0005593 | MI0006328 |
| hsa-miR-124 | MIMAT0000422 | MI0000445 |
| hsa-miR-124* | MIMAT0004591 | MI0000445 |
| hsa-miR-1244 | MIMAT0005896 | MI0006379 |
| hsa-miR-1246 | MIMAT0005898 | MI0006381 |
| hsa-miR-1249 | MIMAT0005901 | MI0006384 |
| hsa-miR-1250 | MIMAT0005902 | MI0006385 |
| hsa-miR-1251 | MIMAT0005903 | MI0006386 |
| hsa-miR-125a-3p | MIMAT0004602 | MI0000469 |
| hsa-miR-125a-5p | MIMAT0000443 | MI0000469 |
| hsa-miR-125b | MIMAT0000423 | MI0000446 |
| hsa-miR-125b-1* | MIMAT0004592 | MI0000446 |
| hsa-miR-125b-2* | MIMAT0004603 | MI0000470 |
| hsa-miR-126 | MIMAT0000445 | MI0000471 |
| hsa-miR-126* | MIMAT0000444 | MI0000471 |
| hsa-miR-1260 | MIMAT0005911 | MI0006394 |
| hsa-miR-1268 | MIMAT0005922 | MI0006405 |
| hsa-miR-127-3p | MIMAT0000446 | MI0000472 |
| hsa-miR-127-5p | MIMAT0004604 | MI0000472 |
| hsa-miR-1270 | MIMAT0005924 | MI0006407 |
| hsa-miR-1271 | MIMAT0005796 | MI0003814 |
| hsa-miR-1274a | MIMAT0005927 | MI0006410 |
| hsa-miR-1274b | MIMAT0005938 | MI0006427 |
| hsa-miR-1275 | MIMAT0005929 | MI0006415 |
| hsa-miR-1276 | MIMAT0005930 | MI0006416 |
| hsa-miR-128 | MIMAT0000424 | MI0000727 |
| hsa-miR-1280 | MIMAT0005946 | MI0006437 |
| hsa-miR-1281 | MIMAT0005939 | MI0006428 |
| hsa-miR-1285 | MIMAT0005876 | MI0006347 |
| hsa-miR-1287 | MIMAT0005878 | MI0006349 |
| hsa-miR-1288 | MIMAT0005942 | MI0006432 |
| hsa-miR-129* | MIMAT0004548 | MI0000252 |
| hsa-miR-129-3p | MIMAT0004605 | MI0000473 |
| hsa-miR-129-5p | MIMAT0000242 | MI0000473 |
| hsa-miR-1290 | MIMAT0005880 | MI0006352 |
| hsa-miR-1291 | MIMAT0005881 | MI0006353 |
| hsa-miR-1295 | MIMAT0005885 | MI0006357 |
| hsa-miR-1296 | MIMAT0005794 | MI0003780 |
| hsa-miR-1299 | MIMAT0005887 | MI0006359 |
| hsa-miR-1300 | MIMAT0005888 | MI0006360 |
| hsa-miR-1301 | MIMAT0005797 | MI0003815 |
| hsa-miR-1303 | MIMAT0005891 | MI0006370 |
| hsa-miR-1305 | MIMAT0005893 | MI0006372 |
| hsa-miR-1306 | MIMAT0005950 | MI0006443 |
| hsa-miR-1307 | MIMAT0005951 | MI0006444 |
| hsa-miR-1308 | MIMAT0005947 | MI0006441 |
| hsa-miR-130a | MIMAT0000425 | MI0000448 |
| hsa-miR-130b | MIMAT0000691 | MI0000748 |
| hsa-miR-130b* | MIMAT0004680 | MI0000748 |
| hsa-miR-132 | MIMAT0000426 | MI0000449 |
| hsa-miR-132* | MIMAT0004594 | MI0000449 |
| hsa-miR-1321 | MIMAT0005952 | MI0006652 |
| hsa-miR-1323 | MIMAT0005795 | MI0003786 |
| hsa-miR-133a | MIMAT0000427 | MI0000451 |
| hsa-miR-133b | MIMAT0000770 | MI0000822 |
| hsa-miR-134 | MIMAT0000447 | MI0000474 |
| hsa-miR-135a | MIMAT0000428 | MI0000452 |
| hsa-miR-135a* | MIMAT0004595 | MI0000452 |
| hsa-miR-135b | MIMAT0000758 | MI0000810 |
| hsa-miR-136 | MIMAT0000448 | MI0000475 |
| hsa-miR-136* | MIMAT0004606 | MI0000475 |
| hsa-miR-137 | MIMAT0000429 | MI0000454 |
| hsa-miR-138 | MIMAT0000430 | MI0000455 |
| hsa-miR-138-1* | MIMAT0004607 | MI0000476 |
| hsa-miR-138-2* | MIMAT0004596 | MI0000455 |
| hsa-miR-139-3p | MIMAT0004552 | MI0000261 |
| hsa-miR-139-5p | MIMAT0000250 | MI0000261 |
| hsa-miR-140-3p | MIMAT0004597 | MI0000456 |
| hsa-miR-140-5p | MIMAT0000431 | MI0000456 |
| hsa-miR-141 | MIMAT0000432 | MI0000457 |
| hsa-miR-141* | MIMAT0004598 | MI0000457 |
| hsa-miR-142-3p | MIMAT0000434 | MI0000458 |
| hsa-miR-142-5p | MIMAT0000433 | MI0000458 |
| hsa-miR-143 | MIMAT0000435 | MI0000459 |
| hsa-miR-143* | MIMAT0004599 | MI0000459 |
| hsa-miR-144 | MIMAT0000436 | MI0000460 |
| hsa-miR-144* | MIMAT0004600 | MI0000460 |
| hsa-miR-145 | MIMAT0000437 | MI0000461 |
| hsa-miR-145* | MIMAT0004601 | MI0000461 |
| hsa-miR-1469 | MIMAT0007347 | MI0007074 |
| hsa-miR-146a | MIMAT0000449 | MI0000477 |
| hsa-miR-146b-3p | MIMAT0004766 | MI0003129 |
| hsa-miR-146b-5p | MIMAT0002809 | MI0003129 |
| hsa-miR-1471 | MIMAT0007349 | MI0007076 |
| hsa-miR-148a | MIMAT0000243 | MI0000253 |
| hsa-miR-148a* | MIMAT0004549 | MI0000253 |
| hsa-miR-148b | MIMAT0000759 | MI0000811 |
| hsa-miR-148b* | MIMAT0004699 | MI0000811 |
| hsa-miR-149 | MIMAT0000450 | MI0000478 |
| hsa-miR-149* | MIMAT0004609 | MI0000478 |
| hsa-miR-150 | MIMAT0000451 | MI0000479 |
| hsa-miR-150* | MIMAT0004610 | MI0000479 |
| hsa-miR-151-3p | MIMAT0000757 | MI0000809 |
| hsa-miR-151-5p | MIMAT0004697 | MI0000809 |
| hsa-miR-152 | MIMAT0000438 | MI0000462 |
| hsa-miR-153 | MIMAT0000439 | MI0000463 |
| hsa-miR-1539 | MIMAT0007401 | MI0007260 |
| hsa-miR-154 | MIMAT0000452 | MI0000480 |
| hsa-miR-154* | MIMAT0000453 | MI0000480 |
| hsa-miR-155 | MIMAT0000646 | MI0000681 |
| hsa-miR-155* | MIMAT0004658 | MI0000681 |
| hsa-miR-15a | MIMAT0000068 | MI0000069 |
| hsa-miR-15a* | MIMAT0004488 | MI0000069 |
| hsa-miR-15b | MIMAT0000417 | MI0000438 |
| hsa-miR-15b* | MIMAT0004586 | MI0000438 |
| hsa-miR-16 | MIMAT0000069 | MI0000115 |
| hsa-miR-16-2* | MIMAT0004518 | MI0000115 |
| hsa-miR-17 | MIMAT0000070 | MI0000071 |
| hsa-miR-17* | MIMAT0000071 | MI0000071 |
| hsa-miR-181a | MIMAT0000256 | MI0000289 |
| hsa-miR-181a* | MIMAT0000270 | MI0000289 |
| hsa-miR-181a-2* | MIMAT0004558 | MI0000269 |
| hsa-miR-181b | MIMAT0000257 | MI0000683 |
| hsa-miR-181c | MIMAT0000258 | MI0000271 |
| hsa-miR-181c* | MIMAT0004559 | MI0000271 |
| hsa-miR-181d | MIMAT0002821 | MI0003139 |
| hsa-miR-182 | MIMAT0000259 | MI0000272 |
| hsa-miR-182* | MIMAT0000260 | MI0000272 |
| hsa-miR-1825 | MIMAT0006765 | MI0008193 |
| hsa-miR-1826 | MIMAT0006766 | MI0008194 |
| hsa-miR-1827 | MIMAT0006767 | MI0008195 |
| hsa-miR-183 | MIMAT0000261 | MI0000273 |

TABLE 1-continued microRNA Accession Numbers. Accession numbers correspond to those listed in the Sanger miRBase version 12.0 database of microRNAs (Griffiths-Jones et al., 2006) and are hereby incorporated by reference in their entirety on Nov. 16, 2010, as well as the sequences represented in each database entry.

| Probe_ID | MicroRNA Accession Number | Precursor Accession Number |
|---|---|---|
| hsa-miR-183* | MIMAT0004560 | MI0000273 |
| hsa-miR-184 | MIMAT0000454 | MI0000481 |
| hsa-miR-185 | MIMAT0000455 | MI0000482 |
| hsa-miR-186 | MIMAT0000456 | MI0000483 |
| hsa-miR-187* | MIMAT0004561 | MI0000274 |
| hsa-miR-188-3p | MIMAT0004613 | MI0000484 |
| hsa-miR-188-5p | MIMAT0000457 | MI0000484 |
| hsa-miR-18a | MIMAT0000072 | MI0000072 |
| hsa-miR-18b | MIMAT0001412 | MI0001518 |
| hsa-miR-18b* | MIMAT0004751 | MI0001518 |
| hsa-miR-190 | MIMAT0000458 | MI0000486 |
| hsa-miR-1909* | MIMAT0007882 | MI0008330 |
| hsa-miR-191 | MIMAT0000440 | MI0000465 |
| hsa-miR-191* | MIMAT0001618 | MI0000465 |
| hsa-miR-1910 | MIMAT0007884 | MI0008331 |
| hsa-miR-1914 | MIMAT0007889 | MI0008335 |
| hsa-miR-1914* | MIMAT0007890 | MI0008335 |
| hsa-miR-1915 | MIMAT0007892 | MI0008336 |
| hsa-miR-1915* | MIMAT0007891 | MI0008336 |
| hsa-miR-192 | MIMAT0000222 | MI0000234 |
| hsa-miR-192* | MIMAT0004543 | MI0000234 |
| hsa-miR-193a-3p | MIMAT0000459 | MI0000487 |
| hsa-miR-193a-5p | MIMAT0004614 | MI0000487 |
| hsa-miR-193b | MIMAT0002819 | MI0003137 |
| hsa-miR-193b* | MIMAT0004767 | MI0003137 |
| hsa-miR-194 | MIMAT0000460 | MI0000732 |
| hsa-miR-194* | MIMAT0004671 | MI0000732 |
| hsa-miR-195 | MIMAT0000461 | MI0000489 |
| hsa-miR-195* | MIMAT0004615 | MI0000489 |
| hsa-miR-196a | MIMAT0000226 | MI0000279 |
| hsa-miR-196b | MIMAT0001080 | MI0001150 |
| hsa-miR-197 | MIMAT0000227 | MI0000239 |
| hsa-miR-198 | MIMAT0000228 | MI0000240 |
| hsa-miR-199a-3p | MIMAT0000232 | MI0000242 |
| hsa-miR-199a-5p | MIMAT0000231 | MI0000242 |
| hsa-miR-199b-5p | MIMAT0000263 | MI0000282 |
| hsa-miR-19a | MIMAT0000073 | MI0000073 |
| hsa-miR-19b | MIMAT0000074 | MI0000074 |
| hsa-miR-19b-1* | MIMAT0004491 | MI0000074 |
| hsa-miR-200a | MIMAT0000682 | MI0000737 |
| hsa-miR-200a* | MIMAT0001620 | MI0000737 |
| hsa-miR-200b | MIMAT0000318 | MI0000342 |
| hsa-miR-200b* | MIMAT0004571 | MI0000342 |
| hsa-miR-200c | MIMAT0000617 | MI0000650 |
| hsa-miR-200c* | MIMAT0004657 | MI0000650 |
| hsa-miR-202 | MIMAT0002811 | MI0003130 |
| hsa-miR-203 | MIMAT0000264 | MI0000283 |
| hsa-miR-204 | MIMAT0000265 | MI0000284 |
| hsa-miR-205 | MIMAT0000266 | MI0000285 |
| hsa-miR-206 | MIMAT0000462 | MI0000490 |
| hsa-miR-208b | MIMAT0004960 | MI0005570 |
| hsa-miR-20a | MIMAT0000075 | MI0000076 |
| hsa-miR-20a* | MIMAT0004493 | MI0000076 |
| hsa-miR-20b | MIMAT0001413 | MI0001519 |
| hsa-miR-21 | MIMAT0000076 | MI0000077 |
| hsa-miR-21* | MIMAT0004494 | MI0000077 |
| hsa-miR-210 | MIMAT0000267 | MI0000286 |
| hsa-miR-211 | MIMAT0000268 | MI0000287 |
| hsa-miR-212 | MIMAT0000269 | MI0000288 |
| hsa-miR-214 | MIMAT0000271 | MI0000290 |
| hsa-miR-214* | MIMAT0004564 | MI0000290 |
| hsa-miR-215 | MIMAT0000272 | MI0000291 |
| hsa-miR-216a | MIMAT0000273 | MI0000292 |
| hsa-miR-216b | MIMAT0004959 | MI0005569 |
| hsa-miR-218 | MIMAT0000275 | MI0000294 |
| hsa-miR-219-5p | MIMAT0000276 | MI0000296 |
| hsa-miR-22 | MIMAT0000077 | MI0000078 |
| hsa-miR-22* | MIMAT0004495 | MI0000078 |
| hsa-miR-221 | MIMAT0000278 | MI0000298 |
| hsa-miR-221* | MIMAT0004568 | MI0000298 |
| hsa-miR-222 | MIMAT0000279 | MI0000299 |
| hsa-miR-222* | MIMAT0004569 | MI0000299 |
| hsa-miR-223 | MIMAT0000280 | MI0000300 |
| hsa-miR-223* | MIMAT0004570 | MI0000300 |
| hsa-miR-224 | MIMAT0000281 | MI0000301 |
| hsa-miR-23a | MIMAT0000078 | MI0000079 |
| hsa-miR-23a* | MIMAT0004496 | MI0000079 |
| hsa-miR-23b | MIMAT0000418 | MI0000439 |
| hsa-miR-23b* | MIMAT0004587 | MI0000439 |
| hsa-miR-24 | MIMAT0000080 | MI0000081 |
| hsa-miR-24-1* | MIMAT0000079 | MI0000080 |
| hsa-miR-25 | MIMAT0000081 | MI0000082 |
| hsa-miR-26a | MIMAT0000082 | MI0000083 |
| hsa-miR-26a-1* | MIMAT0004499 | MI0000083 |
| hsa-miR-26b | MIMAT0000083 | MI0000084 |
| hsa-miR-26b* | MIMAT0004500 | MI0000084 |
| hsa-miR-27a | MIMAT0000084 | MI0000085 |
| hsa-miR-27a* | MIMAT0004501 | MI0000085 |
| hsa-miR-27b | MIMAT0000419 | MI0000440 |
| hsa-miR-28-3p | MIMAT0004502 | MI0000086 |
| hsa-miR-28-5p | MIMAT0000085 | MI0000086 |
| hsa-miR-296-5p | MIMAT0000690 | MI0000747 |
| hsa-miR-298 | MIMAT0004901 | MI0005523 |
| hsa-miR-299-3p | MIMAT0000687 | MI0000744 |
| hsa-miR-299-5p | MIMAT0002890 | MI0000744 |
| hsa-miR-29a | MIMAT0000086 | MI0000087 |
| hsa-miR-29a* | MIMAT0004503 | MI0000087 |
| hsa-miR-29b | MIMAT0000100 | MI0000107 |
| hsa-miR-29b-1* | MIMAT0004514 | MI0000105 |
| hsa-miR-29b-2* | MIMAT0004515 | MI0000107 |
| hsa-miR-29c | MIMAT0000681 | MI0000735 |
| hsa-miR-29c* | MIMAT0004673 | MI0000735 |
| hsa-miR-300 | MIMAT0004903 | MI0005525 |
| hsa-miR-301a | MIMAT0000688 | MI0000745 |
| hsa-miR-301b | MIMAT0004958 | MI0005568 |
| hsa-miR-302c* | MIMAT0000716 | MI0000773 |
| hsa-miR-30a | MIMAT0000087 | MI0000088 |
| hsa-miR-30a* | MIMAT0000088 | MI0000088 |
| hsa-miR-30b | MIMAT0000420 | MI0000441 |
| hsa-miR-30b* | MIMAT0004589 | MI0000441 |
| hsa-miR-30c | MIMAT0000244 | MI0000254 |
| hsa-miR-30c-1* | MIMAT0004674 | MI0000736 |
| hsa-miR-30c-2* | MIMAT0004550 | MI0000254 |
| hsa-miR-30d | MIMAT0000245 | MI0000255 |
| hsa-miR-30d* | MIMAT0004551 | MI0000255 |
| hsa-miR-30e | MIMAT0000692 | MI0000749 |
| hsa-miR-30e* | MIMAT0000693 | MI0000749 |
| hsa-miR-31 | MIMAT0000089 | MI0000089 |
| hsa-miR-31* | MIMAT0004504 | MI0000089 |
| hsa-miR-32 | MIMAT0000090 | MI0000090 |
| hsa-miR-320a | MIMAT0000510 | MI0000542 |
| hsa-miR-320b | MIMAT0005792 | MI0003839 |
| hsa-miR-320c | MIMAT0005793 | MI0003778 |
| hsa-miR-320d | MIMAT0006764 | MI0008192 |
| hsa-miR-323-3p | MIMAT0000755 | MI0000807 |
| hsa-miR-324-3p | MIMAT0000762 | MI0000813 |
| hsa-miR-324-5p | MIMAT0000761 | MI0000813 |
| hsa-miR-326 | MIMAT0000756 | MI0000808 |
| hsa-miR-328 | MIMAT0000752 | MI0000804 |
| hsa-miR-329 | MIMAT0001629 | MI0001726 |
| hsa-miR-330-3p | MIMAT0000751 | MI0000803 |
| hsa-miR-331-3p | MIMAT0000760 | MI0000812 |
| hsa-miR-335 | MIMAT0000765 | MI0000816 |
| hsa-miR-335* | MIMAT0004703 | MI0000816 |
| hsa-miR-337-3p | MIMAT0000754 | MI0000806 |
| hsa-miR-337-5p | MIMAT0004695 | MI0000806 |
| hsa-miR-338-3p | MIMAT0000763 | MI0000814 |
| hsa-miR-338-5p | MIMAT0004701 | MI0000814 |
| hsa-miR-339-3p | MIMAT0004702 | MI0000815 |
| hsa-miR-339-5p | MIMAT0000764 | MI0000815 |
| hsa-miR-33a | MIMAT0000091 | MI0000091 |
| hsa-miR-33b | MIMAT0003301 | MI0003646 |

TABLE 1-continued microRNA Accession Numbers. Accession numbers correspond to those listed in the Sanger miRBase version 12.0 database of microRNAs (Griffiths-Jones et al., 2006) and are hereby incorporated by reference in their entirety on Nov. 16, 2010, as well as the sequences represented in each database entry.

| Probe_ID | MicroRNA Accession Number | Precursor Accession Number |
|---|---|---|
| hsa-miR-33b* | MIMAT0004811 | MI0003646 |
| hsa-miR-340 | MIMAT0004692 | MI0000802 |
| hsa-miR-340* | MIMAT0000750 | MI0000802 |
| hsa-miR-342-3p | MIMAT0000753 | MI0000805 |
| hsa-miR-342-5p | MIMAT0004694 | MI0000805 |
| hsa-miR-345 | MIMAT0000772 | MI0000825 |
| hsa-miR-346 | MIMAT0000773 | MI0000826 |
| hsa-miR-34a | MIMAT0000255 | MI0000268 |
| hsa-miR-34a* | MIMAT0004557 | MI0000268 |
| hsa-miR-34b | MIMAT0004676 | MI0000742 |
| hsa-miR-34b* | MIMAT0000685 | MI0000742 |
| hsa-miR-34c-3p | MIMAT0004677 | MI0000743 |
| hsa-miR-34c-5p | MIMAT0000686 | MI0000743 |
| hsa-miR-361-3p | MIMAT0004682 | MI0000760 |
| hsa-miR-361-5p | MIMAT0000703 | MI0000760 |
| hsa-miR-362-3p | MIMAT0004683 | MI0000762 |
| hsa-miR-362-5p | MIMAT0000705 | MI0000762 |
| hsa-miR-363 | MIMAT0000707 | MI0000764 |
| hsa-miR-365 | MIMAT0000710 | MI0000769 |
| hsa-miR-369-3p | MIMAT0000721 | MI0000777 |
| hsa-miR-369-5p | MIMAT0001621 | MI0000777 |
| hsa-miR-370 | MIMAT0000722 | MI0000778 |
| hsa-miR-371-5p | MIMAT0004687 | MI0000779 |
| hsa-miR-373* | MIMAT0000725 | MI0000781 |
| hsa-miR-374a | MIMAT0000727 | MI0000782 |
| hsa-miR-374b | MIMAT0004955 | MI0005566 |
| hsa-miR-374b* | MIMAT0004956 | MI0005566 |
| hsa-miR-375 | MIMAT0000728 | MI0000783 |
| hsa-miR-376a | MIMAT0000729 | MI0000784 |
| hsa-miR-376a* | MIMAT0003386 | MI0000784 |
| hsa-miR-376b | MIMAT0002172 | MI0002466 |
| hsa-miR-376c | MIMAT0000720 | MI0000776 |
| hsa-miR-377 | MIMAT0000730 | MI0000785 |
| hsa-miR-377* | MIMAT0004689 | MI0000785 |
| hsa-miR-378 | MIMAT0000732 | MI0000786 |
| hsa-miR-378* | MIMAT0000731 | MI0000786 |
| hsa-miR-379 | MIMAT0000733 | MI0000787 |
| hsa-miR-381 | MIMAT0000736 | MI0000789 |
| hsa-miR-382 | MIMAT0000737 | MI0000790 |
| hsa-miR-409-3p | MIMAT0001639 | MI0001735 |
| hsa-miR-409-5p | MIMAT0001638 | MI0001735 |
| hsa-miR-410 | MIMAT0002171 | MI0002465 |
| hsa-miR-411 | MIMAT0003329 | MI0003675 |
| hsa-miR-421 | MIMAT0003339 | MI0003685 |
| hsa-miR-422a | MIMAT0001339 | MI0001444 |
| hsa-miR-423-3p | MIMAT0001340 | MI0001445 |
| hsa-miR-423-5p | MIMAT0004748 | MI0001445 |
| hsa-miR-424 | MIMAT0001341 | MI0001446 |
| hsa-miR-424* | MIMAT0004749 | MI0001446 |
| hsa-miR-425 | MIMAT0003393 | MI0001448 |
| hsa-miR-425* | MIMAT0001343 | MI0001448 |
| hsa-miR-429 | MIMAT0001536 | MI0001641 |
| hsa-miR-431 | MIMAT0001625 | MI0001721 |
| hsa-miR-431* | MIMAT0004757 | MI0001721 |
| hsa-miR-432 | MIMAT0002814 | MI0003133 |
| hsa-miR-433 | MIMAT0001627 | MI0001723 |
| hsa-miR-449a | MIMAT0001541 | MI0001648 |
| hsa-miR-449b | MIMAT0003327 | MI0003673 |
| hsa-miR-450a | MIMAT0001545 | MI0003187 |
| hsa-miR-450b-5p | MIMAT0004909 | MI0005531 |
| hsa-miR-451 | MIMAT0001631 | MI0001729 |
| hsa-miR-452 | MIMAT0001635 | MI0001733 |
| hsa-miR-454 | MIMAT0003885 | MI0003820 |
| hsa-miR-454* | MIMAT0003884 | MI0003820 |
| hsa-miR-455-3p | MIMAT0004784 | MI0003513 |
| hsa-miR-455-5p | MIMAT0003150 | MI0003513 |
| hsa-miR-483-3p | MIMAT0002173 | MI0002467 |
| hsa-miR-483-5p | MIMAT0004761 | MI0002467 |
| hsa-miR-484 | MIMAT0002174 | MI0002468 |
| hsa-miR-485-3p | MIMAT0002176 | MI0002469 |
| hsa-miR-485-5p | MIMAT0002175 | MI0002469 |
| hsa-miR-486-3p | MIMAT0004762 | MI0002470 |
| hsa-miR-486-5p | MIMAT0002177 | MI0002470 |
| hsa-miR-487a | MIMAT0002178 | MI0002471 |
| hsa-miR-487b | MIMAT0003180 | MI0003530 |
| hsa-miR-488 | MIMAT0004763 | MI0003123 |
| hsa-miR-488* | MIMAT0002804 | MI0003123 |
| hsa-miR-489 | MIMAT0002805 | MI0003124 |
| hsa-miR-490-3p | MIMAT0002806 | MI0003125 |
| hsa-miR-490-5p | MIMAT0004764 | MI0003125 |
| hsa-miR-491-5p | MIMAT0002807 | MI0003126 |
| hsa-miR-493 | MIMAT0003161 | MI0003132 |
| hsa-miR-493* | MIMAT0002813 | MI0003132 |
| hsa-miR-494 | MIMAT0002816 | MI0003134 |
| hsa-miR-495 | MIMAT0002817 | MI0003135 |
| hsa-miR-497 | MIMAT0002820 | MI0003138 |
| hsa-miR-498 | MIMAT0002824 | MI0003142 |
| hsa-miR-499-5p | MIMAT0002870 | MI0003183 |
| hsa-miR-500 | MIMAT0004773 | MI0003184 |
| hsa-miR-500* | MIMAT0002871 | MI0003184 |
| hsa-miR-501-3p | MIMAT0004774 | MI0003185 |
| hsa-miR-501-5p | MIMAT0002872 | MI0003185 |
| hsa-miR-502-3p | MIMAT0004775 | MI0003186 |
| hsa-miR-502-5p | MIMAT0002873 | MI0003186 |
| hsa-miR-503 | MIMAT0002874 | MI0003188 |
| hsa-miR-505 | MIMAT0002876 | MI0003190 |
| hsa-miR-505* | MIMAT0004776 | MI0003190 |
| hsa-miR-506 | MIMAT0002878 | MI0003193 |
| hsa-miR-508-5p | MIMAT0004778 | MI0003195 |
| hsa-miR-509-3-5p | MIMAT0004975 | MI0005717 |
| hsa-miR-509-3p | MIMAT0002881 | MI0005717 |
| hsa-miR-509-5p | MIMAT0004779 | MI0003196 |
| hsa-miR-512-3p | MIMAT0002823 | MI0003140 |
| hsa-miR-513a-5p | MIMAT0002877 | MI0003191 |
| hsa-miR-513b | MIMAT0005788 | MI0006648 |
| hsa-miR-513c | MIMAT0005789 | MI0006649 |
| hsa-miR-514 | MIMAT0002883 | MI0003200 |
| hsa-miR-516a-5p | MIMAT0004770 | MI0003181 |
| hsa-miR-516b | MIMAT0002859 | MI0003167 |
| hsa-miR-517a | MIMAT0002852 | MI0003161 |
| hsa-miR-517b | MIMAT0002857 | MI0003165 |
| hsa-miR-518a-5p | MIMAT0005457 | MI0003173 |
| hsa-miR-518c* | MIMAT0002847 | MI0003159 |
| hsa-miR-518e* | MIMAT0005450 | MI0003169 |
| hsa-miR-519d | MIMAT0002853 | MI0003162 |
| hsa-miR-519e* | MIMAT0002828 | MI0003145 |
| hsa-miR-520h | MIMAT0002867 | MI0003175 |
| hsa-miR-525-5p | MIMAT0002838 | MI0003152 |
| hsa-miR-526b | MIMAT0002835 | MI0003150 |
| hsa-miR-532-3p | MIMAT0004780 | MI0003205 |
| hsa-miR-532-5p | MIMAT0002888 | MI0003205 |
| hsa-miR-539 | MIMAT0003163 | MI0003514 |
| hsa-miR-542-3p | MIMAT0003389 | MI0003686 |
| hsa-miR-542-5p | MIMAT0003340 | MI0003686 |
| hsa-miR-543 | MIMAT0004954 | MI0005565 |
| hsa-miR-545 | MIMAT0003165 | MI0003516 |
| hsa-miR-548c-5p | MIMAT0004806 | MI0003630 |
| hsa-miR-550 | MIMAT0004800 | MI0003601 |
| hsa-miR-550* | MIMAT0003257 | MI0003601 |
| hsa-miR-551b | MIMAT0003233 | MI0003575 |
| hsa-miR-551b* | MIMAT0004794 | MI0003575 |
| hsa-miR-552 | MIMAT0003215 | MI0003557 |
| hsa-miR-556-3p | MIMAT0004793 | MI0003562 |
| hsa-miR-557 | MIMAT0003221 | MI0003563 |
| hsa-miR-564 | MIMAT0003228 | MI0003570 |
| hsa-miR-566 | MIMAT0003230 | MI0003572 |
| hsa-miR-572 | MIMAT0003237 | MI0003579 |
| hsa-miR-574-3p | MIMAT0003239 | MI0003581 |
| hsa-miR-574-5p | MIMAT0004795 | MI0003581 |
| hsa-miR-575 | MIMAT0003240 | MI0003582 |
| hsa-miR-576-5p | MIMAT0003241 | MI0003583 |
| hsa-miR-582-3p | MIMAT0004797 | MI0003589 |

TABLE 1-continued microRNA Accession Numbers. Accession numbers correspond to those listed in the Sanger miRBase version 12.0 database of microRNAs (Griffiths-Jones et al., 2006) and are hereby incorporated by reference in their entirety on Nov. 16, 2010, as well as the sequences represented in each database entry.

| Probe_ID | MicroRNA Accession Number | Precursor Accession Number |
| --- | --- | --- |
| hsa-miR-582-5p | MIMAT0003247 | MI0003589 |
| hsa-miR-583 | MIMAT0003248 | MI0003590 |
| hsa-miR-584 | MIMAT0003249 | MI0003591 |
| hsa-miR-585 | MIMAT0003250 | MI0003592 |
| hsa-miR-590-5p | MIMAT0003258 | MI0003602 |
| hsa-miR-592 | MIMAT0003260 | MI0003604 |
| hsa-miR-595 | MIMAT0003263 | MI0003607 |
| hsa-miR-598 | MIMAT0003266 | MI0003610 |
| hsa-miR-601 | MIMAT0003269 | MI0003614 |
| hsa-miR-602 | MIMAT0003270 | MI0003615 |
| hsa-miR-605 | MIMAT0003273 | MI0003618 |
| hsa-miR-610 | MIMAT0003278 | MI0003623 |
| hsa-miR-612 | MIMAT0003280 | MI0003625 |
| hsa-miR-614 | MIMAT0003282 | MI0003627 |
| hsa-miR-615-3p | MIMAT0003283 | MI0003628 |
| hsa-miR-616 | MIMAT0004805 | MI0003629 |
| hsa-miR-617 | MIMAT0003286 | MI0003631 |
| hsa-miR-622 | MIMAT0003291 | MI0003636 |
| hsa-miR-623 | MIMAT0003292 | MI0003637 |
| hsa-miR-624* | MIMAT0003293 | MI0003638 |
| hsa-miR-625 | MIMAT0003294 | MI0003639 |
| hsa-miR-625* | MIMAT0004808 | MI0003639 |
| hsa-miR-627 | MIMAT0003296 | MI0003641 |
| hsa-miR-628-3p | MIMAT0003297 | MI0003642 |
| hsa-miR-628-5p | MIMAT0004809 | MI0003642 |
| hsa-miR-629 | MIMAT0004810 | MI0003643 |
| hsa-miR-629* | MIMAT0003298 | MI0003643 |
| hsa-miR-630 | MIMAT0003299 | MI0003644 |
| hsa-miR-631 | MIMAT0003300 | MI0003645 |
| hsa-miR-633 | MIMAT0003303 | MI0003648 |
| hsa-miR-634 | MIMAT0003304 | MI0003649 |
| hsa-miR-636 | MIMAT0003306 | MI0003651 |
| hsa-miR-638 | MIMAT0003308 | MI0003653 |
| hsa-miR-639 | MIMAT0003309 | MI0003654 |
| hsa-miR-640 | MIMAT0003310 | MI0003655 |
| hsa-miR-641 | MIMAT0003311 | MI0003656 |
| hsa-miR-642 | MIMAT0003312 | MI0003657 |
| hsa-miR-648 | MIMAT0003318 | MI0003663 |
| hsa-miR-650 | MIMAT0003320 | MI0003665 |
| hsa-miR-652 | MIMAT0003322 | MI0003667 |
| hsa-miR-654-3p | MIMAT0004814 | MI0003676 |
| hsa-miR-654-5p | MIMAT0003330 | MI0003676 |
| hsa-miR-656 | MIMAT0003332 | MI0003678 |
| hsa-miR-658 | MIMAT0003336 | MI0003682 |
| hsa-miR-659 | MIMAT0003337 | MI0003683 |
| hsa-miR-660 | MIMAT0003338 | MI0003684 |
| hsa-miR-662 | MIMAT0003325 | MI0003670 |
| hsa-miR-663 | MIMAT0003326 | MI0003672 |
| hsa-miR-663b | MIMAT0005867 | MI0006336 |
| hsa-miR-664 | MIMAT0005949 | MI0006442 |
| hsa-miR-664* | MIMAT0005948 | MI0006442 |
| hsa-miR-665 | MIMAT0004952 | MI0005563 |
| hsa-miR-668 | MIMAT0003881 | MI0003761 |
| hsa-miR-671-5p | MIMAT0003880 | MI0003760 |
| hsa-miR-7 | MIMAT0000252 | MI0000263 |
| hsa-miR-7-1* | MIMAT0004553 | MI0000263 |
| hsa-miR-7-2* | MIMAT0004554 | MI0000264 |
| hsa-miR-708 | MIMAT0004926 | MI0005543 |
| hsa-miR-720 | MIMAT0005954 | MI0006654 |
| hsa-miR-744 | MIMAT0004945 | MI0005559 |
| hsa-miR-744* | MIMAT0004946 | MI0005559 |
| hsa-miR-758 | MIMAT0003879 | MI0003757 |
| hsa-miR-760 | MIMAT0004957 | MI0005567 |
| hsa-miR-765 | MIMAT0003945 | MI0005116 |
| hsa-miR-766 | MIMAT0003888 | MI0003836 |
| hsa-miR-767-5p | MIMAT0003882 | MI0003763 |
| hsa-miR-769-3p | MIMAT0003887 | MI0003834 |
| hsa-miR-769-5p | MIMAT0003886 | MI0003834 |
| hsa-miR-770-5p | MIMAT0003948 | MI0005118 |
| hsa-miR-873 | MIMAT0004953 | MI0005564 |
| hsa-miR-874 | MIMAT0004911 | MI0005532 |
| hsa-miR-876-3p | MIMAT0004925 | MI0005542 |
| hsa-miR-876-5p | MIMAT0004924 | MI0005542 |
| hsa-miR-877 | MIMAT0004949 | MI0005561 |
| hsa-miR-877* | MIMAT0004950 | MI0005561 |
| hsa-miR-885-5p | MIMAT0004947 | MI0005560 |
| hsa-miR-886-3p | MIMAT0004906 | MI0005527 |
| hsa-miR-886-5p | MIMAT0004905 | MI0005527 |
| hsa-miR-887 | MIMAT0004951 | MI0005562 |
| hsa-miR-888 | MIMAT0004916 | MI0005537 |
| hsa-miR-889 | MIMAT0004921 | MI0005540 |
| hsa-miR-890 | MIMAT0004912 | MI0005533 |
| hsa-miR-891a | MIMAT0004902 | MI0005524 |
| hsa-miR-891b | MIMAT0004913 | MI0005534 |
| hsa-miR-892a | MIMAT0004907 | MI0005528 |
| hsa-miR-892b | MIMAT0004918 | MI0005538 |
| hsa-miR-9 | MIMAT0000441 | MI0000468 |
| hsa-miR-9* | MIMAT0000442 | MI0000468 |
| hsa-miR-921 | MIMAT0004971 | MI0005713 |
| hsa-miR-923 | MIMAT0004973 | MI0005715 |
| hsa-miR-92a | MIMAT0000092 | MI0000094 |
| hsa-miR-92a-1* | MIMAT0004507 | MI0000093 |
| hsa-miR-92b | MIMAT0003218 | MI0003560 |
| hsa-miR-92b* | MIMAT0004792 | MI0003560 |
| hsa-miR-93 | MIMAT0000093 | MI0000095 |
| hsa-miR-93* | MIMAT0004509 | MI0000095 |
| hsa-miR-933 | MIMAT0004976 | MI0005755 |
| hsa-miR-934 | MIMAT0004977 | MI0005756 |
| hsa-miR-936 | MIMAT0004979 | MI0005758 |
| hsa-miR-939 | MIMAT0004982 | MI0005761 |
| hsa-miR-940 | MIMAT0004983 | MI0005762 |
| hsa-miR-944 | MIMAT0004987 | MI0005769 |
| hsa-miR-95 | MIMAT0000094 | MI0000097 |
| hsa-miR-96 | MIMAT0000095 | MI0000098 |
| hsa-miR-98 | MIMAT0000096 | MI0000100 |
| hsa-miR-99a | MIMAT0000097 | MI0000101 |
| hsa-miR-99a* | MIMAT0004511 | MI0000101 |
| hsa-miR-99b | MIMAT0000689 | MI0000746 |
| hsa-miR-99b* | MIMAT0004678 | MI0000746 |

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Microarray Analysis of miRNAs from Normal Thyroid Samples and Thyroid Neoplasms miRNAs potentially relevant to carcinogenesis frequently exhibit differential expression in cancer versus normal samples collected from the same tissue type. In addition, miRNAs with differential expression in normal and cancerous samples may be used in the diagnosis of benign and cancerous lesions and in the diagnosis of different types of malignant lesions. To identify miRNAs that may be useful markers for diagnosis of thyroid cancer, for distinguishing benign from cancerous lesions, and for distinguishing among different types of thyroid malignancies, the inventors evaluated miRNA expression in various thyroid tissue samples.

miRNA array expression analysis: miRNA expression profiling was performed by Asuragen, Inc. (Austin, Tex., USA) using the Human miRNA Microarrays (V3) (cat. no. G4471A-021827; Agilent Technologies, Inc., Santa Clara, Calif., USA) according to the manufacturer's recommended protocols. The V3 Human miRNA Microarray contains probes for 866 human and 89 human viral miRNAs from the Sanger miRBase v. 12 (Griffiths-Jones et at, 2006). Total RNA was isolated from each sample, using the mirVana™ miRNA Isolation Kit (Ambion; Austin, Tex., USA). Purified total RNA was quantified using a NanoDrop® ND-1000 spectrophotometer (NanoDrop Technologies; Wilmington, Del., USA). Total RNA (200 ng) from each sample was dephosphorylated and the pCp-Cy3 labeling molecule was ligated to the 3' end of the RNA molecules. The labeled RNA was purified using a Bio-Spin P-6 column (Bio-Rad Laboratories Inc.; Hercules, Calif., USA). Array hybridization, washing, staining, imaging, and signal extraction were performed according to Agilent's recommended procedures.

miRNA array signal processing: The signal processing implemented for the Agilent miRNA array is a multi-step process involving probe specific signal detection calls, background correction, and global normalization. For each probe, the contribution of signal due to background was estimated and removed by the Agilent Feature Extraction software as part of the data file output. Similarly, detection calls were based on the Agilent Feature Extraction software. Arrays within a specific analysis experiment were normalized together according to the VSN method described by Huber et al., 2002.

Background estimate and correction and probe detection: Three types of data are provided to evaluate each hybridization. The "Total Gene Signal" is the total probe signal multiplied by the number of probes per gene and is calculated after the background effects have been accounted for. The "Total Gene Error" is the square root of the square of the total probe error multiplied by the number of probes per gene. The "Total Probe Error" is the robust average for each replicated probe multiplied by the total number of probe replicates. The "Detection Call" is a binary number that indicates if the gene was detected on the miRNA microarray. Probes detected at least once across all samples in the experiment were considered for statistical analysis.

Global normalization: The inventors have found that the Variance Stabilization Normalization (VSN) algorithm provides an ideal balance of accuracy and precision while optimizing sensitivity and specificity of signal. One advantage of VSN is that it accommodates negative values by using the generalized $\log_2$ transformation.

Generalized $\log_2$ transformed: The post-normalized data scale is reported as generalized $\log_2$ data. The distribution of microarray data is typically log normal (i.e., it tends to follow a normal distribution pattern after log transformation). Normal distributed data are amendable to classical statistical treatments, including t-tests and one-way or two-way ANOVA.

For statistical hypothesis testing, a two-sample t-Test, with assumption of equal variance, was applied. This test is used to define which probes are considered to be significantly differentially expressed, or "significant", based on false discovery rate set at 0.05. In addition, differential expression was also evaluated using a standard student t-test and considered statistically significant when p-value≤0.05.

Thirty one fresh, frozen tissue samples from normal thyroid and various thyroid neoplasms were purchased from Asterand (Asterand, plc., Detroit, Mich., USA). Samples were from five normal thyroid tissues (NOR), four hyperplastic nodules (NOD), five follicular adenomas (FA), five follicular thyroid carcinomas (FTC), five papillary thyroid carcinomas (PTC), four follicular variant of papillary thyroid carcinomas (FVPTC), one anaplastic thyroid carcinoma (ATC), and three medullary thyroid carcinomas (MTC) (Table 2).

TABLE 2

Histopathological data and patient information for thyroid tissue samples.

| Sample | Sex | Age at Excision | Ethnicity | Sample Type | Histological Diagnosis | TNM Staging score (Name et al., 1900) | AJCC/UICC Stage Group Greene (2002) | % tumor in sample |
|---|---|---|---|---|---|---|---|---|
| 26 | Female | 53 | Caucasian | Tumor | ATC | T3NXM0 | III | 97 |
| 4 | Female | 41 | Caucasian | Tumor | FA | T3NXM0 | I | 100 |
| 13 | Male | 47 | Caucasian | Tumor | FA | T2NXMX | II | 100 |
| 15 | Female | 68 | Caucasian | Tumor | FA | T3NXM0 | III | 95 |
| 17 | Female | 50 | Caucasian | Tumor | FA | T2N0M0 | II | 100 |
| 22 | Female | 52 | Caucasian | Tumor | FA | T2NXM0 | II | 100 |
| 18 | Male | 58 | Caucasian | Tumor | FTC | T3NXm0 | III | 100 |
| 27 | Female | 52 | Caucasian | Tumor | FTC | T4aNXM0 | IVA | 90 |
| 30 | Female | 79 | Caucasian | Tumor | FTC | T1N1M0 | III | 95 |
| 31 | Female | 75 | Caucasian | Tumor | FTC | T2NXMX | I | 100 |
| 34 | Female | 57 | Caucasian | Tumor | FTC | T1NXMX | I | 95 |
| 16 | Female | 32 | Caucasian | Tumor | FVPTC | T4AN1M0 | I | 95 |
| 25 | Female | 59 | Caucasian | Tumor | FVPTC | TXNXM0 | | 80 |
| 32 | Female | 24 | Caucasian | Tumor | FVPTC | T2NXM0 | I | 90 |
| 33 | Male | 41 | Hispanic | Tumor | FVPTC | T4aN1bMX | I | 70 |
| 19 | Female | 48 | Caucasian | Tumor | MTC | T2N1M0 | | 90 |
| 28 | Female | 54 | Caucasian | Tumor | MTC | T2N0MX | II | 96 |
| 29 | Male | 59 | Caucasian | Tumor | MTC | T1N1MX | III | 85 |
| 6 | Male | 54 | Caucasian | Diseased | NOD | | | 0 |
| 7 | Male | 83 | Caucasian | Diseased | NOD | | | 0 |
| 12 | Female | 88 | Caucasian | Diseased | NOD | | | 0 |
| 21 | Male | 45 | Caucasian | Diseased | NOD | | | 0 |
| 1 | Female | 85 | Caucasian | Normal | NOR | | | 0 |
| 3 | Female | 71 | Caucasian | Normal | NOR | T2NXM0 | II | 0 |

TABLE 2-continued

Histopathological data and patient information for thyroid tissue samples.

| Sample | Sex | Age at Excision | Ethnicity | Sample Type | Histological Diagnosis | TNM Staging score (Name et al., 1900) | AJCC/UICC Stage Group Greene (2002) | % tumor in sample |
|---|---|---|---|---|---|---|---|---|
| 5 | Female | 52 | Caucasian | Normal | NOR | T3N1aM0 | III | 0 |
| 14 | Female | 38 | Caucasian | Normal | NOR | TXN1bM0 | I | 0 |
| 8 | Female | 42 | Caucasian | Tumor | PTC | T3NXM0 | I | 90 |
| 10 | Female | 24 | Caucasian | Tumor | PTC | T2N0M0 | II | 90 |
| 11 | Female | 41 | Caucasian | Tumor | PTC | TXNXM0 | | 95 |
| 23 | Male | 24 | Caucasian | Tumor | PTC | T3N1MX | I | 100 |
| 24 | Male | 29 | Caucasian | Tumor | PTC | T3N1bM0 | I | 90 |

Normal thyroid tissues (NOR),
hyperplastic nodules (NOD),
follicular adenomas (FA),
follicular thyroid carcinomas (FTC),
papillary thyroid carcinomas (PTC),
follicular variant of papillary thyroid carcinomas (FVPTC),
anaplastic thyroid carcinoma (ATC),
medullary thyroid carcinomas (MTC).

Average expression levels of miRNAs in each group, determined from microarray analysis, are shown in Table 3.

TABLE 3

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-let-7a | 14.3 | 100 | 14.6 | 0.5 | 100 | 14.6 | 0.3 | 100 | 14.8 | 0.4 | 100 | 14.8 | 0.1 | 100 | 14.6 | 0.4 | 100 | 15.2 | 0.2 | 100 | 14.9 | 0.3 | 100 |
| hsa-let-7a* | 1.6 | 0 | 1.4 | 0.3 | 20 | 1.5 | 0.5 | 40 | 1.3 | 0.2 | 25 | 1.1 | 0.3 | 0 | 1.2 | 0.2 | 50 | 1.3 | 0.4 | 50 | 1.3 | 0.3 | 20 |
| hsa-let-7b | 13.9 | 100 | 13.6 | 0.6 | 100 | 13.2 | 0.6 | 100 | 13.9 | 0.2 | 100 | 13.3 | 0.4 | 100 | 14.0 | 0.4 | 100 | 14.0 | 0.2 | 100 | 13.8 | 0.4 | 100 |
| hsa-let-7b* | 2.4 | 0 | 2.1 | 1.1 | 20 | 1.7 | 0.4 | 0 | 1.9 | 0.4 | 0 | 1.3 | 0.1 | 0 | 1.6 | 0.5 | 0 | 1.3 | 0.1 | 0 | 1.6 | 0.4 | 0 |
| hsa-let-7c | 10.7 | 100 | 12.1 | 0.7 | 100 | 12.1 | 0.7 | 100 | 12.5 | 0.3 | 100 | 12.8 | 0.4 | 100 | 12.7 | 0.2 | 100 | 13.0 | 0.2 | 100 | 12.4 | 0.4 | 100 |
| hsa-let-7c* | 0.1 | 0 | 0.5 | 0.9 | 0 | −0.1 | 0.6 | 0 | 0.0 | 0.3 | 0 | 0.1 | 0.1 | 0 | 1.0 | 0.2 | 0 | 0.6 | 0.3 | 0 | 1.1 | 1.3 | 20 |
| hsa-let-7d | 11.1 | 100 | 11.7 | 0.6 | 100 | 11.7 | 0.5 | 60 | 12.1 | 0.3 | 100 | 11.3 | 0.7 | 100 | 11.8 | 0.3 | 100 | 12.3 | 0.2 | 100 | 12.0 | 0.4 | 100 |
| hsa-let-7d* | 1.3 | 0 | 2.2 | 1.1 | 100 | 1.3 | 0.9 | 0 | 1.6 | 0.5 | 50 | 0.6 | 0.8 | 33 | 1.5 | 0.3 | 75 | 1.7 | 0.2 | 75 | 1.1 | 0.3 | 40 |
| hsa-let-7e | 12.2 | 100 | 11.4 | 0.6 | 100 | 11.6 | 0.7 | 100 | 12.1 | 0.5 | 100 | 12.8 | 0.2 | 100 | 11.3 | 0.3 | 100 | 11.7 | 0.2 | 100 | 12.2 | 0.2 | 100 |
| hsa-let-7e* | 2.4 | 100 | 2.5 | 1.2 | 80 | 2.4 | 0.6 | 20 | 2.7 | 0.5 | 75 | 3.1 | 0.3 | 100 | 1.7 | 0.5 | 100 | 2.2 | 0.3 | 100 | 2.2 | 0.3 | 40 |
| hsa-let-7f | 13.6 | 100 | 14.1 | 0.6 | 100 | 14.3 | 0.4 | 100 | 14.2 | 0.5 | 100 | 13.9 | 0.1 | 100 | 14.0 | 0.5 | 100 | 14.7 | 0.2 | 100 | 14.4 | 0.5 | 100 |
| hsa-let-7f-1* | 2.5 | 0 | 2.1 | 0.5 | 0 | 1.8 | 0.4 | 0 | 2.1 | 0.5 | 0 | 1.4 | 0.6 | 33 | 1.8 | 0.6 | 0 | 1.4 | 0.1 | 0 | 1.7 | 0.4 | 0 |
| hsa-let-7g | 11.8 | 100 | 12.7 | 0.5 | 100 | 12.7 | 0.3 | 100 | 13.0 | 0.3 | 100 | 12.3 | 0.4 | 100 | 12.8 | 0.3 | 100 | 13.4 | 0.2 | 100 | 13.0 | 0.3 | 100 |
| hsa-let-7g* | −2.1 | 0 | 0.5 | 1.5 | 20 | −1.1 | 0.5 | 0 | −0.2 | 0.1 | 0 | −0.3 | 1.3 | 0 | 0.0 | 0.6 | 0 | −0.1 | 0.5 | 0 | −0.9 | 0.6 | 0 |
| hsa-let-7i | 12.0 | 100 | 13.6 | 0.6 | 100 | 13.5 | 0.4 | 100 | 14.6 | 0.4 | 100 | 12.6 | 0.9 | 100 | 13.5 | 0.2 | 100 | 14.0 | 0.3 | 100 | 14.5 | 0.4 | 100 |
| hsa-let-7i* | 0.1 | 100 | 2.8 | 1.0 | 80 | 3.1 | 1.3 | 100 | 3.7 | 0.7 | 100 | 1.9 | 1.0 | 33 | 2.9 | 1.0 | 100 | 3.6 | 0.4 | 100 | 3.8 | 0.4 | 100 |
| hsa-miR-1 | 3.1 | 100 | 5.9 | 1.4 | 100 | 5.9 | 1.3 | 100 | 7.5 | 1.2 | 100 | 5.2 | 1.0 | 100 | 8.7 | 3.4 | 100 | 9.6 | 3.4 | 100 | 5.4 | 1.4 | 100 |
| hsa-miR-100 | 9.2 | 100 | 11.3 | 1.4 | 100 | 10.6 | 0.8 | 100 | 11.1 | 0.6 | 100 | 10.6 | 0.7 | 67 | 11.7 | 0.2 | 100 | 12.1 | 0.4 | 100 | 11.1 | 0.2 | 20 |
| hsa-miR-100* | 1.3 | 0 | 1.9 | 0.9 | 20 | 1.3 | 0.4 | 0 | 1.5 | 0.2 | 0 | 1.3 | 0.4 | 0 | 1.2 | 0.1 | 0 | 1.7 | 0.4 | 50 | 1.3 | 0.4 | 0 |
| hsa-miR-101 | 7.5 | 100 | 8.3 | 1.1 | 100 | 8.8 | 0.3 | 100 | 8.8 | 0.5 | 100 | 8.8 | 0.3 | 100 | 8.9 | 0.6 | 100 | 9.5 | 0.2 | 100 | 9.1 | 0.7 | 100 |
| hsa-miR-101* | 1.4 | 0 | 1.9 | 0.8 | 40 | 2.2 | 0.2 | 60 | 2.5 | 0.5 | 75 | 2.2 | 0.2 | 67 | 2.4 | 0.5 | 75 | 2.8 | 0.2 | 100 | 2.6 | 0.4 | 80 |
| hsa-miR-103 | 11.6 | 100 | 11.4 | 0.7 | 100 | 11.6 | 0.5 | 100 | 11.7 | 0.3 | 100 | 12.2 | 0.2 | 100 | 11.4 | 0.2 | 100 | 11.7 | 0.2 | 100 | 11.6 | 0.3 | 100 |
| hsa-miR-105 | −0.7 | 0 | −0.8 | 1.6 | 0 | −1.4 | 0.6 | 0 | −1.2 | 0.9 | 0 | 2.0 | 2.5 | 0 | −1.3 | 0.4 | 0 | −1.0 | 0.3 | 0 | −1.1 | 0.5 | 0 |
| hsa-miR-105* | −0.2 | 0 | −0.7 | 0.6 | 0 | 0.4 | 0.6 | 20 | 0.1 | 0.8 | 0 | 0.0 | 0.1 | 0 | 0.2 | 0.5 | 0 | −0.1 | 0.3 | 0 | 0.1 | 1.0 | 20 |
| hsa-miR-106b | 9.9 | 100 | 9.4 | 0.8 | 100 | 9.8 | 0.3 | 100 | 9.9 | 0.3 | 100 | 10.3 | 0.3 | 100 | 9.5 | 0.1 | 100 | 9.7 | 0.3 | 100 | 10.2 | 0.1 | 100 |
| hsa-miR-107 | 11.1 | 100 | 10.9 | 0.8 | 100 | 11.3 | 0.5 | 100 | 10.9 | 0.3 | 100 | 11.5 | 0.1 | 100 | 10.9 | 0.3 | 100 | 11.3 | 0.2 | 100 | 11.0 | 0.3 | 100 |
| hsa-miR-10a | 10.4 | 100 | 8.5 | 1.9 | 100 | 6.7 | 1.0 | 100 | 7.6 | 0.8 | 100 | 11.7 | 0.5 | 100 | 7.6 | 0.4 | 100 | 8.7 | 0.4 | 100 | 7.4 | 0.6 | 100 |
| hsa-miR-10a* | 2.4 | 0 | 1.4 | 1.7 | 0 | 0.5 | 0.4 | 0 | 0.8 | 0.5 | 0 | 3.8 | 0.6 | 100 | 1.1 | 0.4 | 0 | 1.6 | 0.1 | 25 | 1.5 | 0.3 | 0 |
| hsa-miR-10b | 7.7 | 100 | 8.5 | 0.5 | 100 | 8.2 | 0.4 | 100 | 8.5 | 0.6 | 100 | 8.6 | 0.2 | 100 | 8.6 | 0.5 | 100 | 9.1 | 0.2 | 100 | 8.5 | 0.4 | 100 |
| hsa-miR-10b* | 1.8 | 0 | 2.0 | 0.5 | 60 | 0.6 | 0.2 | 20 | 2.8 | 0.6 | 50 | 2.1 | 1.4 | 67 | 3.3 | 0.6 | 100 | 3.3 | 0.6 | 100 | 2.3 | 0.3 | 60 |
| hsa-miR-1180 | 0.4 | 0 | 1.4 | 1.7 | 20 | 1.7 | 0.9 | 20 | 1.5 | 0.5 | 0 | 3.1 | 1.0 | 67 | 3.5 | 0.4 | 100 | 2.4 | 0.1 | 50 | 0.8 | 1.0 | 0 |
| hsa-miR-1181 | 4.0 | 100 | 3.4 | 0.2 | 100 | 4.3 | 1.1 | 100 | 3.7 | 0.4 | 100 | 3.2 | 0.6 | 67 | 4.0 | 0.5 | 100 | 3.5 | 0.4 | 100 | 3.3 | 0.4 | 0 |
| hsa-miR-1182 | 2.2 | 0 | 0.9 | 0.9 | 0 | 1.6 | 1.1 | 20 | 2.2 | 1.1 | 25 | 2.5 | 1.5 | 67 | 4.8 | 0.8 | 100 | 2.9 | 0.4 | 75 | 0.7 | 0.7 | 0 |
| hsa-miR-1183 | 4.0 | 100 | 3.0 | 1.3 | 60 | 3.7 | 0.9 | 80 | 3.8 | 0.9 | 100 | 4.3 | 1.4 | 100 | 6.2 | 0.7 | 100 | 4.6 | 0.5 | 100 | 2.6 | 0.6 | 40 |
| hsa-miR-1185 | 0.9 | 0 | 2.0 | 0.6 | 20 | 1.1 | 0.7 | 20 | 0.4 | 0.5 | 0 | 3.0 | 0.3 | 100 | 0.7 | 0.3 | 0 | 0.9 | 0.2 | 0 | 1.1 | 0.6 | 0 |
| hsa-miR-1201 | 2.5 | 100 | 1.6 | 0.9 | 0 | 2.0 | 0.8 | 20 | 3.7 | 0.3 | 100 | 3.0 | 0.5 | 100 | 1.1 | 0.8 | 0 | 1.4 | 0.2 | 0 | 1.0 | 1.0 | 0 |
| hsa-miR-1202 | 11.2 | 100 | 9.4 | 0.9 | 100 | 10.5 | 1.4 | 100 | 10.6 | 1.6 | 100 | 10.1 | 2.1 | 100 | 13.7 | 0.8 | 100 | 11.0 | 0.4 | 100 | 9.0 | 0.9 | 100 |
| hsa-miR-1203 | −0.4 | 0 | −0.4 | 1.2 | 0 | −0.2 | 1.1 | 0 | 0.0 | 1.0 | 0 | 0.3 | 1.5 | 50 | 2.4 | 1.0 | 50 | 0.4 | 1.0 | 0 | −1.1 | 0.5 | 0 |
| hsa-miR-1207-5p | 9.5 | 100 | 8.7 | 0.8 | 100 | 9.4 | 0.9 | 100 | 9.5 | 0.7 | 100 | 9.3 | 1.6 | 100 | 11.8 | 1.0 | 100 | 9.8 | 0.5 | 100 | 8.2 | 0.7 | 100 |
| hsa-miR-1208 | 0.9 | 0 | 1.2 | 0.8 | 0 | 2.2 | 0.6 | 0 | 1.8 | 0.9 | 25 | 2.3 | 1.0 | 67 | 3.7 | 0.3 | 100 | 2.8 | 0.4 | 75 | 2.0 | 1.0 | 20 |
| hsa-miR-122 | 0.5 | 0 | 0.6 | 0.3 | 0 | 0.5 | 0.6 | 0 | 0.7 | 1.3 | 0 | 4.0 | 3.1 | 33 | 2.2 | 1.3 | 50 | 0.7 | 0.6 | 0 | 0.7 | 1.0 | 0 |
| hsa-miR-122* | −0.7 | 0 | 0.3 | 1.0 | 0 | 0.1 | 0.7 | 0 | 0.1 | 1.1 | 0 | 1.1 | 1.5 | 33 | 0.3 | 0.5 | 0 | −0.2 | 0.5 | 0 | 0.0 | 0.3 | 0 |
| hsa-miR-1224-5p | 5.6 | 100 | 5.0 | 1.5 | 100 | 5.4 | 0.8 | 100 | 5.3 | 0.7 | 100 | 5.7 | 1.1 | 100 | 7.6 | 0.7 | 100 | 5.9 | 0.5 | 100 | 4.3 | 0.5 | 100 |
| hsa-miR-1225-3p | 4.3 | 100 | 3.5 | 0.4 | 80 | 3.8 | 0.3 | 100 | 3.7 | 0.4 | 100 | 3.4 | 0.2 | 100 | 4.1 | 0.3 | 100 | 3.4 | 0.2 | 100 | 3.6 | 0.2 | 100 |
| hsa-miR-1225-5p | 9.8 | 100 | 8.7 | 0.6 | 100 | 9.2 | 0.9 | 100 | 9.5 | 1.0 | 100 | 9.2 | 1.5 | 100 | 11.8 | 1.0 | 100 | 9.8 | 0.4 | 100 | 8.3 | 0.5 | 100 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-1226* | 3.8 | 100 | 3.7 | 0.5 | 80 | 4.2 | 0.6 | 100 | 3.9 | 0.3 | 100 | 4.0 | 0.9 | 100 | 5.7 | 0.5 | 100 | 4.4 | 0.4 | 100 | 3.8 | 0.5 | 100 |
| hsa-miR-1227 | 1.4 | 0 | 1.8 | 1.1 | 20 | 0.5 | 0.5 | 0 | 0.9 | 0.8 | 0 | -0.1 | 0.4 | 0 | 0.1 | 0.6 | 0 | 0.3 | 0.4 | 0 | 0.0 | 0.7 | 0 |
| hsa-miR-1228 | 5.6 | 100 | 4.6 | 0.7 | 100 | 5.1 | 0.3 | 100 | 5.0 | 0.5 | 100 | 4.7 | 0.2 | 100 | 5.8 | 0.6 | 100 | 4.8 | 0.2 | 100 | 4.8 | 0.2 | 100 |
| hsa-miR-1228* | -1.2 | 0 | -0.7 | 1.3 | 0 | -0.4 | 1.0 | 0 | -0.3 | 1.2 | 0 | 0.0 | 1.5 | 0 | 1.9 | 0.7 | 50 | 0.5 | 0.9 | 25 | -1.4 | 0.6 | 0 |
| hsa-miR-1229 | 1.9 | 0 | 2.0 | 0.6 | 0 | 1.8 | 0.5 | 0 | 1.9 | 0.4 | 25 | 1.8 | 0.1 | 0 | 2.3 | 0.3 | 75 | 1.8 | 0.3 | 100 | 1.7 | 0.2 | 40 |
| hsa-miR-1234 | 5.0 | 100 | 3.9 | 1.0 | 80 | 4.6 | 0.2 | 100 | 4.5 | 0.5 | 100 | 3.9 | 0.5 | 100 | 4.7 | 0.6 | 100 | 4.1 | 0.4 | 100 | 4.4 | 0.2 | 100 |
| hsa-miR-1237 | 3.8 | 100 | 2.7 | 0.4 | 20 | 3.0 | 0.3 | 40 | 2.9 | 0.6 | 50 | 2.7 | 0.2 | 33 | 3.3 | 0.5 | 100 | 2.6 | 0.4 | 75 | 2.9 | 0.3 | 60 |
| hsa-miR-1238 | 4.7 | 100 | 3.7 | 0.6 | 80 | 4.1 | 0.2 | 100 | 4.1 | 0.4 | 100 | 3.7 | 0.3 | 100 | 4.1 | 0.4 | 100 | 3.6 | 0.4 | 100 | 4.0 | 0.3 | 100 |
| hsa-miR-124 | 4.2 | 100 | 0.7 | 0.3 | 0 | -0.4 | 1.1 | 0 | -0.1 | 0.4 | 0 | 7.9 | 3.1 | 100 | 1.5 | 1.1 | 25 | 0.6 | 0.5 | 100 | -0.4 | 0.3 | 0 |
| hsa-miR-124* | -1.9 | 0 | -0.7 | 1.0 | 0 | -1.0 | 1.0 | 0 | -1.1 | 0.8 | 0 | 0.2 | 1.7 | 33 | -0.9 | 0.5 | 0 | -1.4 | 0.4 | 0 | -1.5 | 0.3 | 0 |
| hsa-miR-1244 | 1.0 | 0 | 0.4 | 0.8 | 0 | 0.9 | 0.6 | 0 | 1.0 | 0.8 | 25 | 0.9 | 0.7 | 0 | 2.1 | 0.9 | 25 | 1.3 | 1.5 | 50 | 0.5 | 0.5 | 0 |
| hsa-miR-1246 | 7.4 | 100 | 7.1 | 1.2 | 100 | 7.7 | 1.0 | 100 | 7.8 | 1.0 | 100 | 7.9 | 1.9 | 100 | 9.6 | 1.2 | 100 | 9.2 | 0.9 | 100 | 6.9 | 1.4 | 100 |
| hsa-miR-1249 | 5.2 | 100 | 4.0 | 0.6 | 100 | 4.5 | 0.5 | 100 | 4.5 | 0.8 | 100 | 4.2 | 0.7 | 100 | 5.9 | 0.7 | 100 | 4.5 | 0.5 | 100 | 3.9 | 0.4 | 100 |
| hsa-miR-1250 | -1.2 | 0 | -0.5 | 1.3 | 0 | -0.2 | 0.5 | 0 | 0.2 | 0.8 | 0 | 0.9 | 0.3 | 0 | 1.9 | 0.9 | 25 | 0.1 | 0.9 | 0 | -0.3 | 0.7 | 0 |
| hsa-miR-1251 | -2.3 | 0 | 0.5 | 1.4 | 0 | 0.3 | 1.4 | 40 | 0.7 | 0.6 | 75 | 1.5 | 0.4 | 33 | 0.4 | 1.2 | 25 | 1.0 | 0.3 | 25 | -0.1 | 1.5 | 20 |
| hsa-miR-125a-3p | 6.2 | 100 | 5.6 | 0.8 | 100 | 6.1 | 0.7 | 100 | 6.1 | 0.1 | 100 | 6.2 | 0.7 | 100 | 7.3 | 0.4 | 100 | 5.9 | 0.3 | 100 | 5.7 | 0.5 | 100 |
| hsa-miR-125a-5p | 9.3 | 100 | 8.8 | 0.7 | 100 | 8.8 | 0.9 | 100 | 9.0 | 0.3 | 100 | 9.2 | 0.1 | 100 | 8.6 | 0.2 | 100 | 8.8 | 0.2 | 100 | 9.2 | 0.3 | 100 |
| hsa-miR-125b | 10.4 | 100 | 13.2 | 1.0 | 100 | 13.8 | 0.6 | 100 | 14.1 | 0.4 | 100 | 14.0 | 0.7 | 100 | 13.9 | 0.2 | 100 | 14.2 | 0.2 | 100 | 14.4 | 0.3 | 100 |
| hsa-miR-125b-1* | 2.5 | 100 | 0.9 | 1.7 | 20 | 2.2 | 1.1 | 60 | 2.1 | 0.6 | 75 | 2.3 | 1.1 | 67 | 3.1 | 1.3 | 75 | 1.9 | 0.9 | 75 | 0.8 | 0.8 | 20 |
| hsa-miR-125b-2* | 2.7 | 100 | 4.6 | 0.9 | 100 | 4.9 | 1.1 | 100 | 5.3 | 0.3 | 100 | 5.8 | 0.6 | 100 | 5.6 | 0.2 | 100 | 5.6 | 0.2 | 100 | 5.3 | 0.3 | 100 |
| hsa-miR-126 | 10.0 | 100 | 12.7 | 0.7 | 100 | 12.1 | 0.5 | 100 | 12.0 | 0.9 | 100 | 11.7 | 0.3 | 100 | 12.4 | 0.3 | 100 | 12.9 | 0.2 | 100 | 11.9 | 0.4 | 100 |
| hsa-miR-126* | 3.4 | 100 | 6.5 | 1.0 | 100 | 6.2 | 0.4 | 100 | 5.5 | 1.2 | 100 | 5.5 | 0.2 | 100 | 6.2 | 0.3 | 100 | 6.9 | 0.3 | 100 | 5.6 | 0.6 | 100 |
| hsa-miR-1260 | 9.8 | 100 | 8.6 | 0.7 | 100 | 9.5 | 0.6 | 100 | 8.5 | 0.6 | 100 | 8.9 | 0.4 | 100 | 6.5 | 0.8 | 100 | 8.1 | 0.8 | 100 | 8.8 | 0.6 | 100 |
| hsa-miR-1268 | 7.6 | 100 | 7.4 | 0.4 | 100 | 7.8 | 0.5 | 100 | 7.5 | 0.9 | 100 | 7.9 | 0.7 | 100 | 10.2 | 1.3 | 100 | 8.3 | 0.7 | 100 | 6.6 | 0.5 | 100 |
| hsa-miR-127-3p | 5.4 | 100 | 3.4 | 1.0 | 80 | 3.9 | 1.3 | 100 | 4.2 | 0.8 | 100 | 8.9 | 0.4 | 100 | 4.5 | 0.6 | 100 | 5.2 | 0.6 | 100 | 4.1 | 1.4 | 100 |
| hsa-miR-127-5p | -0.2 | 0 | -1.3 | 0.9 | 0 | -1.2 | 0.6 | 0 | -0.4 | 0.4 | 0 | -0.1 | 1.3 | 0 | 1.3 | 0.3 | 25 | -0.3 | 1.0 | 0 | -0.9 | 0.6 | 0 |
| hsa-miR-1270 | 0.0 | 0 | 1.4 | 0.5 | 0 | 1.2 | 1.2 | 0 | 1.4 | 0.6 | 0 | 0.8 | 0.8 | 0 | 2.5 | 0.5 | 50 | 2.1 | 0.2 | 25 | 1.3 | 0.4 | 0 |
| hsa-miR-1271 | 3.3 | 100 | 3.6 | 0.5 | 100 | 3.6 | 0.8 | 100 | 3.9 | 0.4 | 100 | 4.2 | 1.1 | 100 | 4.3 | 0.4 | 100 | 4.4 | 0.2 | 100 | 4.0 | 0.4 | 100 |
| hsa-miR-1274a | 9.6 | 100 | 7.3 | 0.8 | 100 | 8.2 | 0.7 | 100 | 7.4 | 0.7 | 100 | 7.5 | 0.9 | 100 | 4.7 | 1.0 | 100 | 6.6 | 1.3 | 100 | 7.7 | 0.5 | 100 |
| hsa-miR-1274b | 12.6 | 100 | 10.9 | 0.8 | 100 | 11.8 | 0.7 | 100 | 11.1 | 0.6 | 100 | 11.0 | 0.8 | 100 | 8.5 | 0.9 | 100 | 10.2 | 1.2 | 100 | 11.3 | 0.4 | 100 |
| hsa-miR-1275 | 6.9 | 100 | 6.6 | 0.9 | 100 | 7.0 | 1.3 | 100 | 7.2 | 0.3 | 100 | 7.7 | 1.3 | 100 | 8.1 | 0.5 | 100 | 7.4 | 0.4 | 100 | 6.5 | 0.5 | 100 |
| hsa-miR-1276 | -1.0 | 0 | -0.2 | 1.6 | 0 | -0.4 | 0.8 | 0 | -0.4 | 0.6 | 0 | -0.2 | 1.3 | 0 | 2.0 | 0.6 | 25 | 0.1 | 0.6 | 0 | -0.2 | 1.3 | 0 |
| hsa-miR-128 | 6.8 | 100 | 6.5 | 0.6 | 100 | 6.8 | 0.2 | 100 | 6.6 | 0.4 | 100 | 8.3 | 0.9 | 100 | 7.1 | 0.5 | 100 | 7.5 | 0.6 | 100 | 4.0 | 0.2 | 100 |
| hsa-miR-1280 | 7.7 | 100 | 6.9 | 1.4 | 100 | 7.2 | 0.2 | 100 | 6.4 | 0.5 | 100 | 6.9 | 0.2 | 100 | 7.6 | 0.9 | 100 | 7.0 | 1.3 | 100 | 6.7 | 1.0 | 100 |
| hsa-miR-1281 | 4.2 | 100 | 3.5 | 0.5 | 80 | 3.6 | 0.6 | 100 | 3.8 | 0.5 | 100 | 3.3 | 0.4 | 100 | 3.9 | 0.3 | 100 | 3.3 | 0.4 | 100 | 6.7 | 0.3 | 100 |
| hsa-miR-1285 | 2.3 | 100 | 1.9 | 1.0 | 20 | 2.2 | 0.5 | 80 | 1.7 | 0.7 | 25 | 2.9 | 0.3 | 0 | 3.4 | 0.6 | 100 | 2.5 | 0.4 | 100 | 3.5 | 0.3 | 20 |
| hsa-miR-1287 | 1.7 | 0 | 2.1 | 0.9 | 40 | 2.0 | 0.5 | 20 | 1.5 | 0.9 | 0 | 1.9 | 0.3 | 0 | 1.7 | 0.9 | 0 | 2.3 | 0.8 | 75 | 1.7 | 0.4 | 0 |
| hsa-miR-1288 | 5.9 | 100 | 5.4 | 0.5 | 100 | 5.6 | 0.4 | 100 | 5.6 | 0.4 | 100 | 5.1 | 0.3 | 100 | 5.3 | 0.4 | 100 | 5.4 | 0.8 | 100 | 6.3 | 0.7 | 100 |
| hsa-miR-129* | 2.8 | 100 | 2.7 | 0.3 | 100 | 2.7 | 0.9 | 40 | 2.2 | 0.4 | 75 | 5.4 | 3.4 | 67 | 2.1 | 2.0 | 50 | 2.2 | 0.1 | 100 | 2.0 | 0.2 | 100 |
| hsa-miR-129-3p | 4.1 | 100 | 3.1 | 0.8 | 60 | 3.1 | 1.4 | 60 | 2.7 | 0.5 | 75 | 9.2 | 5.5 | 67 | 3.7 | 1.1 | 75 | 4.0 | 1.1 | 100 | 3.3 | 0.6 | 20 |
| hsa-miR-129-5p | 1.8 | 0 | 0.7 | 1.3 | 40 | 0.7 | 1.4 | 20 | -0.8 | 1.0 | 0 | 5.9 | 5.0 | 67 | 2.5 | 0.8 | 50 | 1.5 | 0.6 | 50 | 0.1 | 1.0 | 0 |
| hsa-miR-1290 | 4.9 | 100 | 4.0 | 1.2 | 100 | 4.9 | 0.8 | 20 | 4.2 | 1.0 | 100 | 4.7 | 1.1 | 100 | 5.5 | 1.0 | 100 | 5.9 | 1.6 | 100 | 4.7 | 1.4 | 100 |
| hsa-miR-1291 | 0.6 | 0 | 0.8 | 1.1 | 20 | 1.1 | 1.4 | 20 | 1.7 | 0.7 | 20 | 1.3 | 1.3 | 0 | 3.0 | 0.7 | 100 | 1.6 | 0.7 | 25 | 1.7 | 0.5 | 0 |
| hsa-miR-1295 | 2.0 | 100 | 1.9 | 0.7 | 60 | 3.0 | 0.8 | 60 | 1.6 | 0.9 | 40 | 2.4 | 0.2 | 33 | 2.6 | 0.1 | 50 | 2.4 | 0.2 | 50 | 6.3 | 1.1 | 80 |
| hsa-miR-1296 | -0.8 | 0 | 0.7 | 1.7 | 20 | -0.3 | 0.5 | 40 | 0.2 | 0.3 | 0 | -0.1 | 0.3 | 0 | -0.3 | 0.4 | 0 | -0.5 | 0.6 | 0 | -0.6 | 0.9 | 40 |
| hsa-miR-1299 | 1.7 | 0 | 2.3 | 1.3 | 20 | 2.7 | 0.5 | 20 | 3.2 | 1.2 | 75 | 3.3 | 1.6 | 67 | 4.4 | 0.4 | 100 | 3.4 | 1.6 | 50 | 2.4 | 0.9 | 40 |
| hsa-miR-1300 | 5.5 | 100 | 3.7 | 1.1 | 80 | 4.3 | 0.8 | 100 | 4.6 | 1.2 | 100 | 4.6 | 1.1 | 100 | 7.8 | 0.8 | 100 | 5.7 | 1.4 | 100 | 3.5 | 0.8 | 100 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-1301 | −0.9 | 0 | 0.8 | 0.4 | 0 | 0.8 | 0.8 | 20 | 0.5 | 0.8 | 0 | 3.5 | 0.6 | 100 | 1.6 | 0.3 | 0 | 1.0 | 0.4 | 0 | 0.7 | 0.4 | 0 |
| hsa-miR-1303 | −1.1 | 0 | 0.3 | 1.5 | 0 | −0.3 | 0.6 | 0 | −0.3 | 1.0 | 0 | 0.3 | 0.5 | 0 | 1.7 | 0.6 | 25 | 0.2 | 0.6 | 0 | −0.7 | 0.3 | 0 |
| hsa-miR-1305 | 7.7 | 100 | 7.2 | 0.7 | 100 | 7.5 | 0.3 | 100 | 7.4 | 0.4 | 100 | 7.0 | 0.3 | 100 | 7.1 | 0.5 | 100 | 7.2 | 0.2 | 100 | 8.3 | 0.5 | 100 |
| hsa-miR-1306 | 1.5 | 0 | 1.2 | 0.8 | 0 | 1.7 | 0.6 | 0 | 1.7 | 0.1 | 0 | 1.4 | 0.7 | 0 | 3.0 | 0.3 | 75 | 1.7 | 0.4 | 0 | 0.9 | 0.5 | 0 |
| hsa-miR-1307 | 1.6 | 0 | 1.8 | 1.1 | 40 | 2.1 | 0.5 | 80 | 1.8 | 0.5 | 0 | 2.6 | 0.6 | 100 | 3.4 | 0.4 | 100 | 2.5 | 0.4 | 100 | 1.7 | 0.6 | 40 |
| hsa-miR-1308 | 9.7 | 100 | 8.4 | 1.7 | 100 | 8.0 | 0.6 | 100 | 8.3 | 1.0 | 100 | 9.4 | 1.2 | 100 | 10.0 | 0.9 | 100 | 9.0 | 0.7 | 100 | 7.4 | 0.8 | 100 |
| hsa-miR-130a | 10.2 | 100 | 10.3 | 0.9 | 100 | 10.4 | 1.2 | 100 | 11.3 | 0.2 | 100 | 9.8 | 1.4 | 100 | 11.5 | 0.4 | 100 | 11.6 | 0.3 | 100 | 11.5 | 0.5 | 100 |
| hsa-miR-130b | 7.8 | 100 | 6.6 | 1.1 | 100 | 7.3 | 0.4 | 100 | 6.6 | 0.5 | 100 | 7.4 | 0.6 | 100 | 7.1 | 0.4 | 100 | 7.6 | 0.4 | 100 | 6.5 | 0.2 | 100 |
| hsa-miR-130b* | −0.1 | 0 | 1.0 | 1.1 | 0 | 0.6 | 1.1 | 20 | −0.2 | 0.5 | 0 | 0.3 | 0.5 | 0 | 0.2 | 0.6 | 0 | 0.7 | 0.3 | 50 | −0.1 | 0.9 | 0 |
| hsa-miR-132 | 7.2 | 100 | 5.7 | 0.8 | 100 | 6.1 | 0.4 | 100 | 6.3 | 0.2 | 100 | 9.0 | 1.2 | 100 | 6.3 | 0.6 | 100 | 6.0 | 0.1 | 100 | 6.6 | 0.6 | 100 |
| hsa-miR-132* | 3.5 | 100 | 3.1 | 0.5 | 80 | 3.5 | 0.4 | 100 | 3.3 | 0.4 | 100 | 5.6 | 1.1 | 100 | 2.7 | 0.8 | 75 | 3.3 | 0.5 | 100 | 3.4 | 1.0 | 100 |
| hsa-miR-1321 | 1.3 | 0 | 0.5 | 0.6 | 0 | 1.2 | 0.5 | 0 | 1.3 | 0.7 | 0 | 1.6 | 1.2 | 33 | 3.7 | 0.8 | 100 | 2.1 | 1.0 | 50 | 0.2 | 0.4 | 80 |
| hsa-miR-1323 | 1.6 | 0 | 2.0 | 0.3 | 0 | 1.9 | 0.6 | 0 | 1.7 | 0.5 | 0 | 1.8 | 0.7 | 0 | 2.7 | 0.3 | 50 | 1.8 | 0.4 | 25 | 1.2 | 0.4 | 0 |
| hsa-miR-133a | 2.7 | 0 | 3.5 | 0.6 | 100 | 3.3 | 0.7 | 80 | 5.0 | 1.5 | 100 | 2.8 | 0.6 | 67 | 6.1 | 3.0 | 100 | 6.4 | 3.4 | 100 | 3.3 | 1.1 | 100 |
| hsa-miR-133b | 3.7 | 100 | 6.2 | 1.1 | 100 | 5.8 | 1.3 | 100 | 8.2 | 1.7 | 100 | 5.2 | 1.3 | 100 | 9.4 | 3.0 | 100 | 9.6 | 3.4 | 100 | 5.7 | 1.6 | 100 |
| hsa-miR-134 | 5.8 | 100 | 5.1 | 0.9 | 100 | 5.8 | 0.9 | 100 | 5.8 | 0.9 | 100 | 5.8 | 1.1 | 100 | 8.0 | 0.9 | 100 | 6.1 | 0.5 | 100 | 4.6 | 0.6 | 100 |
| hsa-miR-135a | 1.2 | 0 | 8.0 | 1.2 | 100 | 9.0 | 0.3 | 100 | 8.3 | 1.4 | 100 | 7.8 | 0.7 | 100 | 8.1 | 1.0 | 100 | 8.8 | 0.5 | 100 | 8.5 | 0.8 | 100 |
| hsa-miR-135a* | 4.7 | 100 | 3.7 | 0.5 | 100 | 4.7 | 0.9 | 100 | 4.8 | 0.5 | 100 | 4.2 | 1.3 | 100 | 5.6 | 0.8 | 100 | 5.1 | 0.4 | 100 | 3.6 | 0.3 | 100 |
| hsa-miR-135b | 2.2 | 0 | 9.6 | 1.2 | 40 | 10.0 | 1.7 | 60 | 10.3 | 0.9 | 50 | 9.7 | 0.7 | 100 | 9.0 | 0.4 | 100 | 10.0 | 0.4 | 100 | 10.7 | 0.7 | 60 |
| hsa-miR-136 | 3.3 | 100 | 2.3 | 0.5 | 0 | 2.8 | 1.0 | 0 | 2.5 | 0.4 | 0 | 6.6 | 0.5 | 100 | 2.8 | 0.7 | 100 | 3.6 | 0.5 | 100 | 2.7 | 0.7 | 100 |
| hsa-miR-136* | 1.8 | 0 | 0.9 | 1.1 | 0 | 1.9 | 1.2 | 40 | 1.4 | 0.4 | 0 | 6.4 | 0.5 | 100 | 2.2 | 0.8 | 75 | 3.1 | 0.5 | 100 | 1.7 | 1.2 | 40 |
| hsa-miR-137 | 0.9 | 0 | −0.1 | 0.6 | 0 | 0.4 | 0.8 | 0 | 0.5 | 1.4 | 0 | 5.0 | 3.1 | 100 | 0.5 | 0.6 | 25 | 1.0 | 0.8 | 0 | 1.7 | 0.9 | 20 |
| hsa-miR-138 | 0.1 | 0 | 5.4 | 1.3 | 100 | 4.8 | 1.2 | 80 | 4.9 | 0.8 | 100 | 3.4 | 2.2 | 67 | 6.6 | 0.6 | 100 | 6.6 | 0.5 | 100 | 4.6 | 1.1 | 100 |
| hsa-miR-138-1* | −1.9 | 0 | −1.0 | 0.8 | 0 | −1.3 | 1.2 | 0 | −1.5 | 0.6 | 0 | −0.5 | 0.7 | 0 | 1.3 | 1.2 | 0 | −0.1 | 1.2 | 25 | −1.5 | 0.6 | 0 |
| hsa-miR-138-2* | 1.0 | 0 | 2.2 | 0.7 | 40 | 2.5 | 0.6 | 80 | 1.3 | 1.1 | 25 | 2.1 | 0.4 | 67 | 2.4 | 0.5 | 100 | 2.4 | 0.3 | 25 | 2.6 | 0.9 | 80 |
| hsa-miR-139-3p | 4.0 | 100 | 4.4 | 0.4 | 100 | 4.1 | 0.7 | 100 | 4.9 | 0.3 | 100 | 4.6 | 0.5 | 100 | 5.0 | 0.4 | 100 | 5.0 | 0.3 | 100 | 4.9 | 0.4 | 100 |
| hsa-miR-139-5p | 2.8 | 100 | 6.3 | 0.7 | 100 | 5.3 | 1.1 | 100 | 5.6 | 0.4 | 100 | 5.2 | 0.9 | 100 | 6.9 | 0.3 | 100 | 6.8 | 0.3 | 100 | 5.5 | 0.5 | 100 |
| hsa-miR-140-3p | 8.6 | 100 | 8.4 | 0.5 | 100 | 8.2 | 0.6 | 100 | 8.4 | 0.4 | 100 | 8.4 | 0.1 | 100 | 8.4 | 0.2 | 100 | 8.7 | 0.1 | 100 | 8.1 | 0.2 | 100 |
| hsa-miR-140-5p | 9.0 | 100 | 8.6 | 0.6 | 100 | 8.3 | 0.5 | 100 | 8.5 | 0.5 | 100 | 8.6 | 0.3 | 100 | 8.1 | 0.3 | 100 | 8.6 | 0.1 | 100 | 8.5 | 0.2 | 100 |
| hsa-miR-141 | 2.5 | 100 | 11.1 | 0.8 | 100 | 11.9 | 1.0 | 100 | 11.4 | 0.7 | 100 | 11.7 | 0.5 | 100 | 10.7 | 0.6 | 100 | 11.2 | 0.4 | 100 | 11.7 | 0.3 | 100 |
| hsa-miR-141* | −1.7 | 0 | 3.4 | 0.9 | 80 | 4.2 | 0.5 | 100 | 3.6 | 0.5 | 25 | 3.9 | 0.4 | 67 | 2.7 | 0.6 | 0 | 3.6 | 0.4 | 100 | 4.1 | 0.4 | 20 |
| hsa-miR-142-3p | 10.1 | 100 | 8.3 | 1.9 | 100 | 9.7 | 1.3 | 100 | 9.3 | 1.2 | 100 | 7.8 | 1.1 | 100 | 7.2 | 1.1 | 100 | 8.9 | 1.1 | 100 | 10.0 | 1.4 | 100 |
| hsa-miR-142-5p | 6.6 | 100 | 4.8 | 1.7 | 100 | 5.9 | 1.6 | 100 | 6.1 | 1.3 | 100 | 4.2 | 1.2 | 100 | 4.2 | 1.0 | 100 | 5.7 | 1.1 | 100 | 6.3 | 1.3 | 100 |
| hsa-miR-143 | 5.3 | 100 | 8.1 | 0.6 | 100 | 7.8 | 0.6 | 100 | 7.6 | 0.8 | 75 | 8.1 | 0.5 | 100 | 8.3 | 0.4 | 100 | 8.8 | 0.3 | 100 | 7.3 | 0.3 | 100 |
| hsa-miR-143* | 1.4 | 0 | 4.1 | 0.4 | 100 | 3.6 | 0.6 | 80 | 3.3 | 0.4 | 100 | 4.0 | 0.6 | 100 | 4.0 | 0.5 | 100 | 4.1 | 0.4 | 100 | 3.3 | 0.4 | 100 |
| hsa-miR-144 | 4.4 | 100 | 6.2 | 2.5 | 100 | 7.1 | 1.0 | 100 | 6.9 | 0.5 | 100 | 6.2 | 0.8 | 100 | 7.2 | 1.3 | 100 | 8.2 | 0.3 | 100 | 5.5 | 1.2 | 100 |
| hsa-miR-144* | 3.0 | 100 | 4.4 | 2.2 | 60 | 5.3 | 1.1 | 100 | 5.2 | 0.5 | 100 | 5.1 | 1.4 | 100 | 5.7 | 1.0 | 100 | 6.6 | 0.3 | 100 | 4.1 | 0.9 | 100 |
| hsa-miR-145 | 6.8 | 100 | 10.6 | 0.5 | 100 | 9.8 | 0.9 | 100 | 9.8 | 0.8 | 100 | 10.2 | 0.5 | 100 | 10.7 | 0.2 | 100 | 11.1 | 0.1 | 100 | 9.4 | 0.3 | 100 |
| hsa-miR-145* | 2.4 | 100 | 5.6 | 0.6 | 100 | 5.1 | 0.8 | 100 | 4.8 | 1.1 | 100 | 5.5 | 0.5 | 100 | 5.4 | 0.4 | 100 | 6.2 | 0.4 | 100 | 4.6 | 0.4 | 100 |
| hsa-miR-1469 | −0.8 | 0 | 0.7 | 1.6 | 20 | 1.6 | 0.8 | 20 | 1.3 | 0.8 | 25 | 1.4 | 2.1 | 67 | 3.4 | 0.4 | 100 | 2.2 | 0.7 | 75 | 0.3 | 1.3 | 20 |
| hsa-miR-146a | 8.7 | 100 | 7.7 | 0.8 | 100 | 8.1 | 0.7 | 100 | 8.6 | 0.8 | 100 | 7.4 | 0.3 | 100 | 7.0 | 0.2 | 100 | 7.9 | 0.8 | 100 | 8.7 | 1.4 | 100 |
| hsa-miR-146b-3p | −2.1 | 0 | −0.5 | 1.4 | 0 | −1.1 | 0.6 | 0 | 2.5 | 1.3 | 75 | −1.1 | 0.2 | 0 | −1.1 | 0.4 | 0 | −0.9 | 0.2 | 0 | 3.7 | 1.1 | 100 |
| hsa-miR-146b-5p | 9.0 | 100 | 8.5 | 2.0 | 100 | 7.9 | 1.6 | 100 | 13.2 | 1.1 | 100 | 7.2 | 1.2 | 100 | 7.6 | 0.8 | 100 | 7.5 | 0.5 | 100 | 14.4 | 0.9 | 100 |
| hsa-miR-1471 | 3.2 | 100 | 2.6 | 1.3 | 40 | 3.3 | 1.0 | 60 | 3.8 | 0.9 | 100 | 3.6 | 1.7 | 67 | 5.5 | 0.4 | 100 | 4.5 | 0.3 | 100 | 2.3 | 0.3 | 20 |
| hsa-miR-148a | 10.4 | 100 | 10.6 | 1.4 | 100 | 11.8 | 0.7 | 100 | 10.0 | 0.3 | 100 | 10.7 | 1.4 | 100 | 10.2 | 0.5 | 100 | 11.3 | 0.3 | 100 | 10.1 | 0.4 | 100 |
| hsa-miR-148a* | −0.6 | 0 | 1.8 | 1.2 | 40 | 2.3 | 1.2 | 100 | 0.5 | 0.3 | 25 | 0.9 | 0.8 | 67 | 0.4 | 0.6 | 25 | 1.8 | 0.4 | 100 | 0.2 | 0.9 | 20 |
| hsa-miR-148b | 6.7 | 100 | 8.2 | 1.3 | 100 | 8.8 | 0.9 | 100 | 7.9 | 0.9 | 100 | 9.6 | 0.6 | 100 | 8.3 | 0.6 | 100 | 9.0 | 0.4 | 100 | 7.8 | 0.7 | 100 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-148b* | 1.1 | 0 | 1.3 | 0.4 | 20 | 1.3 | 0.6 | 40 | 1.2 | 0.7 | 50 | 1.6 | 0.2 | 33 | 1.1 | 0.5 | 0 | 1.4 | 0.1 | 75 | 1.2 | 0.5 | 40 |
| hsa-miR-149 | 5.3 | 100 | 4.3 | 1.0 | 100 | 4.7 | 0.8 | 100 | 4.0 | 0.2 | 100 | 4.8 | 0.9 | 100 | 3.8 | 0.4 | 100 | 4.0 | 0.2 | 100 | 3.9 | 0.7 | 100 |
| hsa-miR-149* | 1.7 | 0 | 0.8 | 1.6 | 20 | 1.5 | 1.1 | 20 | 1.6 | 1.1 | 25 | 1.9 | 1.7 | 67 | 4.7 | 0.6 | 100 | 2.8 | 0.6 | 100 | 0.3 | 0.6 | 0 |
| hsa-miR-150 | 9.6 | 100 | 8.9 | 1.7 | 100 | 8.9 | 2.4 | 100 | 9.9 | 1.5 | 100 | 7.7 | 1.9 | 100 | 8.7 | 0.3 | 100 | 9.6 | 1.4 | 100 | 10.3 | 1.2 | 100 |
| hsa-miR-150* | 5.1 | 100 | 4.1 | 0.6 | 100 | 5.0 | 1.0 | 100 | 5.0 | 0.8 | 100 | 4.9 | 1.6 | 100 | 7.5 | 0.7 | 100 | 5.6 | 0.6 | 100 | 3.9 | 0.6 | 100 |
| hsa-miR-151-3p | 6.5 | 100 | 7.1 | 0.6 | 100 | 7.1 | 0.6 | 100 | 7.7 | 0.5 | 100 | 7.7 | 0.3 | 100 | 7.5 | 0.3 | 100 | 7.6 | 0.2 | 100 | 7.7 | 0.3 | 100 |
| hsa-miR-151-5p | 9.2 | 100 | 10.0 | 0.6 | 100 | 10.2 | 0.8 | 100 | 10.9 | 0.6 | 100 | 11.0 | 0.2 | 100 | 10.5 | 0.3 | 100 | 11.1 | 0.2 | 100 | 10.9 | 0.3 | 100 |
| hsa-miR-152 | 6.7 | 100 | 7.2 | 1.1 | 100 | 7.6 | 0.8 | 100 | 6.4 | 0.2 | 100 | 6.6 | 0.5 | 100 | 7.8 | 0.5 | 100 | 7.9 | 0.2 | 100 | 6.2 | 0.5 | 100 |
| hsa-miR-153 | 3.9 | 100 | 0.6 | 1.6 | 40 | 0.8 | 1.5 | 20 | 1.5 | 0.9 | 25 | 8.1 | 1.1 | 100 | 1.4 | 0.8 | 25 | 2.3 | 0.3 | 100 | 1.6 | 0.5 | 20 |
| hsa-miR-1539 | 2.8 | 0 | 2.4 | 0.7 | 40 | 2.1 | 0.4 | 0 | 2.2 | 0.3 | 0 | 1.8 | 0.2 | 0 | 2.9 | 0.5 | 50 | 1.9 | 0.3 | 0 | 2.1 | 0.1 | 0 |
| hsa-miR-154 | 3.4 | 100 | 2.3 | 0.9 | 100 | 2.5 | 1.0 | 40 | 2.5 | 0.4 | 50 | 6.9 | 0.2 | 100 | 2.7 | 1.6 | 75 | 3.9 | 0.4 | 100 | 2.3 | 1.4 | 80 |
| hsa-miR-154* | 2.4 | 0 | 1.2 | 0.7 | 20 | 1.3 | 1.6 | 20 | 1.5 | 0.4 | 0 | 4.8 | 0.6 | 100 | 1.0 | 0.8 | 0 | 2.5 | 0.9 | 25 | 1.6 | 1.0 | 20 |
| hsa-miR-155 | 10.2 | 100 | 6.8 | 1.5 | 100 | 7.2 | 1.5 | 100 | 7.5 | 0.7 | 100 | 6.3 | 1.2 | 100 | 5.9 | 0.2 | 100 | 6.6 | 1.2 | 100 | 8.1 | 0.9 | 100 |
| hsa-miR-155* | 1.9 | 0 | 0.7 | 0.3 | 0 | 0.4 | 1.0 | 20 | 0.5 | 0.3 | 0 | 0.3 | 0.2 | 0 | -0.1 | 0.1 | 0 | 0.2 | 0.5 | 0 | 0.6 | 0.6 | 20 |
| hsa-miR-15a | 11.1 | 100 | 10.9 | 0.6 | 100 | 11.7 | 0.4 | 100 | 11.7 | 0.4 | 100 | 11.6 | 0.6 | 100 | 10.5 | 0.5 | 100 | 10.9 | 0.2 | 100 | 12.0 | 0.3 | 100 |
| hsa-miR-15a* | 1.4 | 0 | 1.8 | 0.6 | 60 | 1.9 | 0.5 | 80 | 2.1 | 0.5 | 75 | 1.9 | 0.7 | 67 | 0.9 | 0.3 | 0 | 1.2 | 0.1 | 50 | 2.2 | 0.4 | 100 |
| hsa-miR-15b | 11.2 | 100 | 11.1 | 0.8 | 100 | 11.7 | 0.2 | 100 | 11.7 | 0.5 | 100 | 11.6 | 0.2 | 100 | 11.4 | 0.3 | 100 | 12.0 | 0.3 | 100 | 12.0 | 0.4 | 100 |
| hsa-miR-15b* | 1.5 | 0 | 1.4 | 0.5 | 20 | 1.7 | 1.0 | 60 | 1.1 | 0.4 | 0 | 1.2 | 0.3 | 0 | 1.2 | 0.2 | 0 | 1.5 | 0.2 | 50 | 1.7 | 0.3 | 60 |
| hsa-miR-16 | 12.6 | 100 | 12.6 | 0.6 | 100 | 13.1 | 0.2 | 100 | 13.3 | 0.4 | 100 | 13.2 | 0.5 | 100 | 12.7 | 0.2 | 100 | 13.1 | 0.3 | 100 | 13.5 | 0.2 | 100 |
| hsa-miR-16-2* | 2.5 | 100 | 2.8 | 0.5 | 80 | 3.1 | 0.4 | 100 | 2.9 | 0.4 | 100 | 2.8 | 0.3 | 100 | 2.8 | 0.4 | 100 | 3.5 | 0.1 | 100 | 3.0 | 0.6 | 100 |
| hsa-miR-17 | 8.4 | 100 | 8.6 | 0.6 | 100 | 9.5 | 0.4 | 100 | 9.3 | 0.2 | 100 | 8.6 | 0.7 | 100 | 9.3 | 0.2 | 100 | 9.4 | 0.2 | 100 | 9.5 | 0.1 | 100 |
| hsa-miR-17* | 3.6 | 100 | 4.5 | 0.7 | 100 | 5.6 | 0.4 | 100 | 5.0 | 0.4 | 100 | 4.9 | 0.3 | 100 | 5.1 | 0.5 | 100 | 5.4 | 0.4 | 100 | 5.4 | 0.3 | 100 |
| hsa-miR-181a | 8.8 | 100 | 10.6 | 1.6 | 100 | 10.5 | 0.7 | 100 | 11.2 | 0.8 | 100 | 10.7 | 0.9 | 100 | 10.1 | 0.5 | 100 | 10.1 | 0.5 | 100 | 11.3 | 0.3 | 100 |
| hsa-miR-181a* | 3.2 | 100 | 4.4 | 1.3 | 100 | 4.8 | 0.5 | 100 | 4.2 | 0.7 | 100 | 4.7 | 0.8 | 100 | 3.3 | 0.4 | 100 | 3.5 | 0.5 | 100 | 4.4 | 0.2 | 100 |
| hsa-miR-181a-2* | 3.0 | 100 | 4.8 | 1.8 | 100 | 4.3 | 0.7 | 100 | 5.9 | 1.3 | 100 | 3.3 | 0.7 | 67 | 3.9 | 0.5 | 100 | 4.5 | 0.6 | 100 | 6.2 | 0.7 | 100 |
| hsa-miR-181b | 7.0 | 100 | 8.5 | 1.5 | 100 | 8.3 | 0.9 | 100 | 9.5 | 0.8 | 100 | 8.3 | 0.8 | 100 | 8.2 | 0.4 | 100 | 8.1 | 0.6 | 100 | 9.6 | 0.5 | 100 |
| hsa-miR-181c | 6.3 | 100 | 6.6 | 0.6 | 100 | 6.4 | 0.7 | 100 | 7.5 | 0.4 | 100 | 8.4 | 0.7 | 100 | 7.1 | 0.4 | 100 | 7.1 | 0.4 | 100 | 7.6 | 0.3 | 100 |
| hsa-miR-181c* | 3.8 | 100 | 3.9 | 0.6 | 100 | 3.4 | 0.4 | 100 | 4.5 | 0.5 | 100 | 5.3 | 0.2 | 100 | 4.0 | 0.4 | 100 | 3.9 | 0.5 | 100 | 4.6 | 0.4 | 100 |
| hsa-miR-181d | 5.3 | 100 | 5.7 | 0.6 | 100 | 5.4 | 0.7 | 100 | 6.6 | 0.6 | 100 | 6.9 | 0.1 | 100 | 5.9 | 0.4 | 100 | 5.8 | 0.3 | 100 | 6.7 | 0.3 | 100 |
| hsa-miR-182 | 1.3 | 0 | 3.8 | 1.1 | 100 | 4.5 | 1.4 | 100 | 3.0 | 1.6 | 75 | 5.9 | 0.3 | 100 | 1.8 | 0.8 | 75 | 2.3 | 0.6 | 100 | 2.6 | 1.1 | 100 |
| hsa-miR-182* | 0.4 | 0 | 1.1 | 0.5 | 20 | 1.1 | 0.7 | 20 | 0.6 | 1.0 | 25 | 2.0 | 0.5 | 100 | -0.3 | 0.5 | 0 | 0.0 | 0.2 | 0 | -0.4 | 0.9 | 0 |
| hsa-miR-1825 | 4.2 | 100 | 3.5 | 0.4 | 80 | 3.6 | 0.1 | 100 | 3.7 | 0.5 | 100 | 3.4 | 0.2 | 100 | 3.4 | 0.3 | 100 | 3.2 | 0.2 | 100 | 3.4 | 0.3 | 80 |
| hsa-miR-1826 | 4.4 | 100 | 5.4 | 1.0 | 100 | 5.7 | 0.4 | 100 | 5.5 | 0.7 | 100 | 5.5 | 0.2 | 100 | 6.3 | 0.4 | 100 | 5.9 | 0.3 | 100 | 5.3 | 0.7 | 100 |
| hsa-miR-1827 | 1.6 | 0 | 1.3 | 1.0 | 0 | 1.8 | 0.3 | 20 | 2.1 | 0.6 | 25 | 1.3 | 0.6 | 0 | 1.7 | 0.7 | 25 | 2.2 | 0.7 | 75 | 1.9 | 0.8 | 60 |
| hsa-miR-183 | 6.0 | 100 | 7.6 | 1.2 | 100 | 7.7 | 1.2 | 100 | 6.8 | 1.4 | 100 | 10.5 | 0.6 | 100 | 6.1 | 0.5 | 100 | 6.1 | 0.4 | 100 | 6.3 | 0.2 | 100 |
| hsa-miR-183* | -0.5 | 0 | 1.6 | 1.1 | 20 | 2.1 | 1.2 | 80 | 1.4 | 1.2 | 50 | 4.4 | 0.4 | 100 | 1.4 | 0.7 | 25 | 0.4 | 0.4 | 0 | 0.0 | 1.0 | 20 |
| hsa-miR-184 | 2.0 | 0 | 0.8 | 0.6 | 0 | 1.7 | 0.4 | 20 | 2.1 | 0.8 | 25 | 2.1 | 0.7 | 0 | 2.8 | 0.4 | 75 | 1.7 | 0.3 | 0 | 1.3 | 0.5 | 0 |
| hsa-miR-185 | 7.8 | 100 | 8.1 | 1.0 | 100 | 8.3 | 0.4 | 100 | 8.2 | 0.3 | 100 | 8.1 | 0.3 | 100 | 8.4 | 0.4 | 100 | 8.7 | 0.3 | 100 | 8.2 | 0.3 | 100 |
| hsa-miR-186 | 5.6 | 100 | 6.1 | 0.9 | 100 | 6.4 | 0.4 | 100 | 6.3 | 0.5 | 100 | 6.5 | 0.3 | 100 | 6.9 | 0.5 | 100 | 7.2 | 0.3 | 100 | 6.3 | 0.4 | 100 |
| hsa-miR-187* | 2.6 | 0 | 0.8 | 1.4 | 0 | 1.6 | 1.1 | 20 | 1.8 | 0.7 | 0 | 2.0 | 0.4 | 0 | 4.7 | 0.7 | 100 | 2.8 | 0.4 | 100 | 0.8 | 0.9 | 0 |
| hsa-miR-188-3p | 0.6 | 0 | 0.2 | 1.2 | 20 | 0.3 | 1.1 | 0 | -0.2 | 0.4 | 0 | 0.4 | 0.4 | 0 | -0.3 | 0.5 | 0 | 0.4 | 0.2 | 0 | 0.4 | 0.6 | 0 |
| hsa-miR-188-5p | 5.7 | 100 | 4.7 | 0.3 | 100 | 5.4 | 0.9 | 100 | 5.5 | 0.8 | 100 | 5.6 | 0.9 | 100 | 7.5 | 0.6 | 100 | 5.8 | 0.4 | 100 | 4.7 | 0.4 | 100 |
| hsa-miR-18a | 4.6 | 100 | 4.3 | 1.0 | 80 | 5.2 | 0.4 | 100 | 4.8 | 0.5 | 100 | 4.6 | 0.5 | 100 | 4.5 | 0.4 | 100 | 4.9 | 0.3 | 100 | 4.9 | 0.4 | 100 |
| hsa-miR-18b | 3.6 | 100 | 3.1 | 1.0 | 80 | 3.8 | 0.4 | 100 | 3.4 | 0.4 | 100 | 3.2 | 0.5 | 100 | 3.3 | 0.5 | 100 | 3.7 | 0.2 | 100 | 3.5 | 0.4 | 100 |
| hsa-miR-18b* | 2.4 | 100 | 2.1 | 0.5 | 0 | 1.9 | 0.4 | 0 | 2.1 | 0.2 | 0 | 1.5 | 0.3 | 0 | 1.9 | 0.4 | 0 | 1.7 | 0.3 | 25 | 1.9 | 0.3 | 0 |
| hsa-miR-190 | 2.0 | 0 | 1.5 | 1.2 | 20 | 2.4 | 0.5 | 20 | 1.7 | 0.2 | 0 | 1.5 | 0.3 | 0 | 1.8 | 0.3 | 0 | 2.2 | 0.3 | 75 | 1.6 | 0.3 | 0 |
| hsa-miR-1909* | -0.1 | 0 | 0.0 | 2.4 | 20 | -0.6 | 1.2 | 0 | -0.2 | 0.4 | 0 | 0.0 | 1.6 | 0 | 2.6 | 0.8 | 75 | 0.6 | 0.3 | 0 | -1.2 | 0.4 | 0 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-191 | 0.9 | 0 | 0.7 | 1.7 | 40 | 1.3 | 0.7 | 0 | 1.2 | 0.6 | 25 | 1.3 | 0.2 | 33 | 0.7 | 0.7 | 0 | 1.5 | 0.4 | 50 | 1.7 | 0.4 | 60 |
| hsa-miR-191* | 4.6 | 100 | 3.5 | 0.9 | 80 | 4.0 | 0.2 | 100 | 3.9 | 0.4 | 100 | 3.5 | 0.3 | 100 | 3.9 | 0.4 | 100 | 3.4 | 0.3 | 100 | 3.9 | 0.3 | 100 |
| hsa-miR-1910 | -1.5 | 0 | -0.2 | 2.1 | 20 | -1.7 | 0.2 | 0 | -1.0 | 0.7 | 0 | -1.4 | 0.4 | 0 | -0.7 | 0.6 | 0 | -0.9 | 0.5 | 0 | -1.9 | 0.2 | 0 |
| hsa-miR-1914 | -1.9 | 0 | -0.3 | 2.0 | 20 | -1.7 | 0.6 | 0 | -1.2 | 0.7 | 0 | -1.2 | 0.4 | 0 | -1.6 | 0.3 | 0 | -1.4 | 0.7 | 0 | -1.5 | 0.7 | 0 |
| hsa-miR-1914* | 8.0 | 100 | 7.2 | 0.7 | 100 | 7.5 | 0.3 | 100 | 7.7 | 0.3 | 100 | 7.3 | 0.4 | 100 | 7.8 | 0.4 | 100 | 7.4 | 0.1 | 100 | 8.2 | 0.7 | 100 |
| hsa-miR-1915 | 7.9 | 100 | 7.4 | 0.6 | 100 | 8.1 | 0.6 | 100 | 8.0 | 0.5 | 100 | 7.9 | 0.3 | 100 | 10.1 | 0.5 | 25 | 8.4 | 0.5 | 100 | 7.1 | 0.7 | 100 |
| hsa-miR-1915* | -0.4 | 0 | -0.8 | 1.1 | 0 | -0.1 | 0.9 | 0 | -0.9 | 0.8 | 0 | -0.2 | 1.4 | 0 | 2.3 | 0.5 | 100 | 0.7 | 0.4 | 0 | -1.4 | 0.8 | 0 |
| hsa-miR-192 | 6.8 | 100 | 7.0 | 1.2 | 100 | 7.5 | 1.0 | 100 | 7.3 | 0.1 | 100 | 7.7 | 1.7 | 100 | 7.4 | 0.4 | 100 | 7.9 | 0.2 | 100 | 7.6 | 0.3 | 100 |
| hsa-miR-192* | 0.6 | 0 | 1.4 | 1.2 | 20 | 1.7 | 0.9 | 40 | 1.8 | 0.3 | 0 | 2.0 | 1.4 | 33 | 1.7 | 0.2 | 0 | 2.2 | 0.3 | 100 | 1.9 | 0.3 | 20 |
| hsa-miR-193a-3p | 7.9 | 100 | 7.3 | 1.0 | 100 | 7.1 | 0.5 | 100 | 7.3 | 0.7 | 100 | 6.5 | 1.1 | 100 | 7.3 | 0.3 | 100 | 7.9 | 0.2 | 100 | 7.4 | 0.4 | 100 |
| hsa-miR-193a-5p | 5.4 | 100 | 5.7 | 0.8 | 100 | 4.9 | 0.5 | 100 | 5.4 | 1.0 | 100 | 4.8 | 1.4 | 100 | 6.1 | 0.5 | 100 | 6.0 | 0.2 | 100 | 5.1 | 0.4 | 100 |
| hsa-miR-193b | 7.3 | 100 | 6.5 | 1.0 | 100 | 7.1 | 1.5 | 100 | 6.8 | 0.6 | 100 | 8.0 | 0.5 | 100 | 7.6 | 1.0 | 100 | 8.3 | 0.8 | 100 | 7.0 | 0.8 | 100 |
| hsa-miR-193b* | 2.8 | 100 | 3.2 | 1.1 | 60 | 3.5 | 0.4 | 60 | 3.4 | 0.5 | 50 | 3.7 | 0.7 | 100 | 4.7 | 0.6 | 100 | 4.4 | 0.2 | 100 | 3.1 | 0.3 | 100 |
| hsa-miR-194 | 5.2 | 100 | 5.7 | 1.2 | 100 | 6.3 | 0.9 | 100 | 6.0 | 0.4 | 100 | 6.5 | 1.8 | 100 | 6.3 | 0.4 | 100 | 6.7 | 0.2 | 100 | 6.3 | 0.3 | 100 |
| hsa-miR-194* | -0.5 | 0 | 0.4 | 1.2 | 0 | 0.0 | 0.6 | 20 | 0.3 | 0.1 | 0 | 0.2 | 1.2 | 33 | 1.5 | 0.6 | 75 | 0.5 | 0.2 | 0 | -0.2 | 0.5 | 0 |
| hsa-miR-195 | 11.1 | 100 | 11.0 | 0.8 | 100 | 11.4 | 1.1 | 100 | 10.6 | 0.6 | 100 | 10.7 | 0.7 | 100 | 11.2 | 0.3 | 100 | 11.6 | 0.3 | 100 | 10.6 | 0.4 | 100 |
| hsa-miR-195* | 1.3 | 0 | 1.6 | 1.4 | 60 | 1.1 | 0.9 | 100 | 1.3 | 0.5 | 100 | 1.3 | 0.2 | 33 | 2.0 | 0.3 | 100 | 1.7 | 0.3 | 100 | 0.2 | 0.9 | 0 |
| hsa-miR-196a | 3.6 | 100 | 3.4 | 1.4 | 80 | 1.8 | 0.3 | 0 | 3.3 | 1.8 | 50 | 2.7 | 1.5 | 33 | 1.8 | 0.4 | 75 | 2.2 | 1.6 | 25 | 2.0 | 0.8 | 40 |
| hsa-miR-196b | 1.5 | 0 | 2.6 | 0.4 | 20 | 2.6 | 1.5 | 20 | 2.5 | 0.4 | 25 | 2.0 | 0.2 | 0 | 1.9 | 0.6 | 0 | 1.9 | 0.7 | 25 | 2.1 | 0.2 | 40 |
| hsa-miR-197 | 6.1 | 100 | 5.8 | 0.4 | 100 | 5.7 | 0.3 | 100 | 5.7 | 0.1 | 100 | 5.8 | 0.6 | 100 | 5.8 | 0.6 | 100 | 5.7 | 0.2 | 100 | 5.6 | 0.2 | 100 |
| hsa-miR-198 | 2.8 | 100 | 1.0 | 0.7 | 100 | 1.6 | 1.4 | 100 | 2.4 | 1.3 | 50 | 2.2 | 2.1 | 67 | 4.9 | 0.2 | 100 | 3.0 | 0.8 | 100 | 0.8 | 0.8 | 100 |
| hsa-miR-199a-3p | 11.3 | 100 | 10.0 | 0.8 | 100 | 10.4 | 1.3 | 100 | 10.8 | 0.4 | 100 | 11.2 | 1.2 | 100 | 11.6 | 0.6 | 100 | 12.0 | 0.2 | 100 | 11.0 | 0.7 | 100 |
| hsa-miR-199a-5p | 8.8 | 100 | 8.5 | 0.8 | 100 | 9.0 | 1.3 | 100 | 9.3 | 0.3 | 100 | 9.7 | 1.2 | 100 | 9.9 | 0.6 | 100 | 10.4 | 0.3 | 100 | 9.3 | 0.8 | 100 |
| hsa-miR-199b-5p | 8.0 | 100 | 5.9 | 1.7 | 100 | 7.2 | 1.9 | 100 | 7.3 | 0.6 | 100 | 7.9 | 1.9 | 100 | 9.3 | 0.2 | 100 | 9.7 | 0.2 | 100 | 7.8 | 0.8 | 100 |
| hsa-miR-19a | 7.1 | 100 | 7.5 | 0.9 | 100 | 8.6 | 0.4 | 100 | 8.2 | 0.5 | 100 | 7.5 | 0.3 | 100 | 7.9 | 0.5 | 100 | 8.3 | 0.1 | 100 | 8.5 | 0.5 | 100 |
| hsa-miR-19b | 9.9 | 100 | 10.2 | 0.7 | 100 | 11.2 | 0.5 | 100 | 10.9 | 0.5 | 100 | 10.3 | 0.3 | 100 | 10.7 | 0.2 | 100 | 10.8 | 0.2 | 100 | 11.3 | 0.6 | 13 |
| hsa-miR-19b-1* | 1.3 | 100 | 2.2 | 0.6 | 60 | 3.0 | 0.4 | 100 | 2.8 | 0.6 | 75 | 2.1 | 0.3 | 0 | 2.0 | 0.4 | 0 | 2.5 | 0.5 | 100 | 2.9 | 0.3 | 100 |
| hsa-miR-200a | 1.4 | 0 | 5.6 | 3.1 | 100 | 7.1 | 2.0 | 100 | 10.2 | 0.6 | 100 | 11.3 | 0.3 | 100 | 8.9 | 0.3 | 100 | 9.9 | 0.1 | 100 | 10.2 | 0.5 | 100 |
| hsa-miR-200a* | 0.5 | 0 | 2.1 | 1.8 | 40 | 2.2 | 1.3 | 60 | 5.4 | 0.6 | 100 | 5.7 | 0.3 | 100 | 4.3 | 0.3 | 100 | 4.6 | 0.8 | 100 | 5.3 | 0.6 | 100 |
| hsa-miR-200b | 2.9 | 100 | 7.2 | 3.2 | 100 | 8.3 | 1.8 | 100 | 11.8 | 0.7 | 100 | 12.2 | 0.1 | 67 | 10.2 | 0.1 | 100 | 11.1 | 0.2 | 100 | 11.8 | 0.5 | 100 |
| hsa-miR-200b* | 0.5 | 0 | 2.5 | 2.2 | 40 | 2.6 | 1.4 | 60 | 5.8 | 0.5 | 100 | 6.0 | 0.3 | 100 | 4.9 | 0.3 | 100 | 5.2 | 0.3 | 100 | 5.6 | 0.6 | 100 |
| hsa-miR-200c | 3.0 | 100 | 11.4 | 0.7 | 100 | 12.1 | 0.7 | 100 | 11.7 | 0.3 | 100 | 12.2 | 0.3 | 100 | 11.4 | 0.3 | 100 | 11.7 | 0.3 | 100 | 11.9 | 0.2 | 100 |
| hsa-miR-200c* | -0.8 | 0 | 2.4 | 0.9 | 80 | 2.6 | 0.8 | 100 | 2.1 | 0.5 | 100 | 2.6 | 0.3 | 100 | 1.0 | 0.5 | 0 | 1.9 | 0.3 | 75 | 2.1 | 0.3 | 100 |
| hsa-miR-202 | 4.7 | 100 | 4.4 | 0.7 | 100 | 4.9 | 0.8 | 100 | 4.9 | 0.8 | 100 | 5.1 | 0.7 | 100 | 7.1 | 0.6 | 100 | 5.1 | 0.8 | 100 | 4.3 | 0.5 | 100 |
| hsa-miR-203 | 3.9 | 100 | 5.6 | 0.9 | 100 | 6.9 | 1.5 | 100 | 5.4 | 0.8 | 75 | 3.5 | 2.0 | 100 | 6.1 | 0.8 | 100 | 5.9 | 0.6 | 100 | 6.6 | 1.1 | 100 |
| hsa-miR-204 | 8.7 | 100 | 7.4 | 2.7 | 100 | 7.3 | 1.6 | 100 | 5.4 | 2.1 | 100 | 6.0 | 1.3 | 67 | 8.2 | 0.5 | 100 | 8.7 | 0.8 | 100 | 5.3 | 0.8 | 100 |
| hsa-miR-205 | -1.9 | 0 | 4.8 | 3.4 | 80 | 3.2 | 2.2 | 60 | 4.9 | 1.6 | 100 | 3.9 | 0.7 | 100 | 4.5 | 0.4 | 100 | 5.1 | 0.1 | 100 | 11.8 | 0.5 | 80 |
| hsa-miR-206 | -1.4 | 0 | -0.3 | 1.2 | 0 | 0.3 | 0.6 | 60 | 2.4 | 3.0 | 25 | 0.8 | 1.0 | 0 | 5.3 | 3.2 | 100 | 3.9 | 3.7 | 50 | 5.2 | 3.4 | 80 |
| hsa-miR-208a | 0.6 | 0 | -0.3 | 0.9 | 0 | 0.6 | 0.4 | 0 | 0.9 | 1.2 | 25 | 0.8 | 0.7 | 100 | 1.5 | 3.1 | 25 | 1.7 | 2.4 | 25 | -0.1 | 0.4 | 0 |
| hsa-miR-20a | 9.7 | 100 | 9.9 | 0.6 | 100 | 10.9 | 0.7 | 100 | 10.7 | 0.2 | 100 | 9.8 | 0.8 | 100 | 10.5 | 0.2 | 100 | 10.7 | 0.3 | 100 | 11.0 | 0.4 | 100 |
| hsa-miR-20a* | 2.5 | 0 | 3.6 | 0.6 | 100 | 4.7 | 0.4 | 100 | 4.2 | 0.5 | 100 | 4.1 | 0.2 | 100 | 4.3 | 0.5 | 75 | 5.0 | 0.4 | 100 | 4.6 | 0.6 | 100 |
| hsa-miR-20b | 7.4 | 100 | 7.2 | 0.8 | 100 | 8.2 | 0.4 | 100 | 7.7 | 0.4 | 100 | 7.0 | 0.7 | 100 | 7.8 | 0.3 | 100 | 8.2 | 0.3 | 100 | 8.0 | 0.4 | 100 |
| hsa-miR-21 | 16.0 | 100 | 13.9 | 1.0 | 100 | 14.5 | 0.6 | 100 | 14.9 | 0.6 | 100 | 14.8 | 1.0 | 100 | 13.3 | 0.4 | 100 | 13.5 | 0.5 | 100 | 15.8 | 0.5 | 100 |
| hsa-miR-21* | 7.1 | 100 | 5.3 | 0.6 | 100 | 5.9 | 0.7 | 100 | 6.7 | 0.3 | 100 | 5.9 | 0.7 | 100 | 4.4 | 0.2 | 100 | 5.6 | 2.0 | 100 | 6.8 | 0.6 | 100 |
| hsa-miR-210 | 8.7 | 0 | 4.6 | 1.0 | 100 | 5.5 | 1.7 | 100 | 5.3 | 0.4 | 100 | 8.7 | 2.9 | 100 | 6.4 | 0.2 | 100 | 6.3 | 0.4 | 100 | 5.8 | 0.4 | 100 |
| hsa-miR-211 | 1.3 | 0 | 1.6 | 1.2 | 20 | 0.5 | 0.4 | 0 | 1.4 | 0.4 | 0 | 0.3 | 1.0 | 0 | 0.3 | 0.5 | 0 | 0.9 | 0.6 | 0 | 0.4 | 0.7 | 0 |
| hsa-miR-212 | 5.4 | 100 | 4.6 | 0.5 | 100 | 4.8 | 0.5 | 100 | 4.6 | 0.4 | 100 | 5.9 | 0.8 | 100 | 5.0 | 0.5 | 100 | 4.4 | 0.2 | 100 | 4.9 | 0.6 | 100 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-214 | 8.3 | 100 | 7.5 | 0.8 | 100 | 7.8 | 1.3 | 100 | 8.5 | 0.5 | 100 | 8.9 | 1.3 | 100 | 9.4 | 0.4 | 100 | 9.6 | 0.2 | 100 | 8.2 | 0.8 | 100 |
| hsa-miR-214* | 3.2 | 100 | 2.9 | 0.8 | 40 | 3.1 | 1.4 | 80 | 3.3 | 0.3 | 100 | 3.8 | 1.2 | 100 | 4.0 | 0.6 | 100 | 4.5 | 0.2 | 100 | 3.5 | 0.9 | 100 |
| hsa-miR-215 | 4.6 | 100 | 5.1 | 1.3 | 100 | 5.8 | 1.0 | 100 | 5.3 | 0.3 | 100 | 5.9 | 1.6 | 100 | 5.5 | 0.5 | 100 | 6.2 | 0.3 | 100 | 5.7 | 0.5 | 100 |
| hsa-miR-216a | −0.8 | 0 | 0.7 | 1.4 | 20 | 0.5 | 1.3 | 20 | −0.4 | 1.6 | 0 | 1.9 | 0.8 | 67 | 0.4 | 0.1 | 0 | −0.2 | 0.4 | 0 | −0.7 | 1.1 | 0 |
| hsa-miR-216b | −2.1 | 0 | −1.7 | 0.7 | 0 | −1.9 | 0.4 | 0 | −1.0 | 0.9 | 0 | 0.0 | 1.4 | 33 | −1.0 | 0.4 | 0 | −1.6 | 0.2 | 0 | −1.3 | 0.6 | 0 |
| hsa-miR-218 | 5.0 | 100 | 7.2 | 1.0 | 100 | 7.8 | 0.6 | 100 | 7.8 | 0.8 | 100 | 8.3 | 0.4 | 100 | 8.2 | 0.3 | 100 | 8.9 | 0.3 | 100 | 7.9 | 0.7 | 100 |
| hsa-miR-219-5p | 2.1 | 0 | 3.3 | 1.0 | 60 | 3.4 | 0.6 | 60 | 3.4 | 0.6 | 75 | 3.7 | 0.6 | 100 | 3.3 | 0.8 | 75 | 3.8 | 0.3 | 100 | 3.4 | 0.5 | 80 |
| hsa-miR-22 | 12.8 | 100 | 12.4 | 0.7 | 100 | 12.7 | 0.8 | 100 | 12.1 | 0.2 | 100 | 12.4 | 0.4 | 100 | 12.2 | 0.3 | 100 | 12.3 | 0.2 | 100 | 12.1 | 0.1 | 100 |
| hsa-miR-22* | 4.8 | 100 | 5.3 | 1.0 | 100 | 5.8 | 0.8 | 100 | 4.3 | 0.5 | 100 | 4.5 | 0.3 | 100 | 4.9 | 0.8 | 100 | 5.6 | 0.7 | 100 | 4.9 | 0.5 | 100 |
| hsa-miR-221 | 6.9 | 100 | 8.9 | 2.0 | 100 | 9.0 | 2.1 | 100 | 10.2 | 1.0 | 100 | 9.7 | 0.8 | 100 | 6.9 | 0.4 | 100 | 6.8 | 0.3 | 100 | 10.6 | 0.7 | 100 |
| hsa-miR-221* | 4.8 | 100 | 6.6 | 1.9 | 100 | 6.6 | 1.9 | 100 | 8.1 | 0.9 | 100 | 6.9 | 0.3 | 100 | 5.1 | 0.2 | 100 | 5.0 | 0.4 | 100 | 8.7 | 0.9 | 100 |
| hsa-miR-222 | 6.0 | 100 | 7.5 | 1.3 | 100 | 7.6 | 1.7 | 100 | 9.7 | 0.8 | 100 | 8.1 | 0.7 | 100 | 6.6 | 0.8 | 100 | 5.9 | 0.1 | 100 | 10.2 | 0.6 | 100 |
| hsa-miR-222* | −2.1 | 0 | 0.0 | 1.0 | 0 | 0.0 | 0.7 | 0 | 0.9 | 0.4 | 0 | −0.4 | 0.8 | 0 | −0.8 | 0.3 | 0 | −1.1 | 0.3 | 0 | 0.5 | 0.7 | 40 |
| hsa-miR-223 | 11.3 | 100 | 9.3 | 1.0 | 100 | 9.6 | 0.9 | 100 | 10.7 | 1.3 | 100 | 9.2 | 1.2 | 100 | 9.9 | 0.7 | 100 | 10.9 | 0.9 | 100 | 10.3 | 0.7 | 100 |
| hsa-miR-223* | 2.1 | 0 | 0.7 | 0.5 | 0 | 0.9 | 0.6 | 0 | 1.4 | 1.0 | 50 | 0.8 | 0.4 | 0 | 0.8 | 0.3 | 0 | 1.4 | 0.7 | 50 | 1.3 | 0.4 | 20 |
| hsa-miR-23a | 2.5 | 100 | 5.3 | 0.9 | 100 | 4.7 | 0.7 | 100 | 5.2 | 0.8 | 100 | 6.6 | 0.3 | 100 | 5.7 | 0.2 | 100 | 6.0 | 0.1 | 100 | 5.7 | 0.5 | 100 |
| hsa-miR-23a* | 13.4 | 100 | 12.3 | 0.5 | 100 | 12.6 | 0.6 | 100 | 12.5 | 0.4 | 100 | 13.0 | 0.1 | 100 | 12.7 | 0.2 | 100 | 13.1 | 0.2 | 100 | 12.6 | 0.4 | 100 |
| hsa-miR-23b | 3.1 | 100 | 2.7 | 0.5 | 80 | 3.5 | 0.3 | 100 | 3.6 | 0.4 | 100 | 3.2 | 0.7 | 100 | 4.5 | 0.5 | 100 | 3.5 | 0.3 | 100 | 3.5 | 0.6 | 100 |
| hsa-miR-23b* | 12.2 | 100 | 12.1 | 1.0 | 100 | 11.5 | 1.0 | 100 | 12.6 | 0.4 | 100 | 13.4 | 0.3 | 100 | 12.0 | 0.1 | 100 | 12.6 | 0.2 | 100 | 12.3 | 0.5 | 100 |
| hsa-miR-24 | 3.5 | 100 | 3.6 | 0.8 | 100 | 2.9 | 0.8 | 100 | 4.3 | 0.2 | 100 | 4.6 | 0.3 | 100 | 3.4 | 0.2 | 100 | 4.0 | 0.2 | 100 | 4.0 | 0.6 | 100 |
| hsa-miR-24-1* | 12.5 | 100 | 12.2 | 0.4 | 100 | 12.0 | 0.5 | 100 | 12.6 | 0.4 | 100 | 13.0 | 0.2 | 100 | 12.2 | 0.2' | 100 | 12.5 | 0.3 | 100 | 12.6 | 0.3 | 100 |
| hsa-miR-25 | 5.6 | 100 | 5.3 | 0.8 | 100 | 4.8 | 0.8 | 100 | 5.7 | 0.4 | 100 | 6.6 | 0.3 | 100 | 4.9 | 0.1 | 100 | 5.4 | 0.1 | 100 | 5.7 | 0.5 | 100 |
| hsa-miR-26a | 9.4 | 100 | 9.4 | 0.7 | 100 | 9.7 | 0.2 | 100 | 9.9 | 0.2 | 100 | 10.1 | 0.1 | 100 | 9.8 | 0.3 | 100 | 10.0 | 0.3 | 100 | 9.9 | 0.2 | 100 |
| hsa-miR-26a-1* | 10.4 | 100 | 11.7 | 1.0 | 100 | 11.8 | 0.4 | 100 | 12.3 | 0.4 | 100 | 12.2 | 0.4 | 100 | 12.5 | 0.3 | 100 | 12.8 | 0.2 | 100 | 12.2 | 0.3 | 100 |
| hsa-miR-26b | 0.6 | 0 | 1.4 | 0.3 | 100 | 1.3 | 0.2 | 100 | 1.3 | 0.2 | 50 | 1.3 | 0.2 | 0 | 1.1 | 0.2 | 0 | 1.4 | 0.2 | 0 | 1.3 | 0.3 | 0 |
| hsa-miR-26b* | 10.5 | 100 | 11.3 | 0.5 | 100 | 12.6 | 0.6 | 100 | 12.5 | 0.4 | 100 | 13.0 | 0.1 | 100 | 12.0 | 0.4 | 100 | 12.6 | 0.3 | 100 | 12.6 | 0.3 | 100 |
| hsa-miR-27a | 1.0 | 0 | 2.0 | 0.4 | 20 | 1.7 | 0.4 | 40 | 1.3 | 0.6 | 100 | 1.7 | 0.2 | 100 | 1.3 | 0.3 | 100 | 1.7 | 0.1 | 100 | 1.5 | 0.3 | 40 |
| hsa-miR-27a* | 13.0 | 100 | 11.6 | 0.6 | 100 | 12.0 | 0.6 | 100 | 12.0 | 0.5 | 100 | 12.3 | 0.5 | 100 | 11.7 | 0.3 | 100 | 12.2 | 0.2 | 100 | 12.2 | 0.3 | 100 |
| hsa-miR-27b | −1.5 | 0 | −0.8 | 0.7 | 0 | −1.0 | 0.5 | 0 | −1.3 | 0.4 | 25 | −1.3 | 0.3 | 0 | −1.5 | 0.6 | 0 | −0.9 | 0.6 | 0 | 0.0 | 1.6 | 20 |
| hsa-miR-28-3p | 11.7 | 100 | 11.8 | 1.0 | 100 | 11.3 | 0.9 | 100 | 12.3 | 0.5 | 100 | 12.9 | 0.3 | 100 | 11.8 | 0.3 | 100 | 12.3 | 0.4 | 100 | 12.1 | 0.5 | 100 |
| hsa-miR-28-5p | 1.2 | 0 | 0.9 | 0.6 | 0 | 0.7 | 0.2 | 0 | 1.0 | 0.2 | 25 | 1.0 | 0.3 | 33 | 2.1 | 0.2 | 100 | 1.4 | 0.2 | 100 | 0.5 | 0.2 | 20 |
| hsa-miR-296-5p | 7.7 | 100 | 7.2 | 0.5 | 100 | 7.4 | 0.4 | 100 | 7.3 | 0.6 | 100 | 7.9 | 0.4 | 100 | 7.6 | 0.1 | 100 | 8.0 | 0.1 | 100 | 7.4 | 0.9 | 100 |
| hsa-miR-298 | 3.7 | 100 | 3.2 | 0.3 | 100 | 3.4 | 0.4 | 100 | 3.4 | 0.5 | 100 | 3.2 | 0.2 | 100 | 4.5 | 0.4 | 100 | 3.4 | 0.8 | 100 | 3.1 | 0.2 | 100 |
| hsa-miR-299-3p | 1.5 | 0 | −0.6 | 1.2 | 0 | −0.1 | 0.9 | 0 | 0.5 | 0.9 | 50 | 0.6 | 1.1 | 0 | 1.9 | 0.4 | 50 | 0.8 | 0.8 | 0 | −0.8 | 0.7 | 0 |
| hsa-miR-299-5p | 2.0 | 100 | 0.3 | 0.7 | 0 | 1.2 | 0.9 | 40 | 1.0 | 0.7 | 0 | 0.6 | 0.5 | 0 | 1.7 | 0.6 | 0 | 1.6 | 0.3 | 0 | 1.0 | 0.5 | 0 |
| hsa-miR-29a | 3.1 | 100 | 2.1 | 1.0 | 40 | 2.3 | 1.3 | 40 | 2.3 | 0.5 | 25 | 3.1 | 0.5 | 100 | 2.9 | 1.5 | 50 | 3.8 | 0.4 | 100 | 2.4 | 0.9 | 60 |
| hsa-miR-29a* | 13.6 | 100 | 13.3 | 0.6 | 100 | 13.7 | 0.3 | 100 | 14.0 | 0.3 | 100 | 14.0 | 0.1 | 100 | 13.7 | 0.3 | 100 | 14.0 | 0.3 | 100 | 14.3 | 0.4 | 100 |
| hsa-miR-29b | 1.8 | 0 | 2.0 | 0.4 | 40 | 2.2 | 0.2 | 100 | 2.1 | 0.1 | 75 | 2.1 | 0.3 | 100 | 1.7 | 0.8 | 75 | 2.1 | 0.3 | 100 | 2.4 | 0.6 | 80 |
| hsa-miR-29b-1* | 11.6 | 100 | 11.4 | 0.5 | 100 | 12.3 | 0.6 | 100 | 12.2 | 0.6 | 100 | 12.8 | 0.8 | 100 | 11.6 | 0.7 | 100 | 12.1 | 0.3 | 100 | 12.6 | 0.8 | 100 |
| hsa-miR-29b-2* | 5.0 | 100 | 4.8 | 0.5 | 100 | 5.0 | 0.4 | 100 | 5.3 | 0.6 | 100 | 5.4 | 0.5 | 100 | 3.4 | 0.3 | 100 | 5.3 | 0.7 | 100 | 5.5 | 0.4 | 100 |
| hsa-miR-29c | 0.2 | 0 | 0.9 | 1.7 | 60 | 1.6 | 0.7 | 60 | 1.2 | 0.3 | 25 | 2.7 | 0.9 | 100 | 1.7 | 0.5 | 100 | 2.0 | 0.3 | 100 | 1.0 | 0.4 | 40 |
| hsa-miR-29c* | 11.9 | 100 | 12.8 | 0.7 | 100 | 13.1 | 1.0 | 100 | 12.9 | 0.3 | 100 | 13.5 | 0.9 | 100 | 13.0 | 0.3 | 100 | 13.3 | 0.3 | 100 | 13.1 | 0.4 | 100 |
| hsa-miR-300 | 6.2 | 100 | 7.4 | 1.0 | 100 | 7.5 | 1.0 | 100 | 6.9 | 0.3 | 100 | 8.3 | 0.9 | 100 | 7.5 | 0.3 | 100 | 7.9 | 0.3 | 100 | 7.0 | 0.4 | 100 |
| hsa-miR-301a | −1.2 | 0 | −0.4 | 1.0 | 0 | −1.1 | 1.0 | 0 | −0.7 | 0.8 | 0 | −0.3 | 1.3 | 0 | 0.2 | 0.5 | 0 | −0.4 | 0.8 | 25 | −1.1 | 0.3 | 0 |
| hsa-miR-301b | 5.9 | 100 | 5.6 | 1.1 | 100 | 6.3 | 0.6 | 100 | 5.9 | 0.6 | 75 | 7.6 | 0.3 | 100 | 5.6 | 0.5 | 100 | 5.8 | 0.2 | 100 | 6.0 | 0.5 | 100 |
| hsa-miR-302c* | 2.3 | 100 | 1.6 | 1.2 | 60 | 2.5 | 0.9 | 60 | 1.7 | 0.3 | 75 | 3.1 | 0.7 | 100 | 1.7 | 0.3 | 75 | 2.5 | 0.5 | 100 | 1.6 | 0.2 | 60 |
| hsa-miR-302c** | −0.8 | 0 | −0.3 | 0.5 | 0 | −0.3 | 0.9 | 0 | −0.8 | 0.4 | 0 | −0.2 | 1.3 | 0 | 1.6 | 0.7 | 25 | −0.1 | 0.5 | 0 | −0.8 | 0.6 | 0 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-30a | 13.4 | 100 | 11.2 | 0.5 | 100 | 12.3 | 1.1 | 100 | 11.3 | 0.3 | 100 | 9.8 | 1.5 | 100 | 12.0 | 0.4 | 100 | 12.1 | 0.3 | 100 | 11.4 | 0.7 | 100 |
| hsa-miR-30a* | 10.3 | 100 | 8.0 | 0.5 | 100 | 9.0 | 1.1 | 100 | 8.2 | 0.5 | 100 | 6.6 | 1.6 | 100 | 8.6 | 0.3 | 100 | 9.0 | 0.4 | 100 | 8.3 | 0.8 | 100 |
| hsa-miR-30b | 9.7 | 100 | 11.1 | 0.6 | 100 | 11.5 | 0.6 | 100 | 11.7 | 0.7 | 100 | 12.0 | 0.2 | 100 | 11.7 | 0.5 | 100 | 12.2 | 0.3 | 100 | 11.9 | 0.5 | 100 |
| hsa-miR-30b* | 3.1 | 100 | 4.0 | 0.7 | 100 | 4.1 | 0.5 | 100 | 4.4 | 0.3 | 100 | 4.4 | 0.4 | 100 | 4.3 | 0.4 | 100 | 4.5 | 0.1 | 100 | 4.3 | 0.4 | 100 |
| hsa-miR-30c | 11.1 | 100 | 10.7 | 0.8 | 100 | 11.4 | 0.6 | 100 | 10.5 | 0.5 | 100 | 10.2 | 0.6 | 100 | 11.1 | 0.4 | 100 | 11.5 | 0.1 | 100 | 10.4 | 0.6 | 100 |
| hsa-miR-30c-1* | 2.4 | 100 | 3.1 | 0.7 | 100 | 3.2 | 0.5 | 100 | 2.8 | 0.6 | 100 | 2.7 | 0.5 | 100 | 3.2 | 0.3 | 100 | 3.4 | 0.3 | 100 | 2.8 | 0.2 | 100 |
| hsa-miR-30c-2* | 6.7 | 100 | 5.0 | 0.5 | 100 | 5.9 | 0.9 | 100 | 5.3 | 0.6 | 100 | 3.8 | 1.7 | 100 | 6.0 | 0.3 | 100 | 6.1 | 0.3 | 100 | 5.2 | 0.7 | 100 |
| hsa-miR-30d | 8.9 | 100 | 9.9 | 0.5 | 100 | 10.1 | 0.6 | 100 | 10.4 | 0.8 | 100 | 10.6 | 0.2 | 100 | 10.4 | 0.4 | 100 | 10.4 | 0.2 | 100 | 10.2 | 0.4 | 100 |
| hsa-miR-30d* | 1.1 | 0 | 2.7 | 0.5 | 80 | 3.0 | 0.4 | 100 | 3.1 | 0.6 | 75 | 3.1 | 0.3 | 100 | 2.2 | 0.3 | 100 | 2.9 | 0.2 | 100 | 2.9 | 0.5 | 100 |
| hsa-miR-30e | 8.4 | 100 | 9.5 | 0.7 | 100 | 10.0 | 0.5 | 100 | 9.4 | 0.4 | 100 | 8.9 | 0.3 | 100 | 9.6 | 0.2 | 100 | 9.8 | 0.3 | 100 | 9.5 | 0.3 | 100 |
| hsa-miR-30e* | 7.0 | 100 | 7.4 | 0.8 | 100 | 8.0 | 0.5 | 100 | 7.1 | 0.5 | 100 | 6.7 | 0.5 | 100 | 7.2 | 0.3 | 100 | 8.0 | 0.3 | 100 | 7.3 | 0.5 | 100 |
| hsa-miR-31 | 5.6 | 100 | 4.9 | 3.5 | 80 | 6.7 | 1.7 | 100 | 10.1 | 1.1 | 100 | 3.6 | 2.7 | 67 | 6.8 | 1.8 | 100 | 7.7 | 0.6 | 100 | 10.1 | 0.6 | 100 |
| hsa-miR-31* | 5.0 | 100 | 3.7 | 3.4 | 60 | 5.4 | 1.6 | 100 | 8.5 | 1.1 | 100 | 2.4 | 2.2 | 67 | 5.2 | 1.6 | 100 | 6.0 | 0.6 | 100 | 8.6 | 0.6 | 100 |
| hsa-miR-32 | 2.6 | 100 | 3.8 | 1.0 | 80 | 5.1 | 0.5 | 100 | 3.8 | 0.8 | 100 | 3.7 | 0.7 | 100 | 3.6 | 0.9 | 100 | 4.4 | 0.3 | 100 | 4.5 | 0.8 | 100 |
| hsa-miR-320a | 8.2 | 100 | 7.9 | 0.7 | 100 | 8.4 | 0.2 | 100 | 8.4 | 0.0 | 100 | 8.9 | 0.1 | 100 | 9.2 | 0.3 | 100 | 8.6 | 0.1 | 100 | 8.3 | 0.3 | 100 |
| hsa-miR-320b | 9.7 | 100 | 9.0 | 0.7 | 100 | 9.5 | 0.2 | 100 | 9.6 | 0.2 | 100 | 10.1 | 0.3 | 100 | 10.2 | 0.4 | 100 | 9.8 | 0.1 | 100 | 9.4 | 0.3 | 100 |
| hsa-miR-320c | 9.8 | 100 | 9.0 | 0.7 | 100 | 9.5 | 0.1 | 100 | 9.5 | 0.1 | 100 | 10.0 | 0.4 | 100 | 10.2 | 0.2 | 100 | 9.9 | 0.1 | 100 | 9.3 | 0.4 | 100 |
| hsa-miR-320d | 10.4 | 100 | 9.6 | 0.7 | 100 | 10.0 | 0.2 | 100 | 10.1 | 0.1 | 100 | 10.5 | 0.4 | 100 | 10.7 | 0.3 | 100 | 10.4 | 0.0 | 100 | 9.9 | 0.4 | 100 |
| hsa-miR-323-3p | 0.3 | 0 | -0.2 | 1.0 | 0 | -0.2 | 0.7 | 0 | -0.3 | 0.5 | 0 | 6.9 | 0.1 | 100 | 0.4 | 0.8 | 0 | 1.3 | 1.5 | 25 | 0.0 | 0.7 | 0 |
| hsa-miR-324-3p | 8.7 | 100 | 9.1 | 0.7 | 100 | 9.3 | 0.2 | 100 | 9.1 | 0.4 | 100 | 9.1 | 0.5 | 100 | 9.1 | 0.2 | 100 | 9.2 | 0.2 | 100 | 9.3 | 0.3 | 100 |
| hsa-miR-324-5p | 7.2 | 100 | 8.0 | 0.9 | 100 | 8.2 | 0.8 | 100 | 7.9 | 0.3 | 100 | 9.2 | 0.0 | 100 | 7.9 | 0.2 | 100 | 8.0 | 0.2 | 100 | 8.0 | 0.4 | 100 |
| hsa-miR-326 | 2.4 | 100 | 2.3 | 0.5 | 80 | 1.5 | 0.2 | 100 | 1.6 | 0.2 | 25 | 3.6 | 0.4 | 100 | 1.7 | 0.1 | 25 | 1.9 | 0.2 | 100 | 1.7 | 0.3 | 80 |
| hsa-miR-328 | 3.9 | 100 | 4.0 | 0.6 | 100 | 2.9 | 0.9 | 100 | 3.7 | 0.3 | 100 | 3.9 | 0.4 | 100 | 3.6 | 0.3 | 100 | 3.9 | 0.2 | 100 | 3.2 | 0.5 | 100 |
| hsa-miR-329 | 0.6 | 0 | 0.8 | 1.1 | 0 | 0.5 | 0.5 | 0 | 0.3 | 0.3 | 25 | 4.1 | 0.1 | 100 | 0.5 | 0.5 | 0 | 1.5 | 0.4 | 0 | 0.1 | 0.6 | 0 |
| hsa-miR-330-3p | 5.2 | 100 | 3.7 | 0.4 | 100 | 3.8 | 0.4 | 100 | 3.9 | 0.4 | 100 | 6.3 | 0.5 | 100 | 4.4 | 0.2 | 100 | 4.0 | 0.2 | 100 | 4.0 | 0.3 | 100 |
| hsa-miR-331-3p | 10.2 | 100 | 10.0 | 0.7 | 100 | 10.6 | 0.8 | 100 | 10.2 | 0.4 | 100 | 10.8 | 0.1 | 100 | 10.1 | 0.2 | 100 | 10.5 | 0.2 | 100 | 10.3 | 0.4 | 100 |
| hsa-miR-335 | 5.8 | 100 | 5.9 | 1.2 | 100 | 6.6 | 0.7 | 100 | 5.5 | 0.6 | 100 | 9.1 | 1.6 | 100 | 5.8 | 0.7 | 100 | 6.5 | 0.3 | 100 | 5.8 | 0.9 | 80 |
| hsa-miR-335* | 2.6 | 0 | 2.5 | 0.3 | 20 | 2.5 | 0.2 | 60 | 1.9 | 0.4 | 25 | 3.8 | 0.9 | 100 | 2.0 | 0.2 | 100 | 2.0 | 0.3 | 25 | 2.0 | 0.2 | 40 |
| hsa-miR-337-3p | 1.5 | 0 | 1.9 | 0.9 | 0 | 1.5 | 1.5 | 0 | 1.4 | 0.4 | 0 | 3.2 | 0.4 | 100 | 1.6 | 0.6 | 0 | 2.0 | 0.3 | 50 | 1.4 | 0.6 | 0 |
| hsa-miR-337-5p | 3.3 | 100 | 1.5 | 0.8 | 100 | 2.0 | 1.5 | 20 | 2.0 | 0.5 | 0 | 5.3 | 0.3 | 100 | 2.5 | 0.9 | 75 | 3.3 | 0.4 | 100 | 2.2 | 1.3 | 40 |
| hsa-miR-338-3p | 6.0 | 100 | 6.2 | 0.6 | 100 | 6.7 | 0.9 | 100 | 6.5 | 0.4 | 100 | 9.3 | 0.3 | 100 | 6.9 | 0.8 | 100 | 7.4 | 0.5 | 100 | 7.0 | 0.6 | 100 |
| hsa-miR-338-5p | 1.0 | 0 | 1.9 | 0.6 | 80 | 2.3 | 0.3 | 100 | 2.0 | 0.4 | 50 | 2.1 | 0.4 | 100 | 2.5 | 0.8 | 100 | 2.1 | 0.2 | 100 | 2.4 | 0.6 | 80 |
| hsa-miR-339-3p | 3.6 | 100 | 3.4 | 0.8 | 100 | 3.6 | 0.6 | 100 | 3.4 | 0.6 | 100 | 4.0 | 0.2 | 100 | 3.6 | 0.3 | 100 | 3.7 | 0.2 | 100 | 3.5 | 0.5 | 100 |
| hsa-miR-339-5p | 1.5 | 100 | 1.1 | 1.6 | 40 | 1.9 | 1.3 | 40 | 0.8 | 1.1 | 50 | 0.9 | 0.9 | 25 | 1.5 | 0.1 | 25 | 1.7 | 0.2 | 100 | 1.4 | 0.8 | 60 |
| hsa-miR-33a | 3.2 | 100 | 2.3 | 1.2 | 60 | 3.0 | 0.4 | 100 | 3.0 | 0.5 | 75 | 3.2 | 0.7 | 100 | 2.3 | 0.4 | 75 | 2.9 | 0.1 | 100 | 3.1 | 0.6 | 80 |
| hsa-miR-33b | 0.6 | 0 | 0.8 | 0.9 | 20 | 0.8 | 0.6 | 0 | 0.4 | 0.5 | 0 | 0.7 | 0.4 | 0 | 0.0 | 0.2 | 0 | 0.3 | 0.4 | 0 | 0.5 | 0.2 | 0 |
| hsa-miR-33b* | 2.9 | 100 | 2.7 | 0.5 | 100 | 2.7 | 0.4 | 60 | 2.8 | 0.4 | 25 | 2.7 | 0.6 | 100 | 4.3 | 0.3 | 100 | 3.0 | 0.3 | 100 | 2.5 | 0.2 | 60 |
| hsa-miR-340 | 5.5 | 100 | 5.2 | 1.1 | 100 | 5.8 | 0.4 | 100 | 5.2 | 0.5 | 100 | 6.2 | 0.6 | 100 | 4.7 | 0.5 | 100 | 5.3 | 0.3 | 100 | 5.4 | 0.6 | 100 |
| hsa-miR-340* | 4.4 | 100 | 4.2 | 0.9 | 100 | 4.6 | 0.3 | 100 | 3.9 | 0.7 | 100 | 5.2 | 0.5 | 100 | 3.3 | 0.5 | 100 | 4.3 | 0.2 | 100 | 4.2 | 0.4 | 100 |
| hsa-miR-342-3p | 9.7 | 100 | 9.4 | 0.8 | 100 | 9.3 | 0.6 | 100 | 9.4 | 0.6 | 100 | 10.1 | 0.7 | 100 | 9.2 | 0.3 | 100 | 9.4 | 0.4 | 100 | 9.8 | 0.2 | 100 |
| hsa-miR-342-5p | 5.9 | 100 | 5.0 | 0.9 | 100 | 5.0 | 0.9 | 100 | 5.5 | 0.6 | 100 | 5.8 | 0.4 | 100 | 4.9 | 0.2 | 100 | 5.3 | 0.6 | 100 | 5.8 | 0.2 | 100 |
| hsa-miR-345 | 1.6 | 0 | 3.9 | 1.8 | 100 | 4.1 | 1.9 | 80 | 3.1 | 0.7 | 50 | 2.9 | 1.0 | 100 | 4.3 | 0.2 | 100 | 4.5 | 0.6 | 100 | 2.9 | 0.2 | 100 |
| hsa-miR-346 | -1.4 | 0 | 1.4 | 1.6 | 40 | 0.3 | 0.3 | 0 | 1.2 | 0.2 | 100 | 0.1 | 1.2 | 0 | 0.3 | 1.0 | 0 | 1.0 | 0.2 | 0 | 0.5 | 0.6 | 0 |
| hsa-miR-34a | 11.3 | 100 | 11.9 | 0.5 | 100 | 12.0 | 0.6 | 100 | 12.3 | 0.3 | 100 | 10.6 | 0.8 | 100 | 10.9 | 0.2 | 100 | 10.9 | 0.1 | 100 | 12.6 | 0.3 | 100 |
| hsa-miR-34a* | 3.8 | 100 | 4.5 | 0.3 | 100 | 4.6 | 0.4 | 100 | 4.8 | 0.3 | 100 | 3.1 | 0.6 | 100 | 3.7 | 0.3 | 100 | 3.7 | 0.2 | 100 | 5.1 | 0.2 | 100 |
| hsa-miR-34b | 4.6 | 100 | 1.6 | 1.1 | 0 | 1.4 | 0.7 | 20 | 1.5 | 0.8 | 0 | 1.2 | 1.6 | 33 | 2.1 | 1.0 | 25 | 1.9 | 0.5 | 50 | 1.3 | 0.6 | 0 |
| hsa-miR-34b* | 8.4 | 100 | 6.8 | 0.5 | 100 | 7.2 | 0.4 | 100 | 7.3 | 0.4 | 100 | 6.0 | 0.8 | 100 | 6.6 | 0.4 | 100 | 6.5 | 0.1 | 100 | 7.6 | 0.5 | 100 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-34c-3p | 2.0 | 100 | -1.4 | 0.8 | 0 | -0.7 | 0.6 | 0 | -1.1 | 0.5 | 0 | -0.2 | 1.6 | 0 | 1.7 | 0.3 | 75 | -0.3 | 0.7 | 0 | -1.4 | 0.2 | 0 |
| hsa-miR-34c-5p | 7.4 | 100 | 3.1 | 0.6 | 100 | 3.9 | 0.7 | 100 | 3.3 | 1.1 | 100 | 3.4 | 1.6 | 67 | 4.1 | 0.8 | 100 | 3.8 | 0.4 | 100 | 3.4 | 0.8 | 100 |
| hsa-miR-361-3p | 6.3 | 100 | 6.8 | 0.5 | 100 | 6.6 | 0.3 | 100 | 6.8 | 0.5 | 100 | 6.8 | 0.2 | 100 | 6.9 | 0.4 | 100 | 7.4 | 0.1 | 100 | 7.3 | 0.2 | 100 |
| hsa-miR-361-5p | 9.0 | 100 | 8.7 | 0.5 | 100 | 8.5 | 0.4 | 100 | 8.7 | 0.4 | 100 | 9.2 | 0.5 | 100 | 8.7 | 0.2 | 100 | 8.8 | 0.1 | 100 | 8.7 | 0.2 | 100 |
| hsa-miR-362-3p | 6.3 | 100 | 5.6 | 0.9 | 100 | 6.1 | 0.4 | 100 | 5.2 | 0.4 | 100 | 5.9 | 0.6 | 100 | 5.8 | 0.5 | 100 | 6.3 | 0.3 | 100 | 5.8 | 0.6 | 100 |
| hsa-miR-362-5p | 6.6 | 100 | 5.6 | 1.0 | 100 | 6.0 | 0.7 | 100 | 5.3 | 0.3 | 100 | 5.9 | 0.6 | 100 | 5.7 | 0.3 | 100 | 5.8 | 0.2 | 100 | 5.6 | 0.0 | 100 |
| hsa-miR-363 | 7.3 | 100 | 5.9 | 0.9 | 100 | 5.8 | 0.6 | 100 | 5.9 | 0.9 | 100 | 5.5 | 0.9 | 100 | 6.4 | 0.3 | 100 | 6.9 | 0.3 | 100 | 4.7 | 0.9 | 100 |
| hsa-miR-365 | 7.7 | 100 | 8.6 | 1.2 | 100 | 8.8 | 0.5 | 100 | 7.9 | 0.4 | 100 | 9.0 | 0.3 | 100 | 8.7 | 0.6 | 100 | 9.8 | 0.5 | 100 | 8.2 | 0.6 | 100 |
| hsa-miR-369-3p | 0.8 | 0 | 0.7 | 1.1 | 0 | 0.9 | 0.5 | 0 | 0.7 | 0.2 | 0 | 2.9 | 0.7 | 67 | 0.5 | 0.5 | 0 | 0.4 | 0.4 | 0 | 0.9 | 0.4 | 0 |
| hsa-miR-369-5p | 1.3 | 0 | 1.2 | 1.1 | 0 | 1.6 | 0.7 | 20 | 0.9 | 0.5 | 0 | 5.3 | 0.7 | 100 | 1.5 | 0.6 | 25 | 2.1 | 0.3 | 75 | 1.5 | 0.8 | 20 |
| hsa-miR-370 | 1.8 | 0 | 0.4 | 1.7 | 0 | 1.8 | 0.7 | 0 | 2.1 | 1.1 | 25 | 4.8 | 0.4 | 100 | 3.8 | 0.5 | 100 | 2.4 | 0.5 | 100 | 1.1 | 0.8 | 0 |
| hsa-miR-371-5p | 4.6 | 100 | 3.6 | 0.8 | 80 | 4.2 | 0.7 | 100 | 3.8 | 0.8 | 100 | 4.1 | 0.9 | 100 | 6.1 | 0.5 | 100 | 4.5 | 0.5 | 100 | 2.8 | 0.4 | 60 |
| hsa-miR-373* | 2.2 | 100 | 0.9 | 1.7 | 20 | 1.9 | 0.7 | 60 | 1.1 | 0.5 | 0 | 1.3 | 1.6 | 67 | 3.2 | 1.0 | 75 | 1.9 | 0.3 | 100 | 0.2 | 0.7 | 0 |
| hsa-miR-374a | 7.5 | 100 | 8.3 | 0.9 | 100 | 8.7 | 0.5 | 100 | 8.6 | 0.8 | 100 | 8.7 | 0.4 | 100 | 8.4 | 0.6 | 100 | 9.2 | 0.2 | 100 | 9.1 | 0.4 | 100 |
| hsa-miR-374b | 7.0 | 100 | 7.6 | 0.7 | 100 | 7.8 | 0.5 | 100 | 8.1 | 0.8 | 100 | 8.1 | 0.5 | 100 | 8.0 | 0.5 | 100 | 8.5 | 0.2 | 100 | 8.4 | 0.2 | 100 |
| hsa-miR-374b* | 1.0 | 0 | 1.5 | 0.4 | 0 | 1.5 | 0.4 | 20 | 1.0 | 0.8 | 25 | 1.6 | 0.3 | 0 | 1.2 | 0.5 | 0 | 1.8 | 0.2 | 75 | 1.7 | 0.3 | 20 |
| hsa-miR-375 | 1.3 | 0 | 2.1 | 2.6 | 60 | 1.9 | 2.1 | 40 | 6.3 | 1.3 | 100 | 13.9 | 0.4 | 100 | 4.0 | 2.1 | 75 | 4.9 | 1.1 | 100 | 6.7 | 1.2 | 100 |
| hsa-miR-376a | 5.1 | 100 | 3.2 | 1.1 | 60 | 4.2 | 1.5 | 100 | 4.1 | 0.4 | 100 | 8.5 | 0.7 | 100 | 4.8 | 0.9 | 100 | 5.8 | 0.4 | 100 | 4.2 | 1.3 | 100 |
| hsa-miR-376a* | 1.5 | 0 | 0.8 | 0.7 | 0 | 1.5 | 0.5 | 0 | 0.9 | 0.2 | 0 | 4.6 | 0.4 | 100 | 1.2 | 0.3 | 0 | 1.5 | 0.3 | 0 | 1.1 | 0.4 | 0 |
| hsa-miR-376b | 2.4 | 0 | 0.6 | 0.9 | 0 | 0.9 | 1.2 | 20 | 0.6 | 0.2 | 0 | 3.4 | 1.4 | 25 | 0.8 | 0.7 | 0 | 1.5 | 0.4 | 25 | 1.2 | 0.6 | 20 |
| hsa-miR-376c | 5.9 | 100 | 3.9 | 1.1 | 100 | 4.6 | 1.4 | 100 | 4.8 | 0.5 | 100 | 9.2 | 0.8 | 100 | 5.4 | 0.8 | 100 | 6.3 | 0.4 | 100 | 4.9 | 0.6 | 100 |
| hsa-miR-377 | 4.0 | 100 | 2.5 | 1.2 | 40 | 3.5 | 1.4 | 80 | 3.3 | 0.3 | 75 | 7.5 | 0.5 | 100 | 3.5 | 0.8 | 75 | 4.5 | 0.6 | 100 | 3.5 | 1.4 | 80 |
| hsa-miR-377* | 0.9 | 0 | 0.5 | 0.9 | 0 | 0.3 | 0.4 | 0 | 0.0 | 1.0 | 0 | 2.9 | 0.2 | 100 | -0.2 | 0.4 | 0 | 0.2 | 0.4 | 0 | -0.1 | 0.3 | 0 |
| hsa-miR-378 | 5.2 | 100 | 4.5 | 0.8 | 100 | 4.6 | 0.5 | 100 | 5.0 | 0.4 | 100 | 4.8 | 0.7 | 100 | 6.2 | 1.5 | 100 | 6.0 | 1.9 | 100 | 4.8 | 0.2 | 100 |
| hsa-miR-378* | 3.7 | 100 | 2.9 | 0.6 | 60 | 2.5 | 0.2 | 60 | 3.3 | 0.3 | 75 | 3.0 | 0.8 | 100 | 3.9 | 1.7 | 100 | 4.1 | 2.0 | 100 | 2.9 | 0.4 | 80 |
| hsa-miR-379 | 2.8 | 100 | 1.0 | 0.9 | 20 | 1.5 | 1.7 | 40 | 1.7 | 0.9 | 25 | 6.2 | 0.1 | 100 | 2.7 | 0.9 | 75 | 3.1 | 0.5 | 100 | 1.9 | 0.4 | 60 |
| hsa-miR-381 | 4.0 | 100 | 2.5 | 1.2 | 40 | 1.6 | 1.4 | 80 | 2.8 | 0.6 | 75 | 4.9 | 0.3 | 100 | 5.4 | 1.2 | 100 | 4.5 | 0.6 | 100 | 3.5 | 1.4 | 80 |
| hsa-miR-382 | 3.7 | 100 | 2.0 | 1.1 | 20 | 2.4 | 1.6 | 50 | 2.8 | 0.4 | 50 | 7.3 | 0.3 | 100 | 4.1 | 1.2 | 100 | 4.3 | 0.5 | 100 | 2.7 | 0.3 | 60 |
| hsa-miR-409-3p | 2.3 | 0 | 1.2 | 1.2 | 20 | 1.7 | 0.9 | 20 | 1.8 | 0.4 | 50 | 6.5 | 0.2 | 100 | 2.2 | 0.4 | 75 | 2.6 | 0.6 | 100 | 1.5 | 0.2 | 40 |
| hsa-miR-409-5p | 4.2 | 100 | 2.3 | 1.1 | 60 | 2.3 | 1.3 | 20 | 2.8 | 0.6 | 25 | 7.2 | 0.3 | 100 | 2.6 | 1.6 | 75 | 2.3 | 1.6 | 75 | 2.6 | 0.4 | 80 |
| hsa-miR-410 | 1.2 | 0 | 0.6 | 0.5 | 0 | 0.5 | 0.7 | 0 | 0.4 | 0.6 | 0 | 0.3 | 0.1 | 100 | 0.3 | 1.1 | 0 | 0.4 | 0.5 | 0 | 0.4 | 0.6 | 60 |
| hsa-miR-411 | 3.0 | 100 | 1.6 | 0.4 | 20 | 1.8 | 0.7 | 0 | 1.7 | 0.7 | 50 | 4.9 | 0.1 | 100 | 4.1 | 1.2 | 75 | 3.1 | 1.2 | 25 | 1.9 | 1.2 | 0 |
| hsa-miR-421 | 1.3 | 0 | 0.4 | 1.2 | 20 | 1.2 | 0.7 | 0 | 1.0 | 0.9 | 0 | 8.2 | 0.1 | 100 | 2.2 | 1.0 | 50 | 4.3 | 0.5 | 75 | 1.9 | 1.1 | 60 |
| hsa-miR-422a | 2.5 | 100 | 2.4 | 1.2 | 20 | 2.8 | 0.8 | 0 | 2.2 | 0.7 | 25 | 4.8 | 0.2 | 100 | 1.3 | 1.1 | 25 | 2.6 | 0.6 | 25 | 0.9 | 1.1 | 0 |
| hsa-miR-422a | -0.2 | 0 | 1.4 | 1.2 | 40 | 2.0 | 0.4 | 80 | 1.3 | 0.2 | 0 | 3.5 | 0.5 | 100 | 2.3 | 0.5 | 75 | 2.7 | 0.1 | 100 | 2.5 | 1.1 | 60 |
| hsa-miR-423-3p | 2.6 | 100 | 3.4 | 0.3 | 100 | 3.6 | 0.2 | 100 | 2.2 | 0.7 | 50 | 2.0 | 1.4 | 67 | 3.6 | 0.4 | 100 | 2.8 | 0.3 | 100 | 0.8 | 1.1 | 100 |
| hsa-miR-423-5p | 5.6 | 100 | 6.6 | 0.3 | 100 | 6.8 | 0.2 | 100 | 3.5 | 0.4 | 100 | 3.6 | 0.1 | 100 | 3.6 | 0.3 | 100 | 3.5 | 0.1 | 100 | 3.4 | 0.2 | 100 |
| hsa-miR-424 | 7.6 | 100 | 9.1 | 0.7 | 100 | 10.0 | 1.4 | 100 | 6.9 | 0.3 | 100 | 6.9 | 0.2 | 100 | 7.2 | 0.3 | 100 | 7.1 | 0.1 | 100 | 6.8 | 0.2 | 100 |
| hsa-miR-424* | 2.2 | 100 | 2.9 | 1.1 | 60 | 2.9 | 1.4 | 80 | 10.8 | 1.4 | 100 | 8.4 | 1.2 | 100 | 8.8 | 0.4 | 100 | 10.0 | 0.5 | 100 | 10.5 | 0.7 | 100 |
| hsa-miR-425 | 7.7 | 100 | 7.3 | 0.9 | 100 | 7.5 | 0.3 | 100 | 3.8 | 0.9 | 100 | 3.1 | 1.9 | 67 | 5.3 | 0.7 | 100 | 3.8 | 0.3 | 100 | 3.0 | 0.5 | 100 |
| hsa-miR-425* | 4.1 | 100 | 3.2 | 0.6 | 80 | 3.5 | 0.2 | 100 | 7.5 | 0.2 | 100 | 7.8 | 0.1 | 67 | 7.0 | 0.4 | 100 | 7.4 | 0.2 | 100 | 7.7 | 0.5 | 100 |
| hsa-miR-429 | -0.1 | 0 | 4.7 | 3.0 | 60 | 5.9 | 2.2 | 80 | 3.4 | 0.2 | 75 | 3.1 | 0.2 | 100 | 3.3 | 0.3 | 100 | 3.1 | 0.3 | 100 | 3.4 | 0.3 | 100 |
| hsa-miR-431 | 2.3 | 0 | 1.0 | 1.2 | 0 | 1.2 | 0.2 | 0 | 9.2 | 0.8 | 100 | 10.3 | 0.3 | 100 | 7.6 | 0.2 | 100 | 8.6 | 0.1 | 100 | 9.0 | 0.5 | 100 |
| hsa-miR-431* | 2.5 | 100 | 2.1 | 0.5 | 20 | 1.6 | 1.1 | 0 | 1.0 | 0.8 | 0 | 5.0 | 1.1 | 100 | 1.1 | 0.5 | 0 | 1.8 | 1.5 | 25 | 1.0 | 0.6 | 0 |
| hsa-miR-432 | 2.8 | 0 | 1.8 | 0.7 | 40 | 2.1 | 0.6 | 20 | 1.5 | 1.4 | 25 | 2.9 | 0.1 | 100 | 1.9 | 0.7 | 25 | 1.4 | 0.2 | 25 | 1.6 | 0.8 | 20 |
| hsa-miR-433 | -1.5 | 0 | -0.7 | 1.3 | 0 | -1.5 | 0.6 | 0 | -1.2 | 0.6 | 0 | 7.6 | 0.4 | 100 | 3.3 | 0.6 | 75 | 3.0 | 0.7 | 100 | 2.0 | 0.7 | 100 |
| hsa-miR-449a | 4.5 | 100 | 2.3 | 0.6 | 40 | 3.5 | 1.2 | 80 | 4.1 | 0.8 | 100 | 4.1 | 0.6 | 67 | -0.4 | 0.9 | 0 | -0.6 | 0.6 | 0 | -1.2 | 0.8 | 20 |
| hsa-miR-449b | 1.2 | 0 | 0.6 | 0.3 | 0 | 1.1 | 0.9 | 20 | 1.2 | 0.3 | 100 | 3.4 | 0.8 | 100 | 3.4 | 1.3 | 75 | 3.2 | 0.2 | 100 | 3.4 | 0.5 | 100 |

TABLE 3-continued

Normalized array data for miRNA expression in thyroid tissue sample groups.

| miRNA | ATC Avg | ATC SD | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|---|
| hsa-miR-450a | 2.0 | 1.3 | 0 | 4.8 | 1.3 | 100 | 5.5 | 1.6 | 80 | 6.0 | 1.8 | 100 | 3.5 | 0.8 | 100 | 4.1 | 0.7 | 100 | 5.4 | 0.4 | 100 | 5.5 | 0.7 | 100 |
| hsa-miR-450b-5p | 0.9 | 0.4 | 0 | 1.3 | 0.4 | 0 | 1.3 | 0.5 | 0 | 1.6 | 0.8 | 25 | 0.4 | 0.7 | 0 | 0.5 | 0.3 | 0 | 0.8 | 0.5 | 0 | 1.2 | 0.4 | 0 |
| hsa-miR-451 | 12.0 | 2.0 | 100 | 13.4 | 2.0 | 100 | 14.0 | 1.1 | 100 | 14.4 | 0.9 | 100 | 13.9 | 1.4 | 100 | 14.9 | 0.6 | 100 | 15.5 | 0.2 | 100 | 12.9 | 0.8 | 100 |
| hsa-miR-452 | 1.6 | 0.8 | 0 | 4.2 | 0.8 | 100 | 3.9 | 0.8 | 100 | 4.3 | 0.5 | 100 | 5.1 | 2.3 | 100 | 4.6 | 0.4 | 100 | 5.0 | 0.3 | 100 | 4.5 | 0.4 | 100 |
| hsa-miR-454 | 5.5 | 0.9 | 100 | 5.5 | 0.9 | 100 | 6.3 | 0.2 | 100 | 5.8 | 0.6 | 100 | 6.7 | 0.2 | 100 | 6.0 | 0.5 | 100 | 6.5 | 0.3 | 100 | 6.1 | 0.2 | 100 |
| hsa-miR-454* | 1.2 | 0.7 | 0 | 1.8 | 0.7 | 20 | 1.5 | 0.2 | 0 | 1.1 | 0.8 | 0 | 1.4 | 0.5 | 0 | 1.0 | 0.5 | 0 | 1.1 | 0.2 | 0 | 1.2 | 0.3 | 0 |
| hsa-miR-455-3p | 5.7 | 0.9 | 100 | 5.7 | 0.9 | 100 | 6.7 | 1.0 | 100 | 6.1 | 0.8 | 100 | 5.4 | 1.2 | 100 | 6.4 | 0.1 | 100 | 6.9 | 0.1 | 100 | 6.4 | 0.2 | 100 |
| hsa-miR-455-5p | 2.3 | 1.1 | 0 | 3.3 | 1.1 | 80 | 4.0 | 1.0 | 100 | 3.6 | 0.6 | 100 | 2.7 | 1.6 | 67 | 4.2 | 0.2 | 100 | 4.7 | 0.1 | 100 | 3.8 | 0.4 | 100 |
| hsa-miR-483-3p | 2.6 | 1.0 | 0 | 2.0 | 1.0 | 20 | 0.8 | 0.6 | 0 | 1.7 | 0.4 | 0 | 1.3 | 0.8 | 0 | 1.4 | 0.3 | 0 | 1.3 | 0.5 | 0 | 0.4 | 0.3 | 0 |
| hsa-miR-483-5p | 6.2 | 0.8 | 100 | 5.0 | 0.8 | 100 | 5.7 | 1.2 | 100 | 6.2 | 1.2 | 100 | 6.4 | 1.9 | 100 | 8.5 | 0.8 | 100 | 6.9 | 0.2 | 100 | 4.5 | 0.8 | 100 |
| hsa-miR-484 | 5.0 | 0.8 | 100 | 4.7 | 0.8 | 100 | 5.1 | 0.4 | 100 | 4.3 | 0.5 | 100 | 5.4 | 0.6 | 100 | 4.5 | 0.2 | 100 | 4.9 | 0.2 | 100 | 4.6 | 0.3 | 100 |
| hsa-miR-485-3p | 1.1 | 1.9 | 0 | 0.3 | 1.9 | 0 | -0.1 | 0.7 | 0 | 0.1 | 0.9 | 0 | 4.3 | 0.4 | 100 | -0.1 | 0.9 | 0 | 0.9 | 0.9 | 25 | -0.2 | 0.5 | 0 |
| hsa-miR-485-5p | 0.5 | 1.1 | 0 | -0.3 | 1.1 | 0 | -0.6 | 0.4 | 0 | -0.4 | 1.0 | 0 | 4.0 | 0.4 | 100 | 0.0 | 0.9 | 0 | 0.2 | 0.6 | 0 | -0.5 | 0.5 | 0 |
| hsa-miR-486-3p | -1.8 | 1.8 | 0 | -0.1 | 1.8 | 40 | 0.6 | 0.8 | 40 | -0.1 | 1.0 | 0 | 3.4 | 0.4 | 100 | 2.2 | 1.0 | 100 | 2.6 | 1.1 | 100 | 0.1 | 1.0 | 20 |
| hsa-miR-486-5p | 5.4 | 1.9 | 100 | 7.0 | 1.9 | 100 | 7.2 | 1.0 | 100 | 7.8 | 0.9 | 100 | 7.8 | 1.2 | 100 | 8.6 | 0.7 | 100 | 8.8 | 0.5 | 100 | 6.0 | 0.9 | 100 |
| hsa-miR-487a | 1.1 | 1.1 | 0 | -0.5 | 1.1 | 0 | -0.5 | 0.6 | 0 | -0.3 | 0.9 | 0 | 4.8 | 0.3 | 100 | 0.2 | 0.6 | 0 | 0.9 | 0.9 | 25 | -0.8 | 1.0 | 0 |
| hsa-miR-487b | 4.9 | 0.5 | 100 | 4.1 | 0.5 | 100 | 4.7 | 0.6 | 100 | 4.1 | 0.4 | 100 | 9.7 | 0.2 | 100 | 3.6 | 1.2 | 100 | 4.7 | 0.6 | 100 | 4.6 | 0.7 | 100 |
| hsa-miR-488 | 1.3 | 1.8 | 0 | 2.3 | 1.8 | 40 | 2.0 | 2.2 | 40 | 1.2 | 0.2 | 25 | 0.4 | 1.0 | 0 | 0.3 | 0.8 | 75 | 0.2 | 0.4 | 0 | 0.5 | 0.6 | 0 |
| hsa-miR-488* | -0.2 | 1.2 | 0 | 0.6 | 1.2 | 20 | 0.3 | 1.1 | 0 | -0.1 | 1.3 | 0 | -0.9 | 0.4 | 0 | -0.7 | 0.4 | 0 | -0.4 | 0.4 | 0 | -0.7 | 0.3 | 0 |
| hsa-miR-489 | 2.5 | 1.6 | 100 | 2.8 | 1.6 | 60 | 2.9 | 1.2 | 75 | 2.9 | 0.4 | 75 | 2.1 | 0.8 | 33 | 2.4 | 0.5 | 50 | 2.8 | 0.6 | 100 | 3.1 | 0.4 | 100 |
| hsa-miR-490-3p | 0.1 | 0.9 | 0 | -0.7 | 0.9 | 0 | -0.4 | 0.9 | 0 | -0.4 | 0.8 | 0 | 1.5 | 1.6 | 33 | 1.7 | 0.4 | 0 | 0.2 | 0.6 | 0 | -1.1 | 0.7 | 0 |
| hsa-miR-490-5p | 0.7 | 0.9 | 0 | 1.3 | 0.9 | 100 | 0.9 | 0.8 | 0 | 1.4 | 0.7 | 0 | 2.0 | 0.9 | 67 | 3.4 | 0.3 | 100 | 2.3 | 0.8 | 50 | 1.1 | 0.5 | 0 |
| hsa-miR-491-5p | -1.3 | 1.0 | 0 | 1.6 | 1.0 | 60 | 0.9 | 0.6 | 60 | 1.7 | 0.5 | 75 | 1.6 | 0.4 | 100 | 1.7 | 0.4 | 100 | 1.9 | 0.2 | 100 | 1.5 | 0.3 | 100 |
| hsa-miR-493 | -1.0 | 1.1 | 0 | -0.1 | 1.1 | 0 | -0.1 | 1.3 | 0 | -0.2 | 1.3 | 0 | 1.0 | 1.4 | 0 | 2.9 | 0.7 | 100 | -0.4 | 0.7 | 0 | -0.7 | 0.8 | 0 |
| hsa-miR-493* | 3.2 | 0.7 | 100 | 1.7 | 0.7 | 20 | 2.2 | 0.4 | 40 | 2.0 | 0.4 | 25 | 5.4 | 0.4 | 100 | 1.7 | 1.3 | 50 | 3.0 | 0.5 | 0 | 2.2 | 0.9 | 40 |
| hsa-miR-494 | 8.7 | 0.8 | 100 | 7.5 | 0.8 | 100 | 8.1 | 0.6 | 100 | 8.4 | 1.0 | 100 | 7.9 | 0.2 | 100 | 8.6 | 1.1 | 100 | 7.5 | 0.3 | 100 | 7.9 | 0.5 | 100 |
| hsa-miR-495 | 3.1 | 0.9 | 100 | 1.9 | 0.9 | 20 | 2.4 | 1.2 | 40 | 2.5 | 0.5 | 25 | 6.9 | 0.3 | 67 | 2.6 | 1.0 | 75 | 3.6 | 0.8 | 100 | 2.5 | 1.0 | 60 |
| hsa-miR-497 | 9.2 | 1.0 | 100 | 9.4 | 1.0 | 100 | 9.6 | 1.1 | 100 | 8.8 | 0.3 | 100 | 8.9 | 0.7 | 100 | 9.6 | 0.1 | 100 | 9.8 | 0.3 | 100 | 8.7 | 0.7 | 100 |
| hsa-miR-498 | 2.0 | 1.1 | 100 | 1.3 | 1.1 | 60 | 1.4 | 0.6 | 0 | 1.7 | 0.6 | 0 | 1.9 | 0.8 | 33 | 3.8 | 0.5 | 100 | 2.3 | 1.6 | 25 | 1.0 | 0.5 | 0 |
| hsa-miR-499-5p | 2.1 | 0.9 | 0 | 3.6 | 0.9 | 100 | 4.3 | 1.1 | 80 | 3.8 | 0.6 | 75 | 4.5 | 0.6 | 100 | 5.3 | 1.8 | 100 | 5.8 | 0.2 | 100 | 3.7 | 0.6 | 100 |
| hsa-miR-500 | 5.0 | 0.7 | 100 | 4.6 | 0.7 | 100 | 5.0 | 0.4 | 100 | 4.6 | 0.3 | 100 | 5.2 | 0.5 | 100 | 4.9 | 0.0 | 100 | 4.8 | 0.3 | 100 | 5.3 | 0.5 | 100 |
| hsa-miR-500* | 5.9 | 0.8 | 100 | 4.9 | 0.8 | 100 | 4.9 | 0.4 | 100 | 4.4 | 0.2 | 100 | 3.8 | 0.5 | 100 | 5.4 | 0.2 | 100 | 5.3 | 0.7 | 100 | 4.5 | 0.6 | 100 |
| hsa-miR-501-3p | 4.5 | 0.8 | 100 | 3.4 | 0.8 | 100 | 3.5 | 0.4 | 100 | 3.0 | 0.2 | 100 | 4.6 | 0.4 | 100 | 4.6 | 0.2 | 100 | 3.9 | 0.3 | 100 | 2.8 | 0.3 | 100 |
| hsa-miR-501-5p | 4.6 | 0.5 | 100 | 4.3 | 0.5 | 100 | 4.4 | 0.1 | 100 | 4.1 | 0.1 | 100 | 4.6 | 0.3 | 100 | 4.6 | 0.1 | 100 | 4.5 | 0.1 | 100 | 4.7 | 0.7 | 100 |
| hsa-miR-502-3p | 6.2 | 0.8 | 100 | 5.4 | 0.8 | 100 | 5.3 | 0.5 | 100 | 4.9 | 0.5 | 100 | 5.5 | 0.6 | 100 | 5.9 | 0.2 | 100 | 5.8 | 0.2 | 100 | 4.9 | 0.2 | 100 |
| hsa-miR-502-5p | 4.6 | 0.6 | 100 | 3.9 | 0.6 | 100 | 3.9 | 0.6 | 100 | 3.3 | 0.3 | 100 | 4.0 | 0.5 | 67 | 4.0 | 0.2 | 100 | 4.1 | 0.2 | 100 | 3.7 | 0.7 | 100 |
| hsa-miR-503 | 4.0 | 0.7 | 100 | 4.6 | 0.7 | 100 | 4.9 | 1.0 | 100 | 6.1 | 0.3 | 100 | 3.5 | 1.6 | 67 | 3.7 | 0.7 | 100 | 4.5 | 0.2 | 100 | 5.7 | 0.5 | 100 |
| hsa-miR-505 | 5.5 | 0.7 | 100 | 5.1 | 0.7 | 100 | 4.9 | 0.3 | 100 | 4.8 | 0.5 | 100 | 6.0 | 0.7 | 100 | 5.1 | 0.2 | 100 | 5.4 | 0.2 | 100 | 4.8 | 0.3 | 100 |
| hsa-miR-505* | 4.7 | 0.8 | 100 | 4.1 | 0.8 | 100 | 3.8 | 0.2 | 100 | 3.9 | 0.4 | 100 | 5.1 | 0.9 | 100 | 4.1 | 0.3 | 100 | 4.2 | 0.3 | 100 | 4.0 | 0.3 | 100 |
| hsa-miR-506 | -0.3 | 1.7 | 0 | 0.5 | 1.7 | 0 | -0.4 | 0.5 | 0 | 0.4 | 1.0 | 0 | -0.5 | 0.7 | 0 | -0.6 | 0.8 | 0 | -0.6 | 0.5 | 0 | 1.0 | 1.5 | 20 |
| hsa-miR-508-5p | -2.2 | 0.6 | 0 | -0.3 | 0.6 | 0 | -1.1 | 0.5 | 0 | -0.9 | 0.2 | 0 | -0.3 | 0.8 | 0 | 0.2 | 1.0 | 25 | -0.4 | 0.6 | 0 | -0.7 | 0.5 | 0 |
| hsa-miR-509-3-5p | 0.0 | 0.9 | 0 | -0.2 | 0.9 | 0 | -0.8 | 0.5 | 0 | 0.5 | 0.6 | 0 | -0.2 | 0.4 | 0 | -0.6 | 0.3 | 0 | 0.0 | 0.4 | 0 | 0.7 | 1.3 | 20 |
| hsa-miR-509-3p | 0.1 | 1.7 | 0 | -0.3 | 1.7 | 0 | -0.5 | 0.6 | 0 | 0.9 | 1.2 | 25 | 0.1 | 1.1 | 0 | 0.0 | 0.5 | 0 | -0.4 | 0.5 | 0 | 1.2 | 1.4 | 20 |
| hsa-miR-509-5p | -0.6 | 1.2 | 0 | 0.6 | 1.2 | 60 | 0.0 | 0.9 | 0 | 1.0 | 0.8 | 100 | 0.1 | 0.7 | 0 | 1.2 | 0.4 | 100 | 0.7 | 0.3 | 100 | 0.7 | 0.9 | 100 |
| hsa-miR-512-3p | 0.4 | 1.7 | 100 | 3.6 | 1.7 | 60 | 3.1 | 1.7 | 60 | 4.3 | 0.5 | 100 | 4.5 | 0.2 | 100 | 5.1 | 0.4 | 100 | 4.8 | 0.5 | 100 | 4.0 | 0.4 | 100 |
| hsa-miR-513a-5p | 3.9 | 0.5 | 100 | 3.4 | 0.5 | 60 | 3.7 | 0.4 | 60 | 4.4 | 0.2 | 100 | 4.1 | 0.2 | 100 | 5.5 | 0.3 | 100 | 4.3 | 0.3 | 100 | 3.9 | 0.7 | 100 |
| hsa-miR-513b | 3.3 | 0.6 | 100 | 2.8 | 0.6 | 60 | 3.2 | 0.2 | 100 | 3.7 | 0.3 | 100 | 3.2 | 0.4 | 100 | 4.1 | 0.7 | 100 | 3.2 | 0.4 | 100 | 3.1 | 0.2 | 100 |

TABLE 3-continued

Normalized array data for miRNA expression in thyroid tissue sample groups.

| miRNA | ATC Avg | ATC % | EA Avg | EA SD | EA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-513c | 2.3 | 100 | 2.2 | 0.5 | 60 | 2.3 | 0.1 | 60 | 3.0 | 0.1 | 75 | 2.5 | 0.3 | 100 | 3.2 | 0.7 | 75 | 2.3 | 0.3 | 75 | 2.7 | 0.6 | 80 |
| hsa-miR-514 | 0.9 | 0 | 1.7 | 1.1 | 20 | 0.5 | 0.2 | 0 | 1.9 | 1.2 | 50 | 1.0 | 1.1 | 33 | 0.7 | 0.5 | 0 | 0.9 | 0.3 | 0 | 2.9 | 0.9 | 80 |
| hsa-miR-516a-5p | 2.2 | 0 | 2.0 | 0.5 | 60 | 2.4 | 0.9 | 80 | 2.8 | 0.6 | 75 | 2.2 | 2.3 | 67 | 3.6 | 1.0 | 75 | 3.4 | 1.1 | 75 | 1.4 | 0.7 | 20 |
| hsa-miR-516b | 0.7 | 0 | -0.1 | 0.8 | 0 | 0.7 | 0.8 | 0 | 0.8 | 0.7 | 0 | 0.8 | 1.4 | 0 | 2.8 | 0.6 | 75 | 1.1 | 0.8 | 0 | 0.0 | 0.3 | 0 |
| hsa-miR-517a | 1.2 | 0 | 0.9 | 1.2 | 0 | 0.0 | 0.8 | 0 | 0.2 | 0.3 | 0 | 1.1 | 1.3 | 33 | 0.0 | 0.6 | 0 | 0.2 | 0.6 | 0 | -0.5 | 0.5 | 0 |
| hsa-miR-517b | 1.3 | 0 | 1.0 | 1.3 | 0 | 0.7 | 0.3 | 0 | 0.1 | 0.6 | 0 | 1.5 | 0.9 | 33 | 0.7 | 0.5 | 0 | 0.9 | 0.4 | 0 | 0.6 | 0.6 | 0 |
| hsa-miR-518a-5p | 0.5 | 0 | 0.2 | 0.5 | 0 | -0.3 | 1.0 | 0 | 0.4 | 0.6 | 0 | 0.2 | 1.2 | 0 | 2.1 | 0.5 | 25 | 0.9 | 0.8 | 0 | -0.5 | 0.4 | 0 |
| hsa-miR-518c* | 0.3 | 0 | -0.1 | 0.8 | 0 | -0.1 | 0.5 | 0 | 0.5 | 0.7 | 0 | 0.2 | 0.8 | 0 | 2.0 | 0.5 | 25 | 0.6 | 0.7 | 0 | -0.5 | 0.6 | 0 |
| hsa-miR-518e* | 0.5 | 0 | -0.3 | 1.2 | 0 | 0.2 | 1.0 | 0 | 0.8 | 1.0 | 0 | 0.4 | 0.7 | 0 | 2.0 | 0.3 | 25 | 1.0 | 0.4 | 0 | 0.7 | 0.4 | 0 |
| hsa-miR-519d | 1.7 | 0 | 1.1 | 1.3 | 0 | 0.3 | 0.6 | 0 | 0.4 | 1.0 | 0 | 0.4 | 0.5 | 0 | 0.8 | 0.2 | 0 | 0.7 | 0.2 | 0 | 0.7 | 0.4 | 0 |
| hsa-miR-519e* | 1.6 | 0 | 1.5 | 0.8 | 40 | 2.1 | 0.7 | 20 | 1.6 | 0.5 | 25 | 1.6 | 0.5 | 0 | 2.4 | 0.4 | 25 | 1.8 | 0.5 | 0 | 1.6 | 0.4 | 0 |
| hsa-miR-520h | 0.6 | 0 | 0.6 | 1.1 | 0 | 0.4 | 0.5 | 0 | 0.3 | 2.5 | 0 | 0.3 | 0.4 | 0 | -0.2 | 0.3 | 0 | 0.1 | 0.5 | 0 | 0.2 | 0.5 | 0 |
| hsa-miR-525-5p | 1.2 | 0 | 0.5 | 0.7 | 0 | 0.5 | 0.6 | 0 | 0.9 | 2.5 | 25 | 0.9 | 0.6 | 0 | 2.2 | 0.5 | 0 | 0.8 | 0.6 | 0 | 0.1 | 0.4 | 0 |
| hsa-miR-526b | 1.2 | 0 | 1.1 | 0.5 | 0 | 1.2 | 1.0 | 0 | 1.3 | 1.1 | 25 | 2.0 | 0.9 | 67 | 3.5 | 0.5 | 100 | 1.9 | 0.4 | 50 | 0.3 | 0.7 | 0 |
| hsa-miR-532-3p | 6.0 | 100 | 5.7 | 0.9 | 100 | 5.9 | 0.6 | 100 | 5.1 | 0.1 | 100 | 6.0 | 0.5 | 100 | 5.9 | 0.2 | 100 | 6.2 | 0.2 | 100 | 5.3 | 0.2 | 100 |
| hsa-miR-532-5p | 7.6 | 100 | 6.7 | 0.8 | 100 | 6.8 | 0.7 | 100 | 6.3 | 0.2 | 100 | 7.2 | 0.5 | 100 | 7.1 | 0.2 | 100 | 7.1 | 0.2 | 100 | 6.5 | 0.2 | 100 |
| hsa-miR-539 | 2.1 | 0 | 1.5 | 0.2 | 0 | 1.2 | 0.4 | 0 | 1.3 | 0.2 | 0 | 6.5 | 0.3 | 100 | 1.7 | 0.3 | 25 | 1.7 | 0.5 | 25 | 1.3 | 0.4 | 0 |
| hsa-miR-542-3p | 3.3 | 100 | 5.4 | 1.5 | 100 | 6.0 | 1.8 | 100 | 7.0 | 1.3 | 100 | 4.2 | 1.1 | 100 | 4.9 | 0.4 | 100 | 5.8 | 0.3 | 100 | 6.4 | 0.8 | 100 |
| hsa-miR-542-5p | 3.9 | 100 | 5.9 | 1.4 | 100 | 6.3 | 1.5 | 100 | 7.3 | 1.1 | 100 | 4.6 | 1.3 | 100 | 5.6 | 0.3 | 100 | 6.3 | 0.3 | 100 | 6.8 | 0.9 | 100 |
| hsa-miR-543 | 2.0 | 0 | 1.1 | 0.5 | 0 | 1.5 | 0.8 | 0 | 0.9 | 0.8 | 0 | 5.3 | 0.1 | 100 | 1.2 | 0.9 | 50 | 2.1 | 0.9 | 50 | 1.3 | 0.6 | 0 |
| hsa-miR-545 | 1.6 | 0 | 1.7 | 0.7 | 40 | 1.8 | 0.3 | 40 | 2.5 | 0.4 | 50 | 2.0 | 0.4 | 67 | 1.5 | 0.3 | 0 | 1.7 | 0.2 | 50 | 1.9 | 0.3 | 40 |
| hsa-miR-548c-5p | 2.4 | 0 | 1.9 | 0.3 | 20 | 2.0 | 0.3 | 20 | 2.2 | 0.0 | 50 | 1.7 | 0.3 | 67 | 1.9 | 0.2 | 0 | 2.3 | 0.2 | 100 | 2.2 | 0.4 | 40 |
| hsa-miR-550 | 2.9 | 100 | 2.0 | 0.6 | 0 | 2.4 | 0.5 | 0 | 2.5 | 0.5 | 50 | 2.3 | 0.5 | 67 | 3.7 | 0.2 | 100 | 2.4 | 0.3 | 100 | 2.0 | 0.3 | 20 |
| hsa-miR-550* | 4.1 | 100 | 3.1 | 0.2 | 80 | 2.9 | 0.7 | 60 | 2.8 | 0.4 | 75 | 3.6 | 0.6 | 100 | 2.8 | 0.2 | 100 | 2.8 | 0.2 | 100 | 3.2 | 0.4 | 80 |
| hsa-miR-551b | 2.6 | 100 | 6.0 | 2.6 | 100 | 4.9 | 0.7 | 100 | 9.0 | 0.8 | 100 | 3.4 | 1.3 | 100 | 5.3 | 0.5 | 100 | 5.2 | 0.5 | 100 | 10.0 | 0.6 | 100 |
| hsa-miR-551b* | -0.3 | 0 | -0.6 | 1.3 | 0 | 0.0 | 0.6 | 0 | -0.8 | 0.8 | 0 | 0.1 | 2.1 | 0 | 2.7 | 0.1 | 100 | 0.9 | 1.0 | 50 | -0.3 | 1.3 | 0 |
| hsa-miR-552 | 0.2 | 0 | 0.0 | 0.3 | 0 | -0.3 | 0.8 | 0 | -0.3 | 0.4 | 0 | 2.1 | 1.8 | 67 | -0.1 | 0.3 | 0 | -0.2 | 0.5 | 0 | 0.0 | 0.2 | 0 |
| hsa-miR-556-3p | 1.6 | 0 | 1.3 | 0.3 | 0 | 0.5 | 0.4 | 0 | 0.9 | 0.4 | 0 | 0.6 | 1.0 | 33 | 0.4 | 0.3 | 0 | 0.6 | 0.5 | 0 | 0.7 | 0.2 | 0 |
| hsa-miR-557 | 4.5 | 100 | 4.7 | 0.3 | 100 | 4.7 | 0.5 | 100 | 4.7 | 0.6 | 100 | 5.6 | 0.4 | 100 | 6.2 | 0.8 | 100 | 5.0 | 0.5 | 100 | 4.0 | 0.6 | 100 |
| hsa-miR-564 | 4.5 | 100 | 5.2 | 0.7 | 100 | 5.3 | 0.5 | 100 | 5.7 | 0.5 | 100 | 5.3 | 0.4 | 100 | 5.9 | 0.3 | 100 | 5.6 | 0.4 | 100 | 5.7 | 0.4 | 100 |
| hsa-miR-566 | 0.9 | 0 | 0.4 | 1.5 | 0 | 0.3 | 1.0 | 0 | 1.1 | 0.7 | 0 | 1.0 | 1.6 | 0 | 3.2 | 0.9 | 75 | 1.3 | 0.5 | 0 | -0.2 | 0.6 | 0 |
| hsa-miR-572 | 4.9 | 100 | 5.0 | 0.6 | 100 | 5.2 | 0.6 | 100 | 5.2 | 0.8 | 100 | 4.9 | 0.9 | 100 | 7.9 | 1.0 | 100 | 5.6 | 0.9 | 100 | 4.1 | 0.5 | 100 |
| hsa-miR-574-3p | 5.7 | 100 | 6.1 | 0.7 | 100 | 6.0 | 0.4 | 100 | 6.2 | 0.1 | 100 | 6.6 | 0.0 | 100 | 6.8 | 0.1 | 100 | 6.8 | 0.1 | 100 | 6.2 | 0.4 | 100 |
| hsa-miR-574-5p | 6.1 | 100 | 5.8 | 0.7 | 100 | 5.8 | 0.6 | 100 | 6.7 | 0.2 | 100 | 6.3 | 0.2 | 100 | 7.5 | 0.6 | 100 | 6.7 | 0.3 | 100 | 6.4 | 0.3 | 100 |
| hsa-miR-575 | 8.3 | 100 | 7.7 | 0.7 | 100 | 8.4 | 0.8 | 100 | 8.3 | 0.4 | 100 | 8.3 | 1.4 | 100 | 10.2 | 0.7 | 100 | 8.5 | 0.6 | 100 | 7.8 | 0.8 | 100 |
| hsa-miR-576-5p | 0.6 | 0 | 1.1 | 0.7 | 20 | 1.5 | 1.1 | 20 | 0.7 | 0.5 | 0 | 0.1 | 0.4 | 0 | 0.8 | 0.3 | 0 | 0.4 | 0.5 | 0 | 1.0 | 0.3 | 0 |
| hsa-miR-582-3p | 4.0 | 100 | -1.0 | 1.1 | 0 | -0.9 | 0.7 | 0 | -0.8 | 0.5 | 0 | 0.2 | 0.3 | 0 | -1.4 | 0.3 | 0 | -1.2 | 0.3 | 0 | -1.4 | 0.4 | 0 |
| hsa-miR-582-5p | 8.4 | 100 | 3.5 | 0.4 | 80 | 4.0 | 1.6 | 80 | 3.5 | 0.8 | 75 | 6.1 | 0.2 | 100 | 3.2 | 0.6 | 100 | 4.3 | 0.4 | 100 | 3.7 | 0.5 | 100 |
| hsa-miR-583 | 1.2 | 0 | 0.5 | 0.8 | 20 | 0.5 | 1.4 | 20 | 0.9 | 1.0 | 0 | 1.3 | 1.1 | 33 | 2.6 | 0.6 | 75 | 1.3 | 0.4 | 0 | -0.6 | 0.5 | 0 |
| hsa-miR-584 | 2.4 | 100 | 2.8 | 0.4 | 60 | 3.5 | 1.3 | 60 | 2.8 | 0.9 | 25 | 3.1 | 0.4 | 100 | 4.4 | 0.5 | 100 | 3.4 | 0.3 | 100 | 2.0 | 0.4 | 40 |
| hsa-miR-585 | 0.4 | 0 | 2.4 | 1.0 | 40 | 2.1 | 1.1 | 40 | 2.1 | 0.4 | 25 | 1.4 | 0.1 | 0 | 2.7 | 0.6 | 75 | 2.2 | 0.6 | 75 | 1.5 | 1.8 | 40 |
| hsa-miR-590-5p | 6.4 | 100 | 6.2 | 0.9 | 100 | 6.9 | 0.4 | 100 | 6.8 | 0.6 | 100 | 6.8 | 0.4 | 100 | 6.0 | 0.3 | 100 | 6.3 | 0.1 | 100 | 6.9 | 0.6 | 100 |
| hsa-miR-592 | 4.7 | 100 | 2.0 | 0.7 | 0 | 2.4 | 1.1 | 40 | 2.4 | 0.9 | 50 | 7.5 | 1.2 | 100 | 1.7 | 0.3 | 0 | 2.5 | 0.3 | 100 | 2.0 | 0.6 | 40 |
| hsa-miR-595 | 0.4 | 0 | 1.6 | 1.1 | 20 | 0.2 | 0.2 | 0 | 1.3 | 0.7 | 0 | 1.1 | 0.6 | 0 | 1.8 | 0.4 | 100 | 1.2 | 0.5 | 0 | 0.5 | 0.3 | 0 |
| hsa-miR-598 | 5.1 | 100 | 5.4 | 1.0 | 100 | 5.7 | 0.8 | 100 | 6.1 | 0.6 | 100 | 8.0 | 0.3 | 100 | 5.6 | 0.5 | 100 | 6.2 | 0.4 | 100 | 5.8 | 0.4 | 100 |
| hsa-miR-601 | 3.2 | 100 | 2.6 | 0.5 | 20 | 3.6 | 0.8 | 100 | 3.5 | 0.9 | 75 | 3.3 | 1.3 | 67 | 5.6 | 0.5 | 100 | 3.9 | 0.5 | 100 | 2.6 | 0.7 | 80 |
| hsa-miR-602 | 2.8 | 0 | 2.4 | 0.5 | 20 | 3.2 | 0.7 | 60 | 2.3 | 0.5 | 25 | 2.2 | 0.9 | 33 | 3.9 | 0.5 | 100 | 2.7 | 0.4 | 100 | 1.9 | 0.4 | 0 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-605 | 3.8 | 100 | 2.0 | 1.2 | 40 | 2.3 | 1.2 | 40 | 1.7 | 1.1 | 25 | 1.5 | 0.6 | 0 | 3.7 | 1.0 | 75 | 2.2 | 0.9 | 50 | 1.1 | 0.6 | 0 |
| hsa-miR-610 | 3.5 | 100 | 1.7 | 0.7 | 20 | 2.3 | 0.9 | 20 | 2.4 | 0.9 | 25 | 2.6 | 1.0 | 67 | 4.5 | 0.6 | 100 | 2.8 | 0.7 | 100 | 1.8 | 0.6 | 0 |
| hsa-miR-612 | -1.8 | 0 | -0.6 | 0.8 | 0 | -0.5 | 0.5 | 0 | -0.8 | 0.4 | 0 | -0.7 | 0.4 | 0 | 0.4 | 0.9 | 50 | -0.7 | 0.4 | 0 | -1.2 | 0.5 | 0 |
| hsa-miR-614 | -0.1 | 0 | 0.1 | 0.9 | 0 | 0.0 | 0.7 | 0 | 0.2 | 0.4 | 0 | 0.7 | 0.8 | 0 | 2.1 | 0.7 | 25 | 0.9 | 0.2 | 0 | -0.1 | 0.8 | 0 |
| hsa-miR-615-3p | -1.0 | 0 | 0.8 | 1.6 | 20 | 0.0 | 0.3 | 0 | 0.1 | 1.0 | 0 | 0.2 | 0.7 | 0 | 0.3 | 0.3 | 0 | 0.0 | 0.2 | 0 | -0.4 | 0.4 | 0 |
| hsa-miR-616 | -1.0 | 0 | -1.1 | 1.0 | 0 | -0.1 | 0.3 | 0 | -0.8 | 1.0 | 0 | 0.0 | 1.1 | 0 | 1.7 | 0.5 | 100 | -0.1 | 0.6 | 0 | -0.4 | 0.4 | 0 |
| hsa-miR-617 | -0.4 | 0 | 0.8 | 0.9 | 0 | -0.2 | 0.8 | 0 | 0.9 | 0.8 | 0 | 1.2 | 0.6 | 0 | 3.3 | 0.3 | 100 | 1.6 | 0.6 | 25 | -1.2 | 0.6 | 0 |
| hsa-miR-622 | 1.3 | 0 | 2.6 | 0.9 | 40 | 1.3 | 0.7 | 0 | 3.0 | 0.8 | 50 | 3.5 | 1.4 | 67 | 5.2 | 0.5 | 100 | 3.9 | 0.7 | 100 | 0.5 | 0.5 | 40 |
| hsa-miR-623 | 4.4 | 100 | 2.1 | 0.9 | 40 | 2.9 | 1.0 | 40 | 2.2 | 1.1 | 25 | 2.3 | 1.6 | 67 | 5.0 | 0.5 | 100 | 3.1 | 0.8 | 100 | 2.4 | 0.7 | 0 |
| hsa-miR-624* | 3.5 | 100 | 2.0 | 0.9 | 40 | 2.1 | 0.7 | 40 | 1.8 | 0.4 | 25 | 1.9 | 0.3 | 100 | 1.6 | 0.6 | 75 | 3.1 | 1.1 | 100 | 1.0 | 1.1 | 0 |
| hsa-miR-625 | 1.3 | 0 | 4.8 | 0.2 | 100 | 2.0 | 0.5 | 60 | 5.7 | 0.3 | 100 | 4.3 | 0.6 | 100 | 5.0 | 0.2 | 100 | 2.3 | 0.2 | 100 | 2.0 | 0.2 | 80 |
| hsa-miR-625* | 6.1 | 100 | 2.2 | 0.8 | 20 | 5.0 | 0.9 | 100 | 2.2 | 0.1 | 25 | 1.9 | 0.5 | 33 | 2.4 | 0.4 | 25 | 5.5 | 0.3 | 100 | 6.2 | 0.3 | 100 |
| hsa-miR-627 | 2.6 | 0 | 2.3 | 0.5 | 60 | 2.1 | 0.3 | 0 | 3.1 | 0.5 | 75 | 2.7 | 0.3 | 100 | 3.0 | 0.3 | 100 | 1.9 | 0.1 | 25 | 2.1 | 0.4 | 40 |
| hsa-miR-628-3p | 2.7 | 100 | 3.1 | 1.1 | 80 | 2.9 | 0.4 | 80 | 3.1 | 0.1 | 75 | 3.6 | 0.3 | 100 | 3.3 | 0.4 | 100 | 3.1 | 0.1 | 100 | 3.1 | 0.4 | 100 |
| hsa-miR-628-5p | 2.3 | 100 | 3.7 | 0.7 | 100 | 3.4 | 0.5 | 100 | 3.6 | 0.6 | 100 | 4.7 | 0.3 | 100 | 3.3 | 0.3 | 100 | 3.7 | 0.2 | 100 | 3.8 | 0.6 | 100 |
| hsa-miR-629 | 3.3 | 100 | 2.0 | 0.6 | 60 | 3.7 | 0.6 | 80 | 3.6 | 0.2 | 100 | 2.7 | 0.5 | 100 | 3.8 | 0.5 | 100 | 4.4 | 0.1 | 100 | 3.8 | 0.4 | 100 |
| hsa-miR-629* | 2.3 | 100 | 2.4 | 0.4 | 100 | 2.3 | 0.8 | 80 | 2.7 | 0.5 | 80 | 2.3 | 0.7 | 100 | 2.4 | 0.9 | 100 | 2.5 | 0.1 | 100 | 2.9 | 0.6 | 100 |
| hsa-miR-630 | 2.4 | 100 | 4.4 | 0.4 | 100 | 3.1 | 0.8 | 100 | 2.3 | 0.5 | 50 | 2.7 | 0.7 | 100 | 2.7 | 0.6 | 100 | 2.3 | 0.4 | 100 | 2.3 | 0.4 | 100 |
| hsa-miR-631 | 5.5 | 100 | 1.2 | 0.9 | 20 | 5.4 | 1.2 | 100 | 5.5 | 1.1 | 100 | 5.3 | 1.2 | 33 | 6.8 | 0.6 | 100 | 6.0 | 0.4 | 100 | 4.0 | 1.1 | 80 |
| hsa-miR-633 | 0.2 | 0 | 0.6 | 1.7 | 20 | 0.8 | 0.9 | 0 | 0.3 | 1.7 | 0 | 1.1 | 2.2 | 0 | 4.0 | 0.9 | 100 | 2.1 | 0.9 | 25 | -0.9 | 0.8 | 0 |
| hsa-miR-634 | 0.3 | 0 | 0.6 | 0.8 | 0 | 0.5 | 0.4 | 0 | 0.4 | 0.3 | 0 | 0.2 | 0.4 | 33 | -0.1 | 0.5 | 0 | 0.2 | 0.5 | 0 | 0.6 | 1.3 | 20 |
| hsa-miR-636 | 2.6 | 100 | 2.8 | 0.6 | 40 | 2.5 | 0.9 | 40 | 2.2 | 0.3 | 50 | 1.7 | 0.1 | 0 | 2.1 | 0.5 | 25 | 1.9 | 0.1 | 25 | 2.3 | 1.3 | 60 |
| hsa-miR-638 | 2.8 | 100 | 2.3 | 0.4 | 0 | 2.3 | 0.3 | 0 | 2.2 | 0.4 | 0 | 1.8 | 0.3 | 0 | 2.3 | 0.3 | 50 | 1.9 | 0.3 | 50 | 2.0 | 0.1 | 0 |
| hsa-miR-639 | 8.4 | 100 | 8.3 | 0.5 | 100 | 8.4 | 0.6 | 100 | 8.5 | 0.7 | 100 | 8.1 | 1.0 | 100 | 11.0 | 1.0 | 100 | 8.9 | 0.6 | 100 | 7.3 | 0.5 | 100 |
| hsa-miR-640 | 0.0 | 0 | -1.1 | 0.7 | 0 | -0.6 | 0.7 | 0 | -1.3 | 0.7 | 0 | -0.2 | 0.6 | 0 | 1.0 | 0.5 | 50 | 0.5 | 1.0 | 25 | -0.5 | 0.7 | 0 |
| hsa-miR-641 | -1.1 | 0 | 0.2 | 1.6 | 20 | -0.5 | 1.0 | 0 | -0.1 | 0.8 | 0 | 0.1 | 0.6 | 0 | 1.5 | 0.5 | 0 | 0.0 | 1.0 | 0 | -1.2 | 0.1 | 0 |
| hsa-miR-642 | -0.1 | 0 | 0.4 | 0.6 | 20 | 0.5 | 0.4 | 0 | 0.6 | 0.2 | 0 | 0.9 | 0.4 | 0 | 0.7 | 0.2 | 100 | 0.8 | 0.5 | 50 | 0.3 | 0.5 | 0 |
| hsa-miR-648 | -1.9 | 0 | -0.6 | 1.3 | 0 | -0.9 | 0.4 | 0 | -1.3 | 0.9 | 0 | 0.7 | 0.9 | 0 | -0.9 | 0.3 | 0 | -0.9 | 0.3 | 0 | -0.7 | 0.6 | 0 |
| hsa-miR-650 | 1.6 | 0 | 0.4 | 1.4 | 0 | 1.1 | 1.2 | 20 | 1.2 | 1.3 | 25 | 1.8 | 1.3 | 33 | 4.1 | 0.5 | 100 | 2.3 | 1.2 | 50 | 0.0 | 0.7 | 0 |
| hsa-miR-652 | 2.2 | 100 | 2.1 | 0.8 | 40 | 2.6 | 0.8 | 80 | 1.6 | 0.7 | 50 | 1.9 | 0.2 | 67 | 2.8 | 0.5 | 75 | 2.6 | 0.6 | 100 | 2.2 | 0.7 | 80 |
| hsa-miR-654-3p | 5.3 | 100 | 5.9 | 1.2 | 100 | 6.2 | 0.8 | 100 | 5.4 | 0.4 | 100 | 7.5 | 0.3 | 100 | 6.4 | 1.0 | 100 | 6.6 | 0.2 | 100 | 5.2 | 1.2 | 100 |
| hsa-miR-654-5p | 3.6 | 100 | 2.3 | 1.1 | 40 | 2.3 | 1.5 | 60 | 2.5 | 0.4 | 75 | 6.3 | 0.5 | 0 | 3.1 | 1.0 | 75 | 4.0 | 0.2 | 100 | 2.7 | 0.3 | 80 |
| hsa-miR-656 | 2.7 | 100 | 2.0 | 1.3 | 60 | 2.4 | 0.8 | 40 | 2.2 | 0.4 | 25 | 4.3 | 0.3 | 67 | 4.1 | 0.4 | 100 | 3.0 | 0.4 | 100 | 2.0 | 0.5 | 60 |
| hsa-miR-658 | 1.6 | 0 | 0.8 | 0.2 | 60 | 0.8 | 0.4 | 0 | 2.1 | 1.1 | 50 | 2.1 | 0.6 | 100 | 0.4 | 0.4 | 100 | 0.5 | 0.8 | 0 | 0.6 | 0.3 | 0 |
| hsa-miR-659 | -0.1 | 0 | -0.1 | 0.9 | 0 | 0.1 | 0.7 | 0 | 0.0 | 0.3 | 0 | 0.2 | 0.9 | 33 | 1.2 | 0.6 | 25 | 0.2 | 0.8 | 0 | -0.7 | 0.3 | 0 |
| hsa-miR-660 | 3.7 | 100 | 2.4 | 0.8 | 40 | 3.0 | 1.2 | 60 | 3.3 | 0.9 | 100 | 3.5 | 1.5 | 67 | 5.5 | 0.7 | 100 | 3.8 | 0.7 | 100 | 1.4 | 0.9 | 0 |
| hsa-miR-662 | 8.2 | 100 | 7.4 | 1.0 | 100 | 7.7 | 0.7 | 100 | 6.8 | 0.5 | 100 | 7.9 | 0.6 | 100 | 7.6 | 0.8 | 100 | 7.8 | 0.2 | 100 | 7.2 | 0.3 | 100 |
| hsa-miR-663 | 1.2 | 0 | 1.5 | 0.7 | 0 | 1.6 | 0.4 | 0 | 1.7 | 0.4 | 0 | 1.9 | 0.8 | 0 | 3.6 | 0.2 | 25 | 2.3 | 0.3 | 25 | 1.0 | 0.2 | 0 |
| hsa-miR-663b | 6.5 | 100 | 4.4 | 1.1 | 100 | 5.6 | 1.2 | 40 | 5.8 | 1.1 | 100 | 5.5 | 1.9 | 100 | 8.6 | 0.8 | 100 | 6.2 | 0.5 | 100 | 4.1 | 0.8 | 100 |
| hsa-miR-664 | 0.4 | 0 | 1.8 | 2.1 | 60 | 1.2 | 0.7 | 0 | 1.8 | 1.8 | 50 | 3.9 | 1.0 | 33 | 4.1 | 1.1 | 50 | 2.0 | 0.8 | 75 | 1.0 | 2.6 | 40 |
| hsa-miR-664* | 5.6 | 100 | 63 | 0.8 | 100 | 6.1 | 0.9 | 100 | 5.8 | 0.5 | 100 | 6.3 | 0.4 | 67 | 5.8 | 0.5 | 100 | 6.2 | 0.2 | 100 | 5.9 | 0.4 | 100 |
| hsa-miR-665 | 5.0 | 100 | 5.1 | 1.0 | 100 | 5.0 | 1.1 | 100 | 5.2 | 0.4 | 100 | 5.6 | 0.2 | 100 | 6.4 | 0.8 | 100 | 5.5 | 0.3 | 100 | 4.8 | 0.4 | 100 |
| hsa-miR-668 | 1.9 | 0 | 3.9 | 1.5 | 80 | 2.8 | 0.9 | 60 | 4.0 | 1.0 | 100 | 3.9 | 0.6 | 100 | 4.5 | 0.2 | 100 | 3.6 | 0.5 | 100 | 3.6 | 0.4 | 100 |
| hsa-miR-671-5p | -2.1 | 0 | 0.5 | 1.7 | 20 | -1.0 | 0.5 | 0 | -0.9 | 0.8 | 0 | 1.3 | 0.4 | 100 | -0.5 | 0.3 | 0 | -0.6 | 0.3 | 0 | -1.4 | 0.8 | 0 |
| hsa-miR-7 | 5.0 | 100 | 4.2 | 0.6 | 100 | 4.9 | 1.0 | 100 | 5.1 | 1.0 | 100 | 5.1 | 1.8 | 100 | 7.2 | 0.6 | 100 | 5.8 | 0.2 | 100 | 3.7 | 0.7 | 100 |
| hsa-miR-7-1* | 9.4 | 100 | 8.7 | 4.3 | 100 | 8.8 | 2.6 | 100 | 7.2 | 2.6 | 100 | 13.9 | 1.0 | 100 | 11.0 | 1.8 | 100 | 11.4 | 0.5 | 100 | 7.3 | 1.7 | 100 |
| hsa-miR-7-2* | 3.8 | 100 | 4.2 | 0.9 | 100 | 4.8 | 0.2 | 100 | 4.6 | 0.7 | 50 | 6.9 | 0.4 | 100 | 4.1 | 0.4 | 100 | 4.9 | 1.0 | 100 | 4.9 | 0.5 | 100 |
| hsa-miR-7* | -1.0 | 0 | 3.6 | 2.4 | 80 | 2.9 | 1.8 | 80 | 1.8 | 1.6 | 50 | 1.6 | 2.0 | 33 | 3.8 | 1.2 | 100 | 4.7 | 0.6 | 100 | 1.1 | 1.3 | 20 |

TABLE 3-continued

Normalized array data for miRNA expression in thyroid tissue sample groups.

| miRNA | ATC Avg | ATC % | FA Avg | FA SD | FA % | FTC Avg | FTC SD | FTC % | FVPTC Avg | FVPTC SD | FVPTC % | MTC Avg | MTC SD | MTC % | NOD Avg | NOD SD | NOD % | NOR Avg | NOR SD | NOR % | PTC Avg | PTC SD | PTC % |
|---|---|---|---|---|---|---|---|---|---|---|---|---|---|---|---|---|---|---|---|---|---|---|---|
| hsa-miR-708 | 0.9 | 0 | 2.1 | 0.9 | 20 | 1.2 | 1.0 | 0 | 1.3 | 1.0 | 0 | 1.1 | 2.0 | 33 | 2.6 | 0.4 | 100 | 2.2 | 0.4 | 75 | 1.5 | 0.4 | 0 |
| hsa-miR-720 | 14.5 | 100 | 12.8 | 0.9 | 100 | 13.2 | 0.6 | 100 | 12.8 | 0.5 | 100 | 12.5 | 0.7 | 100 | 10.2 | 0.8 | 100 | 11.8 | 1.0 | 100 | 12.9 | 0.3 | 100 |
| hsa-miR-744 | 2.8 | 0 | 4.2 | 1.1 | 100 | 4.5 | 0.8 | 100 | 5.1 | 0.3 | 100 | 5.2 | 0.4 | 100 | 4.5 | 0.5 | 100 | 5.1 | 0.1 | 100 | 4.8 | 0.4 | 100 |
| hsa-miR-744* | −1.0 | 0 | 1.7 | 1.1 | 40 | 1.0 | 1.1 | 0 | 0.8 | 1.1 | 0 | 1.1 | 0.2 | 0 | 0.6 | 0.4 | 0 | 0.7 | 0.5 | 0 | 0.7 | 0.6 | 20 |
| hsa-miR-758 | 1.7 | 0 | 0.5 | 1.6 | 0 | 0.9 | 1.6 | 0 | 0.4 | 0.9 | 0 | 5.0 | 0.1 | 100 | 0.3 | 1.1 | 25 | 1.0 | 0.6 | 25 | 0.6 | 0.6 | 0 |
| hsa-miR-760 | 2.9 | 100 | 2.5 | 0.8 | 60 | 3.5 | 0.9 | 80 | 2.8 | 0.3 | 50 | 2.6 | 0.8 | 67 | 4.3 | 0.4 | 100 | 3.1 | 0.4 | 100 | 2.8 | 1.0 | 80 |
| hsa-miR-765 | 4.2 | 100 | 3.0 | 1.0 | 40 | 3.7 | 1.1 | 100 | 4.0 | 1.1 | 100 | 4.5 | 1.7 | 100 | 6.6 | 0.7 | 100 | 4.9 | 0.6 | 100 | 2.3 | 0.7 | 40 |
| hsa-miR-766 | 4.5 | 100 | 4.0 | 0.3 | 100 | 3.8 | 0.6 | 100 | 4.0 | 0.4 | 100 | 4.2 | 0.3 | 100 | 4.4 | 0.3 | 100 | 3.9 | 0.5 | 100 | 3.8 | 0.4 | 100 |
| hsa-miR-767-5p | −1.1 | 0 | −0.1 | 1.2 | 0 | 0.6 | 0.3 | 20 | 0.2 | 1.1 | 0 | 1.1 | 0.6 | 33 | 0.2 | 0.4 | 0 | 0.6 | 0.5 | 50 | 0.6 | 1.1 | 0 |
| hsa-miR-769-3p | 3.1 | 100 | 1.7 | 1.2 | 0 | 1.7 | 0.6 | 20 | 1.8 | 0.4 | 25 | 2.3 | 0.3 | 100 | 3.3 | 0.2 | 100 | 2.0 | 0.2 | 100 | 1.1 | 0.5 | 0 |
| hsa-miR-769-5p | 6.4 | 100 | 4.7 | 0.6 | 100 | 4.9 | 0.3 | 100 | 5.0 | 0.3 | 100 | 5.7 | 0.3 | 100 | 4.6 | 0.2 | 100 | 4.9 | 0.2 | 100 | 5.0 | 0.5 | 100 |
| hsa-miR-770-5p | 3.0 | 100 | 2.9 | 0.5 | 60 | 3.3 | 0.6 | 60 | 2.6 | 0.3 | 50 | 3.2 | 0.2 | 100 | 3.2 | 0.4 | 100 | 2.9 | 0.2 | 100 | 3.0 | 0.6 | 100 |
| hsa-miR-873 | 5.5 | 100 | 2.8 | 1.6 | 60 | 1.6 | 1.4 | 60 | 0.9 | 1.5 | 0 | 3.4 | 3.1 | 67 | 3.3 | 0.8 | 100 | 4.3 | 0.6 | 100 | 0.8 | 0.8 | 20 |
| hsa-miR-874 | 4.8 | 100 | 7.1 | 1.6 | 100 | 7.2 | 1.0 | 100 | 6.3 | 0.6 | 100 | 6.4 | 0.3 | 100 | 7.0 | 0.3 | 100 | 7.0 | 0.2 | 100 | 6.3 | 0.3 | 100 |
| hsa-miR-876-3p | 2.4 | 100 | 1.8 | 2.0 | 60 | 1.3 | 0.5 | 0 | 0.8 | 0.9 | 0 | 2.6 | 2.2 | 67 | 1.7 | 0.5 | 25 | 2.9 | 0.4 | 100 | 0.4 | 0.5 | 0 |
| hsa-miR-876-5p | 1.8 | 0 | 1.2 | 0.4 | 20 | 0.9 | 0.4 | 0 | 1.1 | 0.4 | 0 | 1.1 | 1.0 | 33 | 0.8 | 0.4 | 0 | 1.3 | 0.4 | 25 | 0.8 | 0.7 | 0 |
| hsa-miR-877 | 2.3 | 0 | 1.6 | 1.1 | 20 | 2.7 | 0.7 | 80 | 2.3 | 0.9 | 25 | 3.1 | 1.3 | 100 | 4.5 | 0.6 | 100 | 3.2 | 0.7 | 100 | 1.4 | 1.2 | 20 |
| hsa-miR-877* | 3.1 | 100 | 2.9 | 0.5 | 60 | 3.0 | 0.6 | 100 | 3.0 | 0.3 | 75 | 2.9 | 0.4 | 67 | 4.7 | 0.4 | 100 | 3.2 | 0.7 | 100 | 2.7 | 0.3 | 60 |
| hsa-miR-885-5p | 0.7 | 0 | 2.7 | 2.5 | 60 | 0.9 | 1.4 | 0 | 0.6 | 0.8 | 0 | 1.1 | 0.4 | 0 | 0.9 | 2.4 | 25 | 1.5 | 2.4 | 25 | −0.1 | 0.2 | 0 |
| hsa-miR-886-3p | 7.3 | 100 | 8.7 | 0.7 | 100 | 7.7 | 1.3 | 100 | 9.2 | 0.5 | 100 | 7.5 | 0.5 | 100 | 8.2 | 0.5 | 100 | 8.3 | 1.0 | 100 | 8.4 | 0.8 | 100 |
| hsa-miR-886-5p | −2.2 | 0 | −1.3 | 1.2 | 0 | −1.2 | 0.5 | 0 | −1.1 | 1.0 | 0 | −0.9 | 0.9 | 0 | 0.2 | 1.0 | 0 | −0.3 | 1.0 | 0 | −1.7 | 0.3 | 0 |
| hsa-miR-887 | 3.1 | 100 | 3.2 | 0.7 | 100 | 3.3 | 0.6 | 100 | 3.2 | 0.3 | 100 | 3.2 | 0.9 | 100 | 4.0 | 0.3 | 100 | 3.9 | 0.5 | 100 | 2.8 | 0.5 | 100 |
| hsa-miR-888 | 0.2 | 0 | −0.2 | 0.4 | 0 | 0.4 | 1.9 | 20 | 0.0 | 0.8 | 0 | 2.3 | 3.4 | 33 | −0.2 | 0.9 | 0 | −0.7 | 0.5 | 0 | −0.4 | 1.0 | 0 |
| hsa-miR-889 | 0.5 | 0 | −0.6 | 1.0 | 0 | 0.0 | 0.3 | 0 | −0.2 | 0.8 | 0 | 3.8 | 0.5 | 100 | −0.3 | 0.1 | 0 | 0.0 | 0.2 | 0 | 0.1 | 0.4 | 0 |
| hsa-miR-890 | 0.3 | 0 | −1.1 | 0.8 | 0 | −0.4 | 1.1 | 0 | −0.2 | 0.6 | 0 | 2.6 | 2.0 | 67 | 0.1 | 0.7 | 0 | −0.7 | 0.5 | 0 | −0.8 | 0.7 | 0 |
| hsa-miR-891a | −1.7 | 0 | −1.0 | 2.0 | 0 | −1.6 | 0.9 | 0 | −1.1 | 0.4 | 0 | 0.0 | 2.7 | 33 | −0.6 | 0.4 | 0 | −1.6 | 0.5 | 0 | −1.5 | 0.7 | 0 |
| hsa-miR-891b | 0.2 | 0 | 0.6 | 0.9 | 0 | 0.6 | 1.2 | 20 | 0.5 | 0.3 | 0 | 2.5 | 3.2 | 33 | 0.1 | 0.8 | 0 | 0.0 | 0.3 | 0 | 0.0 | 1.3 | 0 |
| hsa-miR-892a | −0.7 | 0 | 0.9 | 1.2 | 0 | 0.7 | 0.5 | 0 | 0.4 | 0.3 | 0 | 1.5 | 1.1 | 33 | 0.3 | 0.4 | 0 | 0.5 | 0.9 | 25 | 0.4 | 0.4 | 0 |
| hsa-miR-892b | 5.0 | 100 | 4.7 | 0.5 | 100 | 5.0 | 0.3 | 100 | 4.8 | 0.4 | 100 | 4.6 | 0.1 | 100 | 4.7 | 0.2 | 100 | 4.7 | 0.2 | 100 | 5.8 | 0.8 | 100 |
| hsa-miR-9 | 5.1 | 100 | 0.6 | 1.2 | 0 | 1.2 | 0.5 | 0 | 0.4 | 0.7 | 0 | 4.7 | 1.6 | 100 | 1.1 | 0.4 | 0 | 1.9 | 0.3 | 50 | 1.0 | 0.7 | 20 |
| hsa-miR-9* | 7.1 | 100 | 0.9 | 1.7 | 20 | 1.8 | 1.0 | 0 | 1.0 | 1.2 | 0 | 5.3 | 1.8 | 100 | 1.6 | 0.2 | 50 | 2.1 | 0.7 | 50 | 2.1 | 1.1 | 20 |
| hsa-miR-921 | −1.3 | 0 | −0.9 | 0.9 | 0 | −0.8 | 1.0 | 0 | −0.6 | 1.2 | 0 | 0.1 | 0.9 | 0 | 1.7 | 0.5 | 50 | 0.4 | 0.9 | 0 | −0.6 | 0.4 | 0 |
| hsa-miR-923 | 13.3 | 100 | 12.4 | 0.7 | 100 | 12.7 | 1.1 | 100 | 14.3 | 1.5 | 100 | 12.9 | 0.2 | 100 | 14.0 | 1.8 | 100 | 13.3 | 0.9 | 100 | 12.6 | 0.7 | 100 |
| hsa-miR-92a | 7.8 | 100 | 8.6 | 0.7 | 100 | 9.3 | 0.3 | 100 | 9.2 | 0.1 | 100 | 8.8 | 0.4 | 100 | 9.4 | 0.1 | 100 | 9.4 | 1.1 | 100 | 9.3 | 0.2 | 100 |
| hsa-miR-92a-1* | 0.3 | 0 | 0.2 | 0.8 | 0 | 0.5 | 0.5 | 0 | 0.9 | 0.8 | 0 | 0.6 | 0.4 | 0 | −0.1 | 0.3 | 0 | 0.9 | 1.1 | 25 | 0.8 | 0.3 | 0 |
| hsa-miR-92b | 0.8 | 0 | 1.4 | 0.9 | 0 | 1.0 | 0.6 | 20 | 0.9 | 1.3 | 0 | 0.5 | 0.2 | 0 | 1.2 | 0.3 | 0 | 0.7 | 0.1 | 0 | 0.9 | 0.6 | 20 |
| hsa-miR-92b* | −2.1 | 0 | −0.9 | 1.2 | 0 | −0.8 | 0.3 | 0 | −1.3 | 1.3 | 0 | −0.9 | 0.7 | 0 | 3.0 | 0.6 | 100 | 1.0 | 2.2 | 50 | −1.9 | 0.7 | 0 |
| hsa-miR-93 | 7.6 | 100 | 8.0 | 0.7 | 100 | 8.5 | 0.3 | 100 | 8.7 | 0.6 | 100 | 8.8 | 0.3 | 100 | 8.5 | 0.3 | 100 | 8.8 | 0.2 | 100 | 8.7 | 0.2 | 100 |
| hsa-miR-93* | −0.6 | 0 | 1.2 | 0.5 | 60 | 1.2 | 0.2 | 60 | 0.8 | 0.6 | 75 | 1.5 | 0.5 | 75 | 0.7 | 0.5 | 75 | 1.1 | 0.5 | 75 | 0.6 | 0.4 | 40 |
| hsa-miR-933 | 3.1 | 100 | 2.2 | 0.7 | 100 | 2.3 | 0.4 | 100 | 2.4 | 0.6 | 50 | 1.9 | 0.4 | 67 | 2.7 | 0.4 | 100 | 2.1 | 0.4 | 75 | 2.4 | 0.3 | 80 |
| hsa-miR-934 | −2.4 | 0 | −1.3 | 1.5 | 0 | −1.1 | 1.3 | 0 | −1.4 | 1.1 | 0 | −0.4 | 1.0 | 0 | 2.1 | 0.7 | 100 | −0.5 | 1.0 | 0 | −1.8 | 0.7 | 0 |
| hsa-miR-936 | 2.1 | 0 | 0.9 | 1.1 | 20 | 1.7 | 1.0 | 0 | 1.3 | 1.7 | 25 | 3.1 | 1.6 | 67 | 4.5 | 0.6 | 100 | 2.6 | 0.5 | 50 | 1.3 | 0.5 | 0 |
| hsa-miR-939 | 7.3 | 100 | 6.1 | 0.6 | 100 | 6.8 | 0.7 | 100 | 6.7 | 0.5 | 100 | 6.6 | 0.9 | 100 | 8.9 | 0.4 | 100 | 7.4 | 0.8 | 100 | 5.8 | 0.4 | 100 |
| hsa-miR-940 | 7.0 | 100 | 6.0 | 0.8 | 100 | 7.0 | 0.7 | 100 | 6.6 | 0.4 | 100 | 6.5 | 1.1 | 100 | 8.9 | 0.4 | 100 | 6.9 | 0.7 | 100 | 6.1 | 0.1 | 100 |
| hsa-miR-944 | 0.7 | 0 | 0.6 | 0.8 | 0 | 0.2 | 0.4 | 0 | 0.7 | 0.2 | 0 | 0.0 | 0.1 | 0 | 0.5 | 0.3 | 0 | 0.5 | 0.3 | 0 | 0.8 | 0.8 | 20 |
| hsa-miR-95 | 6.4 | 100 | 7.3 | 0.7 | 100 | 7.8 | 0.4 | 100 | 7.5 | 0.8 | 100 | 9.4 | 0.7 | 100 | 7.9 | 0.6 | 100 | 8.4 | 0.5 | 100 | 7.5 | 0.3 | 100 |
| hsa-miR-96 | 7.4 | 100 | 8.9 | 0.9 | 100 | 9.5 | 1.1 | 100 | 8.4 | 1.7 | 100 | 11.0 | 0.5 | 100 | 7.1 | 0.4 | 100 | 7.5 | 0.4 | 100 | 8.2 | 0.5 | 100 |

TABLE 3-continued

Normalized array data for miRNA expression in thyroid tissue sample groups.

| miRNA | ATC | | | FA | | | FTC | | | FVPTC | | | MTC | | | NOD | | | NOR | | | PTC | | |
|---|---|---|---|---|---|---|---|---|---|---|---|---|---|---|---|---|---|---|---|---|---|---|---|---|
| | Avg | SD | % | Avg | SD | % | Avg | SD | % | Avg | SD | % | Avg | SD | % | Avg | SD | % | Avg | SD | % | Avg | SD | % |
| hsa-miR-98 | 7.2 | | 100 | 8.4 | 0.9 | 100 | 8.7 | 0.6 | 100 | 8.2 | 0.7 | 100 | 8.4 | 0.2 | 100 | 8.2 | 0.5 | 100 | 8.9 | 0.3 | 100 | 8.2 | 0.7 | 100 |
| hsa-miR-99a | 8.0 | | 100 | 10.8 | 1.0 | 100 | 11.0 | 0.8 | 100 | 11.4 | 0.3 | 100 | 11.6 | 0.6 | 100 | 11.5 | 0.2 | 100 | 11.9 | 0.2 | 100 | 11.2 | 0.4 | 100 |
| hsa-miR-99a* | −1.8 | | 0 | 1.7 | 0.6 | 60 | 1.8 | 1.3 | 60 | 1.0 | 1.1 | 50 | 1.8 | 0.9 | 67 | 1.3 | 0.7 | 50 | 2.0 | 0.1 | 100 | 1.5 | 0.5 | 60 |
| hsa-miR-99b | 8.8 | | 100 | 8.6 | 0.7 | 100 | 8.3 | 0.6 | 100 | 8.9 | 0.5 | 100 | 9.5 | 0.1 | 100 | 8.5 | 0.3 | 100 | 8.8 | 0.1 | 100 | 8.9 | 0.2 | 100 |
| hsa-miR-99b* | 1.2 | | 0 | 2.1 | 0.7 | 0 | 1.7 | 0.5 | 20 | 2.0 | 0.6 | 25 | 2.0 | 0.4 | 33 | 2.9 | 0.3 | 100 | 2.2 | 0.4 | 50 | 2.3 | 0.4 | 40 |

Avg, Average expression level in the sample set;
SD, standard deviation;
%, percentage of samples with expression level above background.

Example 2 miRNA Expression Profiling Distinguishes Normal Thyroid Tissue and Hyperplastic Thyroid Nodules A total of 415 human miRNAs were expressed above background level in the normal thyroid tissue samples, representing 48% of the human miRNAs present on the arrays. A total of 409 miRNAs were expressed above background level in the hyperplastic thyroid nodules samples, representing 47% of the miRNAs present on the arrays.

A total of 173 human miRNAs were significantly differentially expressed between the normal tissue samples and the hyperplastic nodules specimens ($p<0.05$) (Table 4). Among these, 89 miRNAs were overexpressed (Log 2 diff (NOD vs NOR)≥1), and 14 were underexpressed (Log 2 diff (NOD vs NOR)≤1) by at least 2-fold in NOD compared to NOR. Of these, hsa-miR-1202, -934, and -663 were overexpressed by more than five-fold in NOD vs NOR.

TABLE 4

MicroRNAs significantly differentially expressed between NOD and NOR samples.

| miRNA | NOD AVG | NOD SD | NOR AVG | NOR SD | NOD vs NOR ttest | Log2Diff | Fold change |
|---|---|---|---|---|---|---|---|
| hsa-miR-1202 | 13.75 | 0.81 | 11.03 | 0.86 | 3.65E−03 | 2.71 | 6.6 |
| hsa-miR-934 | 2.09 | 0.71 | −0.51 | 1.01 | 5.57E−03 | 2.60 | 6.1 |
| hsa-miR-663 | 8.63 | 0.75 | 6.18 | 0.82 | 4.50E−03 | 2.45 | 5.5 |
| hsa-miR-572 | 7.90 | 1.01 | 5.63 | 0.90 | 1.52E−02 | 2.28 | 4.9 |
| hsa-miR-1300 | 7.80 | 0.79 | 5.66 | 1.41 | 3.82E−02 | 2.14 | 4.4 |
| hsa-miR-1207-5p | 11.83 | 1.05 | 9.76 | 0.49 | 1.17E−02 | 2.07 | 4.2 |
| hsa-miR-34c-3p | 1.72 | 0.30 | −0.35 | 0.70 | 1.66E−03 | 2.07 | 4.2 |
| hsa-miR-940 | 8.91 | 0.72 | 6.86 | 0.69 | 6.45E−03 | 2.05 | 4.1 |
| hsa-miR-1203 | 2.45 | 0.50 | 0.42 | 0.97 | 9.81E−03 | 2.03 | 4.1 |
| hsa-miR-638 | 10.95 | 1.00 | 8.93 | 0.61 | 1.35E−02 | 2.02 | 4.1 |
| hsa-miR-1909* | 2.64 | 0.78 | 0.62 | 0.25 | 2.69E−03 | 2.02 | 4.0 |
| hsa-miR-936 | 4.55 | 0.65 | 2.56 | 0.47 | 2.46E−03 | 1.99 | 4.0 |
| hsa-miR-1225-5p | 11.79 | 0.95 | 9.85 | 0.45 | 1.00E−02 | 1.95 | 3.9 |
| hsa-miR-149* | 4.68 | 0.59 | 2.76 | 0.59 | 3.67E−03 | 1.92 | 3.8 |
| hsa-miR-187* | 4.73 | 0.70 | 2.81 | 0.38 | 3.02E−03 | 1.92 | 3.8 |
| hsa-miR-198 | 4.90 | 0.65 | 2.98 | 0.64 | 5.61E−03 | 1.92 | 3.8 |
| hsa-miR-150* | 7.49 | 0.70 | 5.58 | 0.63 | 6.61E−03 | 1.92 | 3.8 |
| hsa-miR-202 | 7.06 | 0.56 | 5.14 | 0.80 | 7.72E−03 | 1.92 | 3.8 |
| hsa-miR-648 | 4.14 | 0.46 | 2.26 | 1.24 | 3.00E−02 | 1.87 | 3.7 |
| hsa-miR-134 | 8.00 | 0.93 | 6.13 | 0.47 | 1.16E−02 | 1.86 | 3.6 |
| hsa-miR-631 | 3.97 | 0.56 | 2.11 | 0.89 | 1.20E−02 | 1.86 | 3.6 |
| hsa-miR-623 | 4.95 | 0.55 | 3.09 | 0.84 | 1.00E−02 | 1.86 | 3.6 |
| hsa-miR-1276 | 2.01 | 0.65 | 0.15 | 0.60 | 5.63E−03 | 1.86 | 3.6 |
| hsa-miR-1268 | 10.19 | 1.33 | 8.34 | 0.66 | 4.65E−02 | 1.86 | 3.6 |
| hsa-miR-551b* | 2.72 | 0.65 | 0.88 | 1.01 | 2.22E−02 | 1.84 | 3.6 |
| hsa-miR-566 | 3.15 | 0.92 | 1.31 | 0.55 | 1.40E−02 | 1.84 | 3.6 |
| hsa-miR-1182 | 4.76 | 0.77 | 2.94 | 0.45 | 6.33E−03 | 1.82 | 3.5 |
| hsa-miR-1250 | 1.91 | 0.52 | 0.10 | 0.88 | 1.22E−02 | 1.81 | 3.5 |
| hsa-miR-616 | 1.69 | 0.53 | −0.08 | 0.59 | 4.27E−03 | 1.77 | 3.4 |
| hsa-miR-493 | 2.93 | 0.73 | 1.16 | 0.73 | 1.42E−02 | 1.76 | 3.4 |
| hsa-miR-659 | 5.53 | 0.63 | 3.79 | 0.65 | 8.34E−03 | 1.74 | 3.3 |
| hsa-miR-302c* | 1.62 | 0.71 | −0.10 | 0.48 | 6.98E−03 | 1.72 | 3.3 |
| hsa-miR-601 | 5.60 | 0.53 | 3.90 | 0.46 | 2.84E−03 | 1.69 | 3.2 |
| hsa-miR-371-5p | 6.14 | 0.47 | 4.45 | 0.52 | 2.97E−03 | 1.69 | 3.2 |
| hsa-miR-765 | 6.63 | 0.70 | 4.95 | 0.59 | 1.01E−02 | 1.69 | 3.2 |
| hsa-miR-188-5p | 7.46 | 0.63 | 5.77 | 0.44 | 4.60E−03 | 1.68 | 3.2 |
| hsa-miR-575 | 10.16 | 0.66 | 8.50 | 0.60 | 9.92E−03 | 1.66 | 3.2 |
| hsa-miR-610 | 4.46 | 0.57 | 2.80 | 0.72 | 1.13E−02 | 1.66 | 3.2 |
| hsa-miR-1224-5p | 7.60 | 0.65 | 5.95 | 0.48 | 6.56E−03 | 1.65 | 3.1 |
| hsa-miR-1915 | 10.06 | 0.49 | 8.41 | 0.52 | 3.72E−03 | 1.65 | 3.1 |
| hsa-miR-516b | 2.78 | 0.32 | 1.14 | 0.79 | 8.69E−03 | 1.63 | 3.1 |
| hsa-miR-526b | 3.54 | 0.53 | 1.91 | 0.43 | 3.12E−03 | 1.63 | 3.1 |
| hsa-miR-617 | 3.26 | 0.35 | 1.64 | 0.66 | 4.92E−03 | 1.62 | 3.1 |
| hsa-miR-1321 | 3.74 | 0.75 | 2.13 | 1.05 | 4.68E−02 | 1.61 | 3.1 |
| hsa-miR-518c* | 2.24 | 0.52 | 0.63 | 0.75 | 1.20E−02 | 1.61 | 3.1 |
| hsa-miR-483-5p | 8.47 | 0.79 | 6.87 | 0.23 | 8.35E−03 | 1.60 | 3.0 |
| hsa-miR-127-5p | 8.12 | 0.52 | 7.36 | 0.45 | 2.53E−02 | 1.59 | 3.0 |
| hsa-miR-1183 | 6.22 | 0.69 | 4.64 | 0.50 | 9.83E−03 | 1.58 | 3.0 |
| hsa-miR-939 | 8.91 | 0.42 | 7.35 | 0.82 | 1.50E−02 | 1.56 | 3.0 |
| hsa-miR-490-3p | 1.74 | 0.41 | 0.19 | 0.61 | 5.55E−03 | 1.55 | 2.9 |
| hsa-miR-877* | 4.73 | 0.40 | 3.20 | 0.72 | 9.85E−03 | 1.54 | 2.9 |
| hsa-miR-1303 | 1.71 | 0.56 | 0.18 | 0.58 | 8.93E−03 | 1.53 | 2.9 |
| hsa-miR-640 | 1.49 | 0.46 | −0.04 | 0.54 | 4.90E−03 | 1.53 | 2.9 |
| hsa-miR-424* | 5.34 | 0.66 | 3.82 | 0.28 | 5.36E−03 | 1.52 | 2.9 |
| hsa-miR-1915* | 2.26 | 0.54 | 0.74 | 0.45 | 4.94E−03 | 1.52 | 2.9 |
| hsa-miR-498 | 3.77 | 0.49 | 2.26 | 0.47 | 4.41E−03 | 1.50 | 2.8 |
| hsa-miR-671-5p | 7.24 | 0.57 | 5.77 | 0.20 | 2.82E−03 | 1.47 | 2.8 |
| hsa-miR-1249 | 5.93 | 0.74 | 4.49 | 0.51 | 1.85E−02 | 1.44 | 2.7 |

TABLE 4-continued

MicroRNAs significantly differentially expressed between NOD and NOR samples.

| miRNA | NOD AVG | NOD SD | NOR AVG | NOR SD | NOD vs NOR ttest | Log2Diff | Fold change |
|---|---|---|---|---|---|---|---|
| hsa-miR-1291 | 2.48 | 0.82 | 1.45 | 0.57 | 2.45E−02 | 1.43 | 2.7 |
| hsa-miR-1228* | 1.90 | 0.73 | 0.49 | 0.88 | 4.82E−02 | 1.41 | 2.7 |
| hsa-miR-370 | 3.80 | 0.49 | 2.41 | 0.50 | 7.31E−03 | 1.39 | 2.6 |
| hsa-miR-525-5p | 2.15 | 0.49 | 0.77 | 0.60 | 1.16E−02 | 1.39 | 2.6 |
| hsa-miR-125a-3p | 7.33 | 0.40 | 5.95 | 0.29 | 1.36E−03 | 1.39 | 2.6 |
| hsa-miR-622 | 5.23 | 0.37 | 3.86 | 0.82 | 2.20E−02 | 1.38 | 2.6 |
| hsa-miR-662 | 3.58 | 0.21 | 2.26 | 0.34 | 5.85E−04 | 1.33 | 2.5 |
| hsa-miR-1226* | 5.72 | 0.46 | 4.41 | 0.38 | 4.72E−03 | 1.31 | 2.5 |
| hsa-miR-550 | 3.70 | 0.30 | 2.40 | 0.27 | 6.78E−04 | 1.31 | 2.5 |
| hsa-miR-769-3p | 3.34 | 0.64 | 2.04 | 0.20 | 8.01E−03 | 1.30 | 2.5 |
| hsa-miR-583 | 2.59 | 0.74 | 1.29 | 0.37 | 2.02E−02 | 1.30 | 2.5 |
| hsa-miR-1306 | 2.97 | 0.34 | 1.68 | 0.44 | 3.68E−03 | 1.29 | 2.4 |
| hsa-miR-921 | 1.67 | 0.51 | 0.39 | 0.89 | 4.67E−02 | 1.29 | 2.4 |
| hsa-miR-33b* | 4.27 | 0.51 | 3.00 | 0.35 | 5.89E−03 | 1.28 | 2.4 |
| hsa-miR-373* | 3.17 | 0.97 | 1.91 | 0.35 | 4.98E−02 | 1.26 | 2.4 |
| hsa-miR-877 | 4.47 | 0.65 | 3.24 | 0.44 | 2.00E−02 | 1.23 | 2.3 |
| hsa-miR-557 | 6.23 | 0.77 | 5.01 | 0.53 | 4.06E−02 | 1.22 | 2.3 |
| hsa-miR-760 | 4.31 | 0.36 | 3.09 | 0.41 | 4.29E−03 | 1.21 | 2.3 |
| hsa-miR-1469 | 3.39 | 0.42 | 2.18 | 0.70 | 2.54E−02 | 1.21 | 2.3 |
| hsa-miR-614 | 2.05 | 0.67 | 0.86 | 0.38 | 2.09E−02 | 1.19 | 2.3 |
| hsa-miR-602 | 3.88 | 0.51 | 2.69 | 0.44 | 1.22E−02 | 1.19 | 2.3 |
| hsa-miR-513a-5p | 5.52 | 0.43 | 4.33 | 0.26 | 3.25E−03 | 1.19 | 2.3 |
| hsa-miR-184 | 2.83 | 0.43 | 1.66 | 0.43 | 7.87E−03 | 1.18 | 2.3 |
| hsa-miR-298 | 1.93 | 0.38 | 0.75 | 0.85 | 4.40E−02 | 1.18 | 2.3 |
| hsa-miR-1180 | 3.54 | 0.41 | 2.38 | 0.14 | 1.69E−03 | 1.16 | 2.2 |
| hsa-miR-490-5p | 3.39 | 0.29 | 2.28 | 0.77 | 3.62E−02 | 1.11 | 2.2 |
| hsa-miR-296-5p | 4.51 | 0.68 | 3.44 | 0.22 | 2.50E−02 | 1.07 | 2.1 |
| hsa-miR-518e* | 2.03 | 0.27 | 0.96 | 0.41 | 4.61E−03 | 1.07 | 2.1 |
| hsa-miR-654-5p | 4.06 | 0.36 | 2.99 | 0.39 | 6.73E−03 | 1.06 | 2.1 |
| hsa-miR-1539 | 2.93 | 0.48 | 1.88 | 0.41 | 1.51E−02 | 1.05 | 2.1 |
| hsa-miR-194* | 1.50 | 0.63 | 0.45 | 0.25 | 2.09E−02 | 1.05 | 2.1 |
| hsa-miR-340* | 3.30 | 0.54 | 4.31 | 0.21 | 1.29E−02 | −1.01 | 2.0 |
| hsa-miR-10a | 7.62 | 0.10 | 8.66 | 0.40 | 2.48E−03 | −1.04 | 2.1 |
| hsa-miR-429 | 7.59 | 0.20 | 8.64 | 0.10 | 9.14E−05 | −1.05 | 2.1 |
| hsa-miR-582-5p | 3.22 | 0.58 | 4.27 | 0.39 | 2.28E−02 | −1.06 | 2.1 |
| hsa-miR-365 | 8.74 | 0.64 | 9.80 | 0.45 | 3.53E−02 | −1.06 | 2.1 |
| hsa-miR-200a | 8.86 | 0.32 | 9.93 | 0.13 | 7.60E−04 | −1.07 | 2.1 |
| hsa-miR-148a | 10.18 | 0.47 | 11.27 | 0.26 | 6.55E−03 | −1.08 | 2.1 |
| hsa-miR-876-3p | 1.74 | 0.54 | 2.91 | 0.40 | 1.29E−02 | −1.18 | 2.3 |
| hsa-miR-424 | 8.84 | 0.42 | 10.03 | 0.50 | 1.09E−02 | −1.19 | 2.3 |
| hsa-miR-450a | 4.07 | 0.66 | 5.36 | 0.44 | 1.73E−02 | −1.29 | 2.4 |
| hsa-miR-148a* | 0.37 | 0.58 | 1.75 | 0.37 | 6.80E−03 | −1.39 | 2.6 |
| hsa-miR-720 | 10.25 | 0.79 | 11.85 | 0.99 | 4.50E−02 | −1.60 | 3.0 |
| hsa-miR-1260 | 6.50 | 0.87 | 8.14 | 0.77 | 3.13E−02 | −1.63 | 3.1 |
| hsa-miR-29b-1* | 3.36 | 0.34 | 5.26 | 0.67 | 2.23E−03 | −1.90 | 3.7 |

AVG, average expression among samples in a group;
SD, standard deviation.

Example 3 miRNA Expression Profiling Distinguishes Normal Thyroid Tissue and Follicular Adenoma A total of 415 human miRNAs were expressed above background level in the normal thyroid tissue samples, representing 48% of the human miRNAs present on the arrays. A total of 334 miRNAs were expressed above background level in the follicular adenoma samples, representing 39% of the miRNAs present on the arrays.

A total of 114 human miRNAs were significantly differentially expressed between the normal samples and the FA specimens (p<0.05) (Table 5). Among these, six miRNAs were overexpressed (Log 2 diff (FA vs NOR)≤1), and 79 were underexpressed (Log 2 diff (FA vs NOR)≥1) by at least two-fold in FA compared to NOR. Of these, five miRNAs, (hsa-miR-200a, -206, -200b, -429, and -199b-5p, were underexpressed by 10- to 20-fold in FA vs NOR, and six miRNAs (hsa-miR-200b*, -486-3p, -376a, -200a*, -376c, and -381) were underexpressed by 5- to 10-fold in the FA samples compared to the NOR samples (Table 5).

TABLE 5

MicroRNAs significantly differentially expressed between FA and NOR samples.

| miRNA | NOR AVG | NOR SD | FA AVG | FA SD | FA vs NOR ttest | Log2Diff | Fold change |
|---|---|---|---|---|---|---|---|
| hsa-miR-222 | 5.87 | 0.13 | 7.51 | 1.30 | 4.27E−02 | 1.63 | 3.10 |
| hsa-miR-182 | 2.28 | 0.58 | 3.85 | 1.11 | 3.85E−02 | 1.57 | 2.97 |

TABLE 5-continued

MicroRNAs significantly differentially expressed between FA and NOR samples.

| miRNA | NOR AVG | NOR SD | FA AVG | FA SD | FA vs NOR ttest | FA vs NOR Log2Diff | Fold change |
|---|---|---|---|---|---|---|---|
| hsa-miR-96 | 7.46 | 0.37 | 8.94 | 0.88 | 1.71E−02 | 1.48 | 2.79 |
| hsa-miR-1227 | 0.32 | 0.43 | 1.77 | 1.08 | 4.10E−02 | 1.45 | 2.73 |
| hsa-miR-182* | 0.03 | 0.20 | 1.08 | 0.53 | 7.55E−03 | 1.06 | 2.08 |
| hsa-miR-34a | 10.87 | 0.11 | 11.88 | 0.50 | 5.60E−03 | 1.01 | 2.01 |
| hsa-miR-1915 | 8.41 | 0.52 | 7.41 | 0.57 | 3.07E−02 | −1.00 | 2.00 |
| hsa-miR-30a* | 8.99 | 0.37 | 7.99 | 0.47 | 1.00E−02 | −1.00 | 2.00 |
| hsa-miR-128 | 7.50 | 0.42 | 6.49 | 0.63 | 2.97E−02 | −1.01 | 2.02 |
| hsa-miR-151-5p | 11.05 | 0.25 | 10.03 | 0.57 | 1.31E−02 | −1.02 | 2.03 |
| hsa-miR-20b | 8.20 | 0.29 | 7.17 | 0.76 | 3.85E−02 | −1.04 | 2.05 |
| hsa-miR-188-5p | 5.77 | 0.44 | 4.71 | 0.32 | 3.83E−03 | −1.06 | 2.09 |
| hsa-miR-95 | 8.36 | 0.53 | 7.29 | 0.74 | 4.68E−02 | −1.07 | 2.10 |
| hsa-miR-1207-5p | 9.76 | 0.49 | 8.69 | 0.76 | 4.59E−02 | −1.07 | 2.10 |
| hsa-miR-1225-5p | 9.85 | 0.45 | 8.71 | 0.57 | 1.40E−02 | −1.14 | 2.20 |
| hsa-miR-30b | 12.22 | 0.28 | 11.09 | 0.62 | 1.17E−02 | −1.14 | 2.20 |
| hsa-miR-137 | 1.01 | 0.78 | −0.13 | 0.61 | 4.26E−02 | −1.14 | 2.21 |
| hsa-miR-30c-2* | 6.15 | 0.27 | 5.00 | 0.53 | 6.12E−03 | −1.15 | 2.21 |
| hsa-miR-610 | 2.80 | 0.72 | 1.65 | 0.67 | 4.30E−02 | −1.15 | 2.22 |
| hsa-miR-455-3p | 6.91 | 0.12 | 5.74 | 0.95 | 4.64E−02 | −1.17 | 2.25 |
| hsa-miR-338-3p | 7.41 | 0.48 | 6.20 | 0.59 | 1.31E−02 | −1.21 | 2.32 |
| hsa-miR-432 | 2.98 | 0.71 | 1.76 | 0.66 | 3.21E−02 | −1.22 | 2.34 |
| hsa-miR-10b* | 3.27 | 0.63 | 2.05 | 0.49 | 1.35E−02 | −1.23 | 2.34 |
| hsa-miR-136 | 3.60 | 0.47 | 2.33 | 0.52 | 6.55E−03 | −1.27 | 2.41 |
| hsa-miR-26b | 12.58 | 0.26 | 11.30 | 0.54 | 3.67E−03 | −1.28 | 2.42 |
| hsa-miR-516b | 1.14 | 0.79 | −0.14 | 0.79 | 4.63E−02 | −1.28 | 2.43 |
| hsa-miR-601 | 3.90 | 0.46 | 2.62 | 0.55 | 7.22E−03 | −1.28 | 2.43 |
| hsa-miR-130a | 11.60 | 0.31 | 10.32 | 0.86 | 2.59E−02 | −1.29 | 2.44 |
| hsa-miR-939 | 7.35 | 0.82 | 6.06 | 0.56 | 2.66E−02 | −1.29 | 2.44 |
| hsa-miR-154* | 2.47 | 0.92 | 1.17 | 0.72 | 4.83E−02 | −1.30 | 2.46 |
| hsa-miR-493* | 2.96 | 0.54 | 1.66 | 0.68 | 1.76E−02 | −1.30 | 2.46 |
| hsa-miR-299-3p | 1.65 | 0.31 | 0.33 | 0.73 | 1.23E−02 | −1.32 | 2.49 |
| hsa-miR-20a* | 4.96 | 0.36 | 3.60 | 0.59 | 5.18E−03 | −1.35 | 2.56 |
| hsa-miR-516a-5p | 3.37 | 1.12 | 2.00 | 0.46 | 3.93E−02 | −1.37 | 2.59 |
| hsa-miR-135a* | 5.11 | 0.38 | 3.73 | 0.52 | 3.00E−03 | −1.39 | 2.61 |
| hsa-miR-455-5p | 4.70 | 0.09 | 3.31 | 1.14 | 4.77E−02 | −1.39 | 2.62 |
| hsa-miR-659 | 3.79 | 0.65 | 2.36 | 0.93 | 3.69E−02 | −1.42 | 2.68 |
| hsa-miR-150* | 5.58 | 0.63 | 4.08 | 0.64 | 9.64E−03 | −1.50 | 2.83 |
| hsa-miR-671-5p | 5.77 | 0.20 | 4.25 | 0.59 | 1.75E−03 | −1.52 | 2.87 |
| hsa-miR-1915* | 0.74 | 0.45 | −0.82 | 1.08 | 3.14E−02 | −1.56 | 2.95 |
| hsa-miR-223 | 10.86 | 0.87 | 9.28 | 0.97 | 3.90E−02 | −1.58 | 2.98 |
| hsa-miR-877 | 3.24 | 0.44 | 1.65 | 1.12 | 3.34E−02 | −1.59 | 3.01 |
| hsa-miR-154 | 3.92 | 0.39 | 2.33 | 0.87 | 1.21E−02 | −1.59 | 3.01 |
| hsa-miR-1208 | 2.84 | 0.36 | 1.22 | 0.79 | 7.05E−03 | −1.62 | 3.07 |
| hsa-miR-639 | 0.53 | 1.01 | −1.10 | 0.71 | 2.51E−02 | −1.63 | 3.09 |
| hsa-miR-630 | 6.04 | 0.36 | 4.40 | 0.94 | 1.33E−02 | −1.64 | 3.13 |
| hsa-miR-214* | 4.54 | 0.23 | 2.90 | 0.79 | 5.39E−03 | −1.64 | 3.13 |
| hsa-miR-1321 | 2.13 | 1.05 | 0.48 | 0.58 | 1.97E−02 | −1.65 | 3.13 |
| hsa-miR-218 | 8.86 | 0.27 | 7.21 | 0.99 | 1.52E−02 | −1.65 | 3.15 |
| hsa-miR-1202 | 11.03 | 0.86 | 9.38 | 0.66 | 1.30E−02 | −1.66 | 3.16 |
| hsa-miR-299-5p | 3.80 | 0.43 | 2.13 | 1.01 | 1.89E−02 | −1.66 | 3.17 |
| hsa-miR-936 | 2.56 | 0.47 | 0.89 | 1.06 | 2.28E−02 | −1.67 | 3.18 |
| hsa-miR-654-3p | 3.97 | 0.25 | 2.28 | 1.11 | 2.18E−02 | −1.68 | 3.21 |
| hsa-miR-210 | 6.28 | 0.41 | 4.60 | 1.04 | 1.93E−02 | −1.69 | 3.22 |
| hsa-miR-663 | 6.18 | 0.82 | 4.45 | 1.10 | 3.52E−02 | −1.73 | 3.31 |
| hsa-miR-127-3p | 5.22 | 0.57 | 3.44 | 1.00 | 1.62E−02 | −1.78 | 3.43 |
| hsa-miR-495 | 3.64 | 0.76 | 1.86 | 0.95 | 1.87E−02 | −1.78 | 3.43 |
| hsa-miR-411 | 2.19 | 0.44 | 0.40 | 1.22 | 2.83E−02 | −1.79 | 3.45 |
| hsa-miR-337-5p | 3.33 | 0.35 | 1.52 | 0.79 | 3.90E−03 | −1.82 | 3.52 |
| hsa-miR-483-5p | 6.87 | 0.23 | 5.02 | 0.82 | 3.40E−03 | −1.86 | 3.62 |
| hsa-miR-193b | 8.34 | 0.80 | 6.47 | 1.01 | 2.02E−02 | −1.86 | 3.64 |
| hsa-miR-1471 | 4.55 | 0.27 | 2.62 | 1.29 | 2.29E−02 | −1.93 | 3.80 |
| hsa-miR-765 | 4.95 | 0.59 | 3.01 | 1.05 | 1.37E−02 | −1.93 | 3.82 |
| hsa-miR-198 | 2.98 | 0.64 | 1.05 | 0.66 | 3.00E−03 | −1.94 | 3.83 |
| hsa-miR-199a-5p | 10.41 | 0.25 | 8.46 | 0.81 | 2.53E−03 | −1.95 | 3.86 |
| hsa-miR-187* | 2.81 | 0.38 | 0.84 | 1.40 | 3.15E−02 | −1.96 | 3.90 |
| hsa-miR-377 | 4.48 | 0.60 | 2.50 | 1.15 | 1.73E−02 | −1.98 | 3.96 |
| hsa-miR-199a-3p | 12.04 | 0.17 | 10.02 | 0.83 | 2.12E−03 | −2.01 | 4.04 |
| hsa-miR-1182 | 2.94 | 0.45 | 0.89 | 0.88 | 3.83E−03 | −2.06 | 4.16 |
| hsa-miR-1246 | 9.20 | 0.88 | 7.09 | 1.23 | 2.40E−02 | −2.11 | 4.30 |
| hsa-miR-379 | 3.13 | 0.51 | 1.02 | 0.89 | 4.16E−03 | −2.11 | 4.31 |
| hsa-miR-214 | 9.59 | 0.15 | 7.46 | 0.79 | 1.22E−03 | −2.13 | 4.39 |
| hsa-miR-499-5p | 5.78 | 1.61 | 3.65 | 0.86 | 3.72E−02 | −2.13 | 4.39 |
| hsa-miR-136* | 3.09 | 0.50 | 0.94 | 1.05 | 7.30E−03 | −2.16 | 4.46 |
| hsa-miR-381 | 4.34 | 0.54 | 1.97 | 1.13 | 6.47E−03 | −2.37 | 5.18 |
| hsa-miR-376c | 6.27 | 0.41 | 3.88 | 1.05 | 3.81E−03 | −2.39 | 5.24 |

TABLE 5-continued

MicroRNAs significantly differentially expressed between FA and NOR samples.

| miRNA | NOR AVG | NOR SD | FA AVG | FA SD | FA vs NOR ttest | FA vs NOR Log2Diff | Fold change |
|---|---|---|---|---|---|---|---|
| hsa-miR-200a* | 4.59 | 0.21 | 2.10 | 1.76 | 2.75E-02 | -2.49 | 5.61 |
| hsa-miR-376a | 5.80 | 0.39 | 3.25 | 1.14 | 3.94E-03 | -2.55 | 5.87 |
| hsa-miR-486-3p | 2.60 | 1.12 | -0.11 | 1.75 | 3.23E-02 | -2.70 | 6.51 |
| hsa-miR-200b* | 5.18 | 0.30 | 2.47 | 2.18 | 4.45E-02 | -2.72 | 6.57 |
| hsa-miR-199b-5p | 9.67 | 0.16 | 5.87 | 1.73 | 3.51E-03 | -3.79 | 13.87 |
| hsa-miR-429 | 8.64 | 0.10 | 4.75 | 3.02 | 3.90E-02 | -3.89 | 14.80 |
| hsa-miR-200b | 11.06 | 0.20 | 7.16 | 3.18 | 4.65E-02 | -3.89 | 14.87 |
| hsa-miR-206 | 3.86 | 3.71 | -0.30 | 1.16 | 4.71E-02 | -4.17 | 17.96 |
| hsa-miR-200a | 9.93 | 0.13 | 5.59 | 3.11 | 2.85E-02 | -4.34 | 20.18 |

AVG, average expression among samples in a group;
SD, standard deviation.

Example 4 miRNA Expression Profiling Distinguishes Normal Thyroid Tissue and Follicular Thyroid Carcinoma A total of 415 human miRNAs were expressed above background level in the normal thyroid tissue samples, representing 48% of the human miRNAs present on the arrays. A total of 353 miRNAs were expressed above background level in the follicular thyroid carcinoma samples, representing 41% of the miRNAs present on the arrays.

A total of 100 human miRNAs were significantly differentially expressed between the normal samples and the follicular carcinoma specimens (p<0.05) (Table 6). Among these, 13 miRNAs were overexpressed (Log 2 diff (FTC vs NOR)≥1) and 36 were underexpressed (Log 2 diff (FTC vs NOR)≤1) by at least 2-fold in FTC compared to NOR. Of these, eight miRNAs (hsa-miR-375, -200a, -200b, -429, -873, -200b*, -199b-5p, and -200a*) were underexpressed by 5- to 10-fold in the FTC samples compared to the NOR samples (Table 6).

TABLE 6

MicroRNAs significantly differentially expressed between FTC and NOR samples.

| miRNA | NOR AVG | NOR SD | FTC AVG | FTC SD | FTC vs NOR ttest | FTC vs NOR Log2Diff | Fold change |
|---|---|---|---|---|---|---|---|
| hsa-miR-182 | 2.28 | 0.58 | 4.50 | 1.38 | 2.02E-02 | 2.23 | 4.7 |
| hsa-miR-96 | 7.46 | 0.37 | 9.53 | 1.14 | 1.06E-02 | 2.07 | 4.2 |
| hsa-miR-183* | 0.43 | 0.40 | 2.14 | 1.17 | 2.78E-02 | 1.71 | 3.3 |
| hsa-miR-1274a | 6.64 | 1.28 | 8.23 | 0.72 | 4.99E-02 | 1.59 | 3.0 |
| hsa-miR-183 | 6.09 | 0.54 | 7.67 | 1.17 | 4.18E-02 | 1.58 | 3.0 |
| hsa-miR-1274b | 10.21 | 1.23 | 11.77 | 0.70 | 4.80E-02 | 1.55 | 2.9 |
| hsa-miR-720 | 11.85 | 0.99 | 13.21 | 0.64 | 4.07E-02 | 1.36 | 2.6 |
| hsa-miR-1260 | 8.14 | 0.77 | 9.49 | 0.60 | 2.05E-02 | 1.35 | 2.6 |
| hsa-miR-181a* | 3.51 | 0.54 | 4.80 | 0.73 | 2.23E-02 | 1.29 | 2.4 |
| hsa-miR-34a | 10.87 | 0.11 | 12.03 | 0.62 | 8.67E-03 | 1.15 | 2.2 |
| hsa-miR-222* | -1.15 | 0.34 | -0.04 | 0.74 | 2.86E-02 | 1.11 | 2.2 |
| hsa-miR-182* | 0.03 | 0.20 | 1.12 | 0.70 | 1.95E-02 | 1.10 | 2.1 |
| hsa-miR-21 | 13.52 | 0.47 | 14.52 | 0.58 | 2.74E-02 | 1.00 | 2.0 |
| hsa-let-7g* | -0.08 | 0.50 | -1.09 | 0.50 | 1.98E-02 | -1.01 | 2.0 |
| hsa-miR-595 | 1.19 | 0.38 | 0.18 | 0.21 | 1.35E-03 | -1.01 | 2.0 |
| hsa-miR-1308 | 8.98 | 0.67 | 7.97 | 0.57 | 4.49E-02 | -1.01 | 2.0 |
| hsa-miR-452 | 4.97 | 0.26 | 3.94 | 0.77 | 3.95E-02 | -1.03 | 2.0 |
| hsa-miR-143 | 8.85 | 0.35 | 7.81 | 0.76 | 4.12E-02 | -1.04 | 2.1 |
| hsa-miR-365 | 9.80 | 0.45 | 8.76 | 0.49 | 1.34E-02 | -1.04 | 2.1 |
| hsa-miR-363 | 6.85 | 0.30 | 5.78 | 0.59 | 1.31E-02 | -1.07 | 2.1 |
| hsa-miR-218 | 8.86 | 0.27 | 7.78 | 0.57 | 1.03E-02 | -1.08 | 2.1 |
| hsa-miR-145* | 6.15 | 0.36 | 5.06 | 0.76 | 3.38E-02 | -1.09 | 2.1 |
| hsa-miR-10a* | 1.64 | 0.08 | 0.55 | 0.39 | 9.90E-04 | -1.10 | 2.1 |
| hsa-miR-23b* | 3.98 | 0.18 | 2.87 | 0.81 | 3.37E-02 | -1.11 | 2.2 |
| hsa-miR-193a-5p | 6.04 | 0.25 | 4.90 | 0.52 | 5.20E-03 | -1.14 | 2.2 |
| hsa-miR-224 | 5.97 | 0.07 | 4.74 | 0.67 | 8.56E-03 | -1.23 | 2.4 |
| hsa-miR-487a | 0.85 | 0.93 | -0.49 | 0.56 | 3.13E-02 | -1.34 | 2.5 |
| hsa-miR-145 | 11.11 | 0.39 | 9.75 | 0.89 | 2.61E-02 | -1.35 | 2.6 |
| hsa-miR-490-5p | 2.28 | 0.77 | 0.89 | 0.77 | 3.23E-02 | -1.38 | 2.6 |
| hsa-miR-154 | 3.92 | 0.39 | 2.45 | 1.01 | 3.00E-02 | -1.47 | 2.8 |
| hsa-miR-451 | 15.49 | 0.22 | 14.03 | 1.07 | 3.22E-02 | -1.47 | 2.8 |
| hsa-miR-100 | 12.09 | 0.35 | 10.62 | 0.75 | 8.97E-03 | -1.48 | 2.8 |
| hsa-miR-1246 | 9.20 | 0.88 | 7.69 | 0.96 | 4.51E-02 | -1.51 | 2.9 |
| hsa-miR-139-5p | 6.80 | 0.26 | 5.29 | 1.11 | 3.35E-02 | -1.52 | 2.9 |
| hsa-miR-199a-3p | 12.04 | 0.17 | 10.44 | 1.29 | 4.63E-02 | -1.59 | 3.0 |
| hsa-miR-486-5p | 8.85 | 0.51 | 7.25 | 0.96 | 2.05E-02 | -1.60 | 3.0 |

TABLE 6-continued

MicroRNAs significantly differentially expressed between FTC and NOR samples.

| miRNA | NOR AVG | NOR SD | FTC AVG | FTC SD | FTC vs NOR ttest | Log2Diff | Fold change |
|---|---|---|---|---|---|---|---|
| hsa-miR-876-3p | 2.91 | 0.40 | 1.27 | 0.55 | 1.60E−03 | −1.64 | 3.1 |
| hsa-miR-138 | 6.63 | 0.55 | 4.85 | 1.20 | 3.00E−02 | −1.78 | 3.4 |
| hsa-miR-214 | 9.59 | 0.15 | 7.78 | 1.27 | 2.68E−02 | −1.81 | 3.5 |
| hsa-miR-486-3p | 2.60 | 1.12 | 0.61 | 0.84 | 1.82E−02 | −1.99 | 4.0 |
| hsa-miR-10a | 8.66 | 0.40 | 6.67 | 1.02 | 8.21E−03 | −1.99 | 4.0 |
| hsa-miR-200a* | 4.59 | 0.21 | 2.23 | 1.29 | 9.07E−03 | −2.37 | 5.2 |
| hsa-miR-199b-5p | 9.67 | 0.16 | 7.23 | 1.94 | 4.28E−02 | −2.43 | 5.4 |
| hsa-miR-200b* | 5.18 | 0.30 | 2.61 | 1.38 | 8.66E−03 | −2.58 | 6.0 |
| hsa-miR-873 | 4.26 | 0.29 | 1.64 | 1.40 | 8.29E−03 | −2.62 | 6.2 |
| hsa-miR-429 | 8.64 | 0.10 | 5.86 | 2.18 | 4.08E−02 | −2.77 | 6.8 |
| hsa-miR-200b | 11.06 | 0.20 | 8.28 | 1.82 | 1.99E−02 | −2.78 | 6.9 |
| hsa-miR-200a | 9.93 | 0.13 | 7.09 | 2.00 | 2.70E−02 | −2.84 | 7.2 |
| hsa-miR-375 | 4.86 | 1.12 | 1.85 | 2.10 | 3.74E−02 | −3.01 | 8.0 |

AVG, average expression among samples in a group;
SD, standard deviation.

Example 5 miRNA Expression Profiling Distinguishes Normal Thyroid Tissue and Papillary Thyroid Carcinoma A total of 415 human miRNAs were expressed above background level in the normal thyroid tissue samples, representing 48% of the human miRNAs present on the arrays. A total of 354 miRNAs were expressed above background level in the papillary thyroid carcinoma samples, representing 41% of the miRNAs present on the arrays.

A total of 219 human miRNAs were significantly differentially expressed between the normal samples and the papillary carcinoma specimens ($p<0.05$) (Table 7). Among these, 22 miRNAs were overexpressed (Log 2 diff (PTC vs NOR)≥1) and 121 were underexpressed (Log 2 diff (PTC vs NOR)≤1) by at least 2-fold in PTC compared to NOR. Of these, hsa-miR-146b-5p was overexpressed by more than 110-fold in the PTC samples; five miRNAs (hsa-miR-551b, -146b-3p, -222, -221, and -221*) were overexpressed by 10- to 30-fold in the PTC samples, and three miRNAs (hsa-miR-31*, -31, and -21) were overexpressed by 5- to 10-fold in the PTC samples. Among the miRNAs that were expressed at lower average levels in PTC samples, six miRNAs (hsa-miR-1, -7, -206, -7, -2*, -873, and -204) were underexpressed by 10- to 20-fold, and thirteen miRNAs were underexpressed by 5- and 10-fold in the PTC samples.

TABLE 7

MicroRNAs significantly differentially expressed between PTC and NOR samples.

| miRNA | NOR AVG | NOR SD | PTC AVG | PTC SD | NOR vs PTC ttest | Log2Diff | Fold change |
|---|---|---|---|---|---|---|---|
| hsa-miR-1 | 9.59 | 3.43 | 5.41 | 1.45 | 4.14E−02 | 4.18 | 18.2 |
| hsa-miR-7 | 11.38 | 0.51 | 7.30 | 1.72 | 2.70E−03 | 4.08 | 16.9 |
| hsa-miR-206 | 3.86 | 3.71 | −0.07 | 0.40 | 4.79E−02 | 3.93 | 15.2 |
| hsa-miR-7-2* | 4.72 | 0.59 | 1.08 | 1.28 | 1.21E−03 | 3.65 | 12.5 |
| hsa-miR-873 | 4.26 | 0.29 | 0.81 | 0.78 | 7.17E−05 | 3.45 | 10.9 |
| hsa-miR-204 | 8.70 | 0.83 | 5.26 | 0.80 | 4.03E−04 | 3.45 | 10.9 |
| hsa-miR-631 | 2.11 | 0.89 | −0.92 | 0.83 | 1.12E−03 | 3.03 | 8.2 |
| hsa-miR-92b* | 1.01 | 2.20 | −1.87 | 0.74 | 2.71E−02 | 2.88 | 7.4 |
| hsa-miR-486-5p | 8.85 | 0.51 | 6.05 | 0.90 | 9.11E−04 | 2.80 | 7.0 |
| hsa-miR-144 | 8.24 | 0.32 | 5.48 | 1.15 | 2.51E−03 | 2.76 | 6.8 |
| hsa-miR-765 | 4.95 | 0.59 | 2.28 | 0.68 | 4.49E−04 | 2.67 | 6.4 |
| hsa-miR-451 | 15.49 | 0.22 | 12.86 | 0.80 | 4.10E−04 | 2.63 | 6.2 |
| hsa-miR-144* | 6.62 | 0.32 | 4.08 | 0.88 | 9.59E−04 | 2.54 | 5.8 |
| hsa-miR-876-3p | 2.91 | 0.40 | 0.41 | 0.55 | 1.24E−04 | 2.51 | 5.7 |
| hsa-miR-486-3p | 2.60 | 1.12 | 0.10 | 1.00 | 9.44E−03 | 2.50 | 5.7 |
| hsa-miR-149* | 2.76 | 0.59 | 0.27 | 0.56 | 3.42E−04 | 2.49 | 5.6 |
| hsa-miR-659 | 3.79 | 0.65 | 1.42 | 0.91 | 3.34E−03 | 2.37 | 5.2 |
| hsa-miR-483-5p | 6.87 | 0.23 | 4.52 | 0.79 | 7.40E−04 | 2.35 | 5.1 |
| hsa-miR-1246 | 9.20 | 0.88 | 6.87 | 1.37 | 2.19E−02 | 2.33 | 5.0 |
| hsa-miR-648 | 2.26 | 1.24 | −0.03 | 0.72 | 1.00E−02 | 2.29 | 4.9 |
| hsa-miR-1182 | 2.94 | 0.45 | 0.68 | 0.68 | 7.17E−04 | 2.26 | 4.8 |
| hsa-miR-1471 | 4.55 | 0.27 | 2.31 | 0.52 | 1.15E−04 | 2.24 | 4.7 |
| hsa-miR-936 | 2.56 | 0.47 | 0.34 | 0.48 | 2.16E−04 | 2.22 | 4.7 |
| hsa-miR-1915* | 0.74 | 0.45 | −1.44 | 0.82 | 2.19E−03 | 2.18 | 4.5 |
| hsa-miR-1300 | 5.66 | 1.41 | 3.48 | 0.76 | 2.05E−02 | 2.18 | 4.5 |
| hsa-miR-363 | 6.85 | 0.30 | 4.69 | 0.85 | 2.01E−03 | 2.16 | 4.5 |
| hsa-miR-198 | 2.98 | 0.64 | 0.85 | 0.77 | 2.99E−03 | 2.14 | 4.4 |
| hsa-miR-663 | 6.18 | 0.82 | 4.09 | 0.76 | 5.54E−03 | 2.08 | 4.2 |
| hsa-miR-499-5p | 5.78 | 1.61 | 3.72 | 0.45 | 2.79E−02 | 2.06 | 4.2 |

TABLE 7-continued

MicroRNAs significantly differentially expressed between PTC and NOR samples.

| miRNA | NOR AVG | NOR SD | PTC AVG | PTC SD | NOR vs PTC ttest | Log2Diff | Fold change |
|---|---|---|---|---|---|---|---|
| hsa-miR-623 | 3.09 | 0.84 | 1.05 | 1.06 | 1.64E−02 | 2.04 | 4.1 |
| hsa-miR-630 | 6.04 | 0.36 | 4.01 | 1.11 | 1.01E−02 | 2.03 | 4.1 |
| hsa-miR-1183 | 4.64 | 0.50 | 2.62 | 0.61 | 1.04E−03 | 2.03 | 4.1 |
| hsa-miR-671-5p | 5.77 | 0.20 | 3.74 | 0.72 | 1.04E−03 | 2.03 | 4.1 |
| hsa-miR-1202 | 11.03 | 0.86 | 9.02 | 0.95 | 1.31E−02 | 2.01 | 4.0 |
| hsa-miR-138 | 6.63 | 0.55 | 4.62 | 1.08 | 1.19E−02 | 2.01 | 4.0 |
| hsa-miR-187* | 2.81 | 0.38 | 0.80 | 0.86 | 3.72E−03 | 2.00 | 4.0 |
| hsa-miR-422a | 2.78 | 0.27 | 0.82 | 1.09 | 1.04E−02 | 1.96 | 3.9 |
| hsa-miR-1321 | 2.13 | 1.05 | 0.17 | 0.39 | 5.88E−03 | 1.96 | 3.9 |
| hsa-miR-516a-5p | 3.37 | 1.12 | 1.43 | 0.65 | 1.34E−02 | 1.94 | 3.8 |
| hsa-miR-1228* | 0.49 | 0.88 | −1.42 | 0.60 | 5.86E−03 | 1.91 | 3.8 |
| hsa-miR-1469 | 2.18 | 0.70 | 0.27 | 1.30 | 3.42E−02 | 1.91 | 3.8 |
| hsa-miR-493 | 1.16 | 0.73 | −0.73 | 0.79 | 7.59E−03 | 1.90 | 3.7 |
| hsa-miR-199b-5p | 9.67 | 0.16 | 7.78 | 1.31 | 2.61E−02 | 1.88 | 3.7 |
| hsa-miR-1909* | 0.62 | 0.25 | −1.25 | 0.45 | 1.54E−04 | 1.87 | 3.7 |
| hsa-miR-583 | 1.29 | 0.37 | −0.56 | 0.48 | 4.00E−04 | 1.85 | 3.6 |
| hsa-miR-1291 | 1.56 | 0.68 | −0.24 | 0.49 | 2.41E−03 | 1.80 | 3.5 |
| hsa-miR-877 | 3.24 | 0.44 | 1.45 | 1.15 | 2.28E−02 | 1.79 | 3.5 |
| hsa-miR-1268 | 8.34 | 0.66 | 6.57 | 0.52 | 2.81E−03 | 1.77 | 3.4 |
| hsa-miR-145 | 11.11 | 0.39 | 9.37 | 0.28 | 1.05E−04 | 1.73 | 3.3 |
| hsa-miR-152 | 7.88 | 0.23 | 6.19 | 0.48 | 3.69E−04 | 1.69 | 3.2 |
| hsa-miR-1224-5p | 5.95 | 0.48 | 4.26 | 0.47 | 1.11E−03 | 1.69 | 3.2 |
| hsa-miR-150* | 5.58 | 0.63 | 3.89 | 0.62 | 5.16E−03 | 1.68 | 3.2 |
| hsa-miR-373* | 1.91 | 0.35 | 0.24 | 0.68 | 3.14E−03 | 1.67 | 3.2 |
| hsa-miR-371-5p | 4.45 | 0.52 | 2.81 | 0.43 | 1.24E−03 | 1.64 | 3.1 |
| hsa-miR-365 | 9.80 | 0.45 | 8.16 | 0.64 | 3.40E−03 | 1.64 | 3.1 |
| hsa-miR-345 | 4.50 | 0.63 | 2.86 | 0.49 | 3.03E−03 | 1.64 | 3.1 |
| hsa-miR-638 | 8.93 | 0.61 | 7.32 | 0.50 | 3.27E−03 | 1.61 | 3.1 |
| hsa-miR-1180 | 2.38 | 0.14 | 0.78 | 0.98 | 1.52E−02 | 1.60 | 3.0 |
| hsa-miR-939 | 7.35 | 0.82 | 5.75 | 0.45 | 7.25E−03 | 1.60 | 3.0 |
| hsa-miR-381 | 4.34 | 0.54 | 2.75 | 1.08 | 3.15E−02 | 1.59 | 3.0 |
| hsa-miR-526b | 1.91 | 0.43 | 0.32 | 0.75 | 7.06E−03 | 1.59 | 3.0 |
| hsa-miR-145* | 6.15 | 0.36 | 4.58 | 0.41 | 4.99E−04 | 1.58 | 3.0 |
| hsa-miR-1225-5p | 9.85 | 0.45 | 8.28 | 0.48 | 1.56E−03 | 1.57 | 3.0 |
| hsa-miR-134 | 6.13 | 0.47 | 4.56 | 0.60 | 3.81E−03 | 1.57 | 3.0 |
| hsa-miR-1207-5p | 9.76 | 0.49 | 8.19 | 0.66 | 5.75E−03 | 1.57 | 3.0 |
| hsa-miR-1308 | 8.98 | 0.67 | 7.42 | 0.76 | 1.50E−02 | 1.56 | 2.9 |
| hsa-miR-148a* | 1.75 | 0.37 | 0.21 | 0.94 | 1.80E−02 | 1.55 | 2.9 |
| hsa-miR-572 | 5.63 | 0.90 | 4.08 | 0.45 | 1.20E−02 | 1.54 | 2.9 |
| hsa-miR-298 | 0.75 | 0.85 | −0.78 | 0.66 | 1.81E−02 | 1.53 | 2.9 |
| hsa-miR-143 | 8.85 | 0.35 | 7.32 | 0.28 | 1.67E−04 | 1.53 | 2.9 |
| hsa-miR-566 | 1.31 | 0.55 | −0.20 | 0.64 | 6.95E−03 | 1.52 | 2.9 |
| hsa-miR-135a* | 5.11 | 0.38 | 3.61 | 0.32 | 3.36E−04 | 1.50 | 2.8 |
| hsa-miR-1203 | 0.42 | 0.97 | −1.06 | 0.52 | 2.10E−02 | 1.48 | 2.8 |
| hsa-miR-138-1* | −0.09 | 1.17 | −1.55 | 0.61 | 4.52E−02 | 1.46 | 2.7 |
| hsa-miR-622 | 3.86 | 0.82 | 2.40 | 0.69 | 2.31E−02 | 1.45 | 2.7 |
| hsa-miR-195* | 1.65 | 0.33 | 0.21 | 0.87 | 1.73E−02 | 1.44 | 2.7 |
| hsa-miR-214 | 9.59 | 0.15 | 8.16 | 0.85 | 1.33E−02 | 1.43 | 2.7 |
| hsa-miR-652 | 6.64 | 0.19 | 5.22 | 0.29 | 6.92E−05 | 1.43 | 2.7 |
| hsa-miR-886-5p | −0.28 | 1.12 | −1.68 | 0.30 | 2.98E−02 | 1.40 | 2.6 |
| hsa-miR-584 | 3.41 | 0.30 | 2.03 | 0.45 | 1.15E−03 | 1.38 | 2.6 |
| hsa-miR-329 | 1.45 | 0.43 | 0.08 | 0.64 | 8.19E−03 | 1.37 | 2.6 |
| hsa-miR-299-5p | 3.80 | 0.43 | 2.45 | 0.92 | 3.16E−02 | 1.35 | 2.5 |
| hsa-miR-518a-5p | 0.89 | 0.75 | −0.45 | 0.45 | 1.23E−02 | 1.34 | 2.5 |
| hsa-miR-934 | −0.51 | 1.01 | −1.85 | 0.68 | 4.92E−02 | 1.34 | 2.5 |
| hsa-miR-490-3p | 0.19 | 0.61 | −1.13 | 0.67 | 1.82E−02 | 1.32 | 2.5 |
| hsa-miR-1915 | 8.41 | 0.52 | 7.09 | 0.28 | 1.76E−03 | 1.32 | 2.5 |
| hsa-miR-193b | 8.34 | 0.80 | 7.03 | 0.79 | 4.44E−02 | 1.31 | 2.5 |
| hsa-miR-129-5p | 1.45 | 0.57 | 0.15 | 0.60 | 1.27E−02 | 1.31 | 2.5 |
| hsa-miR-10a | 8.66 | 0.40 | 7.36 | 0.58 | 6.93E−03 | 1.30 | 2.5 |
| hsa-miR-370 | 2.41 | 0.50 | 1.11 | 0.79 | 2.49E−02 | 1.30 | 2.5 |
| hsa-miR-411 | 2.19 | 0.44 | 0.89 | 0.65 | 1.16E−02 | 1.30 | 2.5 |
| hsa-miR-193b* | 4.44 | 0.44 | 3.15 | 0.31 | 1.24E−03 | 1.29 | 2.5 |
| hsa-miR-139-5p | 6.80 | 0.26 | 5.51 | 0.53 | 3.02E−03 | 1.29 | 2.4 |
| hsa-miR-126* | 6.87 | 0.34 | 5.58 | 0.62 | 7.53E−03 | 1.29 | 2.4 |
| hsa-miR-601 | 3.90 | 0.46 | 2.62 | 0.73 | 1.87E−02 | 1.28 | 2.4 |
| hsa-miR-662 | 2.26 | 0.34 | 0.98 | 0.16 | 1.47E−04 | 1.27 | 2.4 |
| hsa-miR-148b | 9.01 | 0.40 | 7.77 | 0.67 | 1.46E−02 | 1.24 | 2.4 |
| hsa-miR-498 | 2.26 | 0.47 | 1.03 | 0.60 | 1.18E−02 | 1.23 | 2.3 |
| hsa-miR-148a | 11.27 | 0.26 | 10.07 | 0.84 | 2.97E−02 | 1.20 | 2.3 |
| hsa-miR-516b | 1.14 | 0.79 | −0.04 | 0.28 | 1.67E−02 | 1.18 | 2.3 |
| hsa-miR-617 | 1.64 | 0.66 | 0.47 | 0.50 | 1.86E−02 | 1.17 | 2.3 |
| hsa-miR-490-5p | 2.28 | 0.77 | 1.10 | 0.47 | 2.58E−02 | 1.17 | 2.3 |
| hsa-miR-485-3p | 0.94 | 0.89 | −0.23 | 0.51 | 4.11E−02 | 1.17 | 2.2 |

TABLE 7-continued

MicroRNAs significantly differentially expressed between PTC and NOR samples.

| miRNA | NOR AVG | NOR SD | PTC AVG | PTC SD | NOR vs PTC ttest | Log2Diff | Fold change |
|---|---|---|---|---|---|---|---|
| hsa-miR-518c* | 0.63 | 0.75 | −0.49 | 0.55 | 3.58E−02 | 1.12 | 2.2 |
| hsa-miR-199a-5p | 10.41 | 0.25 | 9.29 | 0.76 | 2.80E−02 | 1.11 | 2.2 |
| hsa-miR-616 | −0.08 | 0.59 | −1.19 | 0.58 | 2.53E−02 | 1.11 | 2.2 |
| hsa-miR-640 | −0.04 | 0.54 | −1.15 | 0.15 | 2.86E−03 | 1.11 | 2.2 |
| hsa-miR-188-5p | 5.77 | 0.44 | 4.66 | 0.39 | 4.83E−03 | 1.11 | 2.2 |
| hsa-miR-30c | 11.51 | 0.24 | 10.41 | 0.58 | 1.01E−02 | 1.10 | 2.1 |
| hsa-miR-501-3p | 3.91 | 0.68 | 2.83 | 0.27 | 1.34E−02 | 1.08 | 2.1 |
| hsa-miR-34c-3p | −0.35 | 0.70 | −1.42 | 0.20 | 1.32E−02 | 1.07 | 2.1 |
| hsa-miR-887 | 3.89 | 0.46 | 2.82 | 0.46 | 1.02E−02 | 1.07 | 2.1 |
| hsa-miR-199a-3p | 12.04 | 0.17 | 10.98 | 0.71 | 2.31E−02 | 1.06 | 2.1 |
| hsa-miR-557 | 5.01 | 0.53 | 3.95 | 0.56 | 2.36E−02 | 1.06 | 2.1 |
| hsa-miR-29b-2* | 2.05 | 0.28 | 0.99 | 0.44 | 4.23E−03 | 1.06 | 2.1 |
| hsa-miR-497 | 9.77 | 0.27 | 8.74 | 0.47 | 6.23E−03 | 1.03 | 2.0 |
| hsa-miR-1910 | −0.88 | 0.50 | −1.90 | 0.24 | 4.81E−03 | 1.02 | 2.0 |
| hsa-miR-124 | 0.64 | 0.46 | −0.38 | 0.31 | 5.68E−03 | 1.02 | 2.0 |
| hsa-miR-654-5p | 2.99 | 0.39 | 1.98 | 0.52 | 1.46E−02 | 1.01 | 2.0 |
| hsa-miR-130b | 7.56 | 0.39 | 6.55 | 0.21 | 1.54E−03 | 1.01 | 2.0 |
| hsa-miR-195 | 11.57 | 0.26 | 10.57 | 0.40 | 3.44E−03 | 1.00 | 2.0 |
| hsa-miR-892b | 4.74 | 0.18 | 5.77 | 0.82 | 4.49E−02 | −1.04 | 2.0 |
| hsa-miR-34b* | 6.54 | 0.12 | 7.62 | 0.54 | 6.35E−03 | −1.08 | 2.1 |
| hsa-miR-1305 | 7.19 | 0.23 | 8.28 | 0.53 | 6.82E−03 | −1.09 | 2.1 |
| hsa-miR-15a | 10.87 | 0.25 | 12.01 | 0.32 | 6.19E−04 | −1.14 | 2.2 |
| hsa-miR-181a | 10.09 | 0.53 | 11.28 | 0.33 | 4.32E−03 | −1.19 | 2.3 |
| hsa-miR-503 | 4.49 | 0.24 | 5.74 | 0.81 | 2.20E−02 | −1.24 | 2.4 |
| hsa-miR-34a* | 3.71 | 0.15 | 5.07 | 0.21 | 1.22E−05 | −1.36 | 2.6 |
| hsa-miR-181b | 8.08 | 0.58 | 9.59 | 0.52 | 4.57E−03 | −1.51 | 2.8 |
| hsa-miR-222* | −1.15 | 0.34 | 0.46 | 0.73 | 4.92E−03 | −1.61 | 3.0 |
| hsa-miR-181a-2* | 4.53 | 0.63 | 6.23 | 0.66 | 5.62E−03 | −1.70 | 3.3 |
| hsa-miR-34a | 10.87 | 0.11 | 12.59 | 0.24 | 3.29E−06 | −1.72 | 3.3 |
| hsa-miR-375 | 4.86 | 1.12 | 6.74 | 1.20 | 4.70E−02 | −1.88 | 3.7 |
| hsa-miR-514 | 0.86 | 0.32 | 2.93 | 0.86 | 2.70E−03 | −2.07 | 4.2 |
| hsa-miR-21 | 13.52 | 0.47 | 15.85 | 0.45 | 1.36E−04 | −2.32 | 5.0 |
| hsa-miR-31 | 7.66 | 0.63 | 10.14 | 0.64 | 6.61E−04 | −2.49 | 5.6 |
| hsa-miR-31* | 6.00 | 0.62 | 8.58 | 0.56 | 3.21E−04 | −2.57 | 6.0 |
| hsa-miR-221* | 5.03 | 0.35 | 8.71 | 0.86 | 9.54E−05 | −3.68 | 12.9 |
| hsa-miR-221 | 6.75 | 0.27 | 10.60 | 0.73 | 2.24E−05 | −3.85 | 14.4 |
| hsa-miR-222 | 5.87 | 0.13 | 10.25 | 0.58 | 1.75E−06 | −4.37 | 20.7 |
| hsa-miR-146b-3p | −0.93 | 0.25 | 3.73 | 1.12 | 8.80E−05 | −4.65 | 25.2 |
| hsa-miR-551b | 5.24 | 0.48 | 9.98 | 0.58 | 3.63E−06 | −4.74 | 26.7 |
| hsa-miR-146b-5p | 7.54 | 0.54 | 14.41 | 0.92 | 3.58E−06 | −6.87 | 116.6 |

AVG, average expression among samples in a group;
SD, standard deviation.

Example 6 miRNA Expression Profiling Distinguishes Normal Thyroid Tissue and the Follicular Variant of Papillary Thyroid Carcinoma A total of 415 human miRNAs were expressed above background level in the normal thyroid tissue samples, representing 48% of the human miRNAs present on the arrays. A total of 346 miRNAs were expressed above background level in the follicular variant of papillary thyroid carcinoma samples, representing 40% of the miRNAs present on the arrays.

A total of 126 human miRNAs were significantly differentially expressed between the normal samples and the follicular variant of papillary carcinoma specimens (p<0.05). Among these, 14 miRNAs were overexpressed (Log 2 diff (FVPTC vs NOR)≥1) and 50 were underexpressed (Log 2 diff (FVPTC vs NOR)≤1) by at least 2-fold in FVPTC compared to NOR (Table 8). Of these, hsa-miR-146b-5p was overexpressed by 50-fold in the FVPTC samples, hsa-miR-222, -551b, -221, and -146b-3p were overexpressed by 10- to 14-fold in the FVPTC samples, and hsa-miR-221*, -31*, and -31) were overexpressed by 5- to 10-fold in the FVPTC samples. Among the miRNAs that were expressed at lower average levels in FVPTC samples, hsa-miR-7 and -873 were underexpressed by 10- to 20-fold in the FVPTC samples, and hsa-miR-204, -7-2*, and -199b-5p were underexpressed by 5- to 10-fold in the FVPTC samples.

TABLE 8

MicroRNAs significantly differentially expressed between FVPTC and NOR samples.

| miRNA | NOR | | FVPTC | | FVPTC vs NOR | | |
|---|---|---|---|---|---|---|---|
| | AVG | SD | AVG | SD | ttest | Log2Diff | Fold change |
| hsa-miR-146b-5p | 7.54 | 0.54 | 13.20 | 1.09 | 8.62E−05 | 5.66 | 50.5 |
| hsa-miR-222 | 5.87 | 0.13 | 9.66 | 0.79 | 7.99E−05 | 3.79 | 13.8 |
| hsa-miR-551b | 5.24 | 0.48 | 8.99 | 0.76 | 1.64E−04 | 3.75 | 13.4 |
| hsa-miR-221 | 6.75 | 0.27 | 10.19 | 0.98 | 5.17E−04 | 3.44 | 10.9 |
| hsa-miR-146b-3p | −0.93 | 0.25 | 2.46 | 1.30 | 2.17E−03 | 3.39 | 10.5 |
| hsa-miR-221* | 5.03 | 0.35 | 8.06 | 0.85 | 5.98E−04 | 3.03 | 8.2 |
| hsa-miR-31* | 6.00 | 0.62 | 8.47 | 1.06 | 6.94E−03 | 2.46 | 5.5 |
| hsa-miR-31 | 7.66 | 0.63 | 10.06 | 1.12 | 9.65E−03 | 2.40 | 5.3 |
| hsa-miR-222* | −1.15 | 0.34 | 0.85 | 0.42 | 3.21E−02 | 2.00 | 4.0 |
| hsa-miR-503 | 4.49 | 0.24 | 6.07 | 1.04 | 2.58E−02 | 1.57 | 3.0 |
| hsa-miR-34a | 10.87 | 0.11 | 12.33 | 0.27 | 5.15E−05 | 1.46 | 2.7 |
| hsa-miR-21 | 13.52 | 0.47 | 14.94 | 0.64 | 1.18E−02 | 1.42 | 2.7 |
| hsa-miR-181b | 8.08 | 0.58 | 9.48 | 0.84 | 3.36E−02 | 1.40 | 2.6 |
| hsa-miR-34a* | 3.71 | 0.15 | 4.76 | 0.31 | 8.68E−04 | 1.05 | 2.1 |
| hsa-miR-29c* | 7.86 | 0.25 | 6.86 | 0.34 | 3.09E−03 | −1.00 | 2.0 |
| hsa-miR-30c | 11.51 | 0.24 | 10.51 | 0.51 | 1.21E−02 | −1.01 | 2.0 |
| hsa-miR-210 | 6.28 | 0.41 | 5.26 | 0.39 | 1.12E−02 | −1.02 | 2.0 |
| hsa-miR-362-3p | 6.25 | 0.35 | 5.23 | 0.41 | 8.68E−03 | −1.03 | 2.0 |
| hsa-miR-193b* | 4.44 | 0.44 | 3.41 | 0.46 | 1.75E−02 | −1.03 | 2.0 |
| hsa-miR-532-3p | 6.16 | 0.20 | 5.10 | 0.09 | 5.91E−05 | −1.06 | 2.1 |
| hsa-miR-136 | 3.60 | 0.47 | 2.50 | 0.44 | 1.41E−02 | −1.10 | 2.1 |
| hsa-miR-199a-5p | 10.41 | 0.25 | 9.31 | 0.27 | 1.03E−03 | −1.10 | 2.1 |
| hsa-miR-455-5p | 4.70 | 0.09 | 3.57 | 0.63 | 1.21E−02 | −1.13 | 2.2 |
| hsa-miR-214 | 9.59 | 0.15 | 8.46 | 0.48 | 3.98E−03 | −1.14 | 2.2 |
| hsa-miR-377 | 4.48 | 0.60 | 3.32 | 0.35 | 1.54E−02 | −1.16 | 2.2 |
| hsa-miR-329 | 1.45 | 0.43 | 0.28 | 0.26 | 3.62E−03 | −1.17 | 2.2 |
| hsa-miR-495 | 3.64 | 0.76 | 2.45 | 0.45 | 3.56E−02 | −1.19 | 2.3 |
| hsa-miR-199a-3p | 12.04 | 0.17 | 10.82 | 0.41 | 1.50E−03 | −1.21 | 2.3 |
| hsa-miR-369-5p | 2.10 | 0.30 | 0.89 | 0.48 | 5.32E−03 | −1.21 | 2.3 |
| hsa-miR-652 | 6.64 | 0.19 | 5.43 | 0.43 | 2.14E−02 | −1.21 | 2.3 |
| hsa-miR-139-5p | 6.80 | 0.26 | 5.57 | 0.68 | 1.51E−02 | −1.23 | 2.3 |
| hsa-miR-214* | 4.54 | 0.23 | 3.31 | 0.30 | 5.87E−04 | −1.23 | 2.3 |
| hsa-miR-148a | 11.27 | 0.26 | 10.02 | 0.33 | 9.76E−04 | −1.24 | 2.4 |
| hsa-miR-148a* | 1.75 | 0.37 | 0.48 | 0.48 | 5.82E−03 | −1.28 | 2.4 |
| hsa-miR-22* | 5.56 | 0.65 | 4.29 | 0.52 | 2.22E−02 | −1.28 | 2.4 |
| hsa-miR-143 | 8.85 | 0.35 | 7.56 | 0.83 | 2.92E−02 | −1.28 | 2.4 |
| hsa-miR-337-5p | 3.33 | 0.35 | 2.04 | 0.52 | 6.37E−03 | −1.29 | 2.4 |
| hsa-miR-145 | 11.11 | 0.39 | 9.81 | 0.83 | 3.00E−02 | −1.29 | 2.5 |
| hsa-miR-144 | 8.24 | 0.32 | 6.93 | 0.46 | 3.39E−03 | −1.31 | 2.5 |
| hsa-miR-144* | 6.62 | 0.32 | 5.25 | 1.07 | 4.89E−02 | −1.38 | 2.6 |
| hsa-miR-154 | 3.92 | 0.39 | 2.54 | 0.38 | 2.26E−03 | −1.38 | 2.6 |
| hsa-miR-379 | 3.13 | 0.51 | 1.74 | 0.86 | 3.16E−02 | −1.39 | 2.6 |
| hsa-miR-345 | 4.50 | 0.63 | 3.11 | 0.68 | 2.39E−02 | −1.39 | 2.6 |
| hsa-miR-376c | 6.27 | 0.41 | 4.84 | 0.47 | 3.70E−03 | −1.43 | 2.7 |
| hsa-miR-654-3p | 3.97 | 0.25 | 2.50 | 0.40 | 7.43E−04 | −1.47 | 2.8 |
| hsa-miR-152 | 7.88 | 0.23 | 6.38 | 0.23 | 8.99E−05 | −1.50 | 2.8 |
| hsa-miR-299-5p | 3.80 | 0.43 | 2.29 | 0.48 | 3.53E−03 | −1.51 | 2.8 |
| hsa-miR-9 | 1.92 | 0.34 | 0.41 | 0.75 | 1.04E−02 | −1.51 | 2.8 |
| hsa-miR-381 | 4.34 | 0.54 | 2.81 | 0.74 | 1.53E−02 | −1.54 | 2.9 |
| hsa-miR-193b | 8.34 | 0.80 | 6.75 | 0.59 | 1.90E−02 | −1.58 | 3.0 |
| hsa-miR-1915* | 0.74 | 0.45 | −0.87 | 0.78 | 1.17E−02 | −1.60 | 3.0 |
| hsa-miR-551b* | 0.88 | 1.01 | −0.79 | 0.69 | 3.42E−02 | −1.67 | 3.2 |
| hsa-miR-136* | 3.09 | 0.50 | 1.39 | 0.40 | 1.87E−03 | −1.70 | 3.2 |
| hsa-miR-376a | 5.80 | 0.39 | 4.10 | 0.40 | 9.12E−04 | −1.71 | 3.3 |
| hsa-miR-138 | 6.63 | 0.55 | 4.85 | 0.81 | 1.07E−02 | −1.78 | 3.4 |
| hsa-miR-639 | 0.53 | 1.01 | −1.31 | 0.68 | 2.38E−02 | −1.83 | 3.6 |
| hsa-miR-365 | 9.80 | 0.45 | 7.90 | 0.40 | 7.41E−04 | −1.90 | 3.7 |
| hsa-miR-876-3p | 2.91 | 0.40 | 0.79 | 0.91 | 5.28E−03 | −2.12 | 4.4 |
| hsa-miR-129-5p | 1.45 | 0.57 | −0.79 | 1.02 | 8.52E−03 | −2.24 | 4.7 |
| hsa-miR-199b-5p | 9.67 | 0.16 | 7.31 | 0.64 | 3.76E−04 | −2.36 | 5.1 |
| hsa-miR-7-2* | 4.72 | 0.59 | 1.75 | 1.62 | 1.38E−02 | −2.97 | 7.8 |
| hsa-miR-204 | 8.70 | 0.83 | 5.44 | 2.07 | 2.63E−02 | −3.27 | 9.6 |
| hsa-miR-873 | 4.26 | 0.29 | 0.89 | 1.45 | 3.88E−03 | −3.37 | 10.3 |
| hsa-miR-7 | 11.38 | 0.51 | 7.22 | 2.56 | 1.90E−02 | −4.16 | 17.9 |

AVG, average expression among samples in a group;
SD, standard deviation.

Example 7 miRNA Expression Profiling Distinguishes Normal Thyroid Tissue and Anaplastic Thyroid Carcinoma A total of 415 human miRNAs were expressed above background level in the normal thyroid tissue samples, representing 48% of the human miRNAs present on the arrays. A total of 330 miRNAs were expressed above background level in the anaplastic thyroid cancer sample, representing 38% of the miRNAs present on the arrays.

A total of 178 human miRNAs were significantly differentially expressed between the normal samples and the anaplastic thyroid carcinoma specimen ($p<0.05$). Among these, 32 miRNAs were overexpressed (Log 2 diff (ATC vs NOR)$\geq 1$) and 124 were underexpressed (Log 2 diff (ATC vs NOR)$\leq 1$) by at least 2-fold in ATC compared to NOR. Of these, hsa-miR-582-3p and hsa-miR-9* were overexpressed by 30- to 40-fold in the ATC sample, hsa-miR-582-5p, -34c-5p, 124 were overexpressed by 10- to 20-fold in the ATC sample, and hsa-miR-9, -34b, -21, and -210 were overexpressed by 5- to 10-fold in the ATC sample (Table 9). Among the miRNAs that were expressed at lower average levels in the ATC sample, eight (miR-429, -141, -200c, 200a, -200b, -135b, -135a, and -205) were underexpressed by 100- to 420-fold, hsa-miR-138 and hsa-miR-7-2* were underexpressed by 50- to 100-fold, and twenty two miRNAs were expressed at levels between 10- and 40-fold lower in the ATC specimen compared to the NOR samples (Table 9).

TABLE 9

MicroRNAs significantly differentially expressed between ATC and NOR samples.

| miRNA | NOR AVG | NOR SD | ATC | ATC vs NOR ttest | Log2Diff | Fold change |
|---|---|---|---|---|---|---|
| hsa-miR-582-3p | −1.21 | 0.32 | 3.97 | 6.88E−04 | 5.18 | 36.3 |
| hsa-miR-9* | 2.09 | 0.66 | 7.14 | 6.51E−03 | 5.05 | 33.2 |
| hsa-miR-582-5p | 4.27 | 0.39 | 8.42 | 2.40E−03 | 4.15 | 17.7 |
| hsa-miR-34c-5p | 3.81 | 0.36 | 7.37 | 3.18E−03 | 3.55 | 11.7 |
| hsa-miR-124 | 0.64 | 0.46 | 4.16 | 6.56E−03 | 3.52 | 11.5 |
| hsa-miR-9 | 1.92 | 0.34 | 5.05 | 3.66E−03 | 3.13 | 8.7 |
| hsa-miR-34b | 1.95 | 0.51 | 4.65 | 1.81E−02 | 2.70 | 6.5 |
| hsa-miR-21 | 13.52 | 0.47 | 16.00 | 1.84E−02 | 2.48 | 5.6 |
| hsa-miR-210 | 6.28 | 0.41 | 8.74 | 1.25E−02 | 2.45 | 5.5 |
| hsa-miR-592 | 2.46 | 0.28 | 4.74 | 5.25E−03 | 2.28 | 4.9 |
| hsa-miR-34b* | 6.54 | 0.12 | 8.43 | 7.36E−04 | 1.89 | 3.7 |
| hsa-miR-10a | 8.66 | 0.40 | 10.38 | 3.16E−03 | 1.72 | 3.3 |
| hsa-miR-153 | 2.34 | 0.28 | 3.92 | 1.50E−02 | 1.58 | 3.0 |
| hsa-miR-769-5p | 4.90 | 0.24 | 6.42 | 1.08E−02 | 1.52 | 2.9 |
| hsa-miR-550* | 2.80 | 0.18 | 4.14 | 7.27E−03 | 1.34 | 2.5 |
| hsa-miR-30a* | 8.99 | 0.37 | 10.32 | 4.79E−02 | 1.33 | 2.5 |
| hsa-miR-149 | 3.96 | 0.22 | 5.28 | 1.25E−02 | 1.32 | 2.5 |
| hsa-miR-449a | 3.23 | 0.21 | 4.52 | 1.17E−02 | 1.29 | 2.4 |
| hsa-miR-30a | 12.09 | 0.31 | 13.36 | 3.57E−02 | 1.27 | 2.4 |
| hsa-miR-873 | 4.26 | 0.29 | 5.52 | 3.14E−02 | 1.26 | 2.4 |
| hsa-miR-132 | 6.00 | 0.15 | 7.21 | 5.18E−03 | 1.21 | 2.3 |
| hsa-miR-191* | 3.42 | 0.27 | 4.58 | 3.01E−02 | 1.16 | 2.2 |
| hsa-miR-656 | 0.48 | 0.26 | 1.64 | 2.72E−02 | 1.16 | 2.2 |
| hsa-miR-330-3p | 4.00 | 0.04 | 5.15 | 1.78E−04 | 1.15 | 2.2 |
| hsa-miR-1201 | 1.35 | 0.21 | 2.48 | 1.69E−02 | 1.13 | 2.2 |
| hsa-miR-769-3p | 2.04 | 0.20 | 3.15 | 1.57E−02 | 1.11 | 2.2 |
| hsa-let-7b* | 1.31 | 0.14 | 2.41 | 5.36E−03 | 1.10 | 2.1 |
| hsa-miR-431* | 1.38 | 0.23 | 2.46 | 2.45E−02 | 1.09 | 2.1 |
| hsa-miR-1238 | 3.64 | 0.23 | 4.72 | 2.45E−02 | 1.08 | 2.1 |
| hsa-let-7f-1* | 1.41 | 0.12 | 2.48 | 3.84E−03 | 1.07 | 2.1 |
| hsa-miR-425* | 3.06 | 0.27 | 4.08 | 4.45E−02 | 1.02 | 2.0 |
| hsa-miR-519d | 0.74 | 0.21 | 1.74 | 2.42E−02 | 1.00 | 2.0 |
| hsa-miR-30e* | 8.03 | 0.28 | 7.03 | 4.75E−02 | −1.00 | 2.0 |
| hsa-miR-7-1* | 4.85 | 0.15 | 3.84 | 9.18E−03 | −1.01 | 2.0 |
| hsa-miR-16-2* | 3.48 | 0.10 | 2.46 | 2.96E−03 | −1.02 | 2.0 |
| hsa-miR-361-3p | 7.35 | 0.12 | 6.33 | 5.16E−03 | −1.03 | 2.0 |
| hsa-miR-1271 | 4.37 | 0.19 | 3.33 | 1.60E−02 | −1.03 | 2.0 |
| hsa-miR-338-5p | 2.10 | 0.17 | 1.05 | 1.07E−02 | −1.06 | 2.1 |
| hsa-miR-574-3p | 6.79 | 0.11 | 5.72 | 3.21E−03 | −1.07 | 2.1 |
| hsa-miR-30c-1* | 3.43 | 0.11 | 2.37 | 3.00E−03 | −1.07 | 2.1 |
| hsa-miR-624* | 2.34 | 0.17 | 1.27 | 1.05E−02 | −1.07 | 2.1 |
| hsa-miR-151-3p | 7.63 | 0.21 | 6.52 | 1.73E−02 | −1.10 | 2.1 |
| hsa-let-7d | 12.26 | 0.22 | 11.15 | 1.99E−02 | −1.12 | 2.2 |
| hsa-miR-192 | 7.92 | 0.21 | 6.79 | 1.62E−02 | −1.13 | 2.2 |
| hsa-let-7f | 14.71 | 0.25 | 13.56 | 2.54E−02 | −1.15 | 2.2 |
| hsa-miR-152 | 7.88 | 0.23 | 6.73 | 2.11E−02 | −1.15 | 2.2 |
| hsa-miR-628-5p | 4.41 | 0.12 | 3.25 | 2.99E−03 | −1.16 | 2.2 |
| hsa-miR-146b-3p | −0.93 | 0.25 | −2.10 | 2.34E−02 | −1.18 | 2.3 |
| hsa-miR-19a | 8.30 | 0.13 | 7.12 | 4.24E−03 | −1.18 | 2.3 |
| hsa-miR-455-3p | 6.91 | 0.12 | 5.69 | 2.94E−03 | −1.22 | 2.3 |
| hsa-miR-93 | 8.83 | 0.24 | 7.61 | 1.87E−02 | −1.23 | 2.3 |
| hsa-miR-652 | 6.64 | 0.19 | 5.34 | 9.13E−03 | −1.30 | 2.5 |
| hsa-miR-1471 | 4.55 | 0.27 | 3.24 | 2.35E−02 | −1.30 | 2.5 |
| hsa-miR-214 | 9.59 | 0.15 | 8.28 | 4.62E−03 | −1.31 | 2.5 |

TABLE 9-continued

MicroRNAs significantly differentially expressed between ATC and NOR samples.

| | NOR | | | ATC vs NOR | | |
|---|---|---|---|---|---|---|
| miRNA | AVG | SD | ATC | ttest | Log2Diff | Fold change |
| hsa-miR-214* | 4.54 | 0.23 | 3.23 | 1.42E−02 | −1.31 | 2.5 |
| hsa-miR-628-3p | 3.68 | 0.24 | 2.32 | 1.43E−02 | −1.36 | 2.6 |
| hsa-miR-10b | 9.05 | 0.24 | 7.70 | 1.55E−02 | −1.36 | 2.6 |
| hsa-miR-101* | 2.81 | 0.23 | 1.44 | 1.32E−02 | −1.37 | 2.6 |
| hsa-miR-130a | 11.60 | 0.31 | 10.22 | 2.80E−02 | −1.38 | 2.6 |
| hsa-miR-30b* | 4.51 | 0.11 | 3.11 | 1.50E−03 | −1.39 | 2.6 |
| hsa-miR-30e | 9.84 | 0.26 | 8.44 | 1.64E−02 | −1.40 | 2.6 |
| hsa-miR-29c | 13.27 | 0.21 | 11.87 | 9.34E−03 | −1.40 | 2.6 |
| hsa-miR-138-2* | 2.44 | 0.25 | 1.03 | 1.54E−02 | −1.42 | 2.7 |
| hsa-miR-374b | 8.47 | 0.18 | 7.05 | 6.07E−03 | −1.42 | 2.7 |
| hsa-miR-30d | 10.39 | 0.18 | 8.94 | 5.49E−03 | −1.45 | 2.7 |
| hsa-miR-194 | 6.65 | 0.22 | 5.17 | 9.14E−03 | −1.48 | 2.8 |
| hsa-miR-668 | −0.59 | 0.34 | −2.09 | 2.96E−02 | −1.51 | 2.8 |
| hsa-miR-192* | 2.15 | 0.28 | 0.63 | 1.67E−02 | −1.52 | 2.9 |
| hsa-miR-423-5p | 7.13 | 0.09 | 5.61 | 6.53E−04 | −1.52 | 2.9 |
| hsa-miR-1826 | 5.89 | 0.33 | 4.37 | 2.59E−02 | −1.53 | 2.9 |
| hsa-miR-215 | 6.16 | 0.28 | 4.58 | 1.47E−02 | −1.57 | 3.0 |
| hsa-miR-186 | 7.19 | 0.27 | 5.62 | 1.40E−02 | −1.58 | 3.0 |
| hsa-miR-424* | 3.82 | 0.28 | 2.24 | 1.49E−02 | −1.58 | 3.0 |
| hsa-let-7g | 13.44 | 0.18 | 11.83 | 3.81E−03 | −1.60 | 3.0 |
| hsa-miR-193b* | 4.44 | 0.44 | 2.81 | 4.42E−02 | −1.63 | 3.1 |
| hsa-miR-199a-5p | 10.41 | 0.25 | 8.77 | 1.02E−02 | −1.64 | 3.1 |
| hsa-miR-92a | 9.43 | 0.12 | 7.77 | 1.13E−03 | −1.66 | 3.2 |
| hsa-miR-767-5p | 0.57 | 0.17 | −1.10 | 3.23E−03 | −1.67 | 3.2 |
| hsa-miR-374a | 9.21 | 0.22 | 7.52 | 6.08E−03 | −1.69 | 3.2 |
| hsa-miR-199b-5p | 9.67 | 0.16 | 7.97 | 2.44E−03 | −1.70 | 3.2 |
| hsa-miR-29c* | 7.86 | 0.25 | 6.15 | 8.89E−03 | −1.71 | 3.3 |
| hsa-miR-219-5p | 3.84 | 0.31 | 2.13 | 1.67E−02 | −1.71 | 3.3 |
| hsa-miR-665 | 3.57 | 0.46 | 1.87 | 4.48E−02 | −1.71 | 3.3 |
| hsa-miR-98 | 8.93 | 0.29 | 7.22 | 1.35E−02 | −1.7+ | 3.3 |
| hsa-miR-32 | 4.42 | 0.32 | 2.63 | 1.60E−02 | −1.79 | 3.5 |
| hsa-miR-29b-2* | 2.05 | 0.28 | 0.24 | 1.01E−02 | −1.81 | 3.5 |
| hsa-miR-30d* | 2.94 | 0.23 | 1.12 | 5.64E−03 | −1.82 | 3.5 |
| hsa-miR-151-5p | 11.05 | 0.25 | 9.21 | 6.98E−03 | −1.84 | 3.6 |
| hsa-miR-17* | 5.45 | 0.45 | 3.60 | 3.44E−02 | −1.84 | 3.6 |
| hsa-miR-1301 | 0.99 | 0.35 | −0.92 | 1.66E−02 | −1.92 | 3.8 |
| hsa-miR-95 | 8.36 | 0.53 | 6.41 | 4.68E−02 | −1.95 | 3.9 |
| hsa-miR-1208 | 2.84 | 0.36 | 0.87 | 1.64E−02 | −1.96 | 3.9 |
| hsa-miR-101 | 9.47 | 0.24 | 7.49 | 4.90E−03 | −1.97 | 3.9 |
| hsa-miR-7 | 11.38 | 0.51 | 9.39 | 3.99E−02 | −1.98 | 4.0 |
| hsa-miR-1180 | 2.38 | 0.14 | 0.37 | 9.38E−04 | −2.01 | 4.0 |
| hsa-let-7i | 14.01 | 0.31 | 11.99 | 9.81E−03 | −2.02 | 4.1 |
| hsa-miR-1270 | 2.09 | 0.22 | 0.05 | 3.75E−03 | −2.04 | 4.1 |
| hsa-let-7g* | −0.08 | 0.50 | −2.14 | 3.50E−02 | −2.06 | 4.2 |
| hsa-miR-26b | 12.58 | 0.26 | 10.52 | 5.54E−03 | −2.06 | 4.2 |
| hsa-miR-365 | 9.80 | 0.45 | 7.72 | 2.56E−02 | −2.08 | 4.2 |
| hsa-miR-203 | 5.95 | 0.57 | 3.85 | 4.60E−02 | −2.09 | 4.3 |
| hsa-miR-744 | 5.09 | 0.12 | 2.84 | 4.85E−04 | −2.25 | 4.7 |
| hsa-miR-874 | 7.04 | 0.24 | 4.78 | 3.53E−03 | −2.26 | 4.8 |
| hsa-miR-148a* | 1.75 | 0.37 | −0.55 | 1.17E−02 | −2.31 | 4.9 |
| hsa-let-7c | 12.99 | 0.19 | 10.68 | 1.75E−03 | −2.31 | 5.0 |
| hsa-miR-148b | 9.01 | 0.40 | 6.69 | 1.35E−02 | −2.32 | 5.0 |
| hsa-miR-346 | 0.98 | 0.17 | −1.38 | 1.06E−03 | −2.36 | 5.1 |
| hsa-miR-542-5p | 6.26 | 0.30 | 3.91 | 5.96E−03 | −2.36 | 5.1 |
| hsa-miR-455-5p | 4.70 | 0.09 | 2.32 | 1.83E−04 | −2.37 | 5.2 |
| hsa-miR-26a | 12.78 | 0.23 | 10.36 | 2.56E−03 | −2.42 | 5.3 |
| hsa-miR-20a* | 4.96 | 0.36 | 2.51 | 8.79E−03 | −2.44 | 5.4 |
| hsa-miR-542-3p | 5.78 | 0.29 | 3.33 | 4.84E−03 | −2.45 | 5.5 |
| hsa-miR-424 | 10.03 | 0.50 | 7.56 | 2.18E−02 | −2.46 | 5.5 |
| hsa-miR-30b | 12.22 | 0.28 | 9.75 | 4.09E−03 | −2.48 | 5.6 |
| hsa-miR-551b | 5.24 | 0.48 | 2.61 | 1.65E−02 | −2.63 | 6.2 |
| hsa-miR-143* | 4.15 | 0.36 | 1.36 | 6.18E−03 | −2.79 | 6.9 |
| hsa-miR-345 | 4.50 | 0.63 | 1.63 | 2.61E−02 | −2.88 | 7.3 |
| hsa-miR-126 | 12.90 | 0.21 | 10.01 | 1.13E−03 | −2.89 | 7.4 |
| hsa-miR-100 | 12.09 | 0.35 | 9.15 | 5.03E−03 | −2.94 | 7.7 |
| hsa-miR-125b-2* | 5.60 | 0.17 | 2.65 | 5.45E−04 | −2.95 | 7.7 |
| hsa-miR-1469 | 2.18 | 0.70 | −0.80 | 3.20E−02 | −2.98 | 7.9 |
| hsa-miR-422a | 2.78 | 0.27 | −0.25 | 2.09E−03 | −3.03 | 8.1 |
| hsa-miR-491-5p | 1.89 | 0.17 | −1.33 | 4.87E−04 | −3.22 | 9.3 |
| hsa-miR-1251 | 0.97 | 0.29 | −2.26 | 2.08E−03 | −3.23 | 9.4 |
| hsa-miR-450a | 5.36 | 0.44 | 1.98 | 6.34E−03 | −3.38 | 10.4 |
| hsa-miR-452 | 4.97 | 0.26 | 1.57 | 1.41E−03 | −3.40 | 10.6 |
| hsa-miR-126* | 6.87 | 0.34 | 3.44 | 2.81E−03 | −3.43 | 10.8 |

TABLE 9-continued

MicroRNAs significantly differentially expressed between ATC and NOR samples.

| | NOR | | | ATC vs NOR | | |
|---|---|---|---|---|---|---|
| miRNA | AVG | SD | ATC | ttest | Log2Diff | Fold change |
| hsa-miR-486-5p | 8.85 | 0.51 | 5.35 | 8.93E−03 | −3.50 | 11.3 |
| hsa-miR-224 | 5.97 | 0.07 | 2.46 | 2.48E−05 | −3.51 | 11.4 |
| hsa-let-7i* | 3.60 | 0.44 | 0.07 | 5.56E−03 | −3.53 | 11.5 |
| hsa-miR-451 | 15.49 | 0.22 | 11.96 | 7.29E−04 | −3.53 | 11.6 |
| hsa-miR-143 | 8.85 | 0.35 | 5.31 | 2.93E−03 | −3.54 | 11.7 |
| hsa-miR-144* | 6.62 | 0.32 | 3.04 | 2.06E−03 | −3.59 | 12.0 |
| hsa-miR-99a* | 1.97 | 0.14 | −1.76 | 1.50E−04 | −3.72 | 13.2 |
| hsa-miR-145* | 6.15 | 0.36 | 2.37 | 2.53E−03 | −3.78 | 13.8 |
| hsa-miR-125b | 14.25 | 0.19 | 10.44 | 3.62E−04 | −3.81 | 14.0 |
| hsa-miR-144 | 8.24 | 0.32 | 4.43 | 1.80E−03 | −3.81 | 14.0 |
| hsa-miR-218 | 8.86 | 0.27 | 5.04 | 1.10E−03 | −3.82 | 14.1 |
| hsa-miR-99a | 11.86 | 0.17 | 8.00 | 2.39E−04 | −3.87 | 14.6 |
| hsa-miR-139-5p | 6.80 | 0.26 | 2.79 | 7.91E−04 | −4.01 | 16.1 |
| hsa-miR-200a* | 4.59 | 0.21 | 0.46 | 3.96E−04 | −4.13 | 17.5 |
| hsa-miR-145 | 11.11 | 0.39 | 6.78 | 2.14E−03 | −4.32 | 20.0 |
| hsa-miR-512-3p | 4.77 | 0.48 | 0.39 | 3.76E−03 | −4.38 | 20.8 |
| hsa-miR-486-3p | 2.60 | 1.12 | −1.82 | 3.85E−02 | −4.41 | 21.3 |
| hsa-miR-200b* | 5.18 | 0.30 | 0.48 | 7.91E−04 | −4.70 | 26.0 |
| hsa-miR-141* | 3.63 | 0.39 | −1.68 | 1.16E−03 | −5.31 | 39.6 |
| hsa-miR-7-2* | 4.72 | 0.59 | −1.00 | 3.21E−03 | −5.72 | 52.9 |
| hsa-miR-138 | 6.63 | 0.55 | 0.09 | 1.73E−03 | −6.53 | 92.7 |
| hsa-miR-205 | 5.13 | 0.14 | −1.95 | 2.14E−05 | −7.08 | 135.0 |
| hsa-miR-135a | 8.83 | 0.52 | 1.19 | 9.30E−04 | −7.64 | 198.8 |
| hsa-miR-135b | 10.03 | 0.43 | 2.20 | 5.09E−04 | −7.83 | 227.4 |
| hsa-miR-200b | 11.06 | 0.20 | 2.93 | 4.36E−05 | −8.13 | 279.8 |
| hsa-miR-200a | 9.93 | 0.13 | 1.45 | 1.16E−05 | −8.48 | 357.2 |
| hsa-miR-200c | 11.68 | 0.25 | 3.00 | 7.51E−05 | −8.67 | 408.7 |
| hsa-miR-141 | 11.19 | 0.42 | 2.51 | 3.35E−04 | −8.68 | 411.2 |
| hsa-miR-429 | 8.64 | 0.10 | −0.05 | 5.15E−06 | −8.69 | 413.4 |

AVG, average expression among samples in a group;
SD, standard deviation.

Example 8 miRNA Expression Profiling Distinguishes Normal Thyroid Tissue and Medullary Thyroid Carcinoma A total of 415 human miRNAs were expressed above background level in the normal thyroid samples, representing 48% of the human miRNAs present on the arrays. A total of 418 miRNAs were expressed above background level in the medullary thyroid carcinoma samples, representing 48% of the miRNAs present on the arrays.

A total of 165 human miRNAs were significantly differentially expressed between the normal samples and the medullary thyroid carcinomas (p<0.05) (Table 10). Among these, 91 miRNAs were overexpressed (Log 2 diff (MTC vs NOR)≥1) and 30 were underexpressed (Log 2 diff (MTC vs NOR)≤1) by at least 2-fold in MTC compared to NOR. Of these, hsa-miR-375 and hsa-miR-124 were over-expressed between 100- and 520-fold in the MTC samples, twenty one miRNAs were overexpressed by 10- to 54-fold in the MTC samples, and thirty one miRNAs were overexpressed by 5- to 10-fold in the MTC samples compared to the NOR samples. Among the miRNAs that were expressed at lower average levels in the MTC samples, hsa-miR-31 and hsa-miR-31* were underexpressed by more than 10-fold in the MTC samples, and six miRNAs (hsa-miR-138, -7-2*, -204, -30a*, -30c-2*, and -30a) were underexpressed by 5- to 10-fold in the MTC specimens (Table 10).

TABLE 10

MicroRNAs significantly differentially expressed between MTC and NOR samples.

| | NOR | | MTC | | MTC vs NOR | | |
|---|---|---|---|---|---|---|---|
| miRNA | AVG | SD | AVG | SD | ttest | Log2Diff | Fold change |
| hsa-miR-375 | 4.86 | 1.12 | 13.86 | 0.40 | 4.71E−05 | 9.01 | 515.1 |
| hsa-miR-124 | 0.64 | 0.46 | 7.86 | 3.11 | 5.21E−03 | 7.22 | 149.4 |
| hsa-miR-153 | 2.34 | 0.28 | 8.11 | 1.07 | 1.26E−04 | 5.77 | 54.5 |
| hsa-miR-323-3p | 1.27 | 1.48 | 6.93 | 0.13 | 1.33E−03 | 5.66 | 50.6 |
| hsa-miR-410 | 2.89 | 1.19 | 8.20 | 0.14 | 6.54E−04 | 5.31 | 39.7 |
| hsa-miR-592 | 2.46 | 0.28 | 7.50 | 1.19 | 3.85E−04 | 5.04 | 32.9 |
| hsa-miR-487b | 4.75 | 0.63 | 9.75 | 0.19 | 4.62E−05 | 5.00 | 32.0 |
| hsa-miR-409-3p | 2.35 | 1.61 | 7.21 | 0.31 | 3.96E−03 | 4.87 | 29.2 |
| hsa-miR-539 | 1.69 | 0.51 | 6.53 | 0.34 | 3.23E−05 | 4.83 | 28.5 |
| hsa-miR-433 | −0.64 | 0.60 | 4.13 | 0.61 | 1.46E−04 | 4.77 | 27.3 |
| hsa-miR-432 | 2.98 | 0.71 | 7.61 | 0.36 | 1.58E−04 | 4.63 | 24.7 |

TABLE 10-continued

MicroRNAs significantly differentially expressed between MTC and NOR samples.

| miRNA | NOR AVG | NOR SD | MTC AVG | MTC SD | MTC vs NOR ttest | Log2Diff | Fold change |
|---|---|---|---|---|---|---|---|
| hsa-miR-409-5p | 0.42 | 0.53 | 4.92 | 0.15 | 3.23E−05 | 4.50 | 22.6 |
| hsa-miR-183 | 6.09 | 0.54 | 10.49 | 0.69 | 2.13E−04 | 4.40 | 21.2 |
| hsa-miR-758 | 1.00 | 0.63 | 5.04 | 0.13 | 1.22E−04 | 4.03 | 16.4 |
| hsa-miR-382 | 2.57 | 0.59 | 6.53 | 0.24 | 1.16E−04 | 3.96 | 15.6 |
| hsa-miR-487a | 0.85 | 0.93 | 4.79 | 0.32 | 1.00E−03 | 3.94 | 15.3 |
| hsa-miR-183* | 0.43 | 0.40 | 4.36 | 0.40 | 5.10E−05 | 3.93 | 15.2 |
| hsa-miR-485-5p | 0.22 | 0.44 | 4.03 | 0.40 | 7.66E−05 | 3.81 | 14.0 |
| hsa-miR-889 | 0.00 | 0.19 | 3.79 | 0.54 | 4.36E−05 | 3.79 | 13.9 |
| hsa-miR-127-3p | 5.22 | 0.57 | 8.88 | 0.37 | 2.12E−04 | 3.66 | 12.7 |
| hsa-miR-182 | 2.28 | 0.58 | 5.90 | 0.30 | 1.93E−04 | 3.63 | 12.3 |
| hsa-miR-96 | 7.46 | 0.37 | 11.01 | 0.48 | 1.07E−04 | 3.55 | 11.7 |
| hsa-miR-485-3p | 0.94 | 0.89 | 4.27 | 0.37 | 1.83E−03 | 3.33 | 10.1 |
| hsa-miR-136* | 3.09 | 0.50 | 6.41 | 0.51 | 3.53E−04 | 3.32 | 10.0 |
| hsa-miR-890 | −0.66 | 0.49 | 2.63 | 1.99 | 2.22E−02 | 3.29 | 9.8 |
| hsa-miR-495 | 3.64 | 0.76 | 6.93 | 0.28 | 8.90E−04 | 3.29 | 9.8 |
| hsa-miR-543 | 2.07 | 0.93 | 5.30 | 0.05 | 2.10E−03 | 3.23 | 9.4 |
| hsa-miR-9* | 2.09 | 0.66 | 5.31 | 1.78 | 1.93E−02 | 3.21 | 9.3 |
| hsa-miR-431 | 1.78 | 1.51 | 5.00 | 1.06 | 2.65E−02 | 3.21 | 9.3 |
| hsa-miR-369-5p | 2.10 | 0.30 | 5.27 | 0.72 | 4.65E−04 | 3.17 | 9.0 |
| hsa-miR-376a* | 1.53 | 0.33 | 4.63 | 0.44 | 1.18E−04 | 3.10 | 8.6 |
| hsa-miR-379 | 3.13 | 0.51 | 6.20 | 0.14 | 1.73E−04 | 3.07 | 8.4 |
| hsa-miR-377 | 4.48 | 0.60 | 7.51 | 0.55 | 1.02E−03 | 3.03 | 8.2 |
| hsa-miR-10a | 8.66 | 0.40 | 11.69 | 0.52 | 3.28E−04 | 3.03 | 8.2 |
| hsa-miR-136 | 3.60 | 0.47 | 6.61 | 0.51 | 4.48E−04 | 3.01 | 8.0 |
| hsa-miR-381 | 4.34 | 0.54 | 7.34 | 0.33 | 3.96E−04 | 2.99 | 8.0 |
| hsa-miR-132 | 6.00 | 0.15 | 8.97 | 1.15 | 3.28E−03 | 2.97 | 7.8 |
| hsa-miR-376c | 6.27 | 0.41 | 9.21 | 0.81 | 1.39E−03 | 2.94 | 7.7 |
| hsa-miR-154 | 3.92 | 0.39 | 6.86 | 0.17 | 6.85E−05 | 2.94 | 7.7 |
| hsa-miR-221 | 6.75 | 0.27 | 9.68 | 0.79 | 8.60E−04 | 2.93 | 7.6 |
| hsa-miR-377* | 0.16 | 0.39 | 2.94 | 0.16 | 9.44E−05 | 2.78 | 6.9 |
| hsa-miR-9 | 1.92 | 0.34 | 4.69 | 1.56 | 1.66E−02 | 2.77 | 6.8 |
| hsa-miR-376a | 5.80 | 0.39 | 8.51 | 0.67 | 1.05E−03 | 2.70 | 6.5 |
| hsa-miR-329 | 1.45 | 0.43 | 4.13 | 0.15 | 1.67E−04 | 2.68 | 6.4 |
| hsa-miR-411 | 2.19 | 0.44 | 4.80 | 0.24 | 2.66E−04 | 2.61 | 6.1 |
| hsa-miR-335 | 6.48 | 0.33 | 9.06 | 1.56 | 2.08E−02 | 2.58 | 6.0 |
| hsa-miR-7 | 11.38 | 0.51 | 13.88 | 0.95 | 6.11E−03 | 2.50 | 5.7 |
| hsa-miR-1301 | 0.99 | 0.35 | 3.45 | 0.62 | 1.09E−03 | 2.46 | 5.5 |
| hsa-miR-369-3p | 0.42 | 0.36 | 2.85 | 0.71 | 1.82E−03 | 2.43 | 5.4 |
| hsa-miR-493* | 2.96 | 0.54 | 5.39 | 0.45 | 1.52E−03 | 2.43 | 5.4 |
| hsa-miR-154* | 2.47 | 0.92 | 4.83 | 0.62 | 1.25E−02 | 2.36 | 5.1 |
| hsa-miR-370 | 2.41 | 0.50 | 4.77 | 0.36 | 1.02E−03 | 2.35 | 5.1 |
| hsa-miR-330-3p | 4.00 | 0.04 | 6.34 | 0.46 | 1.34E−04 | 2.34 | 5.1 |
| hsa-miR-654-3p | 3.97 | 0.25 | 6.30 | 0.51 | 4.55E−04 | 2.33 | 5.0 |
| hsa-miR-132* | 3.33 | 0.54 | 5.58 | 1.13 | 1.61E−02 | 2.25 | 4.8 |
| hsa-miR-222 | 5.87 | 0.13 | 8.06 | 0.71 | 1.53E−03 | 2.18 | 4.5 |
| hsa-miR-10a* | 1.64 | 0.08 | 3.82 | 0.57 | 5.66E−04 | 2.18 | 4.5 |
| hsa-miR-1185 | 0.91 | 0.24 | 3.03 | 0.54 | 8.66E−04 | 2.11 | 4.3 |
| hsa-miR-216a | −0.17 | 0.41 | 1.88 | 0.79 | 6.21E−03 | 2.06 | 4.2 |
| hsa-miR-7-1* | 4.85 | 0.15 | 6.88 | 0.44 | 3.26E−04 | 2.03 | 4.1 |
| hsa-miR-337-5p | 3.33 | 0.35 | 5.33 | 0.33 | 6.01E−04 | 2.00 | 4.0 |
| hsa-miR-182* | 0.03 | 0.20 | 2.00 | 0.20 | 4.96E−05 | 1.97 | 3.9 |
| hsa-miR-376b | 1.52 | 0.42 | 3.45 | 1.39 | 4.32E−02 | 1.93 | 3.8 |
| hsa-miR-338-3p | 7.41 | 0.48 | 9.34 | 0.35 | 2.08E−03 | 1.93 | 3.8 |
| hsa-miR-221* | 5.03 | 0.35 | 6.93 | 0.33 | 7.96E−04 | 1.90 | 3.7 |
| hsa-miR-668 | −0.59 | 0.34 | 1.30 | 0.42 | 1.20E−03 | 1.89 | 3.7 |
| hsa-miR-582-5p | 4.27 | 0.39 | 6.13 | 0.18 | 6.29E−04 | 1.86 | 3.6 |
| hsa-miR-663b | 2.05 | 0.54 | 3.88 | 1.00 | 2.54E−02 | 1.83 | 3.6 |
| hsa-miR-598 | 6.22 | 0.44 | 7.98 | 0.33 | 2.27E−03 | 1.76 | 3.4 |
| hsa-miR-301a | 5.82 | 0.22 | 7.56 | 0.34 | 4.35E−04 | 1.74 | 3.3 |
| hsa-miR-335* | 2.05 | 0.24 | 3.78 | 0.88 | 1.19E−02 | 1.73 | 3.3 |
| hsa-miR-326 | 1.90 | 0.22 | 3.61 | 0.14 | 7.52E−05 | 1.71 | 3.3 |
| hsa-miR-429 | 8.64 | 0.10 | 10.32 | 0.28 | 9.10E−05 | 1.68 | 3.2 |
| hsa-miR-656 | 0.48 | 0.26 | 2.09 | 0.62 | 4.97E−03 | 1.61 | 3.0 |
| hsa-miR-642 | −0.92 | 0.34 | 0.65 | 0.41 | 2.47E−03 | 1.57 | 3.0 |
| hsa-miR-431* | 1.38 | 0.23 | 2.93 | 0.05 | 9.91E−05 | 1.55 | 2.9 |
| hsa-miR-212 | 4.43 | 0.21 | 5.93 | 0.76 | 1.18E−02 | 1.50 | 2.8 |
| hsa-miR-299-3p | 1.65 | 0.31 | 3.11 | 0.45 | 3.83E−03 | 1.46 | 2.7 |
| hsa-miR-299-5p | 3.80 | 0.43 | 5.22 | 0.48 | 9.19E−03 | 1.42 | 2.7 |
| hsa-miR-582-3p | −1.21 | 0.32 | 0.19 | 0.32 | 2.17E−03 | 1.41 | 2.7 |
| hsa-miR-181c* | 3.92 | 0.47 | 5.32 | 0.15 | 4.54E−03 | 1.40 | 2.6 |
| hsa-miR-181c | 7.07 | 0.37 | 8.44 | 0.26 | 2.93E−03 | 1.37 | 2.6 |
| hsa-miR-200a | 9.93 | 0.13 | 11.26 | 0.29 | 3.98E−04 | 1.33 | 2.5 |
| hsa-miR-654-5p | 2.99 | 0.39 | 4.30 | 0.31 | 4.98E−03 | 1.31 | 2.5 |

TABLE 10-continued

MicroRNAs significantly differentially expressed between MTC and NOR samples.

| miRNA | NOR AVG | NOR SD | MTC AVG | MTC SD | MTC vs NOR ttest | Log2Diff | Fold change |
|---|---|---|---|---|---|---|---|
| hsa-miR-324-5p | 7.97 | 0.19 | 9.24 | 0.04 | 9.68E−05 | 1.27 | 2.4 |
| hsa-miR-24-1* | 5.38 | 0.10 | 6.56 | 0.18 | 9.92E−05 | 1.18 | 2.3 |
| hsa-miR-337-3p | 2.03 | 0.33 | 3.15 | 0.43 | 1.12E−02 | 1.12 | 2.2 |
| hsa-miR-200a* | 4.59 | 0.21 | 5.71 | 0.26 | 1.44E−03 | 1.12 | 2.2 |
| hsa-miR-200b | 11.06 | 0.20 | 12.17 | 0.08 | 2.78E−04 | 1.11 | 2.2 |
| hsa-let-7e | 11.75 | 0.21 | 12.78 | 0.21 | 1.44E−03 | 1.03 | 2.0 |
| hsa-miR-181d | 5.85 | 0.44 | 6.86 | 0.09 | 1.19E−02 | 1.01 | 2.0 |
| hsa-let-7d* | 1.66 | 0.34 | 0.59 | 0.75 | 4.86E−02 | −1.08 | 2.1 |
| hsa-let-7g | 13.44 | 0.18 | 12.32 | 0.43 | 4.98E−03 | −1.12 | 2.2 |
| hsa-miR-126 | 12.90 | 0.21 | 11.72 | 0.25 | 1.04E−03 | −1.18 | 2.3 |
| hsa-miR-20b | 8.20 | 0.29 | 7.02 | 0.70 | 2.62E−02 | −1.19 | 2.3 |
| hsa-miR-205 | 5.13 | 0.14 | 3.92 | 0.71 | 1.82E−02 | −1.21 | 2.3 |
| hsa-miR-625 | 5.52 | 0.34 | 4.29 | 0.64 | 2.02E−02 | −1.23 | 2.3 |
| hsa-miR-152 | 7.88 | 0.23 | 6.62 | 0.52 | 7.12E−03 | −1.26 | 2.4 |
| hsa-miR-1270 | 2.09 | 0.22 | 0.79 | 0.81 | 2.61E−02 | −1.30 | 2.5 |
| hsa-miR-30c | 11.51 | 0.24 | 10.16 | 0.57 | 7.44E−03 | −1.35 | 2.6 |
| hsa-miR-30e* | 8.03 | 0.28 | 6.67 | 0.55 | 7.04E−03 | −1.36 | 2.6 |
| lisa-miR-363 | 6.85 | 0.30 | 5.49 | 0.86 | 2.99E−02 | −1.36 | 2.6 |
| hsa-let-7i | 14.01 | 0.31 | 12.62 | 0.95 | 3.66E−02 | −1.39 | 2.6 |
| hsa-miR-126* | 6.87 | 0.34 | 5.45 | 0.16 | 1.22E−03 | −1.41 | 2.7 |
| hsa-miR-100 | 12.09 | 0.35 | 10.63 | 0.66 | 1.19E−02 | −1.46 | 2.8 |
| hsa-miR-455-3p | 6.91 | 0.12 | 5.44 | 1.18 | 4.95E−02 | −1.48 | 2.8 |
| hsa-miR-542-3p | 5.78 | 0.29 | 4.19 | 1.06 | 3.18E−02 | −1.59 | 3.0 |
| hsa-miR-139-5p | 6.80 | 0.26 | 5.21 | 0.90 | 1.83E−02 | −1.59 | 3.0 |
| hsa-miR-345 | 4.50 | 0.63 | 2.88 | 0.99 | 4.31E−02 | −1.62 | 3.1 |
| hsa-let-7i* | 3.60 | 0.44 | 1.85 | 0.98 | 2.29E−02 | −1.75 | 3.4 |
| hsa-miR-450a | 5.36 | 0.44 | 3.51 | 0.77 | 9.42E−03 | −1.85 | 3.6 |
| hsa-miR-551b | 5.24 | 0.48 | 3.35 | 1.29 | 3.99E−02 | −1.88 | 3.7 |
| hsa-miR-144 | 8.24 | 0.32 | 6.21 | 0.85 | 6.40E−03 | −2.03 | 4.1 |
| hsa-miR-30a | 12.09 | 0.31 | 9.76 | 1.51 | 2.66E−02 | −2.33 | 5.0 |
| hsa-miR-30c-2* | 6.15 | 0.27 | 3.81 | 1.75 | 4.18E−02 | −2.33 | 5.0 |
| hsa-miR-30a* | 8.99 | 0.37 | 6.59 | 1.57 | 2.88E−02 | −2.40 | 5.3 |
| hsa-miR-204 | 8.70 | 0.83 | 6.03 | 1.35 | 2.21E−02 | −2.68 | 6.4 |
| hsa-miR-7-2* | 4.72 | 0.59 | 1.55 | 2.02 | 2.83E−02 | −3.17 | 9.0 |
| hsa-miR-138 | 6.63 | 0.55 | 3.44 | 2.17 | 3.36E−02 | −3.18 | 9.1 |
| hsa-miR-31* | 6.00 | 0.62 | 2.44 | 2.19 | 2.44E−02 | −3.57 | 11.9 |
| hsa-miR-31 | 7.66 | 0.63 | 3.63 | 2.73 | 3.23E−02 | −4.03 | 16.3 |

AVG, average expression among samples in a group;
SD, standard deviation

Example 9 miRNA Expression Profiling Distinguishes Hyperplastic Thyroid Nodules and Follicular Adenoma A total of 160 human miRNAs were significantly differentially expressed between the hyperplastic nodule samples and the follicular adenomas (p<0.05) (Table 11). Among these, 11 miRNAs were overexpressed (Log 2 diff (FA vs NOD)≥1) and 128 were underexpressed (Log 2 diff (FA vs NOD)≤1) by at least 2-fold in FA compared to NOD samples. Of these, hsa-miR-1274a, -720, and -1274b were overexpressed by 5- to 6-fold in the FA compared to the NOD samples. Among the miRNAs that were expressed at lower average levels in the FA samples, hsa-miR-206 and hsa-miR-1202 were underexpressed by 20- to 50-fold in the FA samples, sixteen miRNAs were underexpressed by 10- to 20-fold, and forty seven miRNAs were underexpressed by 5- to 10-fold in the FA specimens compared to the NOD samples.

TABLE 11

MicroRNAs significantly differentially expressed between FA and NOD samples.

| miRNA | NOD AVG | NOD SD | FA AVG | FA SD | FA vs NOD ttest | Log2Diff | Fold change |
|---|---|---|---|---|---|---|---|
| hsa-miR-1274a | 4.74 | 1.03 | 7.33 | 0.79 | 3.72E−03 | 2.59 | 6.0 |
| hsa-miR-720 | 10.25 | 0.79 | 12.76 | 0.87 | 2.80E−03 | 2.51 | 5.7 |
| hsa-miR-1274b | 8.53 | 0.95 | 10.86 | 0.82 | 5.49E−03 | 2.33 | 5.0 |
| hsa-miR-1260 | 6.50 | 0.87 | 8.62 | 0.71 | 5.13E−03 | 2.12 | 4.3 |
| hsa-mill-182 | 1.79 | 0.79 | 3.85 | 1.11 | 1.69E−02 | 2.06 | 4.2 |
| hsa-miR-96 | 7.09 | 0.38 | 8.94 | 0.88 | 6.06E−03 | 1.85 | 3.6 |
| hsa-miR-1227 | 0.13 | 0.61 | 1.77 | 1.08 | 3.12E−02 | 1.64 | 3.1 |

TABLE 11-continued

MicroRNAs significantly differentially expressed between FA and NOD samples.

| miRNA | NOD AVG | NOD SD | FA AVG | FA SD | FA vs NOD ttest | Log2Diff | Fold change |
|---|---|---|---|---|---|---|---|
| hsa-miR-183 | 6.08 | 0.43 | 7.62 | 1.20 | 4.65E−02 | 1.54 | 2.9 |
| hsa-miR-29b-1* | 3.36 | 0.34 | 4.78 | 0.51 | 2.08E−03 | 1.42 | 2.7 |
| hsa-miR-200c* | 1.03 | 0.53 | 2.41 | 0.94 | 3.54E−02 | 1.38 | 2.6 |
| hsa-miR-182* | −0.26 | 0.47 | 1.08 | 0.53 | 5.57E−03 | 1.34 | 2.5 |
| hsa-miR-30c-2* | 6.01 | 0.27 | 5.00 | 0.53 | 1.13E−02 | −1.01 | 2.0 |
| hsa-miR-513c | 3.19 | 0.70 | 2.19 | 0.55 | 4.58E−02 | −1.01 | 2.0 |
| hsa-miR-1270 | 2.47 | 0.46 | 1.35 | 0.54 | 1.30E−02 | −1.12 | 2.2 |
| hsa-miR-320d | 10.69 | 0.29 | 9.56 | 0.73 | 2.34E−02 | −1.13 | 2.2 |
| hsa-miR-1228 | 5.75 | 0.58 | 4.59 | 0.67 | 3.00E−02 | −1.16 | 2.2 |
| hsa-miR-28-3p | 2.09 | 0.21 | 0.93 | 0.64 | 1.11E−02 | −1.16 | 2.2 |
| hsa-miR-320b | 10.20 | 0.36 | 9.03 | 0.72 | 2.16E−02 | −1.17 | 2.2 |
| hsa-miR-320c | 10.20 | 0.21 | 9.02 | 0.68 | 1.29E−02 | −1.19 | 2.3 |
| hsa-miR-130a | 11.54 | 0.35 | 10.32 | 0.86 | 3.36E−02 | −1.22 | 2.3 |
| hsa-miR-513b | 4.08 | 0.67 | 2.85 | 0.56 | 1.96E−02 | −1.23 | 2.3 |
| hsa-miR-501-3p | 4.63 | 0.23 | 3.36 | 0.76 | 1.50E−02 | −1.27 | 2.4 |
| hsa-miR-10b* | 3.33 | 0.58 | 2.05 | 0.49 | 8.73E−03 | −1.28 | 2.4 |
| hsa-miR-320a | 9.16 | 0.27 | 7.87 | 0.70 | 1.09E−02 | −1.29 | 2.4 |
| hsa-miR-296-5p | 4.51 | 0.68 | 3.19 | 0.33 | 6.47E−03 | −1.31 | 2.5 |
| hsa-miR-299-3p | 1.73 | 0.56 | 0.33 | 0.73 | 1.64E−02 | −1.40 | 2.6 |
| hsa-miR-199a-5p | 9.93 | 0.57 | 8.46 | 0.81 | 1.85E−02 | −1.47 | 2.8 |
| hsa-miR-557 | 6.23 | 0.77 | 4.74 | 0.33 | 5.73E−03 | −1.49 | 2.8 |
| hsa-miR-432 | 3.26 | 0.58 | 1.76 | 0.66 | 9.17E−03 | −1.50 | 2.8 |
| hsa-miR-1285 | 3.38 | 0.58 | 1.86 | 0.97 | 2.91E−02 | −1.52 | 2.9 |
| hsa-miR-602 | 3.88 | 0.51 | 2.36 | 0.50 | 2.87E−03 | −1.52 | 2.9 |
| hsa-miR-33b* | 4.27 | 0.51 | 2.73 | 0.50 | 2.53E−03 | −1.55 | 2.9 |
| hsa-miR-1275 | 8.12 | 0.52 | 6.56 | 0.86 | 1.53E−02 | −1.56 | 3.0 |
| hsa-miR-199a-3p | 11.61 | 0.24 | 10.02 | 0.83 | 8.00E−03 | −1.59 | 3.0 |
| hsa-miR-1307 | 3.37 | 0.39 | 1.77 | 1.06 | 2.50E−02 | −1.60 | 3.0 |
| hsa-miR-584 | 4.38 | 0.49 | 2.76 | 0.44 | 1.22E−03 | −1.61 | 3.1 |
| hsa-miR-516a-5p | 3.63 | 0.99 | 2.00 | 0.46 | 1.34E−02 | −1.63 | 3.1 |
| hsa-miR-122 | 2.20 | 1.35 | 0.56 | 0.32 | 3.16E−02 | −1.64 | 3.1 |
| hsa-miR-525-5p | 2.15 | 0.49 | 0.50 | 0.66 | 4.32E−03 | −1.66 | 3.2 |
| hsa-miR-769-3p | 3.34 | 0.64 | 1.68 | 0.57 | 4.48E−03 | −1.66 | 3.2 |
| hsa-miR-379 | 2.70 | 0.88 | 1.02 | 0.89 | 2.51E−02 | −1.68 | 3.2 |
| hsa-miR-1244 | 2.06 | 0.85 | 0.37 | 0.82 | 1.89E−02 | −1.69 | 3.2 |
| hsa-miR-1306 | 2.97 | 0.34 | 1.23 | 0.76 | 4.09E−03 | −1.74 | 3.3 |
| hsa-miR-574-5p | 7.52 | 0.63 | 5.79 | 0.68 | 5.47E−03 | −1.74 | 3.3 |
| hsa-miR-550 | 3.70 | 0.30 | 1.95 | 0.59 | 1.07E−03 | −1.75 | 3.4 |
| hsa-miR-125a-3p | 7.33 | 0.40 | 5.56 | 0.75 | 3.92E−03 | −1.77 | 3.4 |
| hsa-miR-760 | 4.31 | 0.36 | 2.54 | 0.81 | 5.08E−03 | −1.77 | 3.4 |
| hsa-miR-877* | 4.73 | 0.40 | 2.93 | 0.51 | 6.85E−04 | −1.81 | 3.5 |
| hsa-miR-210 | 6.41 | 0.24 | 4.60 | 1.04 | 1.19E−02 | −1.82 | 3.5 |
| hsa-miR-23a* | 4.50 | 0.50 | 2.67 | 0.90 | 8.55E−03 | −1.82 | 3.5 |
| hsa-miR-1249 | 5.93 | 0.74 | 4.05 | 0.56 | 3.22E−03 | −1.88 | 3.7 |
| hsa-miR-135a* | 5.61 | 0.85 | 3.73 | 0.52 | 4.43E−03 | −1.88 | 3.7 |
| hsa-miR-518a-5p | 2.05 | 0.65 | 0.15 | 0.53 | 1.90E−03 | −1.90 | 3.7 |
| hsa-miR-302c* | 1.62 | 0.71 | −0.29 | 0.50 | 2.04E−03 | −1.91 | 3.8 |
| hsa-miR-214 | 9.42 | 0.44 | 7.46 | 0.79 | 3.20E−03 | −1.96 | 3.9 |
| hsa-miR-614 | 2.05 | 0.67 | 0.08 | 0.94 | 9.60E−03 | −1.97 | 3.9 |
| hsa-miR-184 | 2.83 | 0.43 | 0.85 | 0.59 | 7.74E−04 | −1.99 | 4.0 |
| hsa-miR-1226* | 5.72 | 0.46 | 3.70 | 0.47 | 3.51E−04 | −2.03 | 4.1 |
| hsa-miR-583 | 2.59 | 0.74 | 0.54 | 0.77 | 5.12E−03 | −2.04 | 4.1 |
| hsa-miR-654-5p | 4.06 | 0.36 | 2.01 | 1.28 | 1.81E−02 | −2.05 | 4.1 |
| hsa-miR-1299 | 4.40 | 0.44 | 2.34 | 1.29 | 1.96E−02 | −2.06 | 4.2 |
| hsa-miR-639 | 0.97 | 0.48 | −1.10 | 0.71 | 1.64E−02 | −2.07 | 4.2 |
| hsa-miR-513a-5p | 5.52 | 0.43 | 3.44 | 0.48 | 2.74E−04 | −2.08 | 4.2 |
| hsa-miR-490-5p | 3.39 | 0.29 | 1.30 | 0.94 | 3.97E−03 | −2.09 | 4.3 |
| hsa-miR-662 | 3.58 | 0.21 | 1.46 | 0.73 | 8.47E−04 | −2.13 | 4.4 |
| hsa-miR-1180 | 3.54 | 0.41 | 1.41 | 1.66 | 4.20E−02 | −2.13 | 4.4 |
| hsa-miR-1276 | 2.01 | 0.65 | −0.15 | 1.61 | 4.10E−02 | −2.16 | 4.5 |
| hsa-miR-381 | 4.14 | 1.16 | 1.97 | 1.13 | 2.54E−02 | −2.17 | 4.5 |
| hsa-miR-1291 | 2.99 | 0.68 | 0.79 | 1.08 | 9.41E−03 | −2.21 | 4.6 |
| hsa-miR-422a | 3.64 | 0.36 | 1.41 | 1.24 | 1.07E−02 | −2.23 | 4.7 |
| hsa-miR-200a* | 4.34 | 0.33 | 2.10 | 1.76 | 4.24E−02 | −2.24 | 4.7 |
| hsa-miR-373* | 3.17 | 0.97 | 0.91 | 1.67 | 4.86E−02 | −2.26 | 4.8 |
| hsa-miR-518e* | 2.03 | 0.27 | −0.25 | 1.15 | 6.49E−03 | −2.28 | 4.8 |
| hsa-miR-138-1* | 1.32 | 0.49 | −0.97 | 0.85 | 2.04E−03 | −2.29 | 4.9 |
| hsa-miR-518c* | 2.24 | 0.52 | −0.12 | 0.81 | 1.55E−03 | −2.36 | 5.1 |
| hsa-miR-1250 | 1.91 | 0.52 | −0.48 | 1.27 | 9.84E−03 | −2.39 | 5.3 |
| hsa-miR-498 | 3.77 | 0.49 | 1.35 | 1.11 | 5.11E−03 | −2.42 | 5.3 |
| hsa-miR-526b | 3.54 | 0.53 | 1.11 | 0.45 | 1.53E−04 | −2.42 | 5.4 |
| hsa-miR-424* | 5.34 | 0.66 | 2.91 | 1.14 | 7.17E−03 | −2.43 | 5.4 |
| hsa-miR-630 | 6.83 | 0.59 | 4.40 | 0.94 | 2.81E−03 | −2.43 | 5.4 |

TABLE 11-continued

MicroRNAs significantly differentially expressed between FA and NOD samples.

| | NOD | | FA | | FA vs NOD | | |
|---|---|---|---|---|---|---|---|
| miRNA | AVG | SD | AVG | SD | ttest | Log2Diff | Fold change |
| hsa-miR-490-3p | 1.74 | 0.41 | −0.70 | 0.93 | 1.87E−03 | −2.44 | 5.4 |
| hsa-miR-1208 | 3.69 | 0.27 | 1.22 | 0.79 | 5.97E−04 | −2.46 | 5.5 |
| hsa-miR-617 | 3.26 | 0.35 | 0.77 | 0.94 | 1.59E−03 | −2.49 | 5.6 |
| hsa-miR-575 | 10.16 | 0.66 | 7.66 | 0.68 | 8.67E−04 | −2.49 | 5.6 |
| hsa-miR-1246 | 9.63 | 1.16 | 7.09 | 1.23 | 1.63E−02 | −2.53 | 5.8 |
| hsa-miR-1224-5p | 7.60 | 0.65 | 5.05 | 1.45 | 1.45E−02 | −2.55 | 5.9 |
| hsa-miR-298 | 1.93 | 0.38 | −0.62 | 1.18 | 4.51E−03 | −2.55 | 5.9 |
| hsa-miR-371-5p | 6.14 | 0.47 | 3.57 | 0.78 | 6.86E−04 | −2.57 | 5.9 |
| hsa-miR-127-5p | 1.28 | 0.35 | −1.31 | 0.88 | 9.54E−04 | −2.58 | 6.0 |
| hsa-miR-1228* | 1.90 | 0.73 | −0.70 | 1.35 | 1.07E−02 | −2.60 | 6.1 |
| hsa-miR-921 | 1.67 | 0.51 | −0.94 | 0.88 | 1.19E−03 | −2.61 | 6.1 |
| hsa-miR-1915 | 10.06 | 0.49 | 7.41 | 0.57 | 1.59E−04 | −2.65 | 6.3 |
| hsa-miR-622 | 5.23 | 0.37 | 2.58 | 0.92 | 1.06E−03 | −2.65 | 6.3 |
| hsa-miR-202 | 7.06 | 0.56 | 4.38 | 0.70 | 4.36E−03 | −2.68 | 6.4 |
| hsa-miR-638 | 10.95 | 1.00 | 8.26 | 0.52 | 1.16E−03 | −2.70 | 6.5 |
| hsa-miR-1469 | 3.39 | 0.42 | 0.68 | 1.64 | 1.55E−02 | −2.71 | 6.6 |
| hsa-miR-188-5p | 7.46 | 0.63 | 4.71 | 0.32 | 5.89E−05 | −2.74 | 6.7 |
| hsa-miR-631 | 3.97 | 0.56 | 1.22 | 1.73 | 1.91E−02 | −2.75 | 6.7 |
| hsa-miR-566 | 3.15 | 0.92 | 0.39 | 1.49 | 1.45E−02 | −2.77 | 6.8 |
| hsa-miR-1268 | 10.19 | 1.33 | 7.39 | 0.37 | 2.58E−03 | −2.80 | 7.0 |
| hsa-miR-1203 | 2.45 | 0.50 | −0.36 | 1.20 | 3.47E−03 | −2.80 | 7.0 |
| hsa-miR-610 | 4.46 | 0.57 | 1.65 | 0.67 | 3.02E−05 | −2.80 | 7.0 |
| hsa-miR-623 | 4.95 | 0.55 | 2.14 | 0.90 | 9.42E−04 | −2.81 | 7.0 |
| hsa-miR-877 | 4.47 | 0.65 | 1.65 | 1.12 | 3.09E−03 | −2.82 | 7.1 |
| hsa-miR-616 | 1.69 | 0.53 | −1.14 | 1.00 | 1.44E−03 | −2.82 | 7.1 |
| hsa-miR-939 | 8.91 | 0.42 | 6.06 | 0.56 | 6.59E−05 | −2.85 | 7.2 |
| hsa-miR-572 | 7.90 | 1.01 | 5.04 | 0.65 | 1.29E−03 | −2.86 | 7.3 |
| hsa-miR-940 | 8.91 | 0.72 | 6.05 | 0.76 | 7.02E−04 | −2.86 | 7.3 |
| hsa-miR-134 | 8.00 | 0.93 | 5.08 | 0.86 | 1.80E−03 | −2.91 | 7.5 |
| hsa-miR-516b | 2.78 | 0.32 | −0.14 | 0.79 | 2.30E−04 | −2.91 | 7.5 |
| hsa-miR-1471 | 5.53 | 0.37 | 2.62 | 1.29 | 3.42E−03 | −2.92 | 7.5 |
| hsa-miR-601 | 5.60 | 0.53 | 2.62 | 0.55 | 7.49E−05 | −2.97 | 7.9 |
| hsa-miR-671-5p | 7.24 | 0.57 | 4.25 | 0.59 | 1.16E−04 | −2.99 | 7.9 |
| hsa-miR-493 | 2.93 | 0.73 | −0.12 | 1.07 | 1.91E−03 | −3.05 | 8.3 |
| hsa-miR-1915* | 2.26 | 0.54 | −0.82 | 1.08 | 1.30E−03 | −3.08 | 8.5 |
| hsa-miR-1225-5p | 11.79 | 0.95 | 8.71 | 0.57 | 5.05E−04 | −3.08 | 8.5 |
| hsa-miR-34c-3p | 1.72 | 0.30 | −1.38 | 0.78 | 1.53E−04 | −3.09 | 8.5 |
| hsa-miR-1207-5p | 11.83 | 1.05 | 8.69 | 0.76 | 1.20E−03 | −3.14 | 8.8 |
| hsa-miR-659 | 5.53 | 0.63 | 2.36 | 0.93 | 6.76E−04 | −3.17 | 9.0 |
| hsa-miR-1183 | 6.22 | 0.69 | 3.04 | 1.31 | 3.35E−03 | −3.18 | 9.1 |
| hsa-miR-1321 | 3.74 | 0.75 | 0.48 | 0.58 | 1.56E−04 | −3.26 | 9.6 |
| hsa-miR-551b* | 2.72 | 0.65 | −0.64 | 1.29 | 2.18E−03 | −3.36 | 10.2 |
| hsa-miR-199b-5p | 9.26 | 0.23 | 5.87 | 1.73 | 6.41E−03 | −3.38 | 10.4 |
| hsa-miR-370 | 3.80 | 0.49 | 0.41 | 1.72 | 6.93E−03 | −3.40 | 10.5 |
| hsa-miR-934 | 2.09 | 0.71 | −1.31 | 1.49 | 4.19E−03 | −3.40 | 10.5 |
| hsa-miR-150* | 7.49 | 0.70 | 4.08 | 0.64 | 1.19E−04 | −3.42 | 10.7 |
| hsa-miR-483-5p | 8.47 | 0.79 | 5.02 | 0.82 | 3.79E−04 | −3.45 | 11.0 |
| hsa-miR-765 | 6.63 | 0.70 | 3.01 | 1.05 | 6.05E−04 | −3.62 | 12.3 |
| hsa-miR-936 | 4.55 | 0.65 | 0.89 | 1.06 | 5.29E−04 | −3.66 | 12.6 |
| hsa-miR-648 | 4.14 | 0.46 | 0.45 | 1.38 | 1.44E−03 | −3.69 | 12.9 |
| hsa-miR-149* | 4.68 | 0.59 | 0.84 | 1.62 | 2.93E−03 | −3.85 | 14.4 |
| hsa-miR-198 | 4.90 | 0.65 | 1.05 | 0.66 | 4.97E−05 | −3.85 | 14.5 |
| hsa-miR-92b* | 2.96 | 0.56 | −0.89 | 1.18 | 5.65E−04 | −3.86 | 14.5 |
| hsa-miR-1182 | 4.76 | 0.77 | 0.89 | 0.88 | 2.20E−04 | −3.88 | 14.7 |
| hsa-miR-187* | 4.73 | 0.70 | 0.84 | 1.40 | 1.56E−03 | −3.88 | 14.8 |
| hsa-miR-1300 | 7.80 | 0.79 | 3.75 | 1.14 | 5.35E−04 | −4.05 | 16.6 |
| hsa-miR-663 | 8.63 | 0.75 | 4.45 | 1.10 | 3.47E−04 | −4.18 | 18.1 |
| hsa-miR-1202 | 13.75 | 0.81 | 9.38 | 0.66 | 4.28E−05 | −4.37 | 20.7 |
| hsa-miR-206 | 5.33 | 3.16 | −0.30 | 1.16 | 7.27E−03 | −5.63 | 49.6 |

AVG, average expression among samples in a group;
SD, standard deviation

Example 10 miRNA Expression Profiling Distinguishes Hyperplastic Thyroid Nodules and Follicular Thyroid Carcinoma A total of 150 human miRNAs were significantly differentially expressed between the hyperplastic nodule samples and the follicular thyroid carcinoma specimens ($p<0.05$). Among these, 24 miRNAs were overexpressed (Log 2 diff (FTC vs NOD)≥1) and 126 were underexpressed (Log 2 diff (FTC vs NOD)≤1) by at least 2-fold in FTC compared to NOD samples (Table 12). Of these, hsa-miR-1274a was overexpressed by over 10-fold in the FTC samples, and six miRNAs (hsa-miR-1274b, -1260, -720, -182, -142-3p, and -96) were overexpressed by 5- to 10-fold.

TABLE 12

MicroRNAs significantly differentially expressed between FTC and NOD samples.

| miRNA | NOD AVG | NOD SD | FTC AVG | FTC SD | FTC vs NOD ttest | FTC vs NOD Log2Diff | Fold change |
|---|---|---|---|---|---|---|---|
| hsa-miR-1274a | 4.74 | 1.03 | 8.23 | 0.72 | 5.48E−04 | 3.49 | 11.2 |
| hsa-miR-1274b | 8.53 | 0.95 | 11.77 | 0.70 | 6.03E−04 | 3.24 | 9.4 |
| hsa-miR-1260 | 6.50 | 0.87 | 9.49 | 0.60 | 4.85E−04 | 2.99 | 7.9 |
| hsa-miR-720 | 10.25 | 0.79 | 13.21 | 0.64 | 4.31E−04 | 2.96 | 7.8 |
| hsa-miR-182 | 1.79 | 0.79 | 4.50 | 1.38 | 1.03E−02 | 2.72 | 6.6 |
| hsa-miR-142-3p | 7.20 | 1.09 | 9.73 | 1.31 | 1.77E−02 | 2.53 | 5.8 |
| hsa-miR-96 | 7.09 | 0.38 | 9.53 | 1.14 | 4.75E−03 | 2.44 | 5.4 |
| hsa-miR-148a* | 0.37 | 0.58 | 2.35 | 0.67 | 2.32E−03 | 1.98 | 3.9 |
| hsa-miR-29b-1* | 3.36 | 0.34 | 4.98 | 0.44 | 5.07E−04 | 1.62 | 3.1 |
| hsa-miR-148a | 10.18 | 0.47 | 11.79 | 0.72 | 6.39E−03 | 1.60 | 3.0 |
| hsa-miR-183 | 6.08 | 0.43 | 7.67 | 1.17 | 3.69E−02 | 1.60 | 3.0 |
| hsa-miR-181a* | 3.26 | 0.41 | 4.80 | 0.73 | 7.38E−03 | 1.54 | 2.9 |
| hsa-miR-141* | 2.70 | 0.63 | 4.23 | 0.52 | 5.04E−03 | 1.54 | 2.9 |
| hsa-miR-200c* | 1.03 | 0.53 | 2.57 | 0.40 | 1.63E−03 | 1.53 | 2.9 |
| hsa-miR-32 | 3.64 | 0.87 | 5.08 | 0.46 | 1.49E−02 | 1.44 | 2.7 |
| hsa-miR-21* | 4.43 | 0.17 | 5.87 | 0.74 | 7.26E−03 | 1.43 | 2.7 |
| hsa-miR-182* | −0.26 | 0.47 | 1.12 | 0.70 | 1.17E−02 | 1.38 | 2.6 |
| hsa-miR-340* | 3.30 | 0.54 | 4.62 | 0.31 | 2.36E−03 | 1.32 | 2.5 |
| hsa-miR-21 | 13.28 | 0.37 | 14.52 | 0.58 | 7.55E−03 | 1.24 | 2.4 |
| hsa-miR-15a | 10.48 | 0.47 | 11.65 | 0.39 | 4.37E−03 | 1.18 | 2.3 |
| hsa-miR-34a | 10.89 | 0.21 | 12.03 | 0.62 | 1.08E−02 | 1.13 | 2.2 |
| hsa-miR-146a | 6.97 | 0.24 | 8.10 | 0.68 | 1.64E−03 | 1.13 | 2.2 |
| hsa-miR-340 | 4.68 | 0.47 | 5.80 | 0.41 | 6.46E−03 | 1.12 | 2.2 |
| hsa-miR-15a* | 0.91 | 0.35 | 1.93 | 0.52 | 1.22E−02 | 1.02 | 2.0 |
| hsa-miR-23a* | 4.50 | 0.50 | 3.50 | 0.33 | 8.30E−03 | −1.00 | 2.0 |
| hsa-miR-1910 | −0.66 | 0.59 | −1.67 | 0.19 | 7.75E−03 | −1.01 | 2.0 |
| hsa-let-7c* | 0.97 | 0.24 | −0.07 | 0.63 | 1.74E−02 | −1.04 | 2.1 |
| hsa-miR-100 | 11.66 | 0.24 | 10.62 | 0.75 | 3.38E−02 | −1.04 | 2.1 |
| hsa-miR-658 | 1.16 | 0.56 | 0.11 | 0.71 | 4.59E−02 | −1.06 | 2.1 |
| hsa-let-7g* | −0.02 | 0.56 | −1.09 | 0.50 | 1.93E−02 | −1.07 | 2.1 |
| hsa-miR-296-5p | 4.51 | 0.68 | 3.43 | 0.39 | 2.04E−02 | −1.08 | 2.1 |
| hsa-miR-432 | 3.26 | 0.58 | 2.12 | 0.63 | 2.78E−02 | −1.14 | 2.2 |
| hsa-miR-1285 | 3.38 | 0.58 | 2.24 | 0.49 | 1.46E−02 | −1.14 | 2.2 |
| hsa-miR-501-3p | 4.63 | 0.23 | 3.45 | 0.46 | 2.21E−03 | −1.18 | 2.3 |
| hsa-miR-1244 | 2.06 | 0.85 | 0.87 | 0.64 | 4.67E−02 | −1.20 | 2.3 |
| hsa-miR-99b* | 2.95 | 0.29 | 1.74 | 0.46 | 2.55E−03 | −1.21 | 2.3 |
| hsa-miR-193b* | 4.70 | 0.59 | 3.48 | 0.44 | 9.34E−03 | −1.22 | 2.3 |
| hsa-miR-509-5p | 1.19 | 0.42 | −0.04 | 0.93 | 4.58E−02 | −1.23 | 2.4 |
| hsa-miR-193a-5p | 6.14 | 0.51 | 4.90 | 0.52 | 9.03E−03 | −1.24 | 2.4 |
| hsa-miR-1307 | 3.37 | 0.39 | 2.12 | 0.51 | 5.20E−03 | −1.25 | 2.4 |
| hsa-miR-125a-3p | 7.33 | 0.40 | 6.09 | 0.69 | 1.54E−02 | −1.25 | 2.4 |
| hsa-miR-1306 | 2.97 | 0.34 | 1.71 | 0.64 | 9.63E−03 | −1.26 | 2.4 |
| hsa-miR-886-5p | 0.16 | 0.98 | −1.17 | 0.54 | 3.51E−02 | −1.33 | 2.5 |
| hsa-miR-550 | 3.70 | 0.30 | 2.37 | 0.52 | 2.71E−03 | −1.33 | 2.5 |
| hsa-miR-508-5p | 0.24 | 1.03 | −1.13 | 0.51 | 3.41E−02 | −1.37 | 2.6 |
| hsa-miR-708 | 2.61 | 0.40 | 1.22 | 1.04 | 4.23E−02 | −1.38 | 2.6 |
| hsa-miR-28-3p | 2.09 | 0.21 | 0.68 | 0.93 | 2.21E−02 | −1.41 | 2.7 |
| hsa-miR-1249 | 5.93 | 0.74 | 4.52 | 0.53 | 1.22E−02 | −1.42 | 2.7 |
| hsa-miR-1208 | 3.69 | 0.27 | 2.25 | 0.60 | 3.20E−03 | −1.44 | 2.7 |
| hsa-miR-194* | 1.50 | 0.63 | −0.04 | 0.61 | 7.56E−03 | −1.54 | 2.9 |
| hsa-miR-486-3p | 2.16 | 1.04 | 0.61 | 0.84 | 4.16E−03 | −1.55 | 2.9 |
| hsa-miR-1226* | 5.72 | 0.46 | 4.16 | 0.57 | 3.03E−03 | −1.56 | 3.0 |
| hsa-miR-557 | 6.23 | 0.77 | 4.66 | 0.55 | 9.08E−03 | −1.57 | 3.0 |
| hsa-miR-639 | 0.97 | 0.48 | −0.61 | 0.73 | 7.36E−03 | −1.59 | 3.0 |
| hsa-miR-3313* | 4.27 | 0.51 | 2.68 | 0.47 | 1.80E−03 | −1.60 | 3.0 |
| hsa-miR-139-5p | 6.89 | 0.32 | 5.29 | 1.11 | 2.82E−02 | −1.60 | 3.0 |
| hsa-miR-595 | 1.81 | 0.36 | 0.18 | 0.21 | 5.53E−05 | −1.63 | 3.1 |
| hsa-miR-422a | 3.64 | 0.36 | 2.01 | 0.84 | 8.83E−03 | −1.63 | 3.1 |
| hsa-miR-769-3p | 3.34 | 0.64 | 1.71 | 0.57 | 4.78E−03 | −1.63 | 3.1 |
| hsa-miR-214 | 9.42 | 0.44 | 7.78 | 1.27 | 4.54E−03 | −1.63 | 3.1 |
| hsa-miR-525-5p | 2.15 | 0.49 | 0.52 | 0.56 | 2.60E−03 | −1.64 | 3.1 |
| hsa-miR-665 | 4.46 | 0.24 | 2.81 | 0.86 | 7.90E−03 | −1.65 | 3.1 |
| hsa-miR-654-5p | 4.06 | 0.36 | 2.39 | 0.76 | 5.17E−03 | −1.67 | 3.2 |
| hsa-miR-1299 | 4.40 | 0.44 | 2.69 | 0.52 | 1.25E−03 | −1.71 | 3.3 |
| hsa-miR-122 | 2.20 | 1.35 | 0.49 | 0.58 | 3.58E−02 | −1.71 | 3.3 |
| hsa-miR-574-5p | 7.52 | 0.63 | 5.80 | 0.57 | 3.45E−03 | −1.73 | 3.3 |
| hsa-miR-877 | 4.47 | 0.65 | 2.71 | 0.70 | 6.47E−03 | −1.75 | 3.4 |
| hsa-miR-877* | 4.73 | 0.40 | 2.97 | 0.64 | 2.12E−03 | −1.76 | 3.4 |
| hsa-miR-138 | 6.61 | 0.71 | 4.85 | 1.20 | 3.68E−02 | −1.76 | 3.4 |
| hsa-miR-575 | 10.16 | 0.66 | 8.39 | 0.84 | 1.10E−02 | −1.76 | 3.4 |
| hsa-miR-513a-5p | 5.52 | 0.43 | 3.73 | 0.42 | 3.91E−04 | −1.80 | 3.5 |
| hsa-miR-1469 | 3.39 | 0.42 | 1.59 | 0.92 | 9.05E−03 | −1.80 | 3.5 |
| hsa-miR-1180 | 3.54 | 0.41 | 1.72 | 0.88 | 6.77E−03 | −1.82 | 3.5 |

TABLE 12-continued

MicroRNAs significantly differentially expressed between FTC and NOD samples.

| miRNA | NOD AVG | NOD SD | FTC AVG | FTC SD | FTC vs NOD ttest | FTC vs NOD Log2Diff | Fold change |
|---|---|---|---|---|---|---|---|
| hsa-miR-518e* | 2.03 | 0.27 | 0.19 | 0.73 | 2.09E−03 | −1.84 | 3.6 |
| hsa-miR-1291 | 2.99 | 0.68 | 1.11 | 1.41 | 4.57E−02 | −1.88 | 3.7 |
| hsa-miR-1915 | 10.06 | 0.49 | 8.15 | 0.61 | 1.49E−03 | −1.91 | 3.8 |
| hsa-miR-124 | 1.52 | 1.06 | −0.40 | 1.08 | 3.18E−02 | −1.92 | 3.8 |
| hsa-miR-617 | 3.26 | 0.35 | 1.34 | 0.73 | 1.94E−03 | −1.92 | 3.8 |
| hsa-miR-940 | 8.91 | 0.72 | 6.98 | 0.73 | 5.62E−03 | −1.93 | 3.8 |
| hsa-miR-616 | 1.69 | 0.53 | −0.25 | 0.82 | 4.91E−03 | −1.93 | 3.8 |
| hsa-miR-662 | 3.58 | 0.21 | 1.65 | 0.44 | 9.39E−05 | −1.94 | 3.8 |
| hsa-miR4246 | 9.63 | 1.16 | 7.69 | 0.96 | 2.84E−02 | −1.94 | 3.8 |
| hsa-miR-302c* | 1.62 | 0.71 | −0.34 | 0.94 | 1.08E−02 | −1.95 | 3.9 |
| hsa-miR-371-5p | 6.14 | 0.47 | 4.16 | 0.71 | 2.00E−03 | −1.99 | 4.0 |
| hsa-miR-298 | 1.93 | 0.38 | −0.08 | 0.87 | 3.78E−03 | −2.01 | 4.0 |
| hsa-miR-614 | 2.05 | 0.67 | 0.04 | 0.66 | 2.78E−03 | −2.01 | 4.0 |
| hsa-miR-640 | 1.49 | 0.46 | −0.53 | 0.96 | 6.28E−03 | −2.02 | 4.1 |
| hsa-miR-601 | 5.60 | 0.53 | 3.56 | 0.85 | 4.14E−03 | −2.04 | 4.1 |
| hsa-miR-516b | 2.78 | 0.32 | 0.74 | 0.84 | 2.68E−03 | −2.04 | 4.1 |
| hsa-miR-1303 | 1.71 | 0.56 | −0.33 | 0.55 | 9.28E−04 | −2.04 | 4.1 |
| hsa-miR-188-5p | 7.46 | 0.63 | 5.41 | 0.89 | 6.21E−03 | −2.04 | 4.1 |
| hsa-miR-370 | 3.80 | 0.49 | 1.75 | 0.74 | 2.09E−03 | −2.05 | 4.1 |
| hsa-miR-1308 | 10.04 | 0.87 | 7.97 | 0.57 | 3.51E−03 | −2.07 | 4.2 |
| hsa-miR-583 | 2.59 | 0.74 | 0.52 | 1.41 | 3.34E−02 | −2.07 | 4.2 |
| hsa-miR-200a* | 4.34 | 0.33 | 2.23 | 1.29 | 1.61E−02 | −2.12 | 4.3 |
| hsa-miR-202 | 7.06 | 0.56 | 4.93 | 0.81 | 3.08E−03 | −2.13 | 4.4 |
| hsa-miR-1250 | 1.91 | 0.52 | −0.21 | 0.49 | 3.94E−04 | −2.13 | 4.4 |
| hsa-miR-939 | 8.91 | 0.42 | 6.76 | 0.73 | 1.25E−03 | −2.15 | 4.4 |
| hsa-miR-610 | 4.46 | 0.57 | 2.28 | 0.91 | 4.36E−03 | −2.18 | 4.5 |
| hsa-miR-490-3p | 1.74 | 0.41 | −0.44 | 0.85 | 2.29E−03 | −2.18 | 4.5 |
| hsa-miR-1224-5p | 7.60 | 0.65 | 5.41 | 0.82 | 3.46E−03 | −2.19 | 4.6 |
| hsa-miR-134 | 8.00 | 0.93 | 5.80 | 0.88 | 8.16E−03 | −2.20 | 4.6 |
| hsa-miR-1471 | 5.53 | 0.37 | 3.32 | 1.04 | 5.17E−03 | −2.21 | 4.6 |
| hsa-miR-200b* | 4.90 | 0.29 | 2.61 | 1.38 | 1.47E−02 | −2.29 | 4.9 |
| hsa-miR-671-5p | 7.24 | 0.57 | 4.95 | 1.00 | 4.84E−03 | −2.29 | 4.9 |
| hsa-miR-498 | 3.77 | 0.49 | 1.44 | 0.61 | 4.65E−04 | −2.33 | 5.0 |
| hsa-miR-518a-5p | 2.05 | 0.65 | −0.28 | 1.02 | 5.64E−03 | −2.33 | 5.0 |
| hsa-miR-526b | 3.54 | 0.53 | 1.20 | 0.98 | 3.80E−03 | −2.34 | 5.1 |
| hsa-miR-1228* | 1.90 | 0.73 | −0.44 | 1.02 | 6.18E−03 | −2.34 | 5.1 |
| hsa-miR-622 | 5.23 | 0.37 | 2.89 | 0.99 | 2.95E−03 | −2.35 | 5.1 |
| hsa-miR-518c* | 2.24 | 0.52 | −0.12 | 0.50 | 2.22E−04 | −2.36 | 5.1 |
| hsa-miR-1268 | 10.19 | 1.33 | 7.82 | 0.51 | 7.46E−03 | −2.37 | 5.2 |
| hsa-miR-1915* | 2.26 | 0.54 | −0.14 | 0.90 | 2.30E−03 | −2.40 | 5.3 |
| hsa-miR-1276 | 2.01 | 0.65 | −0.39 | 0.80 | 1.89E−03 | −2.40 | 5.3 |
| hsa-miR-1207-5p | 11.83 | 1.05 | 9.42 | 0.95 | 8.58E−03 | −2.41 | 5.3 |
| hsa-miR-424* | 5.34 | 0.66 | 2.93 | 1.11 | 6.68E−03 | −2.41 | 5.3 |
| hsa-miR-34c-3p | 1.72 | 0.30 | −0.70 | 0.62 | 1.92E−04 | −2.42 | 5.4 |
| hsa-miR-127-5p | 1.28 | 0.35 | −1.15 | 0.64 | 2.55E−04 | −2.43 | 5.4 |
| hsa-miR-921 | 1.67 | 0.51 | −0.76 | 1.15 | 6.04E−03 | −2.43 | 5.4 |
| hsa-miR-150* | 7.49 | 0.70 | 5.02 | 0.98 | 3.87E−03 | −2.48 | 5.6 |
| hsa-miR-1321 | 3.74 | 0.75 | 1.25 | 0.46 | 4.63E−04 | −2.49 | 5.6 |
| hsa-miR-1183 | 6.22 | 0.69 | 3.73 | 0.90 | 2.57E−03 | −2.49 | 5.6 |
| hsa-miR-490-5p | 3.39 | 0.29 | 0.89 | 0.77 | 5.25E−04 | −2.50 | 5.6 |
| hsa-miR-659 | 5.53 | 0.63 | 3.03 | 1.18 | 6.73E−03 | −2.50 | 5.6 |
| hsa-miR-1225-5p | 11.79 | 0.95 | 9.24 | 0.94 | 5.06E−03 | −2.55 | 5.9 |
| hsa-miR-638 | 10.95 | 1.00 | 8.39 | 0.59 | 1.91E−03 | −2.56 | 5.9 |
| hsa-miR-138-1* | 1.32 | 0.49 | −1.25 | 1.24 | 6.14E−03 | −2.58 | 6.0 |
| hsa-miR-1203 | 2.45 | 0.50 | −0.22 | 1.05 | 2.43E−03 | −2.67 | 6.3 |
| hsa-miR-572 | 7.90 | 1.01 | 5.22 | 0.61 | 1.64E−03 | −2.68 | 6.4 |
| hsa-miR-551b* | 2.72 | 0.65 | 0.02 | 0.64 | 4.32E−04 | −2.70 | 6.5 |
| hsa-miR-483-5p | 8.47 | 0.79 | 5.75 | 1.18 | 5.68E−03 | −2.72 | 6.6 |
| hsa-miR-566 | 3.15 | 0.92 | 0.32 | 0.98 | 3.15E−03 | −2.83 | 7.1 |
| hsa-miR-936 | 4.55 | 0.65 | 1.69 | 0.95 | 1.40E−03 | −2.86 | 7.2 |
| hsa-miR-623 | 4.95 | 0.55 | 2.08 | 0.72 | 3.08E−04 | −2.88 | 7.3 |
| hsa-miR-765 | 6.63 | 0.70 | 3.72 | 1.08 | 2.33E−03 | −2.91 | 7.5 |
| hsa-miR-493 | 2.93 | 0.73 | −0.08 | 1.31 | 4.78E−03 | −3.00 | 8.0 |
| hsa-miR-648 | 4.14 | 0.46 | 1.11 | 1.21 | 2.26E−03 | −3.02 | 8.1 |
| hsa-miR-663 | 8.63 | 0.75 | 5.58 | 1.19 | 3.01E−03 | −3.05 | 8.3 |
| hsa-miR-187* | 4.73 | 0.70 | 1.60 | 1.16 | 2.23E−03 | −3.13 | 8.7 |
| hsa-miR-631 | 3.97 | 0.56 | 0.83 | 0.94 | 6.30E−04 | −3.15 | 8.9 |
| hsa-miR-149* | 4.68 | 0.59 | 1.51 | 1.12 | 1.43E−03 | −3.18 | 9.0 |
| hsa-miR-1202 | 13.75 | 0.81 | 10.55 | 1.39 | 4.92E−03 | −3.20 | 9.2 |
| hsa-miR-1182 | 4.76 | 0.77 | 1.56 | 1.12 | 1.84E−03 | −3.21 | 9.2 |
| hsa-miR-934 | 2.09 | 0.71 | −1.12 | 1.32 | 3.38E−03 | −3.21 | 9.3 |
| hsa-miR-198 | 4.90 | 0.65 | 1.65 | 1.36 | 3.35E−03 | −3.25 | 9.5 |
| hsa-miR-1909* | 2.64 | 0.78 | −0.64 | 1.16 | 1.93E−03 | −3.28 | 9.7 |

TABLE 12-continued

MicroRNAs significantly differentially expressed between FTC and NOD samples.

| miRNA | NOD AVG | NOD SD | FTC AVG | FTC SD | FTC vs NOD ttest | FTC vs NOD Log2Diff | Fold change |
|---|---|---|---|---|---|---|---|
| hsa-miR-1300 | 7.80 | 0.79 | 4.28 | 0.85 | 3.76E−04 | −3.53 | 11.5 |
| hsa-miR-133b | 9.40 | 3.03 | 5.78 | 1.31 | 4.51E−02 | −3.62 | 12.3 |
| hsa-miR-92b* | 2.96 | 0.56 | −0.83 | 0.95 | 2.07E−04 | −3.80 | 13.9 |
| hsa-miR-206 | 5.33 | 3.16 | 0.29 | 0.60 | 9.35E−03 | −5.04 | 32.9 |

AVG, average expression among samples in a group;
SD, standard deviation

Example 11 miRNA Expression Profiling Distinguishes Hyperplastic Thyroid Nodules and Papillary Thyroid Carcinoma A total of 262 human miRNAs were significantly differentially expressed between the hyperplastic nodule samples the papillary thyroid carcinoma specimens (p<0.05) (Table 13). Among these, 48 miRNAs were overexpressed (Log 2 diff (NOD vs PTC)≤1) and 152 were underexpressed (Log 2 diff (NOD vs PTC)≥1) by at least 2-fold in PTC compared to NOD samples. Of these, hsa-miR-146b-5p was overexpressed by more than 100-fold, seven miRNAs (hsa-miR-146b-3p, -551b, -221, -222, -221*, -31*, and -31) were overexpressed by 10- to 30-fold, and eight miRNAs (hsa-miR-1274a, -1274b, -142-3p, -375, -720, -21, -21*, -181a-2*) were overexpressed by 5- to 10-fold in the PTC specimens compared to the NOD samples. Among the miRNAs that were expressed at lower average levels in the PTC samples, hsa-miR-206 was underexpressed by at least 40-fold, thirty four miRNAs were underexpressed by 10- to 20-fold, and forty seven miRNAs were under-expressed by 5- to 10-fold in the PTC specimens compared to the NOD samples.

TABLE 13

MicroRNAs significantly differentially expressed between PTC and NOD samples.

| miRNA | NOD AVG | NOD SD | PTC AVG | PTC SD | NOD vs PTC ttest | NOD vs PTC Log2 diff | Fold change |
|---|---|---|---|---|---|---|---|
| hsa-miR-206 | 5.33 | 3.16 | −0.07 | 0.40 | 6.31E−03 | −5.39 | 42.1 |
| hsa-miR-631 | 3.97 | 0.56 | −0.92 | 0.83 | 2.03E−05 | −4.90 | 29.8 |
| hsa-miR-92b* | 2.96 | 0.56 | −1.87 | 0.74 | 1.25E−05 | −4.84 | 28.6 |
| hsa-miR-1202 | 13.75 | 0.81 | 9.02 | 0.95 | 9.73E−05 | −4.73 | 26.5 |
| hsa-miR-663 | 8.63 | 0.75 | 4.09 | 0.76 | 4.46E−05 | −4.54 | 23.2 |
| hsa-miR-149* | 4.68 | 0.59 | 0.27 | 0.56 | 8.50E−06 | −4.42 | 21.3 |
| hsa-miR-765 | 6.63 | 0.70 | 2.28 | 0.68 | 3.16E−05 | −4.35 | 20.4 |
| hsa-miR-1300 | 7.80 | 0.79 | 3.48 | 0.76 | 7.05E−05 | −4.32 | 20.0 |
| hsa-miR-936 | 4.55 | 0.65 | 0.34 | 0.48 | 9.70E−06 | −4.21 | 18.5 |
| hsa-miR-648 | 4.14 | 0.46 | −0.03 | 0.72 | 2.15E−05 | −4.17 | 18.0 |
| hsa-miR-659 | 5.53 | 0.63 | 1.42 | 0.91 | 1.22E−04 | −4.11 | 17.3 |
| hsa-miR-1182 | 4.76 | 0.77 | 0.68 | 0.68 | 6.26E−05 | −4.08 | 17.0 |
| hsa-miR-198 | 4.90 | 0.65 | 0.85 | 0.77 | 6.69E−05 | −4.05 | 16.6 |
| hsa-miR-483-5p | 8.47 | 0.79 | 4.52 | 0.79 | 1.45E−04 | −3.95 | 15.5 |
| hsa-miR-934 | 2.09 | 0.71 | −1.85 | 0.68 | 6.15E−05 | −3.94 | 15.3 |
| hsa-miR-187* | 4.73 | 0.70 | 0.80 | 0.86 | 1.61E−04 | −3.93 | 15.2 |
| hsa-miR-623 | 4.95 | 0.55 | 1.05 | 1.06 | 2.88E−04 | −3.91 | 15.0 |
| hsa-miR-1909* | 2.64 | 0.78 | −1.25 | 0.45 | 3.14E−05 | −3.89 | 14.8 |
| hsa-miR-572 | 7.90 | 1.01 | 4.08 | 0.45 | 1.23E−04 | −3.82 | 14.1 |
| hsa-miR-1915* | 2.26 | 0.54 | −1.44 | 0.82 | 1.18E−04 | −3.70 | 13.0 |
| hsa-miR-7 | 10.99 | 1.81 | 7.30 | 1.72 | 1.65E−02 | −3.70 | 13.0 |
| hsa-miR-493 | 2.93 | 0.73 | −0.73 | 0.79 | 1.87E−04 | −3.66 | 12.6 |
| hsa-miR-1207-5p | 11.83 | 1.05 | 8.19 | 0.66 | 3.73E−04 | −3.64 | 12.5 |
| hsa-miR-638 | 10.95 | 1.00 | 7.32 | 0.50 | 1.80E−04 | −3.63 | 12.4 |
| hsa-miR-1268 | 10.19 | 1.33 | 6.57 | 0.52 | 7.63E−05 | −3.62 | 12.3 |
| hsa-miR-1183 | 6.22 | 0.69 | 2.62 | 0.61 | 6.91E−05 | −3.60 | 12.2 |
| hsa-miR-150* | 7.49 | 0.70 | 3.89 | 0.62 | 7.96E−05 | −3.60 | 12.1 |
| hsa-miR-1321 | 3.74 | 0.75 | 0.17 | 0.39 | 3.55E−05 | −3.57 | 11.9 |
| hsa-miR-1225-5p | 11.79 | 0.95 | 8.28 | 0.48 | 1.67E−04 | −3.52 | 11.4 |
| hsa-miR-1203 | 2.45 | 0.50 | −1.06 | 0.52 | 1.79E−05 | −3.50 | 11.3 |
| hsa-miR-671-5p | 7.24 | 0.57 | 3.74 | 0.72 | 1.00E−04 | −3.50 | 11.3 |
| hsa-miR-134 | 8.00 | 0.93 | 4.56 | 0.60 | 2.65E−04 | −3.43 | 10.8 |
| hsa-miR-566 | 3.15 | 0.92 | −0.20 | 0.64 | 3.36E−04 | −3.36 | 10.3 |
| hsa-miR-1224-5p | 7.60 | 0.65 | 4.26 | 0.47 | 4.40E−05 | −3.34 | 10.1 |
| hsa-miR-371-5p | 6.14 | 0.47 | 2.81 | 0.43 | 1.08E−05 | −3.34 | 10.1 |
| hsa-miR-1228* | 1.90 | 0.73 | −1.42 | 0.60 | 1.33E−04 | −3.32 | 10.0 |
| hsa-miR-1291 | 2.99 | 0.68 | −0.24 | 0.49 | 7.16E−05 | −3.23 | 9.4 |
| hsa-miR-1471 | 5.53 | 0.37 | 2.31 | 0.52 | 1.61E−05 | −3.22 | 9.3 |

TABLE 13-continued

MicroRNAs significantly differentially expressed between PTC and NOD samples.

| | NOD | | PTC | | NOD vs PTC | | |
|---|---|---|---|---|---|---|---|
| miRNA | AVG | SD | AVG | SD | ttest | Log2 diff | Fold change |
| hsa-miR-526b | 3.54 | 0.53 | 0.32 | 0.75 | 1.76E−04 | −3.22 | 9.3 |
| hsa-miR-939 | 8.91 | 0.42 | 5.75 | 0.45 | 1.28E−05 | −3.16 | 8.9 |
| hsa-miR-583 | 2.59 | 0.74 | −0.56 | 0.48 | 1.13E−04 | −3.15 | 8.9 |
| hsa-miR-34c-3p | 1.72 | 0.30 | −1.42 | 0.20 | 3.03E−07 | −3.14 | 8.8 |
| hsa-miR-1469 | 3.39 | 0.42 | 0.27 | 1.30 | 2.61E−03 | −3.12 | 8.7 |
| hsa-miR-877 | 4.47 | 0.65 | 1.45 | 1.15 | 2.38E−03 | −3.02 | 8.1 |
| hsa-miR-551b* | 2.72 | 0.65 | −0.28 | 1.25 | 3.56E−03 | −3.00 | 8.0 |
| hsa-miR-601 | 5.60 | 0.53 | 2.62 | 0.73 | 2.51E−04 | −2.98 | 7.9 |
| hsa-miR-1915 | 10.06 | 0.49 | 7.09 | 0.28 | 8.39E−06 | −2.97 | 7.8 |
| hsa-miR-204 | 8.22 | 0.45 | 5.26 | 0.80 | 3.17E−05 | −2.96 | 7.8 |
| hsa-miR-373* | 3.17 | 0.97 | 0.24 | 0.68 | 1.08E−03 | −2.93 | 7.6 |
| hsa-miR-616 | 1.69 | 0.53 | −1.19 | 0.58 | 1.22E−04 | −2.88 | 7.4 |
| hsa-miR-490-3p | 1.74 | 0.41 | −1.13 | 0.67 | 1.37E−04 | −2.87 | 7.3 |
| hsa-miR-138-1* | 1.32 | 0.49 | −1.55 | 0.61 | 1.22E−04 | −2.87 | 7.3 |
| hsa-miR-940 | 8.91 | 0.72 | 6.07 | 0.15 | 5.24E−05 | −2.84 | 7.1 |
| hsa-miR-622 | 5.23 | 0.37 | 2.40 | 0.69 | 1.54E−04 | −2.83 | 7.1 |
| hsa-miR-422a | 3.64 | 0.36 | 0.82 | 1.09 | 1.71E−03 | −2.82 | 7.1 |
| hsa-miR-630 | 6.83 | 0.59 | 4.01 | 1.11 | 2.59E−04 | −2.82 | 7.1 |
| hsa-miR-516b | 2.78 | 0.32 | −0.04 | 0.28 | 2.15E−06 | −2.81 | 7.0 |
| hsa-miR-188-5p | 7.46 | 0.63 | 4.66 | 0.39 | 7.57E−05 | −2.79 | 6.9 |
| hsa-miR-617 | 3.26 | 0.35 | 0.47 | 0.50 | 3.11E−05 | −2.79 | 6.9 |
| hsa-miR-1180 | 3.54 | 0.41 | 0.78 | 0.98 | 1.22E−03 | −2.76 | 6.8 |
| hsa-miR-1246 | 9.63 | 1.16 | 6.87 | 1.37 | 1.50E−02 | −2.76 | 6.8 |
| hsa-miR-498 | 3.77 | 0.49 | 1.03 | 0.60 | 1.55E−04 | −2.73 | 6.7 |
| hsa-miR-518c* | 2.24 | 0.52 | −0.49 | 0.55 | 1.29E−04 | −2.73 | 6.6 |
| hsa-miR-202 | 7.06 | 0.56 | 4.34 | 0.45 | 8.61E−05 | −2.72 | 6.6 |
| hsa-miR-298 | 1.93 | 0.38 | −0.78 | 0.66 | 1.68E−04 | −2.71 | 6.5 |
| hsa-miR-370 | 3.80 | 0.49 | 1.11 | 0.79 | 5.86E−04 | −2.69 | 6.5 |
| hsa-miR-7-2* | 3.76 | 1.18 | 1.08 | 1.28 | 1.43E−02 | −2.69 | 6.4 |
| hsa-miR-610 | 4.46 | 0.57 | 1.81 | 0.58 | 2.45E−04 | −2.65 | 6.3 |
| hsa-miR-640 | 1.49 | 0.46 | −1.15 | 0.15 | 5.34E−06 | −2.64 | 6.3 |
| hsa-miR-1308 | 10.04 | 0.87 | 7.42 | 0.76 | 1.93E−03 | −2.62 | 6.2 |
| hsa-miR-662 | 3.58 | 0.21 | 0.98 | 0.16 | 1.37E−07 | −2.60 | 6.1 |
| hsa-miR-605 | 3.72 | 1.03 | 1.15 | 0.60 | 2.24E−03 | −2.57 | 5.9 |
| hsa-miR-486-5p | 8.61 | 0.71 | 6.05 | 0.90 | 2.38E−03 | −2.56 | 5.9 |
| hsa-miR-518a-5p | 2.05 | 0.65 | −0.45 | 0.45 | 2.43E−04 | −2.51 | 5.7 |
| hsa-miR-873 | 3.30 | 0.83 | 0.81 | 0.78 | 2.40E−03 | −2.49 | 5.6 |
| hsa-miR-302c* | 1.62 | 0.71 | −0.80 | 0.61 | 8.95E−04 | −2.41 | 5.3 |
| hsa-miR-575 | 10.16 | 0.66 | 7.75 | 0.45 | 3.29E−05 | −2.41 | 5.3 |
| hsa-miR-1303 | 1.71 | 0.56 | −0.67 | 0.28 | 6.79E−05 | −2.38 | 5.2 |
| hsa-miR-584 | 4.38 | 0.49 | 2.03 | 0.45 | 1.33E−04 | −2.35 | 5.1 |
| hsa-miR-424* | 5.34 | 0.66 | 2.99 | 0.48 | 4.54E−04 | −2.34 | 5.1 |
| hsa-miR-125b-1* | 3.14 | 1.31 | 0.81 | 0.78 | 1.26E−02 | −2.33 | 5.0 |
| hsa-miR-129-5p | 2.48 | 0.82 | 0.15 | 0.60 | 1.69E−03 | −2.33 | 5.0 |
| hsa-miR-490-5p | 3.39 | 0.29 | 1.10 | 0.47 | 6.65E−05 | −2.28 | 4.9 |
| hsa-miR-557 | 6.23 | 0.77 | 3.95 | 0.56 | 1.33E−03 | −2.28 | 4.9 |
| hsa-miR-769-3p | 3.34 | 0.64 | 1.08 | 0.49 | 5.04E−04 | −2.27 | 4.8 |
| hsa-miR-1250 | 1.91 | 0.52 | −0.34 | 0.68 | 9.37E−04 | −2.26 | 4.8 |
| hsa-miR-921 | 1.67 | 0.51 | −0.58 | 0.37 | 1.15E−04 | −2.25 | 4.8 |
| hsa-miR-1276 | 2.01 | 0.65 | −0.24 | 1.27 | 1.55E−02 | −2.24 | 4.7 |
| hsa-miR-127-5p | 1.28 | 0.35 | −0.95 | 0.60 | 3.29E−04 | −2.22 | 4.7 |
| hsa-miR-516a-5p | 3.63 | 0.99 | 1.43 | 0.65 | 5.13E−03 | −2.20 | 4.6 |
| hsa-miR-614 | 2.05 | 0.67 | −0.10 | 0.84 | 4.18E−03 | −2.15 | 4.4 |
| hsa-miR-451 | 14.94 | 0.59 | 12.86 | 0.80 | 3.55E−03 | −2.08 | 4.2 |
| hsa-miR-525-5p | 2.15 | 0.49 | 0.07 | 0.40 | 2.05E−04 | −2.08 | 4.2 |
| hsa-miR-654-5p | 4.06 | 0.36 | 1.98 | 0.52 | 2.61E−04 | −2.08 | 4.2 |
| hsa-miR-1249 | 5.93 | 0.74 | 3.86 | 0.43 | 1.14E−03 | −2.07 | 4.2 |
| hsa-miR-486-3p | 2.16 | 1.04 | 0.10 | 1.00 | 1.93E−02 | −2.07 | 4.2 |
| hsa-miR-877* | 4.73 | 0.40 | 2.68 | 0.34 | 7.08E−05 | −2.06 | 4.2 |
| hsa-miR-1306 | 2.97 | 0.34 | 0.92 | 0.46 | 1.56E−04 | −2.05 | 4.1 |
| hsa-miR-602 | 3.88 | 0.51 | 1.86 | 0.42 | 3.32E−04 | −2.02 | 4.0 |
| hsa-miR-135a* | 5.61 | 0.85 | 3.61 | 0.32 | 1.70E−03 | −2.00 | 4.0 |
| hsa-miR-1299 | 4.40 | 0.44 | 2.40 | 0.90 | 4.94E−03 | −2.00 | 4.0 |
| hsa-miR-138 | 6.61 | 0.71 | 4.62 | 1.08 | 1.57E−02 | −1.99 | 4.0 |
| hsa-miR-124 | 1.52 | 1.06 | −0.38 | 0.31 | 6.07E−03 | −1.90 | 3.7 |
| hsa-miR-1226* | 5.72 | 0.46 | 3.85 | 0.48 | 6.04E−04 | −1.87 | 3.7 |
| hsa-miR-886-5p | 0.16 | 0.98 | −1.68 | 0.30 | 4.95E−03 | −1.84 | 3.6 |
| hsa-miR-195* | 2.04 | 0.32 | 0.21 | 0.87 | 5.51E−03 | −1.83 | 3.6 |
| hsa-miR-658 | 1.16 | 0.56 | −0.65 | 0.32 | 4.55E−04 | −1.82 | 3.5 |
| hsa-miR-501-3p | 4.63 | 0.23 | 2.83 | 0.27 | 1.35E−05 | −1.81 | 3.5 |
| hsa-miR-33b* | 4.27 | 0.51 | 2.52 | 0.25 | 2.42E−04 | −1.75 | 3.4 |
| hsa-miR-363 | 6.43 | 0.54 | 4.69 | 0.85 | 9.80E−03 | −1.74 | 3.3 |
| hsa-miR-194* | 1.50 | 0.63 | −0.19 | 0.55 | 3.54E−03 | −1.69 | 3.2 |

TABLE 13-continued

MicroRNAs significantly differentially expressed between PTC and NOD samples.

| | NOD | | PTC | | NOD vs PTC | | |
|---|---|---|---|---|---|---|---|
| miRNA | AVG | SD | AVG | SD | ttest | Log2 diff | Fold change |
| hsa-miR-1307 | 3.37 | 0.39 | 1.68 | 0.58 | 1.63E−03 | −1.69 | 3.2 |
| hsa-miR-550 | 3.70 | 0.30 | 2.03 | 0.27 | 4.86E−05 | −1.67 | 3.2 |
| hsa-miR-1285 | 3.38 | 0.58 | 1.71 | 0.43 | 1.58E−03 | −1.67 | 3.2 |
| hsa-miR-1208 | 3.69 | 0.27 | 2.02 | 1.01 | 1.56E−02 | −1.66 | 3.2 |
| hsa-miR-125a-3p | 7.33 | 0.40 | 5.67 | 0.46 | 7.04E−04 | −1.66 | 3.2 |
| hsa-miR-144* | 5.70 | 1.02 | 4.08 | 0.88 | 3.79E−02 | −1.62 | 3.1 |
| hsa-miR-612 | 0.44 | 0.95 | −1.16 | 0.49 | 1.29E−02 | −1.60 | 3.0 |
| hsa-miR-664* | 6.43 | 0.81 | 4.83 | 0.37 | 5.40E−03 | −1.60 | 3.0 |
| hsa-miR-513a-5p | 5.52 | 0.43 | 3.94 | 0.67 | 4.62E−03 | −1.58 | 3.0 |
| hsa-miR-1275 | 8.12 | 0.52 | 6.55 | 0.47 | 2.04E−02 | −1.57 | 3.0 |
| hsa-miR-184 | 2.83 | 0.43 | 1.27 | 0.48 | 1.41E−03 | −1.57 | 3.0 |
| hsa-miR-152 | 7.76 | 0.51 | 6.19 | 0.48 | 2.09E−03 | −1.57 | 3.0 |
| hsa-miR-1244 | 2.06 | 0.85 | 0.50 | 0.47 | 9.53E−03 | −1.57 | 3.0 |
| hsa-miR-193b* | 4.70 | 0.59 | 3.15 | 0.31 | 1.39E−03 | −1.55 | 2.9 |
| hsa-miR-760 | 4.31 | 0.36 | 2.76 | 1.00 | 2.33E−02 | −1.54 | 2.9 |
| hsa-miR-28-3p | 2.09 | 0.21 | 0.55 | 0.88 | 1.16E−02 | −1.54 | 2.9 |
| hsa-miR-639 | 0.97 | 0.48 | −0.51 | 0.72 | 9.83E−03 | −1.48 | 2.8 |
| hsa-miR-345 | 4.32 | 0.16 | 2.86 | 0.49 | 7.72E−03 | −1.45 | 2.7 |
| hsa-miR-122 | 2.20 | 1.35 | 0.75 | 0.22 | 4.67E−02 | −1.45 | 2.7 |
| hsa-miR-1323 | 2.66 | 0.34 | 1.22 | 0.35 | 4.51E−04 | −1.44 | 2.7 |
| hsa-miR-183* | 1.38 | 0.66 | −0.03 | 1.02 | 4.96E−02 | −1.40 | 2.6 |
| hsa-miR-296-5p | 4.51 | 0.68 | 3.13 | 0.22 | 3.49E−03 | −1.38 | 2.6 |
| hsa-miR-139-5p | 6.89 | 0.32 | 5.51 | 0.53 | 2.63E−03 | −1.37 | 2.6 |
| hsa-miR-518e* | 2.03 | 0.27 | 0.67 | 0.38 | 5.35E−04 | −1.36 | 2.6 |
| hsa-miR-145 | 10.71 | 0.24 | 9.37 | 0.28 | 1.30E−04 | −1.33 | 2.5 |
| hsa-miR-876-3p | 1.74 | 0.54 | 0.41 | 0.55 | 8.23E−03 | −1.33 | 2.5 |
| hsa-miR-595 | 1.81 | 0.36 | 0.49 | 0.32 | 5.96E−04 | −1.33 | 2.5 |
| hsa-miR-300 | 0.19 | 0.55 | −1.13 | 0.26 | 1.86E−03 | −1.32 | 2.5 |
| hsa-miR-214 | 9.42 | 0.44 | 8.16 | 0.85 | 3.21E−02 | −1.26 | 2.4 |
| hsa-miR-1910 | −0.66 | 0.59 | −1.90 | 0.24 | 3.33E−03 | −1.25 | 2.4 |
| hsa-miR-432 | 3.26 | 0.58 | 2.03 | 0.77 | 3.41E−02 | −1.23 | 2.3 |
| hsa-miR-1270 | 2.47 | 0.46 | 1.27 | 0.39 | 3.85E−03 | −1.21 | 2.3 |
| hsa-miR-887 | 4.02 | 0.29 | 2.82 | 0.46 | 2.74E−03 | −1.20 | 2.3 |
| hsa-miR-652 | 6.41 | 0.29 | 5.22 | 0.29 | 5.18E−04 | −1.19 | 2.3 |
| hsa-miR-574-5p | 7.52 | 0.63 | 6.36 | 0.28 | 7.18E−03 | −1.16 | 2.2 |
| hsa-miR-708 | 2.61 | 0.40 | 1.48 | 0.42 | 4.83E−03 | −1.13 | 2.2 |
| hsa-miR-512-3p | 5.11 | 0.05 | 4.04 | 0.37 | 7.45E−04 | −1.07 | 2.1 |
| hsa-miR-1826 | 6.34 | 0.42 | 5.33 | 0.70 | 3.97E−02 | −1.01 | 2.0 |
| hsa-miR-483-3p | 1.44 | 0.33 | 0.43 | 0.35 | 3.11E−02 | −1.01 | 2.0 |
| hsa-miR-23a* | 4.50 | 0.50 | 3.49 | 0.59 | 2.96E−02 | −1.01 | 2.0 |
| hsa-miR-143 | 8.32 | 0.44 | 7.32 | 0.28 | 4.28E−03 | −1.00 | 2.0 |
| hsa-let-7i | 13.53 | 0.24 | 14.53 | 0.18 | 1.77E−04 | 1.00 | 2.0 |
| hsa-miR-200e* | 1.03 | 0.53 | 2.06 | 0.34 | 9.62E−03 | 1.02 | 2.0 |
| hsa-miR-34b* | 6.55 | 0.45 | 7.62 | 0.54 | 1.60E−02 | 1.07 | 2.1 |
| hsa-miR-181a* | 3.26 | 0.41 | 4.36 | 0.24 | 1.51E−03 | 1.10 | 2.1 |
| hsa-miR-892b | 4.67 | 0.11 | 5.77 | 0.82 | 3.44E−02 | 1.10 | 2.1 |
| hsa-miR-625 | 5.03 | 0.21 | 6.17 | 0.25 | 1.78E−03 | 1.14 | 2.2 |
| hsa-miR-96 | 7.09 | 0.38 | 8.25 | 0.45 | 4.71E−03 | 1.16 | 2.2 |
| hsa-miR-181a | 10.11 | 0.48 | 11.28 | 0.33 | 3.28E−03 | 1.17 | 2.3 |
| hsa-miR-542-5p | 5.62 | 0.41 | 6.80 | 0.87 | 4.20E−02 | 1.19 | 2.3 |
| hsa-miR-1305 | 7.07 | 0.50 | 8.28 | 0.53 | 1.03E−02 | 1.20 | 2.3 |
| hsa-miR-222* | −0.77 | 0.35 | 0.46 | 0.73 | 1.78E−02 | 1.23 | 2.3 |
| hsa-miR-15a* | 0.91 | 0.35 | 2.18 | 0.39 | 1.47E−03 | 1.27 | 2.4 |
| hsa-miR-200a | 8.86 | 0.32 | 10.22 | 0.52 | 2.60E−03 | 1.36 | 2.6 |
| hsa-miR-34a* | 3.70 | 0.12 | 5.07 | 0.21 | 8.59E−06 | 1.37 | 2.6 |
| hsa-miR-429 | 7.59 | 0.20 | 8.97 | 0.55 | 2.10E−03 | 1.38 | 2.6 |
| hsa-miR-141* | 2.70 | 0.63 | 4.09 | 0.36 | 4.16E−03 | 1.39 | 2.6 |
| hsa-miR-181b | 8.16 | 0.41 | 9.59 | 0.52 | 2.89E−03 | 1.43 | 2.7 |
| hsa-miR-542-3p | 4.93 | 0.37 | 6.39 | 0.81 | 1.27E−02 | 1.46 | 2.8 |
| hsa-miR-450a | 4.07 | 0.66 | 5.54 | 0.74 | 1.71E−02 | 1.47 | 2.8 |
| hsa-miR-15a | 10.48 | 0.47 | 12.01 | 0.32 | 6.22E−04 | 1.54 | 2.9 |
| hsa-miR-200b | 10.22 | 0.06 | 11.78 | 0.50 | 5.00E−04 | 1.55 | 2.9 |
| hsa-miR-150 | 8.70 | 0.28 | 10.28 | 1.21 | 3.99E−02 | 1.58 | 3.0 |
| hsa-miR-135b | 9.05 | 0.63 | 10.66 | 0.71 | 9.24E−03 | 1.61 | 3.1 |
| hsa-miR-424 | 8.84 | 0.42 | 10.51 | 0.68 | 3.60E−03 | 1.67 | 3.2 |
| hsa-miR-34a | 10.89 | 0.21 | 12.59 | 0.24 | 1.02E−05 | 1.70 | 3.2 |
| hsa-miR-146a | 6.97 | 0.24 | 8.74 | 1.29 | 3.18E−02 | 1.77 | 3.4 |
| hsa-miR-503 | 3.72 | 0.73 | 5.74 | 0.81 | 6.05E−03 | 2.02 | 4.1 |
| hsa-miR-29b-1* | 3.36 | 0.34 | 5.53 | 0.38 | 4.45E−05 | 2.17 | 4.5 |
| hsa-miR-142-5p | 4.15 | 0.97 | 6.34 | 1.33 | 2.84E−02 | 2.19 | 4.6 |
| hsa-miR-514 | 0.68 | 0.46 | 2.93 | 0.86 | 2.21E−03 | 2.26 | 4.8 |
| hsa-miR-155 | 5.86 | 0.20 | 8.15 | 0.89 | 1.55E−03 | 2.29 | 4.9 |
| hsa-miR-1260 | 6.50 | 0.87 | 8.82 | 0.47 | 1.35E−03 | 2.32 | 5.0 |

TABLE 13-continued

MicroRNAs significantly differentially expressed between PTC and NOD samples.

| | NOD | | PTC | | NOD vs PTC | | |
|---|---|---|---|---|---|---|---|
| miRNA | AVG | SD | AVG | SD | ttest | Log2 diff | Fold change |
| hsa-miR-181a-2* | 3.90 | 0.52 | 6.23 | 0.66 | 6.88E−04 | 2.33 | 5.0 |
| hsa-miR-21* | 4.43 | 0.17 | 6.77 | 0.63 | 1.87E−04 | 2.34 | 5.1 |
| hsa-miR-21 | 13.28 | 0.37 | 15.85 | 0.45 | 3.80E−05 | 2.57 | 5.9 |
| hsa-miR-720 | 10.25 | 0.79 | 12.95 | 0.34 | 2.14E−04 | 2.70 | 6.5 |
| hsa-miR-375 | 4.00 | 2.15 | 6.74 | 1.20 | 4.45E−02 | 2.74 | 6.7 |
| hsa-miR-142-3p | 7.20 | 1.09 | 9.95 | 1.39 | 1.45E−02 | 2.75 | 6.7 |
| hsa-miR4274b | 8.53 | 0.95 | 11.33 | 0.39 | 5.04E−04 | 2.80 | 7.0 |
| hsa-miR-1274a | 4.74 | 1.03 | 7.71 | 0.50 | 7.32E−04 | 2.97 | 7.8 |
| hsa-miR-31 | 6.80 | 1.81 | 10.14 | 0.64 | 5.96E−03 | 3.34 | 10.1 |
| hsa-miR-31* | 5.23 | 1.63 | 8.58 | 0.56 | 3.42E−03 | 3.35 | 10.2 |
| hsa-miR-221* | 5.14 | 0.24 | 8.71 | 0.86 | 9.54E−05 | 3.57 | 11.9 |
| hsa-miR-222 | 6.60 | 0.81 | 10.25 | 0.58 | 1.01E−04 | 3.65 | 12.6 |
| hsa-miR-221 | 6.94 | 0.35 | 10.60 | 0.73 | 3.82E−05 | 3.66 | 12.7 |
| hsa-miR-551b | 5.32 | 0.11 | 9.98 | 0.58 | 1.09E−06 | 4.65 | 25.2 |
| hsa-miR-146b-3p | −1.13 | 0.41 | 3.73 | 1.12 | 8.22E−05 | 4.85 | 28.9 |
| hsa-miR-146b-5p | 7.65 | 0.79 | 14.41 | 0.92 | 8.03E−06 | 6.76 | 108.5 |

AVG, average expression among samples in a group;
SD, standard deviation

Example 12 miRNA Expression Profiling Distinguishes Hyperplastic Thyroid Nodules and Follicular Variant of Papillary Thyroid Carcinoma A total of 195 human miRNAs were significantly differentially expressed between the hyperplastic nodule samples and the follicular variant papillary thyroid carcinoma specimens (p<0.05) (Table 14). Among these, 40 miRNAs were overexpressed (Log 2 diff (FVPTC vs NOD)≥1) and 117 were underexpressed (Log 2 diff (FVPTC vs NOD)≤1) by at least 2-fold in FVPTC compared to NOD samples. Of these, hsa-miR-146b-5p was overexpressed by more than 40-fold and eleven miRNAs (hsa-miR-551b, -146b-3p, -31, -221, -31*, -222, -221*, -1274a, -1274b, -720, and -503) were overexpressed by 5- to 10-fold in the FVPTC specimens. Among the miRNAs that were expressed at lower average levels in the PTC samples, four (hsa-miR-92b, -631, -551b*, and -934) were underexpressed by 10- to 20-fold, and thirty-three miRNAs were underexpressed by 5- to 10-fold in the FVPTC specimens compared to the NOD samples.

TABLE 14

MicroRNAs significantly differentially expressed between FVPTC and NOD samples.

| | NOD | | FVPTC | | FVPTC vs NOD | | |
|---|---|---|---|---|---|---|---|
| miRNA | AVG | SD | AVG | SD | ttest | Log2Diff | Fold change |
| hsa-miR-146b-5p | 7.65 | 0.79 | 13.20 | 1.09 | 1.70E−04 | 5.56 | 47.0 |
| hsa-miR-551b | 5.32 | 0.11 | 8.99 | 0.76 | 7.57E−05 | 3.66 | 12.7 |
| hsa-miR-146b-3p | −1.13 | 0.41 | 2.46 | 1.30 | 1.90E−03 | 3.59 | 12.0 |
| hsa-miR-31 | 6.80 | 1.81 | 10.06 | 1.12 | 2.21E−02 | 3.26 | 9.6 |
| hsa-miR-221 | 6.94 | 0.35 | 10.19 | 0.98 | 7.90E−04 | 3.26 | 9.6 |
| hsa-miR-31* | 5.23 | 1.63 | 8.47 | 1.06 | 1.59E−02 | 3.23 | 9.4 |
| hsa-miR-222 | 6.60 | 0.81 | 9.66 | 0.79 | 1.66E−03 | 3.06 | 8.4 |
| hsa-miR-221* | 5.14 | 0.24 | 8.06 | 0.85 | 5.89E−04 | 2.92 | 7.6 |
| hsa-miR-1274a | 4.74 | 1.03 | 7.40 | 0.66 | 5.01E−03 | 2.65 | 6.3 |
| hsa-miR-1274b | 8.53 | 0.95 | 11.10 | 0.59 | 3.72E−03 | 2.57 | 5.9 |
| hsa-miR-720 | 10.25 | 0.79 | 12.82 | 0.50 | 1.49E−03 | 2.57 | 5.9 |
| hsa-miR-503 | 3.72 | 0.73 | 6.07 | 1.04 | 1.01E−02 | 2.35 | 5.1 |
| hsa-miR-21* | 4.43 | 0.17 | 6.73 | 0.32 | 1.49E−05 | 2.30 | 4.9 |
| hsa-miR-142-3p | 7.20 | 1.09 | 9.30 | 1.25 | 4.44E−02 | 2.10 | 4.3 |
| hsa-miR-542-3p | 4.93 | 0.37 | 7.01 | 1.32 | 2.26E−02 | 2.08 | 4.2 |
| hsa-miR-1260 | 6.50 | 0.87 | 8.51 | 0.59 | 8.78E−03 | 2.01 | 4.0 |
| hsa-miR-181a-2* | 3.90 | 0.52 | 5.91 | 1.15 | 1.89E−02 | 2.00 | 4.0 |
| hsa-miR-29b-1* | 3.36 | 0.34 | 5.34 | 0.41 | 2.89E−04 | 1.98 | 3.9 |
| hsa-miR-424 | 8.84 | 0.42 | 10.75 | 1.38 | 3.82E−02 | 1.91 | 3.8 |
| hsa-miR-542-5p | 5.62 | 0.41 | 7.34 | 1.07 | 2.37E−02 | 1.72 | 3.3 |
| hsa-miR-21 | 13.28 | 0.37 | 14.94 | 0.64 | 4.05E−03 | 1.66 | 3.2 |
| hsa-miR-146a | 6.97 | 0.24 | 8.61 | 1.03 | 2.11E−02 | 1.64 | 3.1 |
| hsa-miR-222* | −0.77 | 0.35 | 0.85 | 0.42 | 1.01E−03 | 1.62 | 3.1 |
| hsa-miR-155 | 5.86 | 0.20 | 7.48 | 0.68 | 3.79E−03 | 1.62 | 3.1 |
| hsa-miR-200b | 10.22 | 0.06 | 11.82 | 0.67 | 3.26E−03 | 1.60 | 3.0 |
| hsa-miR-429 | 7.59 | 0.20 | 9.17 | 0.77 | 7.30E−03 | 1.59 | 3.0 |
| hsa-miR-34a | 10.89 | 0.21 | 12.33 | 0.27 | 1.42E−04 | 1.44 | 2.7 |
| hsa-miR-200a | 8.86 | 0.32 | 10.20 | 0.62 | 8.20E−03 | 1.34 | 2.5 |

TABLE 14-continued

MicroRNAs significantly differentially expressed between FVPTC and NOD samples.

| | NOD | | FVPTC | | FVPTC vs NOD | | |
|---|---|---|---|---|---|---|---|
| miRNA | AVG | SD | AVG | SD | ttest | Log2Diff | Fold change |
| hsa-miR-181b | 8.16 | 0.41 | 9.48 | 0.84 | 2.97E−02 | 1.33 | 2.5 |
| hsa-miR-15a | 10.48 | 0.47 | 11.73 | 0.60 | 1.67E−02 | 1.25 | 2.4 |
| hsa-miR-15a* | 0.91 | 0.35 | 2.07 | 0.52 | 1.03E−02 | 1.16 | 2.2 |
| hsa-miR-509-3-5p | −0.64 | 0.34 | 0.49 | 0.65 | 2.10E−02 | 1.14 | 2.2 |
| hsa-let-7i | 13.53 | 0.24 | 14.62 | 0.43 | 4.69E−03 | 1.09 | 2.1 |
| hsa-miR-450b-5p | 0.53 | 0.33 | 1.61 | 0.81 | 4.99E−02 | 1.07 | 2.1 |
| hsa-miR-886-3p | 8.15 | 0.52 | 9.21 | 0.51 | 2.81E−02 | 1.06 | 2.1 |
| hsa-miR-34a* | 3.70 | 0.12 | 4.76 | 0.31 | 7.14E−04 | 1.05 | 2.1 |
| hsa-miR-211 | 0.30 | 0.50 | 1.36 | 0.41 | 1.77E−02 | 1.05 | 2.1 |
| hsa-miR-200a* | 4.34 | 0.33 | 5.38 | 0.59 | 2.16E−02 | 1.04 | 2.1 |
| hsa-miR-200c* | 1.03 | 0.53 | 2.07 | 0.45 | 2.51E−02 | 1.03 | 2.0 |
| hsa-let-7e* | 1.65 | 0.54 | 2.67 | 0.53 | 3.61E−02 | 1.02 | 2.0 |
| hsa-miR-1270 | 2.47 | 0.46 | 1.45 | 0.61 | 3.66E−02 | −1.03 | 2.0 |
| hsa-miR-1301 | 1.60 | 0.30 | 0.53 | 0.77 | 4.02E−02 | −1.07 | 2.1 |
| hsa-miR-28-3p | 2.09 | 0.21 | 1.00 | 0.24 | 5.11E−04 | −1.09 | 2.1 |
| hsa-miR-296-5p | 4.51 | 0.68 | 3.36 | 0.54 | 3.93E−02 | −1.15 | 2.2 |
| hsa-miR-210 | 6.41 | 0.24 | 5.26 | 0.39 | 2.47E−03 | −1.15 | 2.2 |
| hsa-miR-513a-5p | 5.52 | 0.43 | 4.37 | 0.17 | 2.54E−03 | −1.15 | 2.2 |
| hsa-miR-658 | 1.16 | 0.56 | −0.02 | 0.28 | 9.21E−03 | −1.18 | 2.3 |
| hsa-miR-194* | 1.50 | 0.63 | 0.30 | 0.10 | 9.44E−03 | −1.19 | 2.3 |
| hsa-miR-345 | 4.32 | 0.16 | 3.11 | 0.68 | 1.39E−02 | −1.20 | 2.3 |
| hsa-miR-550 | 3.70 | 0.30 | 2.49 | 0.55 | 8.02E−03 | −1.21 | 2.3 |
| hsa-miR-432 | 3.26 | 0.58 | 2.04 | 0.63 | 2.92E−02 | −1.22 | 2.3 |
| hsa-miR-125a-3p | 7.33 | 0.40 | 6.11 | 0.06 | 9.03E−04 | −1.22 | 2.3 |
| hsa-miR-664* | 6.43 | 0.81 | 5.17 | 0.37 | 3.05E−02 | −1.25 | 2.4 |
| hsa-miR-1280 | 7.64 | 0.87 | 6.37 | 0.55 | 4.89E−02 | −1.27 | 2.4 |
| hsa-miR-1306 | 2.97 | 0.34 | 1.68 | 0.13 | 4.01E−04 | −1.28 | 2.4 |
| hsa-miR-193b* | 4.70 | 0.59 | 3.41 | 0.46 | 1.38E−02 | −1.29 | 2.4 |
| hsa-miR-139-5p | 6.89 | 0.32 | 5.57 | 0.68 | 1.31E−02 | −1.31 | 2.5 |
| hsa-miR-152 | 7.76 | 0.51 | 6.38 | 0.23 | 2.53E−03 | −1.38 | 2.6 |
| hsa-miR-298 | 1.93 | 0.38 | 0.52 | 0.93 | 3.11E−02 | −1.40 | 2.6 |
| hsa-miR-33b* | 4.27 | 0.51 | 2.82 | 0.44 | 4.91E−03 | −1.46 | 2.7 |
| hsa-miR-1249 | 5.93 | 0.74 | 4.46 | 0.77 | 3.28E−02 | −1.47 | 2.8 |
| hsa-miR-424* | 5.34 | 0.66 | 3.83 | 0.91 | 3.61E−02 | −1.51 | 2.9 |
| hsa-miR-760 | 4.31 | 0.36 | 2.76 | 0.33 | 7.18E−02 | −1.55 | 2.9 |
| hsa-miR-557 | 6.23 | 0.77 | 4.68 | 0.65 | 2.18E−02 | −1.55 | 2.9 |
| hsa-miR-602 | 3.88 | 0.51 | 2.32 | 0.47 | 4.09E−03 | −1.56 | 3.0 |
| hsa-miR-640 | 1.49 | 0.46 | −0.07 | 0.79 | 1.41E−02 | −1.57 | 3.0 |
| hsa-miR-769-3p | 3.34 | 0.64 | 1.76 | 0.44 | 6.54E−03 | −1.58 | 3.0 |
| hsa-miR-1307 | 3.37 | 0.39 | 1.77 | 0.52 | 2.76E−03 | −1.60 | 3.0 |
| hsa-miR-584 | 4.38 | 0.49 | 2.77 | 0.95 | 2.31E−02 | −1.61 | 3.1 |
| hsa-miR-124 | 1.52 | 1.06 | −0.10 | 0.41 | 2.86E−02 | −1.62 | 3.1 |
| hsa-miR-501-3p | 4.63 | 0.23 | 3.01 | 0.18 | 3.06E−05 | −1.62 | 3.1 |
| hsa-miR-518a-5p | 2.05 | 0.65 | 0.40 | 0.87 | 2.26E−02 | −1.65 | 3.1 |
| hsa-miR-1250 | 1.91 | 0.52 | 0.22 | 0.81 | 1.27E−02 | −1.69 | 3.2 |
| hsa-miR-1285 | 3.38 | 0.58 | 1.68 | 0.67 | 8.49E−03 | −1.70 | 3.3 |
| hsa-miR-1308 | 10.04 | 0.87 | 8.34 | 0.99 | 4.15E−02 | −1.70 | 3.3 |
| hsa-miR-877* | 4.73 | 0.40 | 3.03 | 0.31 | 5.35E−04 | −1.71 | 3.3 |
| hsa-miR-1471 | 5.53 | 0.37 | 3.83 | 0.89 | 1.22E−02 | −1.71 | 3.3 |
| hsa-miR-583 | 2.59 | 0.74 | 0.88 | 0.95 | 2.94E−02 | −1.71 | 3.3 |
| hsa-miR-127-5p | 1.28 | 0.35 | −0.44 | 0.41 | 6.91E−04 | −1.72 | 3.3 |
| hsa-miR-518c* | 2.24 | 0.52 | 0.52 | 0.72 | 8.11E−03 | −1.72 | 3.3 |
| hsa-miR-370 | 3.80 | 0.49 | 2.08 | 1.06 | 2.52E−02 | −1.73 | 3.3 |
| hsa-miR-138 | 6.61 | 0.71 | 4.85 | 0.81 | 1.69E−02 | −1.76 | 3.4 |
| hsa-miR-1226* | 5.72 | 0.46 | 3.94 | 0.25 | 5.17E−04 | −1.78 | 3.4 |
| hsa-miR-575 | 10.16 | 0.66 | 8.34 | 0.42 | 3.54E−03 | −1.82 | 3.5 |
| hsa-miR-1208 | 3.69 | 0.27 | 1.83 | 0.93 | 8.66E−03 | −1.86 | 3.6 |
| hsa-miR-525-5p | 2.15 | 0.49 | 0.27 | 0.60 | 2.85E−03 | −1.88 | 3.7 |
| hsa-miR-662 | 3.58 | 0.21 | 1.69 | 0.36 | 9.68E−05 | −1.89 | 3.7 |
| hsa-miR-614 | 2.05 | 0.67 | 0.15 | 0.41 | 2.83E−03 | −1.90 | 3.7 |
| hsa-miR-654-5p | 4.06 | 0.36 | 2.15 | 0.43 | 4.75E−04 | −1.90 | 3.7 |
| hsa-miR-188-5p | 7.46 | 0.63 | 5.53 | 0.82 | 9.83E−03 | −1.93 | 3.8 |
| hsa-miR-516b | 2.78 | 0.32 | 0.84 | 0.74 | 3.05E−03 | −1.93 | 3.8 |
| hsa-miR-490-5p | 3.39 | 0.29 | 1.44 | 0.66 | 1.66E−03 | −1.95 | 3.9 |
| hsa-miR-199b-5p | 9.26 | 0.23 | 7.31 | 0.64 | 1.21E−03 | −1.95 | 3.9 |
| hsa-miR-605 | 3.72 | 1.03 | 1.74 | 1.12 | 4.08E−02 | −1.98 | 3.9 |
| hsa-miR-1180 | 3.54 | 0.41 | 1.53 | 0.70 | 2.58E−03 | −2.01 | 4.0 |
| hsa-miR-566 | 3.15 | 0.92 | 1.14 | 0.67 | 1.23E−02 | −2.01 | 4.0 |
| hsa-miR-1303 | 1.71 | 0.56 | −0.30 | 1.02 | 1.36E−02 | −2.01 | 4.0 |
| hsa-miR-498 | 3.77 | 0.49 | 1.75 | 0.56 | 1.67E−03 | −2.02 | 4.1 |
| hsa-miR-610 | 4.46 | 0.57 | 2.43 | 0.93 | 9.99E−03 | −2.03 | 4.1 |
| hsa-miR-373* | 3.17 | 0.97 | 1.09 | 0.50 | 8.77E−03 | −2.09 | 4.2 |
| hsa-miR-1915 | 10.06 | 0.49 | 7.97 | 0.48 | 8.78E−04 | −2.09 | 4.3 |

TABLE 14-continued

MicroRNAs significantly differentially expressed between FVPTC and NOD samples.

| miRNA | NOD AVG | NOD SD | FVPTC AVG | FVPTC SD | FVPTC vs NOD ttest | Log2Diff | Fold change |
|---|---|---|---|---|---|---|---|
| hsa-miR-1469 | 3.39 | 0.42 | 1.27 | 0.67 | 1.78E-03 | -2.12 | 4.4 |
| hsa-miR-490-3p | 1.74 | 0.41 | -0.38 | 0.84 | 3.95E-03 | -2.12 | 4.4 |
| hsa-miR-877 | 4.47 | 0.65 | 2.34 | 0.85 | 7.32E-03 | -2.13 | 4.4 |
| hsa-miR-601 | 5.60 | 0.53 | 3.46 | 0.87 | 5.55E-03 | -2.14 | 4.4 |
| hsa-miR-1291 | 2.99 | 0.68 | 0.85 | 0.93 | 9.84E-03 | -2.14 | 4.4 |
| hsa-miR-134 | 8.00 | 0.93 | 5.83 | 1.03 | 2.01E-02 | -2.17 | 4.5 |
| hsa-miR-202 | 7.06 | 0.56 | 4.89 | 0.85 | 5.26E-03 | -2.17 | 4.5 |
| hsa-miR-939 | 8.91 | 0.42 | 6.74 | 0.52 | 6.38E-04 | -2.17 | 4.5 |
| hsa-miR-1228* | 1.90 | 0.73 | -0.27 | 1.16 | 1.90E-02 | -2.18 | 4.5 |
| hsa-miR-671-5p | 7.24 | 0.57 | 5.06 | 0.98 | 8.44E-03 | -2.18 | 4.5 |
| hsa-miR-526b | 3.54 | 0.53 | 1.34 | 1.11 | 1.18E-02 | -2.20 | 4.6 |
| hsa-miR-622 | 5.23 | 0.37 | 3.01 | 0.81 | 2.42E-03 | -2.23 | 4.7 |
| hsa-miR-483-5p | 8.47 | 0.79 | 6.22 | 1.20 | 2.05E-02 | -2.25 | 4.8 |
| hsa-miR-659 | 5.53 | 0.63 | 3.28 | 0.92 | 6.76E-03 | -2.25 | 4.8 |
| hsa-miR-639 | 0.97 | 0.48 | -1.31 | 0.68 | 1.53E-03 | -2.28 | 4.9 |
| hsa-miR-921 | 1.67 | 0.51 | -0.63 | 1.15 | 1.08E-02 | -2.30 | 4.9 |
| hsa-miR-1224-5p | 7.60 | 0.65 | 5.30 | 0.72 | 3.22E-03 | -2.30 | 4.9 |
| hsa-miR-422a | 3.64 | 0.36 | 1.34 | 1.23 | 1.15E-02 | -2.30 | 4.9 |
| hsa-miR-371-5p | 6.14 | 0.47 | 3.83 | 0.78 | 2.29E-03 | -2.31 | 5.0 |
| hsa-miR-940 | 8.91 | 0.72 | 6.58 | 0.36 | 1.21E-03 | -2.32 | 5.0 |
| hsa-miR-1225-5p | 11.79 | 0.95 | 9.47 | 1.01 | 1.54E-02 | -2.32 | 5.0 |
| hsa-miR-1276 | 2.01 | 0.65 | -0.35 | 0.81 | 3.85E-03 | -2.36 | 5.1 |
| hsa-miR-1207-5p | 11.83 | 1.05 | 9.46 | 1.03 | 1.79E-02 | -2.37 | 5.2 |
| hsa-miR-617 | 3.26 | 0.35 | 0.87 | 0.83 | 1.80E-03 | -2.39 | 5.2 |
| hsa-miR-302c* | 1.62 | 0.71 | -0.79 | 0.40 | 1.05E-03 | -2.41 | 5.3 |
| hsa-miR-873 | 3.30 | 0.83 | 0.89 | 1.45 | 2.81E-02 | -2.41 | 5.3 |
| hsa-miR-1203 | 2.45 | 0.50 | 0.04 | 0.98 | 4.72E-03 | -2.41 | 5.3 |
| hsa-miR-1321 | 3.74 | 0.75 | 1.29 | 0.74 | 3.54E-03 | -2.45 | 5.5 |
| hsa-miR-1183 | 6.22 | 0.69 | 3.77 | 0.86 | 4.36E-03 | -2.45 | 5.5 |
| hsa-miR-198 | 4.90 | 0.65 | 2.44 | 1.28 | 1.42E-02 | -2.46 | 5.5 |
| hsa-miR-150* | 7.49 | 0.70 | 5.00 | 0.77 | 2.97E-03 | -2.50 | 5.6 |
| hsa-miR-638 | 10.95 | 1.00 | 8.45 | 0.73 | 6.77E-03 | -2.50 | 5.6 |
| hsa-miR-616 | 1.69 | 0.53 | -0.82 | 0.98 | 4.07E-03 | -2.50 | 5.7 |
| hsa-miR-1182 | 4.76 | 0.77 | 2.24 | 1.06 | 8.27E-03 | -2.53 | 5.8 |
| hsa-miR-765 | 6.63 | 0.70 | 4.00 | 1.15 | 7.77E-03 | -2.63 | 6.2 |
| hsa-miR-572 | 7.90 | 1.01 | 5.22 | 0.76 | 5.47E-03 | -2.69 | 6.4 |
| hsa-miR-623 | 4.95 | 0.55 | 2.25 | 1.11 | 4.71E-03 | -2.71 | 6.5 |
| hsa-miR-1268 | 10.19 | 1.33 | 7.45 | 0.90 | 1.42E-02 | -2.74 | 6.7 |
| hsa-miR-34c-3p | 1.72 | 0.30 | -1.06 | 0.54 | 1.05E-04 | -2.78 | 6.9 |
| hsa-miR-204 | 8.22 | 0.45 | 5.44 | 2.07 | 3.92E-02 | -2.78 | 6.9 |
| hsa-miR-1909* | 2.64 | 0.78 | -0.17 | 0.40 | 6.76E-04 | -2.81 | 7.0 |
| hsa-miR-138-1* | 1.32 | 0.49 | -1.51 | 0.57 | 2.83E-04 | -2.83 | 7.1 |
| hsa-miR-663 | 8.63 | 0.75 | 5.77 | 1.09 | 4.93E-03 | -2.87 | 7.3 |
| hsa-miR-187* | 4.73 | 0.70 | 1.85 | 0.71 | 1.18E-03 | -2.88 | 7.4 |
| hsa-miR-648 | 4.14 | 0.46 | 1.22 | 1.33 | 6.09E-03 | -2.92 | 7.6 |
| hsa-miR-149* | 4.68 | 0.59 | 1.62 | 1.06 | 2.37E-03 | -3.06 | 8.4 |
| hsa-miR-493 | 2.93 | 0.73 | -0.16 | 1.28 | 5.71E-03 | -3.09 | 8.5 |
| hsa-miR-1915* | 2.26 | 0.54 | -0.87 | 0.78 | 5.83E-04 | -3.13 | 8.7 |
| hsa-miR-1202 | 13.75 | 0.81 | 10.61 | 1.63 | 1.36E-02 | -3.13 | 8.8 |
| hsa-miR-1300 | 7.80 | 0.79 | 4.60 | 1.19 | 4.21E-03 | -3.20 | 9.2 |
| hsa-miR-936 | 4.55 | 0.65 | 1.33 | 1.65 | 1.10E-02 | -3.22 | 9.3 |
| hsa-miR-129-5p | 2.48 | 0.82 | -0.79 | 1.02 | 2.49E-03 | -3.26 | 9.6 |
| hsa-miR-934 | 2.09 | 0.71 | -1.42 | 1.12 | 1.83E-03 | -3.51 | 11.4 |
| hsa-miR-551b* | 2.72 | 0.65 | -0.79 | 0.69 | 3.15E-04 | -3.51 | 11.4 |
| hsa-miR-631 | 3.97 | 0.56 | 0.26 | 1.72 | 6.31E-03 | -3.71 | 13.1 |
| hsa-miR-92b* | 2.96 | 0.56 | -1.31 | 1.31 | 9.66E-04 | -4.27 | 19.3 |

AVG, average expression among samples in a group;
SD, standard deviation

Example 13 miRNA Expression Profiling Distinguishes Hyperplastic Thyroid Nodules and Anaplastic Thyroid Carcinoma A total of 166 human miRNAs were significantly differentially expressed between the hyperplastic nodule samples and the anaplastic thyroid carcinomas (p<0.05). Among these, 29 miRNAs were overexpressed (Log 2 diff (ATC vs NOD)≥1) and 121 were underexpressed (Log 2 diff (ATC vs NOD)≤1) by at least 2-fold in ATC compared to NOD samples (Table 15). Of these, hsa-miR-9*, -582-3p, and -582-5p were overexpressed by 30- to 50-fold, six miRNAs (hsa-miR-1274a, -155, -720, -1274b, -9, and -1260) were overexpressed by 10- to 30-fold, and six miRNAs (hsa-miR-34c-5p, -592, -10a, -21, -21*, and -210) were overexpressed by 5- to 10-fold in the ATC specimen compared to the NOD samples. Among the miRNAs that were expressed at lower average levels in the ATC sample, nine (hsa-miR-200c, -141, -429, -200a, -200b, -135a, -135b, -138, and -205) were underexpressed by 80- to 300-fold, six miRNAs (hsa-miR-92b, -7-2*, -512-3p, -934, -200b*, and -141*) were underexpressed by 20- to 35-fold, ten miRNAs were underexpressed by 10- to 20-fold, and forty miRNAs were underexpressed by 5- to 10-fold in the ATC specimen compared to the NOD samples.

TABLE 15

MicroRNAs significantly differentially expressed between ATC and NOD samples.

| miRNA | NOD AVG | NOD SD | ATC | ATC vs NOD ttest | Log2Diff | Fold change |
|---|---|---|---|---|---|---|
| hsa-miR-9* | 1.57 | 0.18 | 7.14 | 1.01E−04 | 5.57 | 47.6 |
| hsa-miR-582-3p | −1.38 | 0.31 | 3.97 | 5.78E−04 | 5.35 | 40.9 |
| hsa-miR-582-5p | 3.22 | 0.58 | 8.42 | 3.98E−03 | 5.21 | 36.9 |
| hsa-miR-1274a | 4.74 | 1.03 | 9.62 | 2.44E−02 | 4.88 | 29.5 |
| hsa-miR-155 | 5.86 | 0.20 | 10.25 | 2.90E−04 | 4.39 | 20.9 |
| hsa-miR-720 | 10.25 | 0.79 | 14.50 | 1.69E−02 | 4.25 | 19.0 |
| hsa-miR-1274b | 8.53 | 0.95 | 12.63 | 3.07E−02 | 4.10 | 17.1 |
| hsa-miR-9 | 1.10 | 0.38 | 5.05 | 2.54E−03 | 3.95 | 15.5 |
| hsa-miR-1260 | 6.50 | 0.87 | 9.84 | 4.22E−02 | 3.33 | 10.1 |
| hsa-miR-34c-5p | 4.07 | 0.83 | 7.37 | 3.76E−02 | 3.29 | 9.8 |
| hsa-miR-592 | 1.71 | 0.29 | 4.74 | 2.61E−03 | 3.03 | 8.2 |
| hsa-miR-10a | 7.62 | 0.10 | 10.38 | 1.63E−04 | 2.76 | 6.8 |
| hsa-miR-21 | 13.28 | 0.37 | 16.00 | 6.96E−03 | 2.72 | 6.6 |
| hsa-miR-21* | 4.43 | 0.17 | 7.10 | 7.59E−04 | 2.67 | 6.4 |
| hsa-miR-210 | 6.41 | 0.24 | 8.74 | 3.30E−03 | 2.32 | 5.0 |
| hsa-miR-155* | −0.06 | 0.15 | 1.88 | 1.28E−03 | 1.94 | 3.8 |
| hsa-miR-34b* | 6.55 | 0.45 | 8.43 | 3.29E−02 | 1.88 | 3.7 |
| hsa-miR-769-5p | 4.63 | 0.21 | 6.42 | 4.76E−03 | 1.80 | 3.5 |
| hsa-miR-196a | 1.79 | 0.40 | 3.56 | 2.87E−02 | 1.77 | 3.4 |
| hsa-miR-30a* | 8.56 | 0.34 | 10.32 | 1.95E−02 | 1.77 | 3.4 |
| hsa-miR-146a | 6.97 | 0.24 | 8.68 | 7.38E−03 | 1.71 | 3.3 |
| hsa-miR-296-1* | 3.36 | 0.34 | 5.05 | 2.05E−02 | 1.69 | 3.2 |
| hsa-miR-550* | 2.77 | 0.24 | 4.14 | 1.47E−02 | 1.36 | 2.6 |
| hsa-miR-10a* | 1.13 | 0.36 | 2.44 | 4.83E−02 | 1.31 | 2.5 |
| hsa-miR-223* | 0.82 | 0.32 | 2.11 | 3.55E−02 | 1.29 | 2.4 |
| hsa-miR-27a | 11.74 | 0.32 | 12.98 | 4.06E−02 | 1.24 | 2.4 |
| hsa-miR-556-3p | 0.36 | 0.32 | 1.55 | 4.38E−02 | 1.19 | 2.3 |
| hsa-miR-625 | 5.03 | 0.21 | 6.12 | 1.88E−02 | 1.09 | 2.1 |
| hsa-miR-342-5p | 4.85 | 0.25 | 5.91 | 3.13E−02 | 1.06 | 2.1 |
| hsa-miR-423-3p | 3.59 | 0.14 | 2.56 | 7.23E−03 | −1.02 | 2.0 |
| hsa-miR-30d* | 2.17 | 0.28 | 1.12 | 4.46E−02 | −1.05 | 2.1 |
| hsa-miR-192* | 1.68 | 0.23 | 0.63 | 2.68E−02 | −1.06 | 2.1 |
| hsa-miR-652 | 6.41 | 0.29 | 5.34 | 4.82E−02 | −1.06 | 2.1 |
| hsa-miR-30b* | 4.30 | 0.31 | 3.11 | 4.21E−02 | −1.19 | 2.3 |
| hsa-miR-216a | 0.39 | 0.07 | −0.81 | 6.49E−04 | −1.20 | 2.3 |
| hsa-miR-199b-5p | 9.26 | 0.23 | 7.97 | 1.48E−02 | −1.29 | 2.4 |
| hsa-miR-222* | −0.77 | 0.35 | −2.06 | 4.47E−02 | −1.29 | 2.4 |
| hsa-miR-130a | 11.54 | 0.35 | 10.22 | 4.37E−02 | −1.32 | 2.5 |
| hsa-miR-151-5p | 10.54 | 0.29 | 9.21 | 2.62E−02 | −1.33 | 2.5 |
| hsa-miR-615-3p | 0.33 | 0.29 | −1.03 | 2.54E−02 | −1.35 | 2.6 |
| hsa-miR-564 | 5.89 | 0.30 | 4.52 | 2.60E−02 | −1.37 | 2.6 |
| hsa-miR-29c* | 7.53 | 0.34 | 6.15 | 3.62E−02 | −1.38 | 2.6 |
| hsa-miR-138-2* | 2.41 | 0.31 | 1.03 | 2.79E−02 | −1.38 | 2.6 |
| hsa-miR-654-5p | 4.06 | 0.36 | 2.67 | 3.99E−02 | −1.39 | 2.6 |
| hsa-miR-595 | 1.81 | 0.36 | 0.42 | 4.01E−02 | −1.39 | 2.6 |
| hsa-miR-760 | 4.31 | 0.36 | 2.89 | 3.97E−02 | −1.41 | 2.7 |
| hsa-miR-338-5p | 2.47 | 0.30 | 1.05 | 2.31E−02 | −1.42 | 2.7 |
| hsa-miR-1306 | 2.97 | 0.34 | 1.49 | 3.01E−02 | −1.48 | 2.8 |
| hsa-miR-518e* | 2.03 | 0.27 | 0.53 | 1.53E−02 | −1.49 | 2.8 |
| hsa-miR-127-5p | 1.28 | 0.35 | −0.22 | 3.15E−02 | −1.50 | 2.8 |
| hsa-miR-30d | 10.43 | 0.25 | 8.94 | 1.24E−02 | −1.50 | 2.8 |
| hsa-let-7i | 13.53 | 0.24 | 11.99 | 1.06E−02 | −1.54 | 2.9 |
| hsa-miR-668 | −0.54 | 0.32 | −2.09 | 2.35E−02 | −1.55 | 2.9 |
| hsa-miR-423-5p | 7.16 | 0.31 | 5.61 | 2.03E−02 | −1.55 | 2.9 |
| hsa-miR-877* | 4.73 | 0.40 | 3.14 | 3.81E−02 | −1.59 | 3.0 |
| hsa-miR-542-3p | 4.93 | 0.37 | 3.33 | 3.07E−02 | −1.60 | 3.0 |
| hsa-miR-744* | 0.59 | 0.36 | −1.03 | 2.71E−02 | −1.62 | 3.1 |
| hsa-miR-490-3p | 1.74 | 0.41 | 0.11 | 3.76E−02 | −1.63 | 3.1 |
| hsa-miR-92a | 9.41 | 0.35 | 7.77 | 2.48E−02 | −1.64 | 3.1 |
| hsa-miR-939 | 8.91 | 0.42 | 7.27 | 3.95E−02 | −1.64 | 3.1 |
| hsa-miR-513a-5p | 5.52 | 0.43 | 3.86 | 4.11E−02 | −1.66 | 3.2 |
| hsa-miR-542-5p | 5.62 | 0.41 | 3.91 | 3.43E−02 | −1.71 | 3.3 |
| hsa-miR-708 | 2.61 | 0.40 | 0.87 | 3.12E−02 | −1.73 | 3.3 |
| hsa-miR-99b* | 2.95 | 0.29 | 1.20 | 1.23E−02 | −1.75 | 3.4 |
| hsa-miR-509-5p | 1.19 | 0.42 | −0.56 | 3.45E−02 | −1.75 | 3.4 |
| hsa-miR-498 | 3.77 | 0.49 | 2.00 | 4.93E−02 | −1.76 | 3.4 |
| hsa-miR-1307 | 3.37 | 0.39 | 1.57 | 2.63E−02 | −1.80 | 3.5 |
| hsa-miR-455-5p | 4.20 | 0.25 | 2.32 | 6.39E−03 | −1.88 | 3.7 |

TABLE 15-continued

MicroRNAs significantly differentially expressed between ATC and NOD samples.

| | NOD | | | ATC vs NOD | | |
|---|---|---|---|---|---|---|
| miRNA | AVG | SD | ATC | ttest | Log2Diff | Fold change |
| hsa-miR-30b | 11.67 | 0.45 | 9.75 | 3.16E−02 | −1.93 | 3.8 |
| hsa-miR-518c* | 2.24 | 0.52 | 0.28 | 4.27E−02 | −1.96 | 3.9 |
| hsa-miR-370 | 3.80 | 0.49 | 1.84 | 3.68E−02 | −1.96 | 3.9 |
| hsa-miR-1226* | 5.72 | 0.46 | 3.75 | 3.18E−02 | −1.97 | 3.9 |
| hsa-miR-1826 | 6.34 | 0.42 | 4.37 | 2.44E−02 | −1.97 | 3.9 |
| hsa-miR-617 | 3.26 | 0.35 | 1.28 | 1.48E−02 | −1.98 | 3.9 |
| hsa-miR-584 | 4.38 | 0.49 | 2.38 | 3.46E−02 | −2.00 | 4.0 |
| hsa-let-7c | 12.72 | 0.15 | 10.68 | 1.18E−03 | −2.04 | 4.1 |
| hsa-miR-616 | 1.69 | 0.53 | −0.36 | 4.10E−02 | −2.05 | 4.1 |
| hsa-miR-516b | 2.78 | 0.32 | 0.72 | 1.01E−02 | −2.06 | 4.2 |
| hsa-let-7g* | −0.02 | 0.56 | −2.14 | 4.34E−02 | −2.12 | 4.4 |
| hsa-miR-26a | 12.50 | 0.35 | 10.36 | 1.18E−02 | −2.14 | 4.4 |
| hsa-miR-1915 | 10.06 | 0.49 | 7.91 | 2.98E−02 | −2.15 | 4.4 |
| hsa-miR-874 | 6.97 | 0.13 | 4.78 | 5.77E−04 | −2.19 | 4.6 |
| hsa-miR-671-5p | 7.24 | 0.57 | 5.05 | 4.09E−02 | −2.19 | 4.6 |
| hsa-miR-585 | 2.68 | 0.61 | 0.44 | 4.74E−02 | −2.24 | 4.7 |
| hsa-miR-1471 | 5.53 | 0.37 | 3.24 | 1.13E−02 | −2.29 | 4.9 |
| hsa-miR-526b | 3.54 | 0.53 | 1.18 | 2.90E−02 | −2.36 | 5.1 |
| hsa-miR-202 | 7.06 | 0.56 | 4.70 | 3.31E−02 | −2.36 | 5.1 |
| hsa-miR-662 | 3.58 | 0.21 | 1.17 | 1.94E−03 | −2.42 | 5.3 |
| hsa-miR-126 | 12.43 | 0.25 | 10.01 | 3.28E−03 | −2.42 | 5.3 |
| hsa-miR-1270 | 2.47 | 0.46 | 0.05 | 1.84E−02 | −2.43 | 5.4 |
| hsa-miR-601 | 5.60 | 0.53 | 3.16 | 2.57E−02 | −2.43 | 5.4 |
| hsa-miR-648 | 4.14 | 0.46 | 1.64 | 1.67E−02 | −2.49 | 5.6 |
| hsa-miR-936 | 4.55 | 0.65 | 2.05 | 4.06E−02 | −2.50 | 5.6 |
| hsa-miR-100 | 11.66 | 0.24 | 9.15 | 2.54E−03 | −2.50 | 5.7 |
| hsa-miR-1301 | 1.60 | 0.30 | −0.92 | 4.69E−03 | −2.52 | 5.7 |
| hsa-miR-640 | 1.49 | 0.46 | −1.06 | 1.54E−02 | −2.56 | 5.9 |
| hsa-miR-665 | 4.46 | 0.24 | 1.87 | 2.25E−03 | −2.59 | 6.0 |
| hsa-miR-1915* | 2.26 | 0.54 | −0.36 | 2.29E−02 | −2.62 | 6.1 |
| hsa-miR-143* | 3.99 | 0.50 | 1.36 | 1.84E−02 | −2.64 | 6.2 |
| hsa-miR-345 | 4.32 | 0.16 | 1.63 | 6.01E−04 | −2.69 | 6.4 |
| hsa-miR-490-5p | 3.39 | 0.29 | 0.69 | 3.77E−03 | −2.70 | 6.5 |
| hsa-miR-551b | 5.32 | 0.11 | 2.61 | 1.78E−04 | −2.71 | 6.5 |
| hsa-miR-1299 | 4.40 | 0.44 | 1.68 | 1.17E−02 | −2.72 | 6.6 |
| hsa-miR-1208 | 3.69 | 0.27 | 0.87 | 2.76E−03 | −2.81 | 7.0 |
| hsa-miR-1203 | 2.45 | 0.50 | −0.39 | 1.45E−02 | −2.84 | 7.2 |
| hsa-miR-1303 | 1.71 | 0.56 | −1.15 | 1.96E−02 | −2.86 | 7.3 |
| hsa-miR-921 | 1.67 | 0.51 | −1.27 | 1.44E−02 | −2.94 | 7.7 |
| hsa-miR-125b-2* | 5.61 | 0.18 | 2.65 | 7.20E−04 | −2.95 | 7.7 |
| hsa-miR-1276 | 2.01 | 0.65 | −0.95 | 2.64E−02 | −2.96 | 7.8 |
| hsa-miR-451 | 14.94 | 0.59 | 11.96 | 2.05E−02 | −2.98 | 7.9 |
| hsa-miR-149* | 4.68 | 0.59 | 1.68 | 1.98E−02 | −3.00 | 8.0 |
| hsa-miR-145* | 5.38 | 0.42 | 2.37 | 7.79E−03 | −3.01 | 8.0 |
| hsa-miR-143 | 8.32 | 0.44 | 5.31 | 8.87E−03 | −3.01 | 8.1 |
| hsa-miR-99a* | 1.28 | 0.70 | −1.76 | 3.01E−02 | −3.04 | 8.2 |
| hsa-miR-491-5p | 1.71 | 0.41 | −1.33 | 6.81E−03 | −3.04 | 8.3 |
| hsa-miR-551b* | 2.72 | 0.65 | −0.34 | 2.47E−02 | −3.07 | 8.4 |
| hsa-miR-452 | 4.64 | 0.41 | 1.57 | 6.66E−03 | −3.07 | 8.4 |
| hsa-miR-424* | 5.34 | 0.66 | 2.24 | 2.46E−02 | −3.10 | 8.6 |
| hsa-miR-1228* | 1.90 | 0.73 | −1.22 | 3.15E−02 | −3.12 | 8.7 |
| hsa-miR-1250 | 1.91 | 0.52 | −1.24 | 1.22E−02 | −3.16 | 8.9 |
| hsa-miR-1180 | 3.54 | 0.41 | 0.37 | 6.15E−03 | −3.17 | 9.0 |
| hsa-miR-138-1* | 1.32 | 0.49 | −1.86 | 1.04E−02 | −3.19 | 9.1 |
| hsa-miR-218 | 8.23 | 0.27 | 5.04 | 1.89E−03 | −3.19 | 9.1 |
| hsa-miR-224 | 5.70 | 0.20 | 2.46 | 7.12E−04 | −3.24 | 9.4 |
| hsa-miR-486-5p | 8.61 | 0.71 | 5.35 | 2.59E−02 | −3.26 | 9.6 |
| hsa-miR-125b | 13.93 | 0.24 | 10.44 | 9.63E−04 | −3.48 | 11.2 |
| hsa-miR-99a | 11.53 | 0.24 | 8.00 | 9.00E−04 | −3.53 | 11.6 |
| hsa-miR-631 | 3.97 | 0.56 | 0.20 | 9.12E−03 | −3.78 | 13.7 |
| hsa-miR-200a* | 4.34 | 0.33 | 0.46 | 1.79E−03 | −3.88 | 14.7 |
| hsa-miR-422a | 3.64 | 0.36 | −0.25 | 2.30E−03 | −3.89 | 14.8 |
| hsa-miR-493 | 2.93 | 0.73 | −0.99 | 1.73E−02 | −3.92 | 15.1 |
| hsa-miR-145 | 10.71 | 0.24 | 6.78 | 6.83E−04 | −3.93 | 15.2 |
| hsa-miR-486-3p | 2.16 | 1.04 | −1.82 | 4.19E−02 | −3.98 | 15.8 |
| hsa-miR-139-5p | 6.89 | 0.32 | 2.79 | 1.40E−03 | −4.09 | 17.0 |
| hsa-miR-1469 | 3.39 | 0.42 | −0.80 | 3.04E−03 | −4.19 | 18.3 |
| hsa-miR-141* | 2.70 | 0.63 | −1.68 | 8.48E−03 | −4.38 | 20.8 |
| hsa-miR-200b* | 4.90 | 0.29 | 0.48 | 8.18E−04 | −4.42 | 21.4 |
| hsa-miR-934 | 2.09 | 0.71 | −2.40 | 1.07E−02 | −4.49 | 22.5 |
| hsa-miR-512-3p | 5.11 | 0.05 | 0.39 | 3.03E−06 | −4.72 | 26.3 |
| hsa-miR-7-2* | 3.76 | 1.18 | −1.00 | 3.65E−02 | −4.76 | 27.2 |
| hsa-miR-92b* | 2.96 | 0.56 | −2.10 | 3.91E−03 | −5.06 | 33.4 |

TABLE 15-continued

MicroRNAs significantly differentially expressed between ATC and NOD samples.

| miRNA | NOD AVG | NOD SD | ATC | ATC vs NOD ttest | ATC vs NOD Log2Diff | Fold change |
|---|---|---|---|---|---|---|
| hsa-miR-205 | 4.49 | 0.38 | -1.95 | 6.21E-04 | -6.44 | 86.5 |
| hsa-miR-138 | 6.61 | 0.71 | 0.09 | 3.77E-03 | -6.52 | 91.7 |
| hsa-miR-135b | 9.05 | 0.63 | 2.20 | 2.30E-03 | -6.85 | 115.3 |
| hsa-miR-135a | 8.06 | 0.99 | 1.19 | 8.34E-03 | -6.87 | 117.0 |
| hsa-miR-200b | 10.22 | 0.06 | 2.93 | 1.68E-06 | -7.29 | 156.7 |
| hsa-miR-200a | 8.86 | 0.32 | 1.45 | 2.36E-04 | -7.41 | 169.8 |
| hsa-miR-429 | 7.59 | 0.20 | -0.05 | 5.74E-05 | -7.64 | 199.7 |
| hsa-miR-141 | 10.73 | 0.55 | 2.51 | 9.18E-04 | -8.21 | 297.0 |
| hsa-miR-200c | 11.37 | 0.32 | 3.00 | 1.79E-04 | -8.36 | 329.5 |

AVG, average expression among samples in a group;
SD, standard deviation

Example 14 miRNA Expression Profiling Distinguishes Hyperplastic Thyroid Nodules and Medullary Thyroid Carcinoma A total of 222 human miRNAs were significantly differentially expressed between the hyperplastic nodule samples and the medullary thyroid carcinomas (p<0.05). Among these, 108 miRNAs were overexpressed (Log 2 diff (MTC vs NOD)≥1) and 79 were underexpressed (Log 2 diff (MTC vs NOD)≤1) by at least 2-fold in MTC compared to NOD samples (Table 16). Of these hsa-miR-375 was overexpressed by more than 900-fold, six miRNAs (hsa-miR-153, -323-3p, -124, -487b, -410, and -592) were overexpressed by 50- to 110-fold, thirty five miRNAs were overexpressed by 10- to 30-fold, and twenty three miRNAs were overexpressed by 5- to 10-fold in the MTC specimens compared to the NOD samples. Among the miRNAs that were expressed at lower average levels in the MTC samples, hsa-miR-92b* and hsa-miR-1202 were underexpressed by 10- to 15-fold, and nineteen miRNAs were underexpressed by 5- to 10-fold in the MTC specimens.

TABLE 16

MicroRNAs significantly differentially expressed between MTC and NOD samples.

| miRNA | MTC AVG | MTC SD | NOD AVG | NOD SD | MTC vs NOD ttest | MTC vs NOD Log2Diff | Fold change |
|---|---|---|---|---|---|---|---|
| hsa-miR-375 | 13.86 | 0.40 | 4.00 | 2.15 | 5.95E-04 | 9.87 | 933.7 |
| hsa-miR-153 | 8.11 | 1.07 | 1.40 | 0.85 | 2.38E-04 | 6.71 | 104.7 |
| hsa-miR-323-3p | 6.93 | 0.13 | 0.37 | 0.78 | 3.24E-05 | 6.56 | 94.2 |
| hsa-miR-124 | 7.86 | 3.11 | 1.52 | 1.06 | 1.15E-02 | 6.34 | 80.9 |
| hsa-miR-487b | 9.75 | 0.19 | 3.63 | 1.15 | 3.01E-04 | 6.11 | 69.3 |
| hsa-miR-410 | 8.20 | 0.14 | 2.16 | 1.00 | 1.61E-04 | 6.03 | 65.6 |
| hsa-miR-592 | 7.50 | 1.19 | 1.71 | 0.29 | 2.02E-04 | 5.79 | 55.4 |
| hsa-miR-539 | 6.53 | 0.34 | 1.75 | 0.35 | 9.38E-06 | 4.78 | 27.4 |
| hsa-miR-758 | 5.04 | 0.13 | 0.34 | 1.07 | 7.33E-04 | 4.69 | 25.8 |
| hsa-miR-409-5p | 4.92 | 0.15 | 0.31 | 1.08 | 8.22E-04 | 4.62 | 24.5 |
| hsa-miR-487a | 4.79 | 0.32 | 0.19 | 0.60 | 7.31E-05 | 4.60 | 24.2 |
| hsa-miR-409-3p | 7.21 | 0.31 | 2.64 | 1.02 | 7.34E-04 | 4.58 | 23.9 |
| hsa-miR-137 | 5.03 | 3.11 | 0.46 | 0.60 | 3.16E-02 | 4.57 | 23.7 |
| hsa-miR-433 | 4.13 | 0.61 | -0.44 | 0.89 | 6.41E-04 | 4.56 | 23.7 |
| hsa-miR-127-3p | 8.88 | 0.37 | 4.47 | 0.97 | 7.24E-04 | 4.42 | 21.4 |
| hsa-miR-183 | 10.49 | 0.69 | 6.08 | 0.43 | 1.33E-04 | 4.42 | 21.4 |
| hsa-miR-485-3p | 4.27 | 0.37 | -0.10 | 0.54 | 7.49E-05 | 4.37 | 20.7 |
| hsa-miR-382 | 6.53 | 0.24 | 2.18 | 0.36 | 9.57E-06 | 4.35 | 20.4 |
| hsa-miR-432 | 7.61 | 0.36 | 3.26 | 0.58 | 9.50E-05 | 4.35 | 20.4 |
| hsa-miR-495 | 6.93 | 0.28 | 2.62 | 1.04 | 1.03E-03 | 4.31 | 19.8 |
| hsa-miR-136* | 6.41 | 0.51 | 2.21 | 0.78 | 4.91E-04 | 4.20 | 18.4 |
| hsa-miR-154 | 6.86 | 0.17 | 2.66 | 1.58 | 6.51E-03 | 4.20 | 18.4 |
| hsa-miR-889 | 3.79 | 0.54 | -0.33 | 0.12 | 2.22E-05 | 4.12 | 17.4 |
| hsa-miR-182 | 5.90 | 0.30 | 1.79 | 0.79 | 3.91E-04 | 4.12 | 17.3 |
| hsa-miR-543 | 5.30 | 0.05 | 1.20 | 0.93 | 7.04E-04 | 4.09 | 17.1 |
| hsa-miR-10a | 11.69 | 0.52 | 7.62 | 0.10 | 1.94E-05 | 4.06 | 16.7 |
| hsa-miR-485-5p | 4.03 | 0.40 | -0.01 | 0.88 | 7.69E-04 | 4.04 | 16.5 |
| hsa-miR-377 | 7.51 | 0.55 | 3.54 | 0.80 | 7.58E-04 | 3.98 | 15.8 |
| hsa-miR-96 | 11.01 | 0.48 | 7.09 | 0.38 | 6.96E-05 | 3.92 | 15.1 |
| hsa-miR-431 | 5.00 | 1.06 | 1.13 | 0.48 | 1.20E-03 | 3.86 | 14.6 |
| hsa-miR-376c | 9.21 | 0.81 | 5.35 | 0.89 | 2.00E-03 | 3.86 | 14.5 |
| hsa-miR-136 | 6.61 | 0.51 | 2.79 | 0.73 | 5.87E-04 | 3.81 | 14.1 |
| hsa-miR-154* | 4.83 | 0.62 | 1.04 | 0.80 | 1.06E-03 | 3.79 | 13.8 |
| hsa-miR-369-5p | 5.27 | 0.72 | 1.50 | 0.64 | 7.48E-04 | 3.77 | 13.6 |

TABLE 16-continued

MicroRNAs significantly differentially expressed between MTC and NOD samples.

| miRNA | MTC AVG | MTC SD | NOD AVG | NOD SD | MTC vs NOD ttest | MTC vs NOD Log2Diff | Fold change |
|---|---|---|---|---|---|---|---|
| hsa-miR-9* | 5.31 | 1.78 | 1.57 | 0.18 | 7.66E-03 | 3.73 | 13.3 |
| hsa-miR-493* | 5.39 | 0.45 | 1.70 | 1.26 | 5.06E-03 | 3.69 | 12.9 |
| hsa-miR-376a | 8.51 | 0.67 | 4.83 | 0.87 | 1.75E-03 | 3.68 | 12.8 |
| hsa-miR-329 | 4.13 | 0.15 | 0.51 | 0.46 | 5.07E-05 | 3.61 | 12.2 |
| hsa-miR-9 | 4.69 | 1.56 | 1.10 | 0.38 | 6.08E-03 | 3.59 | 12.0 |
| hsa-miR-411 | 4.80 | 0.24 | 1.27 | 1.11 | 3.20E-03 | 3.53 | 11.6 |
| hsa-miR-379 | 6.20 | 0.14 | 2.70 | 0.88 | 1.13E-03 | 3.49 | 11.2 |
| hsa-miR-376a* | 4.63 | 0.44 | 1.19 | 0.34 | 7.67E-05 | 3.44 | 10.9 |
| hsa-miR-105 | 2.03 | 2.55 | -1.25 | 0.39 | 4.68E-02 | 3.29 | 9.7 |
| hsa-miR-335 | 9.06 | 1.56 | 5.79 | 0.67 | 1.20E-02 | 3.27 | 9.7 |
| hsa-miR-381 | 7.34 | 0.33 | 4.14 | 1.16 | 6.18E-03 | 3.20 | 9.2 |
| hsa-miR-654-3p | 6.30 | 0.51 | 3.13 | 1.00 | 4.39E-03 | 3.17 | 9.0 |
| hsa-miR-377* | 2.94 | 0.16 | -0.19 | 0.38 | 4.51E-05 | 3.14 | 8.8 |
| hsa-miR-183* | 4.36 | 0.40 | 1.38 | 0.66 | 1.03E-03 | 2.98 | 7.9 |
| hsa-miR-582-5p | 6.13 | 0.18 | 3.22 | 0.58 | 4.23E-04 | 2.91 | 7.5 |
| hsa-miR-132* | 5.58 | 1.13 | 2.70 | 0.58 | 6.60E-03 | 2.88 | 7.3 |
| hsa-miR-337-5p | 5.33 | 0.33 | 2.51 | 0.94 | 4.61E-03 | 2.82 | 7.0 |
| hsa-miR-7-1* | 6.88 | 0.44 | 4.08 | 0.43 | 3.90E-04 | 2.80 | 7.0 |
| hsa-miR-1274a | 7.49 | 0.88 | 4.74 | 1.03 | 1.41E-02 | 2.75 | 6.7 |
| hsa-miR-221 | 9.68 | 0.79 | 6.94 | 0.35 | 1.46E-03 | 2.74 | 6.7 |
| hsa-miR-429 | 10.32 | 0.28 | 7.59 | 0.20 | 2.26E-05 | 2.73 | 6.6 |
| hsa-miR-10a* | 3.82 | 0.57 | 1.13 | 0.36 | 5.94E-04 | 2.69 | 6.4 |
| hsa-miR-132 | 8.97 | 1.15 | 6.28 | 0.33 | 6.08E-03 | 2.68 | 6.4 |
| hsa-miR-376b | 3.45 | 1.39 | 0.79 | 0.67 | 1.92E-02 | 2.66 | 6.3 |
| hsa-miR-1274b | 11.05 | 0.81 | 8.53 | 0.95 | 1.43E-02 | 2.52 | 5.7 |
| hsa-miR-338-3p | 9.34 | 0.35 | 6.85 | 0.82 | 4.74E-03 | 2.49 | 5.6 |
| hsa-miR-598 | 7.98 | 0.33 | 5.56 | 0.54 | 1.04E-03 | 2.42 | 5.4 |
| hsa-miR-200a | 11.26 | 0.29 | 8.86 | 0.32 | 1.45E-04 | 2.40 | 5.3 |
| hsa-miR-369-3p | 2.85 | 0.71 | 0.47 | 0.55 | 3.93E-03 | 2.38 | 5.2 |
| hsa-miR-1260 | 8.86 | 0.42 | 6.50 | 0.87 | 8.18E-03 | 2.35 | 5.1 |
| hsa-miR-1185 | 3.03 | 0.54 | 0.69 | 0.26 | 5.87E-04 | 2.34 | 5.1 |
| hsa-miR-182* | 2.00 | 0.20 | -0.26 | 0.47 | 5.90E-04 | 2.26 | 4.8 |
| hsa-miR-720 | 12.50 | 0.70 | 10.25 | 0.79 | 1.13E-02 | 2.26 | 4.8 |
| hsa-miR-663b | 3.88 | 1.00 | 1.76 | 1.12 | 4.96E-02 | 2.12 | 4.3 |
| hsa-miR-29b-1* | 5.39 | 0.51 | 3.36 | 0.34 | 1.36E-03 | 2.03 | 4.1 |
| hsa-miR-301a | 7.56 | 0.34 | 5.60 | 0.52 | 2.39E-03 | 1.97 | 3.9 |
| hsa-miR-200b | 12.17 | 0.08 | 10.22 | 0.06 | 3.03E-07 | 1.95 | 3.9 |
| hsa-miR-330-3p | 6.34 | 0.46 | 4.40 | 0.20 | 5.80E-04 | 1.94 | 3.8 |
| hsa-miR-326 | 3.61 | 0.14 | 1.69 | 0.14 | 8.38E-06 | 1.92 | 3.8 |
| hsa-miR-340* | 5.17 | 0.53 | 3.30 | 0.54 | 6.01E-03 | 1.87 | 3.6 |
| hsa-miR-1301 | 3.45 | 0.62 | 1.60 | 0.30 | 3.09E-03 | 1.85 | 3.6 |
| hsa-miR-668 | 1.30 | 0.42 | -0.54 | 0.32 | 1.18E-03 | 1.85 | 3.6 |
| hsa-miR-335* | 3.78 | 0.88 | 1.95 | 0.33 | 1.14E-02 | 1.83 | 3.6 |
| hsa-miR-221* | 6.93 | 0.33 | 5.14 | 0.24 | 4.13E-04 | 1.79 | 3.4 |
| hsa-miR-656 | 2.09 | 0.62 | 0.40 | 0.38 | 6.24E-03 | 1.69 | 3.2 |
| hsa-miR-24-1* | 6.56 | 0.18 | 4.91 | 0.13 | 3.15E-05 | 1.65 | 3.1 |
| hsa-miR-582-3p | 0.19 | 0.32 | -1.38 | 0.31 | 1.21E-03 | 1.58 | 3.0 |
| hsa-miR-340 | 6.25 | 0.61 | 4.68 | 0.47 | 1.15E-02 | 1.57 | 3.0 |
| hsa-miR-200c* | 2.59 | 0.25 | 1.03 | 0.53 | 5.74E-03 | 1.55 | 2.9 |
| hsa-miR-337-3p | 3.15 | 0.43 | 1.62 | 0.62 | 1.53E-02 | 1.53 | 2.9 |
| hsa-miR-642 | 0.65 | 0.41 | -0.88 | 0.50 | 7.49E-03 | 1.53 | 2.9 |
| hsa-miR-95 | 9.43 | 0.66 | 7.93 | 0.64 | 2.87E-02 | 1.50 | 2.8 |
| hsa-miR-21 | 14.78 | 0.98 | 13.28 | 0.37 | 3.44E-02 | 1.50 | 2.8 |
| hsa-miR-216a | 1.88 | 0.79 | 0.39 | 0.07 | 1.16E-02 | 1.49 | 2.8 |
| hsa-miR-21* | 5.89 | 0.75 | 4.43 | 0.17 | 1.14E-02 | 1.46 | 2.7 |
| hsa-let-7e | 12.78 | 0.21 | 11.33 | 0.40 | 2.33E-03 | 1.45 | 2.7 |
| hsa-miR-301b | 3.14 | 0.72 | 1.72 | 0.31 | 1.51E-02 | 1.42 | 2.7 |
| hsa-let-7e* | 3.07 | 0.28 | 1.65 | 0.54 | 9.38E-03 | 1.42 | 2.7 |
| hsa-miR-181a* | 4.68 | 0.78 | 3.26 | 0.41 | 2.46E-02 | 1.42 | 2.7 |
| hsa-miR-299-3p | 3.11 | 0.45 | 1.73 | 0.56 | 1.82E-02 | 1.38 | 2.6 |
| hsa-miR-23b | 13.42 | 0.15 | 12.04 | 0.09 | 2.24E-05 | 1.37 | 2.6 |
| hsa-miR-148b | 9.64 | 0.55 | 8.27 | 0.62 | 2.97E-02 | 1.37 | 2.6 |
| hsa-miR-200a* | 5.71 | 0.26 | 4.34 | 0.33 | 1.94E-03 | 1.37 | 2.6 |
| hsa-miR-181c | 8.44 | 0.26 | 7.10 | 0.60 | 1.67E-02 | 1.33 | 2.5 |
| hsa-miR-324-5p | 9.24 | 0.04 | 7.92 | 0.20 | 1.16E-04 | 1.32 | 2.5 |
| hsa-miR-181c* | 5.32 | 0.15 | 4.03 | 0.39 | 3.02E-03 | 1.29 | 2.5 |
| hsa-miR-23b* | 4.61 | 0.28 | 3.36 | 0.32 | 3.13E-03 | 1.25 | 2.4 |
| hsa-miR-141* | 3.92 | 0.38 | 2.70 | 0.63 | 3.17E-02 | 1.23 | 2.3 |
| hsa-miR-27b | 12.95 | 0.25 | 11.75 | 0.26 | 1.69E-03 | 1.19 | 2.3 |
| hsa-miR-15a | 11.64 | 0.56 | 10.48 | 0.47 | 2.96E-02 | 1.17 | 2.2 |
| hsa-miR-421 | 3.49 | 0.48 | 2.35 | 0.48 | 2.64E-02 | 1.15 | 2.2 |
| hsa-miR-652 | 7.51 | 0.29 | 6.41 | 0.29 | 4.23E-03 | 1.10 | 2.1 |
| hsa-miR-769-5p | 5.73 | 0.25 | 4.63 | 0.21 | 1.47E-03 | 1.10 | 2.1 |

TABLE 16-continued

MicroRNAs significantly differentially expressed between MTC and NOD samples.

| miRNA | MTC AVG | MTC SD | NOD AVG | NOD SD | MTC vs NOD ttest | MTC vs NOD Log2Diff | Fold change |
|---|---|---|---|---|---|---|---|
| hsa-m1R-200b* | 5.99 | 0.11 | 4.90 | 0.29 | 1.64E−03 | 1.09 | 2.1 |
| hsa-miR-100 | 10.63 | 0.66 | 11.66 | 0.24 | 3.12E−02 | −1.03 | 2.0 |
| hsa-miR-769-3p | 2.27 | 0.15 | 3.34 | 0.64 | 3.81E−02 | −1.08 | 2.1 |
| hsa-miR-1228 | 4.67 | 0.23 | 5.75 | 0.58 | 3.06E−02 | −1.08 | 2.1 |
| hsa-miR-1539 | 1.85 | 0.22 | 2.93 | 0.48 | 1.56E−02 | −1.08 | 2.1 |
| hsa-miR-28-3p | 0.98 | 0.32 | 2.09 | 0.21 | 2.52E−03 | −1.11 | 2.2 |
| hsa-miR-152 | 6.62 | 0.52 | 7.76 | 0.51 | 3.40E−02 | −1.13 | 2.2 |
| hsa-miR-509-5p | 0.06 | 0.66 | 1.19 | 0.42 | 3.77E−02 | −1.14 | 2.2 |
| hsa-miR-125a-3p | 6.16 | 0.72 | 7.33 | 0.40 | 3.89E−02 | −1.17 | 2.2 |
| hsa-miR-639 | −0.25 | 0.59 | 0.97 | 0.48 | 2.99E−02 | −1.22 | 2.3 |
| hsa-miR-585 | 1.44 | 0.15 | 2.68 | 0.61 | 2.07E−02 | −1.23 | 2.4 |
| hsa-miR-525-5p | 0.91 | 0.60 | 2.15 | 0.49 | 2.91E−02 | −1.25 | 2.4 |
| hsa-miR-584 | 3.13 | 0.35 | 4.38 | 0.49 | 1.33E−02 | −1.25 | 2.4 |
| hsa-miR-574-5p | 6.26 | 0.22 | 7.52 | 0.63 | 2.22E−02 | −1.26 | 2.4 |
| hsa-miR-23a* | 3.22 | 0.65 | 4.50 | 0.50 | 3.13E−02 | −1.28 | 2.4 |
| hsa-miR-296-5p | 3.21 | 0.17 | 4.51 | 0.68 | 2.58E−02 | −1.29 | 2.5 |
| hsa-miR-490-5p | 2.00 | 0.91 | 3.39 | 0.29 | 3.26E−02 | −1.38 | 2.6 |
| hsa-miR-1208 | 2.29 | 0.97 | 3.69 | 0.27 | 3.83E−02 | −1.39 | 2.6 |
| hsa-miR-1303 | 0.31 | 0.54 | 1.71 | 0.56 | 2.12E−02 | −1.40 | 2.6 |
| hsa-miR-640 | 0.08 | 0.59 | 1.49 | 0.46 | 1.53E−02 | −1.42 | 2.7 |
| hsa-miR-345 | 2.88 | 0.99 | 4.32 | 0.16 | 3.13E−02 | −1.44 | 2.7 |
| hsa-miR-550 | 2.26 | 0.55 | 3.70 | 0.30 | 6.21E−03 | −1.44 | 2.7 |
| hsa-miR-518c* | 0.79 | 0.80 | 2.24 | 0.52 | 3.24E−02 | −1.45 | 2.7 |
| hsa-miR-513a-5p | 4.06 | 0.74 | 5.52 | 0.43 | 2.04E−02 | −1.46 | 2.8 |
| hsa-miR-33b* | 2.75 | 0.62 | 4.27 | 0.51 | 1.55E−02 | −1.52 | 2.9 |
| hsa-miR-526b | 2.01 | 0.89 | 3.54 | 0.53 | 3.54E−02 | −1.52 | 2.9 |
| hsa-miR-1306 | 1.39 | 0.66 | 2.97 | 0.34 | 8.44E−03 | −1.58 | 3.0 |
| hsa-miR-518e* | 0.42 | 0.71 | 2.03 | 0.27 | 7.96E−03 | −1.60 | 3.0 |
| hsa-miR-921 | 0.06 | 0.95 | 1.67 | 0.51 | 3.29E−02 | −1.61 | 3.0 |
| hsa-miR-139-5p | 5.21 | 0.90 | 6.89 | 0.32 | 1.67E−02 | −1.67 | 3.2 |
| hsa-miR-1226* | 4.04 | 0.87 | 5.72 | 0.46 | 2.03E−02 | −1.68 | 3.2 |
| hsa-miR-1270 | 0.79 | 0.81 | 2.47 | 0.46 | 1.71E−02 | −1.68 | 3.2 |
| hsa-miR-760 | 2.62 | 0.85 | 4.31 | 0.36 | 1.46E−02 | −1.69 | 3.2 |
| hsa-miR-616 | −0.02 | 1.08 | 1.69 | 0.53 | 3.84E−02 | −1.70 | 3.3 |
| hsa-miR-662 | 1.87 | 0.84 | 3.58 | 0.21 | 9.89E−03 | −1.71 | 3.3 |
| hsa-miR-602 | 2.16 | 0.86 | 3.88 | 0.51 | 2.02E−02 | −1.71 | 3.3 |
| hsa-miR-1249 | 4.17 | 0.68 | 5.93 | 0.74 | 2.34E−02 | −1.77 | 3.4 |
| hsa-miR-138-1* | −0.48 | 0.71 | 1.32 | 0.49 | 1.04E−02 | −1.80 | 3.5 |
| hsa-miR-518a-5p | 0.21 | 1.23 | 2.05 | 0.65 | 4.81E−02 | −1.84 | 3.6 |
| hsa-miR-188-5p | 5.61 | 0.88 | 7.46 | 0.63 | 2.23E−02 | −1.85 | 3.6 |
| hsa-miR-877* | 2.86 | 0.40 | 4.73 | 0.40 | 1.73E−03 | −1.87 | 3.7 |
| hsa-miR-610 | 2.56 | 1.05 | 4.46 | 0.57 | 2.65E−02 | −1.89 | 3.7 |
| hsa-miR-498 | 1.86 | 0.85 | 3.77 | 0.49 | 1.28E−02 | −1.90 | 3.7 |
| hsa-miR-516b | 0.84 | 1.36 | 2.78 | 0.32 | 3.64E−02 | −1.94 | 3.8 |
| hsa-miR-202 | 5.12 | 0.65 | 7.06 | 0.56 | 8.22E−03 | −1.94 | 3.8 |
| hsa-miR-1224-5p | 5.65 | 1.15 | 7.60 | 0.65 | 3.47E−02 | −1.94 | 3.8 |
| hsa-miR-551b | 3.35 | 1.29 | 5.32 | 0.11 | 2.53E−02 | −1.97 | 3.9 |
| hsa-miR-371-5p | 4.11 | 0.92 | 6.14 | 0.47 | 1.17E−02 | −2.03 | 4.1 |
| hsa-miR-659 | 3.47 | 1.46 | 5.53 | 0.63 | 4.91E−02 | −2.06 | 4.2 |
| hsa-miR-617 | 1.20 | 0.64 | 3.26 | 0.35 | 2.57E−03 | −2.06 | 4.2 |
| hsa-miR-1203 | 0.29 | 1.50 | 2.45 | 0.50 | 3.95E−02 | −2.16 | 4.5 |
| hsa-miR-1321 | 1.56 | 1.15 | 3.74 | 0.75 | 2.85E−02 | −2.18 | 4.5 |
| hsa-miR-1915 | 7.88 | 1.03 | 10.06 | 0.49 | 1.28E−02 | −2.18 | 4.5 |
| hsa-miR-1276 | −0.18 | 1.32 | 2.01 | 0.65 | 3.22E−02 | −2.18 | 4.5 |
| hsa-miR-204 | 6.03 | 1.35 | 8.22 | 0.45 | 2.65E−02 | −2.19 | 4.6 |
| hsa-miR-134 | 5.80 | 1.10 | 8.00 | 0.93 | 3.46E−02 | −2.19 | 4.6 |
| hsa-miR-30a | 9.76 | 1.51 | 11.96 | 0.40 | 3.47E−02 | −2.20 | 4.6 |
| hsa-miR-1182 | 2.54 | 1.51 | 4.76 | 0.77 | 4.94E−02 | −2.22 | 4.7 |
| hsa-miR-605 | 1.49 | 0.55 | 3.72 | 1.03 | 2.05E−02 | −2.23 | 4.7 |
| hsa-miR-1268 | 7.86 | 0.70 | 10.19 | 1.33 | 4.16E−02 | −2.33 | 5.0 |
| hsa-miR-601 | 3.26 | 1.32 | 5.60 | 0.53 | 2.14E−02 | −2.34 | 5.1 |
| hsa-miR-939 | 6.56 | 0.92 | 8.91 | 0.42 | 5.75E−03 | −2.36 | 5.1 |
| hsa-miR-648 | 1.76 | 1.29 | 4.14 | 0.46 | 1.75E−02 | −2.37 | 5.2 |
| hsa-miR-940 | 6.45 | 1.12 | 8.91 | 0.72 | 1.61E−02 | −2.45 | 5.5 |
| hsa-miR-1915* | −0.22 | 1.39 | 2.26 | 0.54 | 2.05E−02 | −2.48 | 5.6 |
| hsa-miR-934 | −0.44 | 1.00 | 2.09 | 0.71 | 1.07E−02 | −2.53 | 5.8 |
| hsa-miR-623 | 2.34 | 1.63 | 4.95 | 0.55 | 2.77E−02 | −2.61 | 6.1 |
| hsa-miR-150* | 4.87 | 1.63 | 7.49 | 0.70 | 3.22E−02 | −2.62 | 6.2 |
| hsa-miR-1225-5p | 9.17 | 1.49 | 11.79 | 0.95 | 3.52E−02 | −2.62 | 6.2 |
| hsa-miR-1909* | −0.02 | 1.58 | 2.64 | 0.78 | 3.08E−02 | −2.66 | 6.3 |
| hsa-miR-187* | 1.99 | 1.55 | 4.73 | 0.70 | 2.43E−02 | −2.74 | 6.7 |
| hsa-miR-149* | 1.87 | 1.75 | 4.68 | 0.59 | 2.74E−02 | −2.82 | 7.0 |
| hsa-miR-638 | 8.14 | 0.98 | 10.95 | 1.00 | 1.36E−02 | −2.82 | 7.0 |

TABLE 16-continued

MicroRNAs significantly differentially expressed between MTC and NOD samples.

| miRNA | MTC AVG | MTC SD | NOD AVG | NOD SD | MTC vs NOD ttest | Log2Diff | Fold change |
|---|---|---|---|---|---|---|---|
| hsa-miR-631 | 1.11 | 2.20 | 3.97 | 0.56 | 4.97E−02 | −2.86 | 7.3 |
| hsa-miR-572 | 4.86 | 0.86 | 7.90 | 1.01 | 8.63E−03 | −3.05 | 8.3 |
| hsa-miR-663 | 5.54 | 1.91 | 8.63 | 0.75 | 2.96E−02 | −3.09 | 8.5 |
| hsa-miR-138 | 3.44 | 2.17 | 6.61 | 0.71 | 3.77E−02 | −3.17 | 9.0 |
| hsa-miR-1300 | 4.62 | 1.07 | 7.80 | 0.79 | 6.04E−03 | −3.19 | 9.1 |
| hsa-miR-1202 | 10.07 | 2.09 | 13.75 | 0.81 | 2.18E−02 | −3.67 | 12.8 |
| hsa-miR-92b* | −0.87 | 0.66 | 2.96 | 0.56 | 4.05E−04 | −3.83 | 14.3 |

AVG, average expression among samples in a group;
SD, standard deviation

Example 15 miRNA Expression Profiling Distinguishes Follicular Adenoma and Follicular Thyroid Carcinoma A total of 19 human miRNAs were significantly differentially expressed between the follicular adenomas and the follicular thyroid carcinomas (p<0.05) (Table 17). Among these, four (hsa-let-7g* and hsa-miR-196a, -595, and -1227) were expressed at levels that were at least 2-fold higher (Log 2 diff (FA vs FTC)≥1) in FA than in FTC, while seven miRNAs (hsa-miR-32, -19a, -105*, -20a*, -20b, -17*, and -1208) were underexpressed (Log 2 diff (FA vs FTC)≤1) by at least 2-fold in FA compared to FTC samples.

Example 16 miRNA Expression Profiling Distinguishes Follicular Adenoma and Papillary Thyroid Carcinoma A total of 76 human miRNAs were significantly differentially expressed between the follicular adenoma samples and the papillary carcinoma specimens (p<0.05) (Table 18). Among these, 34 miRNAs were overexpressed (Log 2 diff (FA vs PTC)≤1), and fifteen miRNAs were underexpressed by at least 2-fold in PTC samples compared to FA samples (Table 18). Among the miRNAs expressed at a higher level in PTC samples, one miRNA (has-miR-146b-5p) was overexpressed by more than 50-fold; five miRNAs (hsa-miR-31, -31*, -375, -200a, -200b) were overexpressed by 20- to 40-fold; three miRNAs (hsa-miR-146b-3p, -429, and -551b)

TABLE 17

MicroRNAs significantly differentially expressed between FA and FTC samples.

| miRNA | FA AVG | FA SD | FTC AVG | FTC SD | FA vs FTC ttest | Log2Diff | Fold change |
|---|---|---|---|---|---|---|---|
| hsa-let-7g* | 0.54 | 1.49 | −1.09 | 0.50 | 4.90E−02 | 1.63 | 3.1 |
| hsa-miR-196a | 3.38 | 1.42 | 1.82 | 0.34 | 4.34E−02 | 1.56 | 3.0 |
| hsa-miR-595 | 1.61 | 1.13 | 0.18 | 0.21 | 2.35E−02 | 1.43 | 2.7 |
| hsa-miR-1227 | 1.77 | 1.08 | 0.48 | 0.52 | 4.21E−02 | 1.30 | 2.5 |
| hsa-miR-556-3p | 1.32 | 0.33 | 0.50 | 0.43 | 9.26E−03 | 0.83 | 1.8 |
| hsa-miR-326 | 2.27 | 0.49 | 1.53 | 0.24 | 1.62E−02 | 0.75 | 1.7 |
| hsa-miR-1321 | 0.48 | 0.58 | 1.25 | 0.46 | 4.85E−02 | −0.77 | 1.7 |
| hsa-miR-15a | 10.87 | 0.60 | 11.65 | 0.39 | 4.05E−02 | −0.78 | 1.7 |
| hsa-miR-29b | 11.43 | 0.44 | 12.31 | 0.59 | 2.81E−02 | −0.88 | 1.8 |
| hsa-miR-17 | 8.55 | 0.59 | 9.48 | 0.41 | 2.00E−02 | −0.93 | 1.9 |
| hsa-miR-20a | 9.91 | 0.59 | 10.88 | 0.43 | 1.76E−02 | −0.98 | 2.0 |
| hsa-miR-19b | 10.20 | 0.69 | 11.18 | 0.50 | 3.20E−02 | −0.98 | 2.0 |
| hsa-miR-1208 | 1.22 | 0.79 | 2.25 | 0.60 | 4.98E−02 | −1.02 | 2.0 |
| hsa-miR-17* | 4.52 | 0.69 | 5.55 | 0.41 | 2.08E−02 | −1.03 | 2.0 |
| hsa-miR-20b | 7.17 | 0.76 | 8.22 | 0.43 | 2.77E−02 | −1.05 | 2.1 |
| hsa-miR-20a* | 3.60 | 0.59 | 4.73 | 0.24 | 4.27E−03 | −1.12 | 2.2 |
| hsa-miR-105* | −0.75 | 0.57 | 0.39 | 0.42 | 7.15E−03 | −1.14 | 2.2 |
| hsa-miR-19a | 7.45 | 0.87 | 8.60 | 0.40 | 2.84E−02 | −1.14 | 2.2 |
| hsa-miR-32 | 3.80 | 1.01 | 5.08 | 0.46 | 3.22E−02 | −1.28 | 2.4 |

AVG, average expression among samples in a group;
SD, standard deviation were overexpressed by 15- to 20-fold, three miRNAs (hsa-miR-200a*, -200b*, and -222) were overexpressed by 5- to 10-fold, and 22 miRNAs were overexpressed by 2- to 5-fold in the PTC specimens compared to the FA samples. Among the miRNAs expressed at a lower level in PTC compared to FA samples, hsa-mir-885-5p was underexpressed by more than 5-fold, and fourteen miRNAs were underexpressed by 2- to 5-fold.

TABLE 18

MicroRNAs significantly differentially expressed between FA and PTC samples.

| miRNA | FA AVG | FA SD | PTC AVG | PTC SD | FA vs PTC ttest | Log2Diff | Fold change |
|---|---|---|---|---|---|---|---|
| hsa-miR-885-5p | 2.75 | 2.48 | −0.10 | 0.21 | 3.39E−02 | 2.85 | 7.2 |
| hsa-miR-631 | 1.22 | 1.73 | −0.92 | 0.83 | 3.67E−02 | 2.14 | 4.4 |
| hsa-miR-873 | 2.78 | 1.55 | 0.81 | 0.78 | 3.47E−02 | 1.97 | 3.9 |
| hsa-miR-1227 | 1.77 | 1.08 | 0.03 | 0.66 | 1.52E−02 | 1.74 | 3.3 |
| hsa-miR-148a* | 1.83 | 1.23 | 0.21 | 0.94 | 4.73E−02 | 1.62 | 3.1 |
| hsa-miR-183* | 1.57 | 1.10 | −0.03 | 1.02 | 4.48E−02 | 1.60 | 3.0 |
| hsa-miR-483-3p | 1.95 | 0.98 | 0.43 | 0.35 | 1.14E−02 | 1.52 | 2.9 |
| hsa-miR-182* | 1.08 | 0.53 | −0.41 | 0.86 | 1.12E−02 | 1.49 | 2.8 |
| hsa-miR-517a | 0.93 | 1.16 | −0.45 | 0.52 | 4.12E−02 | 1.38 | 2.6 |
| hsa-miR-488* | 0.64 | 1.24 | −0.71 | 0.25 | 4.39E−02 | 1.35 | 2.5 |
| hsa-miR-183 | 7.62 | 1.20 | 6.34 | 0.19 | 4.68E−02 | 1.28 | 2.4 |
| hsa-miR-145 | 10.55 | 0.52 | 9.37 | 0.28 | 2.19E−03 | 1.18 | 2.3 |
| hsa-miR-583 | 0.54 | 0.77 | −0.56 | 0.48 | 2.68E−02 | 1.10 | 2.1 |
| hsa-miR-124 | 0.68 | 0.28 | −0.38 | 0.31 | 4.83E−04 | 1.06 | 2.1 |
| hsa-miR-145* | 5.63 | 0.67 | 4.58 | 0.41 | 1.72E−02 | 1.05 | 2.1 |
| hsa-miR-572 | 5.04 | 0.65 | 4.08 | 0.45 | 2.63E−02 | 0.96 | 1.9 |
| hsa-miR-638 | 8.26 | 0.52 | 7.32 | 0.50 | 2.00E−02 | 0.94 | 1.9 |
| hsa-miR-1268 | 7.39 | 0.37 | 6.57 | 0.52 | 2.03E−02 | 0.82 | 1.8 |
| hsa-miR-557 | 4.74 | 0.33 | 3.95 | 0.56 | 2.56E−02 | 0.79 | 1.7 |
| hsa-miR-143* | 4.11 | 0.42 | 3.34 | 0.37 | 1.42E−02 | 0.78 | 1.7 |
| hsa-miR-1323 | 1.99 | 0.30 | 1.22 | 0.35 | 6.17E−03 | 0.76 | 1.7 |
| hsa-miR-143 | 8.07 | 0.61 | 7.32 | 0.28 | 3.91E−02 | 0.74 | 1.7 |
| hsa-miR-584 | 2.76 | 0.44 | 2.03 | 0.45 | 3.08E−02 | 0.74 | 1.7 |
| hsa-miR-129* | 2.66 | 0.32 | 1.95 | 0.21 | 3.11E−03 | 0.71 | 1.6 |
| hsa-miR-556-3p | 1.32 | 0.33 | 0.67 | 0.22 | 5.88E−03 | 0.66 | 1.6 |
| hsa-miR-326 | 2.27 | 0.49 | 1.66 | 0.29 | 4.35E−02 | 0.61 | 1.5 |
| hsa-miR-196b | 2.63 | 0.43 | 2.13 | 0.22 | 4.94E−02 | 0.50 | 1.4 |
| hsa-miR-335* | 2.48 | 0.31 | 1.99 | 0.18 | 1.44E−02 | 0.49 | 1.4 |
| hsa-miR-449b | 0.58 | 0.28 | 1.08 | 0.28 | 2.27E−02 | −0.50 | 1.4 |
| hsa-miR-34a* | 4.48 | 0.35 | 5.07 | 0.21 | 1.18E−02 | −0.59 | 1.5 |
| hsa-miR-26b | 11.30 | 0.54 | 11.96 | 0.28 | 4.45E−02 | −0.65 | 1.6 |
| hsa-miR-34a | 11.88 | 0.50 | 12.59 | 0.24 | 2.06E−02 | −0.71 | 1.6 |
| hsa-let-7e | 11.41 | 0.64 | 12.15 | 0.24 | 3.95E−02 | −0.75 | 1.7 |
| hsa-miR-29b-1* | 4.78 | 0.51 | 5.53 | 0.38 | 2.94E−02 | −0.75 | 1.7 |
| hsa-miR-34b* | 6.83 | 0.48 | 7.62 | 0.54 | 4.04E−02 | −0.79 | 1.7 |
| hsa-miR-374b | 7.56 | 0.69 | 8.38 | 0.22 | 3.56E−02 | −0.82 | 1.8 |
| hsa-miR-151-5p | 10.03 | 0.57 | 10.90 | 0.35 | 1.95E−02 | −0.87 | 1.8 |
| hsa-miR-15b | 11.08 | 0.77 | 11.96 | 0.35 | 4.80E−02 | −0.88 | 1.8 |
| hsa-miR-17* | 4.52 | 0.69 | 5.43 | 0.32 | 2.86E−02 | −0.91 | 1.9 |
| hsa-miR-16 | 12.60 | 0.59 | 13.53 | 0.18 | 1.02E−02 | −0.92 | 1.9 |
| hsa-miR-17 | 8.55 | 0.59 | 9.48 | 0.14 | 8.75E−03 | −0.93 | 1.9 |
| hsa-let-7i | 13.58 | 0.59 | 14.53 | 0.18 | 8.33E−03 | −0.95 | 1.9 |
| hsa-miR-181c | 6.62 | 0.63 | 7.59 | 0.35 | 1.68E−02 | −0.97 | 2.0 |
| hsa-miR-629 | 1.96 | 0.63 | 2.94 | 0.51 | 2.60E−02 | −0.98 | 2.0 |
| hsa-miR-1914* | 7.19 | 0.66 | 8.19 | 0.68 | 4.53E−02 | −1.00 | 2.0 |
| hsa-miR-29a | 13.29 | 0.55 | 14.31 | 0.37 | 9.50E−03 | −1.01 | 2.0 |
| hsa-miR-20a* | 3.60 | 0.59 | 4.63 | 0.57 | 2.37E−02 | −1.03 | 2.0 |
| hsa-miR-208b | −0.31 | 0.90 | 0.73 | 0.41 | 4.82E−02 | −1.03 | 2.0 |
| hsa-miR-181d | 5.70 | 0.62 | 6.74 | 0.28 | 9.24E−03 | −1.04 | 2.1 |
| hsa-miR-892b | 4.73 | 0.51 | 5.77 | 0.82 | 4.34E−02 | −1.04 | 2.1 |
| hsa-miR-19b | 10.20 | 0.69 | 11.28 | 0.31 | 1.27E−02 | −1.08 | 2.1 |
| hsa-miR-449a | 2.32 | 0.64 | 3.40 | 0.45 | 1.43E−02 | −1.09 | 2.1 |
| hsa-miR-1305 | 7.17 | 0.74 | 8.28 | 0.53 | 2.66E−02 | −1.11 | 2.2 |
| hsa-miR-20a | 9.91 | 0.59 | 11.03 | 0.12 | 3.19E−03 | −1.12 | 2.2 |
| hsa-miR-15a | 10.87 | 0.60 | 12.01 | 0.32 | 5.66E−03 | −1.14 | 2.2 |
| hsa-miR-125b | 13.22 | 0.97 | 14.38 | 0.32 | 3.45E−02 | −1.17 | 2.2 |
| hsa-miR-29b | 11.43 | 0.44 | 12.61 | 0.75 | 1.65E−02 | −1.18 | 2.3 |
| hsa-miR-210 | 4.60 | 1.04 | 5.79 | 0.37 | 4.28E−02 | −1.19 | 2.3 |
| hsa-miR-130a | 10.32 | 0.86 | 11.54 | 0.45 | 2.29E−02 | −1.22 | 2.3 |
| hsa-miR-625 | 4.79 | 0.82 | 6.17 | 0.25 | 7.32E−03 | −1.37 | 2.6 |
| hsa-miR-21* | 5.28 | 0.63 | 6.77 | 0.63 | 5.49E−03 | −1.50 | 2.8 |
| hsa-miR-137 | −0.13 | 0.61 | 1.65 | 0.86 | 5.38E−03 | −1.79 | 3.4 |
| hsa-miR-21 | 13.93 | 0.96 | 15.85 | 0.45 | 3.79E−03 | −1.92 | 3.8 |
| hsa-miR-221* | 6.55 | 1.87 | 8.71 | 0.86 | 4.70E−02 | −2.16 | 4.5 |
| hsa-miR-222 | 7.51 | 1.30 | 10.25 | 0.58 | 2.61E−03 | −2.74 | 6.7 |
| hsa-miR-200b* | 2.47 | 2.18 | 5.62 | 0.59 | 1.41E−02 | −3.15 | 8.9 |
| hsa-miR-200a* | 2.10 | 1.76 | 5.30 | 0.62 | 5.05E−03 | −3.19 | 9.1 |

TABLE 18-continued

MicroRNAs significantly differentially expressed between FA and PTC samples.

| miRNA | FA AVG | FA SD | PTC AVG | PTC SD | FA vs PTC ttest | FA vs PTC Log2Diff | Fold change |
|---|---|---|---|---|---|---|---|
| hsa-miR-551b | 6.03 | 2.55 | 9.98 | 0.58 | 9.86E-03 | -3.94 | 15.4 |
| hsa-miR-429 | 4.75 | 3.02 | 8.97 | 0.55 | 1.53E-02 | -4.22 | 18.6 |
| hsa-miR-146b-3p | -0.55 | 1.45 | 3.73 | 1.12 | 7.98E-04 | -4.28 | 19.4 |
| hsa-miR-200b | 7.16 | 3.18 | 11.78 | 0.50 | 1.25E-02 | -4.61 | 24.5 |
| hsa-miR-200a | 5.59 | 3.11 | 10.22 | 0.52 | 1.12E-02 | -4.62 | 24.6 |
| hsa-miR-375 | 2.08 | 2.60 | 6.74 | 1.20 | 6.59E-03 | -4.66 | 25.3 |
| hsa-miR-31* | 3.69 | 3.42 | 8.58 | 0.56 | 1.35E-02 | -4.89 | 29.6 |
| hsa-miR-31 | 4.88 | 3.49 | 10.14 | 0.64 | 1.06E-02 | -5.26 | 38.3 |
| hsa-miR-146b-5p | 8.50 | 2.02 | 14.41 | 0.92 | 3.45E-04 | -5.90 | 59.8 |

AVG, average expression among samples in a group;
SD, standard deviation

Example 17 miRNA Expression Profiling Distinguishes Follicular Adenoma and the Follicular Variant of Papillary Thyroidcarcinoma A total of 32 human miRNAs were significantly differentially expressed between the follicular adenoma samples and the follicular variant of papillary thyroid carcinoma specimens (p<0.05) (Table 19). Among these, 17 miRNAs were expressed at levels at least 2-fold higher in the FVPTC samples compared to FA samples (Log 2 diff (FA vs FVPTC) ≤1). Of these, hsa-miR-31 was overexpressed by 30-fold, five miRNAs (hsa-miR-31*, -146b-5p, -200b, -200a, and -429) were overexpressed by 20- to 30-fold, two miRNAs (hsa-miR-375, and -200b*) were overexpressed by 10- to 20-fold, and nine miRNAs (hsa-miR-200a*, -146b-3p, -222, -923, -449a, -21*, -503, -135a*, and hsa-let-7i) were overexpressed by 2- to 10-fold in the FVPTC specimens compared to the FA samples.

TABLE 19

MicroRNAs significantly differentially expressed between FA and FVPTC samples.

| miRNA | FA AVG | FA SD | FVPTC AVG | FVPTC SD | FA vs FVPTC ttest | FA vs FVPTC Log2Diff | Fold change |
|---|---|---|---|---|---|---|---|
| hsa-miR-124 | 0.68 | 0.28 | -0.10 | 0.41 | 0.01 | 0.78 | 1.7 |
| hsa-miR-143* | 4.11 | 0.42 | 3.34 | 0.45 | 0.03 | 0.78 | 1.7 |
| hsa-miR-26b* | 2.01 | 0.44 | 1.27 | 0.48 | 0.04 | 0.75 | 1.7 |
| hsa-miR-326 | 2.27 | 0.49 | 1.60 | 0.21 | 0.04 | 0.67 | 1.6 |
| hsa-miR-335* | 2.48 | 0.31 | 1.94 | 0.38 | 0.05 | 0.54 | 1.5 |
| hsa-miR-548c-5p | 1.91 | 0.25 | 2.23 | 0.05 | 0.04 | -0.33 | 1.3 |
| hsa-miR-449b | 0.58 | 0.28 | 1.24 | 0.28 | 0.01 | -0.66 | 1.6 |
| hsa-miR-10b* | 2.05 | 0.49 | 2.81 | 0.46 | 0.05 | -0.77 | 1.7 |
| hsa-miR-20a | 9.91 | 0.59 | 10.68 | 0.25 | 0.05 | -0.78 | 1.7 |
| hsa-miR-513c | 2.19 | 0.55 | 2.98 | 0.11 | 0.03 | -0.79 | 1.7 |
| hsa-miR-516a-5p | 2.00 | 0.46 | 2.82 | 0.56 | 0.05 | -0.82 | 1.8 |
| hsa-miR-574-5p | 5.79 | 0.68 | 6.65 | 0.20 | 0.04 | -0.87 | 1.8 |
| hsa-miR-513b | 2.85 | 0.56 | 3.72 | 0.26 | 0.02 | -0.88 | 1.8 |
| hsa-miR7181c | 6.62 | 0.63 | 7.54 | 0.43 | 0.04 | -0.92 | 1.9 |
| hsa-miR-513a-5p | 3.44 | 0.48 | 4.37 | 0.17 | 0.01 | -0.93 | 1.9 |
| hsa-let-7i | 13.58 | 0.59 | 14.62 | 0.43 | 0.02 | -1.04 | 2.1 |
| hsa-miR-135a* | 3.73 | 0.52 | 4.84 | 0.47 | 0.01 | -1.11 | 2.2 |
| hsa-miR-503 | 4.62 | 0.74 | 6.07 | 1.04 | 0.04 | -1.45 | 2.7 |
| hsa-miR-21* | 5.28 | 0.63 | 6.73 | 0.32 | 0.00 | -1.46 | 2.7 |
| hsa-miR-449a | 2.32 | 0.64 | 4.13 | 0.82 | 0.01 | -1.81 | 3.5 |
| hsa-miR-923 | 12.37 | 0.71 | 14.31 | 1.49 | 0.04 | -1.94 | 3.8 |
| hsa-miR-222 | 7.51 | 1.30 | 9.66 | 0.79 | 0.02 | -2.15 | 4.4 |
| hsa-miR-146b-3p | -0.55 | 1.45 | 2.46 | 1.30 | 0.01 | -3.01 | 8.1 |
| hsa-miR-200a* | 2.10 | 1.76 | 5.38 | 0.59 | 0.01 | -3.28 | 9.7 |
| hsa-miR-200b* | 2.47 | 2.18 | 5.82 | 0.47 | 0.02 | -3.36 | 10.2 |
| hsa-miR-375 | 2.08 | 2.60 | 6.25 | 1.32 | 0.02 | -4.18 | 18.1 |
| hsa-miR-429 | 4.75 | 3.02 | 9.17 | 0.77 | 0.03 | -4.42 | 21.5 |
| hsa-miR-200a | 5.59 | 3.11 | 10.20 | 0.62 | 0.02 | -4.60 | 24.3 |
| hsa-miR-200b | 7.16 | 3.18 | 11.82 | 0.67 | 0.02 | -4.66 | 25.2 |
| hsa-miR-146b-5p | 8.50 | 2.02 | 13.20 | 1.09 | 0.00 | -4.70 | 25.9 |
| hsa-miR-31* | 3.69 | 3.42 | 8.47 | 1.06 | 0.03 | -4.77 | 27.4 |
| hsa-miR-31 | 4.88 | 3.49 | 10.06 | 1.12 | 0.03 | -5.18 | 36.2 |

AVG, average expression among samples in a group;
SD, standard deviation

Example 18 miRNA Expression Profiling Distinguishes Follicular Adenoma and Anaplastic Thyroidcarcinoma A total of 43 human miRNAs were significantly differentially expressed between the follicular adenoma samples and the anaplastic thyroid carcinoma specimens ($p<0.05$) (Table 20). Among these, twenty one miRNAs were expressed at levels at least 2-fold higher (Log 2 diff (ATC vs FA≥1) in the ATC sample compared to FA samples. Of these, hsa-miR-9* was overexpressed by 75-fold, three miRNAs (hsa-miR-582-3p, -582-5p, and -9) were overexpressed by 20- to 30-fold, four miRNAs (hsa-miR-34c-5p, -210, -124, and -34c-3p) were overexpressed by 10- to 20-fold, and thirteen miRNAs were overexpressed by 2- to 10-fold in the ATC specimen compared to the FA samples.

Example 19 miRNA Expression Profiling Distinguishes Anaplastic Thyroid Carcinoma and Medullary Thyroid Carcinoma A total of 114 human miRNAs were significantly differentially expressed between the anaplastic thyroid carcinoma sample and the medullary thyroid carcinoma specimens ($p<0.05$) (Table 21). Among these, 4 miRNAs (hsa-miR-582-3p, -582-5p, -155*, and -7b*) were expressed at levels between 2- and 15-fold higher in the ATC sample compared to MTC samples (Log 2 diff (ATC vs MTC≥1). In addition, 99 miRNAs were underexpressed by at least 2-fold in the ATC compared to the MTC samples. Among these, hsa-miR-375 was underexpressed by more than 6,000 fold, five miRNAs (hsa-miR-429, -200a, -200b, -200c, and -141) were underexpressed by 500- to 1,000-fold, four miRNAs (hsa-miR-135b, -135a, -323-3p, and -205) were underexpressed

TABLE 20

MicroRNAs significantly differentially expressed between FA and ATC samples.

| miRNA | ATC | FA AVG | FA SD | ATC vs FA ttest | ATC vs FA Log2Diff | Fold change |
|---|---|---|---|---|---|---|
| hsa-miR-9* | 7.14 | 0.91 | 1.70 | 2.85E−02 | 6.23 | 75.2 |
| hsa-miR-582-3p | 3.97 | −1.04 | 1.10 | 1.40E−02 | 5.00 | 32.1 |
| hsa-miR-582-5p | 8.42 | 3.51 | 0.40 | 3.64E−04 | 4.91 | 30.1 |
| hsa-miR-9 | 5.05 | 0.57 | 1.18 | 2.53E−02 | 4.48 | 22.4 |
| hsa-miR-34c-5p | 7.37 | 3.10 | 0.57 | 2.42E−03 | 4.27 | 19.2 |
| hsa-miR-210 | 8.74 | 4.60 | 1.04 | 2.23E−02 | 4.14 | 17.7 |
| hsa-miR-124 | 4.16 | 0.68 | 0.28 | 3.36E−04 | 3.48 | 11.1 |
| hsa-miR-34c-3p | 1.95 | −1.38 | 0.78 | 1.79E−02 | 3.33 | 10.1 |
| hsa-miR-592 | 4.74 | 1.97 | 0.74 | 2.69E−02 | 2.77 | 6.8 |
| hsa-miR-30a* | 10.32 | 7.99 | 0.47 | 1.05E−02 | 2.33 | 5.0 |
| hsa-miR-449a | 4.52 | 2.32 | 0.64 | 3.44E−02 | 2.20 | 4.6 |
| hsa-miR-30a | 13.36 | 11.17 | 0.45 | 1.16E−02 | 2.19 | 4.6 |
| hsa-miR-409-3p | 4.20 | 2.34 | 0.54 | 3.40E−02 | 1.86 | 3.6 |
| hsa-miR-769-5p | 6.42 | 4.67 | 0.57 | 4.84E−02 | 1.76 | 3.4 |
| hsa-miR-30c-2* | 6.74 | 5.00 | 0.53 | 4.11E−02 | 1.74 | 3.3 |
| hsa-miR-34b* | 8.43 | 6.83 | 0.48 | 3.80E−02 | 1.60 | 3.0 |
| hsa-miR-330-3p | 5.15 | 3.65 | 0.39 | 2.53E−02 | 1.50 | 2.8 |
| hsa-miR-410 | 2.97 | 1.58 | 0.41 | 3.56E−02 | 1.39 | 2.6 |
| hsa-miR-155* | 1.88 | 0.72 | 0.31 | 2.79E−02 | 1.16 | 2.2 |
| hsa-miR-550* | 4.14 | 3.05 | 0.20 | 7.64E−03 | 1.09 | 2.1 |
| hsa-miR-188-5p | 5.69 | 4.71 | 0.32 | 4.88E−02 | 0.97 | 2.0 |
| hsa-miR-656 | 1.64 | 0.82 | 0.23 | 3.12E−02 | 0.82 | 1.8 |
| hsa-miR-1181 | 4.01 | 3.40 | 0.20 | 4.88E−02 | 0.61 | 1.5 |
| hsa-miR-30d* | 1.12 | 2.67 | 0.50 | 4.55E−02 | −1.56 | 2.9 |
| hsa-miR-1301 | −0.92 | 0.78 | 0.44 | 2.40E−02 | −1.70 | 3.3 |
| hsa-miR-93* | −0.59 | 1.23 | 0.54 | 3.74E−02 | −1.82 | 3.5 |
| hsa-miR-508-5p | −2.20 | −0.35 | 0.58 | 4.27E−02 | −1.85 | 3.6 |
| hsa-miR-452 | 1.57 | 4.17 | 0.76 | 3.52E−02 | −2.60 | 6.0 |
| hsa-miR-126 | 10.01 | 12.69 | 0.69 | 2.34E−02 | −2.68 | 6.4 |
| hsa-miR-143* | 1.36 | 4.11 | 0.42 | 3.82E−03 | −2.76 | 6.8 |
| hsa-miR-143 | 5.31 | 8.07 | 0.61 | 1.48E−02 | −2.76 | 6.8 |
| hsa-miR-224 | 2.46 | 5.32 | 0.92 | 4.74E−02 | −2.86 | 7.3 |
| hsa-miR-200c* | −0.83 | 2.41 | 0.94 | 3.45E−02 | −3.25 | 9.5 |
| hsa-miR-145* | 2.37 | 5.63 | 0.67 | 1.16E−02 | −3.26 | 9.6 |
| hsa-miR-99a* | −1.76 | 1.66 | 0.58 | 5.85E−03 | −3.42 | 10.7 |
| hsa-miR-139-5p | 2.79 | 6.34 | 0.73 | 1.13E−02 | −3.54 | 11.6 |
| hsa-miR-145 | 6.78 | 10.55 | 0.52 | 2.77E−03 | −3.77 | 13.6 |
| hsa-miR-141* | −1.68 | 3.42 | 0.92 | 7.06E−03 | −5.10 | 34.3 |
| hsa-miR-138 | 0.09 | 5.41 | 1.34 | 2.25E−02 | −5.32 | 39.9 |
| hsa-miR-135a | 1.19 | 8.04 | 1.20 | 6.42E−03 | −6.84 | 114.8 |
| hsa-miR-135b | 2.20 | 9.59 | 1.18 | 4.66E−03 | −7.40 | 168.7 |
| hsa-miR-200c | 3.00 | 11.45 | 0.68 | 3.45E−04 | −8.44 | 348.0 |
| hsa-miR-141 | 2.51 | 11.09 | 0.84 | 7.22E−04 | −8.58 | 383.5 |

AVG, average expression among samples in a group;
SD, standard deviation by 50- to 200-fold, thirty nine miRNAs were underexpressed by 10- to 50-fold, and fifty miRNAs were underexpressed by 2- to 50-fold in the ATC sample compared to the MTC specimens.

TABLE 21

MicroRNAs significantly differentially expressed between MTC and ATC samples.

| miRNA | ATC | MTC AVG | SD | ATC vs MTC ttest | Log2Diff | Fold change |
|---|---|---|---|---|---|---|
| hsa-miR-582-3p | 3.97 | 0.19 | 0.32 | 9.51E−03 | 3.78 | 13.7 |
| hsa-miR-582-5p | 8.42 | 6.13 | 0.18 | 8.09E−03 | 2.29 | 4.9 |
| hsa-miR-155* | 1.88 | 0.33 | 0.16 | 1.34E−02 | 1.55 | 2.9 |
| hsa-let-7b* | 2.41 | 1.29 | 0.08 | 6.92E−03 | 1.12 | 2.2 |
| hsa-miR-634 | 2.61 | 1.68 | 0.13 | 2.70E−02 | 0.92 | 1.9 |
| hsa-miR-769-3p | 3.15 | 2.27 | 0.15 | 3.61E−02 | 0.88 | 1.8 |
| hsa-miR-944 | 0.74 | −0.02 | 0.10 | 2.05E−02 | 0.76 | 1.7 |
| hsa-miR-27a | 12.98 | 12.27 | 0.07 | 1.16E−02 | 0.71 | 1.6 |
| hsa-let-7a | 14.35 | 14.77 | 0.07 | 3.12E−02 | −0.42 | 1.3 |
| hsa-miR-431* | 2.46 | 2.93 | 0.05 | 1.54E−02 | −0.47 | 1.4 |
| hsa-miR-331-3p | 10.17 | 10.80 | 0.08 | 1.89E−02 | −0.64 | 1.6 |
| hsa-miR-99b | 8.83 | 9.49 | 0.13 | 4.93E−02 | −0.66 | 1.6 |
| hsa-miR-25 | 9.41 | 10.13 | 0.14 | 4.41E−02 | −0.73 | 1.7 |
| hsa-miR-320a | 8.16 | 8.92 | 0.11 | 2.91E−02 | −0.76 | 1.7 |
| hsa-miR-574-3p | 5.72 | 6.59 | 0.05 | 4.14E−03 | −0.87 | 1.8 |
| hsa-miR-24-1* | 5.59 | 6.56 | 0.18 | 4.39E−02 | −0.97 | 2.0 |
| hsa-miR-585 | 0.44 | 1.44 | 0.15 | 2.76E−02 | −1.00 | 2.0 |
| hsa-miR-146b-3p | −2.10 | −1.08 | 0.19 | 4.53E−02 | −1.02 | 2.0 |
| hsa-miR-423-3p | 2.56 | 3.59 | 0.10 | 1.30E−02 | −1.02 | 2.0 |
| hsa-miR-1826 | 4.37 | 5.46 | 0.15 | 2.37E−02 | −1.09 | 2.1 |
| hsa-miR-326 | 2.42 | 3.61 | 0.14 | 1.68E−02 | −1.20 | 2.3 |
| hsa-miR-98 | 7.22 | 8.44 | 0.17 | 2.44E−02 | −1.22 | 2.3 |
| hsa-miR-454 | 5.50 | 6.74 | 0.18 | 2.69E−02 | −1.24 | 2.4 |
| hsa-miR-23b | 12.17 | 13.42 | 0.15 | 1.84E−02 | −1.24 | 2.4 |
| hsa-miR-27b | 11.68 | 12.95 | 0.25 | 4.96E−02 | −1.27 | 2.4 |
| hsa-miR-423-5p | 5.61 | 6.91 | 0.07 | 4.07E−03 | −1.31 | 2.5 |
| hsa-miR-181c* | 3.75 | 5.32 | 0.15 | 1.26E−02 | −1.57 | 3.0 |
| hsa-miR-182* | 0.43 | 2.00 | 0.20 | 2.10E−02 | −1.57 | 3.0 |
| hsa-miR-20a* | 2.51 | 4.10 | 0.23 | 2.67E−02 | −1.59 | 3.0 |
| hsa-miR-181d | 5.25 | 6.86 | 0.09 | 4.48E−03 | −1.61 | 3.0 |
| hsa-miR-654-5p | 2.67 | 4.30 | 0.31 | 4.50E−02 | −1.63 | 3.1 |
| hsa-miR-30d | 8.94 | 10.62 | 0.25 | 2.78E−02 | −1.68 | 3.2 |
| hsa-miR-26b | 10.52 | 12.22 | 0.12 | 6.91E−03 | −1.70 | 3.3 |
| hsa-miR-126 | 10.01 | 11.72 | 0.25 | 2.75E−02 | −1.71 | 3.3 |
| hsa-miR-151-5p | 9.21 | 11.02 | 0.15 | 9.20E−03 | −1.80 | 3.5 |
| hsa-miR-30d* | 1.12 | 3.11 | 0.30 | 2.94E−02 | −2.00 | 4.0 |
| hsa-miR-126* | 3.44 | 5.45 | 0.16 | 8.72E−03 | −2.02 | 4.0 |
| hsa-miR-377* | 0.92 | 2.94 | 0.16 | 8.50E−03 | −2.03 | 4.1 |
| hsa-miR-324-5p | 7.21 | 9.24 | 0.04 | 4.23E−04 | −2.03 | 4.1 |
| hsa-miR-337-5p | 3.29 | 5.33 | 0.33 | 3.26E−02 | −2.04 | 4.1 |
| hsa-let-7c | 10.68 | 12.76 | 0.42 | 4.99E−02 | −2.08 | 4.2 |
| hsa-miR-181c | 6.32 | 8.44 | 0.26 | 1.89E−02 | −2.11 | 4.3 |
| hsa-miR-744* | −1.03 | 1.10 | 0.21 | 1.28E−02 | −2.13 | 4.4 |
| hsa-miR-221* | 4.78 | 6.93 | 0.33 | 3.06E−02 | −2.15 | 4.4 |
| hsa-miR-652 | 5.34 | 7.51 | 0.29 | 2.25E−02 | −2.16 | 4.5 |
| hsa-miR-1250 | −1.24 | 0.92 | 0.27 | 1.96E−02 | −2.17 | 4.5 |
| hsa-miR-493* | 3.16 | 5.39 | 0.45 | 4.99E−02 | −2.23 | 4.7 |
| hsa-miR-30b | 9.75 | 12.03 | 0.20 | 1.00E−02 | −2.29 | 4.9 |
| hsa-miR-744 | 2.84 | 5.17 | 0.35 | 2.89E−02 | −2.33 | 5.0 |
| hsa-miR-642 | −1.95 | 0.65 | 0.41 | 3.11E−02 | −2.60 | 6.1 |
| hsa-miR-654-3p | 3.59 | 6.30 | 0.51 | 4.43E−02 | −2.71 | 6.5 |
| hsa-miR-143 | 5.31 | 8.13 | 0.51 | 4.03E−02 | −2.83 | 7.1 |
| hsa-miR-598 | 5.11 | 7.98 | 0.33 | 1.71E−02 | −2.86 | 7.3 |
| hsa-miR-370 | 1.84 | 4.77 | 0.36 | 1.97E−02 | −2.93 | 7.6 |
| hsa-miR-491-5p | −1.33 | 1.62 | 0.37 | 2.02E−02 | −2.95 | 7.7 |
| hsa-miR-148b | 6.69 | 9.64 | 0.55 | 4.32E−02 | −2.96 | 7.8 |
| hsa-miR-409-3p | 4.20 | 7.21 | 0.31 | 1.42E−02 | −3.02 | 8.1 |
| hsa-miR-7-1* | 3.84 | 6.88 | 0.44 | 2.73E−02 | −3.05 | 8.3 |
| hsa-miR-145* | 2.37 | 5.48 | 0.47 | 2.88E−02 | −3.10 | 8.6 |
| hsa-miR-376a* | 1.52 | 4.63 | 0.44 | 2.55E−02 | −3.11 | 8.6 |
| hsa-miR-125b-2* | 2.65 | 5.76 | 0.59 | 4.50E−02 | −3.11 | 8.6 |
| hsa-miR-485-3p | 1.15 | 4.27 | 0.37 | 1.83E−02 | −3.13 | 8.7 |
| hsa-miR-543 | 2.04 | 5.30 | 0.05 | 3.40E−04 | −3.25 | 9.5 |
| hsa-miR-218 | 5.04 | 8.29 | 0.43 | 2.21E−02 | −3.25 | 9.5 |
| hsa-miR-889 | 0.51 | 3.79 | 0.54 | 3.45E−02 | −3.28 | 9.7 |
| hsa-miR-136 | 3.27 | 6.61 | 0.51 | 2.94E−02 | −3.34 | 10.1 |
| hsa-miR-758 | 1.69 | 5.04 | 0.13 | 1.87E−03 | −3.35 | 10.2 |

TABLE 21-continued

MicroRNAs significantly differentially expressed between MTC and ATC samples.

| miRNA | ATC | MTC AVG | SD | ATC vs MTC ttest | Log2Diff | Fold change |
|---|---|---|---|---|---|---|
| hsa-miR-338-3p | 5.98 | 9.34 | 0.35 | 1.40E−02 | −3.36 | 10.3 |
| hsa-miR-668 | −2.09 | 1.30 | 0.42 | 1.95E−02 | −3.40 | 10.5 |
| hsa-miR-376a | 5.10 | 8.51 | 0.67 | 4.76E−02 | −3.40 | 10.6 |
| hsa-miR-200c* | −0.83 | 2.59 | 0.25 | 7.31E−03 | −3.42 | 10.7 |
| hsa-miR-379 | 2.77 | 6.20 | 0.14 | 2.26E−03 | −3.42 | 10.7 |
| hsa-miR-145 | 6.78 | 10.23 | 0.51 | 2.77E−02 | −3.45 | 10.9 |
| hsa-miR-154 | 3.41 | 6.86 | 0.17 | 3.09E−03 | −3.45 | 10.9 |
| hsa-miR-329 | 0.64 | 4.13 | 0.15 | 2.44E−03 | −3.48 | 11.2 |
| hsa-miR-411 | 1.30 | 4.80 | 0.24 | 6.16E−03 | −3.50 | 11.3 |
| hsa-miR-485-5p | 0.52 | 4.03 | 0.40 | 1.66E−02 | −3.51 | 11.4 |
| hsa-miR-127-3p | 5.36 | 8.88 | 0.37 | 1.42E−02 | −3.52 | 11.5 |
| hsa-miR-377 | 3.95 | 7.51 | 0.55 | 3.03E−02 | −3.56 | 11.8 |
| hsa-miR-125b | 10.44 | 14.04 | 0.66 | 4.22E−02 | −3.60 | 12.1 |
| hsa-miR-99a | 8.00 | 11.61 | 0.62 | 3.65E−02 | −3.62 | 12.3 |
| hsa-miR-96 | 7.36 | 11.01 | 0.48 | 2.26E−02 | −3.65 | 12.5 |
| hsa-miR-381 | 3.69 | 7.34 | 0.33 | 1.10E−02 | −3.65 | 12.5 |
| hsa-miR-487a | 1.13 | 4.79 | 0.32 | 9.89E−03 | −3.66 | 12.6 |
| hsa-miR-409-5p | 1.23 | 4.92 | 0.15 | 2.18E−03 | −3.69 | 12.9 |
| hsa-miR-1251 | −2.26 | 1.48 | 0.36 | 1.20E−02 | −3.74 | 13.3 |
| hsa-miR-495 | 3.07 | 6.93 | 0.28 | 6.80E−03 | −3.86 | 14.5 |
| hsa-miR-369-5p | 1.32 | 5.27 | 0.72 | 4.19E−02 | −3.94 | 15.4 |
| hsa-miR-512-3p | 0.39 | 4.53 | 0.17 | 2.19E−03 | −4.14 | 17.7 |
| hsa-miR-382 | 2.34 | 6.53 | 0.24 | 4.24E−03 | −4.19 | 18.3 |
| hsa-miR-1301 | −0.92 | 3.45 | 0.62 | 2.58E−02 | −4.38 | 20.8 |
| hsa-miR-539 | 2.09 | 6.53 | 0.34 | 7.81E−03 | −4.43 | 21.6 |
| hsa-miR-183 | 6.00 | 10.49 | 0.69 | 3.02E−02 | −4.49 | 22.5 |
| hsa-miR-182 | 1.33 | 5.90 | 0.30 | 5.51E−03 | −4.58 | 23.8 |
| hsa-miR-136* | 1.78 | 6.41 | 0.51 | 1.57E−02 | −4.63 | 24.8 |
| hsa-miR-432 | 2.85 | 7.61 | 0.36 | 7.50E−03 | −4.76 | 27.1 |
| hsa-miR-487b | 4.94 | 9.75 | 0.19 | 2.15E−03 | −4.81 | 28.1 |
| hsa-miR-183* | −0.51 | 4.36 | 0.40 | 9.08E−03 | −4.87 | 29.2 |
| hsa-miR-410 | 2.97 | 8.20 | 0.14 | 9.35E−04 | −5.22 | 37.3 |
| hsa-miR-486-3p | −1.82 | 3.41 | 0.41 | 7.96E−03 | −5.23 | 37.5 |
| hsa-miR-200a* | 0.46 | 5.71 | 0.26 | 3.23E−03 | −5.25 | 38.0 |
| hsa-miR-200b* | 0.48 | 5.99 | 0.11 | 5.45E−04 | −5.51 | 45.5 |
| hsa-miR-141* | −1.68 | 3.92 | 0.38 | 6.01E−03 | −5.60 | 48.6 |
| hsa-miR-433 | −1.51 | 4.13 | 0.61 | 1.54E−02 | −5.63 | 49.6 |
| hsa-miR-205 | −1.95 | 3.92 | 0.71 | 1.88E−02 | −5.87 | 58.4 |
| hsa-miR-323-3p | 0.30 | 6.93 | 0.13 | 4.76E−04 | −6.63 | 98.9 |
| hsa-miR-135a | 1.19 | 7.85 | 0.66 | 1.28E−02 | −6.66 | 100.8 |
| hsa-miR-135b | 2.20 | 9.73 | 0.72 | 1.20E−02 | −7.53 | 184.7 |
| hsa-miR-141 | 2.51 | 11.67 | 0.50 | 3.94E−03 | −9.16 | 570.9 |
| hsa-miR-200c | 3.00 | 12.22 | 0.28 | 1.20E−03 | −9.22 | 596.9 |
| hsa-miR-200b | 2.93 | 12.17 | 0.08 | 1.11E−04 | −9.24 | 605.5 |
| hsa-miR-200a | 1.45 | 11.26 | 0.29 | 1.13E−03 | −9.81 | 898.5 |
| hsa-miR-429 | −0.05 | 10.32 | 0.28 | 9.54E−04 | −10.37 | 1323.6 |
| hsa-miR-375 | 1.27 | 13.86 | 0.40 | 1.35E−03 | −12.60 | 6201.2 |

AVG, average expression among samples in a group;
SD, standard deviation

Example 20 miRNA Expression Profiling Distinguishes Follicular Thyroid Carcinoma and Papillary Thyroid Carcinoma A total of 79 human miRNAs were significantly differentially expressed between the follicular thyroid carcinoma samples and the papillary thyroid carcinoma specimens (p<0.05) (Table 22). Among these, 27 miRNAs were underexpressed by at least 2-fold in FTC samples compared to PTC samples (Log 2 diff (FTC vs PTC)≤1). Of these, hsa-miR-146b-5p was expressed at a level more than 80-fold lower in FTC samples, five miRNAs (hsa-miR-551b, -375, -146b-3p, -200b, and -31) were expressed at levels 10- to 33-fold lower in FTC; seven miRNAs (hsa-miR-31*, -200a, -429, -200a*, -200b*, -222, and -514) were expressed at levels 5- to 10-fold lower in FTC samples, and fourteen miRNAs were underexpressed by 2- to 5-fold in FTC samples compared to PTC specimens. In addition, a total of 33 miRNAs were expressed at levels 2- to 5-fold higher in FTC compared to PTC samples.

TABLE 22

MicroRNAs significantly differentially expressed between FTC and PTC samples.

| miRNA | FTC AVG | FTC SD | PTC AVG | PTC SD | FTC vs PTC ttest | FTC vs PTC Log2Diff | Fold change |
|---|---|---|---|---|---|---|---|
| hsa-miR-183* | 2.14 | 1.17 | −0.03 | 1.02 | 1.41E-02 | 2.16 | 4.5 |
| hsa-miR-148a* | 2.35 | 0.67 | 0.21 | 0.94 | 3.25E-03 | 2.14 | 4.4 |
| hsa-miR-204 | 7.33 | 1.59 | 5.26 | 0.80 | 3.21E-02 | 2.07 | 4.2 |
| hsa-miR-182 | 4.50 | 1.38 | 2.59 | 1.06 | 3.92E-02 | 1.91 | 3.8 |
| hsa-miR-631 | 0.83 | 0.94 | −0.92 | 0.83 | 1.42E-02 | 1.75 | 3.4 |
| hsa-miR-148a | 11.79 | 0.72 | 10.07 | 0.84 | 8.36E-03 | 1.72 | 3.3 |
| hsa-miR-144 | 7.14 | 0.99 | 5.48 | 1.15 | 4.01E-02 | 1.66 | 3.2 |
| hsa-miR-659 | 3.03 | 1.18 | 1.42 | 0.91 | 4.15E-02 | 1.61 | 3.1 |
| hsa-miR-373* | 1.85 | 0.72 | 0.24 | 0.68 | 6.77E-03 | 1.61 | 3.0 |
| hsa-miR-182* | 1.12 | 0.70 | −0.41 | 0.86 | 1.50E-02 | 1.53 | 2.9 |
| hsa-miR-663 | 5.58 | 1.19 | 4.09 | 0.76 | 4.64E-02 | 1.49 | 2.8 |
| hsa-miR-765 | 3.72 | 1.08 | 2.28 | 0.68 | 3.52E-02 | 1.44 | 2.7 |
| hsa-miR-584 | 3.47 | 1.28 | 2.03 | 0.45 | 4.53E-02 | 1.44 | 2.7 |
| hsa-miR-152 | 7.58 | 0.80 | 6.19 | 0.48 | 1.04E-02 | 1.39 | 2.6 |
| hsa-miR-936 | 1.69 | 0.95 | 0.34 | 0.48 | 2.21E-02 | 1.35 | 2.5 |
| hsa-miR-371-5p | 4.16 | 0.71 | 2.81 | 0.43 | 6.54E-03 | 1.35 | 2.5 |
| hsa-miR-183 | 7.67 | 1.17 | 6.34 | 0.19 | 3.55E-02 | 1.33 | 2.5 |
| hsa-miR-602 | 3.17 | 0.70 | 1.86 | 0.42 | 7.13E-03 | 1.31 | 2.5 |
| hsa-miR-1915* | −0.14 | 0.90 | −1.44 | 0.82 | 4.48E-02 | 1.30 | 2.5 |
| hsa-miR-96 | 9.53 | 1.14 | 8.25 | 0.45 | 4.69E-02 | 1.28 | 2.4 |
| hsa-miR-1268 | 7.82 | 0.51 | 6.57 | 0.52 | 4.97E-03 | 1.25 | 2.4 |
| hsa-miR-1207-5p | 9.42 | 0.95 | 8.19 | 0.66 | 4.43E-02 | 1.23 | 2.4 |
| hsa-miR-134 | 5.80 | 0.88 | 4.56 | 0.60 | 3.21E-02 | 1.23 | 2.4 |
| hsa-miR-1224-5p | 5.41 | 0.82 | 4.26 | 0.47 | 2.64E-02 | 1.15 | 2.2 |
| hsa-miR-572 | 5.22 | 0.61 | 4.08 | 0.45 | 9.89E-03 | 1.14 | 2.2 |
| hsa-miR-135a* | 4.75 | 0.88 | 3.61 | 0.32 | 2.63E-02 | 1.14 | 2.2 |
| hsa-miR-363 | 5.78 | 0.59 | 4.69 | 0.85 | 4.68E-02 | 1.09 | 2.1 |
| hsa-miR-1321 | 1.25 | 0.46 | 0.17 | 0.39 | 3.84E-03 | 1.08 | 2.1 |
| hsa-miR-638 | 8.39 | 0.59 | 7.32 | 0.50 | 1.51E-02 | 1.07 | 2.1 |
| hsa-miR-1915 | 8.15 | 0.61 | 7.09 | 0.28 | 8.14E-03 | 1.05 | 2.1 |
| hsa-miR-939 | 6.76 | 0.73 | 5.75 | 0.45 | 2.98E-02 | 1.01 | 2.0 |
| hsa-miR-652 | 6.19 | 0.81 | 5.22 | 0.29 | 3.47E-02 | 0.98 | 2.0 |
| hsa-miR-30c | 11.38 | 0.57 | 10.41 | 0.58 | 2.89E-02 | 0.97 | 2.0 |
| hsa-miR-940 | 6.98 | 0.73 | 6.07 | 0.15 | 2.63E-02 | 0.91 | 1.9 |
| hsa-miR-876-3p | 1.27 | 0.55 | 0.41 | 0.55 | 3.70E-02 | 0.87 | 1.8 |
| hsa-miR-130b | 7.34 | 0.42 | 6.55 | 0.21 | 5.40E-03 | 0.79 | 1.7 |
| hsa-miR-30c* | 8.01 | 0.50 | 7.25 | 0.46 | 3.87E-02 | 0.75 | 1.7 |
| hsa-miR-190 | 2.39 | 0.50 | 1.64 | 0.29 | 2.04E-02 | 0.75 | 1.7 |
| hsa-miR-34c-3p | −0.70 | 0.62 | −1.42 | 0.20 | 3.90E-02 | 0.72 | 1.6 |
| hsa-miR-662 | 1.65 | 0.44 | 0.98 | 0.16 | 1.37E-02 | 0.67 | 1.6 |
| hsa-miR-501-3p | 3.45 | 0.46 | 2.83 | 0.27 | 2.95E-02 | 0.63 | 1.5 |
| hsa-miR-93* | 1.18 | 0.23 | 0.58 | 0.36 | 1.45E-02 | 0.60 | 1.5 |
| hsa-miR-335* | 2.54 | 0.25 | 1.99 | 0.18 | 3.97E-02 | 0.55 | 1.5 |
| hsa-miR-1271 | 3.63 | 0.23 | 3.98 | 0.16 | 2.57E-02 | −0.35 | 1.3 |
| hsa-miR-16 | 13.11 | 0.21 | 13.53 | 0.18 | 1.07E-02 | −0.41 | 1.3 |
| hsa-miR-34a* | 4.59 | 0.38 | 5.07 | 0.21 | 3.87E-02 | −0.48 | 1.4 |
| hsa-miR-374b | 7.79 | 0.45 | 8.38 | 0.22 | 3.08E-02 | −0.59 | 1.5 |
| hsa-miR-24 | 11.99 | 0.37 | 12.58 | 0.31 | 2.64E-02 | −0.59 | 1.5 |
| hsa-miR-29a | 13.71 | 0.18 | 14.31 | 0.37 | 1.27E-02 | −0.60 | 1.5 |
| hsa-let-7i* | 3.09 | 0.42 | 3.76 | 0.40 | 3.21E-02 | −0.67 | 1.6 |
| hsa-miR-361-3p | 6.60 | 0.33 | 7.27 | 0.20 | 4.77E-03 | −0.67 | 1.6 |
| hsa-miR-1305 | 7.48 | 0.33 | 8.28 | 0.53 | 2.12E-02 | −0.80 | 1.7 |
| hsa-miR-10a* | 0.55 | 0.39 | 1.51 | 0.31 | 2.47E-03 | −0.97 | 2.0 |
| hsa-miR-224 | 4.74 | 0.67 | 5.75 | 0.50 | 2.76E-02 | −1.01 | 2.0 |
| hsa-let-7i | 13.46 | 0.42 | 14.53 | 0.18 | 7.61E-04 | −1.07 | 2.1 |
| hsa-miR-23b* | 2.87 | 0.81 | 4.00 | 0.58 | 3.59E-02 | −1.13 | 2.2 |
| hsa-miR-625 | 5.02 | 0.94 | 6.17 | 0.25 | 2.99E-02 | −1.15 | 2.2 |
| hsa-miR-181c | 6.41 | 0.72 | 7.59 | 0.35 | 1.08E-02 | −1.18 | 2.3 |
| hsa-miR-181c* | 3.42 | 0.81 | 4.63 | 0.41 | 1.77E-02 | −1.21 | 2.3 |
| hsa-miR-137 | 0.41 | 0.80 | 1.65 | 0.86 | 4.54E-02 | −1.25 | 2.4 |
| hsa-miR-181b | 8.27 | 0.94 | 9.59 | 0.52 | 2.60E-02 | −1.32 | 2.5 |
| hsa-miR-21 | 14.52 | 0.58 | 15.85 | 0.45 | 3.76E-03 | −1.32 | 2.5 |
| hsa-miR-181d | 5.41 | 0.66 | 6.74 | 0.28 | 3.20E-03 | −1.33 | 2.5 |
| hsa-miR-509-3-5p | −0.83 | 0.51 | 0.73 | 1.31 | 3.84E-02 | −1.56 | 2.9 |
| hsa-miR-509-3p | −0.52 | 0.58 | 1.16 | 1.39 | 3.77E-02 | −1.67 | 3.2 |
| hsa-miR-181a-2* | 4.29 | 0.66 | 6.23 | 0.66 | 1.62E-03 | −1.94 | 3.8 |
| hsa-miR-514 | 0.50 | 0.21 | 2.93 | 0.86 | 2.70E-04 | −2.43 | 5.4 |
| hsa-miR-222 | 7.63 | 1.65 | 10.25 | 0.58 | 1.03E-02 | −2.61 | 6.1 |
| hsa-miR-200b* | 2.61 | 1.38 | 5.62 | 0.59 | 2.07E-03 | −3.01 | 8.1 |
| hsa-miR-200a* | 2.23 | 1.29 | 5.30 | 0.62 | 1.39E-03 | −3.07 | 8.4 |
| hsa-miR-429 | 5.86 | 2.18 | 8.97 | 0.55 | 1.50E-02 | −3.10 | 8.6 |
| hsa-miR-200a | 7.09 | 2.00 | 10.22 | 0.52 | 9.70E-03 | −3.13 | 8.7 |
| hsa-miR-31* | 5.39 | 1.63 | 8.58 | 0.56 | 3.21E-03 | −3.19 | 9.1 |

TABLE 22-continued

MicroRNAs significantly differentially expressed between FTC and PTC samples.

| miRNA | FTC AVG | FTC SD | PTC AVG | PTC SD | FTC vs PTC ttest | FTC vs PTC Log2Diff | Fold change |
|---|---|---|---|---|---|---|---|
| hsa-miR-31 | 6.66 | 1.68 | 10.14 | 0.64 | 2.51E−03 | −3.49 | 11.2 |
| hsa-miR-200b | 8.28 | 1.82 | 11.78 | 0.50 | 3.22E−03 | −3.49 | 11.3 |
| hsa-miR-146b-3p | −1.06 | 0.61 | 3.73 | 1.12 | 3.12E−05 | −4.79 | 27.6 |
| hsa-miR-375 | 1.85 | 2.10 | 6.74 | 1.20 | 1.95E−03 | −4.89 | 29.6 |
| hsa-miR-551b | 4.93 | 0.73 | 9.98 | 0.58 | 2.03E−06 | −5.05 | 33.0 |
| hsa-miR-146b-5p | 7.93 | 1.61 | 14.41 | 0.92 | 5.20E−05 | −6.47 | 88.9 |

AVG, average expression among samples in a group;
SD, standard deviation

Example 21 miRNA Expression Profiling Distinguishes Follicular Thyroid Carcinoma and the Follicular Variant of Papillary Thyroid Carcinoma A total of 47 human miRNAs were significantly differentially expressed between the follicular thyroid carcinoma samples and the follicular variant of papillary thyroid carcinoma specimens (p<0.05) (Table 23). Among these, seven miRNAs (hsa-miR-148a*, -148a, -22*, -1295, -32, -152, and -1260) were expressed at levels at least 2-fold higher in FTC samples compared to FVPTC samples (Log 2 diff (FTC vs FVPTC)≥1). Among the miRNAs expressed at a lower level in FTC compared to FVPTC samples, two miRNAs (hsa-miR-146b-5p and hsa-miR-375) were underexpressed by 20- to 40-fold, four miRNAs (hsa-miR-551b, -200b, -146b-3p, and -31) were underexpressed by 10- to 20-fold, six miRNAs (has-miR-429, -200b*, -200a*, -200a, -31*, and -133b) were underexpressed by 5- to 10-fold, and nine miRNAs were underexpressed by 2- to 5-fold in FTC samples compared to FVPTC specimens.

TABLE 23

MicroRNAs significantly differentially expressed between FTC and FVPTC samples.

| miRNA | FTC AVG | FTC SD | FVPTC AVG | FVPTC SD | FTC vs FVPTC ttest | FTC vs FVPTC Log2Diff | Fold change |
|---|---|---|---|---|---|---|---|
| hsa-miR-148a* | 2.35 | 0.67 | 0.48 | 0.48 | 2.35E−03 | 1.87 | 3.6 |
| hsa-miR-148a | 11.79 | 0.72 | 10.02 | 0.33 | 2.78E−03 | 1.76 | 3.4 |
| hsa-miR-22* | 5.80 | 0.79 | 4.29 | 0.52 | 1.35E−02 | 1.52 | 2.9 |
| hsa-miR-1295 | 3.03 | 0.84 | 1.59 | 0.89 | 4.10E−02 | 1.44 | 2.7 |
| hsa-miR-32 | 5.08 | 0.46 | 3.82 | 0.79 | 1.94E−02 | 1.27 | 2.4 |
| hsa-miR-152 | 7.58 | 0.80 | 6.38 | 0.23 | 2.39E−02 | 1.20 | 2.3 |
| hsa-miR-1260 | 9.49 | 0.60 | 8.51 | 0.59 | 4.33E−02 | 0.98 | 2.0 |
| hsa-miR-30e* | 8.01 | 0.50 | 7.09 | 0.46 | 2.51E−02 | 0.92 | 1.9 |
| hsa-miR-362-3p | 6.13 | 0.39 | 5.23 | 0.41 | 1.17E−02 | 0.90 | 1.9 |
| hsa-miR-30c | 11.38 | 0.57 | 10.51 | 0.51 | 4.79E−02 | 0.88 | 1.8 |
| hsa-miR-365 | 8.76 | 0.49 | 7.90 | 0.40 | 2.47E−02 | 0.86 | 1.8 |
| hsa-miR-660 | 7.68 | 0.68 | 6.82 | 0.24 | 4.90E−02 | 0.86 | 1.8 |
| hsa-miR-532-3p | 5.86 | 0.60 | 5.10 | 0.09 | 4.13E−02 | 0.76 | 1.7 |
| hsa-miR-130b | 7.34 | 0.42 | 6.61 | 0.04 | 1.09E−02 | 0.73 | 1.7 |
| hsa-miR-190 | 2.39 | 0.50 | 1.73 | 0.22 | 4.49E−02 | 0.66 | 1.6 |
| hsa-miR-335* | 2.54 | 0.25 | 1.94 | 0.38 | 2.39E−02 | 0.60 | 1.5 |
| hsa-miR-501-5p | 4.39 | 0.12 | 4.15 | 0.14 | 2.92E−02 | 0.24 | 1.2 |
| hsa-miR-513b | 3.17 | 0.22 | 3.72 | 0.26 | 1.09E−02 | −0.55 | 1.5 |
| hsa-miR-513a-5p | 3.73 | 0.42 | 4.37 | 0.17 | 2.39E−02 | −0.64 | 1.6 |
| hsa-miR-513c | 2.27 | 0.12 | 2.98 | 0.11 | 3.48E−05 | −0.71 | 1.6 |
| hsa-miR-378* | 2.49 | 0.25 | 3.32 | 0.25 | 1.78E−03 | −0.82 | 1.8 |
| hsa-let-7g* | −1.09 | 0.50 | −0.24 | 0.12 | 1.39E−02 | −0.84 | 1.8 |
| hsa-miR-211 | 0.50 | 0.36 | 1.36 | 0.41 | 1.30E−02 | −0.85 | 1.8 |
| hsa-miR-574-5p | 5.80 | 0.57 | 6.65 | 0.20 | 2.56E−02 | −0.85 | 1.8 |
| hsa-miR-483-3p | 0.84 | 0.56 | 1.71 | 0.42 | 3.86E−02 | −0.86 | 1.8 |
| hsa-miR-346 | 0.27 | 0.31 | 1.18 | 0.24 | 1.75E−03 | −0.91 | 1.9 |
| hsa-miR-181c* | 3.42 | 0.81 | 4.55 | 0.48 | 4.51E−02 | −1.13 | 2.2 |
| hsa-miR-181c | 6.41 | 0.72 | 7.54 | 0.43 | 2.87E−02 | −1.13 | 2.2 |
| hsa-let-7i | 13.46 | 0.42 | 14.62 | 0.43 | 4.79E−03 | −1.16 | 2.2 |
| hsa-miR-595 | 0.18 | 0.21 | 1.35 | 0.71 | 9.19E−03 | −1.17 | 2.2 |
| hsa-miR-181d | 5.41 | 0.66 | 6.61 | 0.55 | 2.32E−02 | −1.20 | 2.3 |
| hsa-miR-509-3-5p | −0.83 | 0.51 | 0.49 | 0.65 | 1.07E−02 | −1.32 | 2.5 |
| hsa-miR-514 | 0.50 | 0.21 | 1.87 | 1.16 | 3.47E−02 | −1.36 | 2.6 |
| hsa-miR-23b* | 2.87 | 0.81 | 4.28 | 0.15 | 1.17E−02 | −1.41 | 2.7 |
| hsa-miR-181a-2* | 4.29 | 0.66 | 5.91 | 1.15 | 3.16E−02 | −1.62 | 3.1 |
| bsa-miR-133b | 5.78 | 1.31 | 8.20 | 1.72 | 4.66E−02 | −2.42 | 5.4 |
| hsa-miR-31* | 5.39 | 1.63 | 8.47 | 1.06 | 1.39E−02 | −3.08 | 8.5 |
| hsa-miR-200a | 7.09 | 2.00 | 10.20 | 0.62 | 2.13E−02 | −3.11 | 8.6 |

TABLE 23-continued

MicroRNAs significantly differentially expressed between FTC and FVPTC samples.

| miRNA | FTC AVG | FTC SD | FVPTC AVG | FVPTC SD | FTC vs FVPTC ttest | FTC vs FVPTC Log2Diff | Fold change |
|---|---|---|---|---|---|---|---|
| hsa-miR-200a* | 2.23 | 1.29 | 5.38 | 0.59 | 2.88E−03 | −3.16 | 8.9 |
| hsa-miR-200b* | 2.61 | 1.38 | 5.82 | 0.47 | 3.17E−03 | −3.22 | 9.3 |
| hsa-miR-429 | 5.86 | 2.18 | 9.17 | 0.77 | 2.44E−02 | −3.31 | 9.9 |
| hsa-miR-31 | 6.66 | 1.68 | 10.06 | 1.12 | 1.06E−02 | −3.41 | 10.6 |
| hsa-miR-146b-3p | −1.06 | 0.61 | 2.46 | 1.30 | 9.87E−04 | −3.52 | 11.5 |
| hsa-miR-200b | 8.28 | 1.82 | 11.82 | 0.67 | 8.09E−03 | −3.54 | 11.6 |
| hsa-miR-551b | 4.93 | 0.73 | 8.99 | 0.76 | 8.21E−05 | −4.06 | 16.6 |
| hsa-miR-375 | 1.85 | 2.10 | 6.25 | 1.32 | 8.35E−03 | −4.40 | 21.2 |
| hsa-miR-146b-5p | 7.93 | 1.61 | 13.20 | 1.09 | 8.37E−04 | −5.27 | 38.5 |

AVG, average expression among samples in a group;
SD, standard deviation

Example 22 miRNA Expression Profiling Distinguishes Follicular Thyroid Carcinoma and Anaplastic Thyroid Carcinoma A total of 73 human miRNAs were significantly differentially expressed between the follicular thyroid carcinoma samples and the anaplastic thyroid carcinoma sample (p<0.05) (Table 24). Among these, 45 miRNAs were expressed by at least 2-fold higher in FTC samples compared to the ATC sample (Log 2 diff (FTC vs ATC)≥1). Among these, four miRNAs (hsa-miR-141, -200c, -135b, and 135a) were upregulated by 200- to 600-fold in FTC, three miRNAs (hsa-miR-141*, -138, -and 200c*) were upregulated by 10- to 60-fold in FTC, twelve miRNAs (hsa-miR-125b, -7i*, -99a, -145, -148*, -126*, -218, -145*, -143, -32, -452, and 551b) were upregulated by 5- to 10-fold in FTC and twenty six miRNAs were upregulated by 2- to 5-fold in FTC specimens compared to the ATC sample. In addition, fifteen miRNAs were expressed at a lower level in FTC compared to the ATC sample. Among these, six miRNAs (hsa-miR-9*, -582-3p, -124, -9, -10a, and 34c-5p) were underexpressed by 10- to 40-fold in FTC samples, and nine miRNAs were underexpressed by 2- to 10-fold in FTC samples compared to the ATC specimen.

TABLE 24

MicroRNAs significantly differentially expressed between FTC and ATC samples.

| miRNA | ATC | FTC AVG | FTC SD | ATC vs FTC ttest | ATC vs FTC Log2Diff | Fold change |
|---|---|---|---|---|---|---|
| hsa-miR-9* | 7.14 | 1.84 | 1.04 | 9.49E−03 | 5.30 | 39.4 |
| hsa-miR-582-3p | 3.97 | −0.87 | 0.67 | 2.70E−03 | 4.84 | 28.6 |
| hsa-miR-124 | 4.16 | −0.40 | 1.08 | 1.83E−02 | 4.55 | 23.4 |
| hsa-miR-9 | 5.05 | 1.18 | 0.28 | 2.13E−04 | 3.87 | 14.7 |
| hsa-miR-10a | 10.38 | 6.67 | 1.02 | 2.93E−02 | 3.71 | 13.1 |
| hsa-miR-34c-5p | 7.37 | 3.90 | 0.69 | 1.04E−02 | 3.47 | 11.1 |
| hsa-miR-34b | 4.65 | 1.45 | 0.70 | 1.41E−02 | 3.20 | 9.2 |
| hsa-miR-34c-3p | 1.95 | −0.70 | 0.62 | 1.71E−02 | 2.66 | 6.3 |
| hsa-miR-10a* | 2.44 | 0.55 | 0.39 | 1.16E−02 | 1.90 | 3.7 |
| hsa-miR-483-3p | 2.61 | 0.84 | 0.56 | 4.53E−02 | 1.77 | 3.4 |
| hsa-miR-196a | 3.56 | 1.82 | 0.34 | 9.34E−03 | 1.74 | 3.3 |
| hsa-miR-769-5p | 6.42 | 4.87 | 0.33 | 1.25E−02 | 1.55 | 2.9 |
| hsa-miR-330-3p | 5.15 | 3.76 | 0.43 | 4.04E−02 | 1.39 | 2.6 |
| hsa-miR-378* | 3.68 | 2.49 | 0.25 | 1.22E−02 | 1.18 | 2.3 |
| hsa-miR-431 | 2.26 | 1.24 | 0.24 | 1.78E−02 | 1.02 | 2.0 |
| hsa-miR-505* | 4.69 | 3.79 | 0.17 | 8.14E−03 | 0.90 | 1.9 |
| hsa-miR-326 | 2.42 | 1.53 | 0.24 | 2.90E−02 | 0.89 | 1.9 |
| hsa-miR-1237 | 3.83 | 3.00 | 0.26 | 4.43E−02 | 0.83 | 1.8 |
| hsa-miR-1238 | 4.72 | 4.11 | 0.20 | 4.79E−02 | 0.61 | 1.5 |
| hsa-miR-1825 | 4.20 | 3.62 | 0.15 | 2.16E−02 | 0.59 | 1.5 |
| hsa-miR-425* | 4.08 | 3.49 | 0.17 | 3.16E−02 | 0.59 | 1.5 |
| hsa-miR-191* | 4.58 | 4.01 | 0.16 | 2.86E−02 | 0.57 | 1.5 |
| hsa-miR-10b* | 1.78 | 2.42 | 0.15 | 1.94E−02 | −0.64 | 1.6 |
| hsa-miR-101* | 1.44 | 2.16 | 0.23 | 4.81E−02 | −0.72 | 1.6 |
| hsa-miR-26a-1* | 0.60 | 1.33 | 0.18 | 1.93E−02 | −0.73 | 1.7 |
| hsa-miR-454 | 5.50 | 6.31 | 0.22 | 3.07E−02 | −0.81 | 1.7 |
| hsa-miR-93 | 7.61 | 8.50 | 0.27 | 3.78E−02 | −0.90 | 1.9 |
| hsa-miR-615-3p | −1.03 | −0.12 | 0.29 | 4.42E−02 | −0.91 | 1.9 |
| hsa-miR-7-1* | 3.84 | 4.81 | 0.22 | 1.62E−02 | −0.98 | 2.0 |
| hsa-miR-423-3p | 2.56 | 3.62 | 0.17 | 5.27E−03 | −1.06 | 2.1 |
| hsa-miR-642 | −1.95 | −0.85 | 0.35 | 4.75E−02 | −1.10 | 2.1 |
| hsa-miR-338-5p | 1.05 | 2.26 | 0.28 | 1.64E−02 | −1.21 | 2.3 |
| hsa-miR-423-5p | 5.61 | 6.84 | 0.17 | 2.93E−03 | −1.23 | 2.3 |

TABLE 24-continued

MicroRNAs significantly differentially expressed between FTC and ATC samples.

| miRNA | ATC | FTC AVG | SD | ATC vs FTC ttest | Log2Diff | Fold change |
|---|---|---|---|---|---|---|
| hsa-miR-101 | 7.49 | 8.83 | 0.34 | 2.38E−02 | −1.33 | 2.5 |
| hsa-miR-1826 | 4.37 | 5.72 | 0.40 | 3.53E−02 | −1.36 | 2.6 |
| hsa-miR-95 | 6.41 | 7.84 | 0.35 | 2.06E−02 | −1.42 | 2.7 |
| hsa-miR-892a | −0.72 | 0.73 | 0.47 | 4.71E−02 | −1.45 | 2.7 |
| hsa-let-7i | 11.99 | 13.46 | 0.42 | 3.34E−02 | −1.47 | 2.8 |
| hsa-miR-19a | 7.12 | 8.60 | 0.40 | 2.88E−02 | −1.48 | 2.8 |
| hsa-miR-92a | 7.77 | 9.25 | 0.33 | 1.51E−02 | −1.48 | 2.8 |
| hsa-miR-26a | 10.36 | 11.85 | 0.41 | 2.99E−02 | −1.48 | 2.8 |
| hsa-miR-30e | 8.44 | 9.98 | 0.49 | 4.45E−02 | −1.54 | 2.9 |
| hsa-miR-346 | −1.38 | 0.27 | 0.31 | 7.94E−03 | −1.65 | 3.1 |
| hsa-miR-19b-1* | 1.32 | 2.96 | 0.45 | 2.83E−02 | −1.65 | 3.1 |
| hsa-miR-767-5p | −1.10 | 0.56 | 0.26 | 4.42E−03 | −1.65 | 3.1 |
| hsa-miR-93* | −0.59 | 1.18 | 0.23 | 2.21E−03 | −1.76 | 3.4 |
| hsa-miR-30b | 9.75 | 11.54 | 0.57 | 4.45E−02 | −1.80 | 3.5 |
| hsa-miR-30d* | 1.12 | 3.02 | 0.36 | 8.57E−03 | −1.91 | 3.8 |
| hsa-miR-17* | 3.60 | 5.55 | 0.41 | 1.18E−02 | −1.95 | 3.9 |
| hsa-miR-126 | 10.01 | 12.06 | 0.55 | 2.72E−02 | −2.05 | 4.1 |
| hsa-miR-143* | 1.36 | 3.56 | 0.60 | 2.91E−02 | −2.20 | 4.6 |
| hsa-miR-20a* | 2.51 | 4.73 | 0.24 | 1.07E−03 | −2.22 | 4.6 |
| hsa-miR-491-5p | −1.33 | 0.93 | 0.67 | 3.76E−02 | −2.26 | 4.8 |
| hsa-miR-224 | 2.46 | 4.74 | 0.67 | 3.62E−02 | −2.28 | 4.9 |
| hsa-miR-551b | 2.61 | 4.93 | 0.73 | 4.41E−02 | −2.32 | 5.0 |
| hsa-miR-452 | 1.57 | 3.94 | 0.77 | 4.84E−02 | −2.37 | 5.2 |
| hsa-miR-32 | 2.63 | 5.08 | 0.46 | 8.20E−03 | −2.46 | 5.5 |
| hsa-miR-143 | 5.31 | 7.81 | 0.76 | 3.93E−02 | −2.51 | 5.7 |
| hsa-miR-145* | 2.37 | 5.06 | 0.76 | 3.14E−02 | −2.69 | 6.5 |
| hsa-miR-218 | 5.04 | 7.78 | 0.57 | 1.17E−02 | −2.74 | 6.7 |
| hsa-miR-126* | 3.44 | 6.22 | 0.37 | 2.45E−03 | −2.78 | 6.9 |
| hsa-miR-148a* | −0.55 | 2.35 | 0.67 | 1.71E−02 | −2.90 | 7.5 |
| hsa-miR-145 | 6.78 | 9.75 | 0.89 | 3.79E−02 | −2.97 | 7.8 |
| hsa-miR-99a | 8.00 | 10.99 | 0.82 | 2.96E−02 | −2.99 | 8.0 |
| hsa-let-7i* | 0.07 | 3.09 | 0.42 | 2.69E−03 | −3.02 | 8.1 |
| hsa-miR-125b | 10.44 | 13.75 | 0.57 | 6.10E−03 | −3.31 | 9.9 |
| hsa-miR-200e* | −0.83 | 2.57 | 0.40 | 1.51E−03 | −3.40 | 10.6 |
| hsa-miR-138 | 0.09 | 4.85 | 1.20 | 2.26E−02 | −4.76 | 27.0 |
| hsa-miR-141* | −1.68 | 4.23 | 0.52 | 4.74E−04 | −5.91 | 60.1 |
| hsa-miR-135a | 1.19 | 8.96 | 0.34 | 2.99E−05 | −7.76 | 217.4 |
| hsa-miR-135b | 2.20 | 10.03 | 1.65 | 1.24E−02 | −7.83 | 228.3 |
| hsa-miR-200c | 3.00 | 12.10 | 0.69 | 2.66E−04 | −9.09 | 546.5 |
| hsa-miR-141 | 2.51 | 11.85 | 0.96 | 8.85E−04 | −9.34 | 649.3 |

AVG, average expression among samples in a group;
SD, standard deviation

Example 23 miRNA Expression Profiling Distinguishes Follicular Thyroid Carcinoma and Medullary Thyroid Carcinoma A total of 136 human miRNAs were significantly differentially expressed between the follicular thyroid carcinoma samples and the medullary thyroid carcinoma (MTC) specimens (p<0.05) (Table 25). Among these, 17 miRNAs were expressed (Log 2 diff (FTC vs MTC)≥1) by 2- to 10-fold higher in FTC samples compared to the MTC samples. In addition, one hundred miRNAs were expressed at a lower level in FTC compared to the MTC samples. Among these hsa-miR-375 was underexpressed by more than 1000-fold in FTC samples, three miRNAs were underexpressed by 100- to 300-fold in FTC samples, forty four miRNAs were underexpressed by 10- to 100-fold, and fifty two miRNAs were underexpressed between 2- and 10-fold in the FTC samples compared to the MTC specimens.

TABLE 25

MicroRNAs significantly differentially expressed between FTC and MTC samples.

| miRNA | FTC AVG | SD | MTC AVG | SD | FTC vs MTC ttest | Log2Diff | Fold change |
|---|---|---|---|---|---|---|---|
| hsa-miR-203 | 6.93 | 1.47 | 3.46 | 2.00 | 2.95E−02 | 3.46 | 11.0 |
| hsa-miR-30a | 12.28 | 1.12 | 9.76 | 1.51 | 3.42E−02 | 2.52 | 5.7 |
| hsa-miR-30a* | 9.03 | 1.12 | 6.59 | 1.57 | 4.10E−02 | 2.44 | 5.4 |
| hsa-miR-34a* | 4.59 | 0.38 | 3.09 | 0.61 | 4.80E−03 | 1.50 | 2.8 |
| hsa-miR-148a* | 2.35 | 0.67 | 0.88 | 0.82 | 3.23E−02 | 1.47 | 2.8 |

TABLE 25-continued

MicroRNAs significantly differentially expressed between FTC and MTC samples.

| miRNA | FTC AVG | FTC SD | MTC AVG | MTC SD | FTC vs MTC ttest | FTC vs MTC Log2Diff | Fold change |
|---|---|---|---|---|---|---|---|
| hsa-miR-34a | 12.03 | 0.62 | 10.62 | 0.71 | 2.60E−02 | 1.40 | 2.6 |
| hsa-miR-32 | 5.08 | 0.46 | 3.71 | 0.68 | 1.33E−02 | 1.38 | 2.6 |
| hsa-miR-30e* | 8.01 | 0.50 | 6.67 | 0.55 | 1.22E−02 | 1.34 | 2.5 |
| hsa-miR-22* | 5.80 | 0.79 | 4.54 | 0.31 | 4.25E−02 | 1.26 | 2.4 |
| hsa-let-7i* | 3.09 | 0.42 | 1.85 | 0.98 | 4.20E−02 | 1.24 | 2.4 |
| hsa-miR-30c | 11.38 | 0.57 | 10.16 | 0.57 | 2.62E−02 | 1.22 | 2.3 |
| hsa-miR-34b* | 7.22 | 0.41 | 6.00 | 0.79 | 2.56E−02 | 1.22 | 2.3 |
| hsa-miR-20b | 8.22 | 0.43 | 7.02 | 0.70 | 2.20E−02 | 1.20 | 2.3 |
| hsa-miR-20a | 10.88 | 0.43 | 9.76 | 0.82 | 4.07E−02 | 1.12 | 2.2 |
| hsa-miR-30e | 9.98 | 0.49 | 8.87 | 0.25 | 1.15E−02 | 1.11 | 2.2 |
| hsa-miR-135a | 8.96 | 0.34 | 7.85 | 0.66 | 1.78E−02 | 1.11 | 2.2 |
| hsa-miR-19a | 8.60 | 0.40 | 7.51 | 0.18 | 5.06E−03 | 1.09 | 2.1 |
| hsa-miR-19b | 11.18 | 0.50 | 10.25 | 0.32 | 2.92E−02 | 0.93 | 1.9 |
| hsa-miR-19b-1* | 2.96 | 0.45 | 2.09 | 0.30 | 2.52E−02 | 0.88 | 1.8 |
| hsa-miR-190 | 2.39 | 0.50 | 1.53 | 0.26 | 3.51E−02 | 0.86 | 1.8 |
| hsa-miR-634 | 2.53 | 0.36 | 1.68 | 0.13 | 8.89E−03 | 0.84 | 1.8 |
| hsa-miR-126* | 6.22 | 0.37 | 5.45 | 0.16 | 1.68E−02 | 0.77 | 1.7 |
| hsa-miR-1234 | 4.56 | 0.24 | 3.90 | 0.47 | 3.76E−02 | 0.65 | 1.6 |
| hsa-miR-20a* | 4.73 | 0.24 | 4.10 | 0.23 | 1.06E−02 | 0.63 | 1.5 |
| hsa-miR-191* | 4.01 | 0.16 | 3.52 | 0.30 | 2.13E−02 | 0.49 | 1.4 |
| hsa-miR-425* | 3.49 | 0.17 | 3.11 | 0.24 | 3.66E−02 | 0.38 | 1.3 |
| hsa-miR-29a | 13.71 | 0.18 | 14.04 | 0.15 | 3.97E−02 | −0.33 | 1.3 |
| hsa-miR-25 | 9.72 | 0.22 | 10.13 | 0.14 | 2.84E−02 | −0.41 | 1.3 |
| hsa-miR-454 | 6.31 | 0.22 | 6.74 | 0.18 | 3.02E−02 | −0.44 | 1.4 |
| hsa-miR-320c | 9.49 | 0.11 | 10.00 | 0.42 | 3.65E−02 | −0.51 | 1.4 |
| hsa-miR-320d | 10.00 | 0.17 | 10.53 | 0.43 | 4.41E−02 | −0.53 | 1.4 |
| hsa-miR-320a | 8.36 | 0.16 | 8.92 | 0.11 | 1.99E−03 | −0.56 | 1.5 |
| hsa-miR-320b | 9.46 | 0.18 | 10.06 | 0.28 | 9.54E−03 | −0.60 | 1.5 |
| hsa-miR-769-5p | 4.87 | 0.33 | 5.73 | 0.25 | 8.46E−03 | −0.86 | 1.8 |
| hsa-miR-595 | 0.18 | 0.21 | 1.11 | 0.62 | 1.78E−02 | −0.93 | 1.9 |
| hsa-miR-557 | 4.66 | 0.55 | 5.61 | 0.40 | 4.13E−02 | −0.95 | 1.9 |
| hsa-miR-628-5p | 3.69 | 0.52 | 4.66 | 0.34 | 2.93E−02 | −0.96 | 2.0 |
| hsa-miR-24 | 11.99 | 0.37 | 13.02 | 0.16 | 4.47E−03 | −1.03 | 2.0 |
| hsa-miR-582-3p | −0.87 | 0.67 | 0.19 | 0.32 | 4.49E−02 | −1.06 | 2.1 |
| hsa-miR-505 | 4.94 | 0.33 | 6.04 | 0.67 | 1.95E−02 | −1.10 | 2.1 |
| hsa-miR-212 | 4.82 | 0.49 | 5.93 | 0.76 | 4.29E−02 | −1.11 | 2.2 |
| hsa-miR-1250 | −0.21 | 0.49 | 0.92 | 0.27 | 1.07E−02 | −1.14 | 2.2 |
| hsa-miR-99b | 8.31 | 0.61 | 9.49 | 0.13 | 1.89E−02 | −1.18 | 2.3 |
| hsa-let-7e | 11.56 | 0.69 | 12.78 | 0.21 | 2.70E−02 | −1.22 | 2.3 |
| hsa-miR-335* | 2.54 | 0.25 | 3.78 | 0.88 | 2.12E−02 | −1.24 | 2.4 |
| hsa-miR-301a | 6.31 | 0.64 | 7.56 | 0.34 | 2.21E−02 | −1.25 | 2.4 |
| hsa-miR-505* | 3.79 | 0.17 | 5.07 | 0.90 | 1.72E−02 | −1.28 | 2.4 |
| hsa-miR-652 | 6.19 | 0.81 | 7.51 | 0.29 | 3.87E−02 | −1.31 | 2.5 |
| hsa-miR-656 | 0.78 | 0.40 | 2.09 | 0.62 | 1.02E−02 | −1.31 | 2.5 |
| hsa-miR-181d | 5.41 | 0.66 | 6.86 | 0.09 | 1.06E−02 | −1.46 | 2.7 |
| hsa-miR-642 | −0.85 | 0.35 | 0.65 | 0.41 | 1.49E−03 | −1.50 | 2.8 |
| hsa-miR-128 | 6.78 | 0.22 | 8.29 | 0.89 | 8.83E−03 | −1.51 | 2.9 |
| hsa-miR-95 | 7.84 | 0.35 | 9.43 | 0.66 | 3.65E−03 | −1.60 | 3.0 |
| hsa-miR-337-3p | 1.54 | 0.34 | 3.15 | 0.43 | 9.77E−04 | −1.62 | 3.1 |
| hsa-miR-27b | 11.31 | 0.86 | 12.95 | 0.25 | 2.08E−02 | −1.64 | 3.1 |
| hsa-miR-23b* | 2.87 | 0.81 | 4.61 | 0.28 | 1.31E−02 | −1.74 | 3.3 |
| hsa-miR-24-1* | 4.76 | 0.85 | 6.56 | 0.18 | 1.23E−02 | −1.81 | 3.5 |
| hsa-miR-216b | −1.86 | 0.39 | 0.04 | 1.44 | 2.70E−02 | −1.90 | 3.7 |
| hsa-miR-181c* | 3.42 | 0.81 | 5.32 | 0.15 | 8.10E−03 | −1.90 | 3.7 |
| hsa-miR-23b | 11.51 | 0.97 | 13.42 | 0.15 | 1.68E−02 | −1.91 | 3.7 |
| hsa-miR-654-5p | 2.39 | 0.76 | 4.30 | 0.31 | 6.80E−03 | −1.91 | 3.8 |
| hsa-miR-299-3p | 1.16 | 0.86 | 3.11 | 0.45 | 1.18E−02 | −1.94 | 3.8 |
| hsa-miR-1185 | 1.08 | 0.45 | 3.03 | 0.54 | 1.43E−03 | −1.95 | 3.9 |
| hsa-miR-369-3p | 0.89 | 0.48 | 2.85 | 0.71 | 3.23E−03 | −1.96 | 3.9 |
| hsa-miR-181c | 6.41 | 0.72 | 8.44 | 0.26 | 3.80E−03 | −2.03 | 4.1 |
| hsa-miR-7-1* | 4.81 | 0.22 | 6.88 | 0.44 | 1.06E−04 | −2.07 | 4.2 |
| hsa-miR-326 | 1.53 | 0.24 | 3.61 | 0.14 | 1.09E−05 | −2.08 | 4.2 |
| hsa-miR-132* | 3.47 | 0.44 | 5.58 | 1.13 | 8.30E−03 | −2.11 | 4.3 |
| hsa-miR-183* | 2.14 | 1.17 | 4.36 | 0.40 | 2.12E−02 | −2.22 | 4.7 |
| hsa-miR-668 | −0.97 | 0.46 | 1.30 | 0.42 | 4.31E−04 | −2.27 | 4.8 |
| hsa-miR-598 | 5.66 | 0.84 | 7.98 | 0.33 | 4.34E−03 | −2.32 | 5.0 |
| hsa-miR-552 | −0.34 | 0.81 | 2.05 | 1.77 | 3.60E−02 | −2.40 | 5.3 |
| hsa-miR-335 | 6.55 | 0.74 | 9.06 | 1.56 | 1.92E−02 | −2.51 | 5.7 |
| hsa-miR-376b | 0.88 | 1.24 | 3.45 | 1.39 | 3.45E−02 | −2.57 | 5.9 |
| hsa-miR-330-3p | 3.76 | 0.43 | 6.34 | 0.46 | 1.90E−04 | −2.58 | 6.0 |
| hsa-miR-338-3p | 6.72 | 0.87 | 9.34 | 0.35 | 2.80E−03 | −2.62 | 6.1 |
| hsa-miR-377* | 0.32 | 0.43 | 2.94 | 0.16 | 5.92E−05 | −2.62 | 6.1 |
| hsa-miR-1301 | 0.82 | 0.78 | 3.45 | 0.62 | 2.63E−03 | −2.63 | 6.2 |

TABLE 25-continued

MicroRNAs significantly differentially expressed between FTC and MTC samples.

| miRNA | FTC AVG | FTC SD | MTC AVG | MTC SD | FTC vs MTC ttest | FTC vs MTC Log2Diff | Fold change |
|---|---|---|---|---|---|---|---|
| hsa-miR-663b | 1.24 | 0.71 | 3.88 | 1.00 | 4.56E−03 | −2.64 | 6.2 |
| hsa-miR-486-3p | 0.61 | 0.84 | 3.41 | 0.41 | 1.81E−03 | −2.80 | 7.0 |
| hsa-miR-183 | 7.67 | 1.17 | 10.49 | 0.69 | 9.61E−03 | −2.82 | 7.1 |
| hsa-miR-299-5p | 2.33 | 1.25 | 5.22 | 0.48 | 9.71E−03 | −2.89 | 7.4 |
| hsa-miR-132 | 6.06 | 0.44 | 8.97 | 1.15 | 1.89E−03 | −2.90 | 7.5 |
| hsa-miR-370 | 1.75 | 0.74 | 4.77 | 0.36 | 6.54E−04 | −3.01 | 8.1 |
| hsa-miR-890 | −0.43 | 1.06 | 2.63 | 1.99 | 2.73E−02 | −3.06 | 8.3 |
| hsa-miR-493* | 2.22 | 1.19 | 5.39 | 0.45 | 4.96E−03 | −3.17 | 9.0 |
| hsa-miR-376a* | 1.45 | 0.46 | 4.63 | 0.44 | 7.49E−05 | −3.18 | 9.1 |
| hsa-miR-10a* | 0.55 | 0.39 | 3.82 | 0.57 | 6.68E−05 | −3.28 | 9.7 |
| hsa-miR-337-5p | 2.00 | 1.50 | 5.33 | 0.33 | 1.03E−02 | −3.33 | 10.1 |
| hsa-miR-200b* | 2.61 | 1.38 | 5.99 | 0.11 | 6.39E−03 | −3.39 | 10.4 |
| hsa-miR-105 | −1.37 | 0.57 | 2.03 | 2.55 | 2.34E−02 | −3.40 | 10.6 |
| hsa-miR-9* | 1.84 | 1.04 | 5.31 | 1.78 | 1.19E−02 | −3.46 | 11.0 |
| hsa-miR-200a* | 2.23 | 1.29 | 5.71 | 0.26 | 4.24E−03 | −3.48 | 11.2 |
| hsa-miR-9 | 1.18 | 0.28 | 4.69 | 1.56 | 2.09E−03 | −3.51 | 11.4 |
| hsa-miR-122 | 0.49 | 0.58 | 4.01 | 3.14 | 4.24E−02 | −3.52 | 11.5 |
| hsa-miR-154* | 1.30 | 1.62 | 4.83 | 0.62 | 1.23E−02 | −3.53 | 11.6 |
| hsa-miR-329 | 0.53 | 0.46 | 4.13 | 0.15 | 1.38E−05 | −3.60 | 12.1 |
| hsa-miR-411 | 1.20 | 0.91 | 4.80 | 0.24 | 6.04E−04 | −3.60 | 12.1 |
| hsa-miR-369-5p | 1.55 | 0.73 | 5.27 | 0.72 | 4.19E−04 | −3.71 | 13.1 |
| hsa-miR-431 | 1.24 | 0.24 | 5.00 | 1.06 | 2.06E−04 | −3.75 | 13.5 |
| hsa-miR-136 | 2.84 | 0.99 | 6.61 | 0.51 | 9.79E−04 | −3.77 | 13.6 |
| hsa-miR-543 | 1.52 | 0.78 | 5.30 | 0.05 | 1.92E−04 | −3.78 | 13.7 |
| hsa-miR-889 | −0.01 | 0.31 | 3.79 | 0.54 | 1.30E−03 | −3.80 | 13.9 |
| hsa-miR-200b | 8.28 | 1.82 | 12.17 | 0.08 | 1.15E−02 | −3.89 | 14.8 |
| hsa-miR-654-3p | 2.33 | 1.51 | 6.30 | 0.51 | 5.21E−03 | −3.97 | 15.6 |
| hsa-miR-377 | 3.50 | 1.40 | 7.51 | 0.55 | 3.55E−03 | −4.01 | 16.2 |
| hsa-miR-200a | 7.09 | 2.00 | 11.26 | 0.29 | 1.33E−02 | −4.17 | 18.0 |
| hsa-miR-376a | 4.21 | 1.52 | 8.51 | 0.67 | 4.00E−03 | −4.30 | 19.7 |
| hsa-miR-485-3p | −0.08 | 0.71 | 4.27 | 0.37 | 7.28E−05 | −4.35 | 20.4 |
| hsa-miR-154 | 2.45 | 1.01 | 6.86 | 0.17 | 3.48E−04 | −4.41 | 21.2 |
| hsa-miR-409-5p | 0.50 | 0.73 | 4.92 | 0.15 | 5.49E−05 | −4.42 | 21.4 |
| hsa-miR-429 | 5.86 | 2.18 | 10.32 | 0.28 | 1.44E−02 | −4.45 | 21.9 |
| hsa-miR-758 | 0.53 | 0.92 | 5.04 | 0.13 | 1.82E−03 | −4.50 | 22.7 |
| hsa-miR-495 | 2.43 | 1.15 | 6.93 | 0.28 | 6.54E−04 | −4.50 | 22.7 |
| hsa-miR-136* | 1.87 | 1.17 | 6.41 | 0.51 | 8.12E−04 | −4.54 | 23.2 |
| hsa-miR-485-5p | −0.57 | 0.44 | 4.03 | 0.40 | 6.27E−06 | −4.60 | 24.2 |
| hsa-miR-137 | 0.41 | 0.80 | 5.03 | 3.11 | 1.62E−02 | −4.62 | 24.6 |
| hsa-miR-376c | 4.56 | 1.42 | 9.21 | 0.81 | 2.23E−03 | −4.65 | 25.1 |
| hsa-miR-379 | 1.51 | 1.69 | 6.20 | 0.14 | 3.58E−03 | −4.68 | 25.7 |
| hsa-miR-382 | 1.70 | 0.95 | 6.53 | 0.24 | 1.52E−04 | −4.83 | 28.5 |
| hsa-miR-381 | 2.42 | 1.55 | 7.34 | 0.33 | 1.93E−03 | −4.92 | 30.2 |
| hsa-miR-409-3p | 2.27 | 1.27 | 7.21 | 0.31 | 6.57E−04 | −4.94 | 30.7 |
| hsa-miR-127-3p | 3.94 | 1.28 | 8.88 | 0.37 | 7.24E−04 | −4.95 | 30.9 |
| hsa-miR-10a | 6.67 | 1.02 | 11.69 | 0.52 | 2.40E−04 | −5.02 | 32.4 |
| hsa-miR-487b | 4.72 | 0.62 | 9.75 | 0.19 | 1.08E−05 | −5.03 | 32.7 |
| hsa-miR-7 | 8.81 | 2.62 | 13.88 | 0.95 | 2.00E−02 | −5.06 | 33.4 |
| hsa-miR-592 | 2.37 | 1.05 | 7.50 | 1.19 | 6.87E−04 | −5.13 | 35.1 |
| hsa-miR-487a | −0.49 | 0.56 | 4.79 | 0.32 | 6.17E−06 | −5.27 | 38.7 |
| hsa-miR-539 | 1.16 | 0.38 | 6.53 | 0.34 | 9.86E−07 | −5.37 | 41.4 |
| hsa-miR-432 | 2.12 | 0.63 | 7.61 | 0.36 | 1.04E−05 | −5.48 | 44.7 |
| hsa-miR-433 | −1.53 | 0.62 | 4.13 | 0.61 | 1.55E−05 | −5.66 | 50.5 |
| hsa-miR-410 | 1.83 | 0.71 | 8.20 | 0.14 | 5.78E−06 | −6.36 | 82.3 |
| hsa-miR-323-3p | −0.16 | 0.72 | 6.93 | 0.13 | 3.36E−06 | −7.09 | 135.9 |
| hsa-miR-153 | 0.84 | 1.52 | 8.11 | 1.07 | 3.66E−03 | −7.27 | 154.0 |
| hsa-miR-124 | −0.40 | 1.08 | 7.86 | 3.11 | 1.32E−03 | −8.26 | 305.6 |
| hsa-miR-375 | 1.85 | 2.10 | 13.86 | 0.40 | 7.72E−05 | −12.01 | 4137.9 |

AVG, average expression among samples in a group;
SD, standard deviation

Example 24 miRNA Expression Profiling Distinguishes Papillary Thyroid Carcinoma and the Follicular Variant of Papillary Thyroid Carcinoma A total of 48 human miRNAs were significantly differentially expressed between the papillary thyroid carcinoma samples and the follicular variant of papillary thyroid carcinoma specimens ($p<0.05$) (Table 26). Among these, 28 miRNAs were overexpressed by 2- to 5-fold (Log 2 diff (FVPTC vs PTC)≥1) in the FVPTC samples compared to the PTC samples (Table 26).

TABLE 26

MicroRNAs significantly differentially expressed between FVPTC and PTC samples.

| miRNA | FVPTC | | PTC | | FVPTC vs PTC | | Fold change |
| --- | --- | --- | --- | --- | --- | --- | --- |
| | AVG | SD | AVG | SD | ttest | Log2Diff | |
| hsa-miR-659 | 3.28 | 0.92 | 1.42 | 0.91 | 1.92E−02 | 1.86 | 3.6 |
| hsa-miR-486-5p | 7.79 | 0.98 | 6.05 | 0.90 | 2.74E−02 | 1.74 | 3.3 |
| hsa-miR-765 | 4.00 | 1.15 | 2.28 | 0.68 | 2.58E−02 | 1.72 | 3.3 |
| hsa-miR-483-5p | 6.22 | 1.20 | 4.52 | 0.79 | 3.69E−02 | 1.70 | 3.3 |
| hsa-miR-663 | 5.77 | 1.09 | 4.09 | 0.76 | 2.98E−02 | 1.67 | 3.2 |
| hsa-miR-1182 | 2.24 | 1.06 | 0.68 | 0.68 | 3.09E−02 | 1.56 | 2.9 |
| hsa-miR-451 | 14.40 | 0.88 | 12.86 | 0.80 | 2.94E−02 | 1.53 | 2.9 |
| hsa-miR-1471 | 3.83 | 0.89 | 2.31 | 0.52 | 1.48E−02 | 1.52 | 2.9 |
| hsa-miR-583 | 0.88 | 0.95 | −0.56 | 0.48 | 2.10E−02 | 1.43 | 2.7 |
| hsa-miR-516a-5p | 2.82 | 0.56 | 1.43 | 0.65 | 1.18E−02 | 1.39 | 2.6 |
| hsa-miR-149* | 1.62 | 1.06 | 0.27 | 0.56 | 4.27E−02 | 1.35 | 2.6 |
| hsa-miR-566 | 1.14 | 0.67 | −0.20 | 0.64 | 1.76E−02 | 1.35 | 2.5 |
| hsa-miR-298 | 0.52 | 0.93 | −0.78 | 0.66 | 4.24E−02 | 1.31 | 2.5 |
| hsa-miR-483-3p | 1.71 | 0.42 | 0.43 | 0.35 | 1.55E−03 | 1.28 | 2.4 |
| hsa-miR-125b-1* | 2.05 | 0.58 | 0.81 | 0.78 | 3.34E−02 | 1.24 | 2.4 |
| hsa-miR-135a* | 4.84 | 0.47 | 3.61 | 0.32 | 2.32E−03 | 1.23 | 2.3 |
| hsa-miR-1183 | 3.77 | 0.86 | 2.62 | 0.61 | 4.95E−02 | 1.16 | 2.2 |
| hsa-miR-638 | 8.45 | 0.73 | 7.32 | 0.50 | 2.72E−02 | 1.14 | 2.2 |
| hsa-miR-572 | 5.22 | 0.76 | 4.08 | 0.45 | 2.70E−02 | 1.14 | 2.2 |
| hsa-miR-1321 | 1.29 | 0.74 | 0.17 | 0.39 | 2.11E−02 | 1.12 | 2.2 |
| hsa-miR-150* | 5.00 | 0.77 | 3.89 | 0.62 | 4.80E−02 | 1.10 | 2.1 |
| hsa-miR-640 | −0.07 | 0.79 | −1.15 | 0.15 | 1.93E−02 | 1.08 | 2.1 |
| hsa-miR-1909* | −0.17 | 0.40 | −1.25 | 0.45 | 7.16E−03 | 1.07 | 2.1 |
| hsa-miR-1224-5p | 5.30 | 0.72 | 4.26 | 0.47 | 3.38E−02 | 1.04 | 2.1 |
| hsa-miR-371-5p | 3.83 | 0.78 | 2.81 | 0.43 | 3.89E−02 | 1.03 | 2.0 |
| hsa-miR-518c* | 0.52 | 0.72 | −0.49 | 0.55 | 4.92E−02 | 1.01 | 2.0 |
| hsa-miR-939 | 6.74 | 0.52 | 5.75 | 0.45 | 1.85E−02 | 0.99 | 2.0 |
| hsa-miR-211 | 1.36 | 0.41 | 0.39 | 0.66 | 3.87E−02 | 0.97 | 2.0 |
| hsa-miR-1910 | −0.98 | 0.72 | −1.90 | 0.24 | 2.97E−02 | 0.92 | 1.9 |
| hsa-miR-1296 | 0.24 | 0.31 | −0.65 | 0.51 | 1.87E−02 | 0.89 | 1.9 |
| hsa-miR-516b | 0.84 | 0.74 | −0.04 | 0.28 | 4.27E−02 | 0.88 | 1.8 |
| hsa-miR-1915 | 7.97 | 0.48 | 7.09 | 0.28 | 1.03E−02 | 0.87 | 1.8 |
| hsa-miR-595 | 1.35 | 0.71 | 0.49 | 0.32 | 4.33E−02 | 0.86 | 1.8 |
| hsa-miR-1306 | 1.68 | 0.13 | 0.92 | 0.46 | 1.60E−02 | 0.76 | 1.7 |
| hsa-miR-346 | 1.18 | 0.24 | 0.46 | 0.56 | 4.87E−02 | 0.72 | 1.6 |
| hsa-miR-662 | 1.69 | 0.36 | 0.98 | 0.16 | 5.13E−03 | 0.71 | 1.6 |
| hsa-miR-1275 | 7.19 | 0.26 | 6.55 | 0.47 | 4.50E−02 | 0.64 | 1.6 |
| hsa-miR-658 | −0.02 | 0.28 | −0.65 | 0.32 | 1.61E−02 | 0.64 | 1.6 |
| hsa-miR-488* | −0.09 | 0.51 | −0.71 | 0.25 | 4.71E−02 | 0.62 | 1.5 |
| hsa-miR-513b | 3.72 | 0.26 | 3.14 | 0.24 | 1.08E−02 | 0.58 | 1.5 |
| hsa-miR-940 | 6.58 | 0.36 | 6.07 | 0.15 | 2.20E−02 | 0.51 | 1.4 |
| hsa-miR-20a | 10.68 | 0.25 | 11.03 | 0.12 | 2.62E−02 | −0.35 | 1.3 |
| hsa-miR-502-5p | 3.33 | 0.25 | 3.74 | 0.16 | 2.07E−02 | −0.41 | 1.3 |
| hsa-miR-625 | 5.66 | 0.26 | 6.17 | 0.25 | 2.24E−02 | −0.50 | 1.4 |
| hsa-miR-15b* | 1.13 | 0.41 | 1.71 | 0.29 | 4.44E−02 | −0.58 | 1.5 |
| hsa-miR-10a* | 0.79 | 0.52 | 1.51 | 0.31 | 3.30E−02 | −0.73 | 1.7 |
| hsa-miR-1305 | 7.43 | 0.36 | 8.28 | 0.53 | 3.03E−02 | −0.85 | 1.8 |
| hsa-miR-21 | 14.94 | 0.64 | 15.85 | 0.45 | 4.13E−02 | −0.90 | 1.9 |

AVG, average expression among samples in a group;
SD, standard deviation

Example 25 miRNA Expression Profiling Distinguishes Papillary Thyroid Carcinoma and Anaplastic Thyroid Carcinoma A total of 154 human miRNAs were significantly differentially expressed between the papillary thyroid carcinoma samples and the anaplastic thyroid carcinoma specimen (p<0.05) (Table 27). Of these, 89 were expressed by at least 2-fold higher in PTC samples compared to the ATC sample (Log 2 diff (PTC vs ATC)≥1). Among these, eight miRNAs (hsa-miR-141, -429, -200c, -20, -200a, -135b, -551b, and -135a) were overexpressed by 100- to 500-fold in the FTC samples, eight miRNAs (hsa-miR-146b-3p, -141*, -375, -146b-5p, -200b*, -200a*, -138, -and -31) were overexpressed between 20- and 60-fold in PTC samples, and seventy-three miRNAs were overexpressed by 2- to 20-fold in PTC samples compared to the ATC specimen. In addition, forty two miRNAs were underexpressed in the PTC specimens versus the ATC sample. Among these, two miRNAs (hsa-miR-582-3p and -9*) were underexpressed by 30- to 50-fold in PTC samples, eight miRNAs (hsa-miR-582-5p, -873, -124, -9, -34c-5p, -204, -34c-3p, and -34b) were underexpressed in PTC samples by 10- to 30-fold, and thirty two miRNAs were underexpressed by 2- to 10-fold in PTC samples compared to the ATC specimen. Unsupervised clustering, as well as principal component analysis (PCA) (FIG. 1) on all detected probes showed a clear segregation between normal thyroid (Norm) and hyperplastic nodules (Nod), and between medullary thyroid cancer (MED) samples and all the follicular cell-derived neoplasms (FA, FTC, PTC, and fvPTC), correlating with the different origin of the tumors (C-cell versus follicular cell). Pair-wise comparison between the different groups of samples allowed the identification of differentially expressed miRNAs, as discussed in the examples below.

TABLE 27

MicroRNAs significantly differentially expressed between PTC and ATC samples.

| miRNA | ATC | PTC AVG | SD | ATC vs PTC ttest | Log2Diff | Fold change |
|---|---|---|---|---|---|---|
| hsa-miR-582-3p | 3.97 | −1.38 | 0.37 | 1.91E−04 | 5.35 | 40.9 |
| hsa-miR-9* | 7.14 | 2.08 | 1.06 | 1.22E−02 | 5.07 | 33.5 |
| hsa-miR-582-5p | 8.42 | 3.66 | 0.51 | 1.02E−03 | 4.76 | 27.1 |
| hsa-miR-873 | 5.52 | 0.81 | 0.78 | 5.26E−03 | 4.71 | 26.2 |
| hsa-miR-124 | 4.16 | −0.38 | 0.31 | 1.89E−04 | 4.53 | 23.2 |
| hsa-miR-9 | 5.05 | 0.99 | 0.68 | 5.37E−03 | 4.06 | 16.7 |
| hsa-miR-34c-5p | 7.37 | 3.41 | 0.79 | 1.05E−02 | 3.96 | 15.5 |
| hsa-miR-204 | 8.74 | 5.26 | 0.80 | 1.64E−02 | 3.49 | 11.2 |
| hsa-miR-34c-3p | 1.95 | −1.42 | 0.20 | 1.04E−04 | 3.38 | 10.4 |
| hsa-miR-34b | 4.65 | 1.29 | 0.56 | 5.27E−03 | 3.36 | 10.2 |
| hsa-miR-10a | 10.38 | 7.36 | 0.58 | 9.14E−03 | 3.02 | 8.1 |
| hsa-miR-210 | 8.74 | 5.79 | 0.37 | 1.97E−03 | 2.95 | 7.7 |
| hsa-miR-592 | 4.74 | 2.04 | 0.61 | 1.57E−02 | 2.70 | 6.5 |
| hsa-miR-605 | 3.82 | 1.15 | 0.60 | 1.58E−02 | 2.67 | 6.4 |
| hsa-miR-363 | 7.31 | 4.69 | 0.85 | 4.85E−02 | 2.63 | 6.2 |
| hsa-miR-663 | 6.54 | 4.09 | 0.76 | 4.26E−02 | 2.45 | 5.5 |
| hsa-miR-153 | 3.92 | 1.59 | 0.51 | 1.42E−02 | 2.33 | 5.0 |
| hsa-miR-298 | 1.49 | −0.78 | 0.66 | 3.47E−02 | 2.27 | 4.8 |
| hsa-miR-483-3p | 2.61 | 0.43 | 0.35 | 4.52E−03 | 2.19 | 4.5 |
| hsa-miR-769-3p | 3.15 | 1.08 | 0.49 | 1.76E−02 | 2.07 | 4.2 |
| hsa-miR-876-3p | 2.38 | 0.41 | 0.55 | 3.00E−02 | 1.98 | 3.9 |
| hsa-miR-1274a | 9.62 | 7.71 | 0.50 | 2.49E−02 | 1.91 | 3.8 |
| hsa-miR-371-5p | 4.62 | 2.81 | 0.43 | 1.84E−02 | 1.81 | 3.5 |
| hsa-miR-583 | 1.23 | −0.56 | 0.48 | 2.73E−02 | 1.79 | 3.5 |
| hsa-miR-936 | 2.05 | 0.34 | 0.48 | 3.12E−02 | 1.71 | 3.3 |
| hsa-miR-501-3p | 4.53 | 2.83 | 0.27 | 4.34E−03 | 1.71 | 3.3 |
| hsa-miR-517a | 1.20 | −0.45 | 0.52 | 4.45E−02 | 1.65 | 3.1 |
| hsa-miR-720 | 14.50 | 12.95 | 0.34 | 1.42E−02 | 1.55 | 2.9 |
| hsa-miR-939 | 7.27 | 5.75 | 0.45 | 3.64E−02 | 1.52 | 2.9 |
| hsa-miR-1225-5p | 9.76 | 8.28 | 0.48 | 4.84E−02 | 1.48 | 2.8 |
| hsa-miR-769-5p | 6.42 | 5.00 | 0.21 | 3.69E−03 | 1.42 | 2.7 |
| hsa-miR-500* | 5.90 | 4.53 | 0.27 | 9.30E−03 | 1.37 | 2.6 |
| hsa-miR-502-3p | 6.19 | 4.88 | 0.23 | 6.23E−03 | 1.31 | 2.5 |
| hsa-miR-1274b | 12.63 | 11.33 | 0.39 | 3.71E−02 | 1.30 | 2.5 |
| hsa-miR-130b | 7.77 | 6.55 | 0.21 | 6.44E−03 | 1.23 | 2.3 |
| hsa-miR-330-3p | 5.15 | 4.02 | 0.28 | 2.01E−02 | 1.13 | 2.2 |
| hsa-miR-532-5p | 7.58 | 6.51 | 0.17 | 5.08E−03 | 1.06 | 2.1 |
| hsa-miR-656 | 1.64 | 0.58 | 0.26 | 2.08E−02 | 1.06 | 2.1 |
| hsa-miR-135a* | 4.66 | 3.61 | 0.32 | 3.89E−02 | 1.05 | 2.1 |
| hsa-miR-660 | 8.23 | 7.17 | 0.27 | 2.49E−02 | 1.05 | 2.1 |
| hsa-miR-377* | 0.92 | −0.13 | 0.26 | 2.05E−02 | 1.05 | 2.1 |
| hsa-miR-362-5p | 6.59 | 5.62 | 0.05 | 4.62E−05 | 0.98 | 2.0 |
| hsa-miR-10a* | 2.44 | 1.51 | 0.31 | 4.97E−02 | 0.93 | 1.9 |
| hsa-miR-940 | 7.00 | 6.07 | 0.15 | 4.43E−03 | 0.93 | 1.9 |
| hsa-miR-1237 | 3.83 | 2.93 | 0.28 | 4.47E−02 | 0.90 | 1.9 |
| hsa-miR-556-3p | 1.55 | 0.67 | 0.22 | 2.16E−02 | 0.89 | 1.8 |
| hsa-miR-636 | 2.84 | 1.98 | 0.12 | 2.59E−03 | 0.85 | 1.8 |
| hsa-miR-1228 | 5.64 | 4.79 | 0.23 | 2.98E−02 | 0.85 | 1.8 |
| hsa-miR-550 | 2.88 | 2.03 | 0.27 | 4.55E−02 | 0.84 | 1.8 |

TABLE 27-continued

MicroRNAs significantly differentially expressed between PTC and ATC samples.

| miRNA | ATC | PTC AVG | SD | ATC vs PTC ttest | Log2Diff | Fold change |
|---|---|---|---|---|---|---|
| hsa-miR-129* | 2.78 | 1.95 | 0.21 | 2.35E−02 | 0.83 | 1.8 |
| hsa-miR-502-5p | 4.57 | 3.74 | 0.16 | 8.43E−03 | 0.83 | 1.8 |
| hsa-miR-885-5p | 0.68 | −0.10 | 0.21 | 2.91E−02 | 0.78 | 1.7 |
| hsa-miR-1539 | 2.79 | 2.07 | 0.08 | 1.04E−03 | 0.72 | 1.6 |
| hsa-miR-301b | 2.28 | 1.59 | 0.20 | 3.28E−02 | 0.69 | 1.6 |
| hsa-miR-22 | 12.78 | 12.12 | 0.11 | 4.98E−03 | 0.66 | 1.6 |
| hsa-miR-335* | 2.61 | 1.99 | 0.18 | 3.64E−02 | 0.62 | 1.5 |
| hsa-miR-140-5p | 9.04 | 8.48 | 0.15 | 2.69E−02 | 0.56 | 1.5 |
| hsa-miR-25 | 9.41 | 9.92 | 0.16 | 4.50E−02 | −0.51 | 1.4 |
| hsa-miR-1271 | 3.33 | 3.98 | 0.16 | 2.14E−02 | −0.64 | 1.6 |
| hsa-miR-455-3p | 5.69 | 6.39 | 0.19 | 2.73E−02 | −0.70 | 1.6 |
| hsa-miR-624* | 1.27 | 1.98 | 0.17 | 1.85E−02 | −0.71 | 1.6 |
| hsa-miR-192 | 6.79 | 7.63 | 0.27 | 4.62E−02 | −0.84 | 1.8 |
| hsa-miR-423-3p | 2.56 | 3.45 | 0.22 | 2.03E−02 | −0.88 | 1.8 |
| hsa-miR-361-3p | 6.33 | 7.27 | 0.20 | 1.29E−02 | −0.94 | 1.9 |
| hsa-miR-16 | 12.57 | 13.53 | 0.18 | 7.74E−03 | −0.95 | 1.9 |
| hsa-miR-30e | 8.44 | 9.46 | 0.25 | 2.11E−02 | −1.02 | 2.0 |
| hsa-miR-93 | 7.61 | 8.67 | 0.23 | 1.36E−02 | −1.07 | 2.1 |
| hsa-miR-17 | 8.41 | 9.48 | 0.14 | 2.19E−03 | −1.07 | 2.1 |
| hsa-miR-194 | 5.17 | 6.25 | 0.34 | 4.43E−02 | −1.08 | 2.1 |
| hsa-miR-95 | 6.41 | 7.54 | 0.31 | 2.98E−02 | −1.13 | 2.2 |
| hsa-miR-151-3p | 6.52 | 7.67 | 0.26 | 1.57E−02 | −1.15 | 2.2 |
| hsa-miR-93* | −0.59 | 0.58 | 0.36 | 4.34E−02 | −1.16 | 2.2 |
| hsa-miR-181a* | 3.19 | 4.36 | 0.24 | 1.17E−02 | −1.17 | 2.2 |
| hsa-let-7g | 11.83 | 13.03 | 0.30 | 2.29E−02 | −1.20 | 2.3 |
| hsa-miR-1270 | 0.05 | 1.27 | 0.39 | 4.66E−02 | −1.22 | 2.3 |
| hsa-miR-192* | 0.63 | 1.86 | 0.29 | 1.72E−02 | −1.23 | 2.3 |
| hsa-miR-423-5p | 5.61 | 6.84 | 0.25 | 1.03E−02 | −1.23 | 2.3 |
| hsa-miR-29c | 11.87 | 13.10 | 0.40 | 4.63E−02 | −1.23 | 2.4 |
| hsa-miR-30d | 8.94 | 10.20 | 0.41 | 4.79E−02 | −1.27 | 2.4 |
| hsa-miR-181c | 6.32 | 7.59 | 0.35 | 2.91E−02 | −1.27 | 2.4 |
| hsa-miR-34a* | 3.79 | 5.07 | 0.21 | 5.13E−03 | −1.28 | 2.4 |
| hsa-miR-206 | −1.36 | −0.07 | 0.40 | 4.24E−02 | −1.29 | 2.4 |
| hsa-miR-34a | 11.30 | 12.59 | 0.24 | 7.79E−03 | −1.29 | 2.5 |
| hsa-miR-20a | 9.71 | 11.03 | 0.12 | 6.10E−04 | −1.32 | 2.5 |
| hsa-miR-374b | 7.05 | 8.38 | 0.22 | 5.18E−03 | −1.33 | 2.5 |
| hsa-miR-19b | 9.89 | 11.28 | 0.31 | 1.54E−02 | −1.38 | 2.6 |
| hsa-miR-26b | 10.52 | 11.96 | 0.28 | 9.48E−03 | −1.44 | 2.7 |
| hsa-miR-455-5p | 2.32 | 3.78 | 0.44 | 3.86E−02 | −1.46 | 2.8 |
| hsa-miR-874 | 4.78 | 6.26 | 0.25 | 5.97E−03 | −1.48 | 2.8 |
| hsa-miR-181d | 5.25 | 6.74 | 0.28 | 7.95E−03 | −1.49 | 2.8 |
| hsa-miR-19b-1* | 1.32 | 2.85 | 0.25 | 4.93E−03 | −1.54 | 2.9 |
| hsa-miR-374a | 7.52 | 9.09 | 0.41 | 2.50E−02 | −1.57 | 3.0 |
| hsa-miR-92a | 7.77 | 9.35 | 0.16 | 8.31E−04 | −1.58 | 3.0 |
| hsa-miR-499-5p | 2.14 | 3.72 | 0.45 | 3.38E−02 | −1.58 | 3.0 |
| hsa-miR-1301 | −0.92 | 0.69 | 0.39 | 1.97E−02 | −1.61 | 3.1 |
| hsa-miR-151-5p | 9.21 | 10.90 | 0.35 | 1.16E−02 | −1.69 | 3.2 |
| hsa-miR-665 | 1.87 | 3.57 | 0.41 | 1.89E−02 | −1.70 | 3.3 |
| hsa-let-7c | 10.68 | 12.41 | 0.38 | 1.48E−02 | −1.73 | 3.3 |
| hsa-miR-744* | −1.03 | 0.75 | 0.36 | 1.07E−02 | −1.78 | 3.4 |
| hsa-miR-30d* | 1.12 | 2.93 | 0.50 | 3.00E−02 | −1.82 | 3.5 |
| hsa-miR-17* | 3.60 | 5.43 | 0.32 | 6.44E−03 | −1.83 | 3.6 |
| hsa-miR-26a | 10.36 | 12.20 | 0.35 | 8.50E−03 | −1.84 | 3.6 |
| hsa-miR-346 | −1.38 | 0.46 | 0.56 | 3.93E−02 | −1.84 | 3.6 |
| hsa-miR-126 | 10.01 | 11.92 | 0.43 | 1.49E−02 | −1.92 | 3.8 |
| hsa-miR-100 | 9.15 | 11.12 | 0.21 | 1.03E−03 | −1.97 | 3.9 |
| hsa-miR-143* | 1.36 | 3.34 | 0.37 | 8.09E−03 | −1.98 | 3.9 |
| hsa-miR-744 | 2.84 | 4.82 | 0.38 | 9.21E−03 | −1.98 | 4.0 |
| hsa-miR-143 | 5.31 | 7.32 | 0.28 | 2.73E−03 | −2.02 | 4.0 |
| hsa-miR-30b | 9.75 | 11.85 | 0.45 | 1.29E−02 | −2.11 | 4.3 |
| hsa-miR-20a* | 2.51 | 4.63 | 0.57 | 2.81E−02 | −2.12 | 4.3 |
| hsa-miR-126* | 3.44 | 5.58 | 0.62 | 3.42E−02 | −2.14 | 4.4 |
| hsa-miR-145* | 2.37 | 4.58 | 0.41 | 7.75E−03 | −2.20 | 4.6 |
| hsa-miR-181a | 8.77 | 11.28 | 0.33 | 2.31E−03 | −2.51 | 5.7 |
| hsa-miR-222* | −2.06 | 0.46 | 0.73 | 3.39E−02 | −2.52 | 5.7 |
| hsa-let-7i | 11.99 | 14.53 | 0.18 | 1.92E−04 | −2.54 | 5.8 |
| hsa-miR-145 | 6.78 | 9.37 | 0.28 | 1.07E−03 | −2.59 | 6.0 |
| hsa-miR-181b | 6.96 | 9.59 | 0.52 | 1.00E−02 | −2.63 | 6.2 |
| hsa-miR-125b-2* | 2.65 | 5.32 | 0.29 | 1.18E−03 | −2.66 | 6.3 |
| hsa-miR-139-5p | 2.79 | 5.51 | 0.53 | 9.33E−03 | −2.72 | 6.6 |
| hsa-miR-491-5p | −1.33 | 1.51 | 0.34 | 1.54E−03 | −2.84 | 7.2 |
| hsa-miR-200c* | −0.83 | 2.06 | 0.34 | 1.48E−03 | −2.89 | 7.4 |
| hsa-miR-218 | 5.04 | 7.94 | 0.71 | 2.00E−02 | −2.90 | 7.4 |

TABLE 27-continued

MicroRNAs significantly differentially expressed between PTC and ATC samples.

| miRNA | ATC | PTC AVG | PTC SD | ATC vs PTC ttest | ATC vs PTC Log2Diff | Fold change |
|---|---|---|---|---|---|---|
| hsa-miR-542-5p | 3.91 | 6.80 | 0.87 | 3.86E−02 | −2.90 | 7.4 |
| hsa-miR-424 | 7.56 | 10.51 | 0.68 | 1.65E−02 | −2.95 | 7.7 |
| hsa-miR-452 | 1.57 | 4.54 | 0.40 | 2.51E−03 | −2.96 | 7.8 |
| hsa-miR-542-3p | 3.33 | 6.39 | 0.81 | 2.57E−02 | −3.06 | 8.4 |
| hsa-miR-99a | 8.00 | 11.21 | 0.37 | 1.38E−03 | −3.21 | 9.3 |
| hsa-miR-181a-2* | 3.00 | 6.23 | 0.66 | 1.09E−02 | −3.23 | 9.4 |
| hsa-miR-224 | 2.46 | 5.75 | 0.50 | 3.98E−03 | −3.29 | 9.8 |
| hsa-miR-99a* | −1.76 | 1.53 | 0.53 | 4.70E−03 | −3.29 | 9.8 |
| hsa-miR-450a | 1.98 | 5.54 | 0.74 | 1.16E−02 | −3.56 | 11.8 |
| hsa-miR-31* | 4.96 | 8.58 | 0.56 | 4.14E−03 | −3.62 | 12.3 |
| hsa-miR-512-3p | 0.39 | 4.04 | 0.37 | 8.13E−04 | −3.65 | 12.6 |
| hsa-let-7i* | 0.07 | 3.76 | 0.40 | 1.10E−03 | −3.69 | 12.9 |
| hsa-miR-221 | 6.87 | 10.60 | 0.73 | 9.46E−03 | −3.73 | 13.3 |
| hsa-miR-221* | 4.78 | 8.71 | 0.86 | 1.41E−02 | −3.94 | 15.3 |
| hsa-miR-125b | 10.44 | 14.38 | 0.32 | 3.64E−04 | −3.94 | 15.4 |
| hsa-miR-222 | 6.04 | 10.25 | 0.58 | 2.76E−03 | −4.21 | 18.5 |
| hsa-miR-31 | 5.65 | 10.14 | 0.64 | 3.07E−03 | −4.50 | 22.6 |
| hsa-miR-138 | 0.09 | 4.62 | 1.08 | 1.86E−02 | −4.52 | 23.0 |
| hsa-miR-200a* | 0.46 | 5.30 | 0.62 | 2.10E−03 | −4.84 | 28.6 |
| hsa-miR-200b* | 0.48 | 5.62 | 0.59 | 1.34E−03 | −5.13 | 35.1 |
| hsa-miR-146b-5p | 9.04 | 14.41 | 0.92 | 6.08E−03 | −5.37 | 41.3 |
| hsa-miR-375 | 1.27 | 6.74 | 1.20 | 1.41E−02 | −5.47 | 44.4 |
| hsa-miR-141* | −1.68 | 4.09 | 0.36 | 1.31E−04 | −5.77 | 54.4 |
| hsa-miR-146b-3p | −2.10 | 3.73 | 1.12 | 8.99E−03 | −5.83 | 56.9 |
| hsa-miR-135a | 1.19 | 8.54 | 0.82 | 1.23E−03 | −7.35 | 162.8 |
| hsa-miR-551b | 2.61 | 9.98 | 0.58 | 3.21E−04 | −7.37 | 164.9 |
| hsa-miR-135b | 2.20 | 10.66 | 0.71 | 4.00E−04 | −8.46 | 352.2 |
| hsa-miR-200a | 1.45 | 10.22 | 0.52 | 1.05E−04 | −8.77 | 436.0 |
| hsa-miR-200b | 2.93 | 11.78 | 0.50 | 8.68E−05 | −8.85 | 460.1 |
| hsa-miR-200c | 3.00 | 11.91 | 0.17 | 1.27E−06 | −8.91 | 480.0 |
| hsa-miR-429 | −0.05 | 8.97 | 0.55 | 1.14E−04 | −9.02 | 520.5 |
| hsa-miR-141 | 2.51 | 11.71 | 0.34 | 1.53E−05 | −9.19 | 585.7 |

AVG, average expression among samples in a group;
SD, standard deviation

Example 26 miRNA Expression Profiling Distinguishes Papillary Thyroid Carcinoma and Medullary Thyroid Carcinoma A total of 188 human miRNAs were significantly differentially expressed between the papillary thyroid carcinoma samples and the medullary thyroid carcinoma specimens (p<0.05) (Table 28). Of these, 29 miRNAs were expressed at levels at least 2-fold higher in PTC samples compared to the MTC samples Log 2 diff (MTC vs PTC)≤1). Among these, hsa-miR-146b-5p was expressed at a level more than a 100-fold higher in PTC compared to the MTC samples, four miRNAs (hsa-miR-551b, -31, -31*, and -146b-3p) were overexpressed by 25- to 100-fold in PTC samples, and twenty-four miRNAs were overexpressed by 2- to -10-fold in PTC samples compared to the MTC specimens. In addition, 124 miRNAs were underexpressed in PTC samples compared to the MTC specimens. Among those, hsa-miR-124, -375, and -323-3p were underexpressed by 100- to 300-fold in PTC, five miRNAs (hsa-miR-7, -153, -410, -129-3p, and -129-5p) were underexpressed by 50- to 100-fold in PTC, nineteen miRNAs were underexpressed by 20- to 50-fold in PTC, and ninety seven miRNAs were underexpressed by 2- to 20-fold in the PTC samples compared to the MTC specimens.

TABLE 28

MicroRNAs significantly differentially expressed between PTC and MTC samples.

| miRNA | MTC AVG | MTC SD | PTC AVG | PTC SD | MTC vs PTC ttest | MTC vs PTC Log2Diff | Fold change |
|---|---|---|---|---|---|---|---|
| hsa-miR-124 | 7.86 | 3.11 | −0.38 | 0.31 | 8.00E-04 | 8.24 | 301.9 |
| hsa-miR-375 | 13.86 | 0.40 | 6.74 | 1.20 | 6.89E-05 | 7.13 | 139.7 |
| hsa-miR-323-3p | 6.93 | 0.13 | 0.03 | 0.72 | 3.76E-06 | 6.90 | 119.2 |
| hsa-miR-7 | 13.88 | 0.95 | 7.30 | 1.72 | 9.8813-04 | 6.58 | 95.7 |
| hsa-miR-153 | 8.11 | 1.07 | 1.59 | 0.51 | 2.04E-05 | 6.52 | 91.5 |
| hsa-miR-410 | 8.20 | 0.14 | 1.86 | 1.02 | 4.71E-05 | 6.34 | 80.9 |
| hsa-miR-129-3p | 9.17 | 5.52 | 3.31 | 0.56 | 4.70E-02 | 5.86 | 58.3 |
| hsa-miR-129-5p | 5.85 | 5.05 | 0.15 | 0.60 | 3.84E-02 | 5.71 | 52.2 |
| hsa-miR-432 | 7.61 | 0.36 | 2.03 | 0.77 | 2.59E-05 | 5.57 | 47.6 |

TABLE 28-continued

MicroRNAs significantly differentially expressed between PTC and MTC samples.

| miRNA | MTC | | PTC | | MTC vs PTC | | Fold change |
| --- | --- | --- | --- | --- | --- | --- | --- |
| | AVG | SD | AVG | SD | ttest | Log2Diff | |
| hsa-miR-487a | 4.79 | 0.32 | −0.76 | 1.16 | 2.23E−04 | 5.55 | 46.9 |
| hsa-miR-592 | 7.50 | 1.19 | 2.04 | 0.61 | 1.19E−04 | 5.45 | 43.9 |
| hsa-miR-433 | 4.13 | 0.61 | −1.22 | 0.52 | 1.14E−05 | 5.35 | 40.8 |
| hsa-miR-539 | 6.53 | 0.34 | 1.30 | 0.37 | 1.10E−06 | 5.22 | 37.4 |
| hsa-miR-487b | 9.75 | 0.19 | 4.61 | 0.74 | 2.57E−05 | 5.14 | 35.2 |
| hsa-miR-382 | 6.53 | 0.24 | 1.48 | 1.24 | 5.11E−04 | 5.05 | 33.0 |
| hsa-miR-127-3p | 8.88 | 0.37 | 4.10 | 1.39 | 1.29E−03 | 4.79 | 27.6 |
| hsa-miR-136* | 6.41 | 0.51 | 1.67 | 1.19 | 7.01E−04 | 4.74 | 26.7 |
| hsa-miR-381 | 7.34 | 0.33 | 2.75 | 1.08 | 4.31E−04 | 4.59 | 24.0 |
| hsa-miR-409-3p | 7.21 | 0.31 | 2.64 | 1.15 | 6.04E−04 | 4.57 | 23.8 |
| hsa-miR-154 | 6.86 | 0.17 | 2.35 | 1.36 | 1.47E−03 | 4.51 | 22.8 |
| hsa-miR-485-3p | 4.27 | 0.37 | −0.23 | 0.51 | 1.21E−05 | 4.50 | 22.6 |
| hsa-miR-485-5p | 4.03 | 0.40 | −0.47 | 0.52 | 1.37E−05 | 4.50 | 22.6 |
| hsa-miR-409-5p | 4.92 | 0.15 | 0.43 | 0.61 | 1.81E−05 | 4.49 | 22.5 |
| hsa-miR-495 | 6.93 | 0.28 | 2.48 | 1.01 | 3.57E−04 | 4.45 | 21.9 |
| hsa-miR-758 | 5.04 | 0.13 | 0.65 | 0.61 | 2.06E−05 | 4.39 | 20.9 |
| hsa-miR-183* | 4.36 | 0.40 | −0.03 | 1.02 | 4.36E−04 | 4.39 | 20.9 |
| hsa-miR-10a | 11.69 | 0.52 | 7.36 | 0.58 | 4.37E−05 | 4.33 | 20.1 |
| hsa-miR-376c | 9.21 | 0.81 | 4.93 | 1.14 | 1.36E−03 | 4.28 | 19.5 |
| hsa-miR-379 | 6.20 | 0.14 | 1.93 | 1.19 | 9.64E−04 | 4.27 | 19.2 |
| hsa-miR-376a | 8.51 | 0.67 | 4.25 | 1.32 | 2.23E−03 | 4.26 | 19.1 |
| hsa-miR-183 | 10.49 | 0.69 | 6.34 | 0.19 | 1.14E−04 | 4.16 | 17.8 |
| hsa-miR-329 | 4.13 | 0.15 | 0.08 | 0.64 | 4.42E−05 | 4.05 | 16.5 |
| hsa-miR-377 | 7.51 | 0.55 | 3.49 | 1.41 | 3.61E−03 | 4.03 | 16.3 |
| hsa-miR-543 | 5.30 | 0.05 | 1.29 | 0.60 | 3.10E−05 | 4.00 | 16.0 |
| hsa-miR-431 | 5.00 | 1.06 | 1.01 | 0.65 | 5.24E−04 | 3.98 | 15.8 |
| hsa-miR-136 | 6.61 | 0.51 | 2.65 | 0.74 | 1.95E−04 | 3.95 | 15.5 |
| hsa-miR-411 | 4.80 | 0.24 | 0.89 | 0.65 | 6.69E−05 | 3.91 | 15.1 |
| hsa-miR-369-5p | 5.27 | 0.72 | 1.47 | 0.77 | 4.50E−04 | 3.80 | 13.9 |
| hsa-miR-889 | 3.79 | 0.54 | 0.08 | 0.40 | 2.99E−05 | 3.71 | 13.1 |
| hsa-miR-9 | 4.69 | 1.56 | 0.99 | 0.68 | 3.04E−03 | 3.70 | 13.0 |
| hsa-miR-370 | 4.77 | 0.36 | 1.11 | 0.79 | 3.17E−04 | 3.65 | 12.6 |
| hsa-miR-654-3p | 6.30 | 0.51 | 2.68 | 1.10 | 1.92E−03 | 3.62 | 12.3 |
| hsa-miR-376a* | 4.63 | 0.44 | 1.13 | 0.40 | 2.52E−05 | 3.50 | 11.3 |
| hsa-miR-890 | 2.63 | 1.99 | −0.83 | 0.68 | 1.00E−02 | 3.46 | 11.0 |
| hsa-miR-182 | 5.90 | 0.30 | 2.59 | 1.06 | 2.12E−03 | 3.31 | 9.9 |
| hsa-miR-486-3p | 3.41 | 0.41 | 0.10 | 1.00 | 1.77E−03 | 3.31 | 9.9 |
| hsa-miR-335 | 9.06 | 1.56 | 5.76 | 0.92 | 8.37E−03 | 3.31 | 9.9 |
| hsa-miR-122 | 4.01 | 3.14 | 0.75 | 0.22 | 4.99E−02 | 3.26 | 9.6 |
| hsa-miR-9* | 5.31 | 1.78 | 2.08 | 1.06 | 1.68E−02 | 3.23 | 9.4 |
| hsa-miR-154* | 4.83 | 0.62 | 1.61 | 0.96 | 2.20E−03 | 3.21 | 9.3 |
| hsa-miR-493* | 5.39 | 0.45 | 2.22 | 0.95 | 1.79E−03 | 3.17 | 9.0 |
| hsa-miR-337-5p | 5.33 | 0.33 | 2.17 | 1.25 | 5.85E−03 | 3.16 | 9.0 |
| hsa-miR-105 | 2.03 | 2.55 | −1.09 | 0.54 | 3.15E−02 | 3.13 | 8.7 |
| hsa-miR-377* | 2.94 | 0.16 | −0.13 | 0.26 | 1.71E−06 | 3.07 | 8.4 |
| hsa-miR-299-5p | 5.22 | 0.48 | 2.45 | 0.92 | 3.20E−03 | 2.77 | 6.8 |
| hsa-miR-1301 | 3.45 | 0.62 | 0.69 | 0.39 | 2.19E−04 | 2.77 | 6.8 |
| hsa-miR-96 | 11.01 | 0.48 | 8.25 | 0.45 | 1.82E−04 | 2.76 | 6.8 |
| hsa-miR-668 | 1.30 | 0.42 | −1.42 | 0.77 | 1.48E−03 | 2.73 | 6.6 |
| hsa-miR-936 | 3.06 | 1.62 | 0.34 | 0.48 | 1.04E−02 | 2.71 | 6.6 |
| hsa-miR-490-3p | 1.48 | 1.56 | −1.13 | 0.67 | 1.45E−02 | 2.61 | 6.1 |
| hsa-miR-216a | 1.88 | 0.79 | −0.69 | 1.07 | 1.16E−02 | 2.58 | 6.0 |
| hsa-miR-582-5p | 6.13 | 0.18 | 3.66 | 0.51 | 2.17E−04 | 2.47 | 5.5 |
| hsa-miR-182* | 2.00 | 0.20 | −0.41 | 0.86 | 3.64E−03 | 2.41 | 5.3 |
| hsa-miR-132 | 8.97 | 1.15 | 6.57 | 0.65 | 8.37E−03 | 2.39 | 5.3 |
| hsa-miR-1180 | 3.10 | 1.01 | 0.78 | 0.98 | 1.84E−02 | 2.32 | 5.0 |
| hsa-miR-330-3p | 6.34 | 0.46 | 4.02 | 0.28 | 9.61E−05 | 2.32 | 5.0 |
| hsa-miR-654-5p | 4.30 | 0.31 | 1.98 | 0.52 | 4.65E−04 | 2.32 | 5.0 |
| hsa-miR-10a* | 3.82 | 0.57 | 1.51 | 0.31 | 2.61E−04 | 2.31 | 5.0 |
| hsa-miR-338-3p | 9.34 | 0.35 | 7.04 | 0.63 | 1.26E−03 | 2.30 | 4.9 |
| hsa-miR-652 | 7.51 | 0.29 | 5.22 | 0.29 | 3.71E−05 | 2.29 | 4.9 |
| hsa-miR-598 | 7.98 | 0.33 | 5.76 | 0.74 | 3.02E−03 | 2.22 | 4.7 |
| hsa-miR-376b | 3.45 | 1.39 | 1.23 | 0.61 | 1.84E−02 | 2.22 | 4.7 |
| hsa-miR-765 | 4.47 | 1.66 | 2.28 | 0.68 | 3.50E−02 | 2.19 | 4.6 |
| hsa-miR-132* | 5.58 | 1.13 | 3.43 | 0.97 | 2.87E−02 | 2.15 | 4.4 |
| hsa-miR-552 | 2.05 | 1.77 | −0.04 | 0.24 | 3.30E−02 | 2.10 | 4.3 |
| hsa-miR-299-3p | 3.11 | 0.45 | 1.01 | 0.50 | 1.06E−03 | 2.09 | 4.3 |
| hsa-miR-659 | 3.47 | 1.46 | 1.42 | 0.91 | 4.66E−02 | 2.05 | 4.1 |
| hsa-miR-7-1* | 6.88 | 0.44 | 4.87 | 0.48 | 1.10E−03 | 2.01 | 4.0 |
| hsa-miR-1308 | 9.41 | 1.22 | 7.42 | 0.76 | 2.70E−02 | 1.99 | 4.0 |
| hsa-miR-1185 | 3.03 | 0.54 | 1.06 | 0.64 | 4.44E−03 | 1.97 | 3.9 |
| hsa-miR-326 | 3.61 | 0.14 | 1.66 | 0.29 | 4.02E−05 | 1.95 | 3.9 |
| hsa-miR-369-3p | 2.85 | 0.71 | 0.91 | 0.39 | 2.24E−03 | 1.94 | 3.8 |

TABLE 28-continued

MicroRNAs significantly differentially expressed between PTC and MTC samples.

| miRNA | MTC AVG | MTC SD | PTC AVG | PTC SD | MTC vs PTC ttest | MTC vs PTC Log2Diff | Fold change |
|---|---|---|---|---|---|---|---|
| hsa-miR-95 | 9.43 | 0.66 | 7.54 | 0.31 | 1.27E-03 | 1.89 | 3.7 |
| hsa-miR-148b | 9.64 | 0.55 | 7.77 | 0.67 | 6.84E-03 | 1.87 | 3.7 |
| hsa-miR-1182 | 2.54 | 1.51 | 0.68 | 0.68 | 4.85E-02 | 1.86 | 3.6 |
| hsa-miR-583 | 1.28 | 1.13 | −0.56 | 0.48 | 1.60E-02 | 1.84 | 3.6 |
| hsa-miR-648 | 1.76 | 1.29 | −0.03 | 0.72 | 4.16E-02 | 1.79 | 3.5 |
| hsa-miR-335* | 3.78 | 0.88 | 1.99 | 0.18 | 3.57E-03 | 1.79 | 3.5 |
| hsa-miR-337-3p | 3.15 | 0.43 | 1.41 | 0.59 | 4.44E-03 | 1.74 | 3.3 |
| hsa-miR-296-2* | 2.70 | 0.90 | 0.99 | 0.44 | 1.01E-02 | 1.71 | 3.3 |
| hsa-miR-526b | 2.01 | 0.89 | 0.32 | 0.75 | 2.70E-02 | 1.70 | 3.2 |
| hsa-miR-557 | 5.61 | 0.40 | 3.95 | 0.56 | 4.33E-03 | 1.66 | 3.2 |
| hsa-miR-128 | 8.29 | 0.89 | 6.69 | 0.27 | 7.67E-03 | 1.61 | 3.0 |
| hsa-miR-301a | 7.56 | 0.34 | 5.96 | 0.52 | 3.25E-03 | 1.61 | 3.0 |
| hsa-miR-582-3p | 0.19 | 0.32 | −1.38 | 0.37 | 8.97E-04 | 1.58 | 3.0 |
| hsa-miR-301b | 3.14 | 0.72 | 1.59 | 0.20 | 3.01E-03 | 1.55 | 2.9 |
| hsa-miR-1291 | 1.29 | 1.30 | −0.24 | 0.49 | 4.92E-02 | 1.53 | 2.9 |
| hsa-miR-656 | 2.09 | 0.62 | 0.58 | 0.26 | 2.59E-03 | 1.51 | 2.8 |
| hsa-miR-1224-5p | 5.65 | 1.15 | 4.26 | 0.47 | 4.66E-02 | 1.40 | 2.6 |
| hsa-miR-1321 | 1.56 | 1.15 | 0.17 | 0.39 | 4.17E-02 | 1.39 | 2.6 |
| hsa-miR-431* | 2.93 | 0.05 | 1.56 | 0.84 | 3.39E-02 | 1.37 | 2.6 |
| hsa-miR-642 | 0.65 | 0.41 | −0.71 | 0.63 | 1.64E-02 | 1.36 | 2.6 |
| hsa-miR-429 | 10.32 | 0.28 | 8.97 | 0.55 | 8.14E-03 | 1.35 | 2.5 |
| hsa-miR-29c* | 8.32 | 0.89 | 7.00 | 0.39 | 2.47E-02 | 1.32 | 2.5 |
| hsa-miR-371-5p | 4.11 | 0.92 | 2.81 | 0.43 | 3.12E-02 | 1.30 | 2.5 |
| hsa-miR-1268 | 7.86 | 0.70 | 6.57 | 0.52 | 2.35E-02 | 1.29 | 2.4 |
| hsa-miR-518c* | 0.79 | 0.80 | −0.49 | 0.55 | 3.48E-02 | 1.28 | 2.4 |
| hsa-miR-1250 | 0.92 | 0.27 | −0.34 | 0.68 | 2.34E-02 | 1.27 | 2.4 |
| hsa-miR-324-5p | 9.24 | 0.04 | 7.98 | 0.41 | 2.22E-03 | 1.26 | 2.4 |
| hsa-miR-640 | 0.08 | 0.59 | −1.15 | 0.15 | 3.43E-03 | 1.23 | 2.3 |
| hsa-miR-885-5p | 1.10 | 1.01 | −0.10 | 0.21 | 3.60E-02 | 1.20 | 2.3 |
| hsa-miR-505 | 6.04 | 0.67 | 4.84 | 0.28 | 1.10E-02 | 1.19 | 2.3 |
| hsa-miR-769-3p | 2.27 | 0.15 | 1.08 | 0.49 | 6.98E-03 | 1.19 | 2.3 |
| hsa-miR-1285 | 2.87 | 0.34 | 1.71 | 0.43 | 7.47E-03 | 1.16 | 2.2 |
| hsa-miR-1275 | 7.69 | 0.34 | 6.55 | 0.47 | 1.13E-02 | 1.14 | 2.2 |
| hsa-miR-584 | 3.13 | 0.35 | 2.03 | 0.45 | 1.15E-02 | 1.10 | 2.1 |
| hsa-miR-23b | 13.42 | 0.15 | 12.34 | 0.52 | 1.42E-02 | 1.08 | 2.1 |
| hsa-miR-505* | 5.07 | 0.90 | 4.00 | 0.23 | 3.85E-02 | 1.07 | 2.1 |
| hsa-miR-200a | 11.26 | 0.29 | 10.22 | 0.52 | 2.03E-02 | 1.04 | 2.1 |
| hsa-miR-421 | 3.49 | 0.48 | 2.47 | 0.49 | 2.75E-02 | 1.03 | 2.0 |
| hsa-miR-501-3p | 3.85 | 0.36 | 2.83 | 0.27 | 3.66E-03 | 1.02 | 2.0 |
| hsa-miR-340* | 5.17 | 0.53 | 4.16 | 0.42 | 2.39E-02 | 1.01 | 2.0 |
| hsa-miR-1303 | 0.31 | 0.54 | −0.67 | 0.28 | 1.37E-02 | 0.98 | 2.0 |
| hsa-miR-93* | 1.54 | 0.46 | 0.58 | 0.36 | 1.61E-02 | 0.96 | 2.0 |
| hsa-let-7e* | 3.07 | 0.28 | 2.15 | 0.31 | 6.14E-03 | 0.92 | 1.9 |
| hsa-miR-130b | 7.45 | 0.55 | 6.55 | 0.21 | 1.47E-02 | 0.90 | 1.9 |
| hsa-miR-145* | 5.48 | 0.47 | 4.58 | 0.41 | 2.80E-02 | 0.90 | 1.9 |
| hsa-miR-24-1* | 6.56 | 0.18 | 5.68 | 0.52 | 3.36E-02 | 0.88 | 1.8 |
| hsa-miR-145 | 10.23 | 0.51 | 9.37 | 0.28 | 1.99E-02 | 0.85 | 1.8 |
| hsa-miR-484 | 5.42 | 0.61 | 4.57 | 0.29 | 3.43E-02 | 0.85 | 1.8 |
| hsa-miR-181c | 8.44 | 0.26 | 7.59 | 0.35 | 1.12E-02 | 0.84 | 1.8 |
| hsa-miR-628-5p | 4.66 | 0.34 | 3.84 | 0.40 | 2.63E-02 | 0.82 | 1.8 |
| hsa-miR-143 | 8.13 | 0.51 | 7.32 | 0.28 | 2.44E-02 | 0.81 | 1.8 |
| hsa-miR-664* | 5.63 | 0.23 | 4.83 | 0.37 | 1.62E-02 | 0.80 | 1.7 |
| hsa-miR-886-5p | −0.90 | 0.48 | −1.68 | 0.30 | 2.88E-02 | 0.78 | 1.7 |
| hsa-miR-660 | 7.94 | 0.55 | 7.17 | 0.27 | 3.66E-02 | 0.76 | 1.7 |
| hsa-miR-769-5p | 5.73 | 0.25 | 5.00 | 0.21 | 4.68E-03 | 0.72 | 1.7 |
| hsa-miR-181e* | 5.32 | 0.15 | 4.63 | 0.41 | 3.31E-02 | 0.69 | 1.6 |
| hsa-miR-532-5p | 7.19 | 0.46 | 6.51 | 0.17 | 2.10E-02 | 0.68 | 1.6 |
| hsa-miR-454 | 6.74 | 0.18 | 6.07 | 0.19 | 2.79E-03 | 0.67 | 1.6 |
| hsa-miR-500* | 5.20 | 0.47 | 4.53 | 0.27 | 3.91E-02 | 0.67 | 1.6 |
| hsa-miR-320b | 10.06 | 0.28 | 9.39 | 0.34 | 2.94E-02 | 0.67 | 1.6 |
| hsa-miR-532-3p | 5.99 | 0.45 | 5.33 | 0.24 | 3.14E-02 | 0.67 | 1.6 |
| hsa-miR-99b | 9.49 | 0.13 | 8.86 | 0.20 | 2.88E-03 | 0.63 | 1.5 |
| hsa-let-7e | 12.78 | 0.21 | 12.15 | 0.24 | 9.41E-03 | 0.63 | 1.5 |
| hsa-miR-502-3p | 5.50 | 0.33 | 4.88 | 0.23 | 1.78E-02 | 0.62 | 1.5 |
| hsa-miR-320a | 8.92 | 0.11 | 8.30 | 0.30 | 1.49E-02 | 0.62 | 1.5 |
| hsa-miR-28-5p | 7.95 | 0.37 | 7.38 | 0.10 | 1.41E-02 | 0.57 | 1.5 |
| hsa-miR-103 | 12.16 | 0.15 | 11.61 | 0.32 | 3.19E-02 | 0.55 | 1.5 |
| hsa-miR-107 | 11.50 | 0.11 | 10.98 | 0.31 | 3.26E-02 | 0.52 | 1.4 |
| hsa-miR-331-3p | 10.80 | 0.08 | 10.30 | 0.23 | 1.10E-02 | 0.50 | 1.4 |
| hsa-miR-361-3p | 6.76 | 0.17 | 7.27 | 0.20 | 1.08E-02 | −0.51 | 1.4 |
| hsa-miR-92a | 8.81 | 0.44 | 9.35 | 0.16 | 4.07E-02 | −0.54 | 1.5 |
| hsa-miR-30e | 8.87 | 0.25 | 9.46 | 0.25 | 1.85E-02 | −0.59 | 1.5 |
| hsa-let-7g | 12.32 | 0.43 | 13.03 | 0.30 | 3.28E-02 | −0.71 | 1.6 |

TABLE 28-continued

MicroRNAs significantly differentially expressed between PTC and MTC samples.

| miRNA | MTC AVG | MTC SD | PTC AVG | PTC SD | MTC vs PTC ttest | MTC vs PTC Log2Diff | Fold change |
|---|---|---|---|---|---|---|---|
| hsa-miR-19b-1* | 2.09 | 0.30 | 2.85 | 0.25 | 7.79E-03 | -0.77 | 1.7 |
| hsa-miR-576-5p | 0.08 | 0.45 | 0.95 | 0.27 | 1.32E-02 | -0.87 | 1.8 |
| hsa-miR-17 | 8.57 | 0.68 | 9.48 | 0.14 | 2.27E-02 | -0.91 | 1.9 |
| hsa-miR-19a | 7.51 | 0.18 | 8.46 | 0.55 | 3.10E-02 | -0.95 | 1.9 |
| hsa-miR-489 | 2.06 | 0.80 | 3.05 | 0.37 | 4.84E-02 | -0.99 | 2.0 |
| hsa-miR-19b | 10.25 | 0.32 | 11.28 | 0.31 | 4.33E-03 | -1.02 | 2.0 |
| hsa-miR-1288 | 5.08 | 0.30 | 6.26 | 0.70 | 3.53E-02 | -1.18 | 2.3 |
| hsa-miR-181b | 8.33 | 0.79 | 9.59 | 0.52 | 3.24E-02 | -1.26 | 2.4 |
| hsa-miR-20a | 9.76 | 0.82 | 11.03 | 0.12 | 1.15E-02 | -1.27 | 2.4 |
| hsa-miR-1305 | 6.95 | 0.26 | 8.28 | 0.53 | 7.51E-02 | -1.32 | 2.5 |
| hsa-miR-34b* | 6.00 | 0.79 | 7.62 | 0.54 | 1.30E-02 | -1.62 | 3.1 |
| hsa-miR-130a | 9.83 | 1.43 | 11.54 | 0.45 | 4.15E-02 | -1.70 | 3.3 |
| hsa-miR-221* | 6.93 | 0.33 | 8.71 | 0.86 | 1.54E-02 | -1.79 | 3.5 |
| hsa-miR-625 | 4.29 | 0.64 | 6.17 | 0.25 | 8.95E-04 | -1.87 | 3.7 |
| hsa-miR-155 | 6.25 | 1.18 | 8.15 | 0.89 | 3.99E-02 | -1.90 | 3.7 |
| hsa-miR-514 | 1.03 | 1.14 | 2.93 | 0.86 | 3.54E-02 | -1.90 | 3.7 |
| hsa-let-7i | 12.62 | 0.95 | 14.53 | 0.18 | 3.56E-03 | -1.91 | 3.8 |
| hsa-let-7i* | 1.85 | 0.98 | 3.76 | 0.40 | 7.11E-03 | -1.91 | 3.8 |
| hsa-miR-34a | 10.62 | 0.71 | 12.59 | 0.24 | 1.02E-03 | -1.97 | 3.9 |
| hsa-miR-34a* | 3.09 | 0.61 | 5.07 | 0.21 | 4.58E-04 | -1.98 | 3.9 |
| hsa-miR-450a | 3.51 | 0.77 | 5.54 | 0.74 | 9.78E-03 | -2.03 | 4.1 |
| hsa-miR-424 | 8.41 | 1.24 | 10.51 | 0.68 | 1.91E-02 | -2.11 | 4.3 |
| hsa-miR-222 | 8.06 | 0.71 | 10.25 | 0.58 | 3.06E-03 | -2.19 | 4.6 |
| hsa-miR-542-3p | 4.19 | 1.06 | 6.39 | 0.81 | 1.53E-02 | -2.20 | 4.6 |
| hsa-miR-542-5p | 4.60 | 1.34 | 6.80 | 0.87 | 2.82E-02 | -2.20 | 4.6 |
| hsa-miR-503 | 3.46 | 1.63 | 5.74 | 0.81 | 3.53E-02 | -2.27 | 4.8 |
| hsa-miR-181a-2* | 3.33 | 0.74 | 6.23 | 0.66 | 1.16E-03 | -2.90 | 7.5 |
| hsa-miR-203 | 3.46 | 2.00 | 6.60 | 1.11 | 2.66E-02 | -3.14 | 8.8 |
| hsa-miR-146b-3p | -1.08 | 0.19 | 3.73 | 1.12 | 3.79E-04 | -4.81 | 28.1 |
| hsa-miR-31* | 2.44 | 2.19 | 8.58 | 0.56 | 7.76E-04 | -6.14 | 70.6 |
| hsa-miR-31 | 3.63 | 2.73 | 10.14 | 0.64 | 1.71E-02 | -6.51 | 91.3 |
| hsa-miR-551b | 3.35 | 1.29 | 9.98 | 0.58 | 4.92E-05 | -6.62 | 98.5 |
| hsa-miR-146b-5p | 7.19 | 1.17 | 14.41 | 0.92 | 6.71E-05 | -7.21 | 148.4 |

AVG, average expression among samples in a group;
SD, standard deviation

Example 27 miRNA Expression Profiling Distinguishes Anaplastic Thyroid Carcinoma and Follicular Variant of Papillary Thyroid Carcinoma A total of 93 human miRNAs were significantly differentially expressed between the anaplastic thyroid carcinoma sample (ATC) and the follicular variant of papillary thyroid carcinoma specimens (p<0.05) (Table 29). Of these, twenty seven miRNAs were expressed by at least 2-fold higher in the ATC sample compared to the FVPTC samples (Log 2 diff (ATC vs FVPTC)≥1). Among these, one miRNA (hsa-miR-9*) was expressed by more than 70-fold higher in ATC, six miRNAs (hsa-miR-582-5p, -582-3p, -9, -124, -34c-3p, and -210) were overexpressed in ATC by 10- to 30-fold, and twenty miRNAs were overexpressed by 2- to 10-fold in ATC compared to the FVPTC specimens. In addition, fifty three miRNAs were underexpressed by at least two fold in ATC compared to the FVPTC specimens. Among these, eight miRNAs (hsa-miR-429, -200b, -141, -200a, -200c, -135b, -135a, and -205) were underexpressed by 100- to 600-fold in ATC, eight miRNAs (hsa-miR-551 b, -200b*, -141*, -375, -200a*, -138, -31, and -1) were underexpressed by 20- to 80-fold in ATC, six miRNAs (hsa-miR-146b-5p, -512-3p, -125b, -222, -7i*, and -99a) were underexpressed by 10- to 20-fold in ATC, and 31 miRNAs were underexpressed by 2- to 10-fold in the ATC sample compared to the FVPTC specimens.

TABLE 29

MicroRNAs significantly differentially expressed between FVPTC and ATC samples.

| miRNA | ATC ATC | FVPTC AVG | FVPTC SD | ATC vs FVPTC ttest | ATC vs FVPTC Log2Diff | Fold change |
|---|---|---|---|---|---|---|
| hsa-miR-9* | 7.14 | 1.01 | 0.85 | 7.60E-03 | 6.14 | 70.3 |
| hsa-miR-582-5p | 8.42 | 3.55 | 0.77 | 1.10E-02 | 4.87 | 29.3 |
| hsa-miR-582-3p | 3.97 | -0.81 | 0.52 | 3.81E-03 | 4.78 | 27.4 |
| hsa-miR-9 | 5.05 | 0.41 | 0.75 | 1.16E-02 | 4.64 | 24.9 |
| hsa-miR-124 | 4.16 | -0.10 | 0.41 | 2.60E-03 | 4.26 | 19.1 |
| hsa-miR-34c-5p | 7.37 | 3.31 | 1.06 | 4.14E-02 | 4.05 | 16.6 |
| hsa-miR-210 | 8.74 | 5.26 | 0.39 | 4.22E-03 | 3.48 | 11.1 |
| hsa-miR-34b | 4.65 | 1.52 | 0.79 | 3.85E-02 | 3.13 | 8.7 |
| hsa-miR-34c-3p | 1.95 | -1.06 | 0.54 | 1.52E-02 | 3.02 | 8.1 |
| hsa-miR-155 | 10.25 | 7.48 | 0.68 | 3.56E-02 | 2.77 | 6.8 |
| hsa-miR-30a* | 10.32 | 8.17 | 0.45 | 2.34E-02 | 2.16 | 4.5 |
| hsa-miR-30a | 13.36 | 11.32 | 0.28 | 7.06E-03 | 2.04 | 4.1 |
| hsa-miR-376b | 2.37 | 0.60 | 0.24 | 7.44E-03 | 1.77 | 3.4 |
| hsa-miR-501-3p | 4.53 | 3.01 | 0.18 | 4.74E-03 | 1.52 | 2.9 |
| hsa-miR-500* | 5.90 | 4.40 | 0.17 | 4.10E-03 | 1.50 | 2.8 |
| hsa-miR-1201 | 2.48 | 1.00 | 0.35 | 3.19E-02 | 1.48 | 2.8 |
| hsa-miR-769-5p | 6.42 | 4.96 | 0.33 | 2.79E-02 | 1.47 | 2.8 |
| hsa-miR-660 | 8.23 | 6.82 | 0.24 | 1.36E-02 | 1.41 | 2.7 |
| hsa-miR-155* | 1.88 | 0.50 | 0.26 | 1.75E-02 | 1.38 | 2.6 |
| hsa-miR-502-3p | 6.19 | 4.88 | 0.20 | 9.56E-03 | 1.31 | 2.5 |
| hsa-miR-330-3p | 5.15 | 3.87 | 0.31 | 3.48E-02 | 1.28 | 2.4 |
| hsa-miR-362-5p | 6.59 | 5.32 | 0.34 | 4.30E-02 | 1.28 | 2.4 |
| hsa-miR-532-5p | 7.58 | 6.30 | 0.18 | 7.61E-03 | 1.28 | 2.4 |
| hsa-miR-149 | 5.28 | 4.01 | 0.23 | 1.58E-02 | 1.26 | 2.4 |
| hsa-miR-502-5p | 4.57 | 3.33 | 0.25 | 2.21E-02 | 1.23 | 2.4 |

TABLE 29-continued

MicroRNAs significantly differentially expressed between FVPTC and ATC samples.

| miRNA | ATC ATC | FVPTC AVG | FVPTC SD | ATC vs FVPTC ttest | ATC vs FVPTC Log2Diff | Fold change |
|---|---|---|---|---|---|---|
| hsa-miR-130b | 7.77 | 6.61 | 0.04 | 1.16E−04 | 1.16 | 2.2 |
| hsa-miR-656 | 1.64 | 0.50 | 0.26 | 2.93E−02 | 1.14 | 2.2 |
| hsa-miR-132 | 7.21 | 6.25 | 0.18 | 1.71E−02 | 0.96 | 1.9 |
| hsa-miR-532-3p | 6.00 | 5.10 | 0.09 | 2.51E−03 | 0.90 | 1.9 |
| hsa-miR-326 | 2.42 | 1.60 | 0.21 | 4.27E−02 | 0.81 | 1.8 |
| hsa-miR-376a* | 1.52 | 0.94 | 0.15 | 4.22E−02 | 0.58 | 1.5 |
| hsa-miR-197 | 6.10 | 5.66 | 0.07 | 8.74E−03 | 0.45 | 1.4 |
| hsa-miR-625* | 2.59 | 2.18 | 0.08 | 1.69E−02 | 0.41 | 1.3 |
| hsa-miR-320a | 8.16 | 8.38 | 0.03 | 7.87E−03 | −0.22 | 1.2 |
| hsa-miR-192 | 6.79 | 7.32 | 0.09 | 1.51E−02 | −0.54 | 1.4 |
| hsa-miR-513c | 2.33 | 2.98 | 0.11 | 1.19E−02 | −0.65 | 1.6 |
| hsa-miR-26a-1* | 0.60 | 1.29 | 0.18 | 3.93E−02 | −0.69 | 1.6 |
| hsa-miR-23b* | 3.49 | 4.28 | 0.15 | 1.90E−02 | −0.79 | 1.7 |
| hsa-miR-194* | −0.53 | 0.30 | 0.10 | 4.75E−03 | −0.84 | 1.8 |
| hsa-miR-17 | 8.41 | 9.27 | 0.20 | 2.97E−02 | −0.86 | 1.8 |
| hsa-miR-20a | 9.71 | 10.68 | 0.25 | 3.89E−02 | −0.97 | 2.0 |
| hsa-miR-34a | 11.30 | 12.33 | 0.27 | 3.98E−02 | −1.04 | 2.0 |
| hsa-miR-93 | 7.61 | 8.66 | 0.25 | 3.43E−02 | −1.05 | 2.1 |
| hsa-miR-130a | 10.22 | 11.34 | 0.23 | 2.17E−02 | −1.12 | 2.2 |
| hsa-miR-892a | −0.72 | 0.43 | 0.31 | 4.69E−02 | −1.15 | 2.2 |
| hsa-miR-192* | 0.63 | 1.80 | 0.31 | 4.47E−02 | −1.17 | 2.3 |
| hsa-miR-423-5p | 5.61 | 6.89 | 0.29 | 3.01E−02 | −1.28 | 2.4 |
| hsa-miR-30b* | 3.11 | 4.41 | 0.30 | 3.01E−02 | −1.30 | 2.5 |
| hsa-miR-508-5p | −2.20 | −0.86 | 0.25 | 1.68E−02 | −1.34 | 2.5 |
| hsa-miR-17* | 3.60 | 4.99 | 0.39 | 4.83E−02 | −1.39 | 2.6 |
| hsa-miR-92a | 7.77 | 9.23 | 0.13 | 2.09E−03 | −1.46 | 2.7 |
| hsa-miR-19b-1* | 1.32 | 2.79 | 0.34 | 3.16E−02 | −1.47 | 2.8 |
| hsa-miR-585 | 0.44 | 2.14 | 0.40 | 3.27E−02 | −1.70 | 3.2 |
| hsa-miR-20a* | 2.51 | 4.23 | 0.45 | 4.25E−02 | −1.71 | 3.3 |
| hsa-let-7c | 10.68 | 12.54 | 0.33 | 1.56E−02 | −1.86 | 3.6 |
| hsa-let-7g* | −2.14 | −0.24 | 0.12 | 6.89E−04 | −1.89 | 3.7 |
| hsa-miR-886-3p | 7.26 | 9.21 | 0.51 | 4.26E−02 | −1.95 | 3.9 |
| hsa-miR-26a | 10.36 | 12.32 | 0.41 | 2.36E−02 | −1.96 | 3.9 |
| hsa-miR-143* | 1.36 | 3.34 | 0.45 | 2.87E−02 | −1.98 | 3.9 |
| hsa-miR-744 | 2.84 | 5.11 | 0.34 | 9.14E−03 | −2.27 | 4.8 |
| hsa-miR-144 | 4.43 | 6.93 | 0.46 | 1.66E−02 | −2.50 | 5.6 |
| hsa-miR-346 | −1.38 | 1.18 | 0.24 | 2.31E−03 | −2.56 | 5.9 |
| hsa-miR-125b-2* | 2.65 | 5.28 | 0.34 | 5.97E−03 | −2.63 | 6.2 |
| hsa-let-7i | 11.99 | 14.62 | 0.43 | 1.24E−02 | −2.63 | 6.2 |
| hsa-miR-452 | 1.57 | 4.32 | 0.51 | 1.71E−02 | −2.75 | 6.7 |
| hsa-miR-139-5p | 2.79 | 5.57 | 0.68 | 3.57E−02 | −2.78 | 6.9 |
| hsa-miR-200c* | −0.83 | 2.07 | 0.45 | 1.06E−02 | −2.90 | 7.5 |
| hsa-miR-222* | −2.06 | 0.85 | 0.42 | 8.46E−03 | −2.91 | 7.5 |
| hsa-miR-491-5p | −1.33 | 1.65 | 0.46 | 1.03E−02 | −2.99 | 7.9 |
| hsa-miR-145 | 6.78 | 9.81 | 0.83 | 4.68E−02 | −3.03 | 8.2 |
| hsa-miR-221* | 4.78 | 8.06 | 0.85 | 4.13E−02 | −3.29 | 9.8 |
| hsa-miR-99a | 8.00 | 11.35 | 0.30 | 2.09E−03 | −3.36 | 10.3 |
| hsa-let-7i* | 0.07 | 3.66 | 0.74 | 2.29E−02 | −3.58 | 12.0 |
| hsa-miR-222 | 6.04 | 9.66 | 0.79 | 2.64E−02 | −3.62 | 12.3 |
| hsa-miR-125b | 10.44 | 14.14 | 0.44 | 5.03E−03 | −3.69 | 13.0 |
| hsa-miR-512-3p | 0.39 | 4.27 | 0.48 | 5.45E−03 | −3.89 | 14.8 |
| hsa-miR-146b-5p | 9.04 | 13.20 | 1.09 | 4.17E−02 | −4.16 | 17.9 |
| hsa-miR-1 | 3.13 | 7.49 | 1.20 | 4.82E−02 | −4.35 | 20.4 |
| hsa-miR-31 | 5.65 | 10.06 | 1.12 | 3.87E−02 | −4.41 | 21.3 |
| hsa-miR-138 | 0.09 | 4.85 | 0.81 | 1.33E−02 | −4.76 | 27.1 |
| hsa-miR-200a* | 0.46 | 5.38 | 0.59 | 5.00E−03 | −4.92 | 30.3 |
| hsa-miR-375 | 1.27 | 6.25 | 1.32 | 4.28E−02 | −4.99 | 31.7 |
| hsa-miR-141* | −1.68 | 3.56 | 0.53 | 3.04E−03 | −5.23 | 37.7 |
| hsa-miR-200b* | 0.48 | 5.82 | 0.47 | 2.01E−03 | −5.34 | 40.5 |
| hsa-miR-551b | 2.61 | 8.99 | 0.76 | 4.92E−03 | −6.37 | 83.0 |
| hsa-miR-205 | −1.95 | 4.92 | 1.61 | 3.15E−02 | −6.87 | 116.9 |
| hsa-miR-135a | 1.19 | 8.34 | 1.41 | 2.02E−02 | −7.15 | 142.1 |
| hsa-miR-135b | 2.20 | 10.27 | 0.91 | 4.23E−03 | −8.08 | 269.9 |
| hsa-miR-200c | 3.00 | 11.67 | 0.33 | 1.72E−04 | −8.67 | 407.2 |
| hsa-miR-200a | 1.45 | 10.20 | 0.62 | 1.05E−03 | −8.75 | 430.1 |
| hsa-miR-141 | 2.51 | 11.36 | 0.71 | 1.58E−03 | −8.85 | 461.2 |
| hsa-miR-200b | 2.93 | 11.82 | 0.67 | 1.31E−03 | −8.89 | 474.4 |
| hsa-miR-429 | −0.05 | 9.17 | 0.77 | 1.74E−03 | −9.23 | 599.6 |

AVG, average expression among samples in a group;
SD, standard deviation

Example 28 miRNA Expression Profiling Distinguishes the Follicular Variant of Papillary Thyroid Carcinoma and Medullary Thyroid Carcinoma A total of 142 human miRNAs were significantly differentially expressed between the follicular variant of papillary thyroid carcinoma samples and the medullary thyroid carcinoma specimens (p<0.05) (Table 30). Of these, nineteen miRNAs were expressed at levels at least 2-fold higher in the FVPTC samples compared to the MTC specimens (Log 2 diff (FVPTC vs MTC)≥1). Among these, four miRNAs (has-miR-31, -31*, 146b-5p, and -55b) were expressed by 40- to 90-fold higher in FVPTC, hsa-miR-146b-3p) was expresses by at least 10-fold higher in FVPTC, and fourteen miRNAs were expressed by 2- to 10-fold higher in the FVPTC samples compared to the MTC specimens. In addition, ninety six miRNAs were underexpressed by at least two-fold in the FVPTC samples compared to the MTC specimens. Among these, four miRNAs (hsa-miR-124, -375, -323-3p, and -7) were underexpressed by 100- to 250-fold in FVPTC, six miRNAs (hsa-miR-129-5p, -153, -410, -487b, -432, and -433) were underexpressed by 400- to 100-fold in FVPTC, seventeen miRNAs were underexpressed by 20- to 40-fold in FVPTC, seventeen miRNAs were underexpressed by 10- to 20-fold in FVPTC, and 52 miRNAs were underexpressed by 2- to 10-fold in FVPTC samples compared to the MTC specimens.

TABLE 30

MicroRNAs significantly differentially expressed between FVPTC and MTC samples.

| miRNA | FVPTC AVG | FVPTC SD | MTC AVG | MTC SD | FVPTC vs MTC ttest | FVPTC vs MTC Log2Diff | Fold change |
|---|---|---|---|---|---|---|---|
| hsa-miR-31 | 10.06 | 1.12 | 3.63 | 2.73 | 7.28E−03 | 6.43 | 86.3 |
| hsa-miR-31* | 8.47 | 1.06 | 2.44 | 2.19 | 4.45E−03 | 6.03 | 65.3 |
| hsa-miR-146b-5p | 13.20 | 1.09 | 7.19 | 1.17 | 9.10E−04 | 6.01 | 64.3 |
| hsa-miR-551b | 8.99 | 0.76 | 3.35 | 1.29 | 7.34E−04 | 5.63 | 49.6 |
| hsa-miR-146b-3p | 2.46 | 1.30 | −1.08 | 0.19 | 5.96E−03 | 3.55 | 11.7 |
| hsa-miR-542-3p | 7.01 | 1.32 | 4.19 | 1.06 | 2.91E−02 | 2.82 | 7.1 |
| hsa-miR-542-5p | 7.34 | 1.07 | 4.60 | 1.34 | 2.90E−02 | 2.74 | 6.7 |

TABLE 30-continued

MicroRNAs significantly differentially expressed between FVPTC and MTC samples.

| miRNA | FVPTC AVG | FVPTC SD | MTC AVG | MTC SD | FVPTC vs MTC ttest | FVPTC vs MTC Log2Diff | Fold change |
|---|---|---|---|---|---|---|---|
| hsa-miR-503 | 6.07 | 1.04 | 3.46 | 1.63 | 4.80E−02 | 2.60 | 6.1 |
| hsa-miR-181a-2* | 5.91 | 1.15 | 3.33 | 0.74 | 2.01E−02 | 2.58 | 6.0 |
| hsa-miR-1 | 7.49 | 1.20 | 5.17 | 1.04 | 4.47E−02 | 2.32 | 5.0 |
| hsa-let-7i | 14.62 | 0.43 | 12.62 | 0.95 | 1.24E−02 | 2.00 | 4.0 |
| hsa-let-7i* | 3.66 | 0.74 | 1.85 | 0.98 | 3.82E−02 | 1.81 | 3.5 |
| hsa-miR-886-3p | 9.21 | 0.51 | 7.47 | 1.00 | 2.83E−02 | 1.74 | 3.3 |
| hsa-miR-34a | 12.33 | 0.27 | 10.62 | 0.71 | 6.22E−03 | 1.71 | 3.3 |
| hsa-miR-34a* | 4.76 | 0.31 | 3.09 | 0.61 | 4.90E−03 | 1.67 | 3.2 |
| hsa-miR-222 | 9.66 | 0.79 | 8.06 | 0.71 | 3.95E−02 | 1.60 | 3.0 |
| hsa-miR-625 | 5.66 | 0.26 | 4.29 | 0.64 | 1.07E−02 | 1.37 | 2.6 |
| hsa-miR-34b* | 7.29 | 0.41 | 6.00 | 0.79 | 3.54E−02 | 1.29 | 2.4 |
| hsa-miR-222* | 0.85 | 0.42 | −0.37 | 0.76 | 3.93E−02 | 1.22 | 2.3 |
| hsa-miR-944 | 0.72 | 0.21 | −0.02 | 0.10 | 2.56E−03 | 0.74 | 1.7 |
| hsa-miR-19b-1* | 2.79 | 0.34 | 2.09 | 0.30 | 3.82E−02 | 0.70 | 1.6 |
| hsa-miR-585 | 2.14 | 0.40 | 1.44 | 0.15 | 3.80E−02 | 0.70 | 1.6 |
| hsa-let-7b* | 1.95 | 0.36 | 1.29 | 0.08 | 2.99E−02 | 0.65 | 1.6 |
| hsa-let-7b | 13.90 | 0.18 | 13.28 | 0.41 | 4.09E−02 | 0.62 | 1.5 |
| hsa-miR-18b* | 2.07 | 0.24 | 1.52 | 0.31 | 4.35E−02 | 0.55 | 1.5 |
| hsa-miR-548c-5p | 2.23 | 0.05 | 1.70 | 0.27 | 1.02E−02 | 0.53 | 1.4 |
| hsa-miR-513c | 2.98 | 0.11 | 2.52 | 0.29 | 3.00E−02 | 0.46 | 1.4 |
| hsa-miR-574-3p | 6.16 | 0.14 | 6.59 | 0.05 | 3.72E−03 | −0.44 | 1.4 |
| hsa-miR-320b | 9.63 | 0.15 | 10.06 | 0.28 | 4.28E−02 | −0.44 | 1.4 |
| hsa-miR-103 | 11.67 | 0.18 | 12.16 | 0.15 | 1.30E−02 | −0.49 | 1.4 |
| hsa-miR-501-5p | 4.15 | 0.14 | 4.64 | 0.32 | 3.84E−02 | −0.49 | 1.4 |
| hsa-miR-320a | 8.38 | 0.03 | 8.92 | 0.11 | 2.46E−04 | −0.54 | 1.5 |
| hsa-miR-107 | 10.95 | 0.26 | 11.50 | 0.11 | 1.91E−02 | −0.56 | 1.5 |
| hsa-miR-770-5p | 2.61 | 0.27 | 3.18 | 0.21 | 3.07E−02 | −0.57 | 1.5 |
| hsa-miR-502-3p | 4.88 | 0.20 | 5.50 | 0.33 | 2.47E−02 | −0.62 | 1.5 |
| hsa-miR-769-5p | 4.96 | 0.33 | 5.73 | 0.25 | 1.99E−02 | −0.77 | 1.7 |
| hsa-miR-181e* | 4.55 | 0.48 | 5.32 | 0.15 | 4.59E−02 | −0.78 | 1.7 |
| hsa-miR-500* | 4.40 | 0.17 | 5.20 | 0.47 | 2.44E−02 | −0.79 | 1.7 |
| hsa-miR-23b | 12.59 | 0.41 | 13.42 | 0.15 | 2.31E−02 | −0.82 | 1.8 |
| hsa-miR-501-3p | 3.01 | 0.18 | 3.85 | 0.36 | 9.70E−03 | −0.83 | 1.8 |
| hsa-miR-130b | 6.61 | 0.04 | 7.45 | 0.55 | 2.61E−02 | −0.84 | 1.8 |
| hsa-miR-24-1* | 5.70 | 0.42 | 6.56 | 0.18 | 2.19E−02 | −0.86 | 1.8 |
| hsa-miR-532-5p | 6.30 | 0.18 | 7.19 | 0.46 | 1.49E−02 | −0.89 | 1.9 |
| hsa-miR-532-3p | 5.10 | 0.09 | 5.99 | 0.45 | 1.02E−02 | −0.90 | 1.9 |
| hsa-miR-181c | 7.54 | 0.43 | 8.44 | 0.26 | 2.45E−02 | −0.90 | 1.9 |
| hsa-miR-454 | 5.79 | 0.59 | 6.74 | 0.18 | 4.46E−02 | −0.96 | 1.9 |
| hsa-miR-582-3p | −0.81 | 0.52 | 0.19 | 0.32 | 3.39E−02 | −1.00 | 2.0 |
| hsa-miR-628-5p | 3.62 | 0.46 | 4.66 | 0.34 | 2.19E−02 | −1.04 | 2.1 |
| hsa-miR-365 | 7.90 | 0.40 | 8.96 | 0.32 | 1.34E−02 | −1.06 | 2.1 |
| hsa-miR-200a | 10.20 | 0.62 | 11.26 | 0.29 | 4.14E−02 | −1.06 | 2.1 |
| hsa-miR-484 | 4.30 | 0.53 | 5.42 | 0.61 | 4.86E−02 | −1.12 | 2.2 |
| hsa-miR-660 | 6.82 | 0.24 | 7.94 | 0.55 | 1.40E−02 | −1.12 | 2.2 |
| hsa-miR-1285 | 1.68 | 0.67 | 2.87 | 0.34 | 3.89E−02 | −1.19 | 2.3 |
| hsa-miR-340* | 3.95 | 0.67 | 5.17 | 0.53 | 4.94E−02 | −1.22 | 2.3 |
| hsa-miR-193b | 6.75 | 0.59 | 7.99 | 0.51 | 3.39E−02 | −1.24 | 2.4 |
| hsa-miR-505 | 4.79 | 0.33 | 6.04 | 0.67 | 2.16E−02 | −1.25 | 2.4 |
| hsa-miR-421 | 2.20 | 0.69 | 3.49 | 0.48 | 4.07E−02 | −1.29 | 2.4 |
| hsa-miR-324-5p | 7.92 | 0.33 | 9.24 | 0.04 | 1.12E−02 | −1.32 | 2.5 |
| hsa-miR-212 | 4.55 | 0.44 | 5.93 | 0.76 | 2.82E−02 | −1.38 | 2.6 |
| hsa-miR-517b | 0.08 | 0.58 | 1.50 | 0.86 | 4.56E−02 | −1.42 | 2.7 |
| hsa-miR-301b | 1.69 | 0.31 | 3.14 | 0.72 | 1.38E−02 | −1.45 | 2.7 |
| hsa-miR-29c* | 6.86 | 0.34 | 8.32 | 0.89 | 2.77E−02 | −1.46 | 2.8 |
| hsa-miR-29b-2* | 1.18 | 0.35 | 2.70 | 0.90 | 2.53E−02 | −1.52 | 2.9 |
| hsa-miR-656 | 0.50 | 0.26 | 2.09 | 0.62 | 5.28E−03 | −1.59 | 3.0 |
| hsa-miR-301a | 5.93 | 0.56 | 7.56 | 0.34 | 6.97E−03 | −1.63 | 3.1 |
| hsa-miR-128 | 6.57 | 0.42 | 8.29 | 0.89 | 1.80E−02 | −1.72 | 3.3 |
| hsa-miR-148b | 7.91 | 0.86 | 9.64 | 0.55 | 2.91E−02 | −1.73 | 3.3 |
| hsa-miR-337-3p | 1.37 | 0.42 | 3.15 | 0.43 | 2.79E−03 | −1.78 | 3.4 |
| hsa-miR-335* | 1.94 | 0.38 | 3.78 | 0.88 | 1.23E−02 | −1.84 | 3.6 |
| hsa-miR-95 | 7.55 | 0.84 | 9.43 | 0.66 | 2.40E−02 | −1.89 | 3.7 |
| hsa-miR-598 | 6.08 | 0.57 | 7.98 | 0.33 | 3.78E−02 | −1.90 | 3.7 |
| hsa-miR-642 | −1.29 | 0.91 | 0.65 | 0.41 | 1.99E−02 | −1.94 | 3.8 |
| hsa-miR-326 | 1.60 | 0.21 | 3.61 | 0.14 | 3.27E−05 | −2.01 | 4.0 |
| hsa-miR-652 | 5.43 | 0.43 | 7.51 | 0.29 | 8.23E−04 | −2.08 | 4.2 |
| hsa-miR-369-3p | 0.75 | 0.18 | 2.85 | 0.71 | 2.04E−02 | −2.10 | 4.3 |
| hsa-miR-299-3p | 0.98 | 0.74 | 3.11 | 0.45 | 7.29E−03 | −2.13 | 4.4 |
| hsa-miR-654-5p | 2.15 | 0.43 | 4.30 | 0.31 | 7.49E−04 | −2.14 | 4.4 |
| hsa-miR-486-3p | 1.20 | 0.92 | 3.41 | 0.41 | 1.27E−02 | −2.20 | 4.6 |
| hsa-miR-668 | −0.93 | 0.84 | 1.30 | 0.42 | 8.78E−03 | −2.24 | 4.7 |
| hsa-miR-132* | 3.28 | 0.43 | 5.58 | 1.13 | 1.22E−02 | −2.30 | 4.9 |

TABLE 30-continued

MicroRNAs significantly differentially expressed between FVPTC and MTC samples.

| miRNA | FVPTC AVG | FVPTC SD | MTC AVG | MTC SD | FVPTC vs MTC ttest | Log2Diff | Fold change |
|---|---|---|---|---|---|---|---|
| hsa-miR-7-1* | 4.57 | 0.67 | 6.88 | 0.44 | 3.64E-03 | -2.31 | 5.0 |
| hsa-miR-330-3p | 3.87 | 0.31 | 6.34 | 0.46 | 3.55E-04 | -2.47 | 5.5 |
| hsa-miR-582-5p | 3.55 | 0.77 | 6.13 | 0.18 | 2.62E-03 | -2.58 | 6.0 |
| hsa-miR-1185 | 0.44 | 0.42 | 3.03 | 0.54 | 8.29E-04 | -2.58 | 6.0 |
| hsa-miR-96 | 8.40 | 1.66 | 11.01 | 0.48 | 4.92E-02 | -2.61 | 6.1 |
| hsa-miR-370 | 2.08 | 1.06 | 4.77 | 0.36 | 9.02E-03 | -2.69 | 6.5 |
| hsa-miR-132 | 6.25 | 0.18 | 8.97 | 1.15 | 4.92E-03 | -2.71 | 6.6 |
| hsa-miR-338-3p | 6.51 | 0.41 | 9.34 | 0.35 | 2.04E-04 | -2.83 | 7.1 |
| hsa-miR-890 | -0.21 | 0.63 | 2.63 | 1.99 | 4.04E-04 | -2.84 | 7.2 |
| hsa-miR-376b | 0.60 | 0.24 | 3.45 | 1.39 | 8.98E-03 | -2.85 | 7.2 |
| hsa-miR-182 | 2.98 | 1.64 | 5.90 | 0.30 | 3.06E-02 | -2.92 | 7.6 |
| hsa-miR-1301 | 0.53 | 0.77 | 3.45 | 0.62 | 2.99E-03 | -2.93 | 7.6 |
| hsa-miR-299-5p | 2.29 | 0.48 | 5.22 | 0.48 | 5.11E-04 | -2.93 | 7.6 |
| hsa-miR-377* | 0.00 | 1.03 | 2.94 | 0.16 | 4.97E-03 | -2.95 | 7.7 |
| hsa-miR-183* | 1.36 | 1.22 | 4.36 | 0.40 | 1.04E-02 | -3.00 | 8.0 |
| hsa-miR-10a* | 0.79 | 0.52 | 3.82 | 0.57 | 7.18E-05 | -3.04 | 8.2 |
| hsa-miR-337-5p | 2.04 | 0.52 | 5.33 | 0.33 | 2.22E-04 | -3.29 | 9.8 |
| hsa-miR-154* | 1.53 | 0.45 | 4.83 | 0.62 | 4.22E-04 | -3.30 | 9.8 |
| hsa-miR-493* | 1.99 | 0.43 | 5.39 | 0.45 | 1.61E-04 | -3.40 | 10.6 |
| hsa-miR-335 | 5.53 | 0.63 | 9.06 | 1.56 | 8.42E-03 | -3.53 | 11.5 |
| hsa-miR-183 | 6.84 | 1.37 | 10.49 | 0.69 | 8.77E-03 | -3.65 | 12.6 |
| hsa-miR-376a* | 0.94 | 0.15 | 4.63 | 0.44 | 1.72E-05 | -3.69 | 12.9 |
| hsa-miR-654-3p | 2.50 | 0.40 | 6.30 | 0.51 | 9.98E-05 | -3.80 | 13.9 |
| hsa-miR-411 | 0.96 | 0.91 | 4.80 | 0.24 | 9.12E-04 | -3.84 | 14.3 |
| hsa-miR-329 | 0.28 | 0.26 | 4.13 | 0.15 | 3.20E-06 | -3.85 | 14.4 |
| hsa-miR-431 | 1.04 | 0.82 | 5.00 | 1.06 | 2.51E-03 | -3.96 | 15.6 |
| hsa-miR-889 | -0.20 | 0.76 | 3.79 | 0.54 | 6.11E-04 | -3.99 | 15.9 |
| hsa-miR-10a | 7.60 | 0.79 | 11.69 | 0.52 | 5.80E-04 | -4.09 | 17.0 |
| hsa-miR-136 | 2.50 | 0.44 | 6.61 | 0.51 | 8.87E-05 | -4.11 | 17.2 |
| hsa-miR-485-5p | -0.09 | 1.02 | 4.03 | 0.40 | 1.25E-03 | -4.12 | 17.4 |
| hsa-miR-485-3p | 0.13 | 0.91 | 4.27 | 0.37 | 7.61E-04 | -4.14 | 17.7 |
| hsa-miR-377 | 3.32 | 0.35 | 7.51 | 0.55 | 5.86E-05 | -4.19 | 18.3 |
| hsa-miR-9 | 0.41 | 0.75 | 4.69 | 1.56 | 4.56E-03 | -4.27 | 19.3 |
| hsa-miR-9* | 1.01 | 0.85 | 5.31 | 1.78 | 7.67E-03 | -4.30 | 19.6 |
| hsa-miR-154 | 2.54 | 0.38 | 6.86 | 0.17 | 9.35E-06 | -4.32 | 19.9 |
| hsa-miR-543 | 0.93 | 0.40 | 5.30 | 0.05 | 8.61E-06 | -4.37 | 20.6 |
| hsa-miR-376c | 4.84 | 0.47 | 9.21 | 0.81 | 2.71E-04 | -4.37 | 20.7 |
| hsa-miR-369-5p | 0.89 | 0.48 | 5.27 | 0.72 | 1.96E-04 | -4.38 | 20.8 |
| hsa-miR-409-3p | 2.81 | 0.60 | 7.21 | 0.31 | 8.88E-05 | -4.41 | 21.2 |
| hsa-miR-376a | 4.10 | 0.40 | 8.51 | 0.67 | 1.07E-04 | -4.41 | 21.2 |
| hsa-miR-379 | 1.74 | 0.86 | 6.20 | 0.14 | 3.28E-04 | -4.46 | 22.0 |
| hsa-miR-495 | 2.45 | 0.45 | 6.93 | 0.28 | 2.42E-05 | -4.48 | 22.3 |
| hsa-miR-409-5p | 0.42 | 0.59 | 4.92 | 0.15 | 5.62E-05 | -4.50 | 22.6 |
| hsa-miR-137 | 0.50 | 1.37 | 5.03 | 3.11 | 4.53E-02 | -4.52 | 23.0 |
| hsa-miR-381 | 2.81 | 0.74 | 7.34 | 0.33 | 1.97E-04 | -4.53 | 23.1 |
| hsa-miR-758 | 0.44 | 0.95 | 5.04 | 0.13 | 4.53E-04 | -4.60 | 24.2 |
| hsa-miR-127-3p | 4.25 | 0.75 | 8.88 | 0.37 | 1.98E-04 | -4.64 | 24.9 |
| hsa-miR-382 | 1.76 | 0.44 | 6.53 | 0.24 | 1.39E-05 | -4.77 | 27.3 |
| hsa-miR-136* | 1.39 | 0.40 | 6.41 | 0.51 | 2.62E-05 | -5.02 | 32.3 |
| hsa-miR-592 | 2.41 | 0.91 | 7.50 | 1.19 | 1.32E-03 | -5.09 | 34.0 |
| hsa-miR-487a | -0.33 | 0.87 | 4.79 | 0.32 | 2.17E-05 | -5.12 | 34.7 |
| hsa-miR-539 | 1.31 | 0.24 | 6.53 | 0.34 | 2.25E-06 | -5.22 | 37.3 |
| hsa-miR-433 | -1.20 | 0.60 | 4.13 | 0.61 | 8.50E-05 | -5.33 | 40.2 |
| hsa-miR-432 | 2.04 | 0.63 | 7.61 | 0.36 | 3.92E-05 | -5.57 | 47.4 |
| hsa-miR-487b | 4.12 | 0.35 | 9.75 | 0.19 | 2.07E-06 | -5.63 | 49.5 |
| hsa-miR-410 | 1.65 | 0.58 | 8.20 | 0.14 | 7.92E-06 | -6.54 | 93.2 |
| hsa-miR-153 | 1.52 | 0.89 | 8.11 | 1.07 | 2.90E-04 | -6.59 | 96.3 |
| hsa-miR-129-5p | -0.79 | 1.02 | 5.85 | 5.05 | 4.58E-02 | -6.64 | 99.7 |
| hsa-miR-7 | 7.22 | 2.56 | 13.88 | 0.95 | 8.45E-03 | -6.66 | 101.1 |
| hsa-miR-323-3p | -0.32 | 0.52 | 6.93 | 0.13 | 2.72E-06 | -7.24 | 151.3 |
| hsa-miR-375 | 6.25 | 1.32 | 13.86 | 0.40 | 2.20E-04 | -7.61 | 195.5 |
| hsa-miR-124 | -0.10 | 0.41 | 7.86 | 3.11 | 3.39E-03 | -7.96 | 248.9 |

AVG, average expression among samples in a group;
SD, standard deviation

Example 29 miRNA Expression Profiling Distinguishes Hyperplastic Nodules (NOD) and Follicular Cell-Derived Neoplasms (FA, FTC, PTC, and FVPTC)

The inventors sought to determine whether miRNAs could distinguish between benign hyperplastic nodules (NOD) and diseased thyroid nodules (FA, FTC, PTC, and FVPTC), which is of important clinical utility for the preoperative assessment and management of patients with thyroid nodules. miRNA expression profiles of hyperplastic nodules (NOD) and those of the most common follicular cell-derived neoplasms (FA, FTC, FTC, and FVPTC) were compared. A total of 201 human miRNAs were significantly differentially expressed between the hyperplastic nodules and the follicular cell-derived neoplasm specimens ($p<0.05$). Of these, one hundred forty four miRNAs were expressed at levels at least 2-fold higher (Log 2 diff (NOD vs FA, FTC, FTC, and FVPTC)≥1) and twenty-two miRNAs were expressed at levels that were at least 2-fold lower in the NOD specimens as compared to the follicular cell-derived neoplasm specimens (Table 31). Among the miRNAs expressed at higher average levels in NOD, hsa-miR-206 was overexpressed by 27-fold, thirteen miRNAs (hsa-miR-92b*, -1202, -1300, -663, -149*, -631, -936, -187*, -1182, -198, -765, -648, and -934) were overexpressed by 10- to 20-fold, forty five miRNAs were overexpressed by 5- to 10-fold, and eighty five miRNAs were overexpressed by 2- to 5-fold. Among the miRNAs expressed at lower average levels in NOD, five (hsa-miR-1274a, -1274b, -221, -720, and -1260) were underexpressed by at least 5-fold, and seventeen miRNAs were underexpressed by 2- to 5-fold (Table 31).

TABLE 31

MicroRNAs significantly differentially expressed between NOD and follicular cell-derived neoplasms (FA, FTC, PTC, and FVPTC.

| miRNA | NOD Avg | NOD SD | FA, FTC, PTC, FVPTC Avg | FA, FTC, PTC, FVPTC SD | NOD vs FA, FTC, PTC, FVPTC ttest | NOD vs FA, FTC, PTC, FVPTC Log2Diff | Fold change |
|---|---|---|---|---|---|---|---|
| hsa-miR-206 | 4.98 | 3.14 | 0.18 | 1.69 | 2.20E−04 | 4.80 | 27.9 |
| hsa-miR-92b* | 2.62 | 0.57 | −1.40 | 0.96 | 8.67E−08 | 4.01 | 16.1 |
| hsa-miR-1202 | 13.40 | 0.83 | 9.44 | 1.31 | 1.08E−05 | 3.96 | 15.5 |
| hsa-miR-1300 | 7.45 | 0.80 | 3.58 | 1.01 | 4.73E−07 | 3.87 | 14.6 |
| hsa-miR-663 | 8.28 | 0.78 | 4.52 | 1.21 | 7.45E−06 | 3.76 | 13.6 |
| hsa-miR-149* | 4.33 | 0.61 | 0.67 | 1.15 | 4.59E−06 | 3.66 | 12.6 |
| hsa-miR-631 | 3.62 | 0.57 | 0.05 | 1.41 | 7.36E−05 | 3.57 | 11.9 |
| hsa-miR-936 | 4.20 | 0.65 | 0.69 | 1.08 | 3.83E−06 | 3.51 | 11.4 |
| hsa-miR-187* | 4.38 | 0.72 | 0.88 | 1.05 | 3.20E−06 | 3.50 | 11.3 |
| hsa-miR-1182 | 4.41 | 0.79 | 0.92 | 1.03 | 2.57E−06 | 3.50 | 11.3 |
| hsa-miR-198 | 4.55 | 0.67 | 1.07 | 1.11 | 6.22E−06 | 3.48 | 11.2 |
| hsa-miR-765 | 6.28 | 0.71 | 2.80 | 1.14 | 8.81E−06 | 3.48 | 11.1 |
| hsa-miR-648 | 3.78 | 0.49 | 0.33 | 1.13 | 7.27E−06 | 3.46 | 11.0 |
| hsa-miR-934 | 1.75 | 0.72 | −1.58 | 1.03 | 4.80E−06 | 3.33 | 10.0 |
| hsa-miR-483-5p | 8.12 | 0.81 | 4.92 | 1.14 | 2.94E−05 | 3.20 | 9.2 |
| hsa-miR-623 | 4.60 | 0.57 | 1.47 | 0.97 | 4.31E−06 | 3.13 | 8.8 |
| hsa-miR-493 | 2.58 | 0.75 | −0.54 | 0.97 | 5.48E−06 | 3.12 | 8.7 |
| hsa-miR-659 | 5.18 | 0.64 | 2.08 | 1.16 | 4.64E−05 | 3.09 | 8.5 |
| hsa-miR-572 | 7.55 | 1.04 | 4.46 | 0.77 | 8.07E−07 | 3.09 | 8.5 |
| hsa-miR-150* | 7.14 | 0.71 | 4.05 | 0.88 | 1.88E−06 | 3.09 | 8.5 |
| hsa-miR-133b | 9.04 | 3.01 | 5.96 | 1.65 | 7.67E−03 | 3.08 | 8.5 |
| hsa-miR-1909* | 2.29 | 0.80 | −0.76 | 1.29 | 1.90E−04 | 3.06 | 8.3 |
| hsa-miR-551b* | 2.37 | 0.66 | −0.67 | 0.92 | 3.52E−06 | 3.04 | 8.2 |
| hsa-miR-1183 | 5.87 | 0.71 | 2.85 | 1.01 | 1.39E−05 | 3.02 | 8.1 |
| hsa-miR-1207-5p | 11.48 | 1.07 | 8.50 | 0.96 | 1.73E−05 | 2.98 | 7.9 |
| hsa-miR-1321 | 3.39 | 0.78 | 0.41 | 0.67 | 1.02E−07 | 2.98 | 7.9 |
| hsa-miR-1225-5p | 11.44 | 0.97 | 8.48 | 0.86 | 4.37E−06 | 2.96 | 7.8 |
| hsa-miR-1268 | 9.84 | 1.32 | 6.89 | 0.74 | 2.66E−06 | 2.95 | 7.7 |
| hsa-miR-1915* | 1.92 | 0.55 | −1.03 | 0.87 | 2.26E−06 | 2.95 | 7.7 |
| hsa-miR-638 | 10.60 | 1.02 | 7.67 | 0.74 | 1.06E−06 | 2.93 | 7.6 |
| hsa-miR-671-5p | 6.89 | 0.59 | 4.06 | 0.94 | 1.17E−05 | 2.83 | 7.1 |
| hsa-miR-134 | 7.65 | 0.95 | 4.88 | 0.96 | 3.13E−05 | 2.77 | 6.8 |
| hsa-miR-1203 | 2.10 | 0.51 | −0.67 | 0.89 | 6.68E−06 | 2.77 | 6.8 |
| hsa-miR-566 | 2.81 | 0.94 | 0.06 | 0.98 | 4.67E−05 | 2.75 | 6.7 |
| hsa-miR-34c-3p | 1.38 | 0.29 | −1.33 | 0.54 | 4.18E−09 | 2.71 | 6.5 |
| hsa-miR-1 | 8.39 | 3.41 | 5.69 | 1.44 | 1.49E−02 | 2.70 | 6.5 |
| hsa-miR-1224-5p | 7.25 | 0.67 | 4.57 | 1.00 | 5.06E−05 | 2.67 | 6.4 |
| hsa-miR-939 | 8.56 | 0.44 | 5.89 | 0.71 | 4.33E−07 | 2.67 | 6.4 |
| hsa-miR-371-5p | 5.79 | 0.48 | 3.17 | 0.82 | 4.67E−06 | 2.62 | 6.2 |
| hsa-miR-1471 | 5.18 | 0.39 | 2.57 | 1.07 | 1.12E−04 | 2.61 | 6.1 |
| hsa-miR-601 | 5.25 | 0.55 | 2.63 | 0.83 | 6.37E−06 | 2.61 | 6.1 |
| hsa-miR-622 | 4.88 | 0.38 | 2.30 | 0.83 | 5.76E−06 | 2.59 | 6.0 |
| hsa-miR-526b | 3.19 | 0.55 | 0.61 | 0.83 | 7.32E−06 | 2.58 | 6.0 |
| hsa-miR-940 | 8.55 | 0.72 | 6.00 | 0.67 | 8.12E−07 | 2.56 | 5.9 |
| hsa-miR-370 | 3.45 | 0.51 | 0.93 | 1.17 | 4.32E−04 | 2.53 | 5.8 |
| hsa-miR-1228* | 1.57 | 0.73 | −0.96 | 0.97 | 8.07E−05 | 2.52 | 5.7 |
| hsa-miR-133a | 5.79 | 2.96 | 3.29 | 1.14 | 7.48E−03 | 2.50 | 5.7 |
| hsa-miR-202 | 6.71 | 0.59 | 4.21 | 0.72 | 1.98E−06 | 2.50 | 5.7 |
| hsa-miR-877 | 4.11 | 0.66 | 1.62 | 1.03 | 1.61E−04 | 2.49 | 5.6 |

TABLE 31-continued

MicroRNAs significantly differentially expressed between NOD and follicular cell-derived neoplasms (FA, FTC, PTC, and FVPTC.

| miRNA | NOD Avg | NOD SD | FA, FTC, PTC, FVPTC Avg | FA, FTC, PTC, FVPTC SD | NOD vs FA, FTC, PTC, FVPTC ttest | NOD vs FA, FTC, PTC, FVPTC Log2Diff | Fold change |
|---|---|---|---|---|---|---|---|
| hsa-miR-610 | 4.11 | 0.59 | 1.62 | 0.78 | 6.33E−06 | 2.49 | 5.6 |
| hsa-miR-1915 | 9.71 | 0.51 | 7.22 | 0.64 | 4.26E−07 | 2.48 | 5.6 |
| hsa-miR-188-5p | 7.10 | 0.65 | 4.64 | 0.72 | 3.12E−06 | 2.46 | 5.5 |
| hsa-miR-1469 | 3.04 | 0.43 | 0.58 | 1.16 | 5.06E−04 | 2.46 | 5.5 |
| hsa-miR-516b | 2.43 | 0.32 | 0.00 | 0.74 | 2.69E−05 | 2.43 | 5.4 |
| hsa-miR-498 | 3.42 | 0.51 | 0.99 | 0.73 | 3.43E−06 | 2.43 | 5.4 |
| hsa-miR-616 | 1.35 | 0.54 | −1.06 | 0.80 | 1.11E−05 | 2.42 | 5.3 |
| hsa-miR-617 | 2.91 | 0.37 | 0.50 | 0.73 | 2.92E−06 | 2.41 | 5.3 |
| hsa-miR-1291 | 2.65 | 0.69 | 0.28 | 1.03 | 2.95E−05 | 2.36 | 5.1 |
| hsa-miR-1246 | 9.28 | 1.15 | 6.93 | 1.14 | 1.22E−03 | 2.35 | 5.1 |
| hsa-miR-921 | 1.34 | 0.52 | −0.96 | 0.77 | 1.34E−05 | 2.29 | 4.9 |
| hsa-miR-199b-5p | 8.91 | 0.21 | 6.62 | 1.57 | 9.61E−03 | 2.29 | 4.9 |
| hsa-miR-422a | 3.29 | 0.36 | 1.02 | 1.06 | 4.15E−04 | 2.27 | 4.8 |
| hsa-miR-424* | 4.99 | 0.68 | 2.72 | 0.93 | 1.68E−04 | 2.27 | 4.8 |
| hsa-miR-518c* | 1.90 | 0.53 | −0.37 | 0.63 | 1.31E−06 | 2.27 | 4.8 |
| hsa-miR-490-5p | 3.04 | 0.32 | 0.79 | 0.69 | 2.87E−06 | 2.25 | 4.7 |
| hsa-miR-583 | 2.24 | 0.75 | 0.01 | 0.98 | 3.40E−04 | 2.24 | 4.7 |
| hsa-miR-1180 | 3.19 | 0.43 | 0.97 | 1.05 | 5.30E−04 | 2.22 | 4.7 |
| hsa-miR-1276 | 1.67 | 0.65 | −0.54 | 1.02 | 5.04E−04 | 2.21 | 4.6 |
| hsa-miR-575 | 9.81 | 0.66 | 7.61 | 0.67 | 6.71E−06 | 2.20 | 4.6 |
| hsa-miR-129-5p | 2.13 | 0.81 | −0.06 | 1.14 | 1.58E−03 | 2.19 | 4.6 |
| hsa-miR-662 | 3.23 | 0.23 | 1.04 | 0.52 | 6.49E−08 | 2.19 | 4.6 |
| hsa-miR-373* | 2.82 | 0.97 | 0.66 | 1.06 | 1.18E−03 | 2.16 | 4.5 |
| hsa-miR-298 | 1.59 | 0.37 | −0.55 | 0.91 | 1.64E−04 | 2.14 | 4.4 |
| hsa-miR-127-5p | 0.95 | 0.36 | −1.19 | 0.62 | 1.58E−05 | 2.14 | 4.4 |
| hsa-miR-630 | 6.48 | 0.60 | 4.38 | 1.20 | 2.91E−03 | 2.10 | 4.3 |
| hsa-miR-1308 | 9.69 | 0.89 | 7.61 | 1.11 | 2.07E−03 | 2.08 | 4.2 |
| hsa-miR-302c* | 1.28 | 0.71 | −0.79 | 0.58 | 3.09E−06 | 2.07 | 4.2 |
| hsa-miR-1250 | 1.57 | 0.53 | −0.49 | 0.76 | 4.29E−05 | 2.07 | 4.2 |
| hsa-miR-518a-5p | 1.71 | 0.67 | −0.35 | 0.70 | 2.40E−05 | 2.07 | 4.2 |
| hsa-miR-614 | 1.71 | 0.68 | −0.27 | 0.64 | 1.54E−05 | 1.98 | 3.9 |
| hsa-miR-654-5p | 3.71 | 0.37 | 1.73 | 0.77 | 7.02E−05 | 1.98 | 3.9 |
| hsa-miR-605 | 3.37 | 1.05 | 1.41 | 1.05 | 2.70E−03 | 1.96 | 3.9 |
| hsa-miR-1208 | 3.34 | 0.27 | 1.43 | 0.85 | 2.63E−04 | 1.91 | 3.8 |
| hsa-miR-877* | 4.38 | 0.42 | 2.48 | 0.47 | 2.31E−07 | 1.90 | 3.7 |
| hsa-miR-1303 | 1.37 | 0.56 | −0.52 | 0.89 | 5.85E−04 | 1.89 | 3.7 |
| hsa-miR-1226* | 5.37 | 0.48 | 3.50 | 0.47 | 4.23E−07 | 1.87 | 3.7 |
| hsa-miR-769-3p | 2.99 | 0.65 | 1.15 | 0.56 | 8.24E−05 | 1.84 | 3.6 |
| hsa-miR-1299 | 4.04 | 0.46 | 2.23 | 0.99 | 1.85E−03 | 1.82 | 3.5 |
| hsa-miR-640 | 1.16 | 0.46 | −0.65 | 1.02 | 2.56E−03 | 1.81 | 3.5 |
| hsa-miR-525-5p | 1.81 | 0.50 | 0.01 | 0.51 | 1.99E−06 | 1.80 | 3.5 |
| hsa-miR-557 | 5.88 | 0.79 | 4.08 | 0.61 | 4.50E−05 | 1.79 | 3.5 |
| hsa-miR-1249 | 5.58 | 0.76 | 3.80 | 0.61 | 4.46E−05 | 1.79 | 3.4 |
| hsa-miR-873 | 2.95 | 0.83 | 1.19 | 1.42 | 2.74E−02 | 1.76 | 3.4 |
| hsa-miR-513a-5p | 5.17 | 0.43 | 3.43 | 0.55 | 6.89E−06 | 1.74 | 3.3 |
| hsa-miR-486-3p | 1.82 | 1.02 | 0.08 | 1.13 | 9.91E−03 | 1.74 | 3.3 |
| hsa-miR-138 | 6.26 | 0.71 | 4.52 | 1.08 | 6.15E−03 | 1.74 | 3.3 |
| hsa-miR-639 | 0.66 | 0.47 | −1.08 | 0.66 | 7.15E−05 | 1.74 | 3.3 |
| hsa-miR-381 | 3.79 | 1.14 | 2.07 | 1.11 | 1.07E−02 | 1.72 | 3.3 |
| hsa-miR-125b-1* | 2.79 | 1.31 | 1.08 | 1.20 | 1.86E−02 | 1.71 | 3.3 |
| hsa-miR-486-5p | 8.26 | 0.71 | 6.56 | 1.31 | 2.17E−02 | 1.70 | 3.2 |
| hsa-miR-518e* | 1.68 | 0.29 | 0.00 | 0.84 | 7.90E−04 | 1.69 | 3.2 |
| hsa-miR-584 | 4.03 | 0.50 | 2.35 | 0.94 | 2.51E−03 | 1.68 | 3.2 |
| hsa-miR-33b* | 3.92 | 0.53 | 2.27 | 0.42 | 9.85E−07 | 1.65 | 3.1 |
| hsa-miR-1306 | 2.62 | 0.34 | 0.99 | 0.61 | 4.71E−05 | 1.64 | 3.1 |
| hsa-miR-122 | 1.86 | 1.30 | 0.26 | 0.59 | 7.55E−04 | 1.59 | 3.0 |
| hsa-miR-1307 | 3.02 | 0.38 | 1.44 | 0.67 | 2.05E−04 | 1.58 | 3.0 |
| hsa-miR-550 | 3.35 | 0.32 | 1.79 | 0.51 | 8.72E−06 | 1.56 | 3.0 |
| hsa-miR-1285 | 3.03 | 0.59 | 1.48 | 0.65 | 2.53E−03 | 1.55 | 2.9 |
| hsa-miR-125a-3p | 6.98 | 0.40 | 5.43 | 0.59 | 5.87E−05 | 1.55 | 2.9 |
| hsa-miR-516a-5p | 3.28 | 0.99 | 1.73 | 0.79 | 2.51E−03 | 1.55 | 2.9 |
| hsa-miR-214 | 9.06 | 0.45 | 7.52 | 0.91 | 3.71E−03 | 1.54 | 2.9 |
| hsa-miR-499-5p | 4.99 | 1.73 | 3.45 | 0.78 | 9.19E−03 | 1.54 | 2.9 |
| hsa-miR-124 | 1.20 | 1.01 | −0.34 | 0.66 | 8.30E−04 | 1.54 | 2.9 |
| hsa-miR-501-3p | 4.28 | 0.24 | 2.76 | 0.52 | 1.21E−05 | 1.53 | 2.9 |
| hsa-miR-378 | 5.80 | 1.51 | 4.29 | 0.52 | 1.40E−03 | 1.51 | 2.8 |
| hsa-miR-602 | 3.53 | 0.52 | 2.03 | 0.70 | 6.15E−04 | 1.50 | 2.8 |
| hsa-miR-135a* | 5.26 | 0.83 | 3.78 | 0.79 | 3.03E−03 | 1.47 | 2.8 |
| hsa-miR-664* | 6.07 | 0.84 | 4.60 | 0.73 | 1.78E−03 | 1.47 | 2.8 |
| hsa-miR-760 | 3.96 | 0.39 | 2.49 | 0.85 | 3.25E−03 | 1.47 | 2.8 |
| hsa-miR-574-5p | 7.17 | 0.65 | 5.71 | 0.58 | 1.87E−04 | 1.46 | 2.8 |
| hsa-miR-193b* | 4.35 | 0.60 | 2.90 | 0.62 | 3.51E−04 | 1.45 | 2.7 |

TABLE 31-continued

MicroRNAs significantly differentially expressed between NOD and follicular cell-derived neoplasms (FA, FTC, PTC, and FVPTC.

| miRNA | NOD Avg | NOD SD | FA, FTC, PTC, FVPTC Avg | FA, FTC, PTC, FVPTC SD | NOD vs FA, FTC, PTC, FVPTC ttest | NOD vs FA, FTC, PTC, FVPTC Log2Diff | Fold change |
|---|---|---|---|---|---|---|---|
| hsa-miR-512-3p | 4.75 | 0.05 | 3.32 | 1.22 | 3.16E-02 | 1.43 | 2.7 |
| hsa-miR-184 | 2.49 | 0.44 | 1.05 | 1.03 | 1.39E-02 | 1.43 | 2.7 |
| hsa-miR-1244 | 1.73 | 0.83 | 0.32 | 0.66 | 1.22E-03 | 1.41 | 2.7 |
| hsa-miR-194* | 1.17 | 0.64 | −0.21 | 0.67 | 1.18E-03 | 1.38 | 2.6 |
| hsa-miR-1275 | 7.77 | 0.53 | 6.39 | 0.83 | 4.85E-03 | 1.37 | 2.6 |
| hsa-miR-28-3p | 1.74 | 0.21 | 0.41 | 0.66 | 8.18E-04 | 1.33 | 2.5 |
| hsa-miR-432 | 2.91 | 0.59 | 1.58 | 0.62 | 8.38E-04 | 1.33 | 2.5 |
| hsa-miR-296-5p | 4.16 | 0.70 | 2.86 | 0.38 | 2.91E-05 | 1.30 | 2.5 |
| hsa-miR-658 | 0.84 | 0.57 | −0.45 | 0.59 | 6.85E-04 | 1.29 | 2.5 |
| hsa-miR-139-5p | 6.53 | 0.30 | 5.27 | 0.84 | 8.04E-03 | 1.27 | 2.4 |
| hsa-miR-23a* | 4.15 | 0.52 | 2.88 | 0.66 | 1.85E-03 | 1.26 | 2.4 |
| hsa-miR-1270 | 2.13 | 0.49 | 0.92 | 0.67 | 2.79E-03 | 1.21 | 2.3 |
| hsa-miR-210 | 6.06 | 0.22 | 4.87 | 1.07 | 4.08E-02 | 1.19 | 2.3 |
| hsa-miR-612 | 0.15 | 0.90 | −0.98 | 0.52 | 2.36E-03 | 1.13 | 2.2 |
| hsa-miR-199a-3p | 11.25 | 0.25 | 10.14 | 0.89 | 2.27E-03 | 1.12 | 2.2 |
| hsa-miR-708 | 2.26 | 0.40 | 1.16 | 0.87 | 2.30E-02 | 1.10 | 2.1 |
| hsa-miR-378* | 3.57 | 1.66 | 2.49 | 0.48 | 1.82E-02 | 1.08 | 2.1 |
| hsa-miR-10b* | 2.98 | 0.58 | 1.97 | 0.42 | 5.30E-04 | 1.01 | 2.0 |
| hsa-miR-320a | 8.81 | 0.27 | 7.80 | 0.42 | 1.76E-04 | 1.00 | 2.0 |
| hsa-miR-1323 | 2.32 | 0.36 | 1.31 | 0.53 | 1.69E-02 | 1.00 | 2.0 |
| hsa-miR-199a-5p | 9.58 | 0.56 | 8.58 | 0.89 | 4.61E-02 | 0.99 | 2.0 |
| hsa-miR-152 | 7.41 | 0.49 | 6.44 | 0.89 | 4.95E-02 | 0.97 | 2.0 |
| hsa-miR-99b* | 2.60 | 0.27 | 1.64 | 0.53 | 2.28E-03 | 0.96 | 2.0 |
| hsa-miR-15a* | 0.59 | 0.33 | 1.57 | 0.48 | 8.95E-04 | −0.98 | 2.0 |
| hsa-miR-15a | 10.12 | 0.45 | 11.14 | 0.61 | 4.92E-02 | −1.02 | 2.0 |
| hsa-miR-141* | 2.35 | 0.61 | 3.42 | 0.65 | 6.32E-03 | −1.07 | 2.1 |
| hsa-miR-181a* | 2.91 | 0.38 | 4.02 | 0.79 | 1.30E-02 | −1.11 | 2.2 |
| hsa-miR-200c* | 0.71 | 0.51 | 1.88 | 0.58 | 1.19E-03 | −1.17 | 2.2 |
| hsa-miR-146a | 6.62 | 0.21 | 7.85 | 0.98 | 2.23E-02 | −1.23 | 2.3 |
| hsa-miR-34a | 10.54 | 0.23 | 11.79 | 0.50 | 8.70E-05 | −1.24 | 2.4 |
| hsa-miR-21 | 12.93 | 0.34 | 14.39 | 0.95 | 7.19E-03 | −1.46 | 2.7 |
| hsa-miR-155 | 5.51 | 0.19 | 7.01 | 1.22 | 2.54E-02 | −1.50 | 2.8 |
| hsa-miR-503 | 3.37 | 0.73 | 4.88 | 1.00 | 9.46E-03 | −1.51 | 2.9 |
| hsa-miR-21* | 4.08 | 0.15 | 5.72 | 0.85 | 1.08E-03 | −1.64 | 3.1 |
| hsa-miR-182 | 1.45 | 0.76 | 3.09 | 1.41 | 3.61E-02 | −1.64 | 3.1 |
| hsa-miR-96 | 6.74 | 0.37 | 8.38 | 1.11 | 8.80E-03 | −1.65 | 3.1 |
| hsa-miR-29b-1* | 3.01 | 0.32 | 4.73 | 0.49 | 1.48E-06 | −1.72 | 3.3 |
| hsa-miR-222 | 6.24 | 0.80 | 8.30 | 1.65 | 2.57E-02 | −2.06 | 4.2 |
| hsa-miR-142-3p | 6.85 | 1.06 | 8.92 | 1.49 | 1.60E-02 | −2.07 | 4.2 |
| hsa-miR-221* | 4.79 | 0.21 | 7.04 | 1.66 | 1.47E-02 | −2.25 | 4.8 |
| hsa-miR-1260 | 6.15 | 0.87 | 8.47 | 0.65 | 4.63E-06 | −2.31 | 5.0 |
| hsa-miR-720 | 9.90 | 0.79 | 12.52 | 0.59 | 1.58E-07 | −2.63 | 6.2 |
| hsa-miR-221 | 6.58 | 0.33 | 9.22 | 1.65 | 5.23E-03 | −2.63 | 6.2 |
| hsa-miR-1274b | 8.18 | 0.94 | 10.86 | 0.67 | 1.05E-06 | −2.68 | 6.4 |
| hsa-miR-1274a | 4.39 | 1.03 | 7.27 | 0.70 | 8.19E-07 | −2.87 | 7.3 |

Avg, average of expression among samples in a group;
SD, standard deviation.

Example 30 miRNA Expression Profiling Distinguishes Benign and Pre-Malignant Lesions (NOD and FA) From Differentiated Follicular Cell-Derived Carcinomas (FTC, PTC, FVPTC)

The inventors also sought to determine whether miRNA expressions levels could distinguish benign and pre-malignant thyroid conditions from malignant thyroid cancers. miRNA expression profiles from benign hyperplastic nodules (NOD) and pre-malignant follicular adenoma (FA) samples were compared with those from malignant thyroid cancers, in particular differentiated thyroid cancers (FTC, PTC, and FVPTC). A total of 111 human miRNAs were significantly differentially expressed between the NOD+FA samples and the follicular cell-derived carcinoma (FTC, PTC, FVPTC) specimens (p<0.05). Of these, thirty nine miRNAs were expressed at levels at least 2-fold higher (Log 2 diff (NOD+FA vs CANCER)≥1) and twenty one miRNAs were expressed at levels at least 2-fold lower in the NOD+FA samples versus the CANCER specimens (Table 32). Among the miRNAs expressed at higher average levels in the NOD+FA samples, hsa-miR-1 308 was overexpressed by 5-fold, and thirty eight miRNAs were overexpressed by 2- to 5-fold. Among the miRNAs expressed at lower average levels in the NOD+FA samples, hsa-let-7i* was underexpressed by at least 10 fold, three miRNAs (hsa-miR-1244 and -1246, and hsa-let-7i) were underexpressed by 5- to 10-fold, and seventeen miRNAs were underexpresssed by 2- to 5-fold (Table 32).

TABLE 32

MicroRNAs significantly differentially expressed between NOD + FA and differentiated follicular cell-derived carcinomas (CANCER).

| miRNA | NOD + FA | | CANCER | | NOD + FA VS CANCER | | |
|---|---|---|---|---|---|---|---|
| | Avg | SD | Avg | SD | ttest | Log2Diff | Fold change |
| hsa-miR-1308 | 8.77 | 1.60 | 7.45 | 1.23 | 1.71E−03 | 2.34 | 5.1 |
| hsa-miR-136 | 2.16 | 0.62 | 2.26 | 0.94 | 4.90E−03 | 2.03 | 4.1 |
| hsa-miR-135a | 7.67 | 1.01 | 8.21 | 1.15 | 1.22E−03 | 1.88 | 3.7 |
| hsa-miR-10a* | 0.94 | 1.22 | 0.58 | 0.76 | 8.61E−03 | 1.81 | 3.5 |
| hsa-miR-1207-5p | 9.71 | 1.88 | 8.57 | 1.72 | 3.45E−02 | 1.77 | 3.4 |
| hsa-miR-1323 | 1.92 | 0.49 | 1.21 | 1.62 | 2.62E−02 | 1.73 | 3.3 |
| hsa-miR-1306 | 1.64 | 1.10 | 1.03 | 1.01 | 7.46E−03 | 1.65 | 3.1 |
| hsa-miR-138-2* | 1.92 | 0.58 | 1.77 | 0.83 | 9.06E−03 | 1.60 | 3.0 |
| hsa-miR-136* | 1.14 | 1.09 | 1.27 | 0.95 | 2.00E−02 | 1.56 | 2.9 |
| hsa-miR-1290 | 4.31 | 1.31 | 4.23 | 0.81 | 8.30E−03 | 1.55 | 2.9 |
| hsa-miR-127-5p | −0.41 | 1.43 | −1.08 | 0.99 | 1.64E−02 | 1.50 | 2.8 |
| hsa-miR-130a | 10.48 | 0.92 | 10.65 | 0.80 | 8.23E−03 | 1.48 | 2.8 |
| hsa-miR-1 | 6.78 | 2.75 | 5.76 | 1.05 | 4.93E−02 | 1.47 | 2.8 |
| hsa-miR-137 | −0.18 | 0.63 | 0.52 | 1.13 | 4.82E−02 | 1.41 | 2.7 |
| hsa-let-7a | 14.23 | 0.38 | 14.35 | 0.82 | 1.69E−02 | 1.31 | 2.5 |
| hsa-miR-130b | 6.42 | 0.86 | 6.42 | 0.72 | 6.38E−03 | 1.30 | 2.5 |
| hsa-miR-10b* | 2.24 | 0.85 | 2.09 | 0.87 | 2.76E−02 | 1.29 | 2.4 |
| hsa-miR-1285 | 2.16 | 1.13 | 1.48 | 0.94 | 1.58E−02 | 1.26 | 2.4 |
| hsa-miR-129-5p | 1.17 | 1.38 | −0.23 | 0.85 | 3.88E−02 | 1.24 | 2.4 |
| hsa-let-7b | 13.36 | 0.57 | 13.16 | 0.98 | 1.48E−02 | 1.22 | 2.3 |
| hsa-let-7b* | 1.52 | 0.87 | 1.31 | 0.77 | 8.98E−04 | 1.18 | 2.3 |
| hsa-miR-1291 | 1.41 | 1.45 | 0.23 | 1.07 | 2.68E−02 | 1.17 | 2.3 |
| hsa-miR-126 | 12.20 | 0.49 | 11.57 | 0.87 | 2.69E−02 | 1.17 | 2.3 |
| hsa-miR-127-3p | 3.52 | 1.07 | 3.66 | 0.62 | 1.07E−02 | 1.12 | 2.2 |
| hsa-miR-1238 | 3.54 | 0.55 | 3.65 | 0.61 | 5.72E−03 | 1.11 | 2.2 |
| hsa-miR-128 | 6.40 | 0.63 | 6.26 | 0.77 | 1.13E−02 | 1.09 | 2.1 |
| hsa-miR-1270 | 1.49 | 0.78 | 0.90 | 0.61 | 2.83E−02 | 1.07 | 2.1 |
| hsa-miR-1296 | −0.02 | 1.27 | −0.53 | 0.61 | 1.94E−03 | 1.07 | 2.1 |
| hsa-miR-1299 | 2.88 | 1.46 | 2.33 | 1.04 | 4.88E−02 | 1.06 | 2.1 |
| hsa-miR-1305 | 6.75 | 0.60 | 7.33 | 0.83 | 4.77E−02 | 1.05 | 2.1 |
| hsa-miR-132* | 2.56 | 0.50 | 2.98 | 0.62 | 1.75E−02 | 1.05 | 2.1 |
| hsa-miR-10b | 8.17 | 0.45 | 7.96 | 0.48 | 2.49E−02 | 1.04 | 2.1 |
| hsa-miR-129-3p | 3.00 | 1.37 | 2.66 | 0.66 | 5.94E−03 | 1.04 | 2.1 |
| hsa-let-7f | 13.69 | 0.55 | 13.91 | 0.68 | 4.81E−04 | 1.03 | 2.0 |
| hsa-miR-133a | 4.30 | 2.34 | 3.36 | 0.78 | 5.71E−03 | 1.01 | 2.0 |
| hsa-miR-132 | 5.58 | 0.64 | 5.88 | 0.46 | 1.18E−02 | 1.01 | 2.0 |
| hsa-miR-1303 | 0.60 | 1.30 | −0.70 | 0.70 | 3.96E−02 | 1.00 | 2.0 |
| hsa-miR-125b-2* | 4.68 | 0.85 | 4.73 | 0.47 | 4.34E−02 | 0.99 | 2.0 |
| ha-miR-1280 | 6.86 | 1.16 | 6.34 | 0.62 | 2.79E−02 | 0.98 | 2.0 |
| hsa-miR-101 | 8.21 | 0.87 | 8.52 | 0.42 | 2.79E−05 | −1.06 | 2.1 |
| hsa-let-7g* | 0.00 | 1.12 | −0.98 | 0.99 | 9.69E−03 | −1.06 | 2.1 |
| hsa-miR-1237 | 2.63 | 0.55 | 2.53 | 0.45 | 4.99E−02 | −1.09 | 2.1 |
| hsa-miR-1260 | 7.30 | 1.30 | 8.55 | 1.28 | 3.90E−02 | −1.13 | 2.2 |
| hsa-miR-100* | 1.23 | 0.73 | 0.96 | 1.11 | 2.35E−02 | −1.18 | 2.3 |
| hsa-miR-1288 | 4.99 | 0.45 | 5.42 | 1.31 | 3.45E−02 | −1.18 | 2.3 |
| hsa-miR-1275 | 6.88 | 1.09 | 6.48 | 0.99 | 4.21E−03 | −1.28 | 2.4 |
| hsa-miR-133b | 7.22 | 2.64 | 6.03 | 0.50 | 6.41E−03 | −1.31 | 2.5 |
| hsa-miR-126* | 5.95 | 0.84 | 5.36 | 1.13 | 5.54E−03 | −1.40 | 2.6 |
| hsa-miR-1225-3p | 3.39 | 0.49 | 3.29 | 0.77 | 3.00E−04 | −1.43 | 2.7 |
| hsa-miR-1225-5p | 9.70 | 1.80 | 8.54 | 0.71 | 4.18E−05 | −1.49 | 2.8 |
| hsa-let-7d* | 1.51 | 0.88 | 0.95 | 1.35 | 1.41E−02 | −1.55 | 2.9 |
| hsa-let-7d | 11.39 | 0.44 | 11.50 | 1.24 | 5.78E−03 | −1.80 | 3.5 |
| hsa-miR-1227 | 0.71 | 1.17 | 0.12 | 1.53 | 1.13E−02 | −1.81 | 3.5 |
| hsa-miR-1226* | 4.22 | 1.18 | 3.57 | 1.53 | 1.49E−02 | −1.82 | 3.5 |
| hsa-miR-1228 | 4.73 | 0.87 | 4.53 | 1.58 | 3.67E−03 | −2.00 | 4.0 |
| hsa-miR-129* | 2.02 | 0.45 | 1.86 | 2.41 | 3.50E−02 | −2.13 | 4.4 |
| hsa-let-7i | 13.18 | 0.41 | 13.75 | 2.24 | 8.36E−03 | −2.33 | 5.0 |
| hsa-miR-1246 | 7.84 | 1.76 | 7.01 | 1.89 | 5.61E−03 | −2.97 | 7.8 |
| hsa-miR-1244 | 0.78 | 1.17 | 0.42 | 2.05 | 6.90E−03 | −3.08 | 8.5 |
| hsa-let-7i* | 2.50 | 0.92 | 3.07 | 3.20 | 5.38E−03 | −3.58 | 12.0 |

Avg, average of expression among samples in a group;
SD, standard deviation.

Example 31 miRNA Expression Profiling Distinguishes Hyperplastic Nodules (NOD) From Differentiated Follicular Cell-Derived Carcinomas (FTC, PTC, FVPTC)

A total of 291 human miRNAs were significantly differentially expressed between hyperplastic nodules (NOD) and follicular cell-derived carcinoma (FTC, PTC, FVPTC) specimens ($p<0.05$). Of these, one hundred eighty miRNAs were expressed at levels at least 2-fold higher (Log 2 diff (NOD vs CANCER)≥1), and thirty miRNAs were expressed at levels at least 2-fold lower in the NOD specimens (Table 33). Among the miRNAs expressed at higher average levels in NOD, hsa-miR-206 was overexpressed by 20-fold, thirteen miRNAs (hsa-miR-92b*, -631, -1202, -1300, -149*, -633, -936, -765, -648, -187*, -934, -1182, and -198 were overexpressed by 10- to 20-fold, forty five miRNAs were overexpressed by 5- to 10-fold, and one hundred twenty one miRNAs were overexpressed by 2- to 5-fold in the NOD samples. Among the miRNAs expressed at lower average levels in NOD, hsa-miR-146b-5p was underexpressed by at least 15-fold, nine miRNAs (hsa-miR-1274a, -221, -1274b, -720, -146b-3p, -221*, -222, -142-3p, and -1260) were underexpressed by 5- to 10-fold, and twenty miRNAs were underexpressed by 2- to 5-fold (Table 33).

TABLE 33

MicroRNAs significantly differentially expressed between hyperplastic nodules (NOD) and differentiated follicular cell-derived carcinomas (CANCER).

| miRNA | NOD Avg | NOD STD | CANCER Avg | CANCER STD | NOD vs CANCER ttest | NOD vs CANCER Log2diff | Fold change |
|---|---|---|---|---|---|---|---|
| hsa-miR-206 | 4.98 | 3.14 | 0.45 | 1.81 | 1.72E−03 | 4.52 | 23.0 |
| hsa-miR-92b* | 2.62 | 0.57 | −1.49 | 0.94 | 3.82E−07 | 4.11 | 17.3 |
| hsa-miR-631 | 3.62 | 0.57 | −0.24 | 1.23 | 1.81E−05 | 3.86 | 14.6 |
| hsa-miR-1202 | 13.40 | 0.83 | 9.60 | 1.47 | 1.63E−04 | 3.80 | 13.9 |
| hsa-miR-1300 | 7.45 | 0.80 | 3.67 | 0.99 | 3.17E−06 | 3.79 | 13.8 |
| hsa-miR-149* | 4.33 | 0.61 | 0.73 | 1.05 | 7.50E−06 | 3.60 | 12.1 |
| hsa-miR-663 | 8.28 | 0.78 | 4.68 | 1.24 | 5.67E−05 | 3.60 | 12.1 |
| hsa-miR-936 | 4.20 | 0.65 | 0.74 | 1.13 | 2.87E−05 | 3.45 | 11.0 |
| hsa-miR-765 | 6.28 | 0.71 | 2.87 | 1.20 | 6.43E−05 | 3.41 | 10.6 |
| hsa-miR-648 | 3.78 | 0.49 | 0.40 | 1.11 | 2.50E−05 | 3.38 | 10.4 |
| hsa-miR-187* | 4.38 | 0.72 | 1.01 | 0.95 | 7.35E−06 | 3.37 | 10.3 |
| hsa-miR-934 | 1.75 | 0.72 | −1.61 | 0.95 | 7.00E−06 | 3.36 | 10.3 |
| hsa-miR-1182 | 4.41 | 0.79 | 1.06 | 1.08 | 2.99E−05 | 3.35 | 10.2 |
| hsa-miR-198 | 4.55 | 0.67 | 1.21 | 1.23 | 9.58E−05 | 3.34 | 10.1 |
| hsa-miR-7 | 10.64 | 1.81 | 7.39 | 2.27 | 1.89E−02 | 3.25 | 9.5 |
| hsa-miR-1909* | 2.29 | 0.80 | −0.94 | 0.76 | 1.51E−06 | 3.23 | 9.4 |
| hsa-miR-623 | 4.60 | 0.57 | 1.37 | 1.01 | 1.68E−05 | 3.23 | 9.4 |
| hsa-miR-493 | 2.58 | 0.75 | −0.59 | 0.99 | 2.39E−05 | 3.16 | 9.0 |
| hsa-miR-572 | 7.55 | 1.04 | 4.39 | 0.81 | 7.65E−06 | 3.16 | 8.9 |
| hsa-miR-483-5p | 8.12 | 0.81 | 5.02 | 1.24 | 2.69E−04 | 3.10 | 8.6 |
| hsa-miR-659 | 5.18 | 0.64 | 2.13 | 1.26 | 2.90E−04 | 3.05 | 8.3 |
| hsa-miR-133b | 9.04 | 3.01 | 6.03 | 1.83 | 2.24E−02 | 3.02 | 8.1 |
| hsa-miR-638 | 10.60 | 1.02 | 7.60 | 0.80 | 1.18E−05 | 3.00 | 8.0 |
| hsa-miR-1268 | 9.84 | 1.32 | 6.85 | 0.83 | 4.08E−05 | 2.99 | 8.0 |
| hsa-miR-551b* | 2.37 | 0.66 | −0.59 | 0.85 | 8.60E−06 | 2.97 | 7.8 |
| hsa-miR-150* | 7.14 | 0.71 | 4.19 | 0.94 | 2.89E−05 | 2.95 | 7.7 |
| hsa-miR-1183 | 5.87 | 0.71 | 2.93 | 0.93 | 2.68E−05 | 2.94 | 7.7 |
| hsa-miR-1915* | 1.92 | 0.55 | −1.02 | 0.87 | 9.74E−06 | 2.94 | 7.7 |
| hsa-miR-1207-5p | 11.48 | 1.07 | 8.57 | 1.04 | 1.63E−04 | 2.91 | 7.5 |
| hsa-miR-1225-5p | 11.44 | 0.97 | 8.54 | 0.95 | 6.63E−05 | 2.90 | 7.5 |
| hsa-miR-1321 | 3.39 | 0.78 | 0.51 | 0.70 | 2.41E−06 | 2.87 | 7.3 |
| hsa-miR-1203 | 2.10 | 0.51 | −0.69 | 0.84 | 1.25E−05 | 2.79 | 6.9 |
| hsa-miR-671-5p | 6.89 | 0.59 | 4.13 | 1.06 | 1.49E−04 | 2.76 | 6.8 |
| hsa-miR-566 | 2.81 | 0.94 | 0.05 | 0.85 | 3.87E−05 | 2.76 | 6.8 |
| hsa-miR-134 | 7.65 | 0.95 | 4.94 | 1.01 | 2.06E−04 | 2.70 | 6.5 |
| hsa-miR-1224-5p | 7.25 | 0.67 | 4.54 | 0.85 | 2.73E−05 | 2.70 | 6.5 |
| hsa-miR-1 | 8.39 | 3.41 | 5.76 | 1.51 | 3.46E−02 | 2.63 | 6.2 |
| hsa-miR-371-5p | 5.79 | 0.48 | 3.16 | 0.87 | 3.03E−05 | 2.63 | 6.2 |
| hsa-miR-34c-3p | 1.38 | 0.29 | −1.24 | 0.47 | 1.37E−08 | 2.62 | 6.2 |
| hsa-miR-526b | 3.19 | 0.55 | 0.57 | 0.94 | 7.58E−05 | 2.62 | 6.1 |
| hsa-miR-939 | 8.56 | 0.44 | 5.97 | 0.75 | 7.64E−06 | 2.59 | 6.0 |
| hsa-miR-138-1* | 0.99 | 0.50 | −1.57 | 0.74 | 8.42E−06 | 2.57 | 5.9 |
| hsa-miR-622 | 4.88 | 0.38 | 2.33 | 0.83 | 2.42E−05 | 2.55 | 5.9 |
| hsa-miR-1228* | 1.57 | 0.73 | −0.96 | 0.91 | 1.17E−04 | 2.53 | 5.8 |
| hsa-miR-1471 | 5.18 | 0.39 | 2.69 | 1.02 | 2.40E−04 | 2.49 | 5.6 |
| hsa-miR-601 | 5.25 | 0.55 | 2.78 | 0.88 | 8.16E−05 | 2.47 | 5.5 |
| hsa-miR-133a | 5.79 | 2.96 | 3.36 | 1.29 | 2.46E−02 | 2.44 | 5.4 |
| hsa-miR-940 | 8.55 | 0.72 | 6.12 | 0.62 | 4.69E−06 | 2.43 | 5.4 |
| hsa-miR-498 | 3.42 | 0.51 | 0.99 | 0.61 | 1.95E−06 | 2.42 | 5.4 |
| hsa-miR-202 | 6.71 | 0.59 | 4.29 | 0.73 | 1.74E−05 | 2.42 | 5.4 |
| hsa-miR-1291 | 2.65 | 0.69 | 0.23 | 1.07 | 6.31E−04 | 2.42 | 5.3 |
| hsa-miR-1915 | 9.71 | 0.51 | 7.30 | 0.67 | 6.30E−06 | 2.41 | 5.3 |
| hsa-miR-617 | 2.91 | 0.37 | 0.53 | 0.70 | 7.79E−06 | 2.38 | 5.2 |
| hsa-miR-1469 | 3.04 | 0.43 | 0.66 | 1.06 | 5.44E−04 | 2.38 | 5.2 |

TABLE 33-continued

MicroRNAs significantly differentially expressed between hyperplastic nodules (NOD) and differentiated follicular cell-derived carcinomas (CANCER).

| miRNA | NOD Avg | NOD STD | CANCER Avg | CANCER STD | NOD vs CANCER ttest | NOD vs CANCER Log2diff | Fold change |
|---|---|---|---|---|---|---|---|
| hsa-miR-877 | 4.11 | 0.66 | 1.75 | 1.02 | 5.07E−04 | 2.37 | 5.2 |
| hsa-miR-610 | 4.11 | 0.59 | 1.74 | 0.80 | 5.52E−05 | 2.36 | 5.1 |
| hsa-miR-129-5p | 2.13 | 0.81 | −0.23 | 1.09 | 1.04E−03 | 2.36 | 5.1 |
| hsa-miR-188-5p | 7.10 | 0.65 | 4.76 | 0.80 | 6.57E−05 | 2.35 | 5.1 |
| hsa-miR-616 | 1.35 | 0.54 | −0.96 | 0.76 | 3.59E−05 | 2.31 | 5.0 |
| hsa-miR-583 | 2.24 | 0.75 | −0.06 | 1.07 | 1.04E−03 | 2.31 | 4.9 |
| hsa-miR-490-3p | 1.40 | 0.41 | −0.90 | 0.73 | 2.16E−05 | 2.30 | 4.9 |
| hsa-miR-490-5p | 3.04 | 0.32 | 0.74 | 0.62 | 2.64E−06 | 2.30 | 4.9 |
| hsa-miR-422a | 3.29 | 0.36 | 1.01 | 1.05 | 7.08E−05 | 2.28 | 4.9 |
| hsa-miR-1255b | 1.70 | 0.49 | −0.58 | 0.65 | 7.47E−06 | 2.28 | 4.8 |
| hsa-miR-516b | 2.43 | 0.32 | 0.15 | 0.70 | 1.23E−05 | 2.28 | 4.8 |
| hsa-miR-1246 | 9.28 | 1.15 | 7.01 | 1.15 | 3.05E−03 | 2.27 | 4.8 |
| hsa-miR-518c* | 1.90 | 0.53 | −0.36 | 0.62 | 6.04E−05 | 2.25 | 4.8 |
| hsa-miR-1276 | 1.67 | 0.65 | −0.58 | 0.85 | 1.66E−04 | 2.25 | 4.8 |
| hsa-miR-1180 | 3.19 | 0.43 | 0.95 | 0.88 | 1.78E−04 | 2.25 | 4.7 |
| hsa-miR-204 | 7.87 | 0.45 | 5.63 | 1.72 | 2.22E−02 | 2.24 | 4.7 |
| hsa-miR-1308 | 9.69 | 0.89 | 7.45 | 0.82 | 2.38E−05 | 2.23 | 4.7 |
| hsa-miR-370 | 3.45 | 0.51 | 1.23 | 0.86 | 1.79E−04 | 2.23 | 4.7 |
| hsa-miR-921 | 1.34 | 0.52 | −0.88 | 0.78 | 6.77E−05 | 2.22 | 4.7 |
| hsa-miR-662 | 3.23 | 0.23 | 1.03 | 0.46 | 9.15E−08 | 2.21 | 4.6 |
| hsa-miR-424* | 4.99 | 0.68 | 2.79 | 0.89 | 3.49E−05 | 2.20 | 4.6 |
| hsa-miR-873 | 2.95 | 0.83 | 0.76 | 1.15 | 2.81E−03 | 2.19 | 4.6 |
| hsa-miR-302c* | 1.28 | 0.71 | −0.86 | 0.61 | 1.94E−05 | 2.15 | 4.4 |
| hsa-miR-373* | 2.82 | 0.97 | 0.69 | 0.89 | 7.27E−04 | 2.13 | 4.4 |
| hsa-miR-518a-5p | 1.71 | 0.67 | −0.42 | 0.77 | 1.24E−04 | 2.13 | 4.4 |
| hsa-miR-510 | 1.32 | 0.19 | −0.79 | 0.93 | 4.02E−04 | 2.12 | 4.3 |
| hsa-miR-575 | 9.81 | 0.66 | 7.73 | 0.66 | 4.17E−05 | 2.08 | 4.2 |
| hsa-miR-1303 | 1.37 | 0.56 | −0.70 | 0.57 | 7.72E−06 | 2.07 | 4.2 |
| hsa-miR-296-3p | 0.00 | 0.65 | −2.06 | 0.51 | 4.33E−06 | 2.07 | 4.2 |
| hsa-miR-605 | 3.37 | 1.05 | 1.33 | 1.04 | 3.26E−03 | 2.04 | 4.1 |
| hsa-miR-1266 | 1.41 | 0.16 | −0.62 | 0.86 | 2.91E−04 | 2.03 | 4.1 |
| hsa-miR-127-5p | 0.95 | 0.36 | −1.08 | 0.53 | 2.51E−06 | 2.03 | 4.1 |
| hsa-miR-298 | 1.59 | 0.37 | −0.43 | 0.85 | 3.14E−04 | 2.02 | 4.1 |
| hsa-miR-640 | 1.16 | 0.46 | −0.84 | 0.72 | 8.16E−05 | 2.01 | 4.0 |
| hsa-miR-614 | 1.71 | 0.68 | −0.28 | 0.58 | 2.48E−05 | 1.99 | 4.0 |
| hsa-miR-1250 | 1.57 | 0.53 | −0.42 | 0.58 | 1.49E−05 | 1.99 | 4.0 |
| hsa-miR-630 | 6.48 | 0.60 | 4.52 | 1.29 | 1.02E−02 | 1.96 | 3.9 |
| hsa-miR-654-5p | 3.71 | 0.37 | 1.76 | 0.58 | 1.05E−06 | 1.94 | 3.8 |
| hsa-miR-877* | 4.38 | 0.42 | 2.47 | 0.46 | 1.44E−06 | 1.92 | 3.8 |
| hsa-miR-138 | 6.26 | 0.71 | 4.34 | 0.98 | 2.39E−03 | 1.91 | 3.8 |
| hsa-miR-769-3p | 2.99 | 0.65 | 1.10 | 0.56 | 2.87E−05 | 1.89 | 3.7 |
| hsa-miR-557 | 5.88 | 0.79 | 3.99 | 0.66 | 1.74E−04 | 1.89 | 3.7 |
| hsa-miR-199b-5p | 8.91 | 0.21 | 7.03 | 1.36 | 1.60E−02 | 1.88 | 3.7 |
| hsa-miR-525-5p | 1.81 | 0.50 | −0.04 | 0.47 | 4.07E−06 | 1.86 | 3.6 |
| hsa-miR-1226* | 5.37 | 0.48 | 3.57 | 0.47 | 4.41E−06 | 1.80 | 3.5 |
| hsa-miR-124 | 1.20 | 1.01 | −0.57 | 0.59 | 3.40E−04 | 1.77 | 3.4 |
| hsa-miR-1249 | 5.58 | 0.76 | 3.85 | 0.64 | 2.89E−04 | 1.73 | 3.3 |
| hsa-miR-1299 | 4.04 | 0.46 | 2.33 | 0.89 | 2.16E−03 | 1.72 | 3.3 |
| hsa-miR-541 | 0.61 | 0.40 | −1.10 | 0.61 | 7.79E−05 | 1.71 | 3.3 |
| hsa-miR-486-5p | 8.26 | 0.71 | 6.55 | 1.16 | 1.42E−02 | 1.71 | 3.3 |
| hsa-miR-1208 | 3.34 | 0.27 | 1.64 | 0.80 | 8.44E−04 | 1.70 | 3.2 |
| hsa-miR-671-3p | 0.34 | 0.59 | −1.35 | 0.69 | 3.88E−04 | 1.70 | 3.2 |
| hsa-miR-584 | 4.03 | 0.50 | 2.34 | 1.08 | 8.74E−03 | 1.69 | 3.2 |
| hsa-miR-33b* | 3.92 | 0.53 | 2.24 | 0.40 | 3.59E−06 | 1.68 | 3.2 |
| hsa-miR-639 | 0.66 | 0.47 | −1.00 | 0.67 | 3.30E−04 | 1.65 | 3.1 |
| hsa-miR-1254 | 1.14 | 0.36 | −0.48 | 0.71 | 4.63E−04 | 1.63 | 3.1 |
| hsa-miR-513a-5p | 5.17 | 0.43 | 3.57 | 0.53 | 4.65E−05 | 1.61 | 3.0 |
| hsa-miR-501-3p | 4.28 | 0.24 | 2.68 | 0.42 | 2.29E−06 | 1.60 | 3.0 |
| hsa-miR-1306 | 2.62 | 0.34 | 1.03 | 0.58 | 8.73E−05 | 1.59 | 3.0 |
| hsa-miR-122 | 1.86 | 1.30 | 0.29 | 0.67 | 4.08E−03 | 1.57 | 3.0 |
| hsa-miR-675b | 0.16 | 0.91 | −1.40 | 0.47 | 1.99E−04 | 1.57 | 3.0 |
| hsa-miR-486-3p | 1.82 | 1.02 | 0.26 | 0.91 | 9.11E−03 | 1.56 | 3.0 |
| hsa-miR-1307 | 3.02 | 0.38 | 1.46 | 0.53 | 5.61E−05 | 1.56 | 3.0 |
| hsa-miR-1285 | 3.03 | 0.59 | 1.48 | 0.55 | 1.61E−04 | 1.55 | 2.9 |
| hsa-miR-381 | 3.79 | 1.14 | 2.24 | 1.10 | 2.59E−02 | 1.55 | 2.9 |
| hsa-miR-125b-1* | 2.79 | 1.31 | 1.27 | 1.02 | 2.43E−02 | 1.53 | 2.9 |
| hsa-miR-139-5p | 6.53 | 0.30 | 5.03 | 0.77 | 1.68E−03 | 1.51 | 2.8 |
| hsa-miR-516a-5p | 3.28 | 0.99 | 1.77 | 0.89 | 9.99E−03 | 1.51 | 2.8 |
| hsa-miR-664* | 6.07 | 0.84 | 4.57 | 0.67 | 1.70E−03 | 1.50 | 2.8 |
| hsa-miR-220c | 0.55 | 0.18 | −0.94 | 0.53 | 5.27E−05 | 1.49 | 2.8 |
| hsa-miR-518e* | 1.68 | 0.29 | 0.19 | 0.67 | 6.11E−04 | 1.49 | 2.8 |
| hsa-miR-602 | 3.53 | 0.52 | 2.05 | 0.77 | 2.59E−03 | 1.48 | 2.8 |

TABLE 33-continued

MicroRNAs significantly differentially expressed between hyperplastic nodules (NOD) and differentiated follicular cell-derived carcinomas (CANCER).

| miRNA | NOD Avg | NOD STD | CANCER Avg | CANCER STD | NOD vs CANCER ttest | NOD vs CANCER Log2diff | Fold change |
|---|---|---|---|---|---|---|---|
| hsa-miR-550 | 3.35 | 0.32 | 1.87 | 0.47 | 2.57E−05 | 1.48 | 2.8 |
| hsa-miR-194* | 1.17 | 0.64 | −0.30 | 0.46 | 8.51E−05 | 1.47 | 2.8 |
| hsa-miR-499-5p | 4.99 | 1.73 | 3.53 | 0.78 | 2.26E−02 | 1.47 | 2.8 |
| hsa-miR-125a-3p | 6.98 | 0.40 | 5.52 | 0.52 | 9.98E−05 | 1.46 | 2.7 |
| hsa-miR-378 | 5.80 | 1.51 | 4.35 | 0.40 | 3.42E−05 | 1.45 | 2.7 |
| hsa-miR-193b* | 4.35 | 0.60 | 2.92 | 0.41 | 4.05E−05 | 1.43 | 2.7 |
| hsa-miR-512-3p | 4.75 | 0.05 | 3.35 | 1.10 | 2.41E−02 | 1.40 | 2.6 |
| hsa-miR-135b* | 0.11 | 0.63 | −1.28 | 0.64 | 1.36E−03 | 1.40 | 2.6 |
| hsa-miR-885-3p | 0.33 | 0.38 | −1.05 | 0.65 | 1.01E−03 | 1.38 | 2.6 |
| hsa-miR-28-3p | 1.74 | 0.21 | 0.37 | 0.70 | 1.44E−03 | 1.38 | 2.6 |
| hsa-miR-214 | 9.06 | 0.45 | 7.69 | 0.92 | 1.19E−02 | 1.38 | 2.6 |
| hsa-miR-886-5p | −0.11 | 0.91 | −1.48 | 0.59 | 2.23E−03 | 1.37 | 2.6 |
| hsa-miR-520a-5p | 0.68 | 0.37 | −0.68 | 0.56 | 3.30E−03 | 1.37 | 2.6 |
| hsa-miR-611 | −0.08 | 0.42 | −1.43 | 0.57 | 4.58E−04 | 1.36 | 2.6 |
| hsa-miR-574-5p | 7.17 | 0.65 | 5.82 | 0.52 | 4.89E−04 | 1.35 | 2.6 |
| hsa-miR-331-5p | 0.48 | 0.50 | −0.87 | 0.72 | 3.18E−03 | 1.35 | 2.6 |
| hsa-miR-760 | 3.96 | 0.39 | 2.61 | 0.87 | 9.16E−03 | 1.34 | 2.5 |
| hsa-miR-1304 | 0.10 | 0.85 | −1.23 | 0.57 | 1.78E−03 | 1.33 | 2.5 |
| hsa-miR-658 | 0.84 | 0.57 | −0.48 | 0.52 | 4.12E−04 | 1.33 | 2.5 |
| hsa-miR-135a* | 5.26 | 0.83 | 3.95 | 0.83 | 1.32E−02 | 1.31 | 2.5 |
| hsa-miR-708 | 2.26 | 0.40 | 0.96 | 0.78 | 5.73E−03 | 1.31 | 2.5 |
| hsa-miR-1244 | 1.73 | 0.83 | 0.42 | 0.61 | 2.85E−03 | 1.30 | 2.5 |
| hsa-miR-451 | 14.59 | 0.58 | 13.29 | 1.10 | 3.99E−02 | 1.30 | 2.5 |
| hsa-miR-1275 | 7.77 | 0.53 | 6.48 | 0.84 | 1.06E−02 | 1.29 | 2.4 |
| hsa-miR-296-5p | 4.16 | 0.70 | 2.88 | 0.40 | 2.25E−04 | 1.27 | 2.4 |
| hsa-miR-219-2-3p | −0.14 | 0.75 | −1.40 | 0.35 | 1.56E−04 | 1.26 | 2.4 |
| hsa-miR-432 | 2.91 | 0.59 | 1.66 | 0.63 | 2.59E−03 | 1.25 | 2.4 |
| hsa-miR-1270 | 2.13 | 0.49 | 0.90 | 0.73 | 6.53E−03 | 1.23 | 2.3 |
| hsa-miR-938 | −0.36 | 0.55 | −1.59 | 0.49 | 4.82E−04 | 1.23 | 2.3 |
| hsa-miR-184 | 2.49 | 0.44 | 1.26 | 1.10 | 4.77E−02 | 1.23 | 2.3 |
| hsa-miR-1322 | 0.07 | 0.89 | −1.15 | 0.46 | 1.45E−03 | 1.22 | 2.3 |
| hsa-miR-195* | 1.70 | 0.31 | 0.49 | 0.84 | 1.39E−02 | 1.21 | 2.3 |
| hsa-miR-595 | 1.47 | 0.36 | 0.27 | 0.61 | 1.87E−03 | 1.20 | 2.3 |
| hsa-miR-612 | 0.15 | 0.90 | −1.04 | 0.45 | 1.85E−03 | 1.19 | 2.3 |
| hsa-miR-145 | 10.36 | 0.25 | 9.21 | 0.68 | 4.88E−03 | 1.14 | 2.2 |
| hsa-miR-920 | −0.31 | 0.71 | −1.45 | 0.75 | 1.57E−02 | 1.14 | 2.2 |
| hsa-miR-604 | 1.03 | 0.47 | −0.09 | 0.71 | 9.28E−03 | 1.13 | 2.2 |
| hsa-miR-665 | 4.11 | 0.23 | 3.00 | 0.86 | 2.37E−02 | 1.11 | 2.2 |
| hsa-miR-300 | −0.08 | 0.53 | −1.19 | 0.65 | 6.59E−03 | 1.11 | 2.2 |
| hsa-miR-1323 | 2.32 | 0.36 | 1.21 | 0.56 | 1.99E−03 | 1.10 | 2.1 |
| hsa-miR-378* | 3.57 | 1.66 | 2.47 | 0.45 | 3.28E−02 | 1.10 | 2.1 |
| hsa-miR-193a-5p | 5.79 | 0.54 | 4.70 | 0.64 | 7.04E−03 | 1.09 | 2.1 |
| hsa-miR-152 | 7.41 | 0.49 | 6.32 | 0.84 | 2.72E−02 | 1.09 | 2.1 |
| hsa-miR-1470 | 0.88 | 0.44 | −0.21 | 0.75 | 1.51E−02 | 1.09 | 2.1 |
| hsa-miR-363 | 6.07 | 0.52 | 5.01 | 0.94 | 4.73E−02 | 1.07 | 2.1 |
| hsa-miR-18a* | 0.03 | 0.53 | −1.02 | 0.54 | 3.38E−02 | 1.06 | 2.1 |
| hsa-miR-23a* | 4.15 | 0.52 | 3.10 | 0.42 | 7.25E−04 | 1.05 | 2.1 |
| hsa-miR-508-5p | −0.04 | 0.96 | −1.09 | 0.40 | 4.24E−03 | 1.05 | 2.1 |
| hsa-miR-1247 | −0.30 | 0.85 | −1.34 | 0.79 | 3.59E−02 | 1.04 | 2.1 |
| hsa-miR-596 | −0.35 | 0.80 | −1.37 | 0.83 | 4.33E−02 | 1.02 | 2.0 |
| hsa-miR-887 | 3.67 | 0.29 | 2.67 | 0.51 | 1.91E−03 | 1.00 | 2.0 |
| hsa-miR-99b* | 2.60 | 0.27 | 1.61 | 0.50 | 1.72E−03 | 0.99 | 2.0 |
| hsa-miR-513a-3p | 0.56 | 0.52 | −0.43 | 0.64 | 1.19E−02 | 0.99 | 2.0 |
| hsa-miR-567 | 0.38 | 0.82 | −0.60 | 0.49 | 7.32E−03 | 0.98 | 2.0 |
| hsa-miR-222* | −0.97 | 0.32 | 0.06 | 0.65 | 7.78E−03 | −1.03 | 2.0 |
| hsa-miR-34a* | 3.35 | 0.11 | 4.39 | 0.34 | 2.71E−05 | −1.03 | 2.0 |
| hsa-miR-15a* | 0.59 | 0.33 | 1.65 | 0.43 | 3.58E−04 | −1.06 | 2.1 |
| hsa-miR-200c* | 0.71 | 0.51 | 1.83 | 0.44 | 4.76E−04 | −1.12 | 2.2 |
| hsa-miR-181a* | 2.91 | 0.38 | 4.04 | 0.59 | 2.55E−03 | −1.13 | 2.2 |
| hsa-miR-141* | 2.35 | 0.61 | 3.56 | 0.51 | 9.62E−04 | −1.22 | 2.3 |
| hsa-miR-15a | 10.12 | 0.45 | 11.38 | 0.42 | 8.40E−05 | −1.26 | 2.4 |
| hsa-miR-34a | 10.54 | 0.23 | 11.89 | 0.46 | 4.37E−05 | −1.35 | 2.6 |
| hsa-miR-542-3p | 4.58 | 0.36 | 6.01 | 1.31 | 4.97E−02 | −1.43 | 2.7 |
| hsa-miR-146a | 6.62 | 0.21 | 8.05 | 0.99 | 1.21E−02 | −1.43 | 2.7 |
| hsa-miR-181a-2* | 3.55 | 0.49 | 5.02 | 1.17 | 2.85E−02 | −1.47 | 2.8 |
| hsa-miR-424 | 8.49 | 0.39 | 9.98 | 1.13 | 2.10E−02 | −1.49 | 2.8 |
| hsa-miR-450a | 3.72 | 0.63 | 5.23 | 1.28 | 3.88E−02 | −1.51 | 2.9 |
| hsa-miR-96 | 6.74 | 0.37 | 8.33 | 1.20 | 2.12E−02 | −1.59 | 3.0 |
| hsa-miR-155 | 5.51 | 0.19 | 7.21 | 1.11 | 8.65E−03 | −1.70 | 3.2 |
| hsa-miR-503 | 3.37 | 0.73 | 5.12 | 0.99 | 4.93E−03 | −1.75 | 3.4 |
| hsa-miR-21 | 12.93 | 0.34 | 14.69 | 0.77 | 4.84E−04 | −1.76 | 3.4 |
| hsa-miR-29b-1* | 3.01 | 0.32 | 4.86 | 0.45 | 1.05E−06 | −1.85 | 3.6 |

TABLE 33-continued

MicroRNAs significantly differentially expressed between hyperplastic nodules (NOD) and differentiated follicular cell-derived carcinomas (CANCER).

| miRNA | NOD Avg | NOD STD | CANCER Avg | CANCER STD | NOD vs CANCER ttest | NOD vs CANCER Log2diff | Fold change |
|---|---|---|---|---|---|---|---|
| hsa-miR-142-5p | 3.80 | 0.94 | 5.68 | 1.35 | 1.99E−02 | −1.88 | 3.7 |
| hsa-miR-21* | 4.08 | 0.15 | 6.02 | 0.71 | 7.31E−05 | −1.93 | 3.8 |
| hsa-miR-1260 | 6.15 | 0.87 | 8.55 | 0.65 | 1.60E−05 | −2.40 | 5.3 |
| hsa-miR-142-3p | 6.85 | 1.06 | 9.26 | 1.24 | 2.86E−03 | −2.42 | 5.3 |
| hsa-miR-222 | 6.24 | 0.80 | 8.72 | 1.58 | 8.77E−03 | −2.48 | 5.6 |
| hsa-miR-221* | 4.79 | 0.21 | 7.36 | 1.53 | 4.70E−03 | −2.57 | 5.9 |
| hsa-miR-146b-3p | −1.31 | 0.37 | 1.33 | 2.24 | 3.56E−02 | −2.63 | 6.2 |
| hsa-miR-720 | 9.90 | 0.79 | 12.58 | 0.50 | 3.13E−07 | −2.68 | 6.4 |
| hsa-miR-1274b | 8.18 | 0.94 | 11.00 | 0.60 | 1.61E−02 | −2.82 | 7.0 |
| hsa-miR-221 | 6.58 | 0.33 | 9.47 | 1.53 | 2.08E−03 | −2.89 | 7.4 |
| hsa-miR-1274a | 4.39 | 1.03 | 7.38 | 0.67 | 2.84E−06 | −2.99 | 7.9 |
| hsa-miR-146b-5p | 7.29 | 0.77 | 11.33 | 3.20 | 2.62E−02 | −4.03 | 16.4 |

Avg, average of expression among samples in a group;
SD, standard deviation.

Example 32 miRNA Expression Profiling Distinguishes Follicular Adenoma (FA) From Differentiated Follicular Cell-Derived Carcinomas (FTC, PTC, FVPTC)

A total of 94 human miRNAs were significantly differentially expressed between the follicular adenomas and the follicular cell-derived carcinoma (FTC, PTC, FVPTC) specimens (p<0.05). Of these, nineteen miRNAs were expressed at levels 2- to 5-fold higher (Log 2 diff (FA vs CANCER)≥1) in the FA samples. In addition, thirteen miRNAs were expressed at levels at least 2-fold lower in the FA samples (Table 34). Among these, five miRNAs (hsa-miR-31, -31*, -200a, -200b, and -429) were underexpressed by 8- to 20-fold, and eight miRNAs were underexpressed by 2- to 5-fold in the FA samples (Table 34).

TABLE 34

MicroRNAs significantly differentially expressed between follicular adenomas and differentiated follicular cell-derived carcinomas (CANCER).

| miRNA | CANCER Avg | CANCER SD | FA Avg | FA SD | FA vs CANCER ttest | FA vs CANCER Log2Diff | Fold change |
|---|---|---|---|---|---|---|---|
| hsa-miR-885-5p | 0.15 | 0.95 | 2.39 | 2.44 | 8.50E−03 | 2.24 | 4.7 |
| hsa-miR-873 | 0.76 | 1.15 | 2.39 | 1.52 | 2.22E−02 | 1.63 | 3.1 |
| hsa-miR-668 | −1.29 | 0.62 | 0.18 | 1.71 | 1.11E−02 | 1.47 | 2.8 |
| hsa-miR-554 | −1.86 | 0.30 | −0.48 | 1.09 | 3.07E−04 | 1.38 | 2.6 |
| hsa-miR-10a | 6.76 | 0.85 | 8.12 | 1.89 | 4.06E−02 | 1.36 | 2.6 |
| hsa-miR-1227 | 0.12 | 0.66 | 1.40 | 1.09 | 5.85E−03 | 1.28 | 2.4 |
| hsa-miR-220a | −1.15 | 0.69 | 0.11 | 1.16 | 9.35E−03 | 1.26 | 2.4 |
| hsa-miR-1910 | −1.68 | 0.48 | −0.46 | 2.07 | 4.53E−02 | 1.23 | 2.3 |
| hsa-let-7g* | −0.98 | 0.49 | 0.23 | 1.47 | 1.22E−02 | 1.21 | 2.3 |
| hsa-miR-671-3p | −1.35 | 0.69 | −0.25 | 1.10 | 1.72E−02 | 1.11 | 2.2 |
| hsa-miR-1247 | −1.34 | 0.79 | −0.29 | 0.97 | 2.80E−02 | 1.05 | 2.1 |
| hsa-miR-637 | −1.17 | 0.39 | −0.13 | 1.32 | 1.37E−02 | 1.04 | 2.1 |
| hsa-miR-1204 | −1.05 | 0.49 | −0.02 | 1.48 | 2.94E−02 | 1.03 | 2.0 |
| hsa-miR-1468 | −1.84 | 0.59 | −0.81 | 1.29 | 2.64E−02 | 1.03 | 2.0 |
| hsa-miR-371-3p | −0.16 | 0.67 | 0.85 | 1.16 | 2.79E−02 | 1.02 | 2.0 |
| hsa-miR-411* | −1.36 | 0.40 | −0.35 | 1.61 | 3.71E−02 | 1.01 | 2.0 |
| hsa-miR-483-3p | 0.57 | 0.65 | 1.57 | 0.99 | 2.03E−02 | 0.99 | 2.0 |
| hsa-miR-517a | −0.40 | 0.54 | 0.59 | 1.11 | 1.63E−02 | 0.99 | 2.0 |
| hsa-miR-595 | 0.27 | 0.61 | 1.24 | 1.14 | 2.73E−02 | 0.96 | 2.0 |
| hsa-miR-1255b | −0.58 | 0.65 | −1.55 | 1.06 | 2.52E−02 | −0.98 | 2.0 |
| hsa-miR-556-5p | 0.05 | 0.34 | −0.94 | 0.91 | 2.30E−03 | −0.99 | 2.0 |
| hsa-miR-21* | 6.02 | 0.71 | 4.88 | 0.62 | 5.84E−03 | −1.14 | 2.2 |
| hsa-miR-21 | 14.69 | 0.77 | 13.53 | 0.95 | 1.47E−02 | −1.16 | 2.2 |
| hsa-miR-449a | 3.24 | 0.86 | 1.92 | 0.60 | 6.16E−03 | −1.32 | 2.5 |
| hsa-miR-424 | 9.98 | 1.13 | 8.66 | 1.27 | 4.37E−02 | −1.32 | 2.5 |
| hsa-miR-200a* | 3.81 | 1.75 | 1.73 | 1.73 | 3.45E−02 | −2.09 | 4.2 |
| hsa-miR-200b* | 4.18 | 1.76 | 2.08 | 2.15 | 4.39E−02 | −2.11 | 4.3 |
| hsa-miR-429 | 7.50 | 2.05 | 4.35 | 3.00 | 1.82E−02 | −3.14 | 8.8 |
| hsa-miR-200b | 10.12 | 2.06 | 6.77 | 3.16 | 1.45E−02 | −3.35 | 10.2 |
| hsa-miR-200a | 8.67 | 1.95 | 5.20 | 3.08 | 9.08E−03 | −3.47 | 11.1 |

TABLE 34-continued

MicroRNAs significantly differentially expressed between follicular adenomas and differentiated follicular cell-derived carcinomas (CANCER).

| miRNA | CANCER Avg | CANCER SD | FA Avg | FA SD | FA vs CANCER ttest | FA vs CANCER Log2Diff | Fold change |
|---|---|---|---|---|---|---|---|
| hsa-miR-31* | 6.98 | 1.89 | 3.33 | 3.40 | 7.99E−03 | −3.66 | 12.6 |
| hsa-miR-31 | 8.45 | 2.05 | 4.50 | 3.49 | 6.91E−03 | −3.95 | 15.5 |

Avg, average of expression among samples in a group;
SD, standard deviation.

Figure 2A:
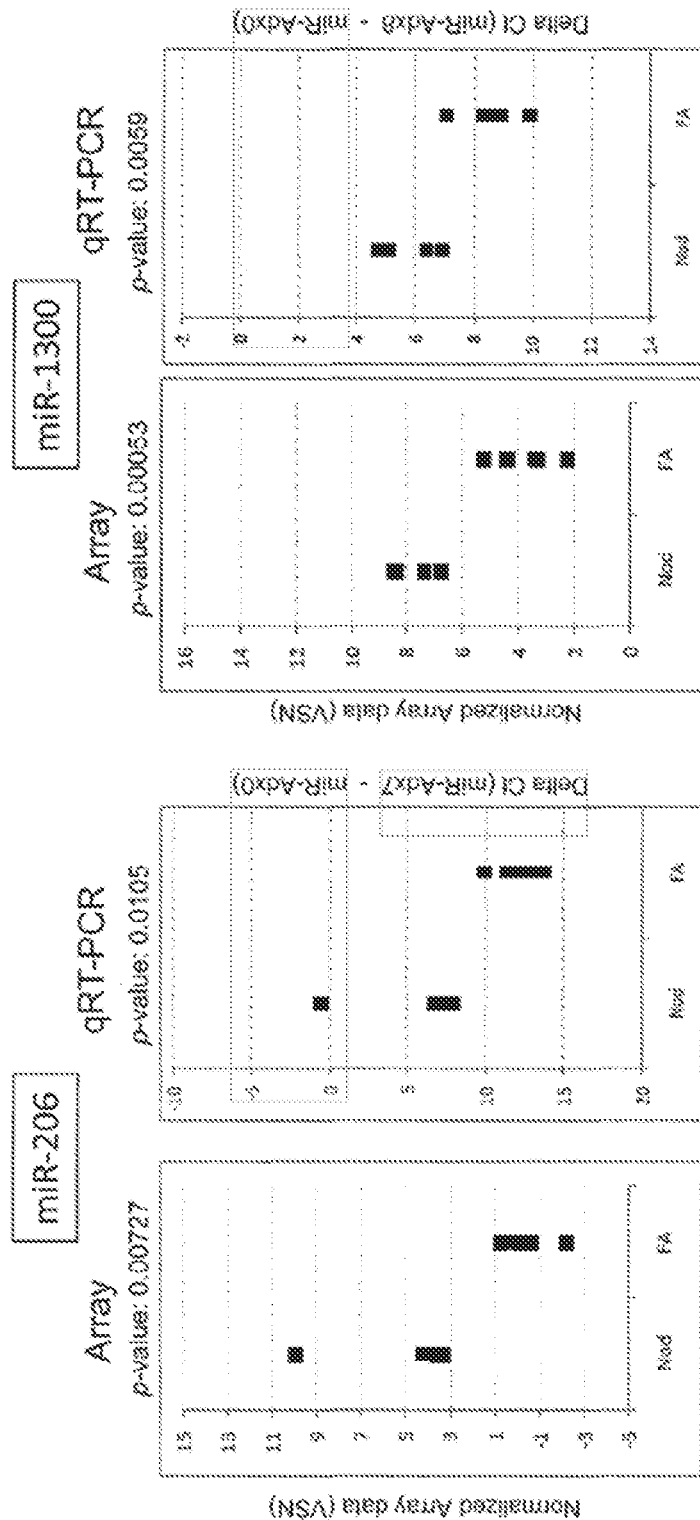
FIG. 2A. Comparison between array and qRT-PCR data for selected miRNAs differentially expressed between hyperplastic nodules (NOD) and follicular adenoma (FA), with associated p-values.
Figure 2B:
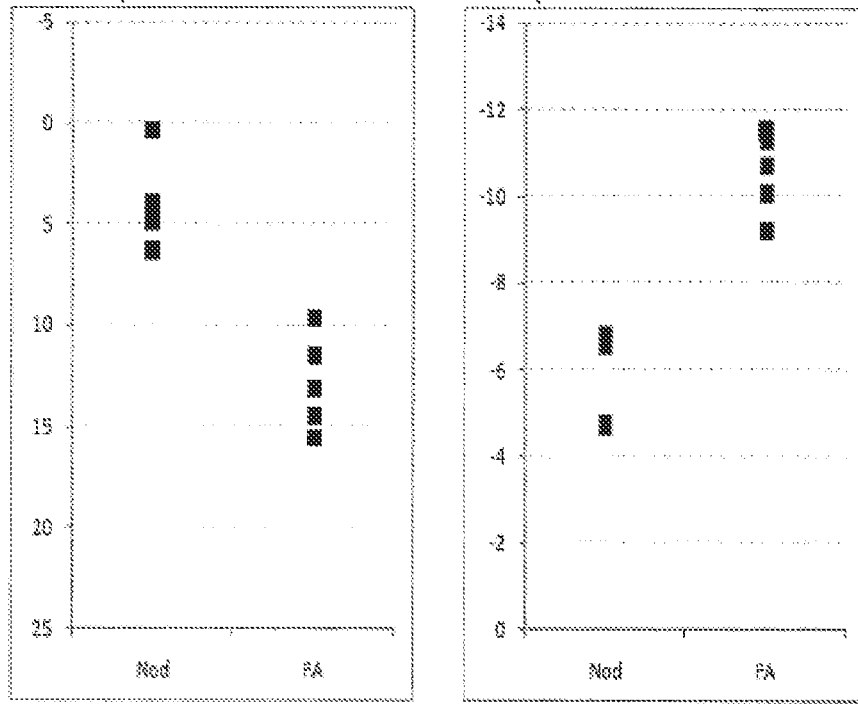
FIG. 2B. Comparison between array and qRT-PCR data for selected combinations of miRNAs differentially expressed between hyperplastic nodules (NOD) and follicular adenoma (FA), with associated p-values.
Figure 3A:
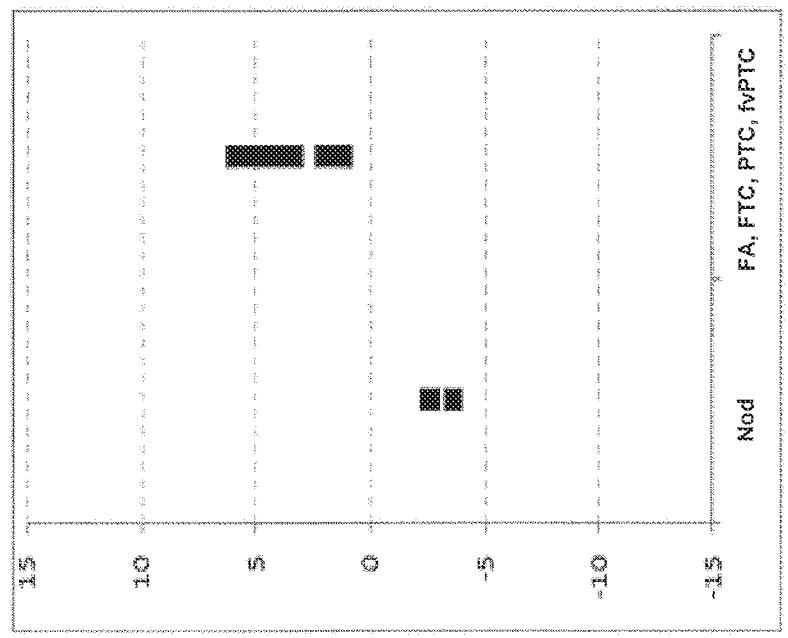
FIGS. 3A, B, and C Examples of combinations of differentially expressed miRNA illustrating the correlation between array and qRT-PCR data. Differentially expressed miRNAs were identified by array analysis and confirmed by qRT-PCR. Differentially expressed miRNAs were selected and combined, as shown in the graphs of the three examples above. The triangles correspond to an additional and independent set of 11 samples (1 Nod, 2 FA, 1 oncocytic FA, 4 PTC, 1 FVPTC, 1 oncocytic FTC, and 1 Hashimoto's thyroiditis (Hash)) that were only tested by qRT-PCR. The grey squares and triangles correspond to samples positive for any of the most common mutations or gene translocations in thyroid cancer.
Figure 3B:
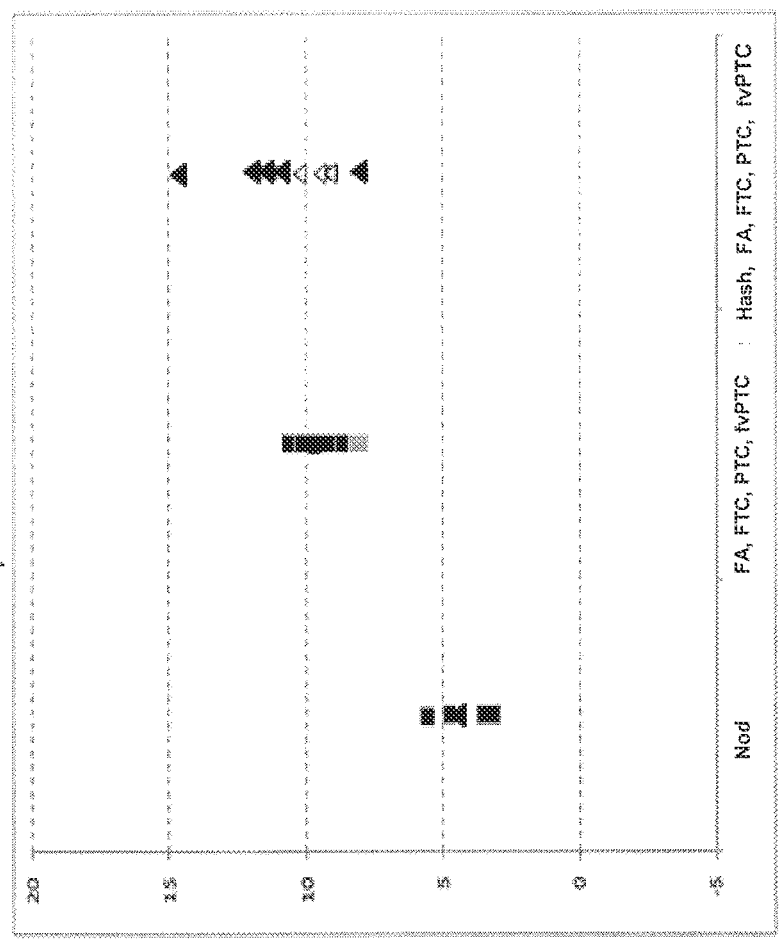
Figure 3B:
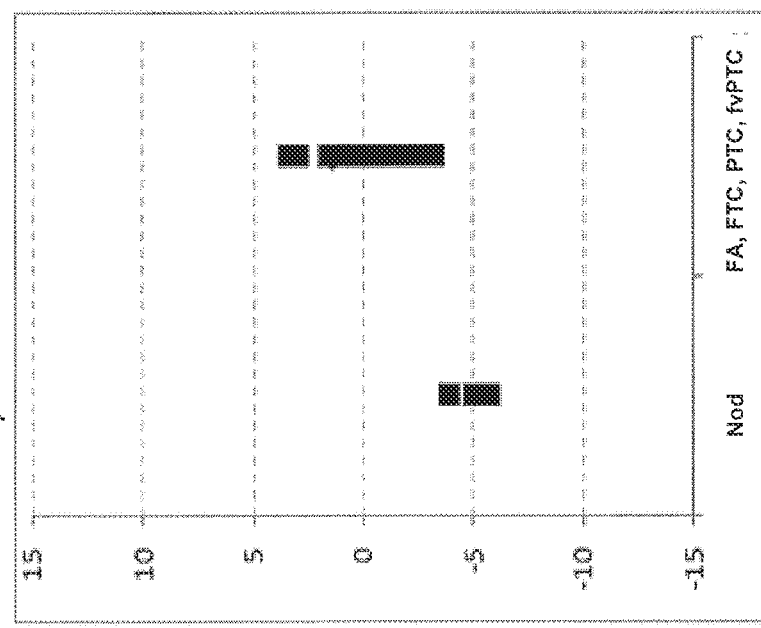
Figure 3C:
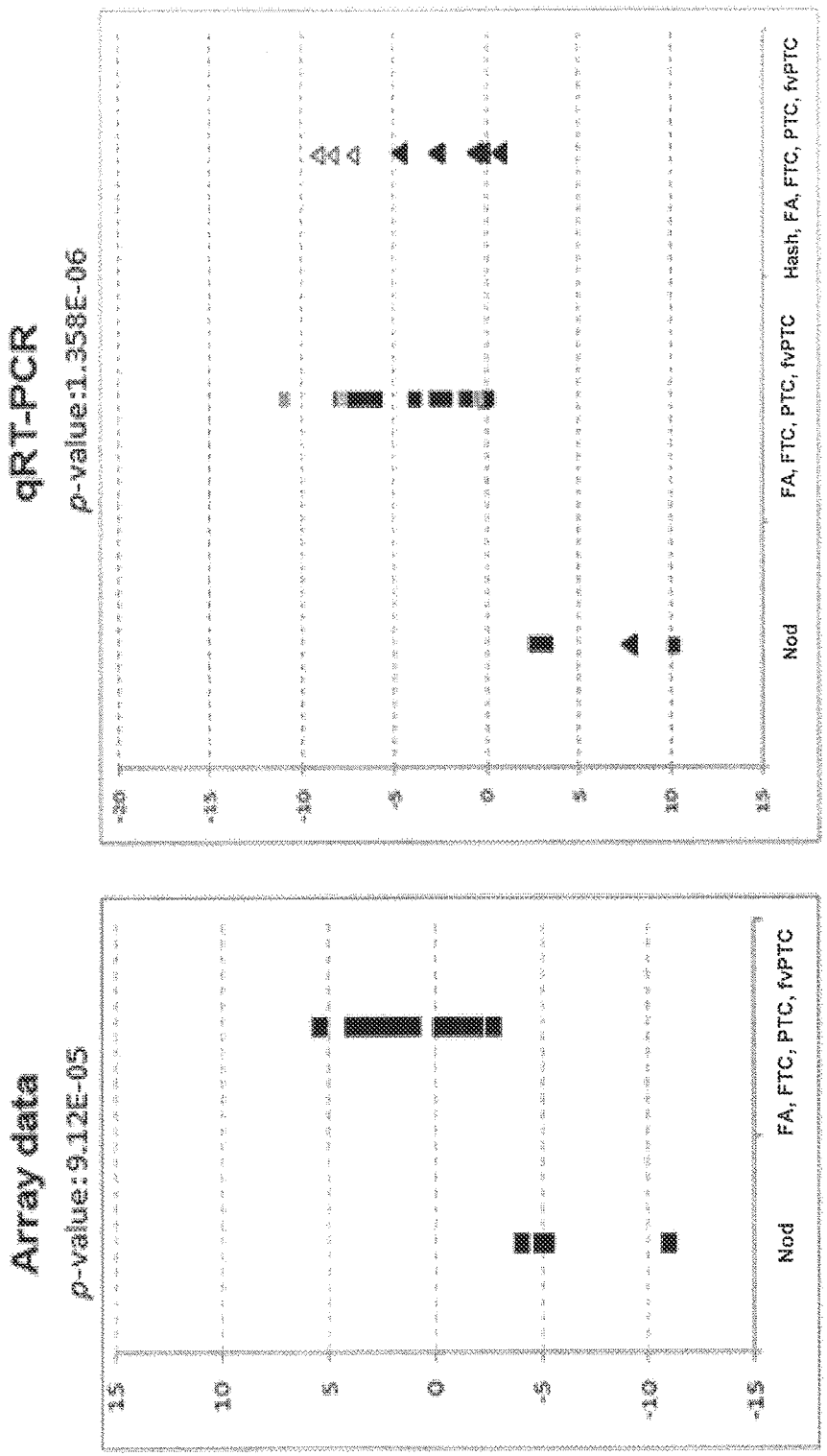

Example 33 qRT-PCR Analysis of Differentially Expressed miRNAS qRT-PCR reactions were performed for 33 of the top most commonly differentially expressed miRNAs between the eight different subgroups of normal and diseased thyroid tissues. qRT-PCR reactions were performed using TaqMan® MicroRNA Assays (Applied Biosystems; Foster City, Calif., USA) according to the manufacturer's instructions. Reactions included 5 ng of total RNA per reaction and were incubated in the 7900HT Fast Real-Time PCR System (Applied Biossystems). The 31 patient samples that were initially evaluated by miRNA microarray expression analysis were also analyzed by qRT-PCR. In addition, an independent set of 11 patient thyroid samples (1 NOD, 2 FA, 1 oncocytic FA, 4 PTC, 1 FVPTC, 1 oncocytic FTC, and 1 Hashimoto's thyroiditis (Hash)) were also analyzed by qRT-PCR. The raw qRT-PCR data obtained for the 42 thyroid samples are shown in Table 35. Two different analyses were performed using the qRT-PCR data. First, the inventors compared the expression levels of each individual miRNA between different groups of samples, as illustrated for miR-206 and miR-1300 in NOD vs. FA samples (FIG. 2A). For these experiments, miRNA expression levels were normalized, using miR-191 as a normalizer, as its expression levels were very similar across the eight subgroups of samples. Second, the inventors determined the expression difference between two miRNAs that were differentially expressed in opposite directions (i.e., one miRNA was overexpressed and one was underexpressed) between two groups of samples. This type of evaluation eliminates the need for normalization and increases the distinction between two particular groups of samples. Examples of the expression difference between two miRNAs are illustrated in FIG. 2B and FIGS. 3A-C for miRNAs distinguishing thyroid nodules from follicular cell-derived thyroid neoplasms (FA, FTC, PTC, and FVPTC). As mutations and gene rearrangements are important for the pathogenesis of thyroid cancer, the 42 samples were analyzed for the presence of the most common DNA mutation (BRAF V600E, NRAS, HRAS, and KRAS) or translocation (RET/PTC1 and 3, and PAX8/PPARγ) found in thyroid cancer, using Asuragen's Luminex-based Research Assay.

Importantly, the accurate classification of the samples was obtained regardless of the mutational status of the samples (FIG. 3). Overall, the relative variations of miRNA expression levels were very similar for array and qRT-PCR data, demonstrating a very good correlation between the two platforms.

TABLE 35

QRT-PCR data for expression of 33 miRNAs in 42 thyroid samples.

| miRNA | | | | | |
|---|---|---|---|---|---|
| miR-96 | 31.6 | 31.5 | 31.4 | 31.5 | 28.8 |
| miR-934 | 39.1 | 40.0 | 40.0 | 36.6 | 37.3 |
| miR-92b* | 31.4 | 31.1 | 30.8 | 10.7 | 30.8 |
| miR-885- | 31.4 | 32.1 | 31.2 | 26.7 | 35.3 |
| miR-720 | 22.1 | 23.7 | 22.5 | 19.9 | 21.4 |
| miR-631 | 32.9 | 31.9 | 31.8 | 32.5 | 33.7 |
| miR-551b | 33.4 | 32.5 | 32.2 | 32.7 | 29.7 |
| miR-513c | 36.0 | 34.6 | 36.6 | 35.8 | 35.2 |
| miR-429 | 25.3 | 24.4 | 24.5 | 24.8 | 23.7 |
| miR-375 | 29.4 | 27.4 | 26.2 | 24.5 | 27.2 |
| miR-31* | 25.9 | 25.5 | 26.3 | 29.6 | 31.4 |
| miR-31 | 22.2 | 22.1 | 23.1 | 25.9 | 27.1 |
| miR-222* | 31.3 | 31.7 | 31.0 | 31.3 | 30.9 |
| miR-222 | 20.1 | 20.2 | 20.4 | 20.5 | 21.9 |
| miR-221* | 30.8 | 31.1 | 30.6 | 31.2 | 31.8 |
| miR-221 | 24.9 | 25.0 | 24.6 | 24.5 | 25.7 |
| miR-22 | 26.4 | 26.4 | 26.4 | 26.2 | 27.3 |
| miR-206 | 28.5 | 27.7 | 27.4 | 20.2 | 32.8 |
| miR- | 26.6 | 26.3 | 26.5 | 27.2 | 25.2 |
| miR-200b | 21.8 | 21.6 | 21.6 | 21.8 | 20.8 |
| miR-200a* | 28.6 | 28.3 | 28.4 | 29.1 | 27.5 |
| miR-200a | 23.8 | 23.6 | 23.7 | 24.2 | 23.1 |
| miR-187* | 36.7 | 36.2 | 35.3 | 36.6 | 36.7 |
| miR-187 | 32.3 | 31.3 | 32.8 | 31.4 | 30.5 |
| miR-182 | 26.4 | 26.9 | 26.3 | 26.1 | 25.1 |
| miR-146b- | 23.1 | 22.5 | 22.6 | 22.1 | 24.0 |
| miR-146b- | 31.1 | 30.2 | 30.6 | 30.4 | 32.9 |
| miR-133b | 27.7 | 27.0 | 26.5 | 21.4 | 28.8 |
| miR-1300 | 26.9 | 27.3 | 25.7 | 25.5 | 29.6 |
| miR- | 18.1 | 20.1 | 18.7 | 16.4 | 18.5 |
| miR-1274a | 20.4 | 22.5 | 21.0 | 18.6 | 20.4 |
| miR-1202 | 26.3 | 26.4 | 25.7 | 26.9 | 28.2 |
| miR-1182 | 35.9 | 34.9 | 34.8 | 36.4 | 37.6 |
| miR-191 | 20.6 | 20.3 | 20.6 | 20.7 | 20.7 |
| miR-24 | 19.3 | 19.2 | 19.0 | 19.1 | 18.5 |
| miR-16 | 17.9 | 18.2 | 17.9 | 17.3 | 18.2 |
| Mutational Histologic | NOD | NOD | NOD | NOD | FA |
| Sample | 6 | 7 | 12 | 21 | 4 |
| 28.6 | 28.7 | 28.7 | 28.9 | 30.6 | 30.7 | 30.3 |
| 38.2 | 33.6 | 28.7 | 39.1 | 34.3 | 35.6 | 32.7 |
| 32.2 | 30.4 | 28.7 | 30.7 | 30.9 | 30.7 | 29.7 |
| 26.4 | 32.0 | 28.7 | 26.3 | 31.9 | 31.8 | 32.4 |
| 19.1 | 19.0 | 28.7 | 19.5 | 21.2 | 19.0 | 20.6 |
| 33.1 | 34.4 | 28.7 | 33.6 | 33.5 | 33.9 | 32.9 |
| 40.0 | 29.6 | 28.7 | 34.2 | 29.1 | 29.1 | 28.9 |
| 38.6 | 33.7 | 28.7 | 34.7 | 35.2 | 31.1 | 34.1 |
| 30.2 | 32.0 | 28.7 | 28.3 | 23.3 | 23.2 | 23.5 |
| 31.5 | 25.5 | 28.7 | 30.0 | 24.5 | 25.0 | 23.8 |
| 35.2 | 23.2 | 28.7 | 25.7 | 24.6 | 22.8 | 25.0 |
| 29.4 | 40.0 | 28.7 | 40.0 | 20.7 | 19.2 | 21.0 |
| 27.8 | 26.3 | 28.7 | 27.7 | 27.6 | 26.8 | 27.2 |
| 18.3 | 17.4 | 19.8 | 20.0 | 17.6 | 17.2 | 17.2 |
| 28.9 | 27.3 | 30.3 | 28.4 | 28.6 | 27.7 | 28.0 |
| 20.5 | 20.9 | 23.0 | 21.8 | 22.3 | 21.6 | 22.2 |
| 26.6 | 26.1 | 26.7 | 26.0 | 27.6 | 26.8 | 27.4 |
| 33.5 | 32.0 | 30.3 | 34.9 | 32.9 | 31.9 | 32.4 |
| 33.0 | 34.1 | 27.4 | 31.3 | 25.7 | 25.2 | 25.5 |
| 24.8 | 24.4 | 23.2 | 25.4 | 20.8 | 20.2 | 20.4 |

TABLE 35-continued

QRT-PCR data for expression of 33 miRNAs in 42 thyroid samples.

| | | | | | | |
|---|---|---|---|---|---|---|
| 33.8 | 34.4 | 30.0 | 32.8 | 27.5 | 26.7 | 27.2 |
| 30.7 | 31.5 | 25.4 | 28.3 | 23.1 | 22.3 | 22.8 |
| 37.3 | 34.9 | 39.3 | 37.3 | 38.7 | 34.1 | 36.3 |
| 32.3 | 25.8 | 30.7 | 32.7 | 29.4 | 26.0 | 31.9 |
| 23.4 | 24.6 | 25.8 | 25.0 | 25.5 | 25.7 | 25.9 |
| 23.1 | 18.1 | 22.1 | 21.6 | 16.5 | 16.7 | 16.6 |
| 31.2 | 26.1 | 30.2 | 28.7 | 24.8 | 25.0 | 24.3 |
| 30.6 | 26.9 | 28.2 | 30.2 | 31.7 | 29.6 | 26.9 |
| 28.7 | 27.7 | 30.4 | 29.8 | 29.3 | 28.9 | 28.7 |
| 16.2 | 16.1 | 17.8 | 16.6 | 18.4 | 16.8 | 17.6 |
| 17.4 | 17.7 | 19.7 | 18.3 | 19.7 | 18.4 | 19.0 |
| 27.9 | 27.1 | 28.4 | 27.4 | 27.9 | 28.2 | 27.7 |
| 37.6 | 39.0 | 36.7 | 36.5 | 37.4 | 35.7 | 35.2 |
| 20.5 | 20.7 | 20.5 | 21.3 | 20.7 | 20.3 | 20.9 |
| 19.8 | 18.4 | 28.7 | 19.6 | 19.5 | 19.0 | 19.4 |
| 17.5 | 17.3 | 18.1 | 18.0 | 17.4 | 16.9 | 17.6 |
| | RET/PTC3 | | | BRAF | | BRAF |
| FA | FA | FA | FA | PTC | PTC | PTC |
| 13 | 15 | 17 | 22 | 8 | 10 | 11 |

| | | | | | | |
|---|---|---|---|---|---|---|
| 30.2 | 29.8 | 28.2 | 31.1 | 30.2 | 31.5 | 26.4 |
| 35.8 | 34.4 | 35.4 | 33.7 | 34.6 | 34.2 | 38.7 |
| 30.6 | 30.4 | 31.4 | 30.6 | 31.5 | 30.6 | 31.9 |
| 31.6 | 31.1 | 32.2 | 29.3 | 33.1 | 31.1 | 31.6 |
| 20.9 | 20.5 | 20.1 | 20.0 | 18.6 | 20.2 | 19.4 |
| 33.6 | 33.7 | 33.6 | 33.9 | 33.4 | 33.4 | 32.8 |
| 27.9 | 28.2 | 29.2 | 28.3 | 31.0 | 29.4 | 34.1 |
| 32.9 | 39.6 | 32.3 | 34.2 | 33.8 | 34.0 | 32.6 |
| 22.6 | 24.5 | 22.4 | 22.3 | 24.0 | 23.6 | 21.3 |
| 22.9 | 25.1 | 25.7 | 22.4 | 25.1 | 24.4 | 17.1 |
| 23.5 | 23.2 | 22.9 | 24.2 | 23.1 | 24.2 | 30.0 |
| 20.0 | 19.4 | 19.3 | 20.9 | 19.4 | 20.7 | 25.5 |
| 26.1 | 27.2 | 25.9 | 27.4 | 26.5 | 27.7 | 29.0 |
| 15.8 | 16.5 | 16.5 | 17.6 | 17.2 | 18.4 | 18.7 |
| 26.4 | 27.5 | 27.2 | 27.4 | 28.0 | 29.6 | 30.5 |
| 20.2 | 21.7 | 20.6 | 21.2 | 21.0 | 22.6 | 23.2 |
| 27.1 | 27.3 | 27.0 | 26.7 | 27.2 | 27.3 | 27.4 |
| 33.8 | 32.6 | 33.2 | 34.2 | 33.0 | 28.5 | 30.8 |
| 24.7 | 26.4 | 24.7 | 24.7 | 25.8 | 25.5 | 24.5 |
| 19.8 | 21.2 | 20.1 | 19.7 | 21.4 | 21.1 | 19.6 |
| 26.5 | 27.6 | 26.6 | 26.2 | 27.9 | 27.4 | 26.3 |
| 21.7 | 23.4 | 22.0 | 21.5 | 23.7 | 23.1 | 21.3 |
| 37.5 | 37.1 | 35.6 | 36.8 | 35.1 | 36.7 | 37.0 |
| 30.0 | 31.5 | 27.3 | 31.5 | 27.3 | 30.4 | 30.0 |
| 25.9 | 24.9 | 23.4 | 26.3 | 25.3 | 26.6 | 22.1 |
| 15.2 | 16.3 | 16.8 | 15.8 | 18.2 | 18.9 | 21.8 |
| 22.8 | 24.7 | 25.3 | 23.7 | 25.7 | 26.1 | 30.4 |
| 30.5 | 30.1 | 28.3 | 24.2 | 28.4 | 27.6 | 30.1 |
| 29.4 | 28.9 | 30.5 | 28.4 | 27.9 | 28.2 | 29.3 |
| 18.1 | 17.7 | 18.1 | 17.3 | 15.7 | 17.0 | 16.3 |
| 19.6 | 19.0 | 19.5 | 19.2 | 17.5 | 18.7 | 18.0 |
| 27.8 | 28.4 | 28.1 | 27.6 | 28.3 | 27.2 | 27.0 |
| 37.1 | 36.5 | 37.4 | 37.9 | 35.4 | 36.1 | 35.6 |
| 20.3 | 20.0 | 20.6 | 20.3 | 20.8 | 20.9 | 20.2 |
| 18.6 | 18.5 | 18.5 | 18.5 | 18.7 | 19.2 | 18.4 |
| 17.3 | 16.8 | 17.0 | 17.4 | 17.6 | 17.3 | 17.7 |
| BRAF | BRAF | RET/PTC3 | BRAF | | RET/PTC1 | |
| PTC | PTC | FVPTC | FVPTC | FVPTC | FVPTC | MTC |
| 23 | 24 | 16 | 25 | 32 | 33 | 19 |

| | | | | | | |
|---|---|---|---|---|---|---|
| 29.2 | 28.8 | 29.5 | 28.1 | 31.5 | 29.1 | 32.4 |
| 21.2 | 21.4 | 21.9 | 21.0 | 25.6 | 21.3 | 26.3 |
| 26.1 | 26.7 | 26.1 | 27.7 | 28.2 | 25.8 | 26.3 |
| 34.7 | 30.6 | 34.6 | 33.3 | 31.8 | 35.4 | 32.2 |
| 25.3 | 24.5 | 28.1 | 27.9 | 30.3 | 32.3 | 27.8 |
| 20.5 | 19.8 | 23.1 | 22.7 | 24.5 | 24.6 | 22.3 |
| 27.2 | 26.3 | 30.7 | 29.9 | 32.4 | 34.5 | 29.4 |
| 21.6 | 21.4 | 25.7 | 24.9 | 28.0 | 29.9 | 24.3 |
| 33.1 | 35.4 | 35.9 | 38.7 | 37.9 | 32.6 | 37.2 |
| 25.5 | 30.5 | 29.7 | 31.4 | 31.8 | 24.9 | 30.7 |
| 23.5 | 23.0 | 24.3 | 26.2 | 25.3 | 23.1 | 26.0 |
| 24.3 | 23.0 | 23.1 | 23.0 | 20.5 | 24.4 | 23.4 |
| 32.8 | 30.4 | 30.7 | 30.7 | 28.9 | 33.0 | 31.1 |
| 31.7 | 28.1 | 29.7 | 30.2 | 31.0 | 32.5 | 28.1 |
| 29.6 | 27.9 | 28.7 | 29.7 | 28.8 | 30.3 | 29.2 |
| 16.8 | 16.0 | 15.5 | 17.3 | 16.7 | 17.0 | 16.1 |
| 18.9 | 17.6 | 17.0 | 19.6 | 17.8 | 19.1 | 18.1 |
| 28.8 | 26.1 | 28.3 | 29.3 | 27.5 | 29.2 | 27.7 |
| 37.9 | 34.6 | 37.3 | 37.0 | 36.3 | 39.1 | 39.2 |
| 20.9 | 20.1 | 20.9 | 21.6 | 21.5 | 21.2 | 21.0 |
| 18.9 | 18.2 | 19.9 | 19.4 | 20.4 | 19.4 | 19.9 |
| 17.6 | 17.2 | 17.8 | 18.3 | 17.9 | 17.9 | 17.4 |
| MTC | MTC | FTC | FTC | FTC | FTC | FTC |
| 28 | 29 | 18 | 27 | 30 | 31 | 34 |

| | | | | | | |
|---|---|---|---|---|---|---|
| 30.6 | 31.2 | 30.8 | 30.7 | 32.4 | 36.2 | 36.6 |
| 40.0 | 38.1 | 39.5 | 36.3 | 39.5 | 39.7 | 40.0 |
| 32.0 | 31.5 | 30.8 | 30.2 | 31.2 | 33.8 | 36.3 |
| 29.7 | 26.5 | 30.8 | 30.7 | 32.0 | 32.9 | 36.6 |
| 18.2 | 21.0 | 21.3 | 20.6 | 21.0 | 25.7 | 21.5 |
| 33.2 | 32.5 | 33.9 | 32.6 | 33.5 | 32.9 | 34.7 |
| 35.4 | 33.8 | 32.9 | 32.6 | 33.3 | 36.3 | 36.9 |
| 35.1 | 38.7 | 35.0 | 38.6 | 40.0 | 39.8 | 40.0 |
| 32.8 | 23.9 | 23.6 | 23.2 | 23.9 | 26.5 | 27.9 |
| 29.0 | 27.5 | 26.6 | 24.3 | 26.8 | 27.0 | 33.4 |
| 27.6 | 26.8 | 26.1 | 26.7 | 25.4 | 28.2 | 30.1 |
| 24.5 | 23.4 | 22.8 | 22.9 | 22.2 | 24.7 | 25.7 |
| 30.9 | 31.9 | 31.0 | 29.3 | 29.2 | 34.3 | 32.8 |
| 20.3 | 21.1 | 21.4 | 20.6 | 21.4 | 40.0 | 40.0 |
| 32.7 | 32.5 | 32.4 | 31.2 | 31.6 | 35.5 | 35.2 |
| 25.0 | 25.6 | 26.4 | 25.6 | 25.0 | 28.9 | 29.4 |
| 27.1 | 26.7 | 27.2 | 26.8 | 27.4 | 30.1 | 31.5 |
| 33.2 | 21.6 | 28.0 | 29.3 | 31.0 | 26.7 | 37.4 |
| 33.6 | 26.3 | 25.5 | 25.3 | 26.2 | 29.3 | 31.8 |
| 29.1 | 21.4 | 21.1 | 20.8 | 21.1 | 23.2 | 25.1 |
| 37.2 | 28.1 | 27.9 | 27.5 | 27.9 | 31.2 | 33.7 |
| 31.6 | 23.6 | 25.3 | 22.9 | 23.2 | 26.2 | 27.8 |
| 35.4 | 37.7 | 38.4 | 39.0 | 38.5 | 36.4 | 38.6 |
| 27.2 | 32.7 | 30.9 | 29.1 | 32.5 | 35.1 | 35.8 |
| 26.6 | 26.8 | 26.4 | 26.2 | 27.5 | 29.0 | 28.1 |
| 21.1 | 23.4 | 21.5 | 23.3 | 24.5 | 22.4 | |
| 29.5 | 32.1 | 32.7 | 30.5 | 31.2 | 34.4 | 32.8 |
| 31.8 | 21.1 | 27.2 | 27.4 | 28.1 | 28.1 | 33.7 |
| 28.0 | 26.7 | 29.5 | 28.5 | 27.8 | 30.2 | 32.8 |
| 15.5 | 16.9 | 17.5 | 17.3 | 18.6 | 21.8 | 18.6 |
| 16.6 | 18.3 | 19.4 | 18.8 | 21.2 | 23.9 | 21.8 |
| 27.1 | 27.0 | 27.6 | 27.7 | 28.5 | 27.8 | 29.9 |
| 35.7 | 35.5 | 37.2 | 35.0 | 37.1 | 36.6 | 40.0 |
| 20.6 | 20.8 | 20.5 | 20.1 | 20.3 | 22.5 | 23.4 |
| 19.2 | 19.3 | 18.9 | 18.8 | 19.0 | 21.9 | 22.1 |
| 17.9 | 17.8 | 17.6 | 17.1 | 17.7 | 21.3 | 21.3 |
| ATC | NOR | NOR | NOR | NOR | NOD | Hashimoto |
| 26 | 1 | 3 | 5 | 14 | 37 | 41 |

TABLE 35-continued

QRT-PCR data for expression of 33 miRNAs in 42 thyroid samples.

| | | | | | | |
|---|---|---|---|---|---|---|
| 31.1 | 29.8 | 29.9 | 33.6 | 30.1 | 28.8 | 30.8 |
| 40.0 | 40.0 | 40.0 | 40.0 | 40.0 | 40.0 | 40.0 |
| 33.8 | 31.7 | 33.8 | 40.0 | 32.1 | 31.5 | 32.1 |
| 27.1 | 25.4 | 24.4 | 30.6 | 25.7 | 25.4 | 25.0 |
| 31.1 | 30.5 | 29.8 | 30.0 | 30.6 | 32.1 | 30.8 |
| 35.1 | 35.5 | 36.8 | 37.9 | 36.2 | 36.2 | 30.7 |
| 29.8 | 30.5 | 35.2 | 31.1 | 29.9 | 27.7 | 29.3 |
| 23.4 | 23.9 | 26.1 | 26.2 | 23.6 | 22.2 | 23.4 |
| 31.6 | 32.2 | 38.7 | 33.0 | 31.7 | 29.8 | 31.3 |
| 26.1 | 26.6 | 32.9 | 26.6 | 26.6 | 24.9 | 26.3 |
| 38.8 | 37.0 | 38.7 | 39.1 | 39.1 | 37.3 | 38.8 |
| 34.7 | 36.2 | 32.0 | 37.5 | 33.0 | 34.1 | 33.5 |
| 27.0 | 26.0 | 23.0 | 29.7 | 27.7 | 28.6 | 28.4 |
| 26.1 | 23.1 | 26.5 | 30.2 | 19.3 | 17.5 | 18.5 |
| 35.6 | 32.8 | 36.2 | 37.6 | 28.9 | 27.0 | 28.1 |
| 28.0 | 34.2 | 34.6 | 31.4 | 32.3 | 33.6 | 31.2 |
| 33.2 | 32.7 | 32.5 | 30.5 | 31.9 | 30.9 | 31.9 |
| 18.6 | 20.4 | 17.5 | 18.8 | 18.5 | 18.7 | 19.3 |
| 21.2 | 23.5 | 21.1 | 21.7 | 21.0 | 20.9 | 21.9 |
| 29.6 | 28.5 | 30.3 | 28.5 | 30.4 | 28.6 | 29.7 |
| 37.2 | 37.0 | 40M | 38.5 | 40.0 | 36.2 | 36.8 |
| 22.4 | 23.4 | 23.4 | 26.8 | 23.0 | 23.0 | 22.8 |
| 23.1 | 22.4 | 21.9 | 24.0 | 21.9 | 21.8 | 21.6 |
| 20.9 | 20.4 | 21.2 | 22.2 | 20.5 | 20.1 | 20.6 |
| oncocytic | FA | FA | FVPTC | BRAF PTC | BRAF PTC | PTC |
| 44 | 35 | 36 | 38 | 40 | 43 | 45 |

| | | | |
|---|---|---|---|
| 35.9 | 30.5 | 40.0 | 37.4 |
| 40.0 | 39.5 | 40.0 | 40.0 |
| 32.7 | 34.7 | 39.9 | 39.5 |
| 34.3 | 35.0 | 40.0 | 40.0 |
| 22.5 | 20.9 | 35.7 | 33.6 |
| 33.6 | 33.9 | 40.0 | 40.0 |
| 32.4 | 39.1 | 40.0 | 40.0 |
| 35.5 | 34.0 | 40.0 | 40.0 |
| 25.7 | 25.5 | 40.0 | 40.0 |
| 25.5 | 25.4 | 40.0 | 40.0 |
| 24.3 | 32.6 | 40.0 | 40.0 |
| 21.0 | 29.4 | 40.0 | 40.0 |
| 28.2 | 34.3 | 40.0 | 40.0 |
| 40.0 | 40.0 | 40.0 | 39.6 |
| 31.4 | 38.6 | 40.0 | 40.0 |
| 24.0 | 30.6 | 39.7 | 40.0 |
| 30.7 | 30.8 | 40.0 | 38.7 |
| 34.4 | 35.5 | 39.5 | 38.2 |
| 29.0 | 28.3 | 40.0 | 40.0 |
| 22.9 | 22.3 | 40.0 | 40.0 |
| 30.3 | 30.6 | 40.0 | 34.4 |
| 25.7 | 25.1 | 40.0 | 40.0 |
| 37.3 | 38.1 | 39.3 | 40.0 |
| 31.5 | 34.3 | 40.0 | 40.0 |
| 28.7 | 24.7 | 40.0 | 40.0 |
| 17.1 | 23.6 | 40.0 | 40.0 |
| 26.1 | 32.7 | 40.0 | 40.0 |
| 31.9 | 30.8 | 40.0 | 40.0 |
| 31.6 | 35.6 | 40.0 | 39.7 |
| 19.1 | 18.3 | 34.4 | 32.7 |
| 21.5 | 21.1 | 39.4 | 34.5 |
| 28.4 | 29.2 | 35.3 | 34.6 |
| 39.5 | 36.6 | 40.0 | 40.0 |
| 22.5 | 22.0 | 40.0 | 39.1 |
| 21.0 | 23.4 | 40.0 | 39.2 |
| 20.5 | 21.5 | 40.0 | 38.4 |
| BRAF PTC | oncocytic | NTC | NTC |
| 46 | 42 | NTC | NTC |

REFERENCES

The following references, to the extent that they provide exemplary procedural or other details supplementary to those set forth herein, are specifically incorporated herein by reference.

U.S. Pat. No. 4,659,774
U.S. Pat. No. 4,682,195
U.S. Pat. No. 4,683,202
U.S. Pat. No. 4,704,362
U.S. Pat. No. 4,816,571
U.S. Pat. No. 4,959,463
U.S. Pat. No. 5,141,813
U.S. Pat. No. 5,143,854
U.S. Pat. No. 5,202,231
U.S. Pat. No. 5,221,619
U.S. Pat. No. 5,223,618
U.S. Pat. No. 5,242,974
U.S. Pat. No. 5,264,566
U.S. Pat. No. 5,288,644
U.S. Pat. No. 5,324,633
U.S. Pat. No. 5,384,261
U.S. Pat. No. 5,405,783
U.S. Pat. No. 5,411,876
U.S. Pat. No. 5,412,087
U.S. Pat. No. 5,413,924
U.S. Pat. No. 5,424,186
U.S. Pat. No. 5,428,148
U.S. Pat. No. 5,429,807
U.S. Pat. No. 5,432,049
U.S. Pat. No. 5,436,327
U.S. Pat. No. 5,445,934
U.S. Pat. No. 5,468,613
U.S. Pat. No. 5,470,710
U.S. Pat. No. 5,470,967
U.S. Pat. No. 5,472,672
U.S. Pat. No. 5,480,980
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,550,044
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146
U.S. Pat. No. 5,580,726
U.S. Pat. No. 5,580,732
U.S. Pat. No. 5,583,013
U.S. Pat. No. 5,593,839
U.S. Pat. No. 5,599,672
U.S. Pat. No. 5,599,695
U.S. Pat. No. 5,602,244
U.S. Pat. No. 5,610,287
U.S. Pat. No. 5,624,711
U.S. Pat. No. 5,631,134
U.S. Pat. No. 5,639,603
U.S. Pat. No. 5,645,897
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,705,629

U.S. Pat. No. 5,744,305
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,871,928
U.S. Pat. No. 5,876,932
U.S. Pat. No. 5,886,165
U.S. Pat. No. 5,919,626
U.S. Pat. No. 5,985,619
U.S. Pat. No. 6,004,755
U.S. Pat. No. 6,087,102
U.S. Pat. No. 6,368,799
U.S. Pat. No. 6,383,749
U.S. Pat. No. 6,403,341
U.S. Pat. No. 6,617,112
U.S. Pat. No. 6,638,717
U.S. Pat. No. 6,720,138
U.S. Pat. No. 6,723,509
U.S. patent appin. Ser. No. 10/667,126
U.S. patent appin. Ser. No. 11/141,707
U.S. patent appin. Ser. No. 11/273,640
U.S. patent appin. Ser. No. 11/567,082
U.S. patent appin. Ser. No. 11/857,948
U.S. Patent appin. Ser. 60/869,295
Andersen et al., Cancer Res., 64(15):5245-5250, 2004.
Carrington and Ambros, Science, 301(5631):336-338, 2003.
Chen et al. Mol. Endocrinol., 19:441-458, 2005.
Cummins et al., In: IRT: Nucleosides and nucleosides, La Jolla Calif., 72, 1996.
Denli et al., Trends Biochem. Sci., 28:196, 2003.
Didenko, Biotechniques, 31(5):1106-16, 1118, 1120-1, 2001.
Emptage et al., Neuron, 29(1):197-208, 2001.
EP 266,032
EP 373 203
EP 785 280
EP 799 897
Froehler et al., Nucleic Acids Res., 14(13):5399-5407, 1986.
Griffey et al., J. Mass Spectrom, 32(3):305-13, 1997.
Griffiths-Jones et al., Nucleic Acids Res., 34:D140-D144, 2006.
Huber et al., Bioinformatics, 18(S1):S96-S104, 2002.
Itakura and Riggs, Science, 209:1401-1405, 1980.
Klostermeier and Millar, Biopolymers, 61(3):159-79, 2001-2002.
Lee et al., Biochim. Biophys. Acta, 1582:175-177, 2002.
Olsen et al., Dev. Biol., 216:671, 1999.
PCT Appin. WO 0138580
PCT Appin. WO 0168255
PCT Appin. WO 03020898
PCT Appin. WO 03022421
PCT Appin. WO 03023058
PCT Appin. WO 03029485
PCT Appin. WO 03040410
PCT Appin. WO 03053586
PCT Appin. WO 03066906
PCT Appin. WO 03067217
PCT Appin. WO 03076928
PCT Appin. WO 03087297
PCT Appin. WO 03091426
PCT Appin. WO 03093810
PCT Appin. WO 03100012
PCT Appin. WO 03100448A1
PCT Appin. WO 04020085
PCT Appin. WO 04027093
PCT Appin. WO 09923256
PCT Appin. WO 09936760
PCT Appin. WO 93/17126
PCT Appin. WO 95/11995
PCT Appin. WO 95/21265
PCT Appin. WO 95/21944
PCT Appin. WO 95/35505
PCT Appin. WO 96/31622
PCT Appin. WO 97/10365
PCT Appin. WO 97/27317
PCT Appin. WO 97/43450
PCT Appin. WO 99/35505
Sambrook et al., In: DNA microaarays: a Molecular Cloning Manual, Cold Spring Harbor Laboratory Press, Cold Spring Harbor, N.Y., 2003.
Sambrook et al., In: Molecular cloning: a Laboratory Manual, $2^{nd}$ Ed., Cold Spring Harbor Laboratory Press, Cold Spring Harbor, N.Y., 1989.
Sambrook et al., In: Molecular cloning: a Laboratory Manual, $3^{rd}$ Ed., Cold Spring Harbor Laboratory Press, Cold Spring Harbor, N.Y., 2001.
Seggerson et al., Dev. Biol., 243:215, 2002.
U.K. Patent 8 803 000

What is claimed is:

1. A method of producing labeled nucleotide sequences from a thyroid sample from a subject, the method comprising contacting the thyroid sample from the subject with labeled primers specific for a group of microRNAs consisting of miR-375, miR-146b-5p, mir-138-1*, and miR-204; and reacting the sample with the labeled primers under conditions to amplify the microRNAs using polymerase chain reaction to produce the labeled nucleotide sequences.

2. The method of claim 1, wherein the label is non-radioactive.

3. The method of claim 1, wherein the label is radioactive.

4. The method of claim 1, wherein the label is a UV spectrum emitting label.

5. The method of claim 1, wherein the label is a fluorescent label.

6. The method of claim 1, wherein the label is an enzymatic label.

* * * * *